US012534446B2

(12) United States Patent
Parham et al.

(10) Patent No.: US 12,534,446 B2
(45) Date of Patent: Jan. 27, 2026

(54) MATERIALS FOR ELECTRONIC DEVICES

(71) Applicant: Merck Patent GmbH, Darmstadt (DE)

(72) Inventors: Amir Parham, Frankfurt am Main (DE); Jonas Kroeber, Frankfurt am Main (DE); Tobias Grossmann, Neubulach (DE); Anja Jatsch, Frankfurt am Main (DE); Christian Eickhoff, Mannheim (DE); Christian Ehrenreich, Darmstadt (DE); Jens Engelhart, Darmstadt (DE)

(73) Assignee: Merck Patent GmbH, Darmstadt (DE)

(*) Notice: Subject to any disclaimer, the term of this patent is extended or adjusted under 35 U.S.C. 154(b) by 1063 days.

(21) Appl. No.: 17/045,190

(22) PCT Filed: Apr. 1, 2019

(86) PCT No.: PCT/EP2019/058174
§ 371 (c)(1),
(2) Date: Oct. 5, 2020

(87) PCT Pub. No.: WO2019/192954
PCT Pub. Date: Oct. 10, 2019

(65) Prior Publication Data

US 2021/0147375 A1 May 20, 2021

(30) Foreign Application Priority Data

Apr. 4, 2018 (EP) .................................... 18165764

(51) Int. Cl.

| | |
|---|---|
| ***C07D 307/91*** | (2006.01) |
| ***C07D 209/86*** | (2006.01) |
| ***C07D 333/76*** | (2006.01) |
| ***H01L 51/00*** | (2006.01) |
| ***H10K 85/30*** | (2023.01) |
| ***H10K 85/40*** | (2023.01) |
| ***H10K 85/60*** | (2023.01) |
| *H10K 50/11* | (2023.01) |
| *H10K 50/15* | (2023.01) |
| *H10K 50/16* | (2023.01) |
| *H10K 101/00* | (2023.01) |
| *H10K 101/10* | (2023.01) |

(52) U.S. Cl.
CPC ......... *C07D 307/91* (2013.01); *C07D 209/86* (2013.01); *C07D 333/76* (2013.01); *H10K 85/342* (2023.02); *H10K 85/346* (2023.02); *H10K 85/40* (2023.02); *H10K 85/633* (2023.02); *H10K 85/636* (2023.02); *H10K 85/6572* (2023.02); *H10K 85/6574* (2023.02); *H10K 85/6576* (2023.02); *H10K 50/11* (2023.02); *H10K 50/15* (2023.02); *H10K 50/16* (2023.02); *H10K 2101/10* (2023.02); *H10K 2101/90* (2023.02)

(58) Field of Classification Search
None
See application file for complete search history.

(56) References Cited

U.S. PATENT DOCUMENTS

| | | | | |
|---|---|---|---|---|
| 10,355,218 | B2 | 7/2019 | Kato | |
| 10,516,112 | B2 | 12/2019 | Kato et al. | |
| 2014/0203216 | A1 | 7/2014 | Elberle et al. | |
| 2015/0322198 | A1* | 11/2015 | Hayer | H05B 33/14 558/290 |
| 2016/0043317 | A1 | 2/2016 | Takada et al. | |
| 2016/0176801 | A1 | 6/2016 | Kato et al. | |
| 2016/0301005 | A1 | 10/2016 | Pfister et al. | |
| 2017/0186969 | A1 | 6/2017 | Kim et al. | |
| 2017/0194569 | A1 | 7/2017 | Kim et al. | |
| 2018/0013068 | A1 | 1/2018 | Parham et al. | |
| 2019/0088878 | A1 | 3/2019 | Parham et al. | |

FOREIGN PATENT DOCUMENTS

| | | | |
|---|---|---|---|
| EP | 3010066 | A1 | 4/2016 |
| JP | 2014-534161 | A | 12/2014 |
| JP | 2016-039187 | A | 3/2016 |
| JP | 2017-501144 | A | 1/2017 |
| KR | 20140043224 | A | 4/2014 |
| KR | 10-2014-0053238 | A | 5/2014 |
| KR | 10-2015-0007476 | A | 1/2015 |
| KR | 10-2016-0017596 | A | 2/2016 |
| KR | 10-2016-0046075 | A | 4/2016 |
| KR | 10-2016-0078506 | A | 7/2016 |
| KR | 2017-0030449 | A | 3/2017 |
| KR | 20170134163 | A | 12/2017 |
| WO | WO-2007072952 | A1 | 6/2007 |
| WO | WO-2011021520 | A1 | 2/2011 |
| WO | WO-2016006709 | A1 | 1/2016 |
| WO | WO-2016006710 | A1 | 1/2016 |
| WO | WO-2017/148564 | A1 * | 9/2017 |
| WO | WO-2017148565 | A1 | 9/2017 |

OTHER PUBLICATIONS

International Preliminary Report on Patentability received for PCT Patent Application No. PCT/EP2019/058174, mailed on Oct. 15, 2020, 16 pages. (8 pages of English Translation and 8 pages of Original Document).
International Search Report for PCT/EP2019/058174 mailed Jun. 6, 2019.
Written Opinion of the International Searching Authority for PCT/EP2019/058174 mailed Jun. 6, 2019.

* cited by examiner

*Primary Examiner* — Jay Yang
(74) *Attorney, Agent, or Firm* — Faegre Drinker Biddle & Reath LLP

(57) ABSTRACT

The present application relates to fluorenylamine compounds, to the use thereof in electronic devices, and to synthesis methods for preparing the fluorenylamine compounds.

15 Claims, No Drawings

MATERIALS FOR ELECTRONIC DEVICES

CROSS-REFERENCE TO RELATED APPLICATIONS

This application is a national stage application (under 35 U.S.C. § 371) of PCT/EP2019/058174, filed Apr. 1, 2019, which claims benefit of European Application No. 18165764.4, filed Apr. 4, 2018, both of which are incorporated herein by reference in their entirety.

The present application relates to fluorenyl compounds containing at least one amino group. The compounds are suitable for use in electronic devices.

Electronic devices in the context of this application are understood to mean what are called organic electronic devices, which contain organic semiconductor materials as functional materials. More particularly, these are understood to mean OLEDs (organic electroluminescent devices). The term OLEDs is understood to mean electronic devices which have one or more layers comprising organic compounds and emit light on application of electrical voltage. The construction and general principle of function of OLEDs are known to those skilled in the art.

In electronic devices, especially OLEDs, there is great interest in an improvement in the performance data, especially lifetime, efficiency and operating voltage. In these aspects, it has not yet been possible to find any entirely satisfactory solution.

There is additionally a search for materials having a high glass transition temperature, a low tendency to crystallization and a high refractive index, especially for use in hole-transporting and emitting layers of OLEDs.

A great influence on the performance data of electronic devices is possessed by emission layers and layers having a hole-transporting function. Novel compounds are also being sought for use in these layers, especially hole-transporting compounds and compounds that can serve as matrix material, especially for phosphorescent emitters, in an emitting layer.

Compounds containing one or more fluorenyl groups bonded to an amino group directly or via spacer groups are known in the prior art as compounds for use in OLEDs, especially for use as hole-transporting compounds.

However, there is still a need for alternative compounds suitable for use in electronic devices. There is also a need for improvement with regard to the performance data in use in electronic devices, especially with regard to lifetime, operating voltage and efficiency.

It has now been found that particular compounds from the abovementioned structure class are of excellent suitability for use in electronic devices, especially for use in OLEDs, even more especially for use therein as hole transport materials and for use as matrix materials for phosphorescent emitters. The compounds preferably lead to high lifetime, high efficiency and low operating voltage of the devices. Further preferably, the compounds have a low tendency to crystallization, a high glass transition temperature and a high refractive index.

The present application thus provides a compound of a formula (I)

Formula (I)

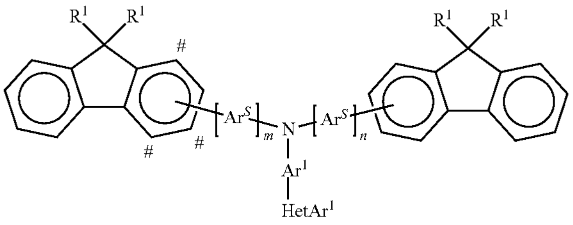

where the free positions on the fluorenyl groups may each be substituted by an $R^2$ radical, and where, in addition:

$R^1$ is the same or different at each instance and is selected from H, D, F, $Si(R^{11})_3$, straight-chain alkyl and alkoxy groups having 1 to 20 carbon atoms and branched or cyclic alkyl or alkoxy groups having 3 to 20 carbon atoms, where two or more $R^1$ radicals may be joined to one another and may form a ring; where the alkyl and alkoxy groups mentioned may each be substituted by one or more $R^{11}$ radicals;

$Ar^S$ is the same or different at each instance and is selected from aromatic ring systems which have 6 to 40 aromatic ring atoms and may be substituted by one or more $R^3$ radicals, and heteroaromatic ring systems which have 5 to 40 aromatic ring atoms and may be substituted by one or more $R^3$ radicals;

$Ar^1$ is selected from aromatic ring systems which have 6 to 40 aromatic ring atoms and may be substituted by one or more $R^4$ radicals, and heteroaromatic ring systems which have 5 to 40 aromatic ring atoms and may be substituted by one or more $R^4$ radicals;

$HetAr^1$ is selected from heteroaromatic ring systems which have 13 to 40 aromatic ring atoms and may be substituted by one or more $R^5$ radicals;

$R^2$, $R^3$, $R^4$, $R^5$ are the same or different at each instance and are selected from H, D, F, $C(=O)R^{11}$, CN, $Si(R^{11})_3$, $N(R^{11})_2$, $P(=O)(R^{11})_2$, $OR^{11}$, $S(=O)R^{11}$, $S(=O)_2R^{11}$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more radicals selected from $R^2$ radicals, two or more radicals selected from $R^3$ radicals, two or more radicals selected from $R^4$ radicals and two or more radicals selected from $R^5$ radicals may in each case be joined to one another and may form a ring; where the alkyl, alkoxy, alkenyl and alkynyl groups mentioned and the aromatic ring systems and heteroaromatic ring systems mentioned may each be substituted by one or more $R^{11}$ radicals; and where one or more $CH_2$ groups in the alkyl, alkoxy, alkenyl and alkynyl groups mentioned may be replaced by $-R^{11}C=CR^{11}-$, $-C\equiv C-$, $Si(R^{11})_2$, $C=O$, $C=NR^{11}$, $-C(=O)O-$, $-C(=O)NR^{11}-$, $NR^{11}$, $P(=O)(R^{11})$, $-O-$, $-S-$, SO or $SO_2$;

$R^{11}$ is the same or different at each instance and is selected from H, D, F, $C(=O)R^{21}$, CN, $Si(R^{21})_3$, $N(R^{21})_2$, $P(=O)(R^{21})_2$, $OR^{21}$, $S(=O)R^{21}$, $S(=O)_2R^{21}$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ radicals may be joined to one another and may form a ring; where the alkyl, alkoxy, alkenyl and alkynyl groups mentioned and the aromatic ring systems and heteroaromatic ring systems mentioned may each be substituted by one or more $R^{21}$ radicals; and where one or more $CH_2$ groups in the alkyl, alkoxy, alkenyl and alkynyl groups mentioned may be replaced by $-R^{21}C{=}CR^{21}-$, $-C{\equiv}C-$, $Si(R^{21})_2$, C═O, $C{=}NR^{21}$, —C(═O)O—, $-C(=O)NR^{21}-$, $NR^{21}$, $P(=O)(R^{21})$, —O—, —S—, SO or $SO_2$;

$R^{21}$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^3$ radicals may be joined to one another and may form a ring; and where the alkyl, alkoxy, alkenyl and alkynyl groups, aromatic ring systems and heteroaromatic ring systems mentioned may be substituted by one or more radicals selected from F and CN;

m, n are the same or different and are selected from 0, 1, 2 and 3, where at least one of the indices m and n is 0; and where the left-hand fluorenyl group is bonded to the $Ar^S$ group or the N via one of the positions marked #.

The circle within the six-membered rings of the formula (I) means that the ring in question is aromatic.

The following is applicable to the indices m and n: if the index in question is 0, the $Ar^S$ group indicated thereby is absent, and the groups that bind to this group are bonded directly to one another. If the index in question is 2, two $Ar^S$ groups are present, which are bonded to one another in such a way that an $-Ar^S-Ar^S-$ unit is present. If the index in question is 3, three $Ar^S$ groups are present, which are bonded to one another in such a way that a $-Ar^S-Ar^S-Ar^S-$ unit is present.

The definitions which follow are applicable to the chemical groups that are used in the present applications. They are applicable unless any more specific definitions are given.

An aryl group in the context of this invention is understood to mean either a single aromatic cycle, i.e. benzene, or a fused aromatic polycycle, for example naphthalene, phenanthrene or anthracene. A fused aromatic polycycle in the context of the present application consists of two or more single aromatic cycles fused to one another. Fusion between cycles is understood here to mean that the cycles share at least one edge with one another. An aryl group in the context of this invention contains 6 to 40 aromatic ring atoms of which none is a heteroatom.

A heteroaryl group in the context of this invention is understood to mean either a single heteroaromatic cycle, for example pyridine, pyrimidine or thiophene, or a fused heteroaromatic polycycle, for example quinoline or carbazole. A fused heteroaromatic polycycle in the context of the present application consists of two or more single aromatic or heteroaromatic cycles that are fused to one another, where at least one of the aromatic and heteroaromatic cycles is a heteroaromatic cycle. Fusion between cycles is understood here to mean that the cycles share at least one edge with one another. A heteroaryl group in the context of this invention contains 5 to 40 aromatic ring atoms of which at least one is a heteroatom. The heteroatoms of the heteroaryl group are preferably selected from N, O and S.

An aryl or heteroaryl group, each of which may be substituted by the abovementioned radicals, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention is a system which does not necessarily contain solely aryl groups, but which may additionally contain one or more non-aromatic rings fused to at least one aryl group. These non-aromatic rings contain exclusively carbon atoms as ring atoms. Examples of groups covered by this definition are tetrahydronaphthalene, fluorene and spirobifluorene. In addition, the term "aromatic ring system" includes systems that consist of two or more aromatic ring systems joined to one another via single bonds, for example biphenyl, terphenyl, 7-phenyl-2-fluorenyl, quaterphenyl and 3,5-diphenyl-1-phenyl. An aromatic ring system in the context of this invention contains 6 to 40 carbon atoms and no heteroatoms in the ring system. The definition of "aromatic ring system" does not include heteroaryl groups.

A heteroaromatic ring system conforms to the abovementioned definition of an aromatic ring system, except that it must contain at least one heteroatom as ring atom. As is the case for the aromatic ring system, the heteroaromatic ring system need not contain exclusively aryl groups and heteroaryl groups, but may additionally contain one or more non-aromatic rings fused to at least one aryl or heteroaryl group. The non-aromatic rings may contain exclusively carbon atoms as ring atoms, or they may additionally contain one or more heteroatoms, where the heteroatoms are preferably selected from N, O and S. One example of such a heteroaromatic ring system is benzopyranyl. In addition, the term "heteroaromatic ring system" is understood to mean systems that consist of two or more aromatic or heteroaromatic ring systems that are bonded to one another via single bonds, for example 4,6-diphenyl-2-triazinyl. A heteroaromatic ring system in the context of this invention contains 5 to 40 ring atoms selected from carbon and heteroatoms, where at least one of the ring atoms is a heteroatom. The heteroatoms of the heteroaromatic ring system are preferably selected from N, O and S.

The terms "heteroaromatic ring system" and "aromatic ring system" as defined in the present application thus differ from one another in that an aromatic ring system cannot have a heteroatom as ring atom, whereas a heteroaromatic ring system must have at least one heteroatom as ring atom.

This heteroatom may be present as a ring atom of a non-aromatic heterocyclic ring or as a ring atom of an aromatic heterocyclic ring.

In accordance with the above definitions, any aryl group is covered by the term "aromatic ring system", and any heteroaryl group is covered by the term "heteroaromatic ring system".

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

$R^1$ is preferably the same or different at each instance, preferably the same, and is selected from straight-chain alkyl groups having 1 to 10 carbon atoms and branched or cyclic alkyl groups having 3 to 10 carbon atoms, where two or more $R^1$ radicals may be joined to one another and may form a ring, and where one or more hydrogen atoms in the alkyl groups may be replaced by D. More preferably, $R^1$ is the same or different at each instance, preferably the same, and is selected from methyl, n-octyl and cyclopentyl; most preferably, $R^1$ is methyl.

Preferred $Ar^S$ groups are selected from benzene, biphenyl, terphenyl, naphthalene, fluorene, indenofluorene, indenocarbazole, spirobifluorene, dibenzofuran, dibenzothiophene, and carbazole, each of which may be substituted by one or more $R^3$ radicals. Most preferably, $Ar^S$ is benzene which may be substituted in each case by one or more $R^3$ radicals. When $Ar^S$ is benzene, $R^3$ is preferably selected from H, methyl and phenyl.

m and n are preferably 0 or 1, where at least one of the indices m and n is 0. More preferably, m and n are both 0.

$Ar^1$ is preferably selected from aromatic ring systems which have 6 to 20 aromatic ring atoms and may be substituted by one or more $R^4$ radicals. Particularly preferred $Ar^1$ groups are selected from benzene, biphenyl, terphenyl, naphthalene, phenylnaphthalene, fluorene, indenofluorene, indenocarbazole, spirobifluorene, dibenzofuran, dibenzothiophene, and carbazole, especially N-arylcarbazole, each of which may be substituted by one or more $R^4$ radicals. Even more preferably, $Ar^1$ is benzene or naphthalene, each of which may be substituted by one or more $R^3$ radicals, most preferably benzene which may be substituted in each case by one or more $R^4$ radicals. When $Ar^1$ is benzene, $R^4$ is preferably selected from H, methyl and phenyl.

Preferred $Ar^1$ groups are shown in the following table:

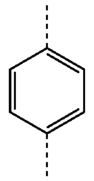
$Ar^1$-1

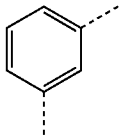
$Ar^1$-2

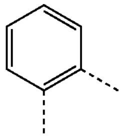
$Ar^1$-3

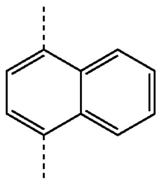
$Ar^1$-4

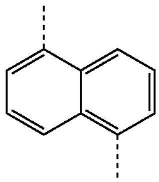
$Ar^1$-5

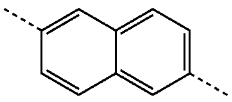
$Ar^1$-6

-continued
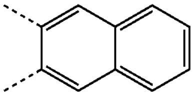
Ar¹-7
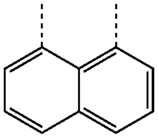
Ar¹-8
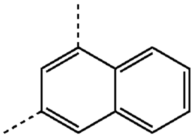
Ar¹-9
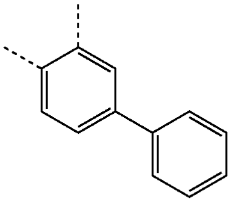
Ar¹-10
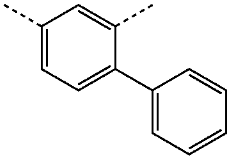
Ar¹-11
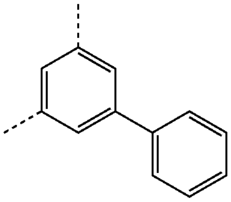
Ar¹-12
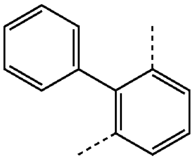
Ar¹-13
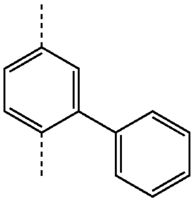
Ar¹-14
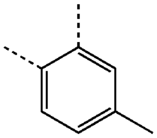
Ar¹-15
-continued
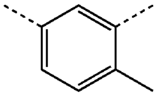
Ar¹-16
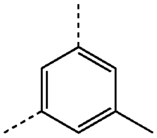
Ar¹-17
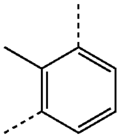
Ar¹-18
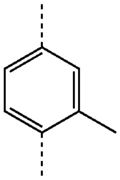
Ar¹-19
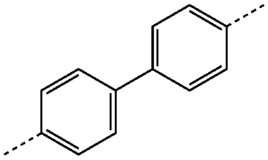
Ar¹-20
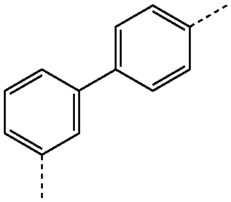
Ar¹-21
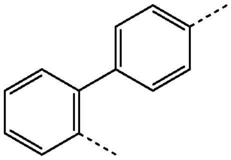
Ar¹-22
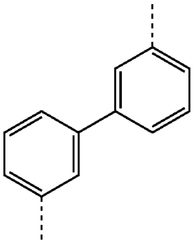
Ar¹-23
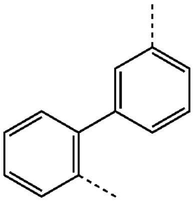
Ar¹-24

-continued
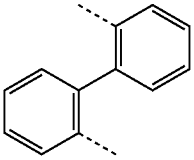
Ar$^1$-25
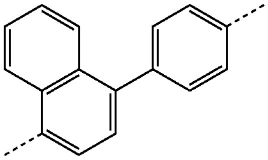
Ar$^1$-26
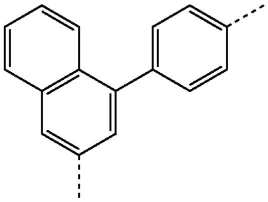
Ar$^1$-27
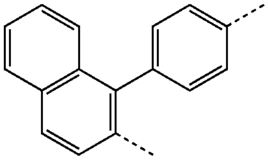
Ar$^1$-28
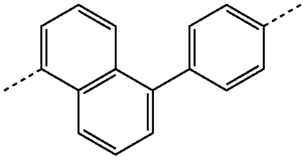
Ar$^1$-29
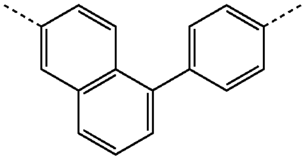
Ar$^1$-30
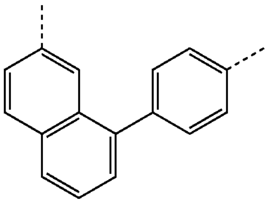
Ar$^1$-31
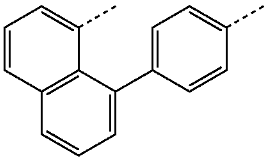
Ar$^1$-32
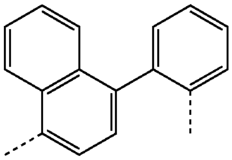
Ar$^1$-33
-continued
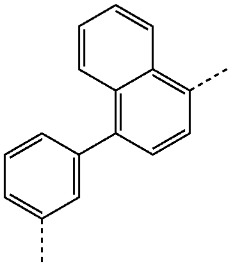
Ar$^1$-34
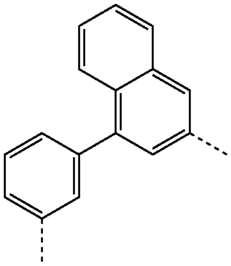
Ar$^1$-35
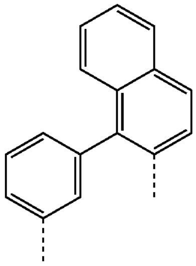
Ar$^1$-36
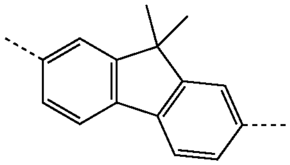
Ar$^1$-37
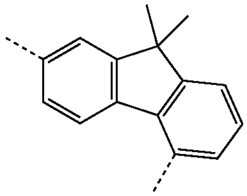
Ar$^1$-38
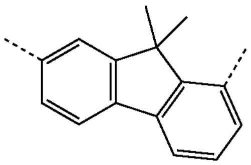
Ar$^1$-39
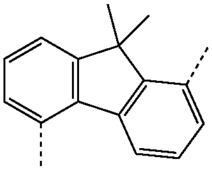
Ar$^1$-40

-continued
Ar$^1$-41
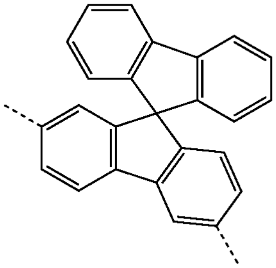
Ar$^1$-42
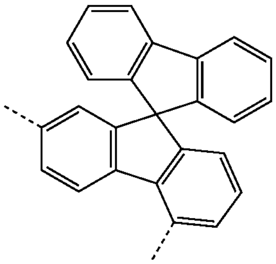
Ar$^1$-43
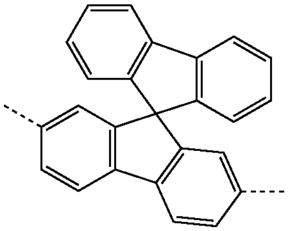
Ar$^1$-44
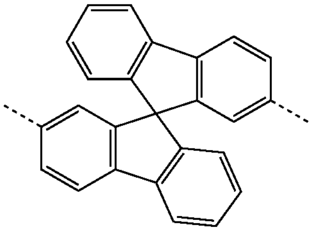
Ar$^1$-45
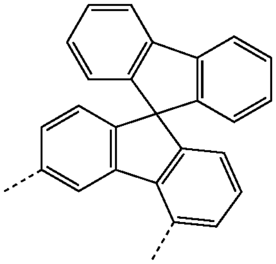
Ar$^1$-46
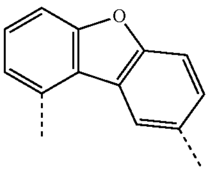
-continued
Ar$^1$-47
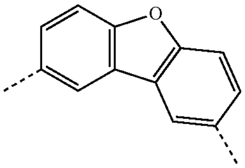
Ar$^1$-48
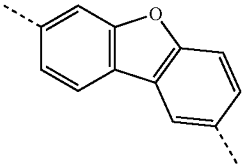
Ar$^1$-49
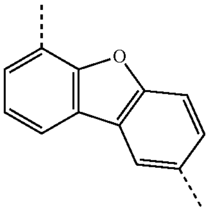
Ar$^1$-50
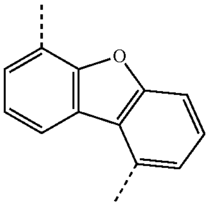
Ar$^1$-51
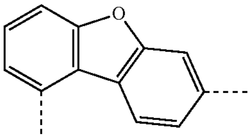
Ar$^1$-52
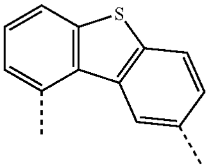
Ar$^1$-53
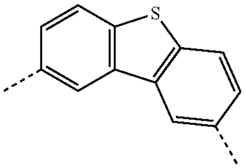
Ar$^1$-54
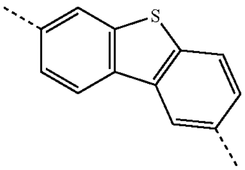

-continued

Ar1-55

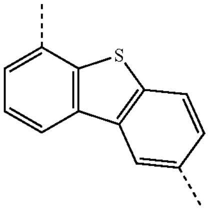

Ar1-56

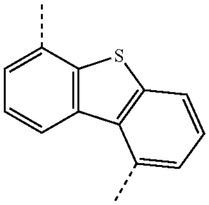

Ar1-57

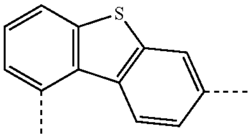

Ar1-58

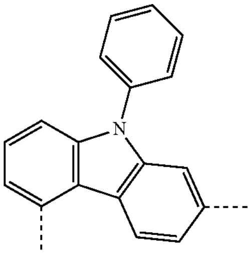

Ar1-59

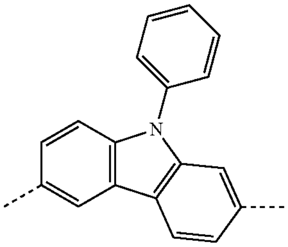

Ar1-60

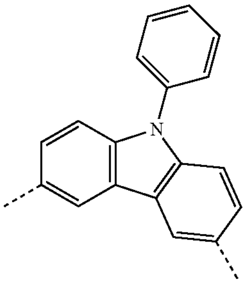

Ar1-61

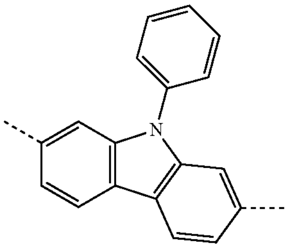

-continued

Ar1-62

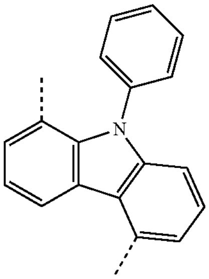

Ar1-63

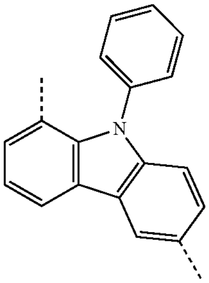

Ar1-64

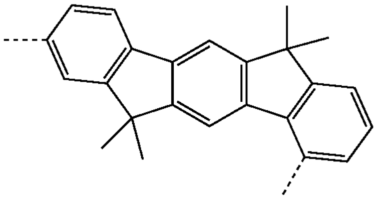

Ar1-65

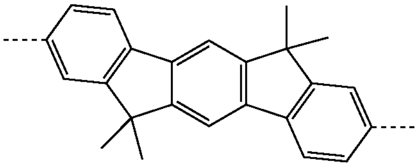

Ar1-66

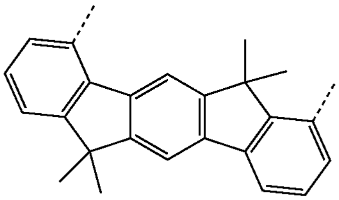

$HetAr^1$ is preferably selected from dibenzofuran, benzonaphthofuran, dibenzothiophene, benzonaphthothiophene, carbazole bonded via one of its carbon atoms, carbazole bonded via its nitrogen atom, benzocarbazole bonded via one of its carbon atoms, and benzocarbazole bonded via its nitrogen atom, more preferably dibenzofuran, dibenzothiophene and carbazole, where carbazole is preferably bonded via one of its carbon atoms, and where the groups mentioned may be substituted by one or more $R^5$ radicals.

The —$Ar^1$-$HetAr^1$ group in formula (I) preferably conforms to the following formula (H-1) or (H-2):

Formula (H-1)

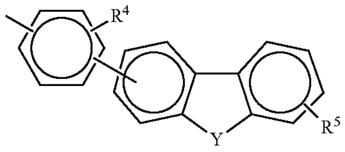

Formula (H-2)

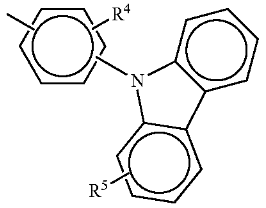

where Y is O, S or $NR^5$, more preferably O, S, or N-Ph where Ph is a phenyl group that may be substituted by one or more $R^{11}$ radicals; and where $R^4$ and $R^5$ are defined as above, and are preferably H or phenyl, more preferably H;

and where the group is bonded to the nitrogen atom in formula (I) via the free bond.

$R^2$, $R^3$, $R^4$, $R^5$ are preferably the same or different at each instance and are selected from H, D, F, CN, $Si(R^{11})_3$, $N(R^{11})_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where said alkyl groups, said aromatic ring systems and said heteroaromatic ring systems may each be substituted by one or more $R^1$ radicals. Most preferably, $R^2$, $R^3$, $R^4$, $R^5$ are the same or different at each instance and are selected from H, aromatic ring systems having 6 to 40 aromatic ring atoms, and heteroaromatic ring systems having 5 to 40 aromatic ring atoms, each of which may substituted by one or more $R^1$ radicals. Most preferably, $R^2$, $R^3$, $R^4$, $R^5$ are the same or different at each instance and are selected from H and phenyl, especially H.

$R^{11}$ is preferably the same or different at each instance and is selected from H, D, F, CN, $Si(R^{21})_3$, $N(R^{21})_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where said alkyl groups, said aromatic ring systems and said heteroaromatic ring systems may each be substituted by one or more $R^{21}$ radicals.

Preferably, the left-hand fluorene group in formula (I) is bonded in the 4 position to the $Ar^S$ group or the N. Preferably, the right-hand fluorene group in formula (I) is bonded in the 4 position or in the 2 position to the $Ar^S$ group or the N.

These positions on the fluorene groups are defined as follows:

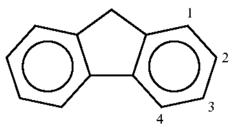

Embodiments of the formula (I) are the following formulae:

Formula (I-A)

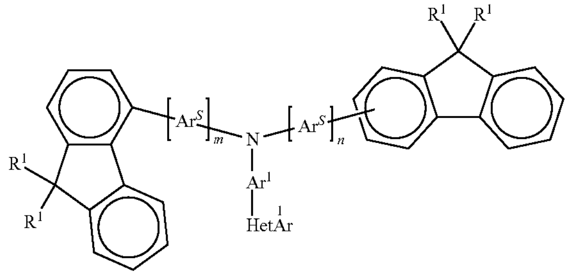

Formula (I-B)

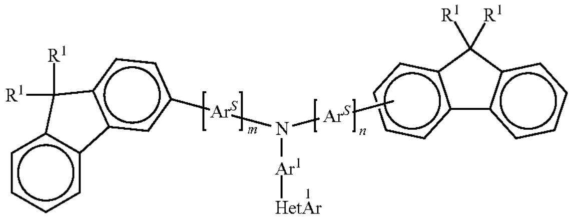

Formula (I-C)

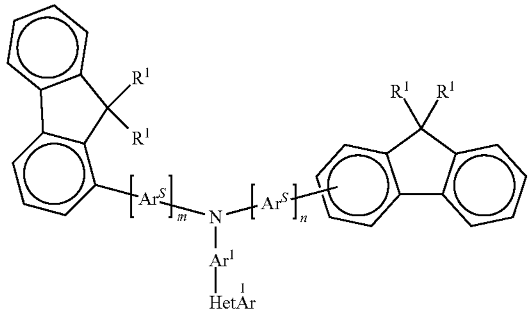

where the groups and indices that occur are defined as above, where the unoccupied positions of the fluorenyl groups may each be substituted by an $R^2$ radical, and where at least one of the indices m and n is 0.

Among these formulae, preference is given to formula (I-A).

Preferred embodiments of the formula (I-A) are the following formulae:

Formula (I-A-1)

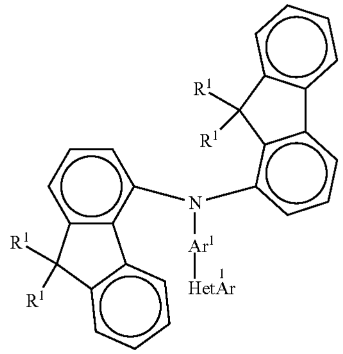

-continued

Formula (I-A-2)

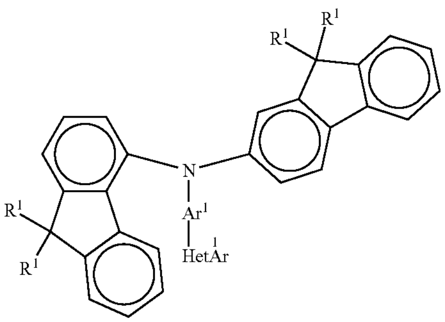

Formula (I-A-3)

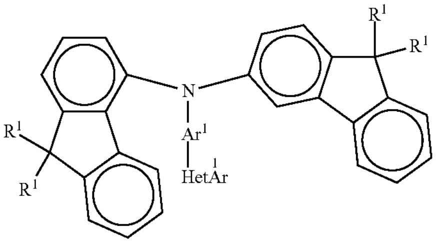

Formula (I-A-4)

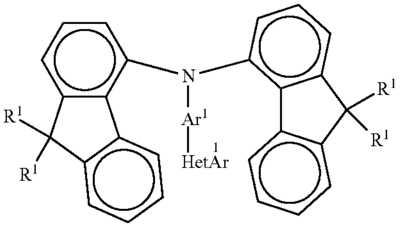

Formula (I-A-5)

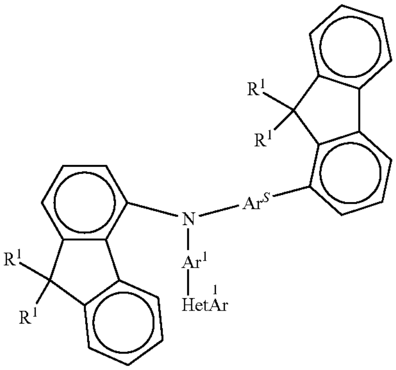

Formula (I-A-6)

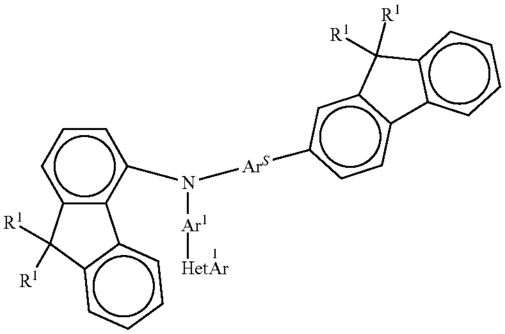

-continued

Formula (I-A-7)

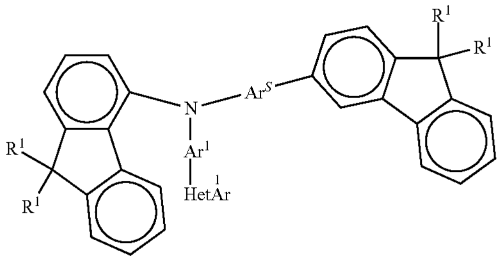

Formula (I-A-8)

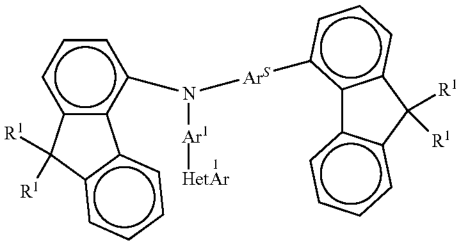

Formula (I-A-9)

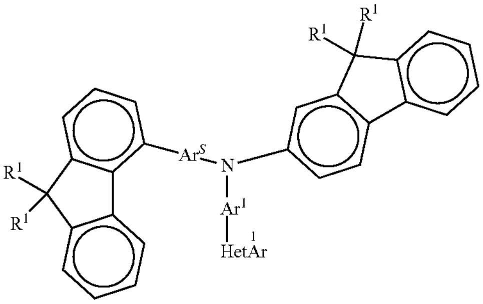

where the variable groups are as defined above, and where the unoccupied positions on the fluorenyl groups may each be substituted by an $R^2$ radical. Preferably, in the formulae, $Ar^S$ is selected from ortho-phenylene, meta-phenylene and para-phenylene, each of which may be substituted by one or more $R^3$ radicals. $R^3$ here is preferably selected from H, alkyl groups having 1 to 10 carbon atoms and aromatic ring systems having 6 to 40 aromatic ring atoms, more preferably from H, methyl and phenyl. In addition, the —$Ar^1$-$HetAr^1$ group preferably conforms to the formula (H-1) or (H-2), more preferably to the formula (H-1).

Preferred embodiments of the formula (I-B) are the following formulae:

Formula (I-B-1)

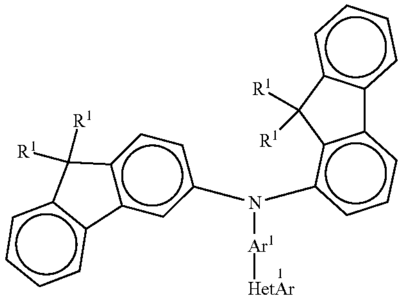

-continued

Formula (I-B-2)

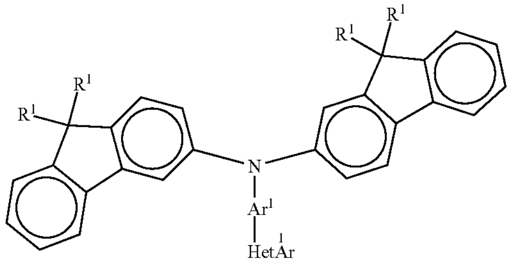

Formula (I-B-3)

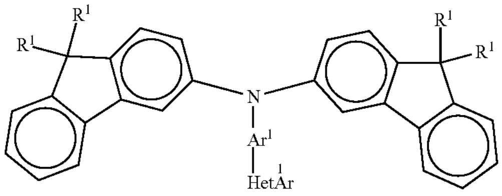

Formula (I-B-4)

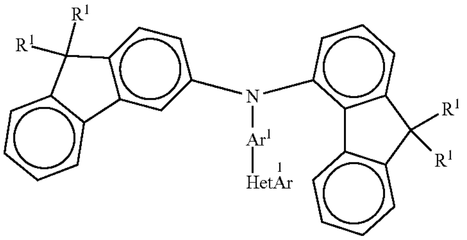

Formula (I-B-5)

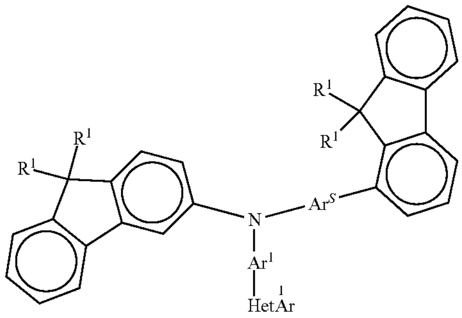

Formula (I-B-6)

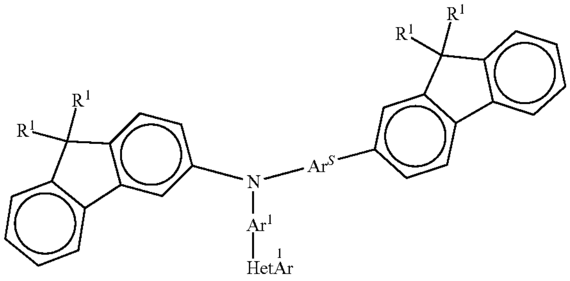

-continued

Formula (I-B-7)

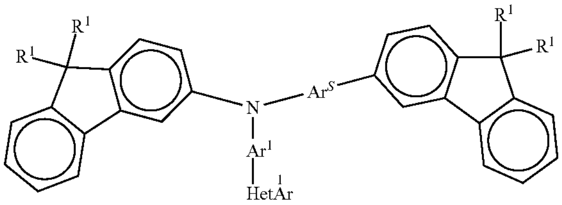

Formula (I-B-8)

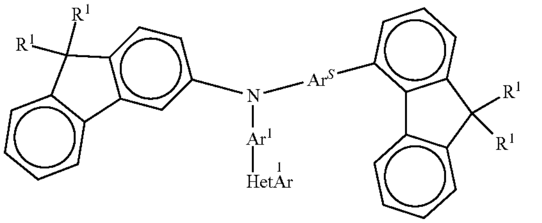

Formula (I-B-9)

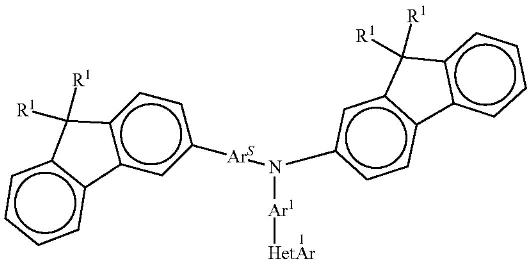

where the variable groups are as defined above, and where the unoccupied positions on the fluorenyl groups may each be substituted by an $R^2$ radical. Preferably, in the formulae, $Ar^S$ is selected from ortho-phenylene, meta-phenylene and para-phenylene, each of which may be substituted by one or more $R^3$ radicals. $R^3$ here is preferably selected from H, alkyl groups having 1 to 10 carbon atoms and aromatic ring systems having 6 to 40 aromatic ring atoms, more preferably from H, methyl and phenyl. In addition, the —$Ar^1$-$HetAr^1$ group preferably conforms to the formula (H-1) or (H-2), more preferably to the formula (H-1).

Preferred embodiments of the formula (I-C) are the following formulae:

Formula (I-C-1)

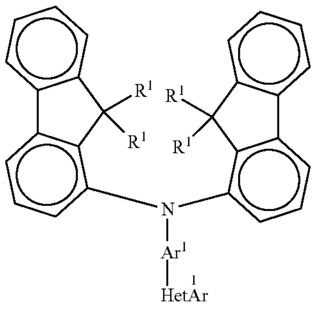

-continued

Formula (I-C-2)

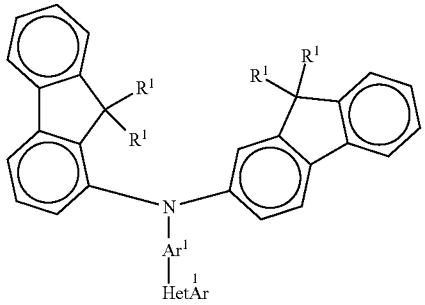

Formula (I-C-3)

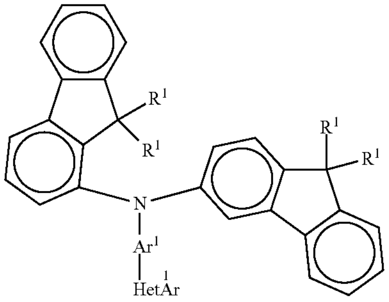

Formula (I-C-4)

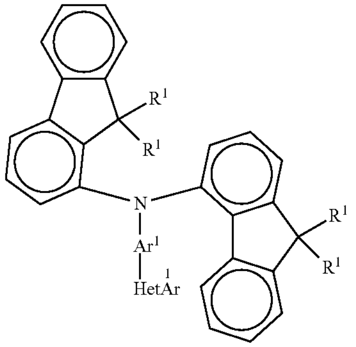

Formula (I-C-5)

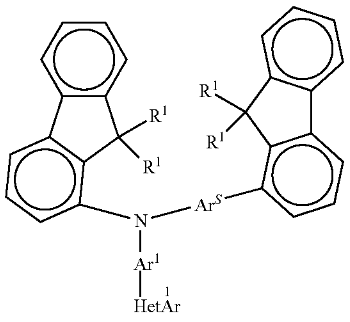

Formula (I-C-6)

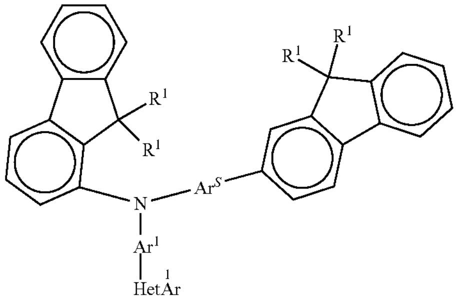

-continued

Formula (I-C-7)

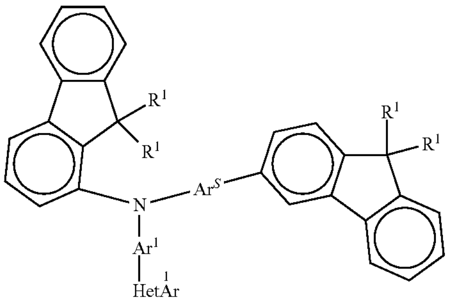

Formula (I-C-8)

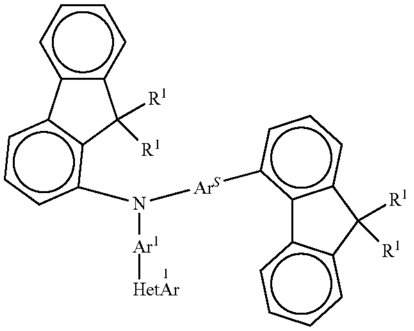

Formula (I-C-9)

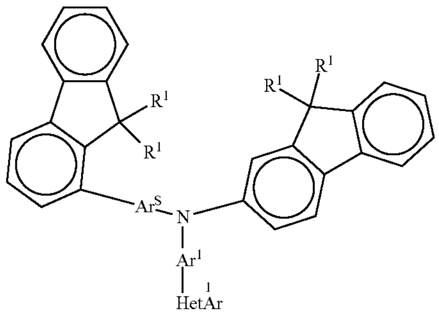

where the variable groups are as defined above, and where the unoccupied positions on the fluorenyl groups may each be substituted by an $R^2$ radical. Preferably, in the formulae, $Ar^S$ is selected from ortho-phenylene, meta-phenylene and para-phenylene, each of which may be substituted by one or more $R^3$ radicals. $R^3$ here is preferably selected from H, alkyl groups having 1 to 10 carbon atoms and aromatic ring systems having 6 to 40 aromatic ring atoms, more preferably from H, methyl and phenyl. In addition, the —$Ar^1$-$HetAr^1$ group preferably conforms to the formula (H-1) or (H-2), more preferably to the formula (H-1).

The following compounds are preferred embodiments of the formula (I):

1
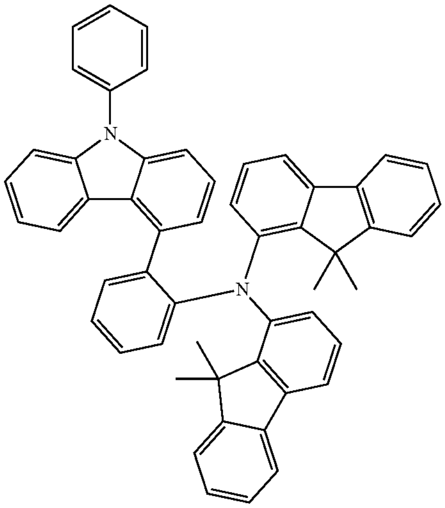
2
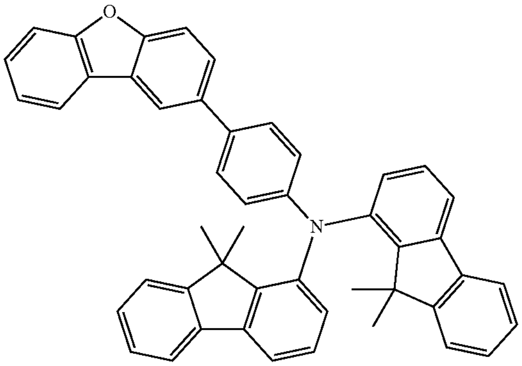
3
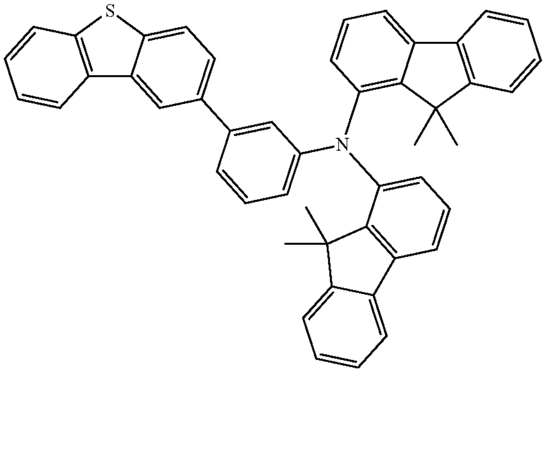
-continued
4
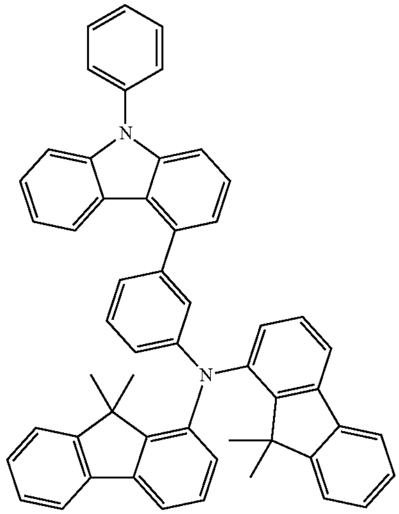
5
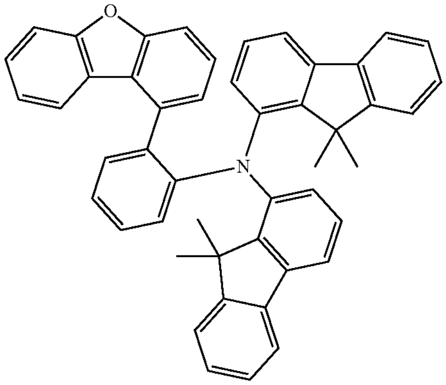
6
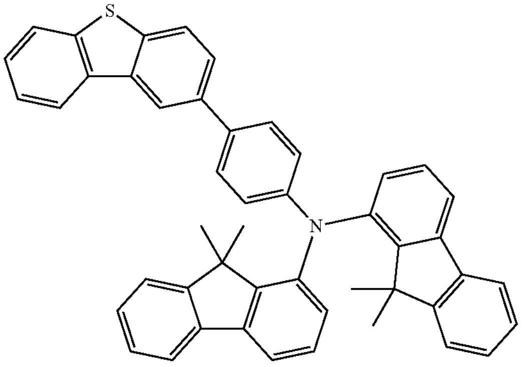

-continued
7
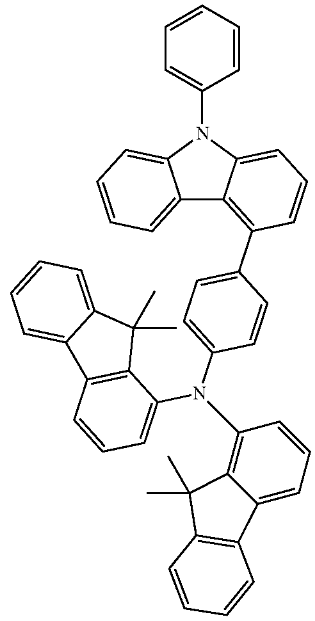
8
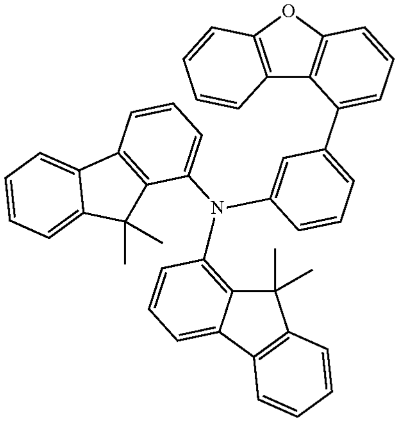
9
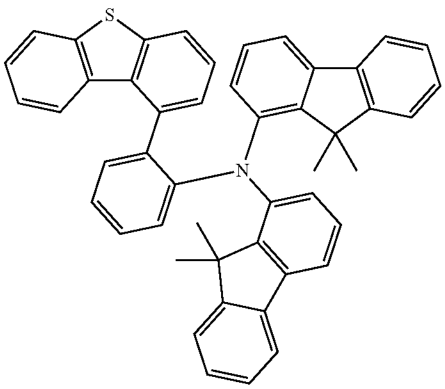
-continued
10
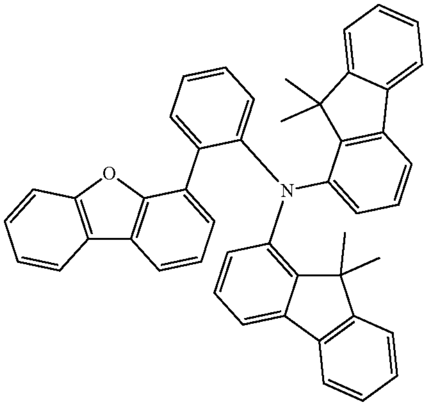
11
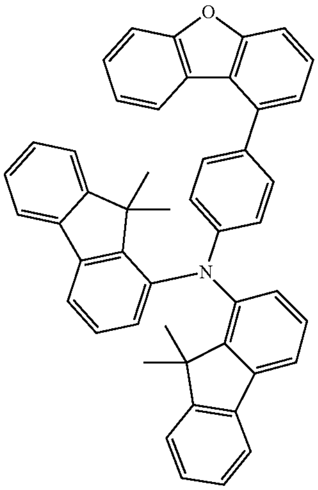
12
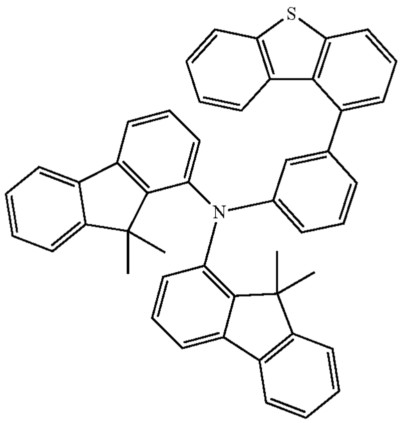

-continued
13
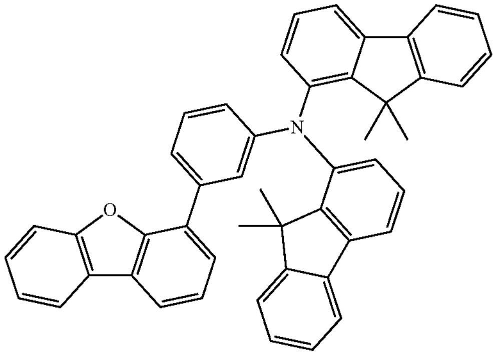
14
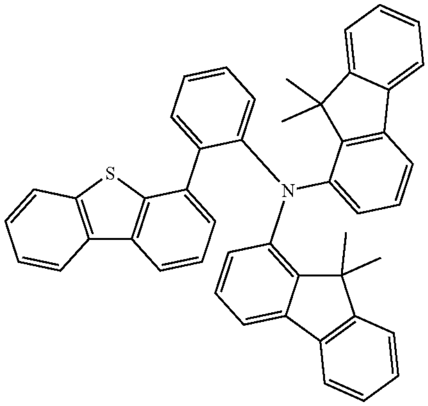
15
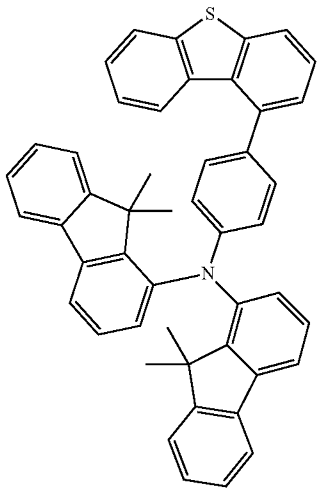
-continued
16
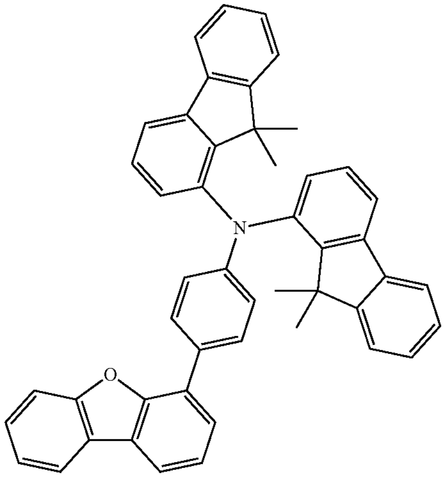
17
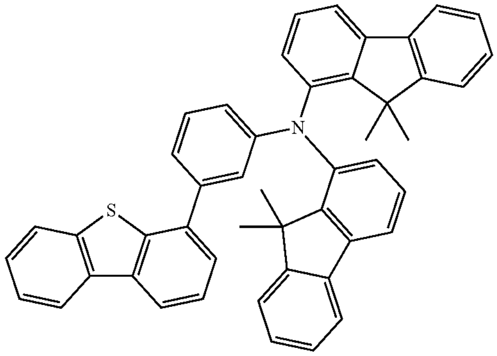
18
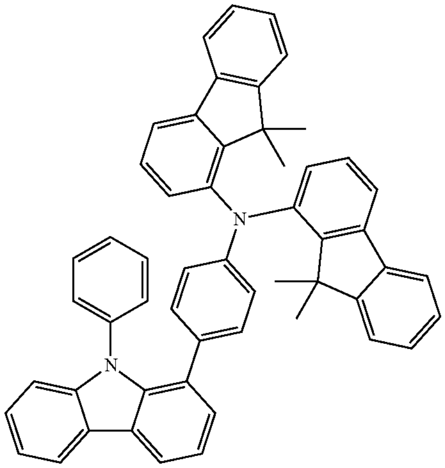
19
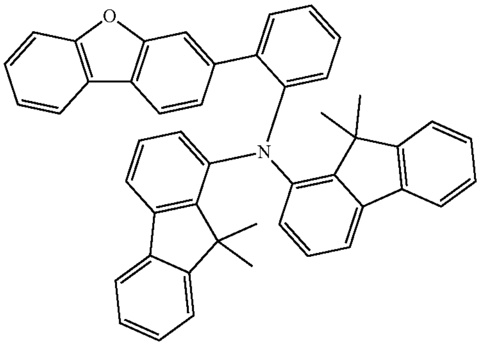

-continued
20
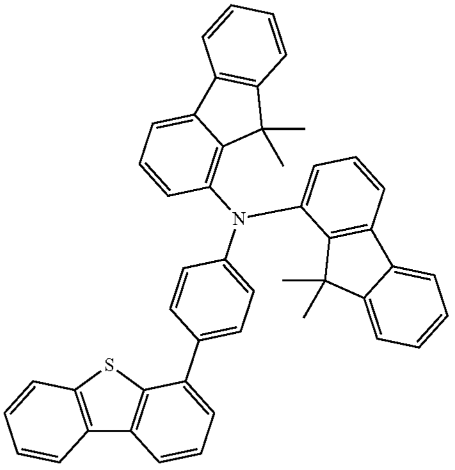
21
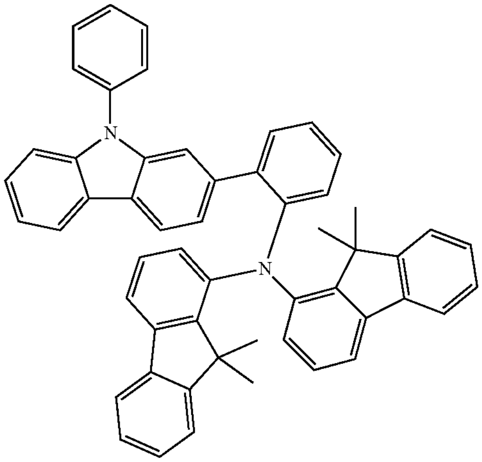
22
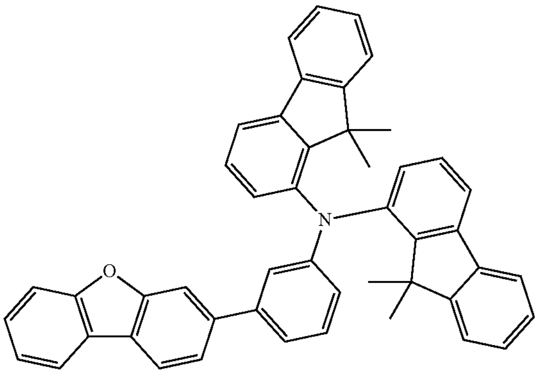
-continued
23
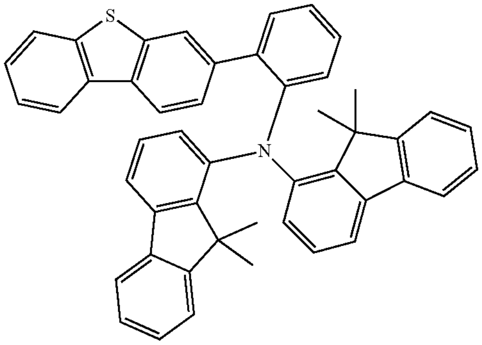
24
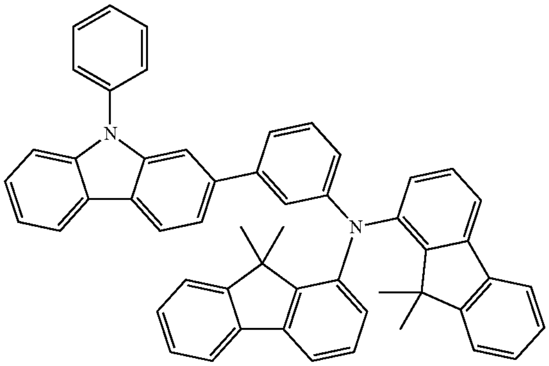
25
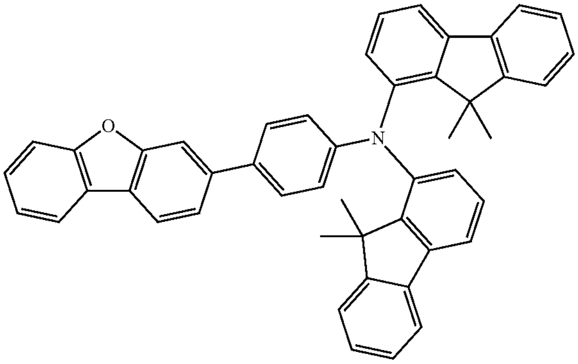
26
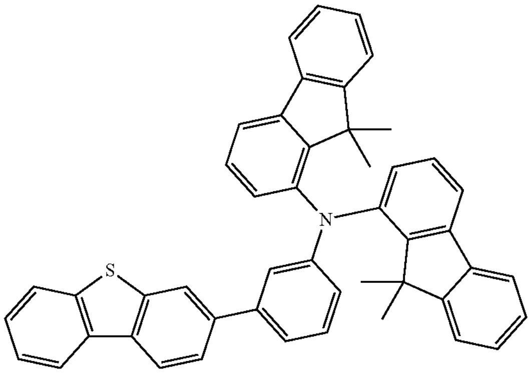

-continued
27
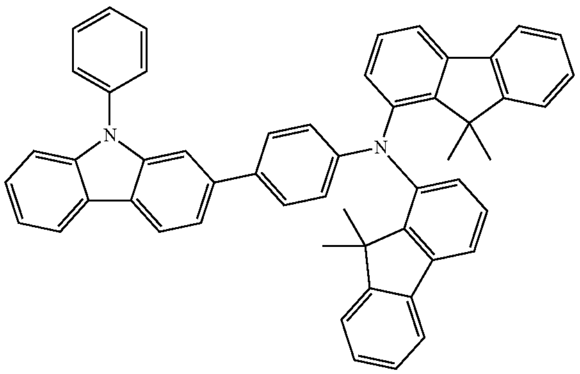
28
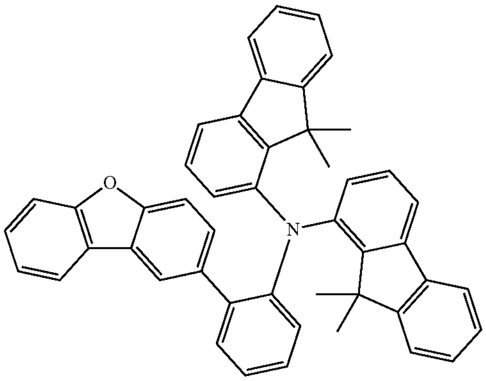
29
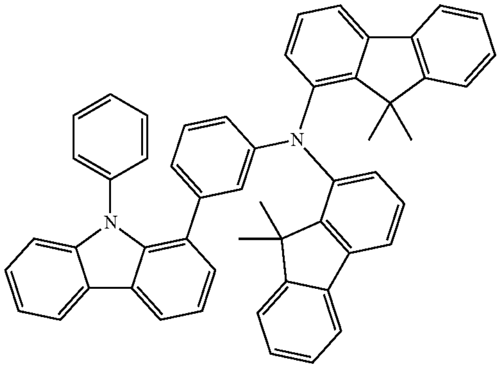
30
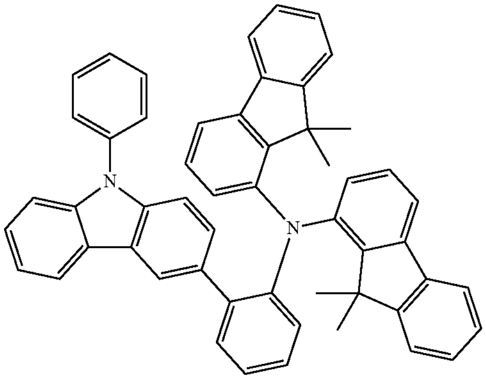
-continued
31
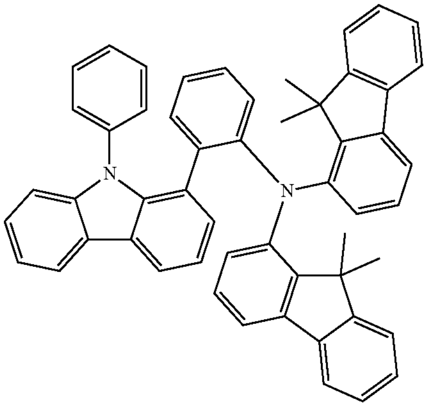
32
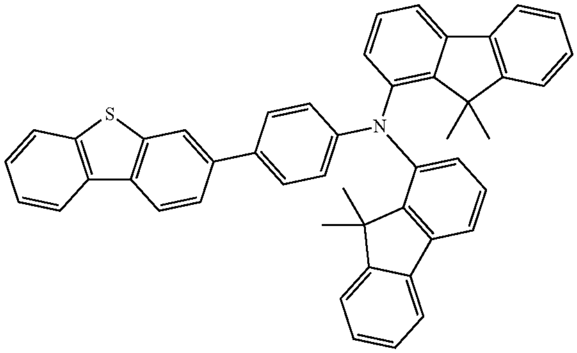
33
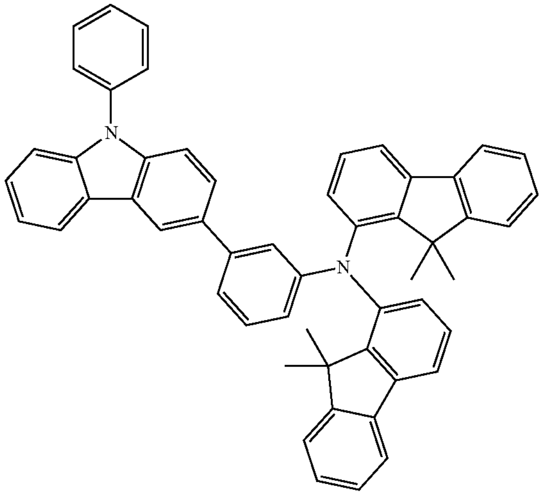

-continued
34
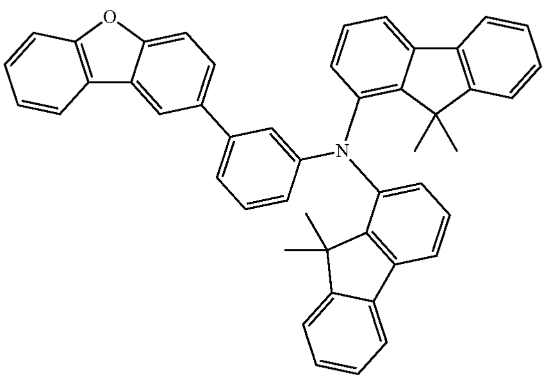
35
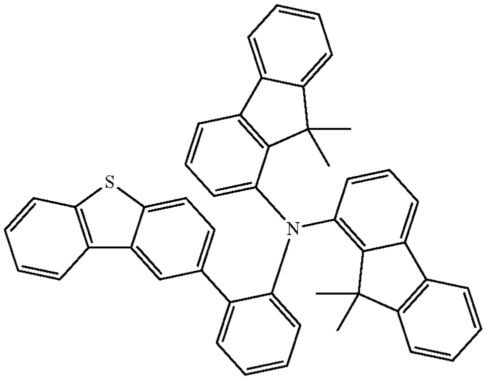
36
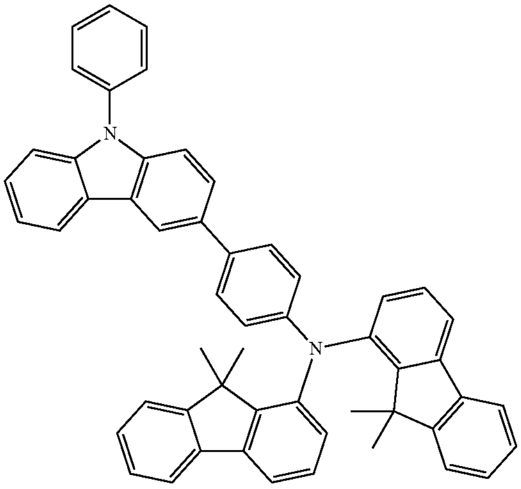
-continued
37
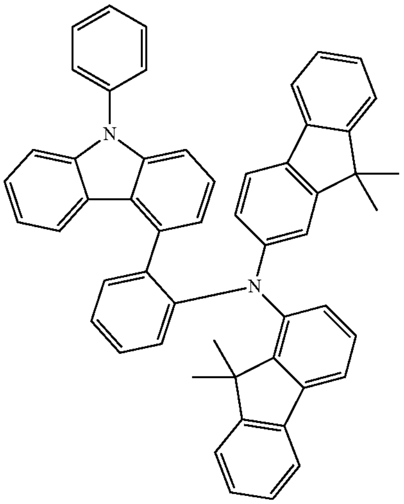
38
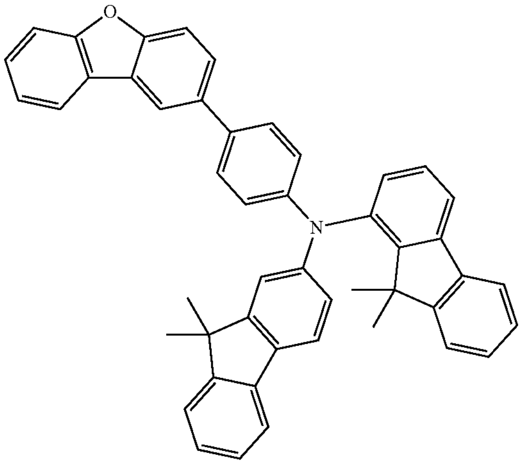
39
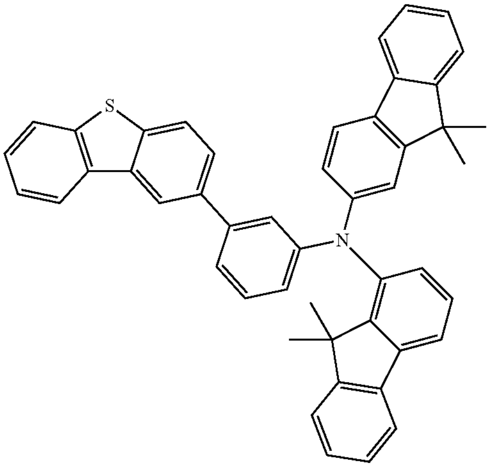

-continued
40
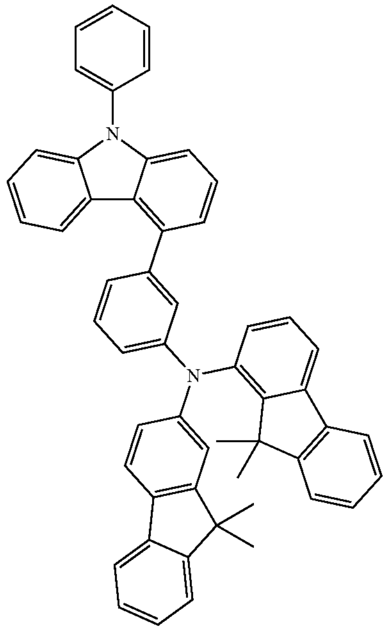
41
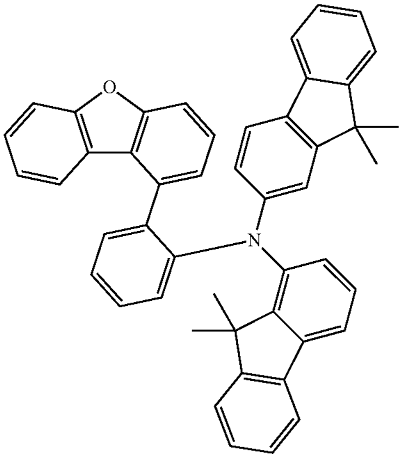
42
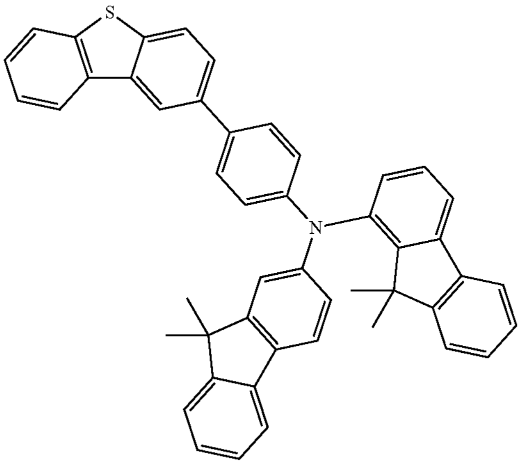
-continued
43
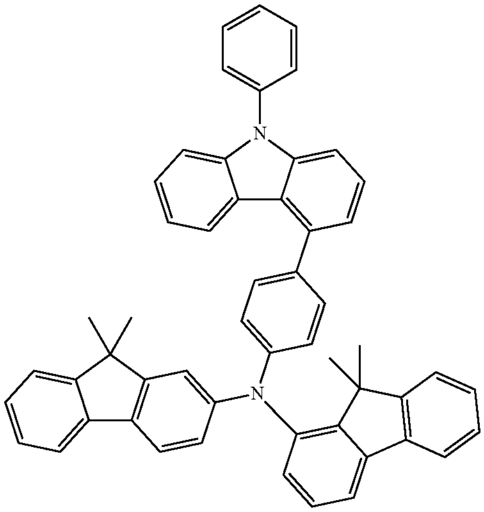
44
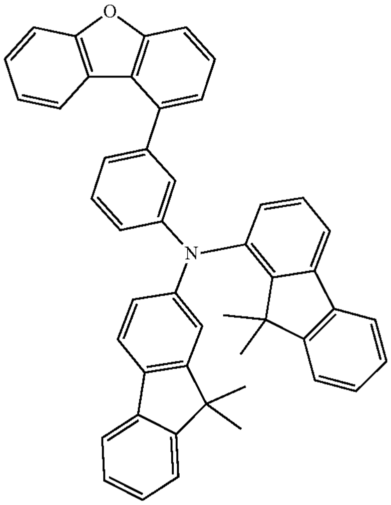
45
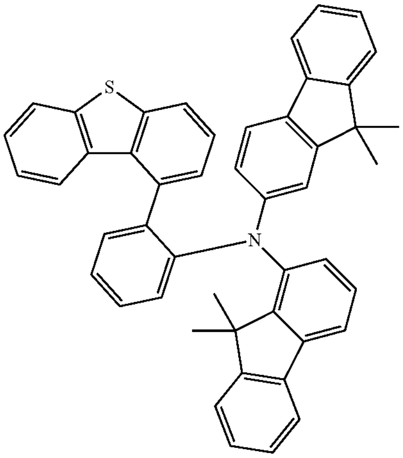

-continued
46
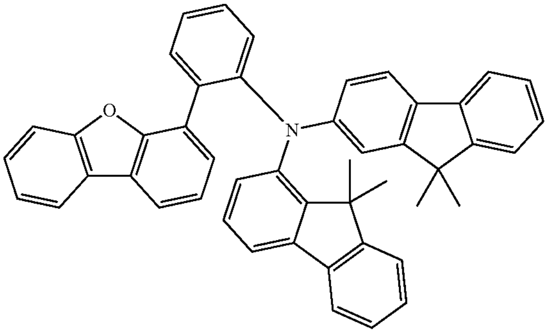
47
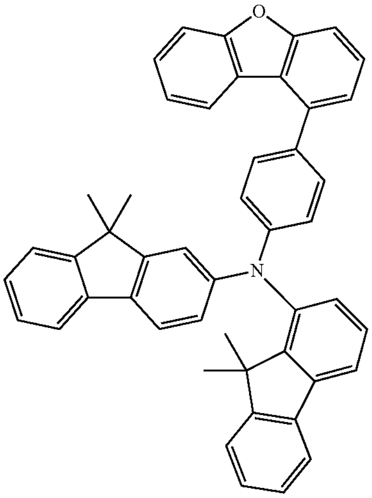
48
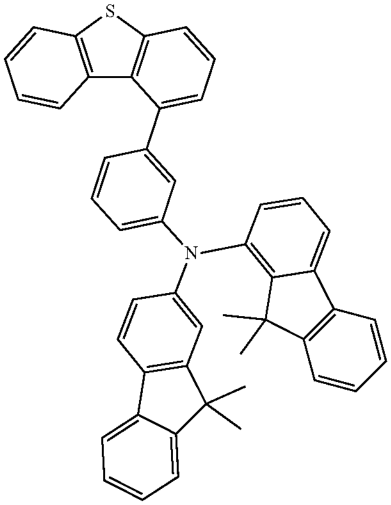
-continued
49
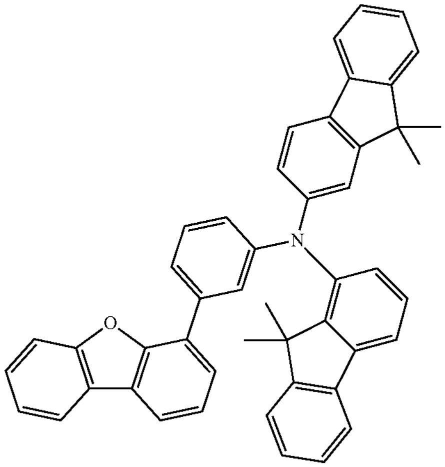
50
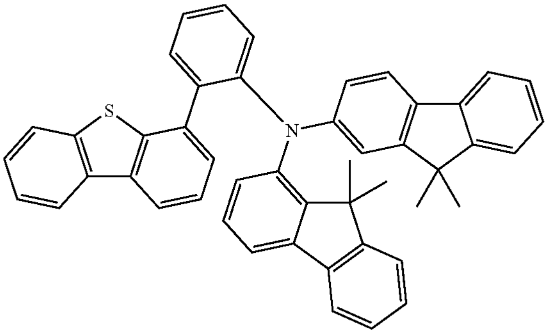
51
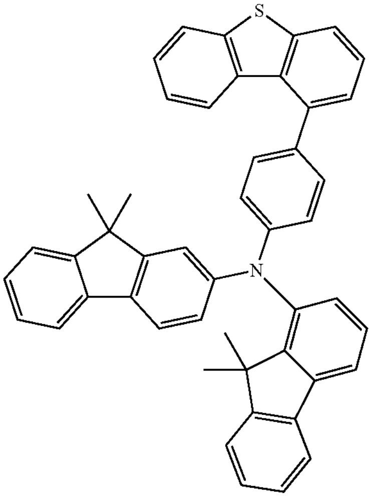

-continued
52
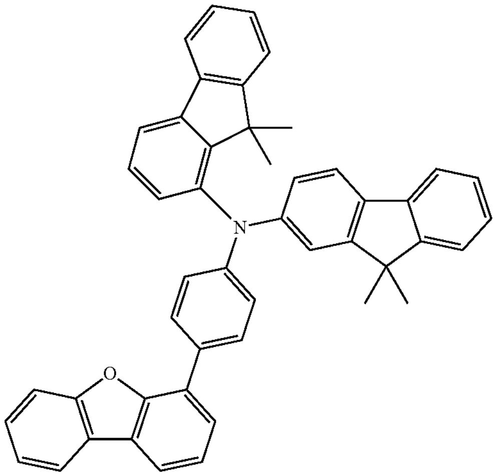
53
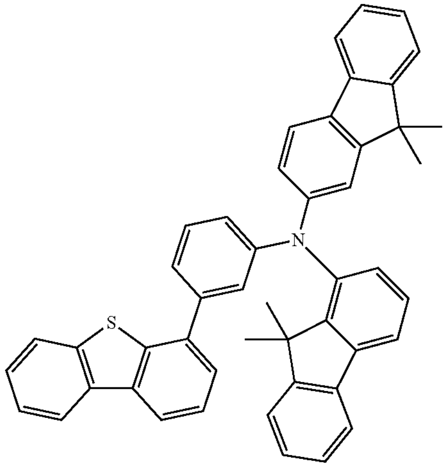
54
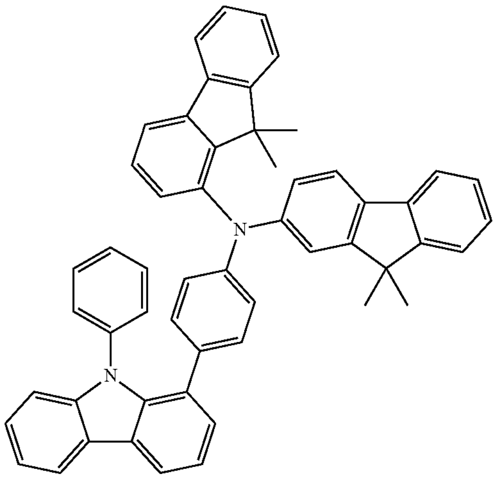
-continued
55
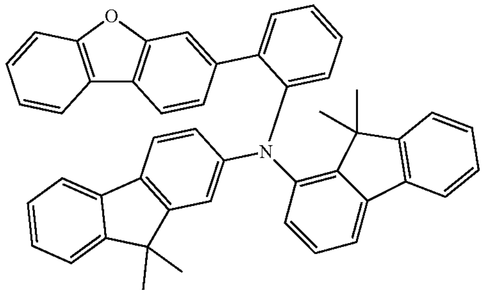
56
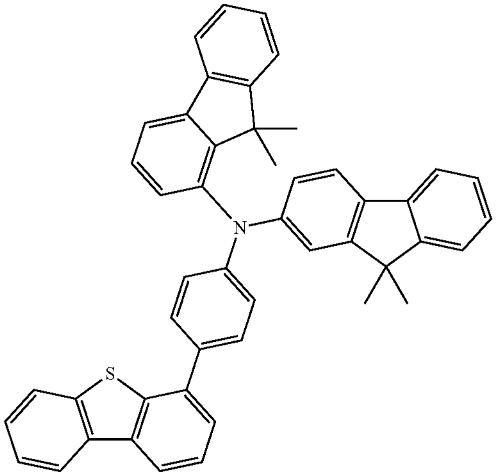
57
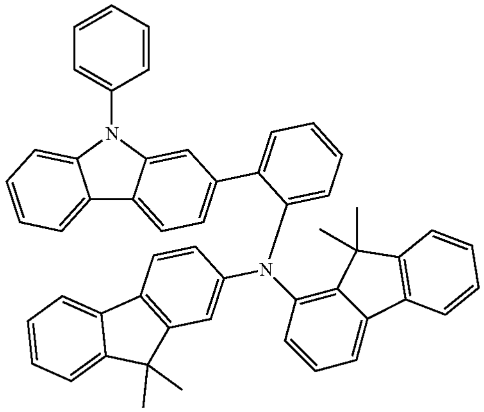
58
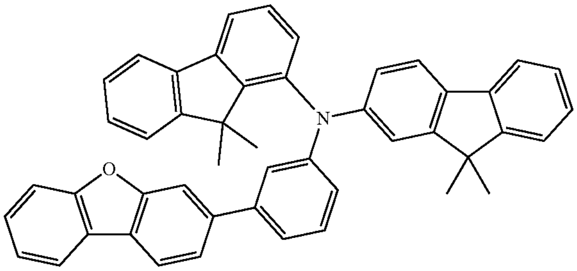

-continued
59
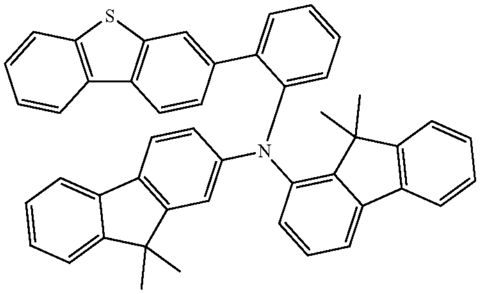
60
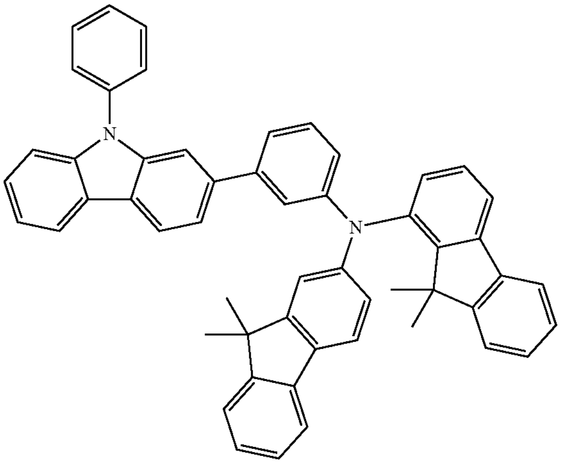
61
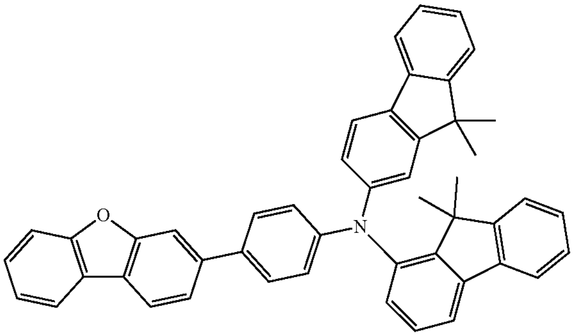
62
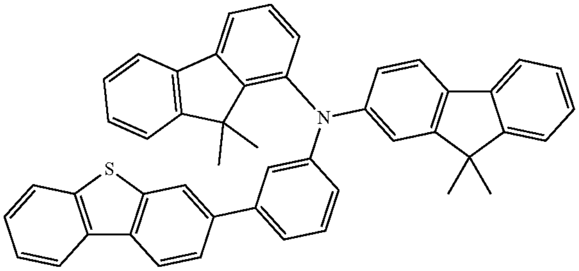
-continued
63
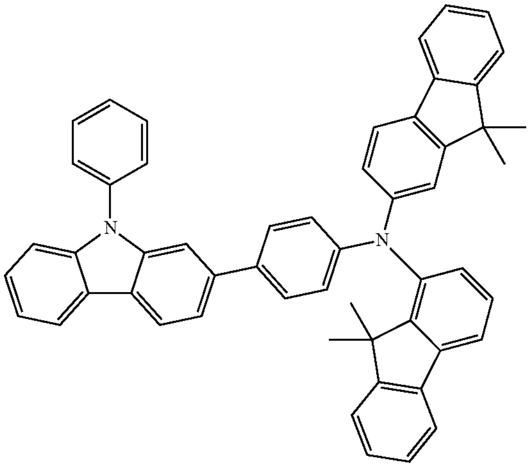
64
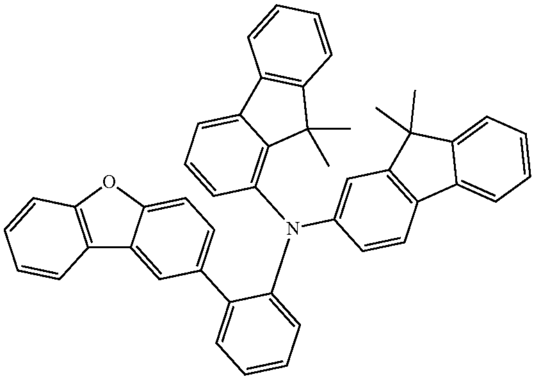
65
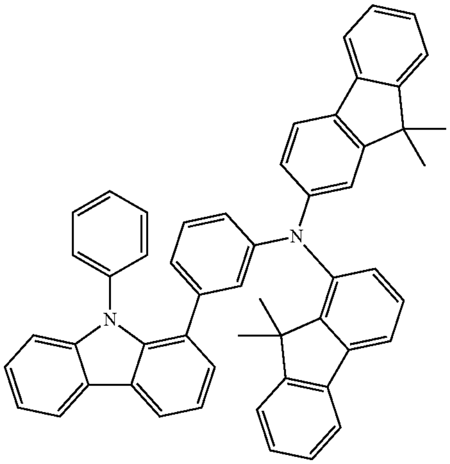

-continued
66
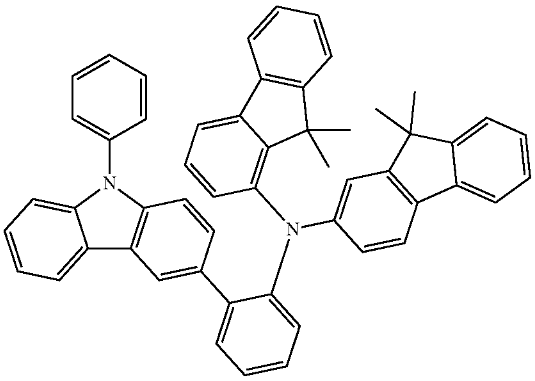
67
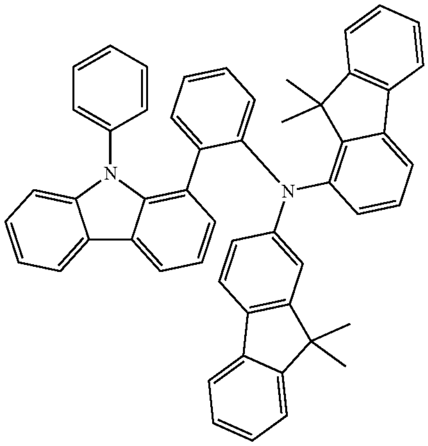
68
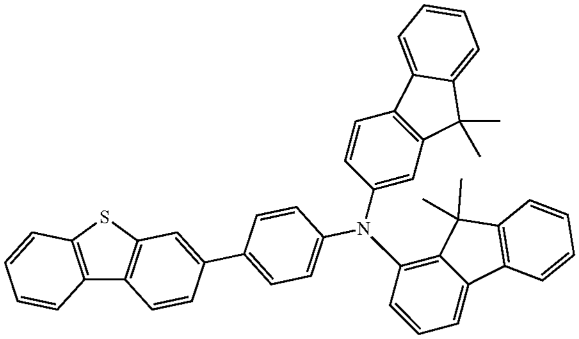
-continued
69
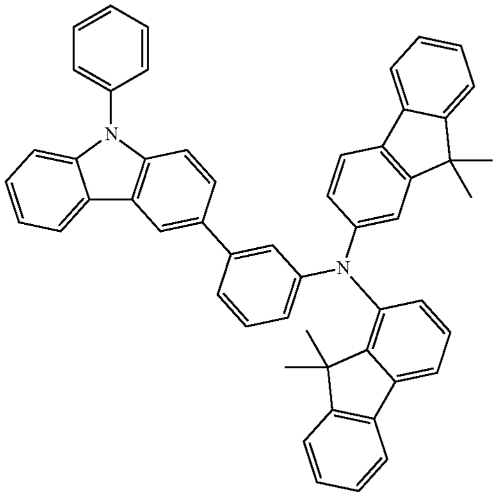
70
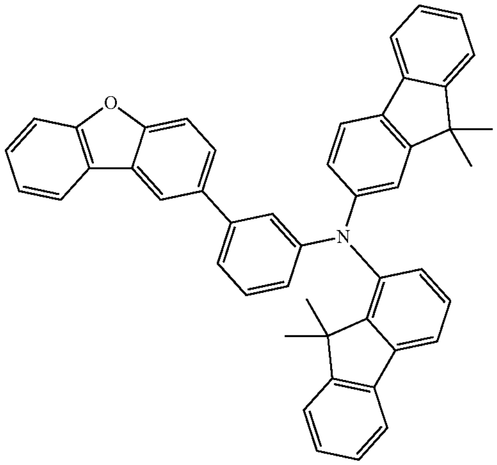
71
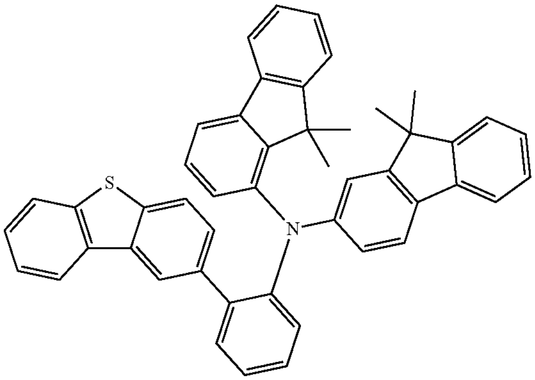

-continued
72
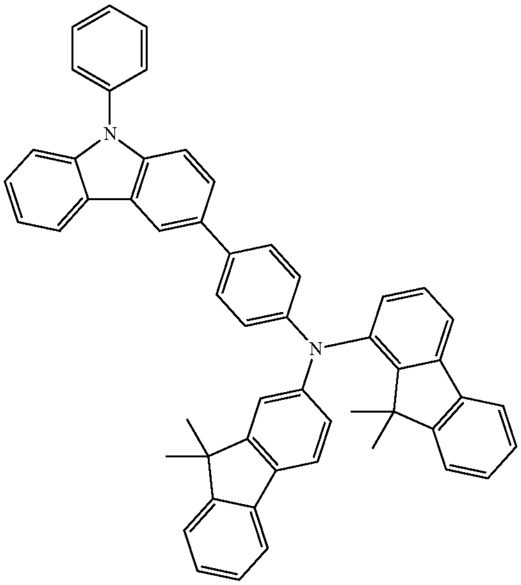
73
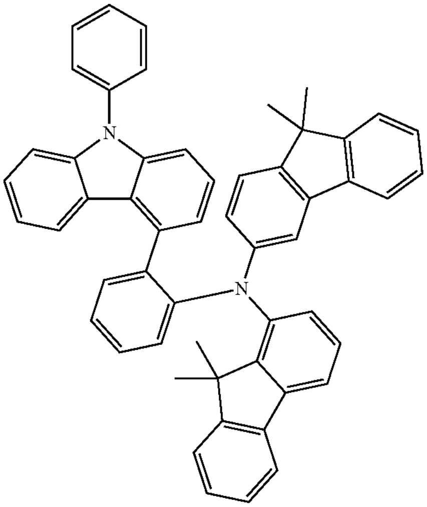
74
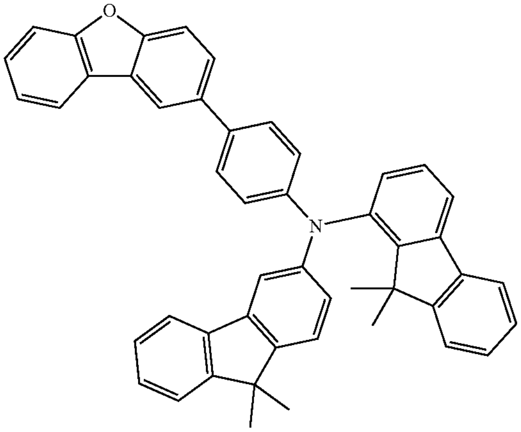
-continued
75
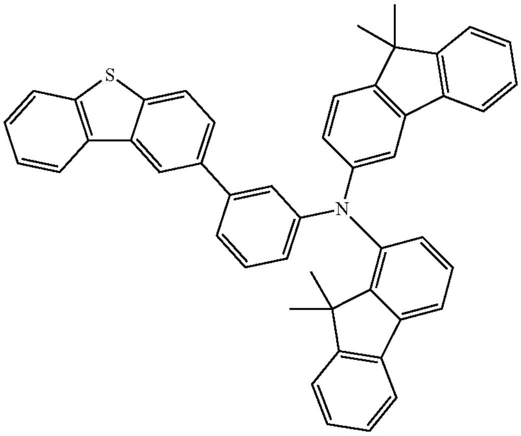
76
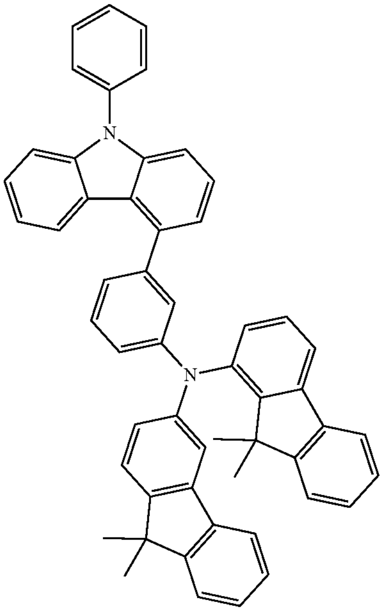
77
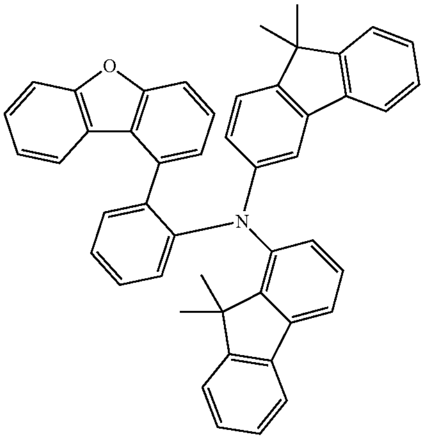

-continued
78
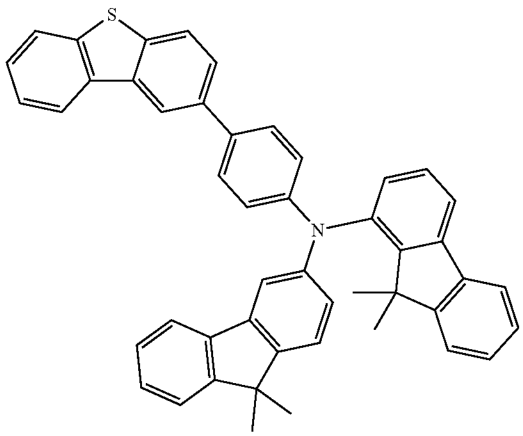
79
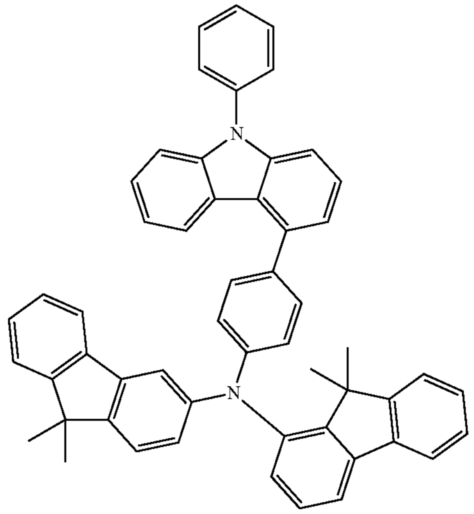
80
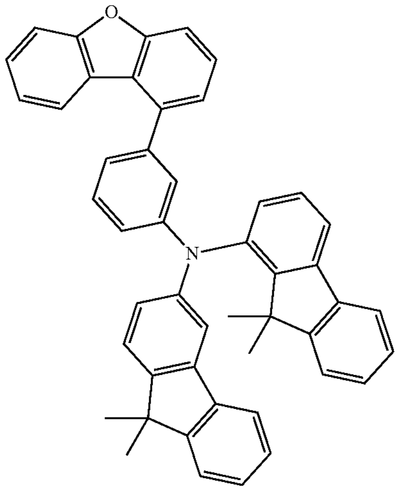
-continued
81
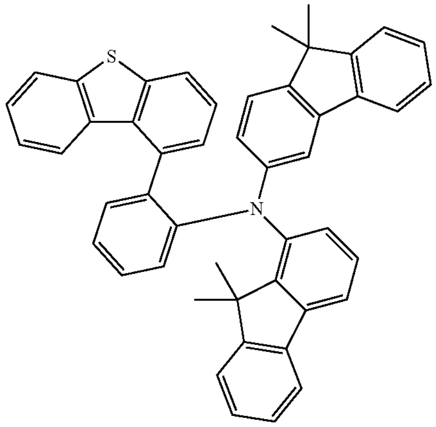
82
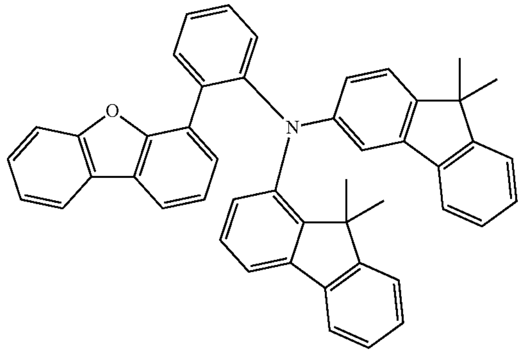
83
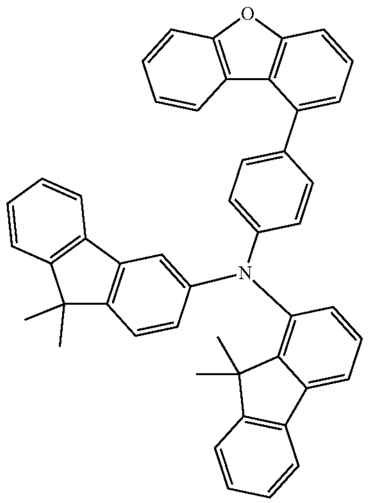

-continued
84
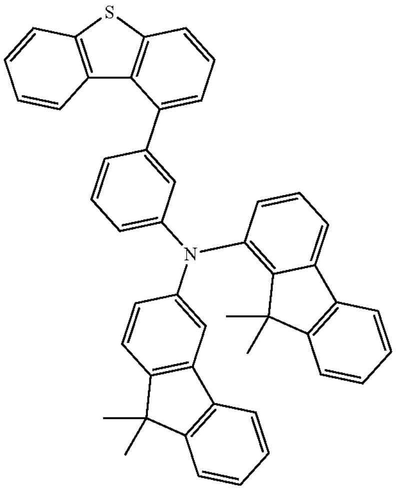
85
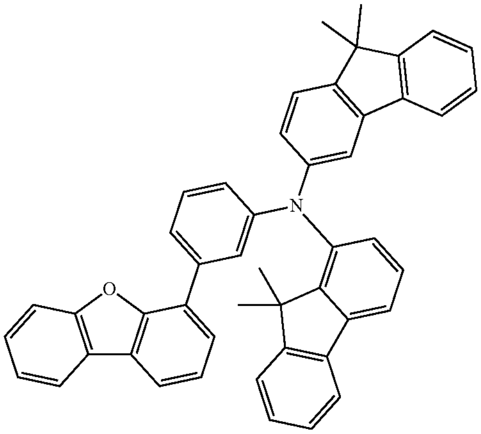
86
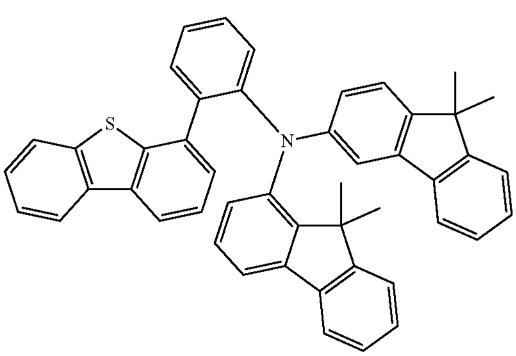
-continued
87
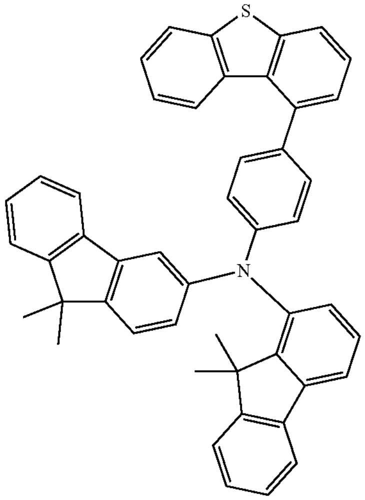
88
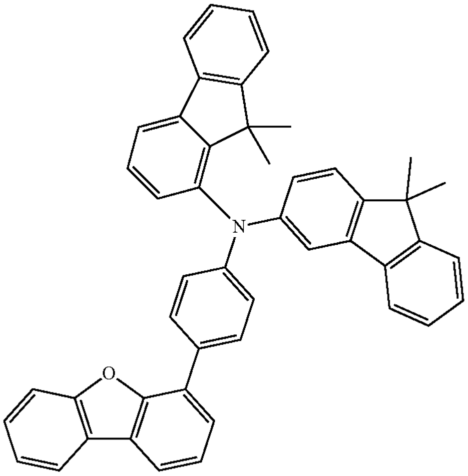
89
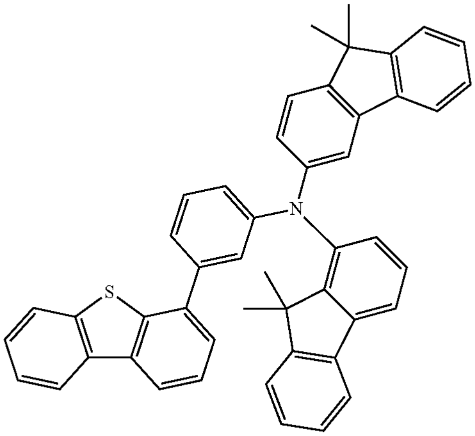

-continued
90
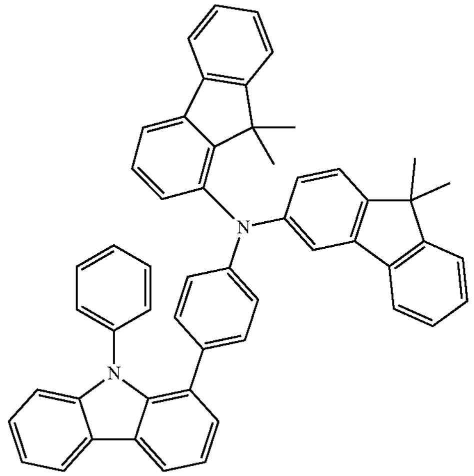
91
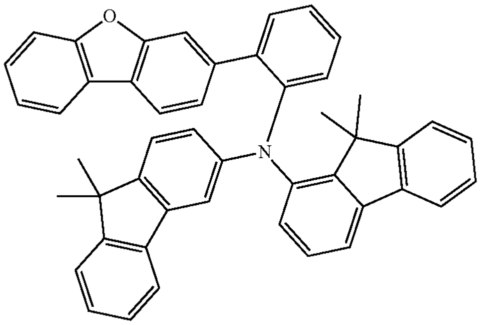
92
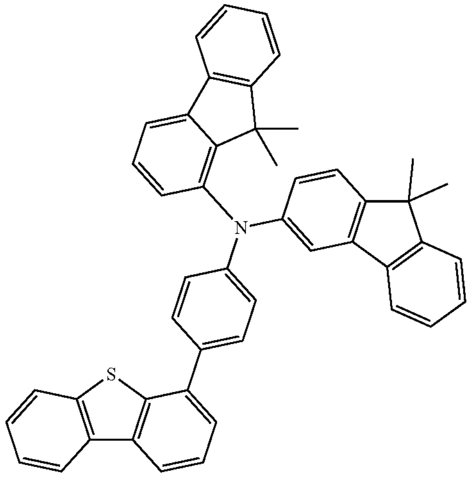
-continued
93
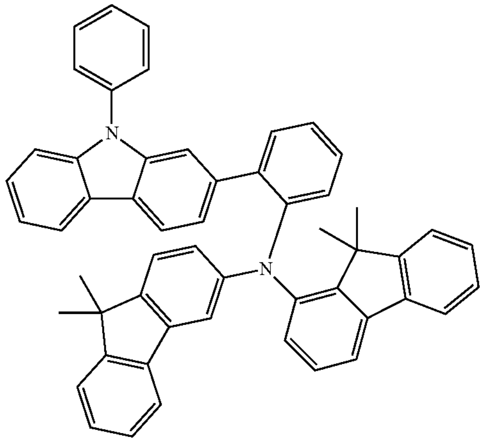
94
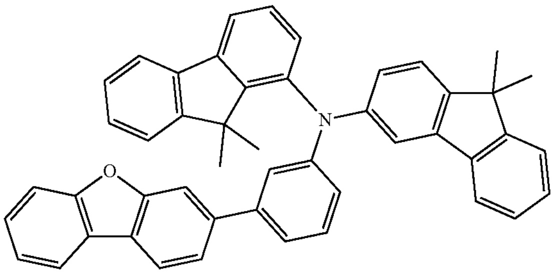
95
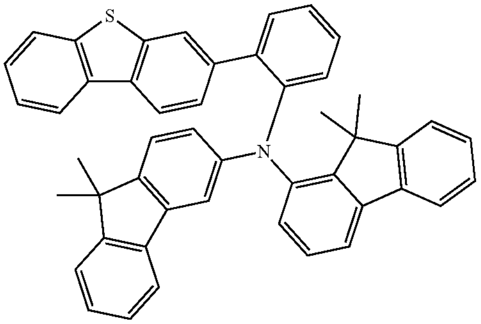
96
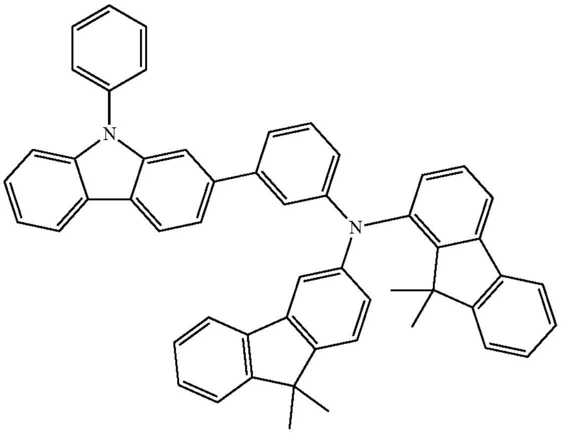

-continued
97
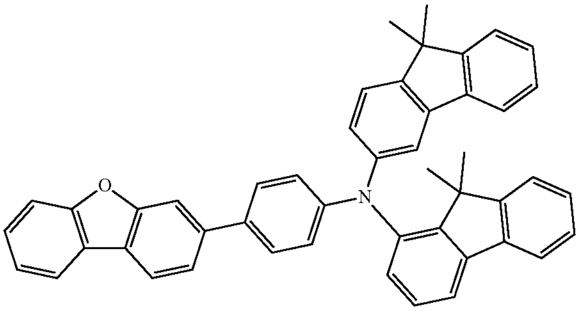
98
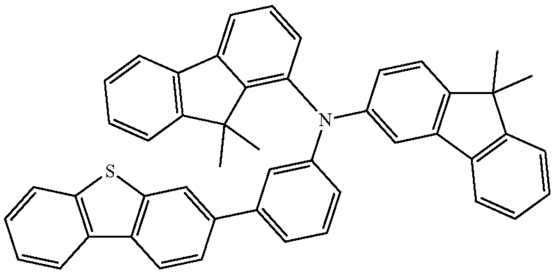
99
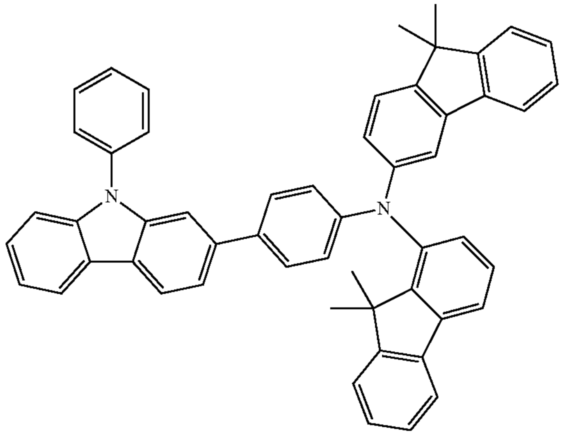
100
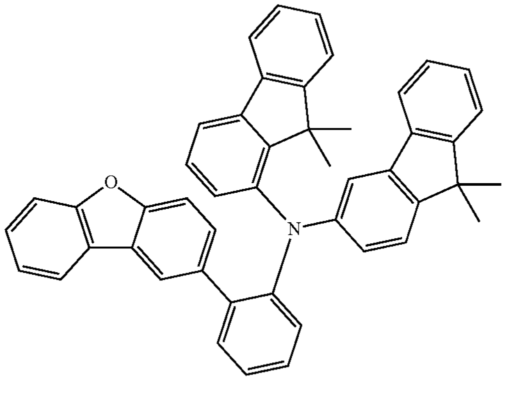
-continued
101
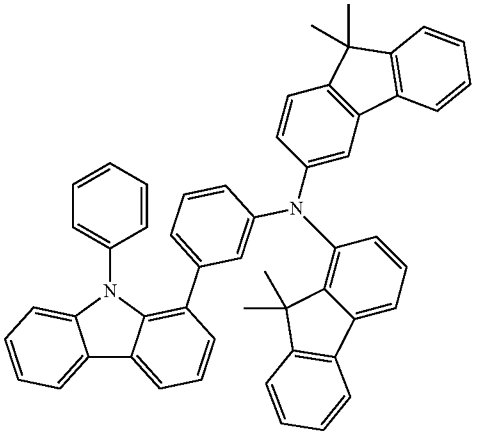
102
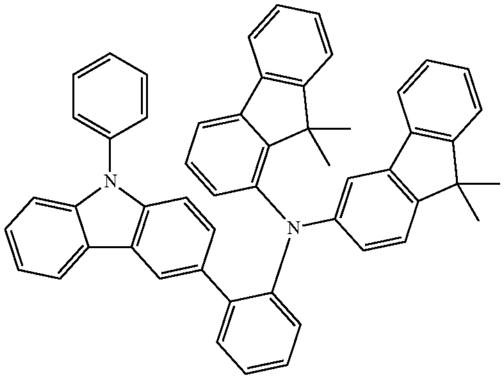
103
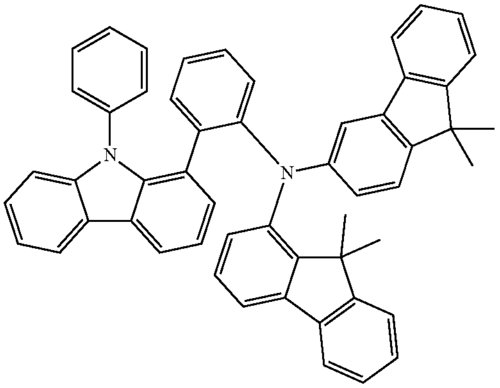
104
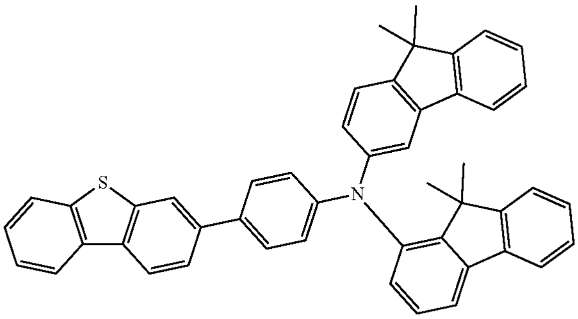

-continued
105
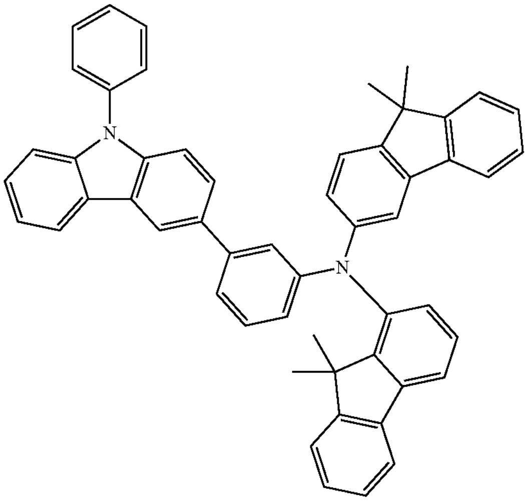
106
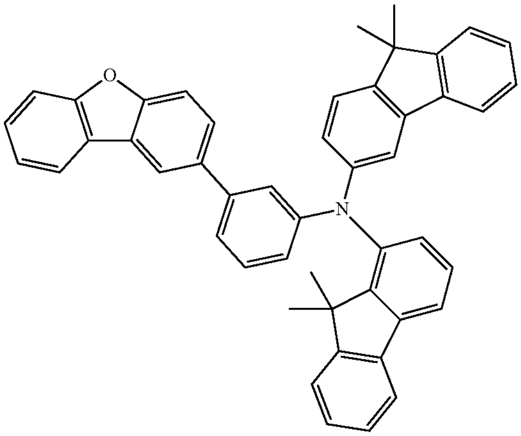
107
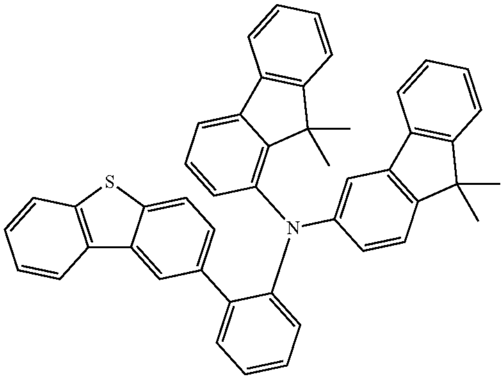
-continued
108
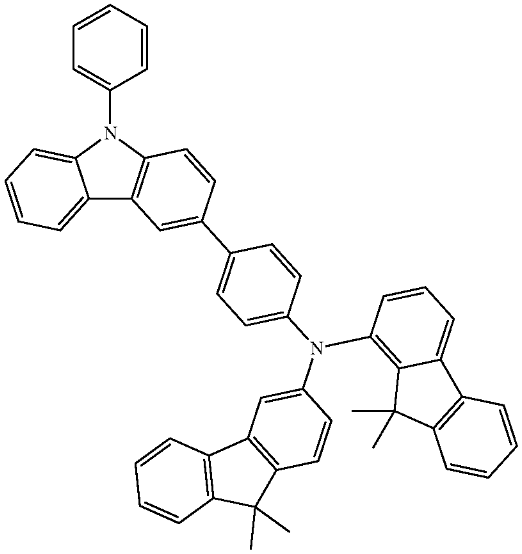
109
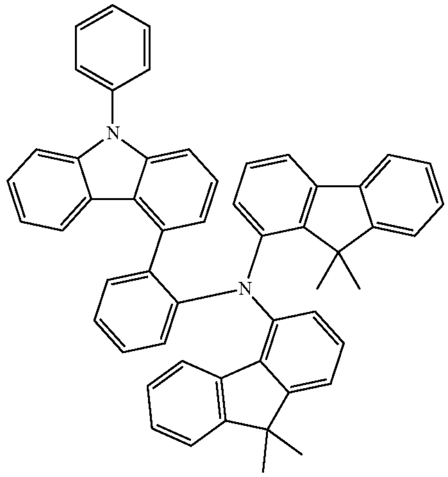
110
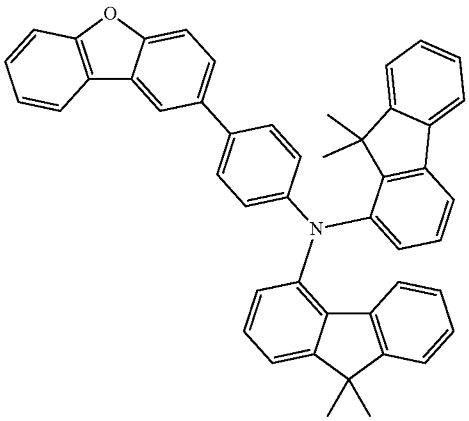

-continued
111
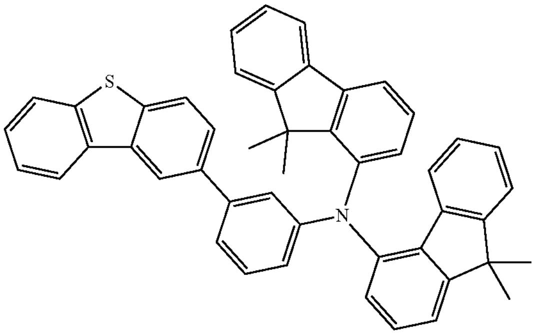
112
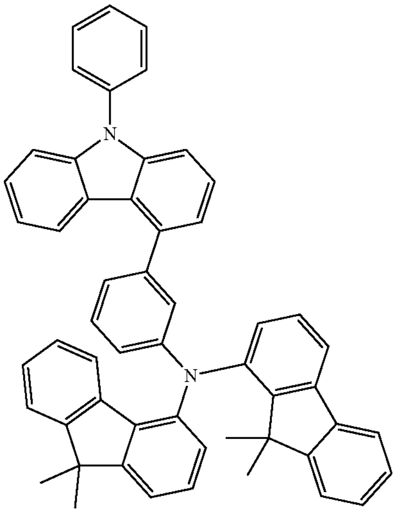
113
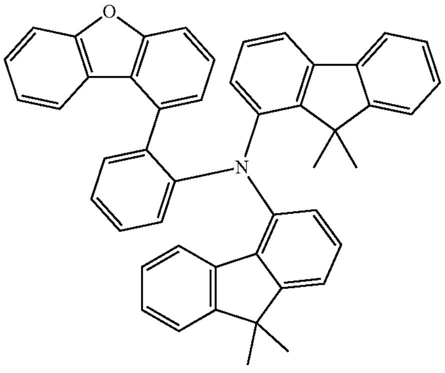
-continued
114
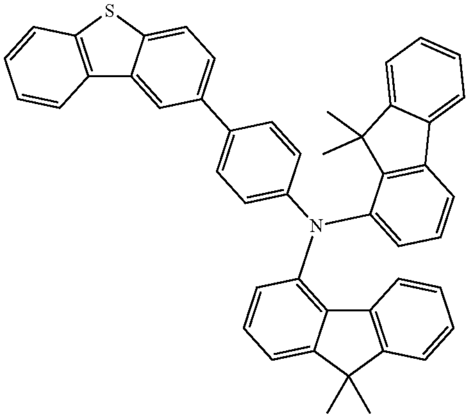
115
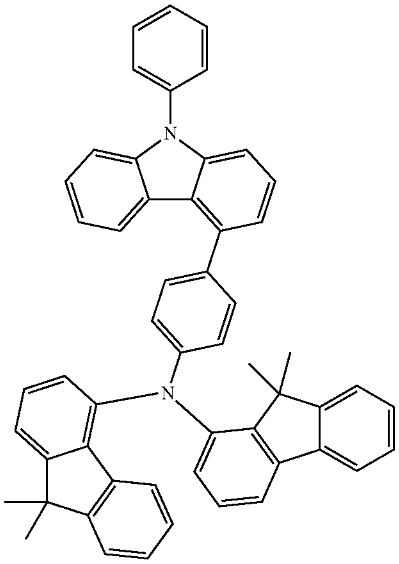
116
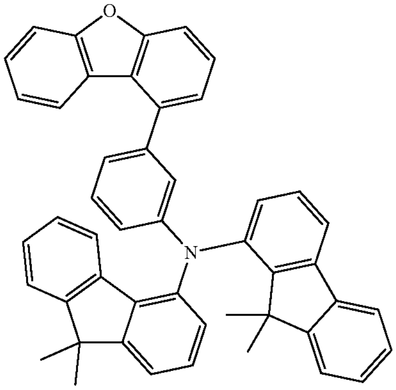

-continued
117
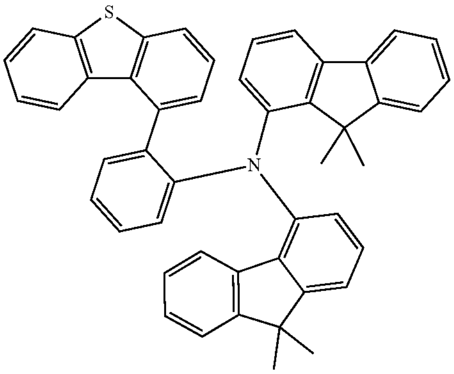
118
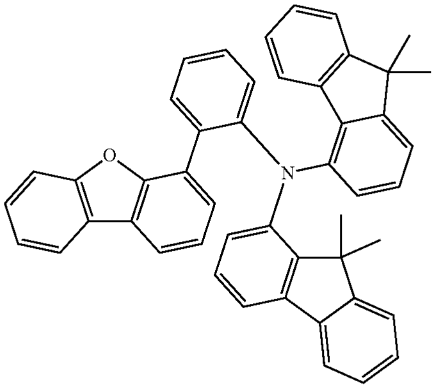
119
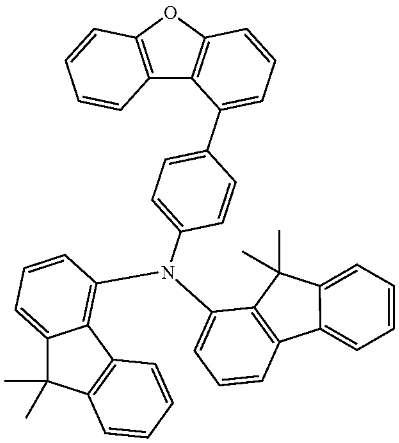
120
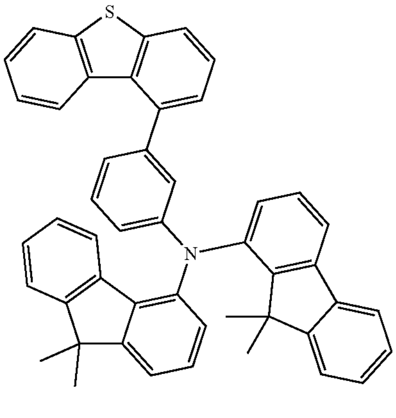
-continued
121
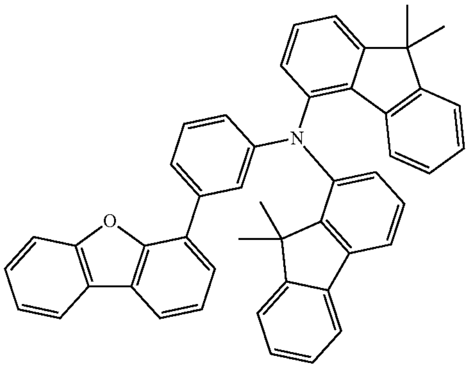
122
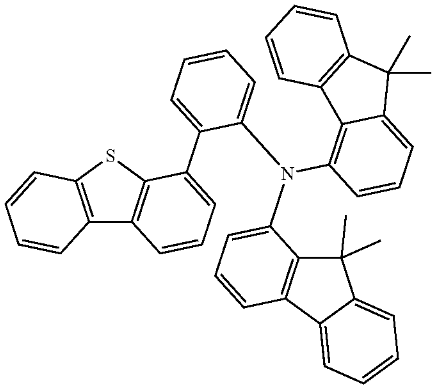
123
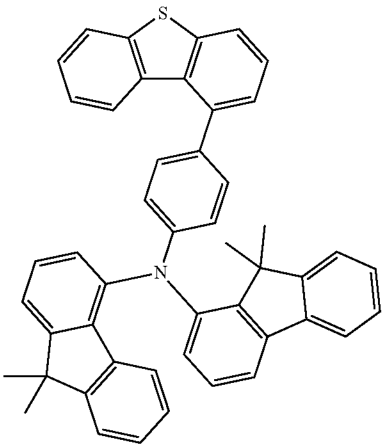
124
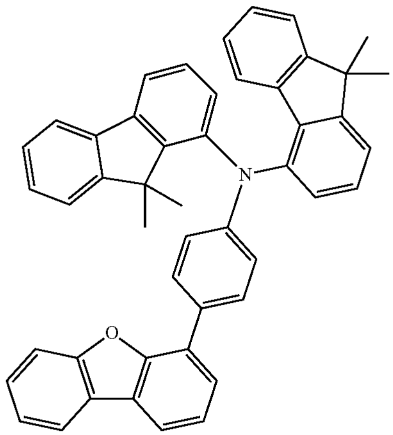

-continued
125
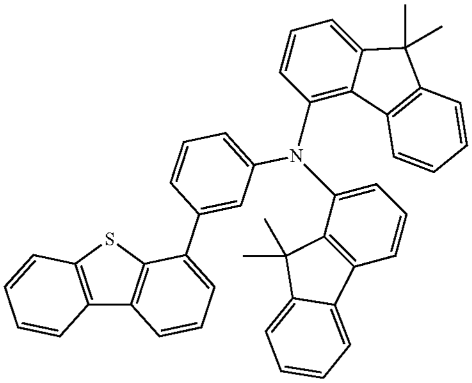
126
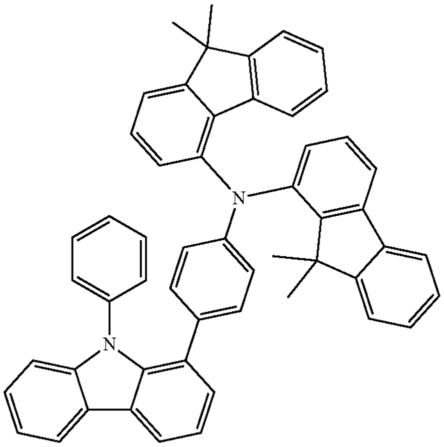
127
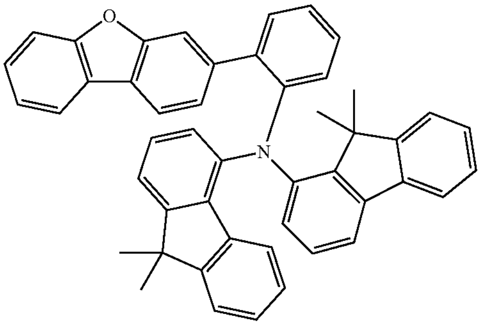
128
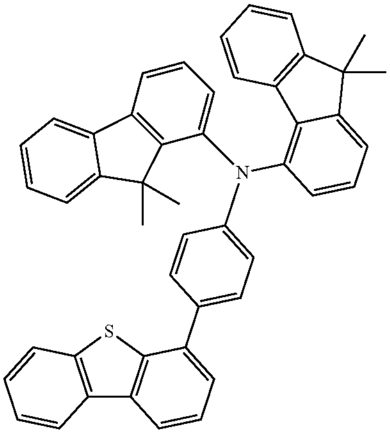
-continued
129
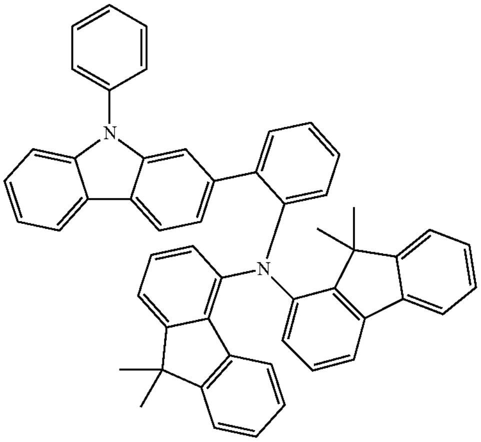
130
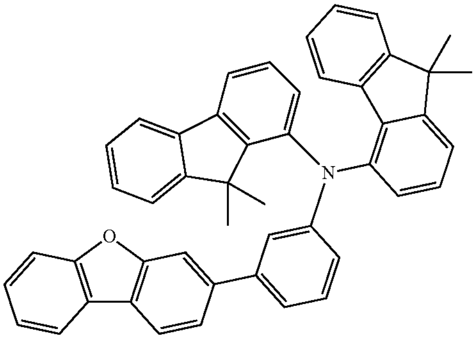
131
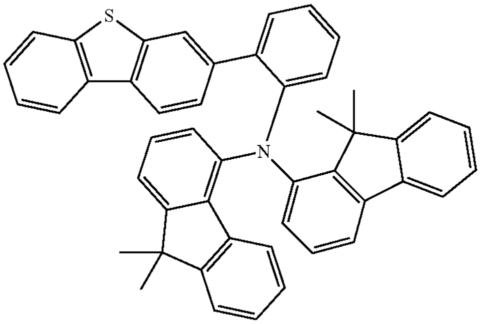
132
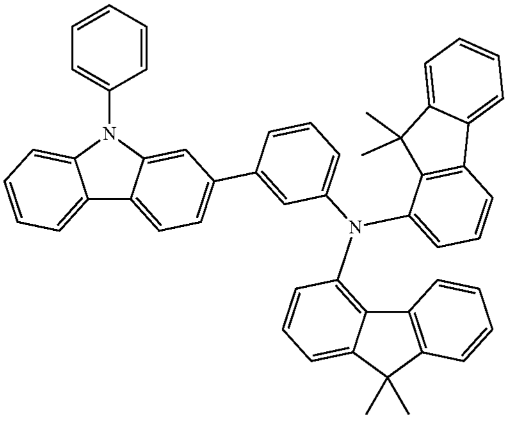

-continued
133
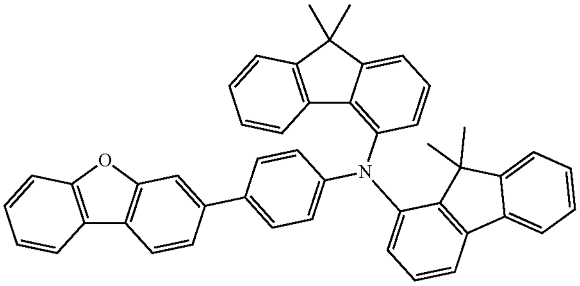
134
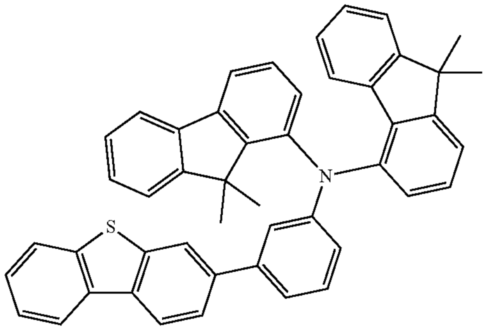
135
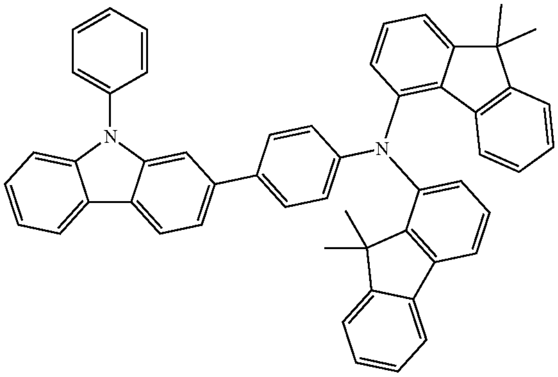
136
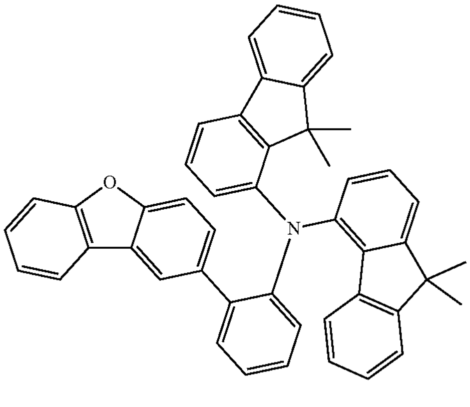
-continued
137
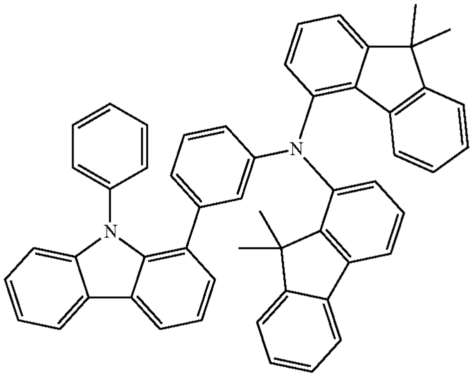
138
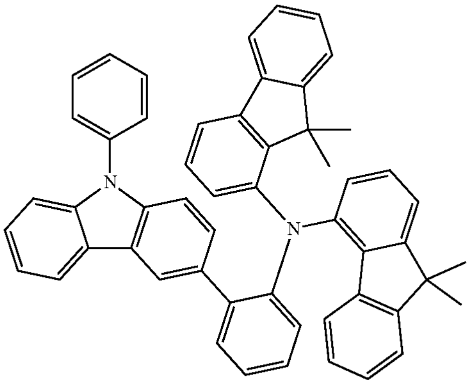
139
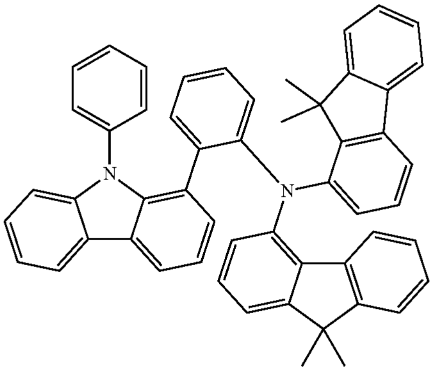
140
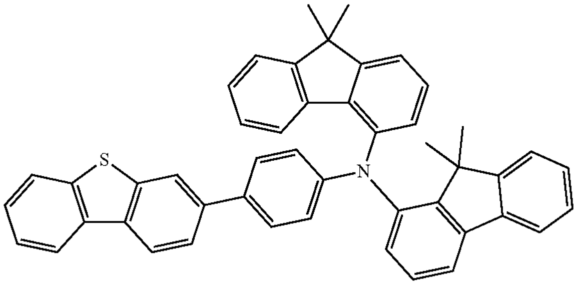

141
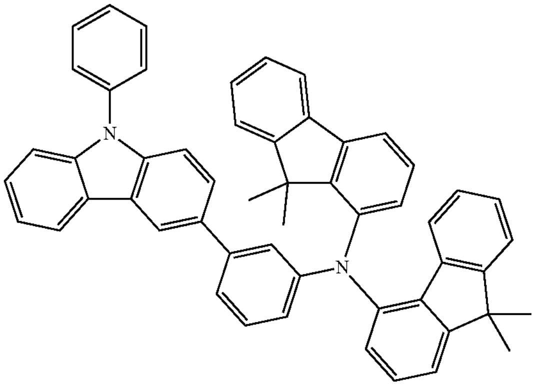
142
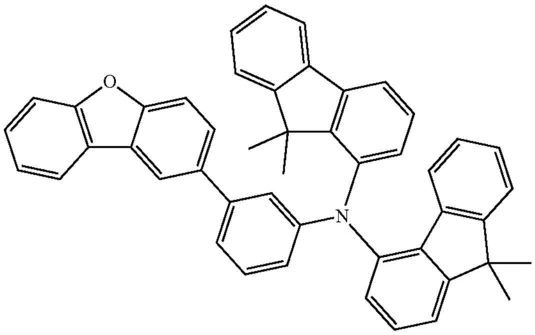
143
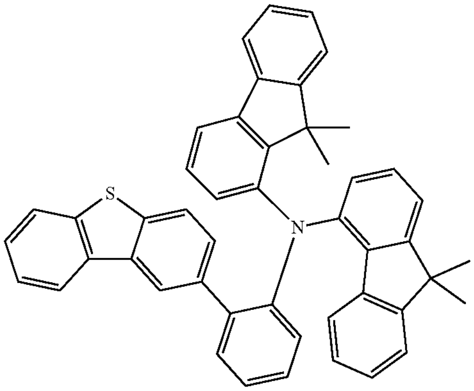
144
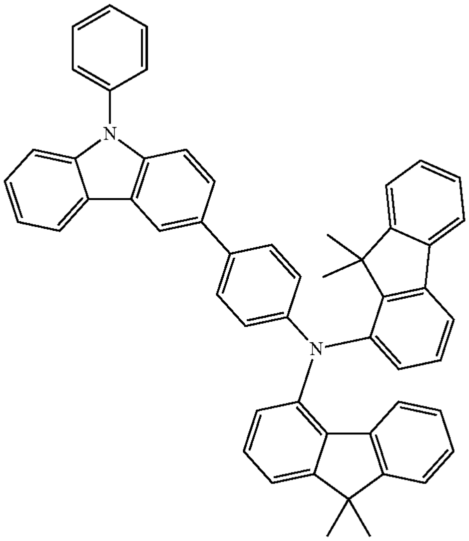
145
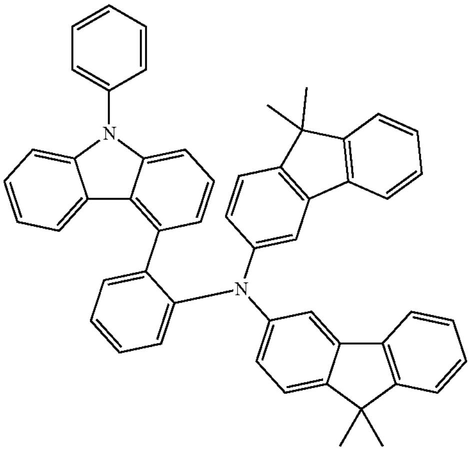
146
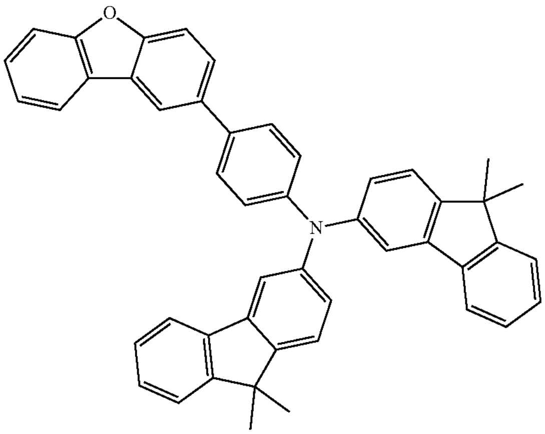

-continued
147
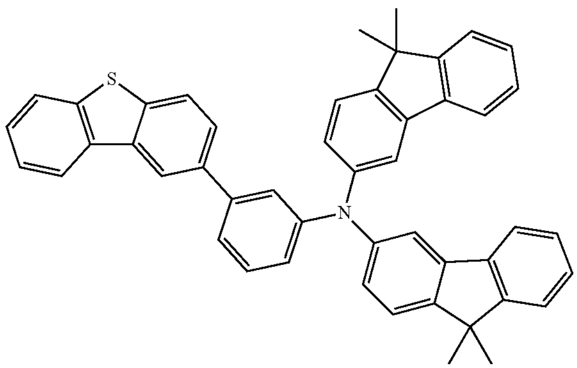
148
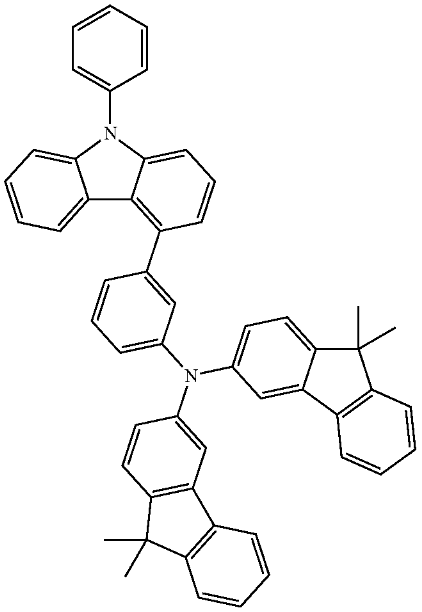
149
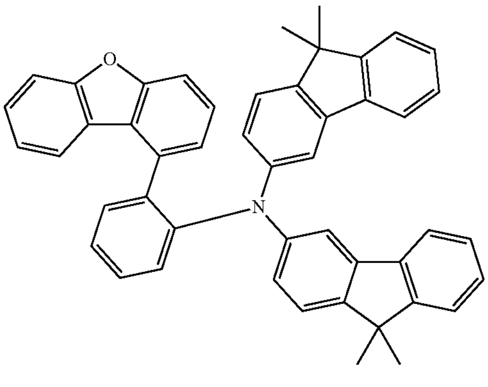
-continued
150
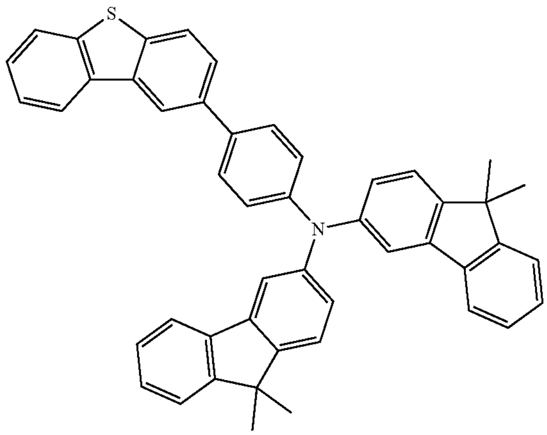
151
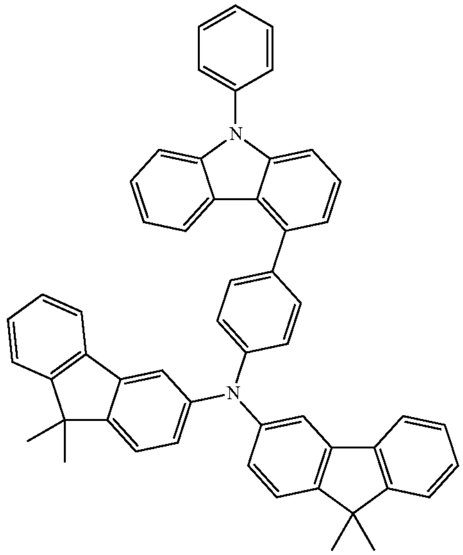
152
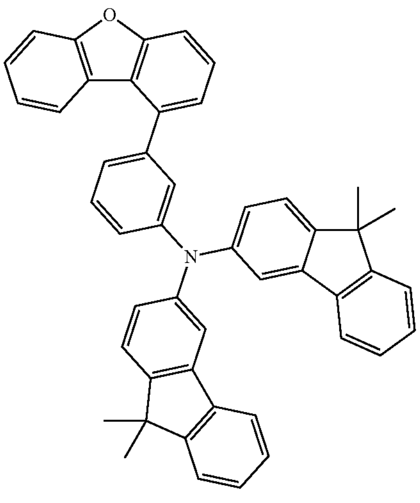

-continued
153
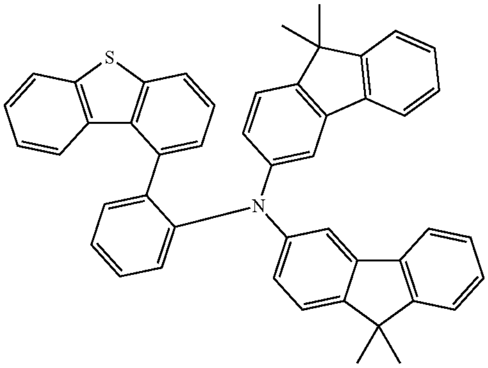
154
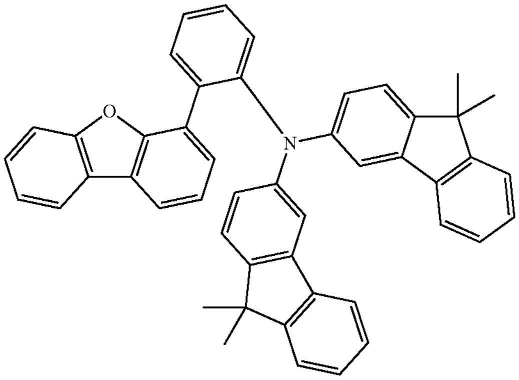
155
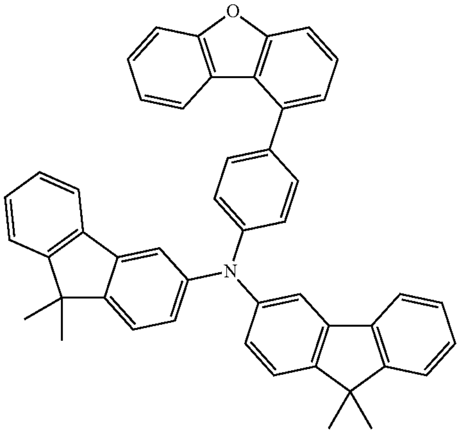
-continued
156
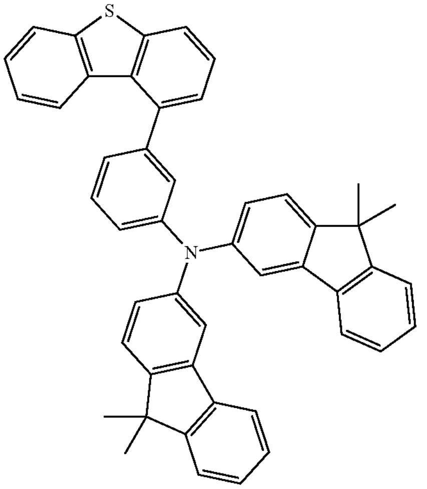
157
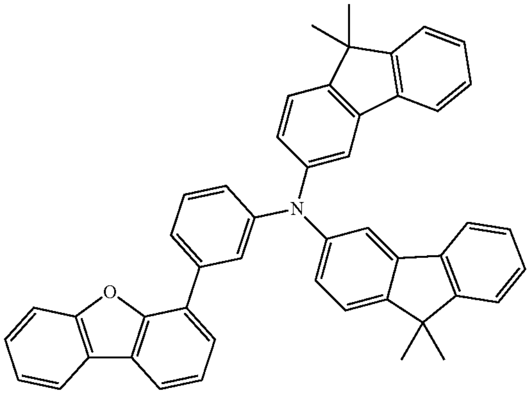
158
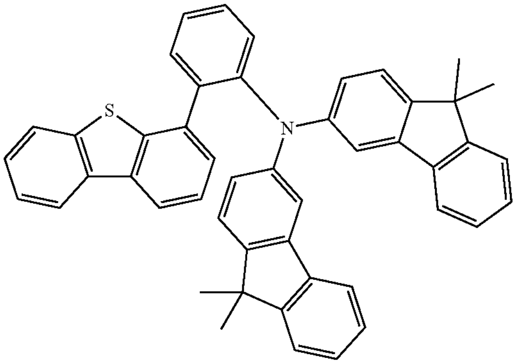

-continued
159
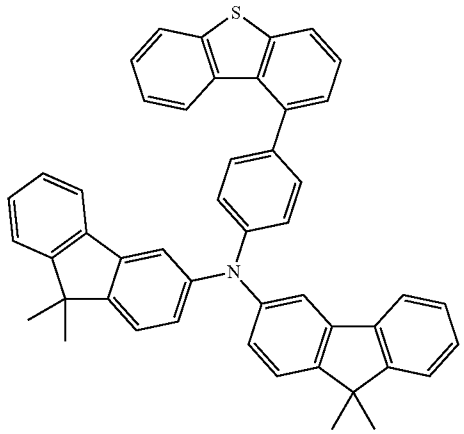
160
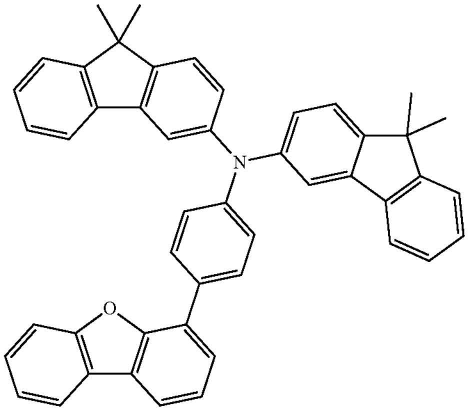
161
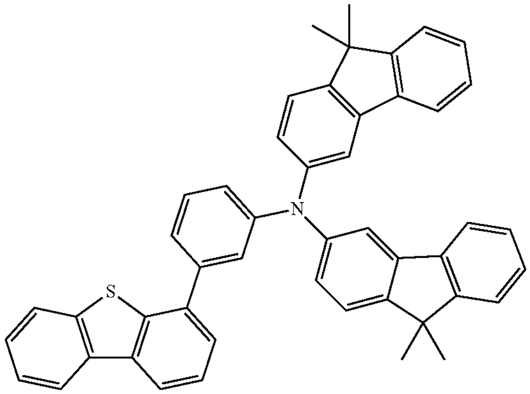
-continued
162
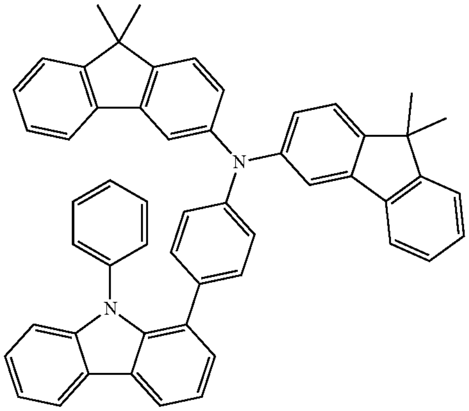
163
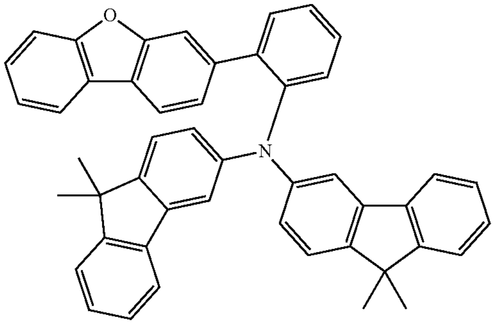
164
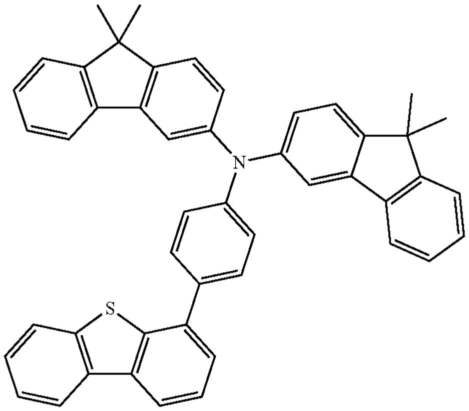
165
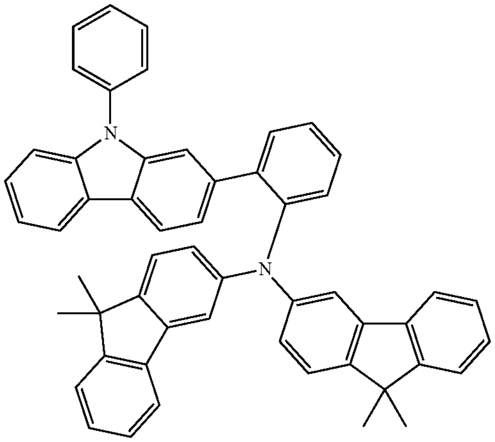

-continued
166
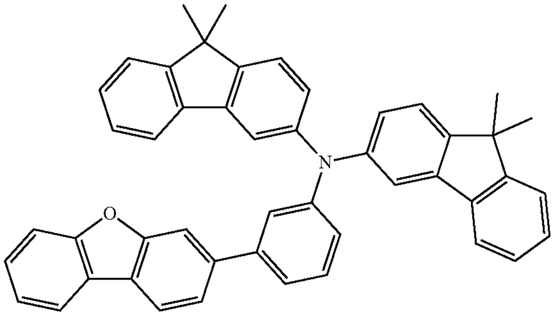
167
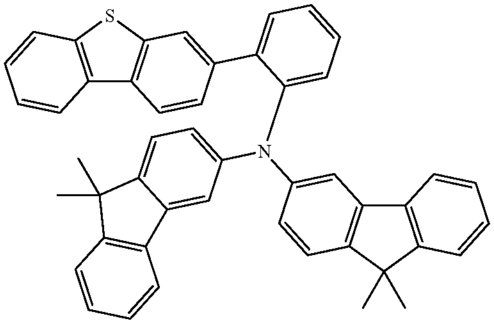
168
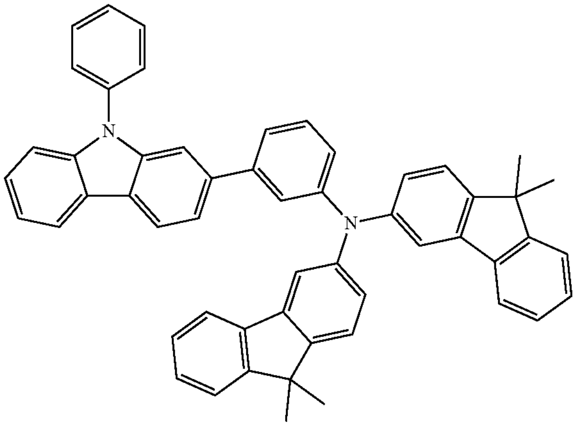
169
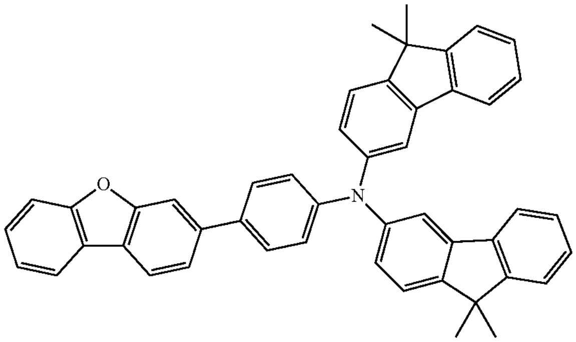
-continued
170
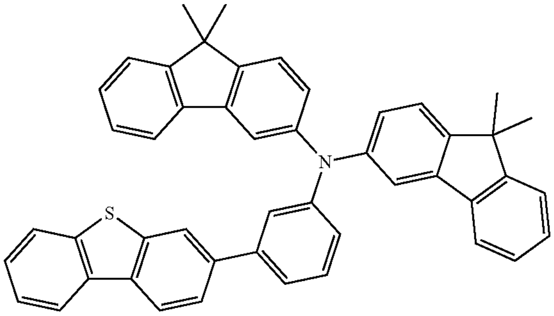
171
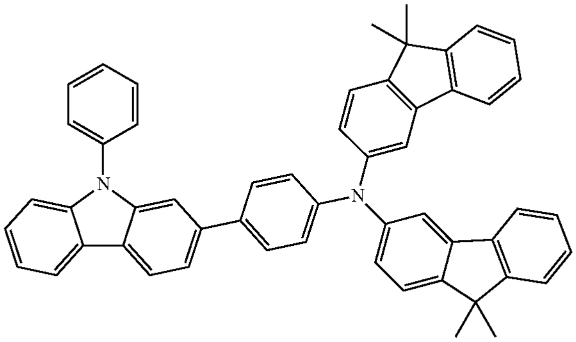
172
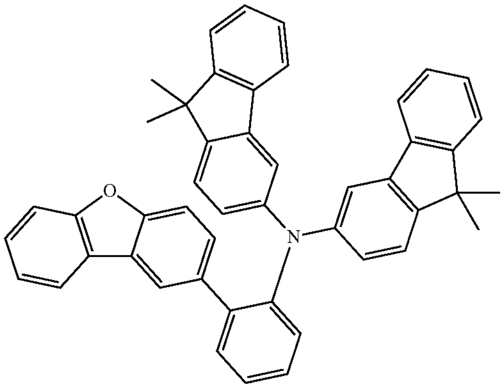
173
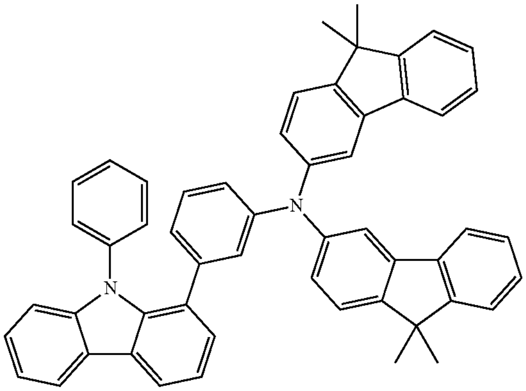

-continued
174
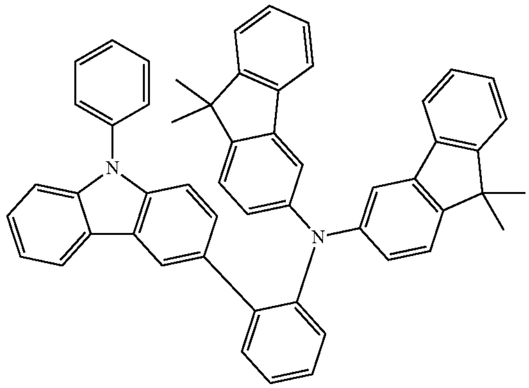
175
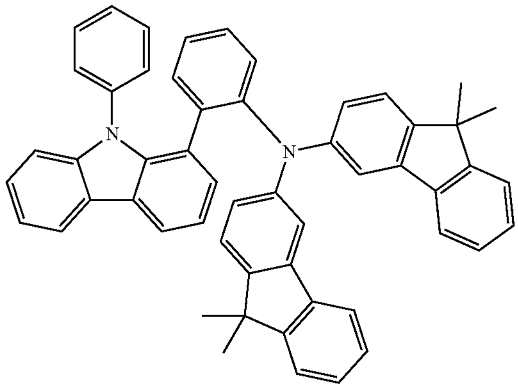
176
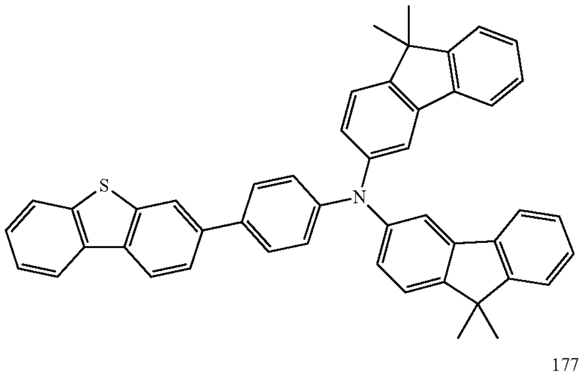
177
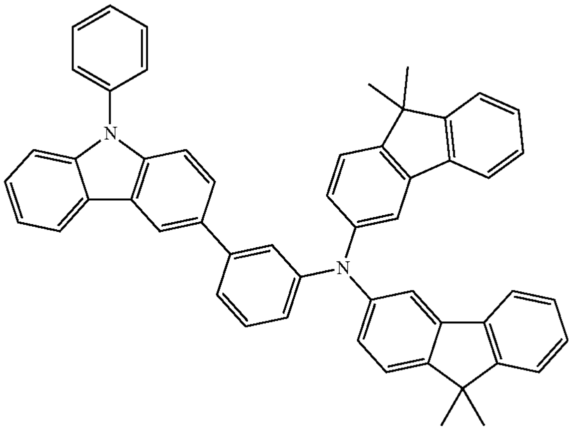
-continued
178
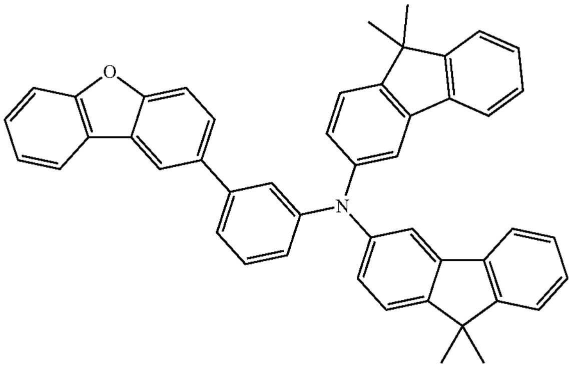
179
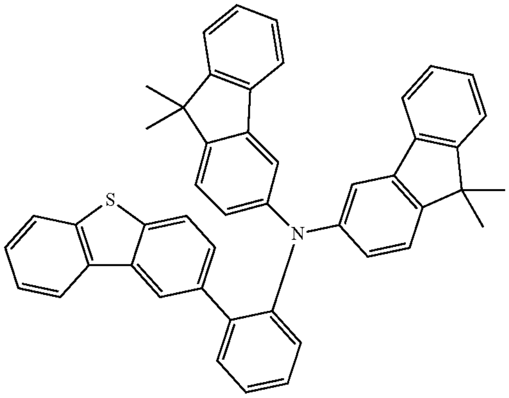
180
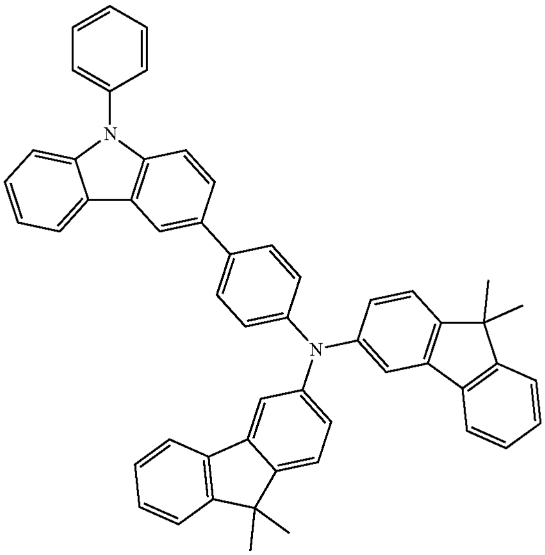

-continued
181
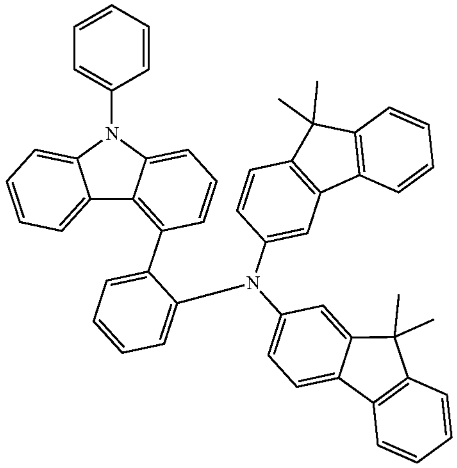
182
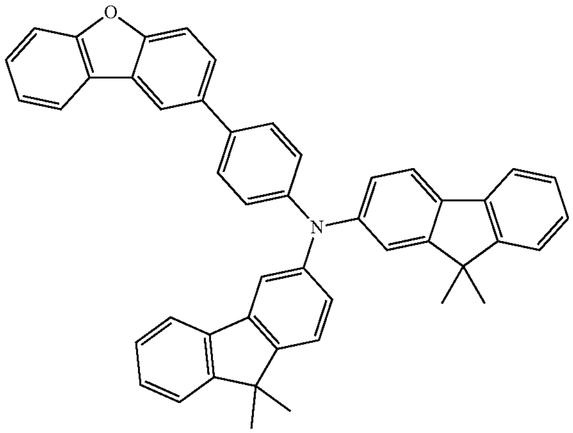
183
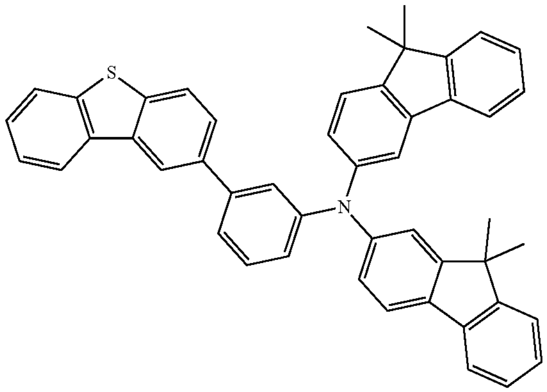
-continued
184
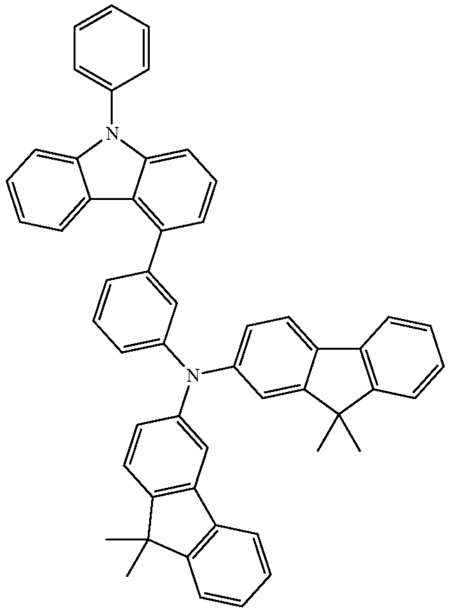
185
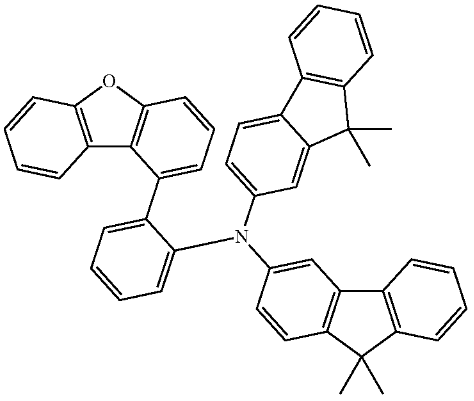
186
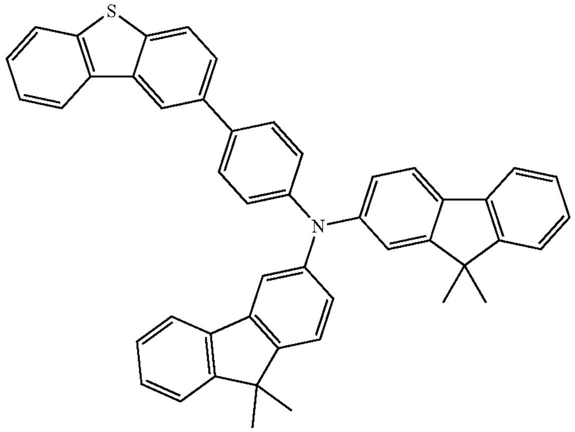

-continued
187
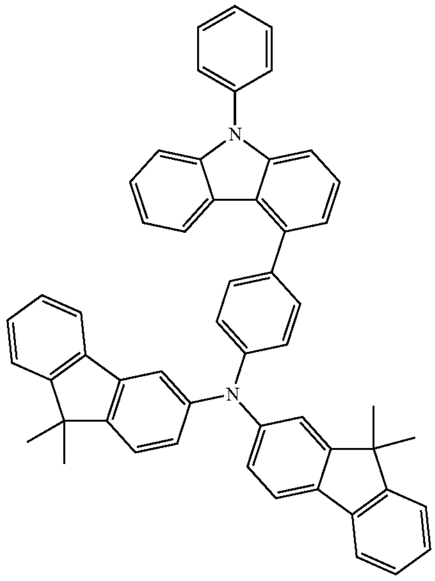
188
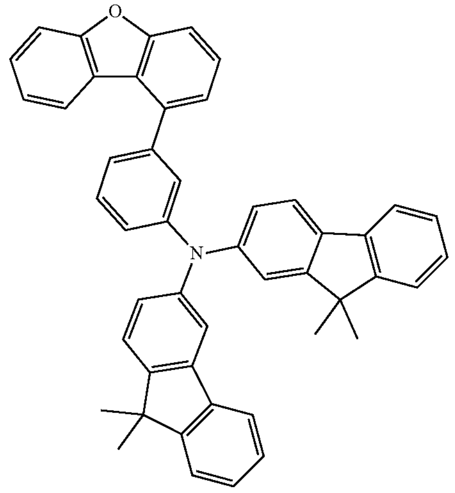
189
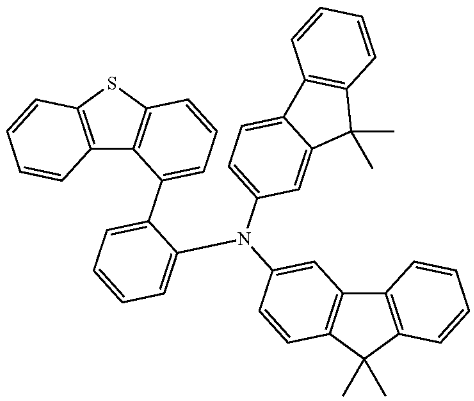
-continued
190
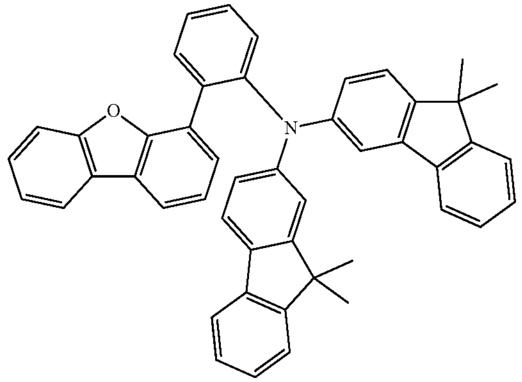
191
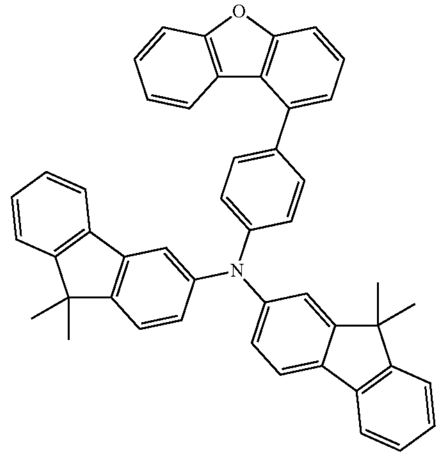
192
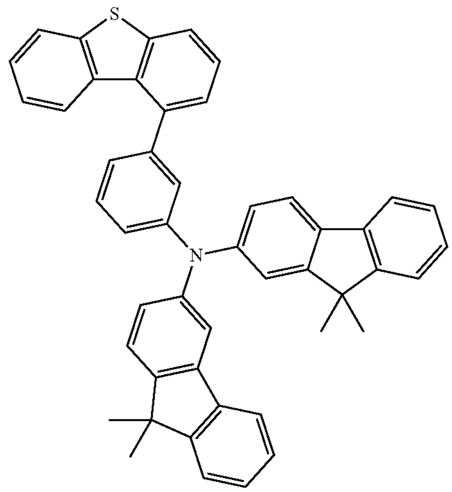

-continued
193
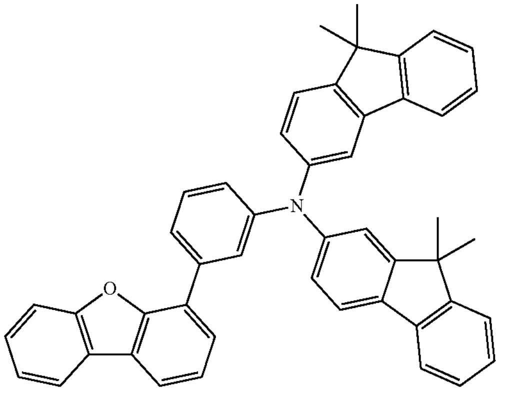
194
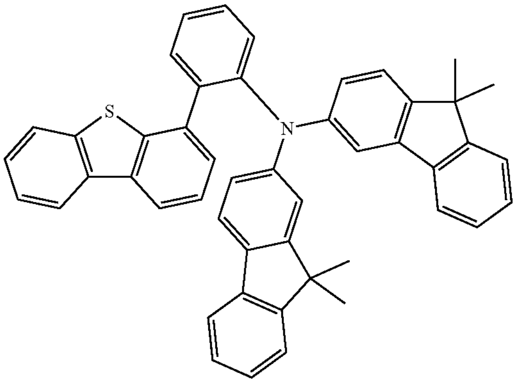
195
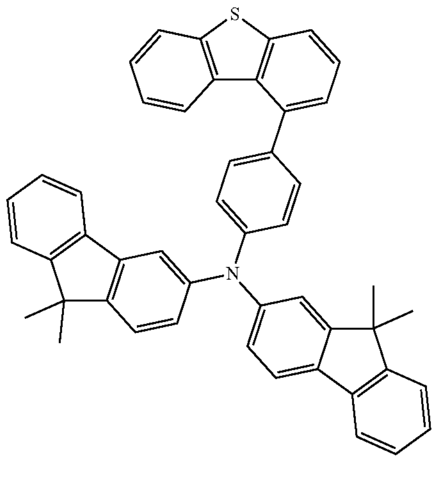
196
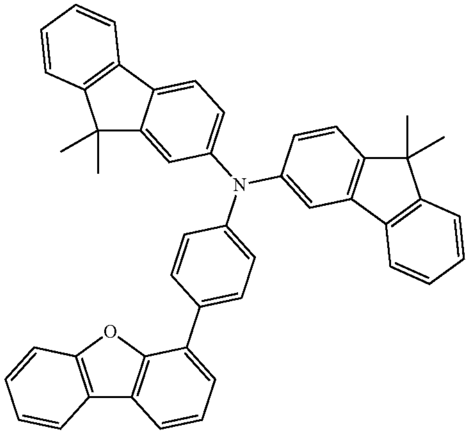
197
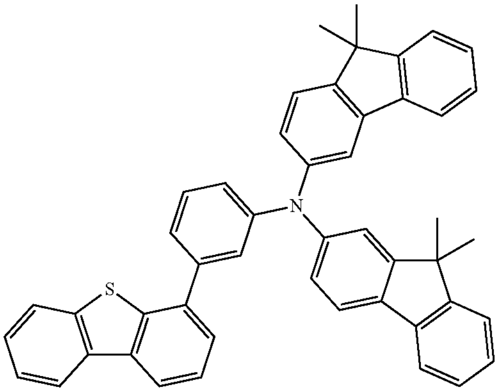
198
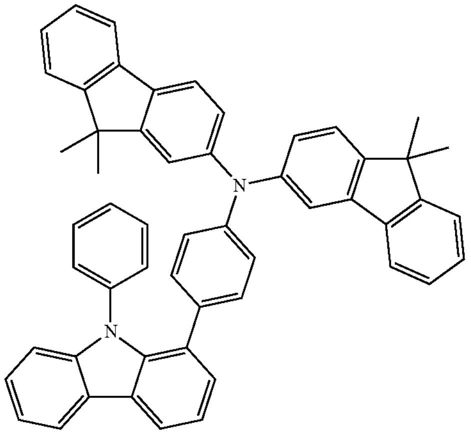
199
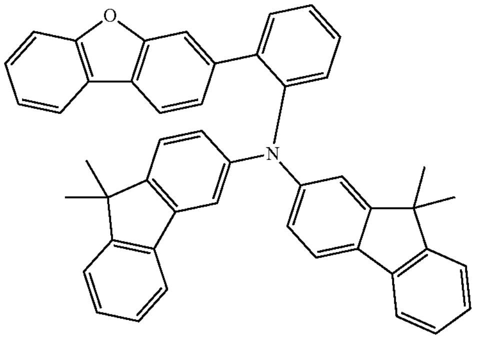

-continued
200
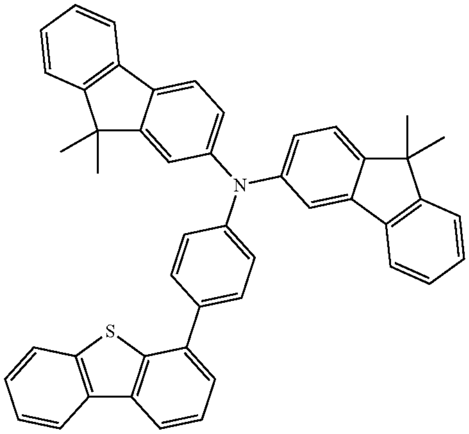
201
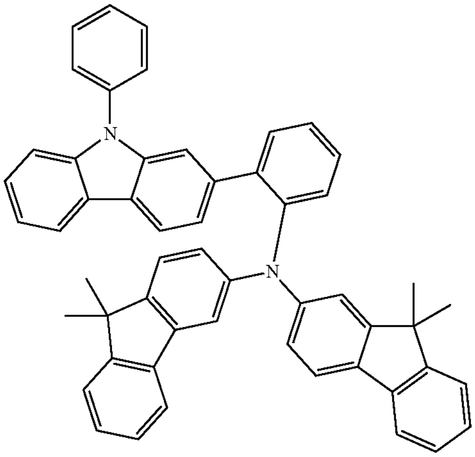
202
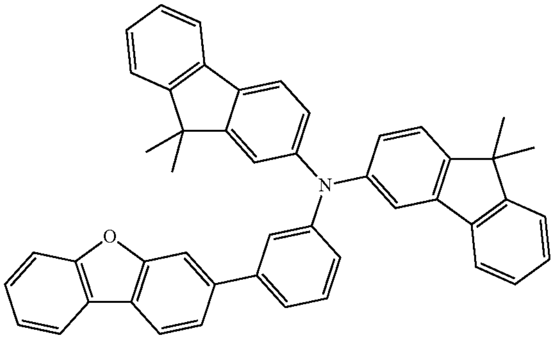
203
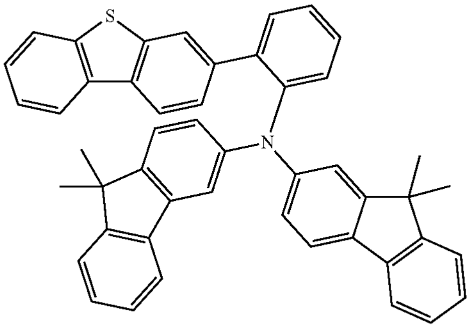
-continued
204
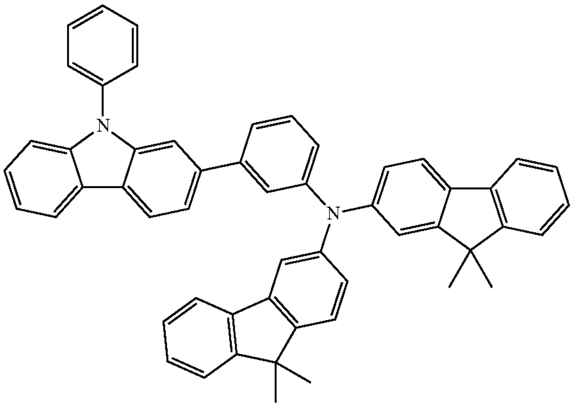
205
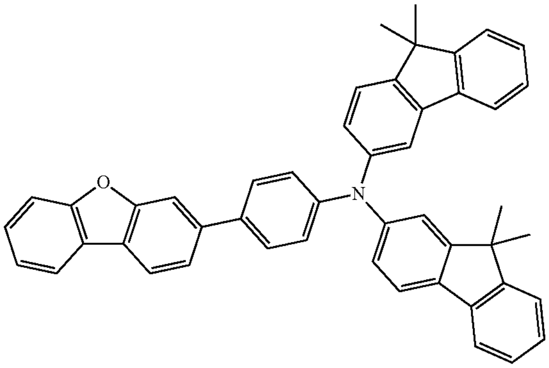
206
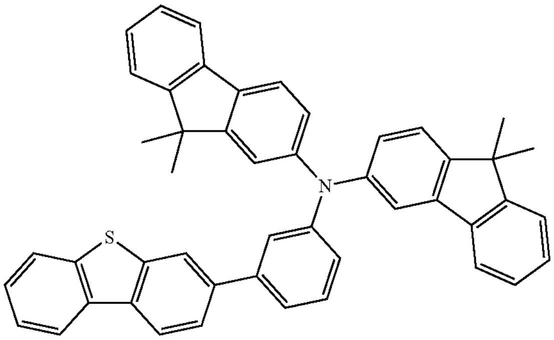
207
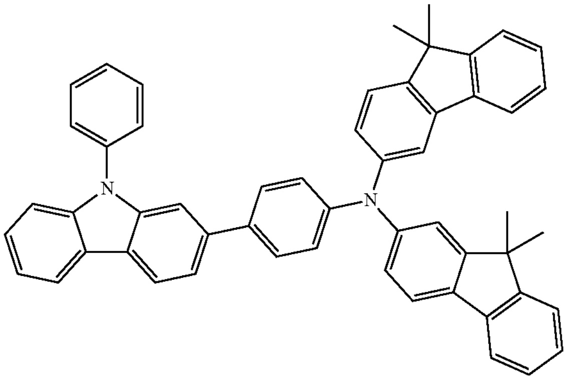

-continued
208
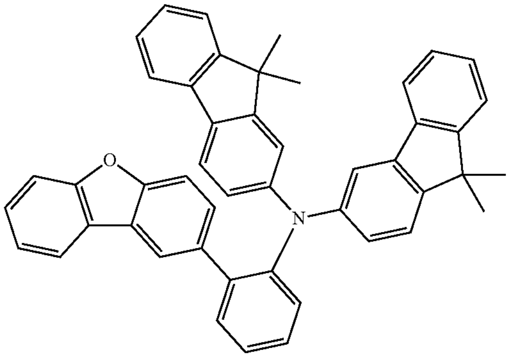
209
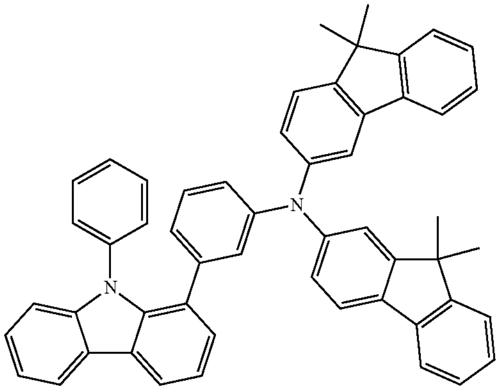
210
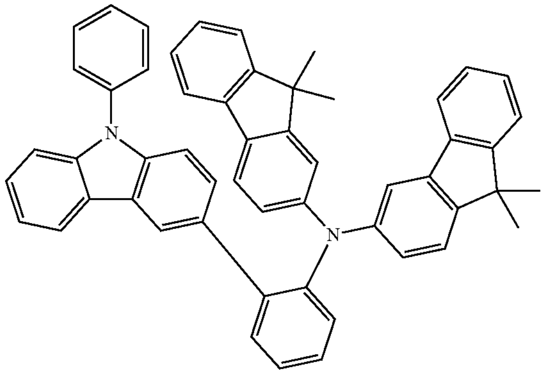
211
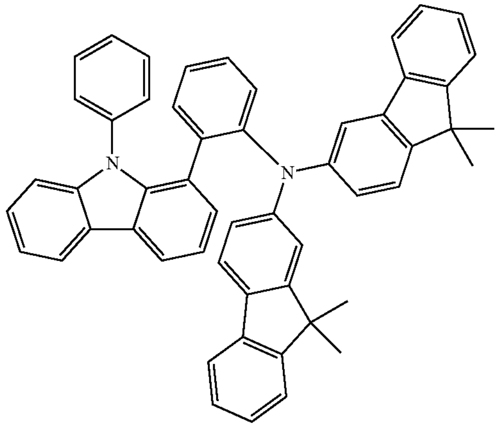
-continued
212
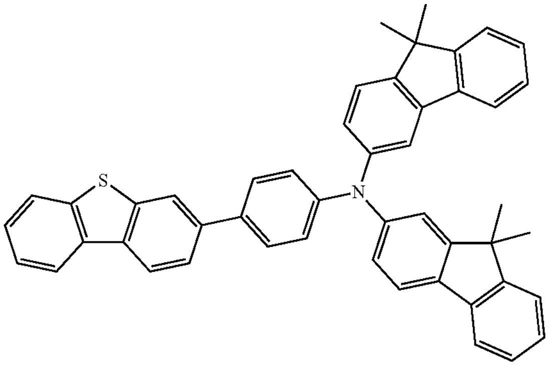
213
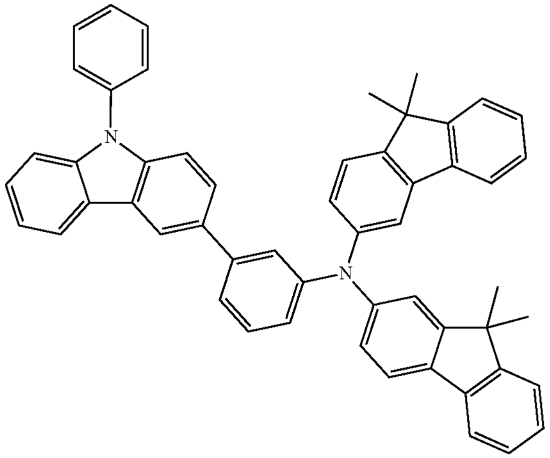
214
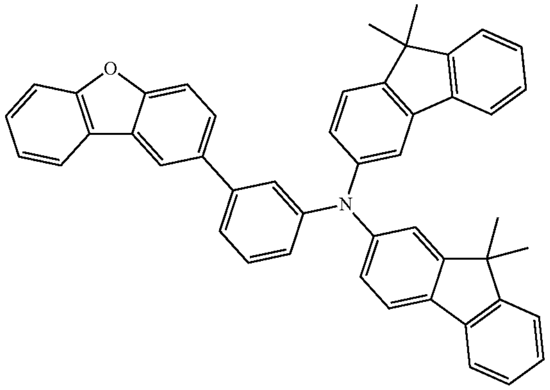
215
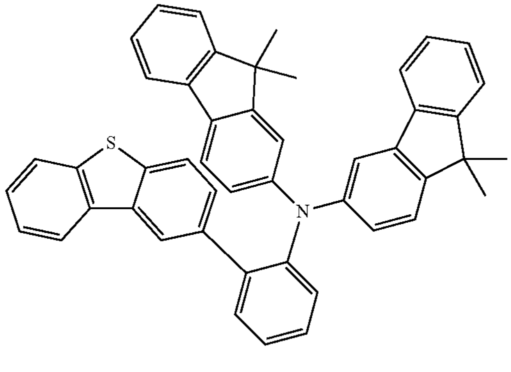

-continued
216
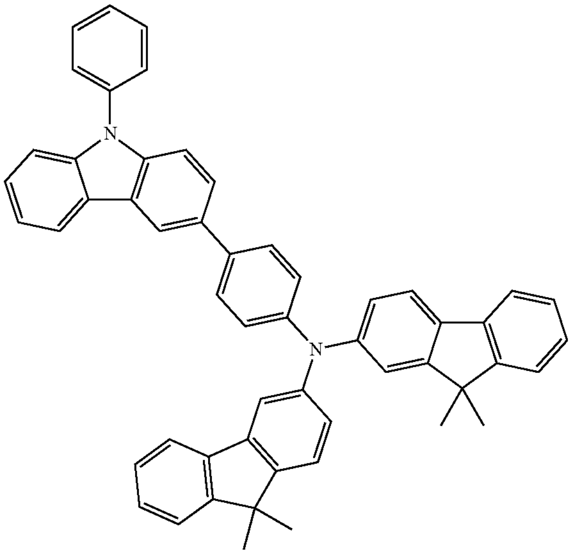
217
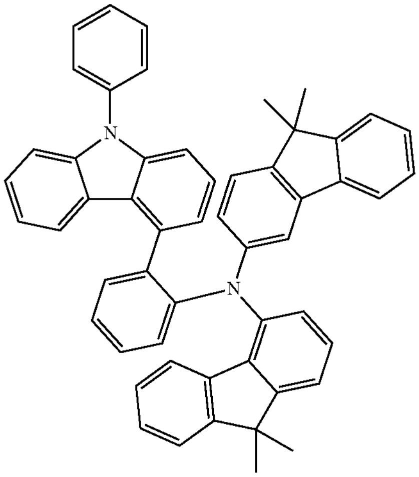
218
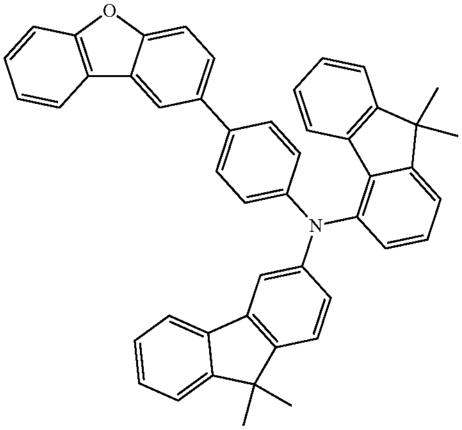
-continued
219
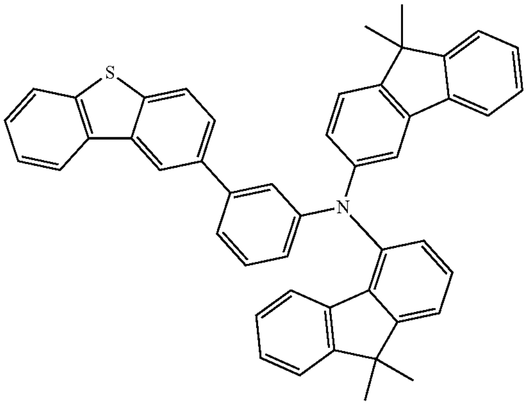
220
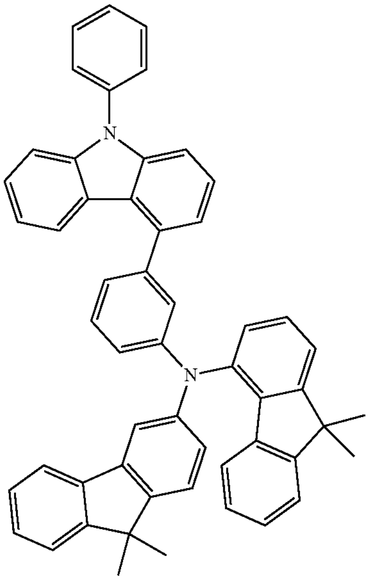
221
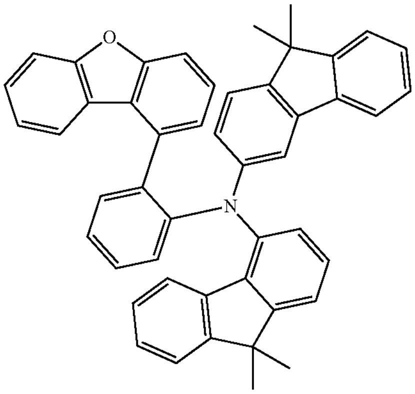

-continued
222
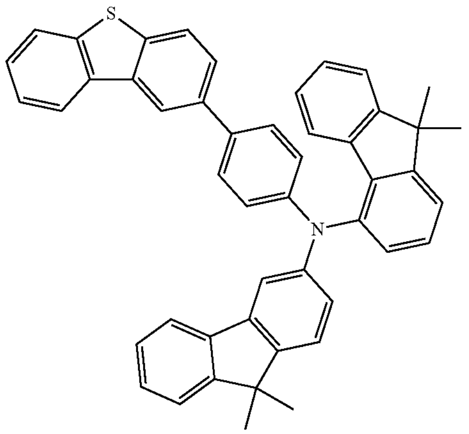
223
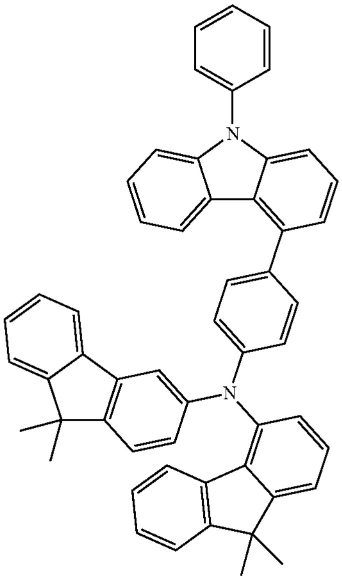
224
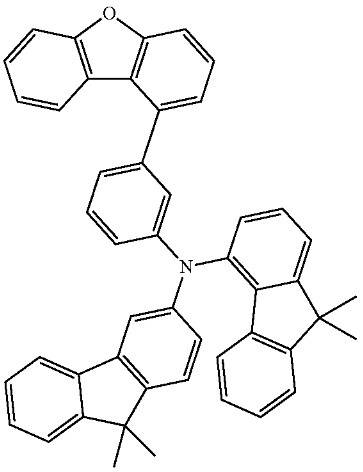
-continued
225
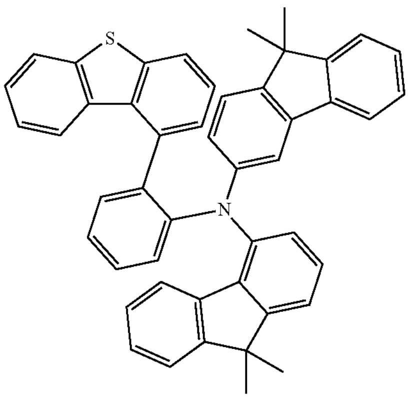
226
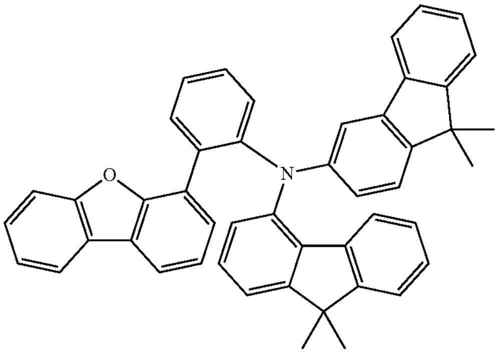
227
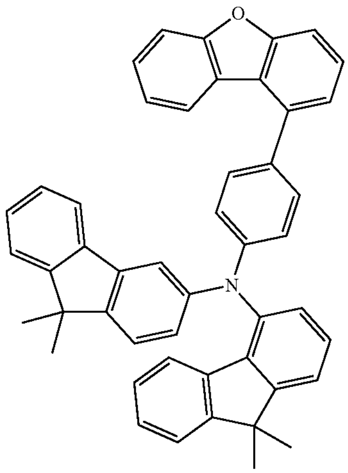

-continued
228
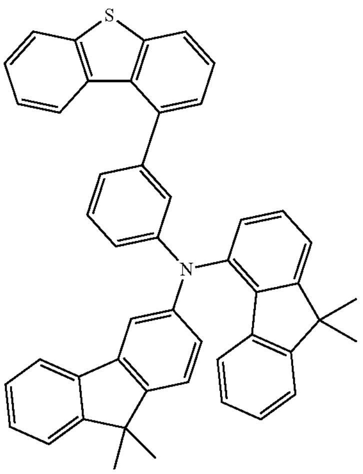
229
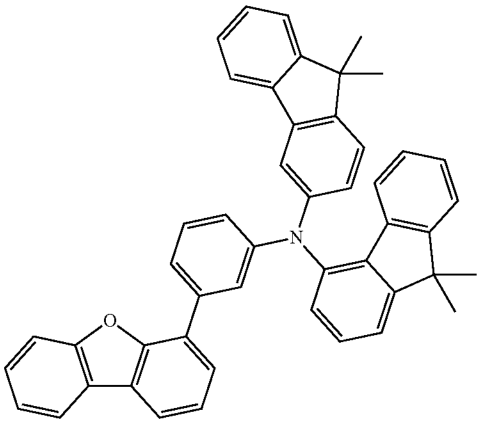
230
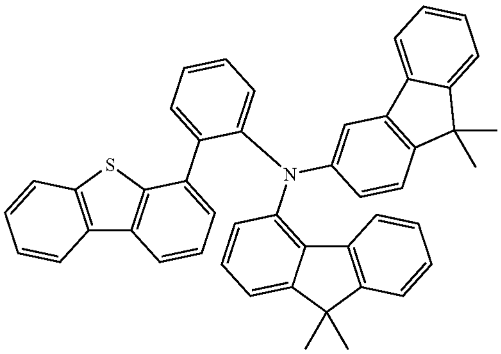
-continued
231
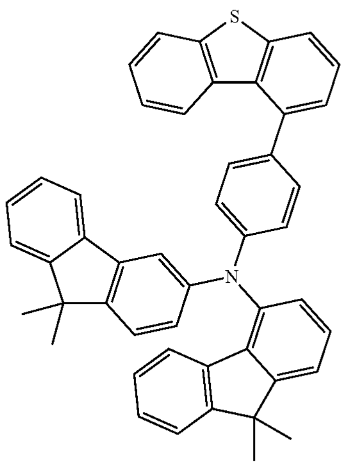
232
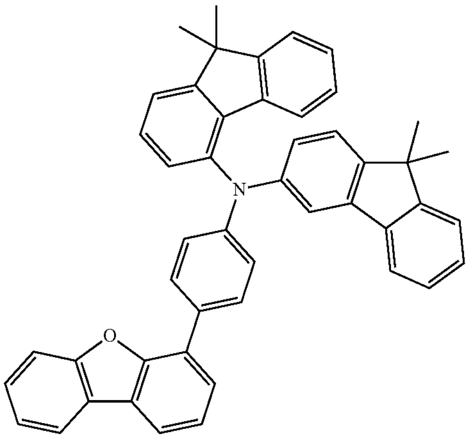
233
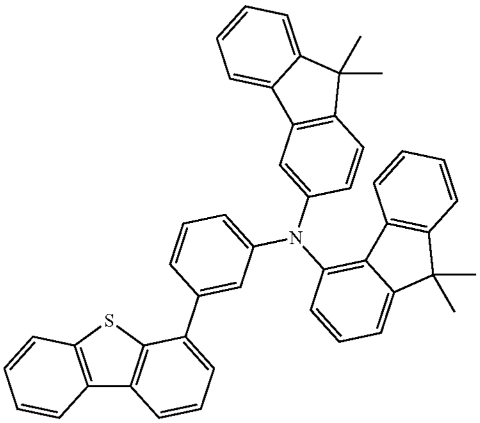

-continued
234
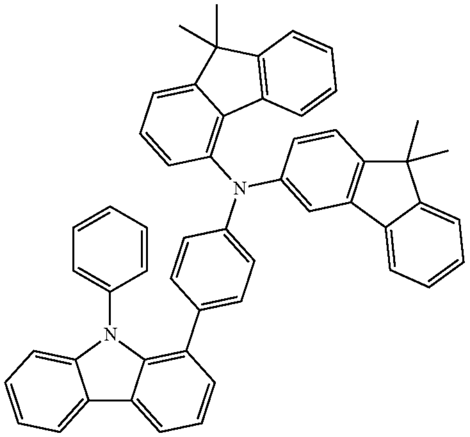
235
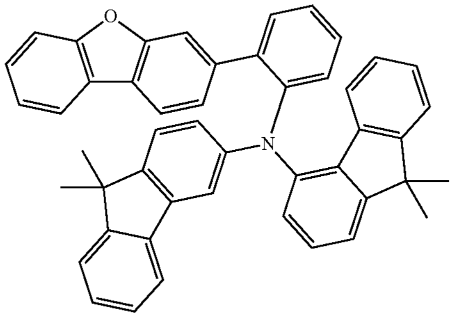
236
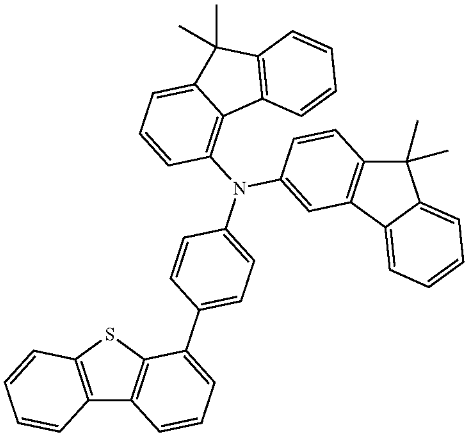
237
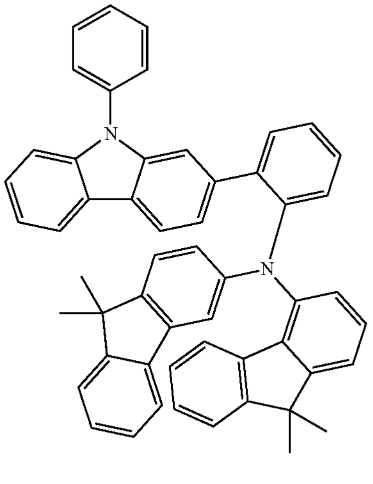
-continued
238
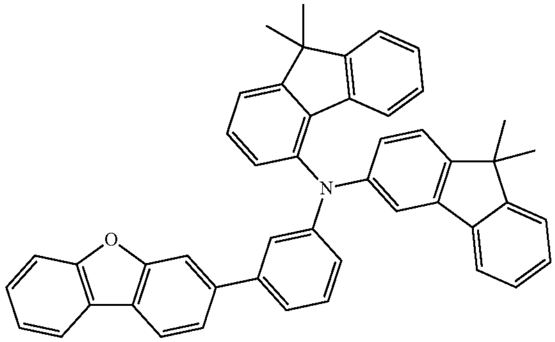
239
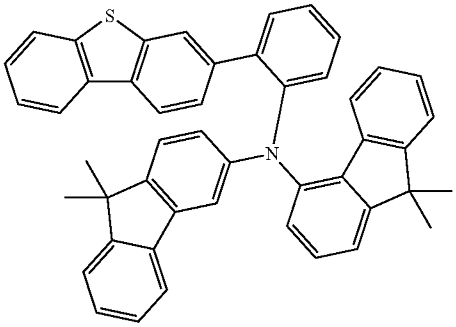
240
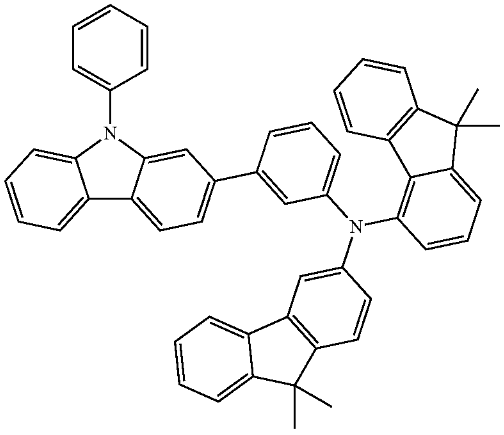
241
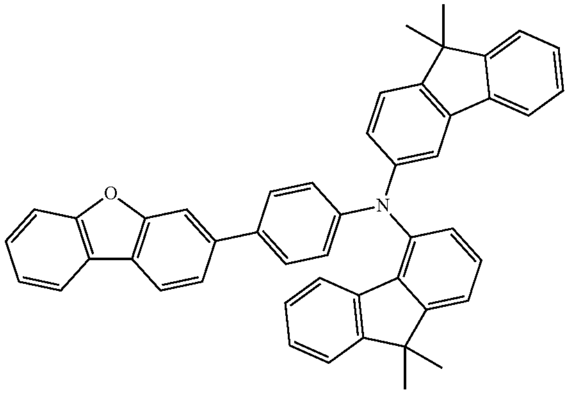

-continued
242
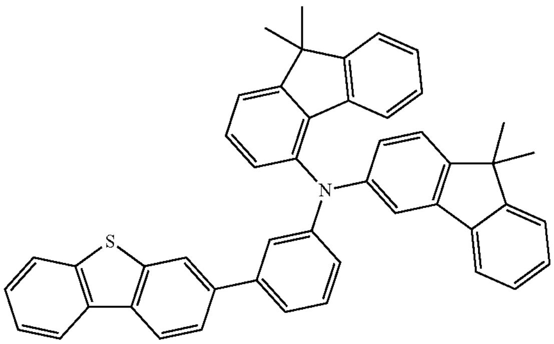
243
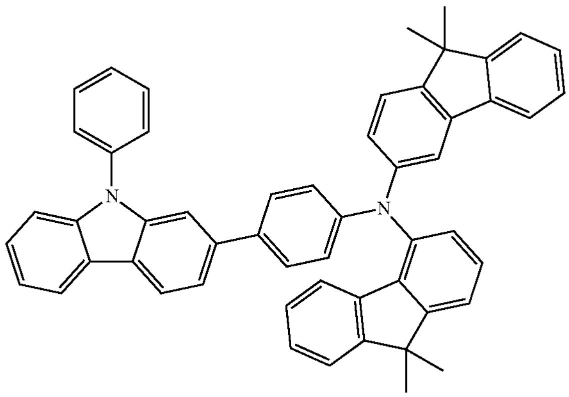
244
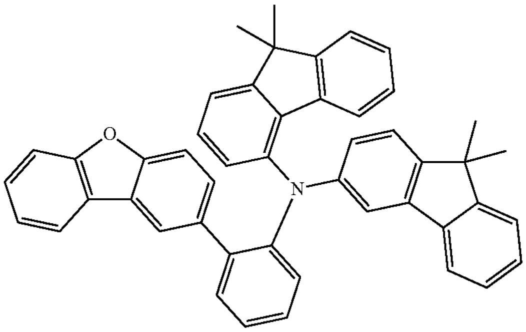
245
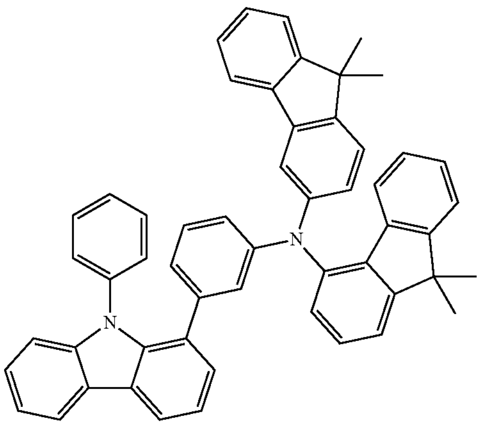
-continued
246
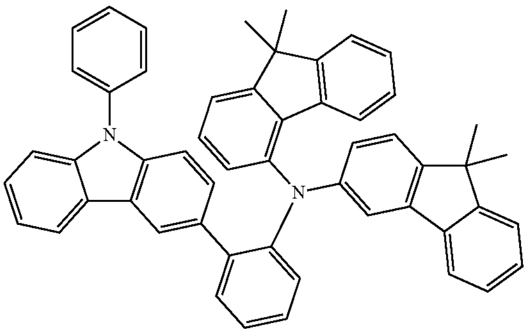
247
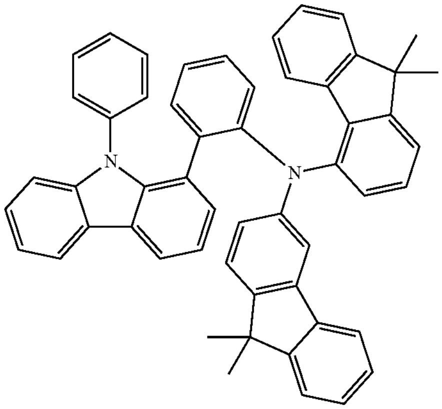
248
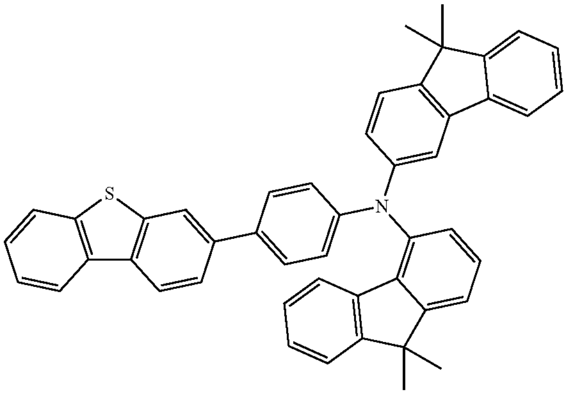

-continued
249
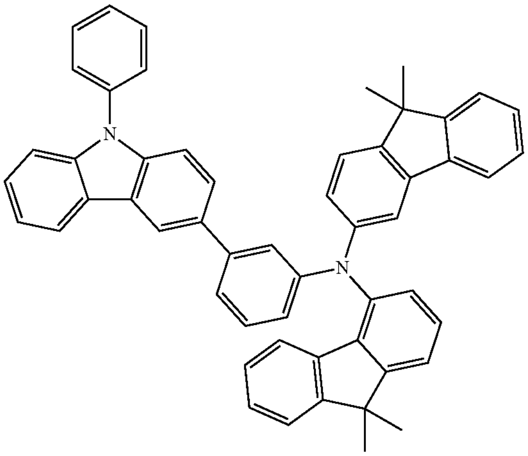
250
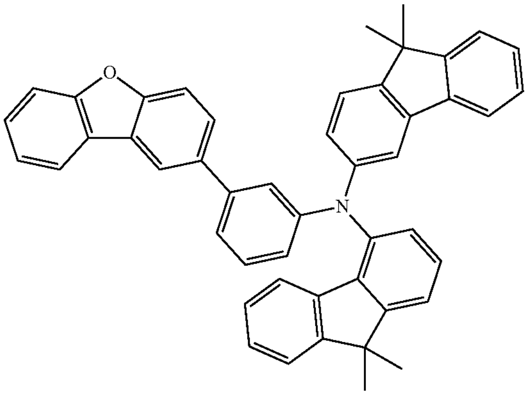
251
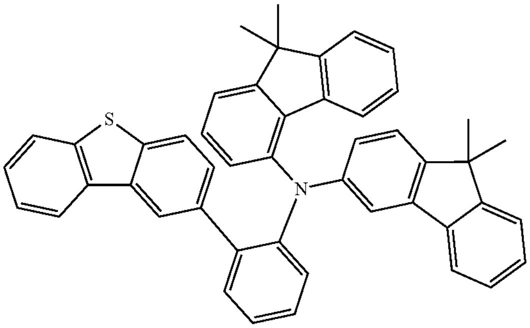
-continued
252
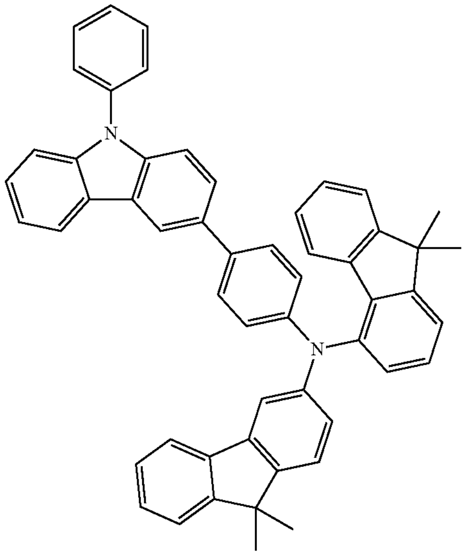
253
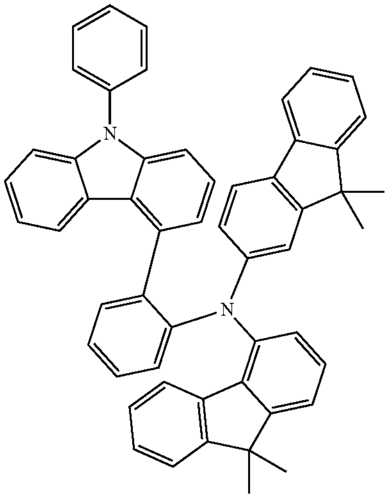
254
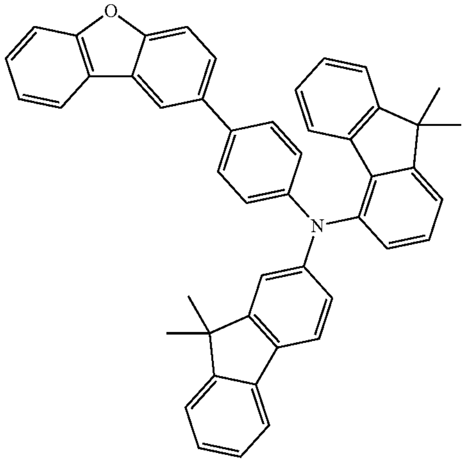

-continued
255
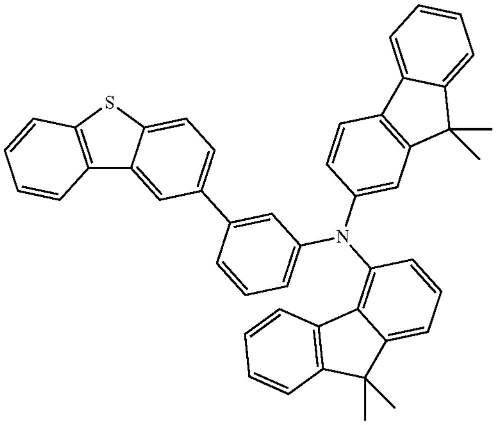
256
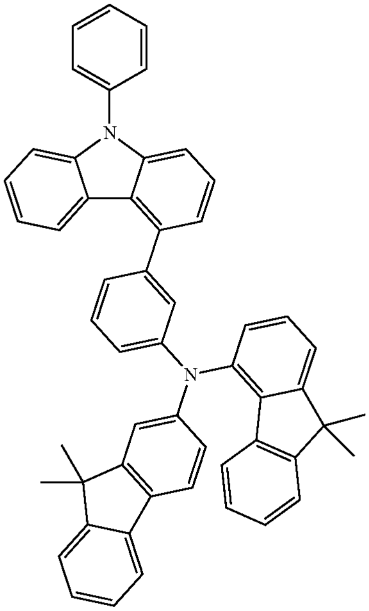
257
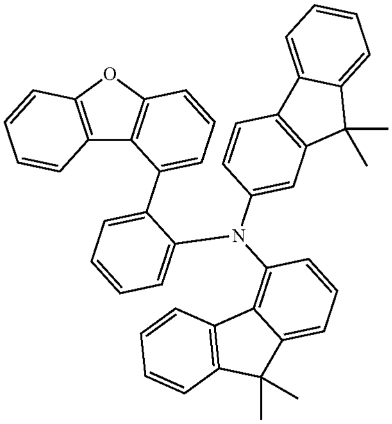
-continued
258
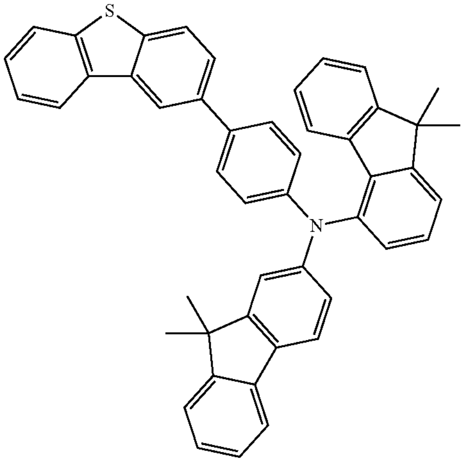
259
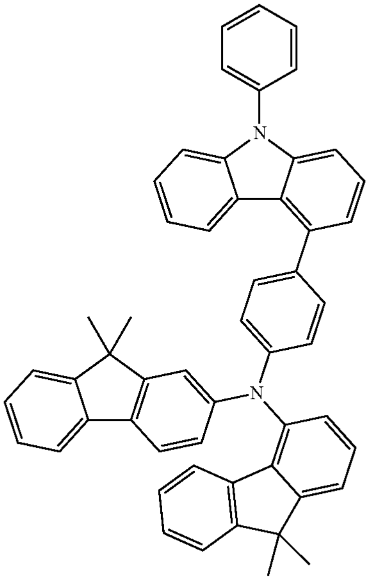
260
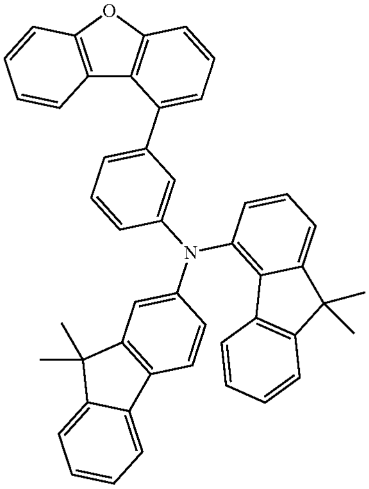

-continued
261
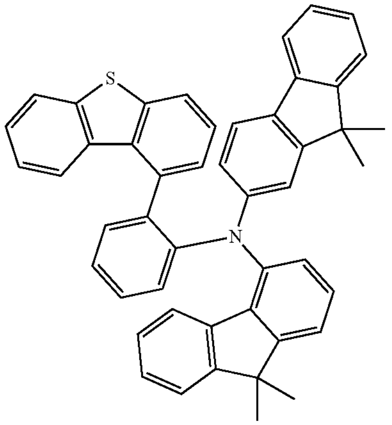
262
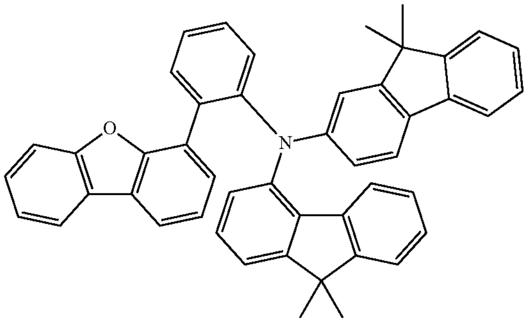
263
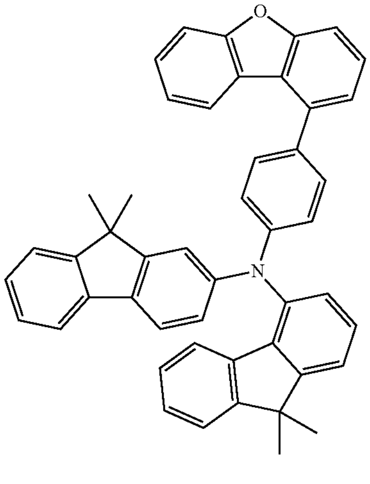
-continued
264
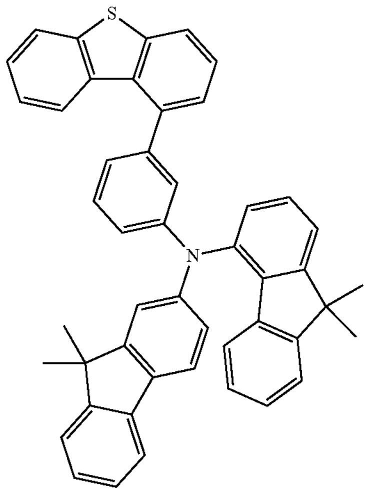
265
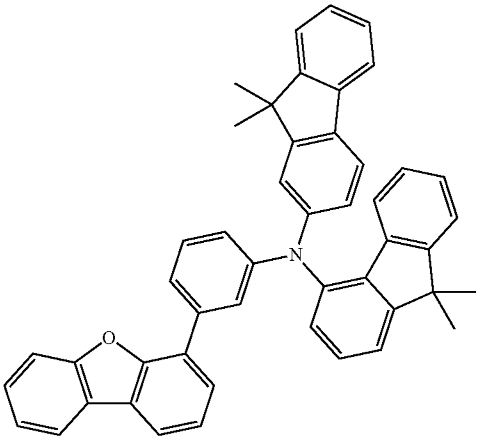
266
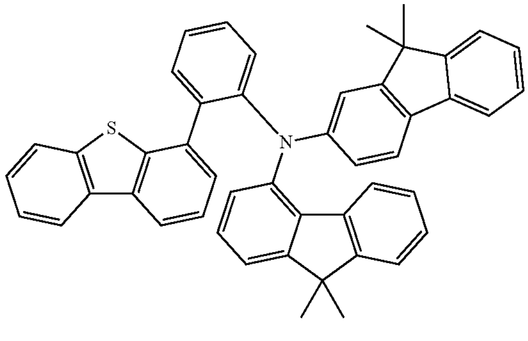

-continued
267
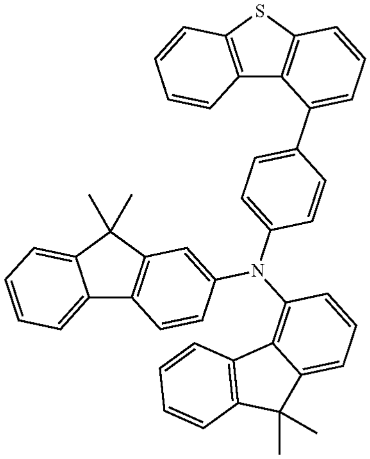
268
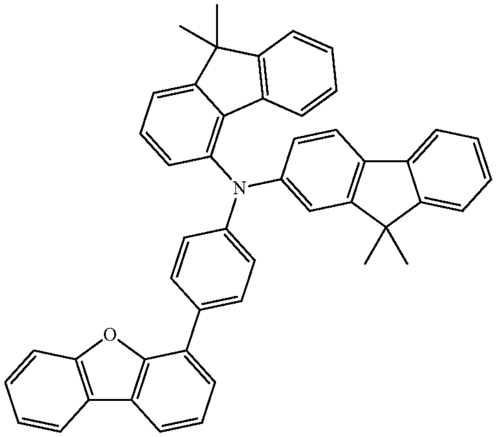
269
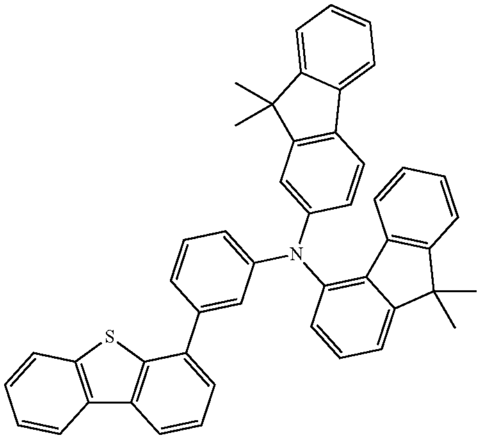
-continued
270
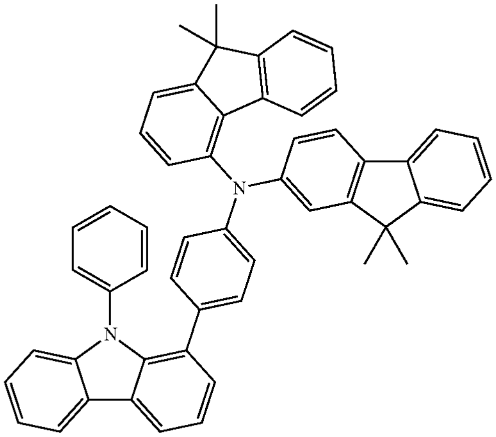
271
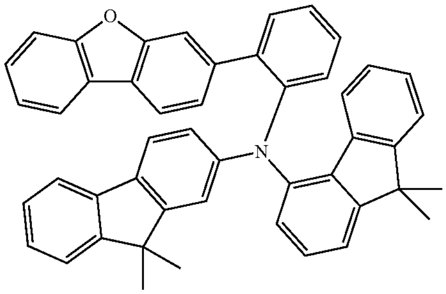
272
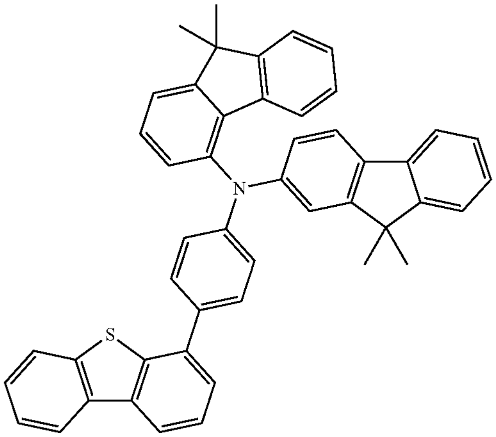
273
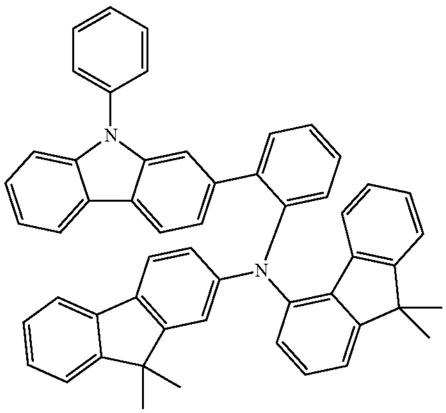

-continued
274
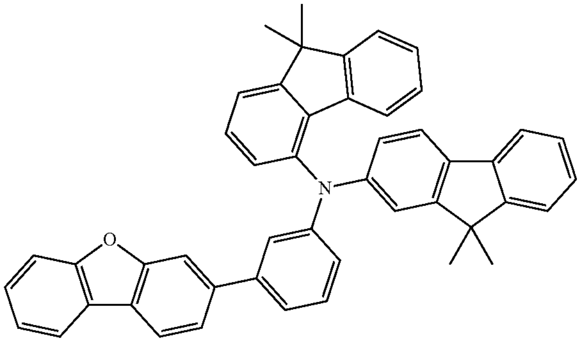
275
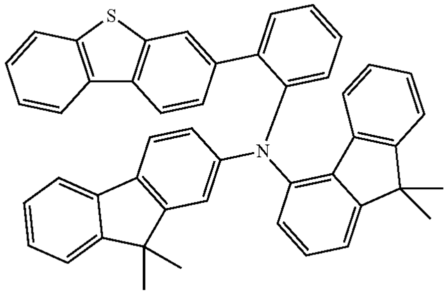
276
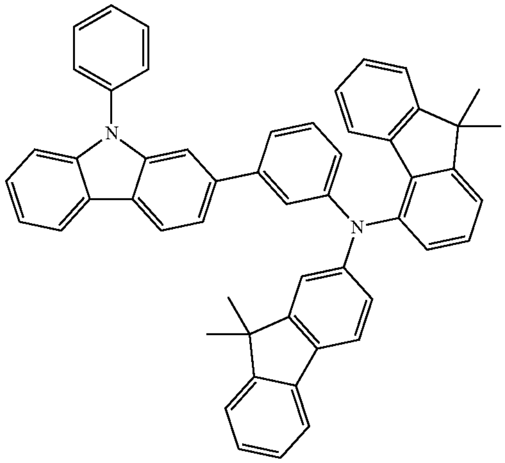
277
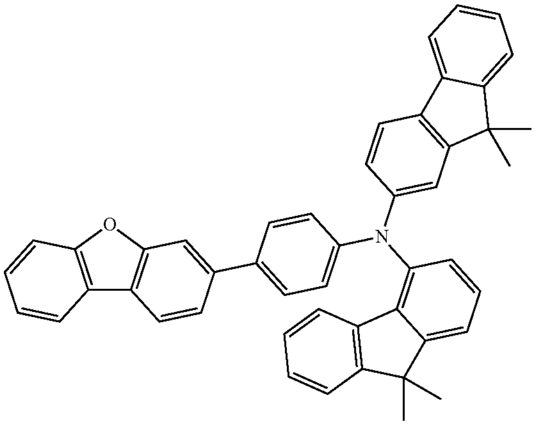
-continued
278
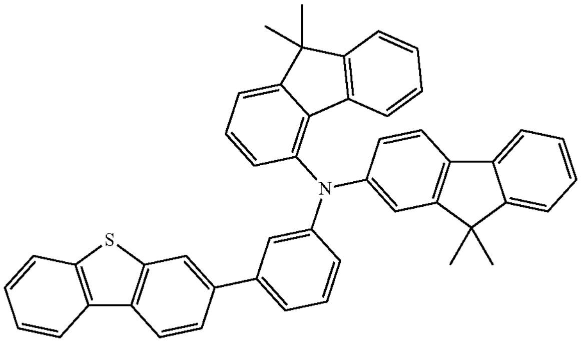
279
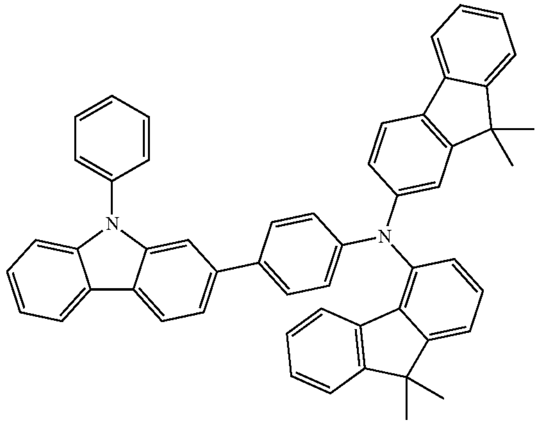
280
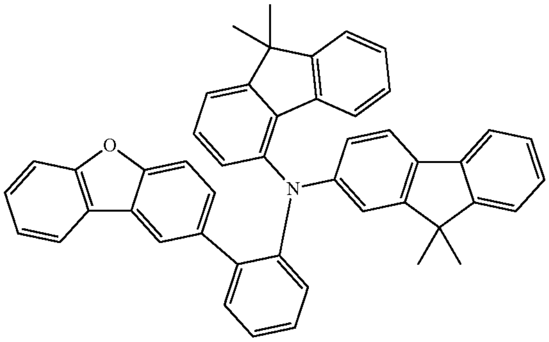
281
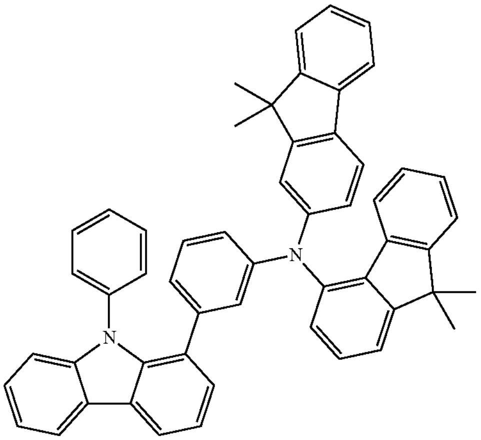

-continued
282
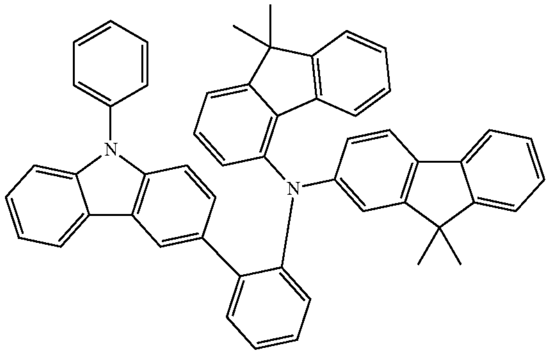
283
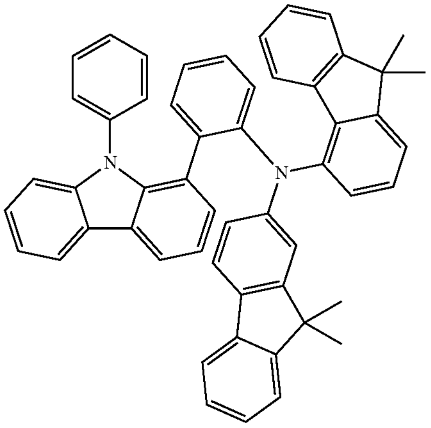
284
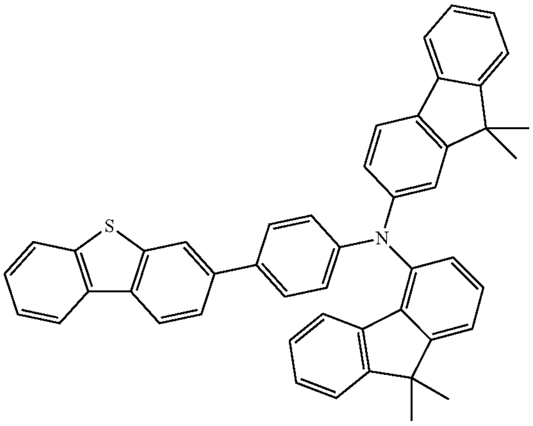
-continued
285
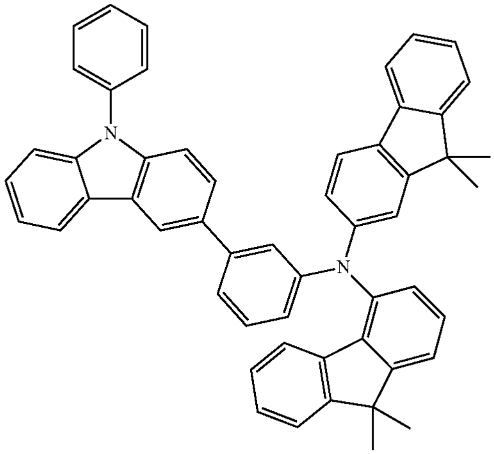
286
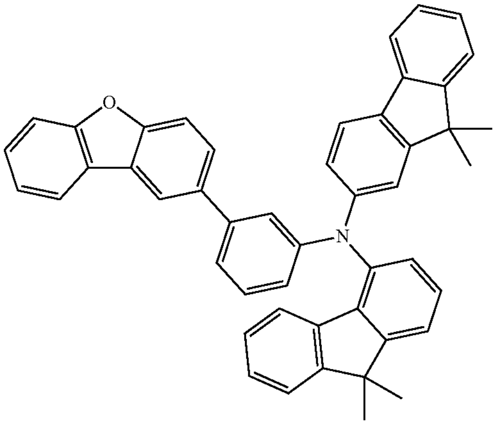
287
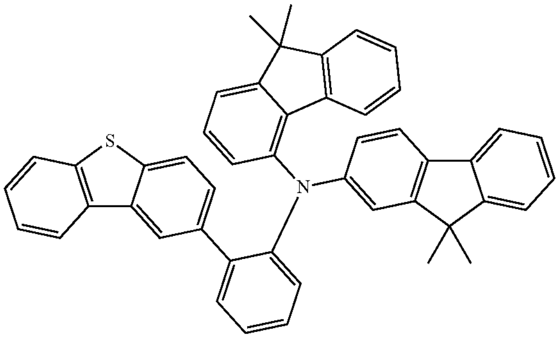

-continued
288
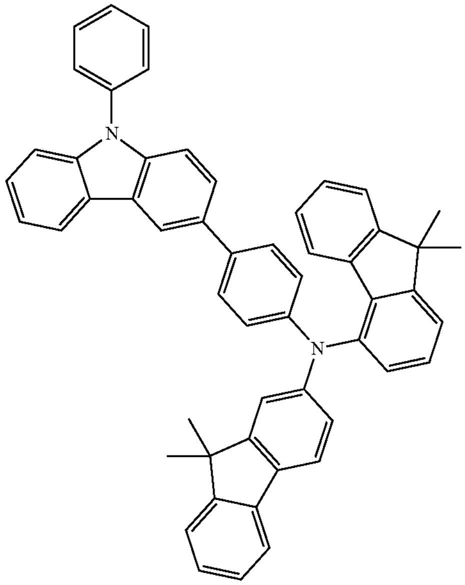
289
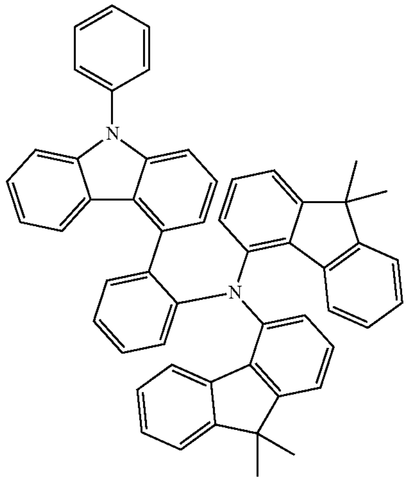
290
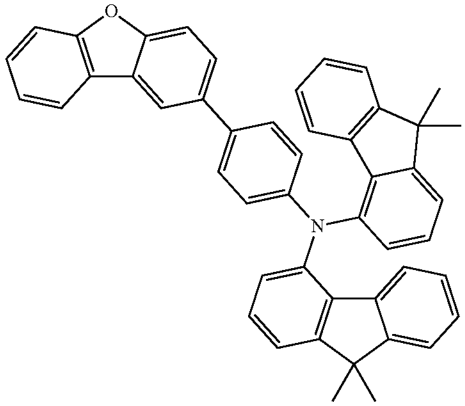
-continued
291
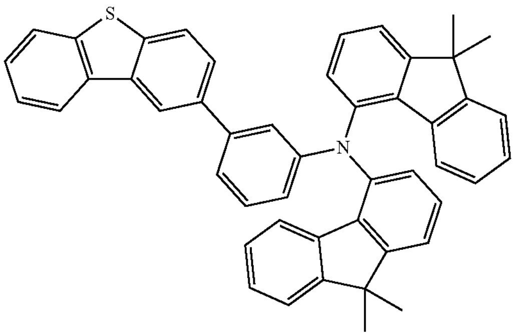
292
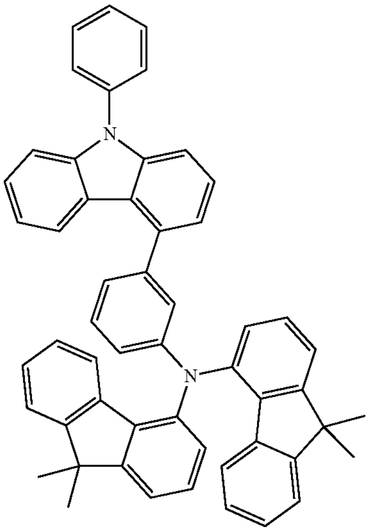
293
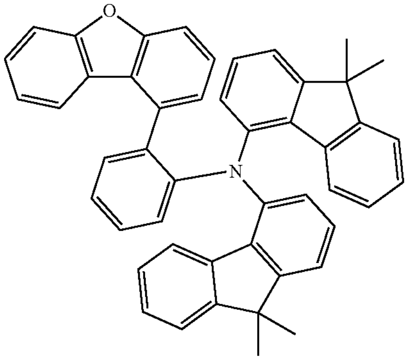
294
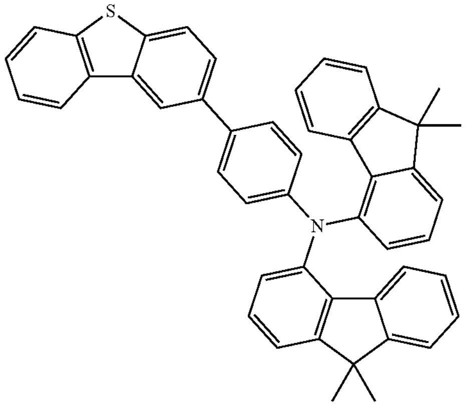

-continued
295
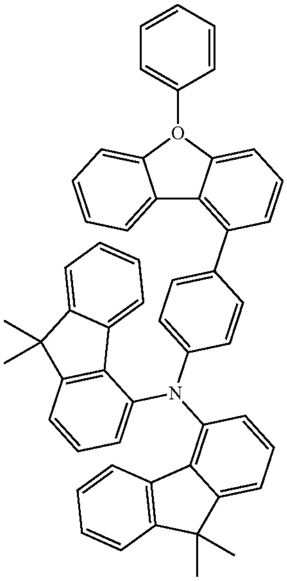
296
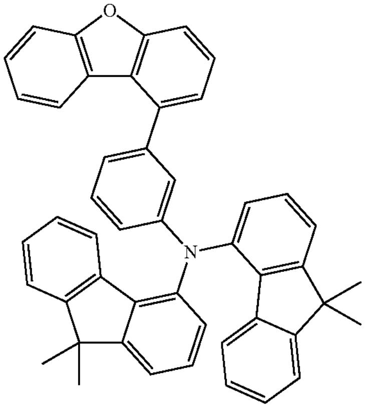
297
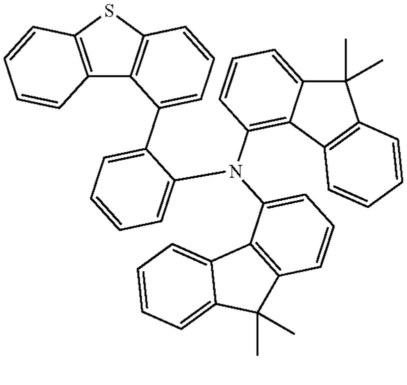
-continued
298
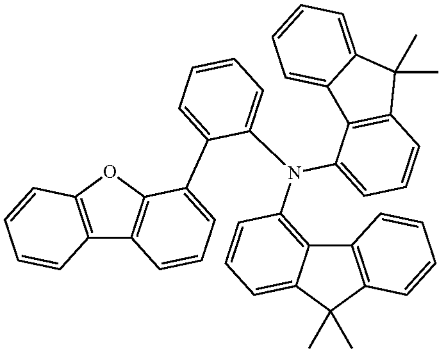
299
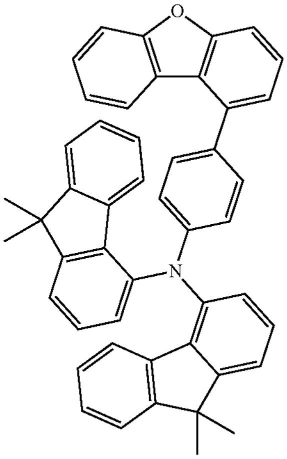
300
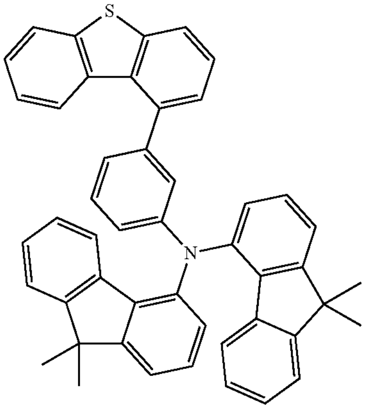
301
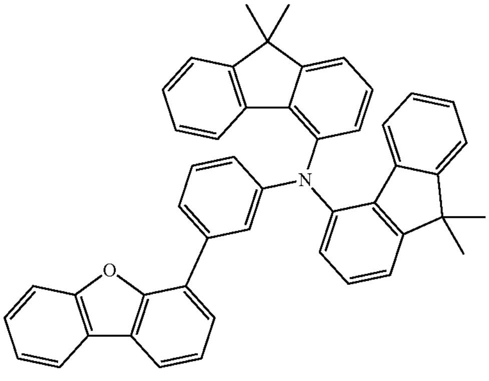

-continued
302
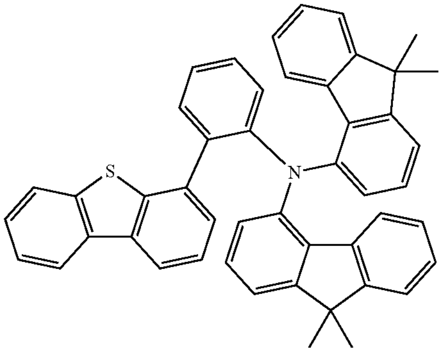
303
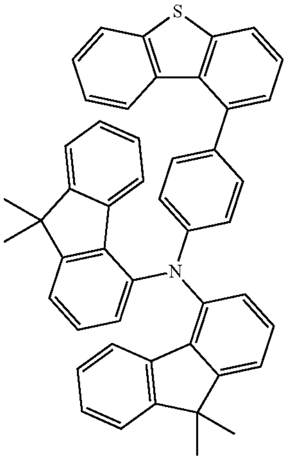
304
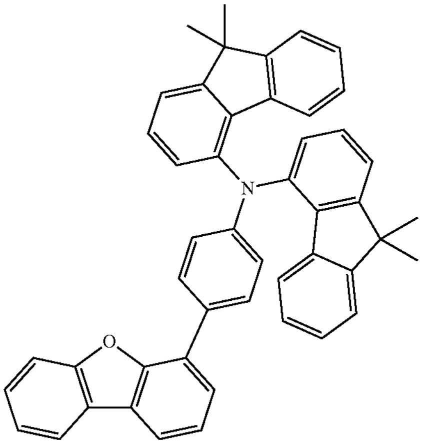
305
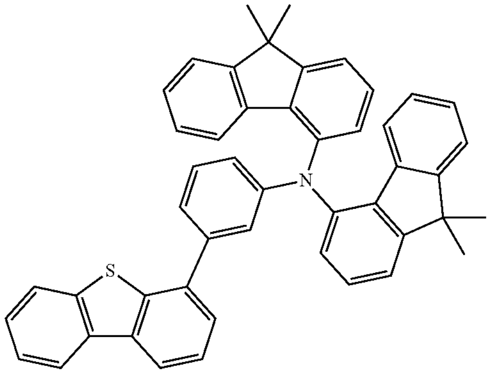
-continued
306
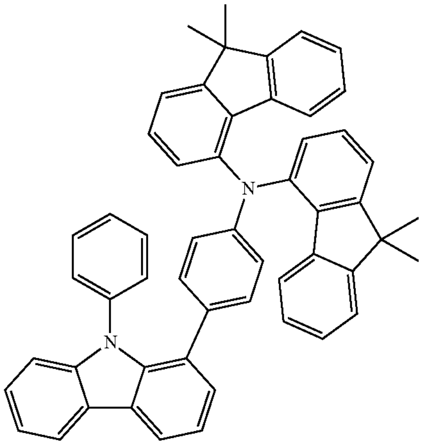
307
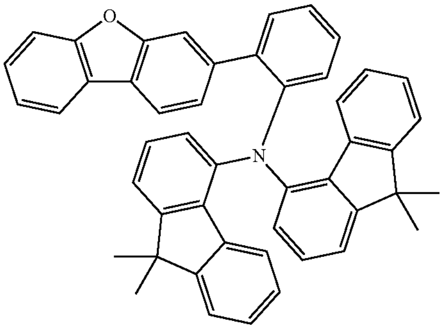
308
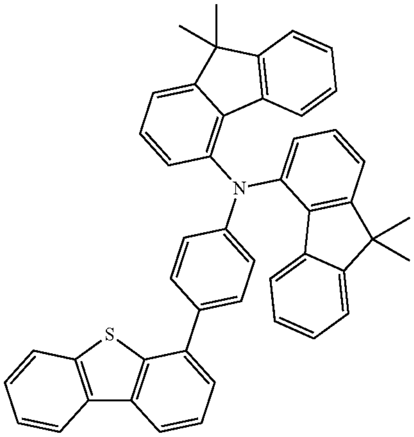

-continued
309
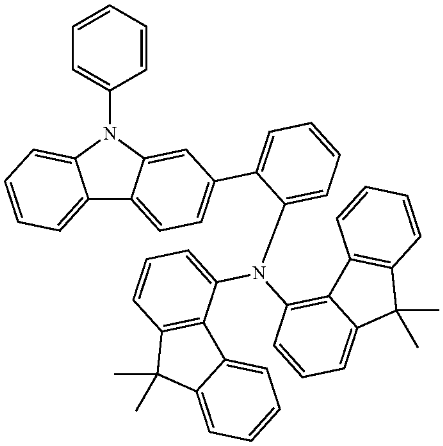
310
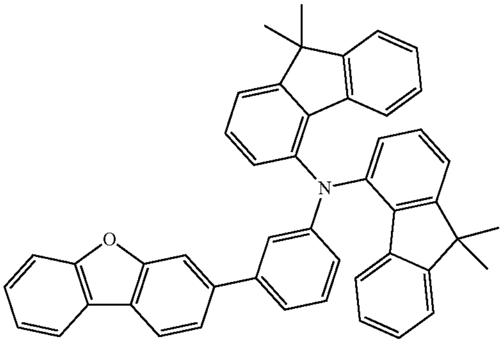
311
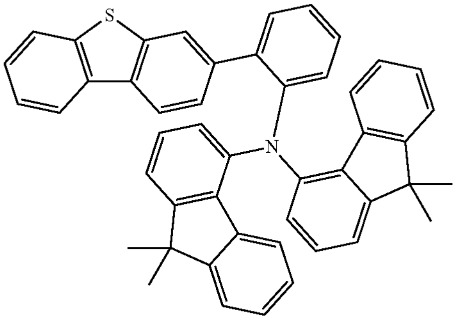
312
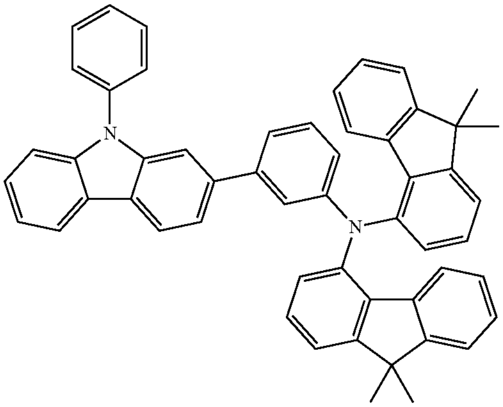
-continued
313
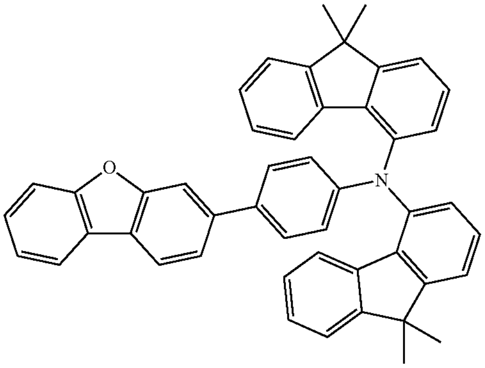
314
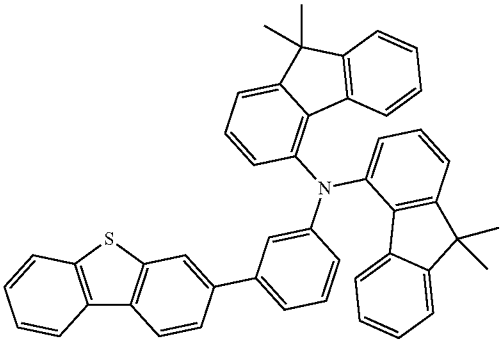
315
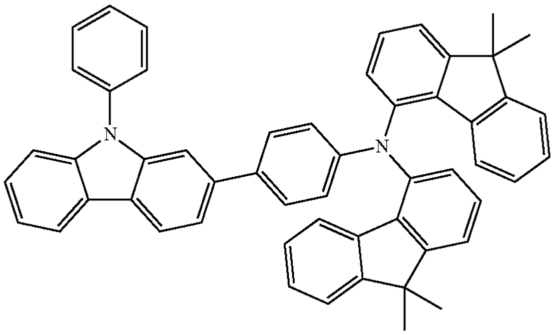
316
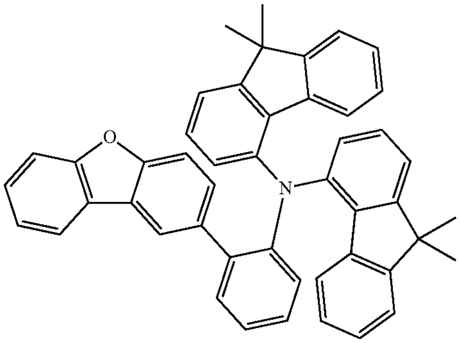

-continued
317
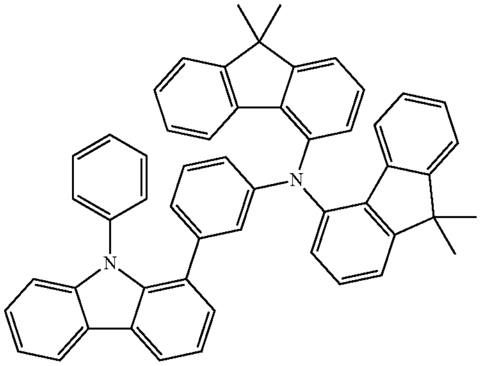
318
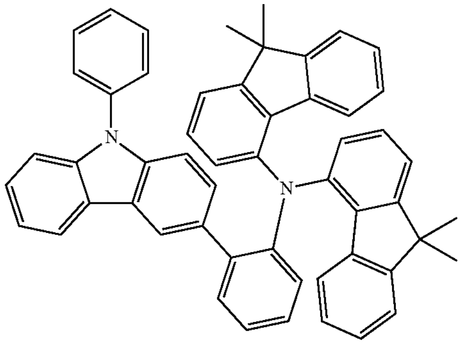
319
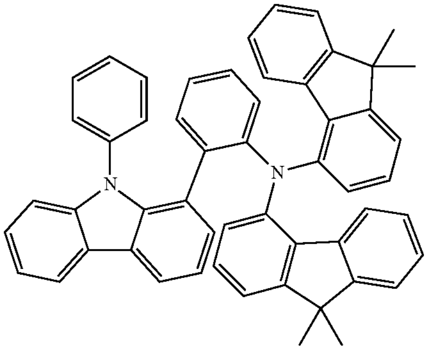
320
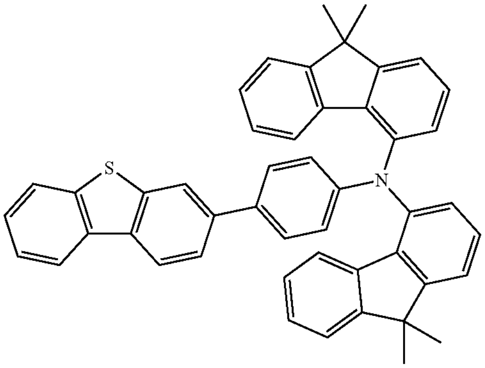
-continued
321
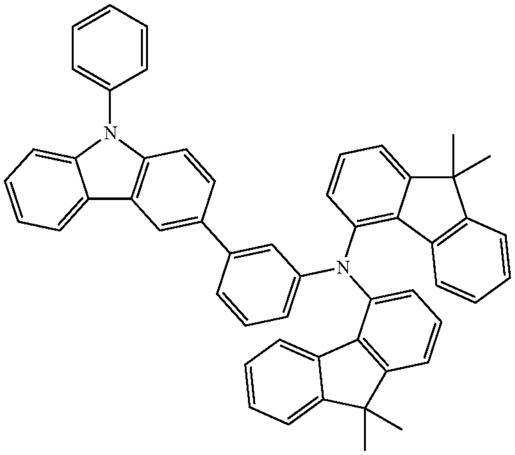
322
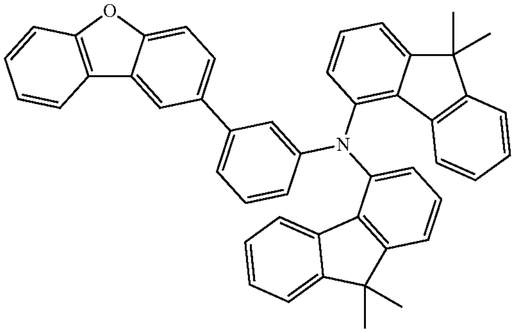
323
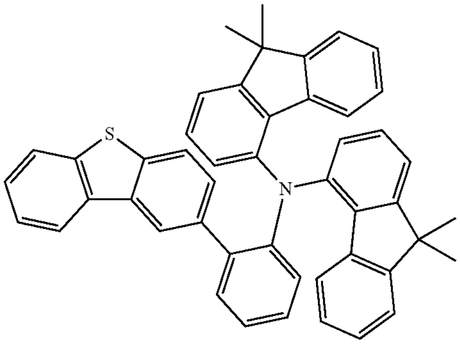

324
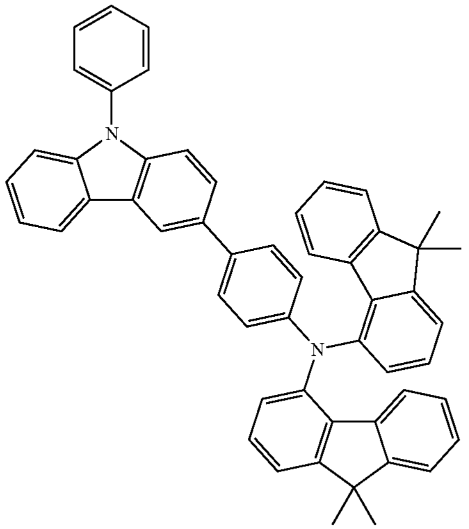
325
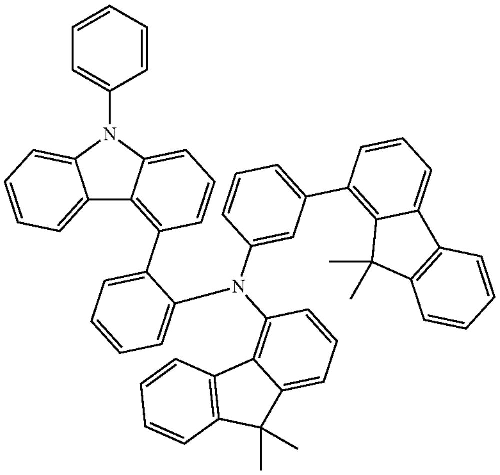
326
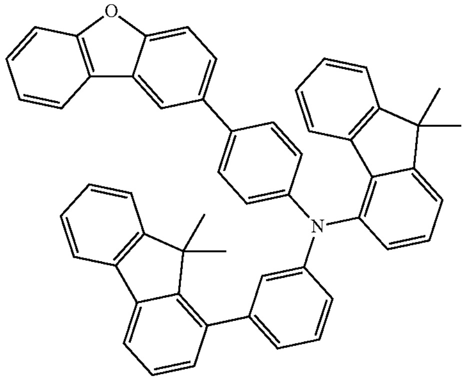
327
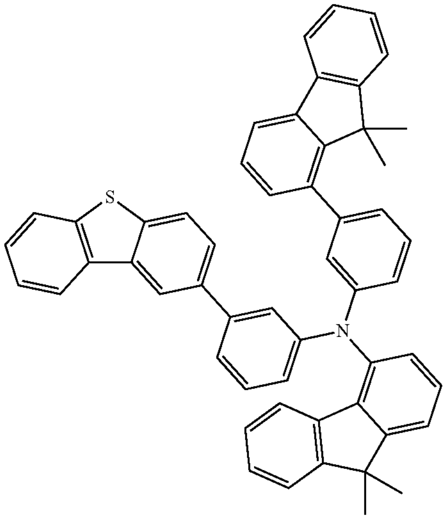
328
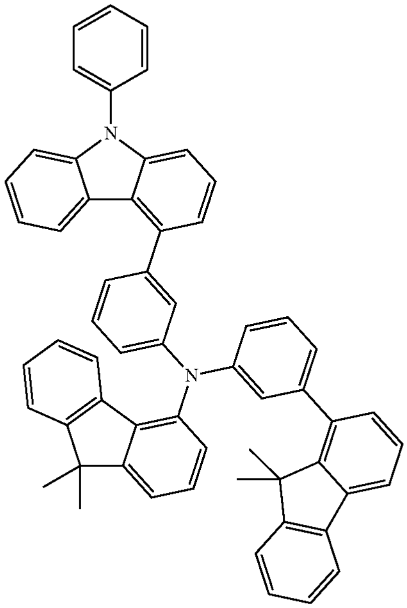
329
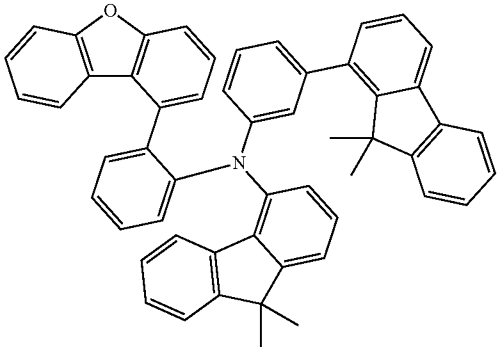

-continued
330
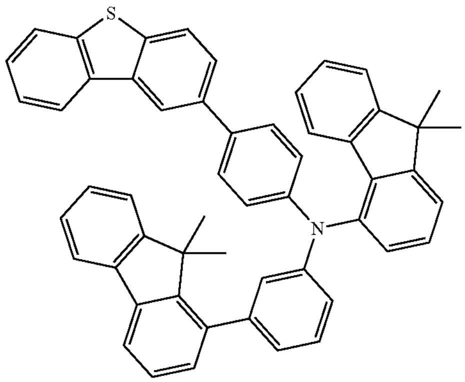
331
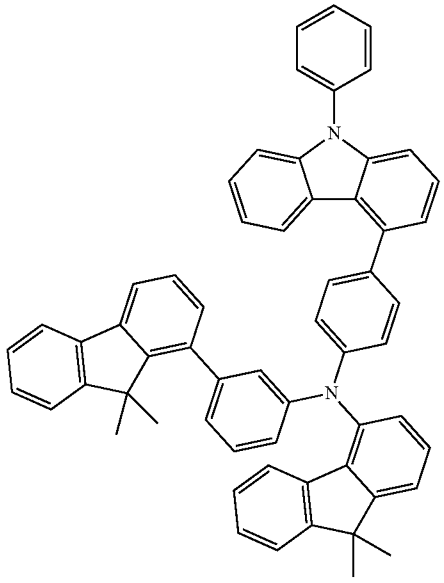
332
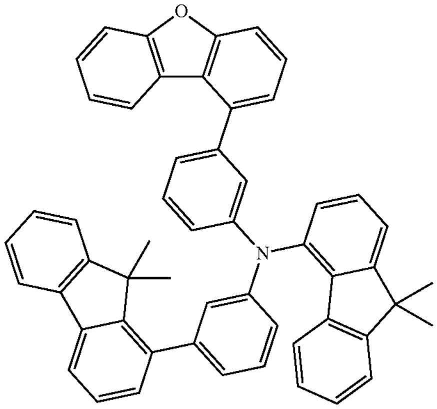
-continued
333
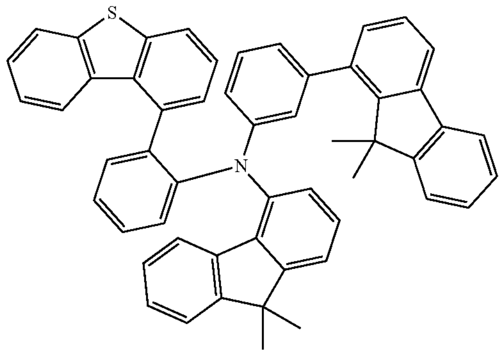
334
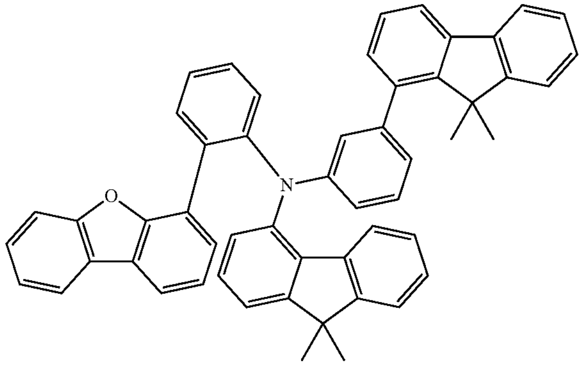
335
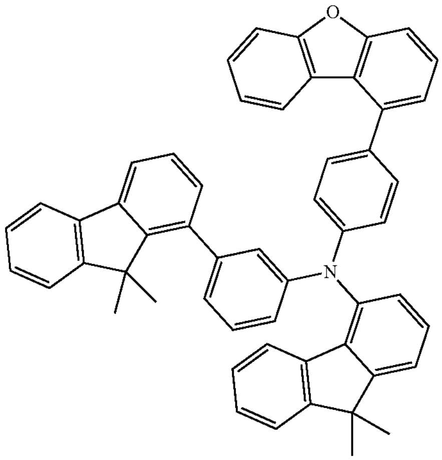
336
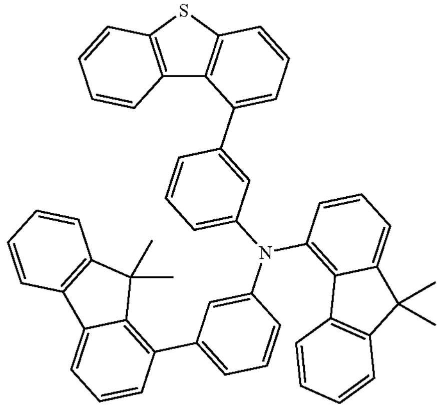

337
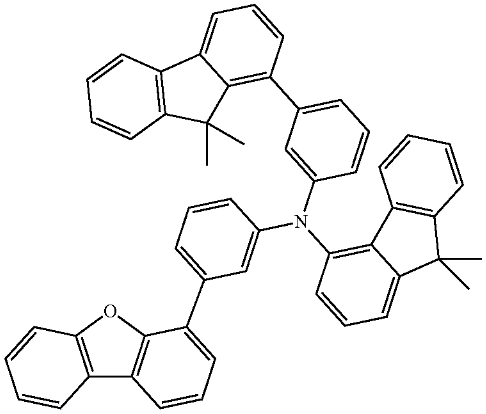
338
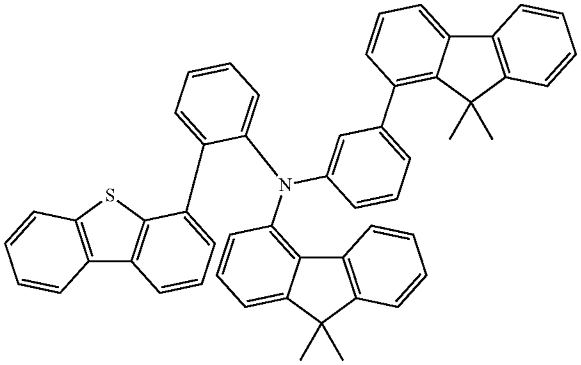
339
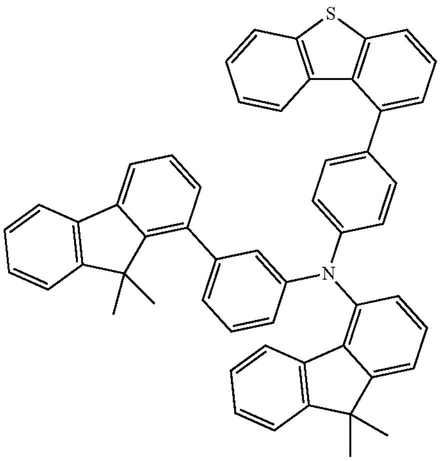
340
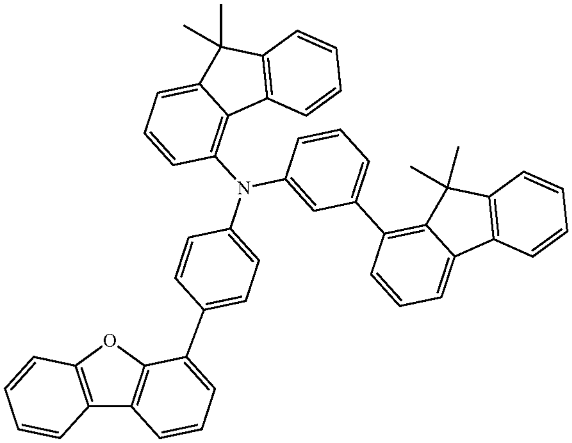
341
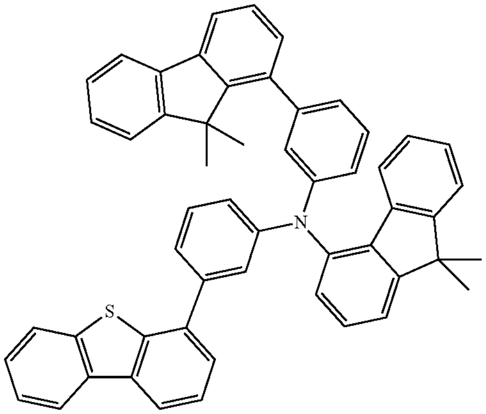
342
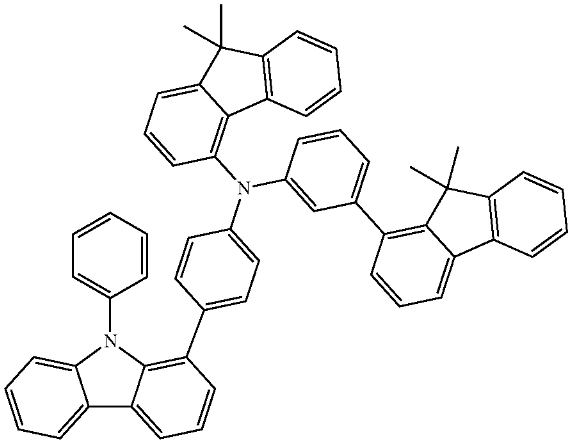

343
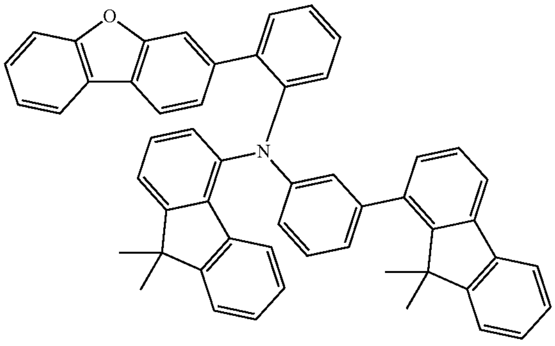
344
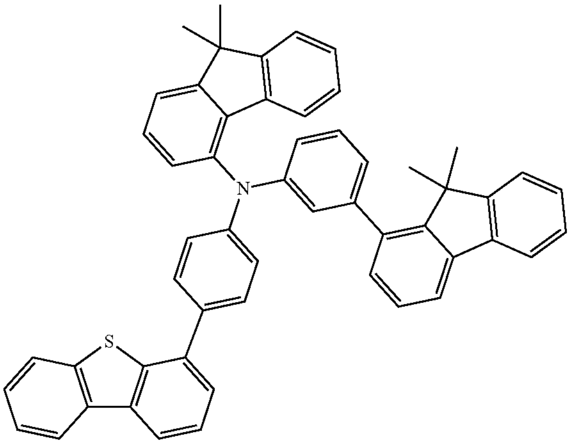
345
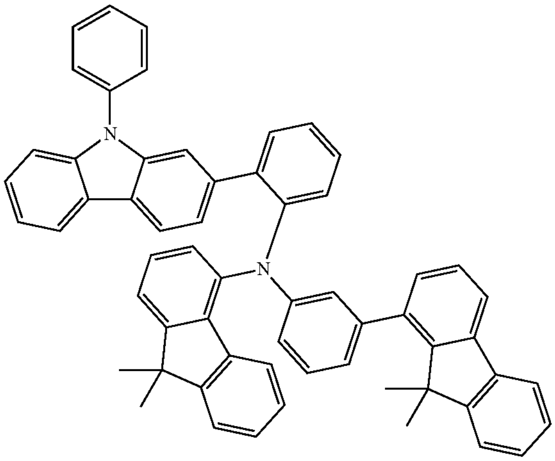
346
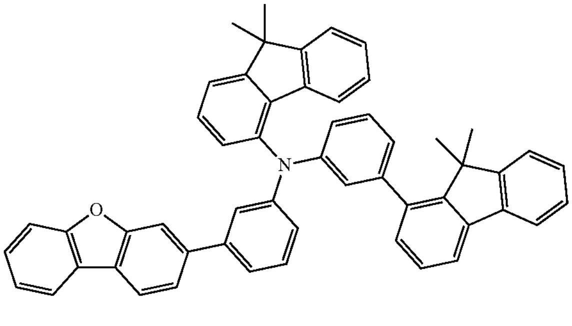
347
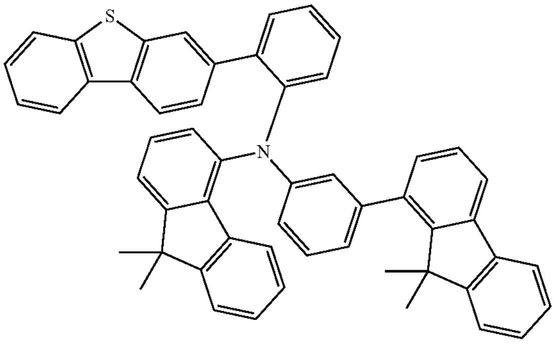
348
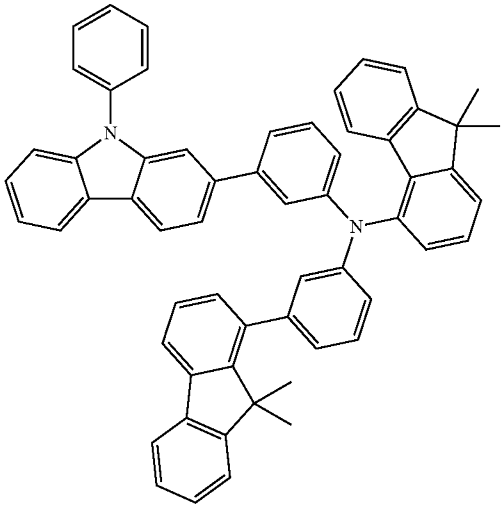
349
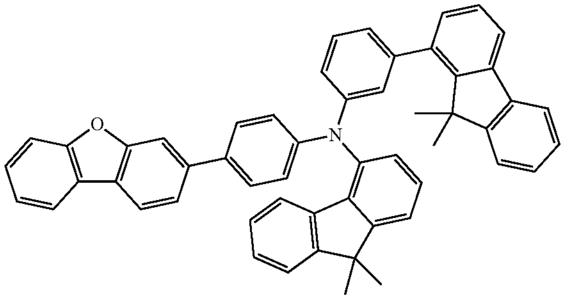
350
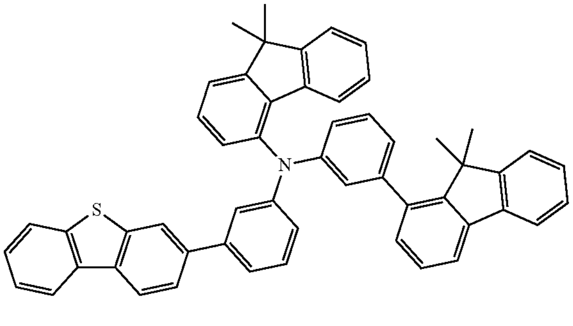

-continued
351
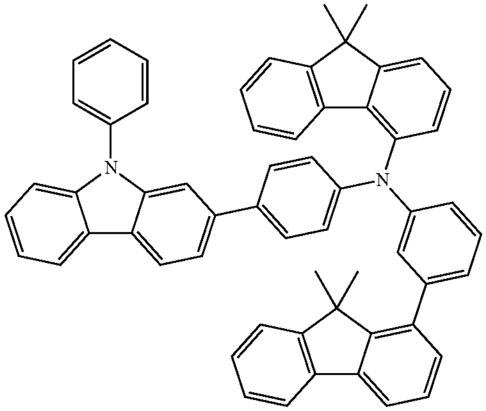
352
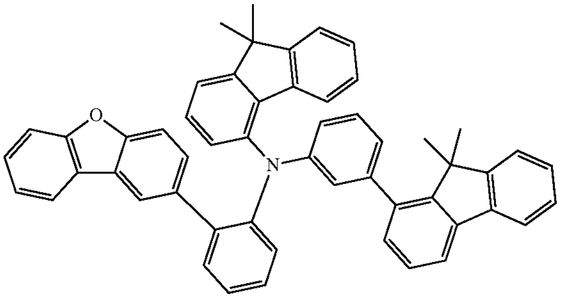
353
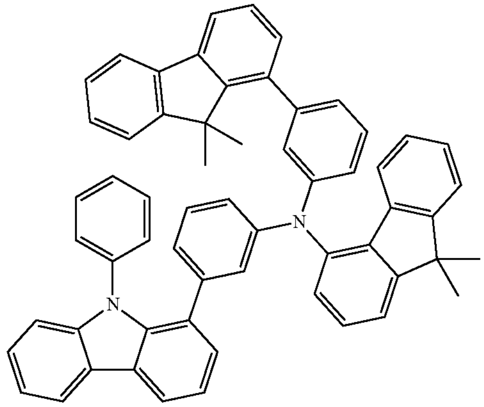
354
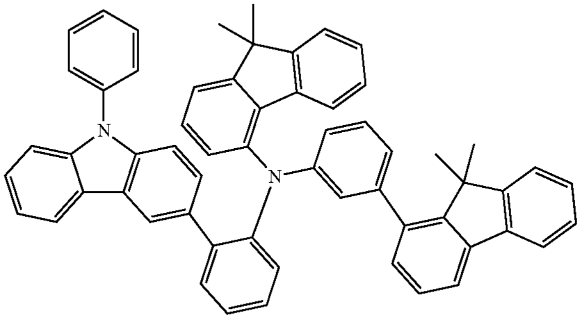
-continued
355
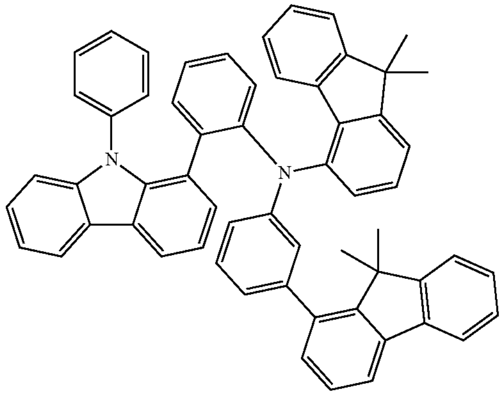
356
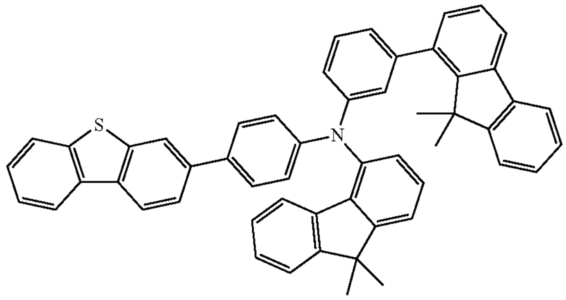
357
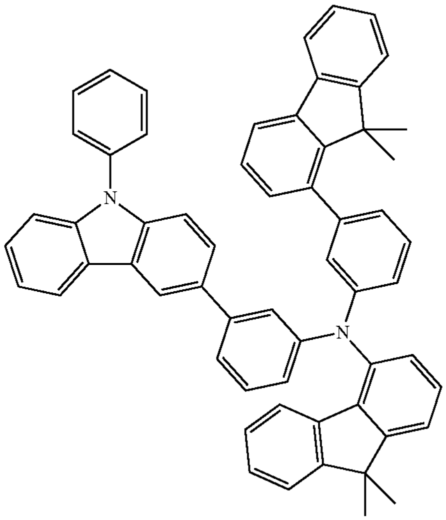

358
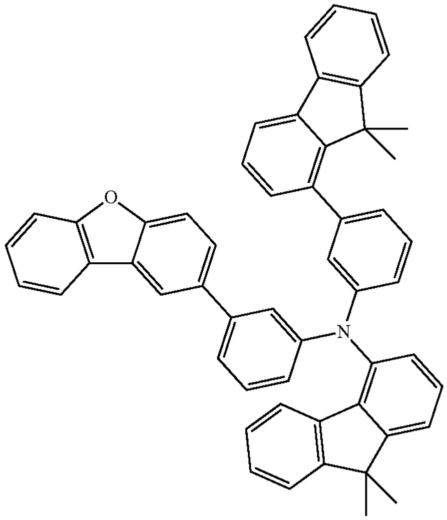
359
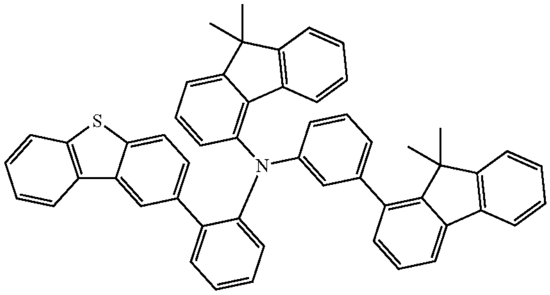
360
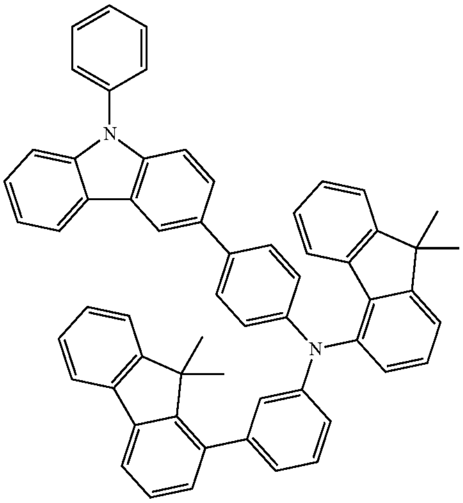
361
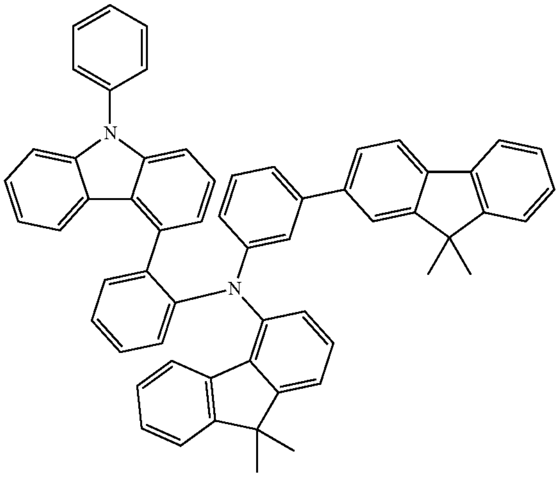
362
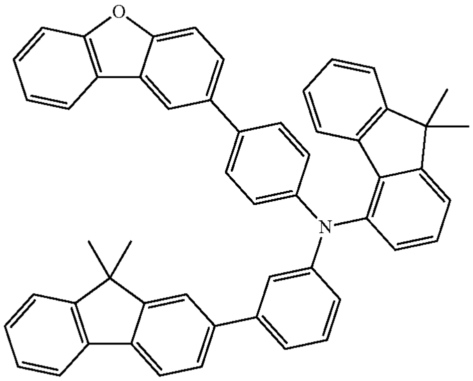
363
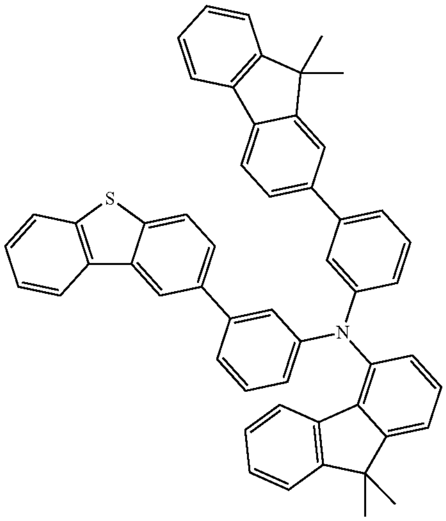

-continued
364
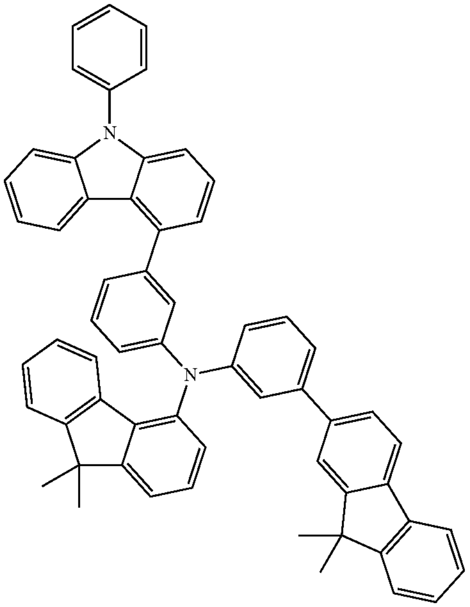
365
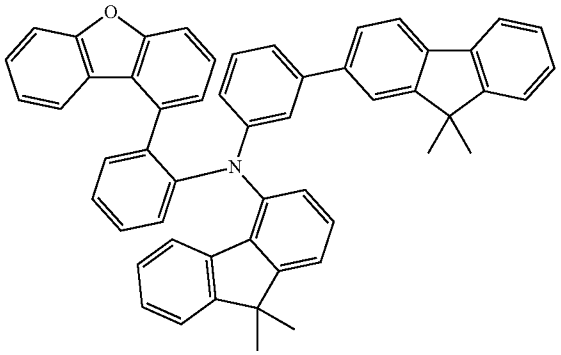
366
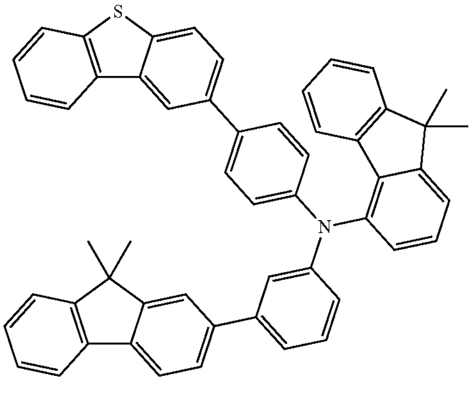
-continued
367
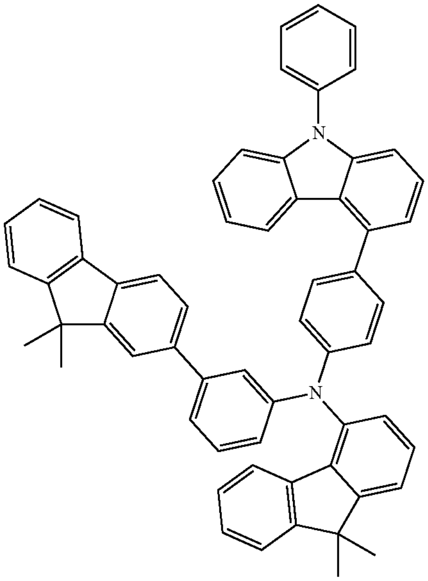
368
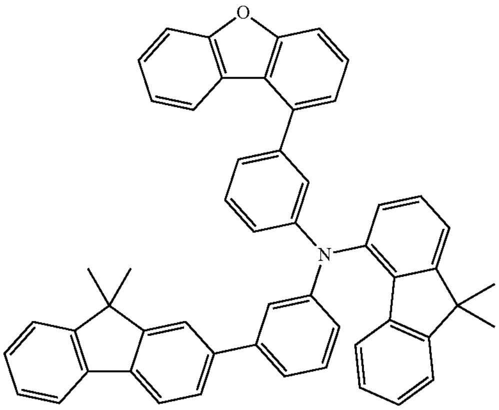
369
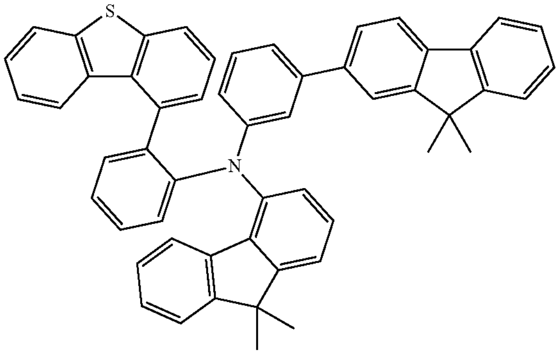

-continued
370
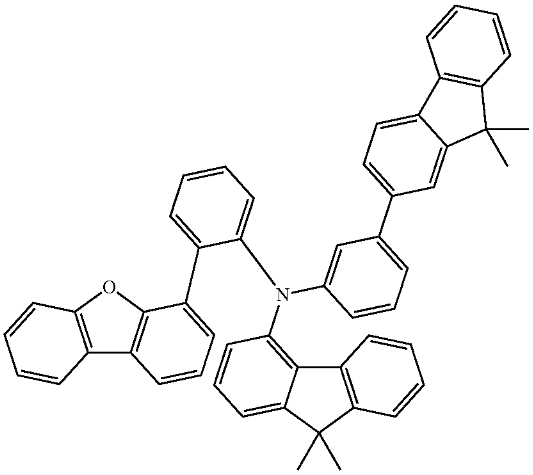
371
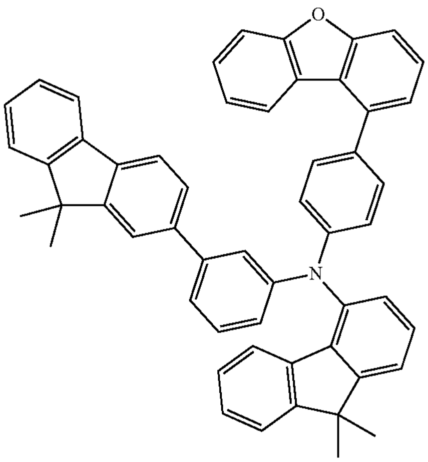
372
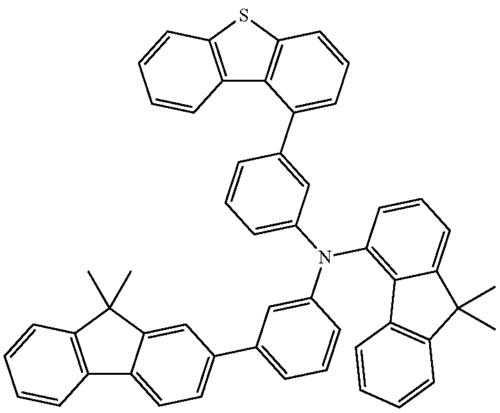
373
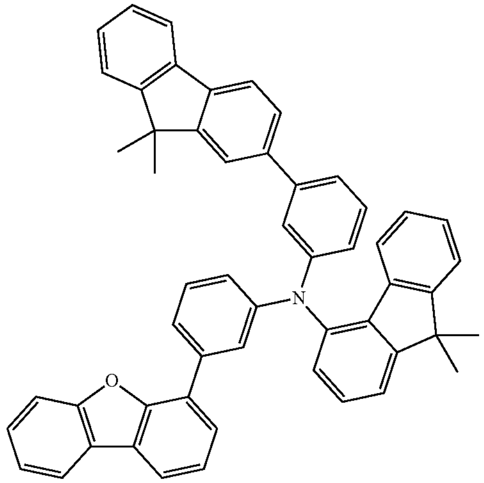
374
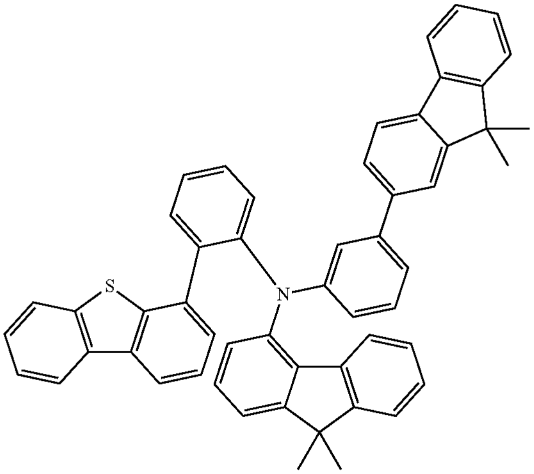
375
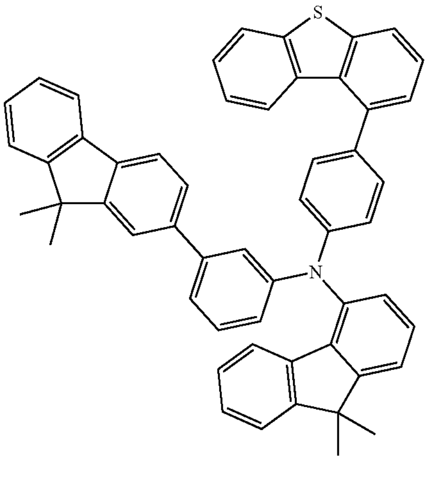

-continued
376
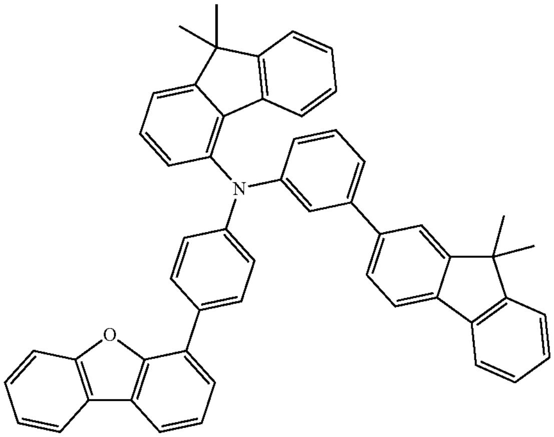
377
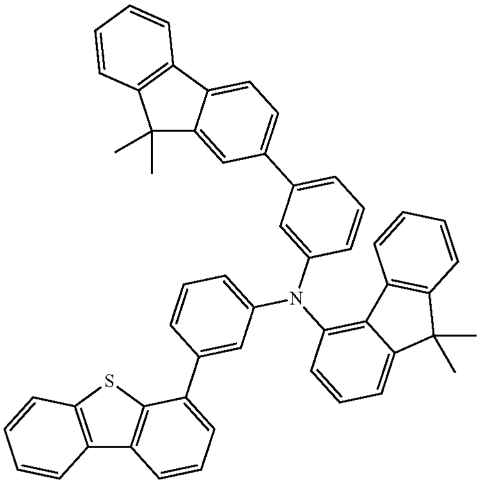
378
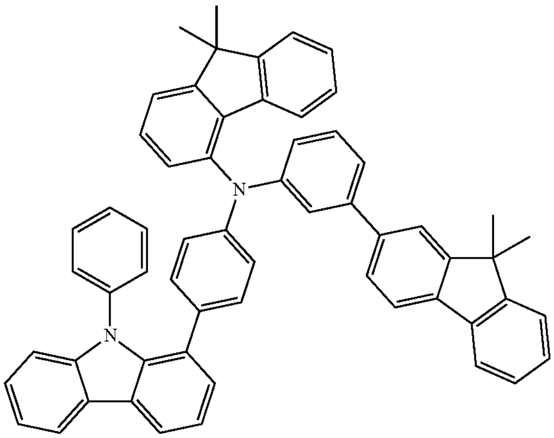
-continued
379
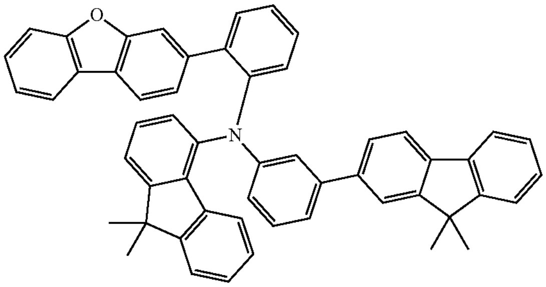
380
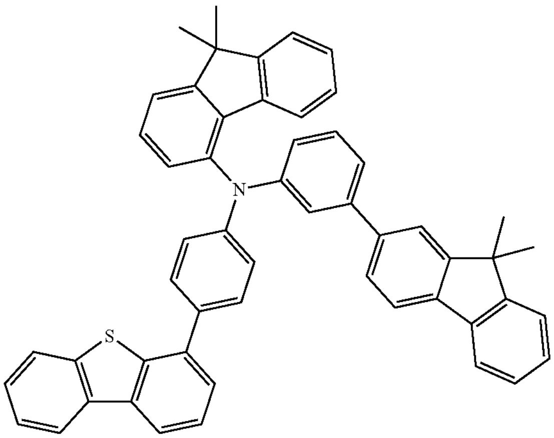
381
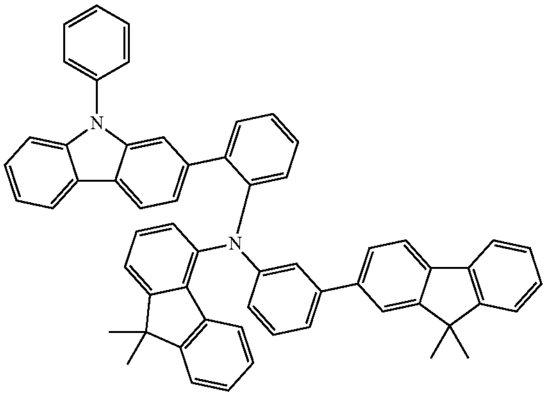
382
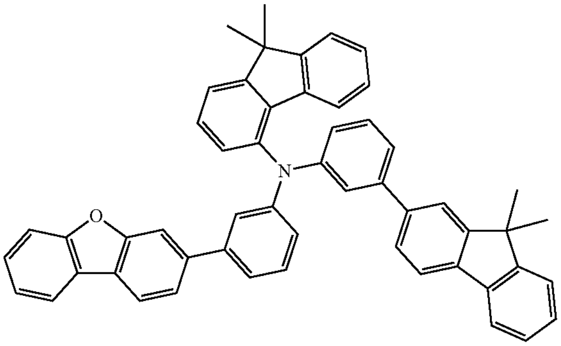

-continued
383
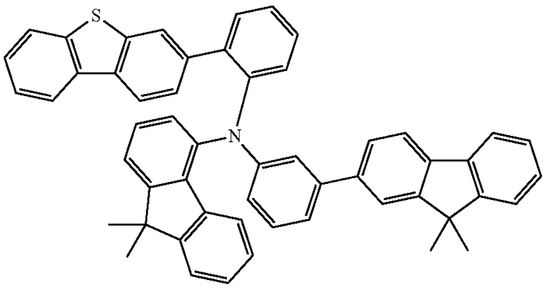
384
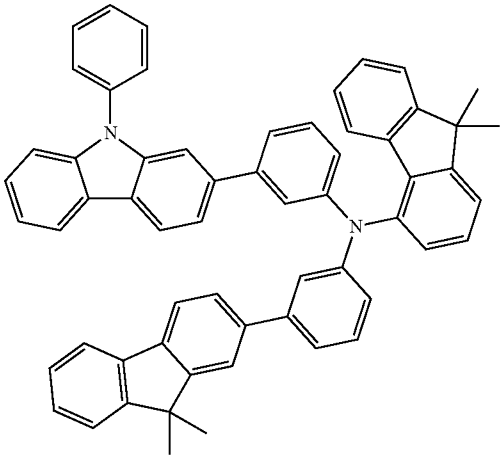
385
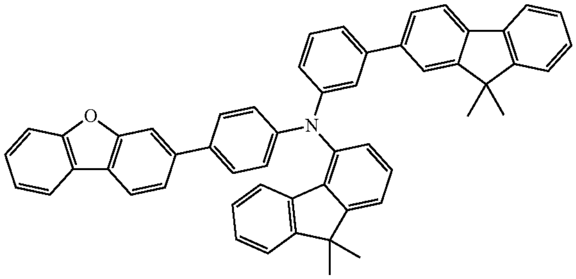
386
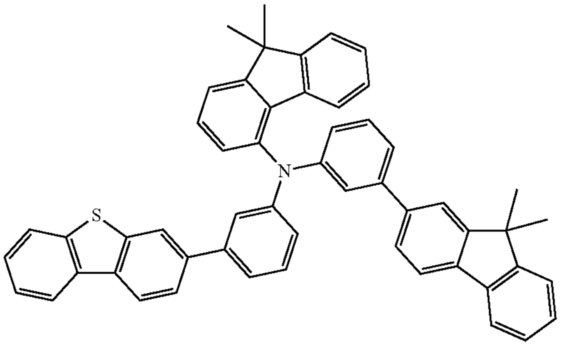
-continued
387
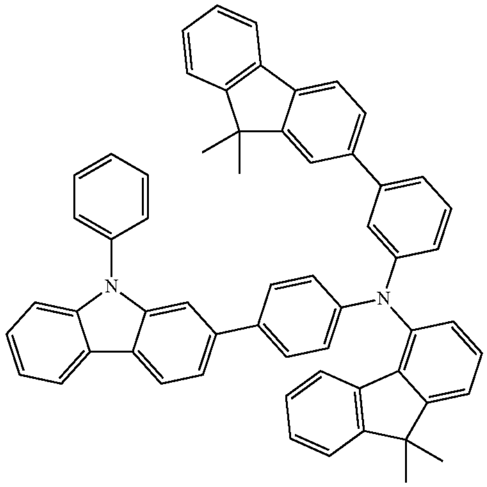
388
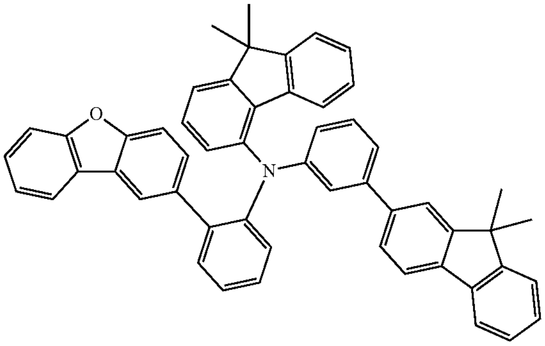
389
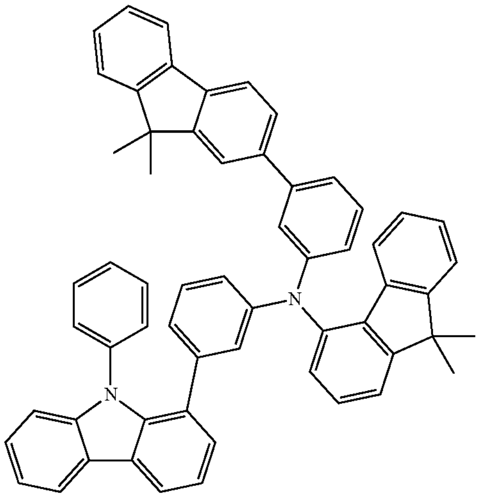

-continued
390
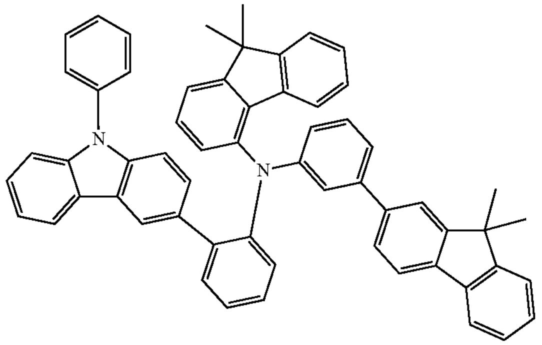
391
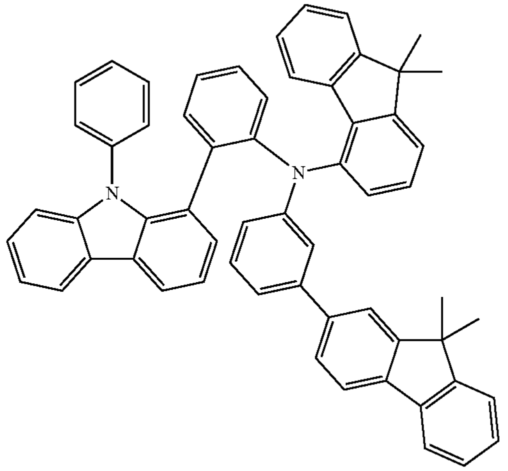
392
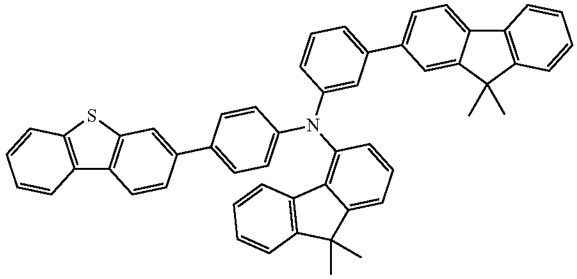
-continued
393
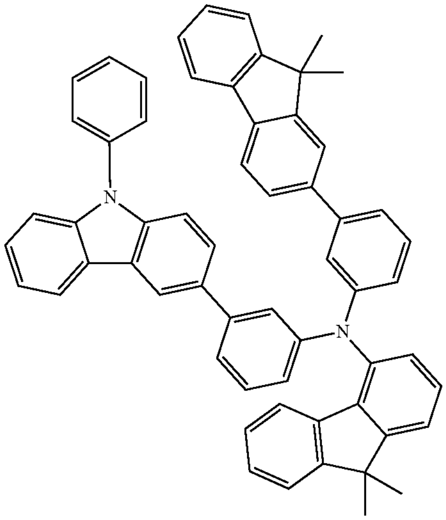
394
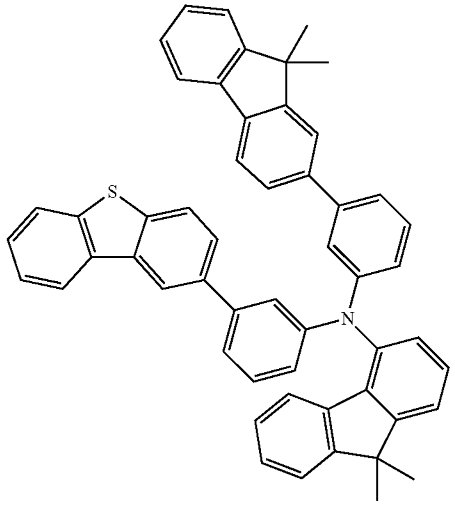
395
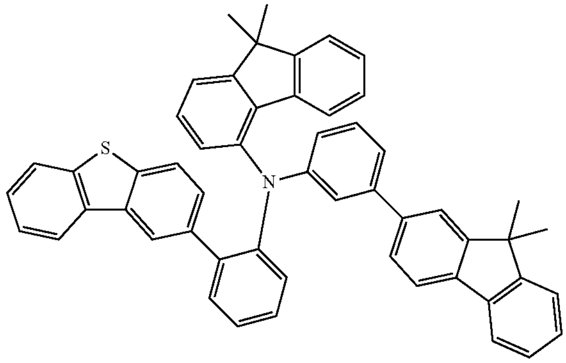

-continued
396
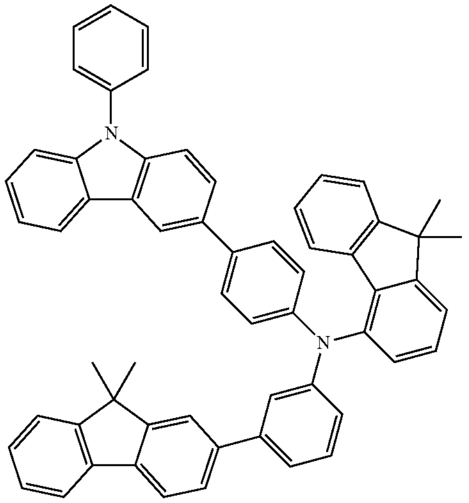
397
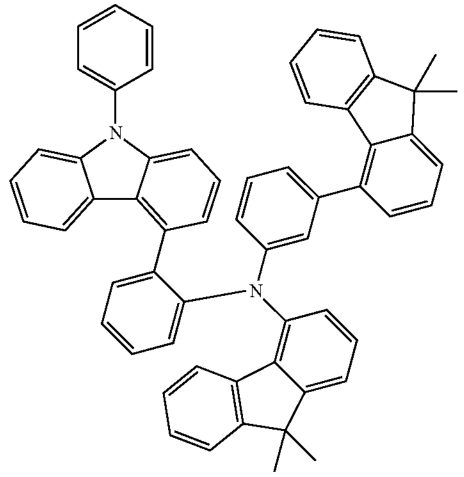
398
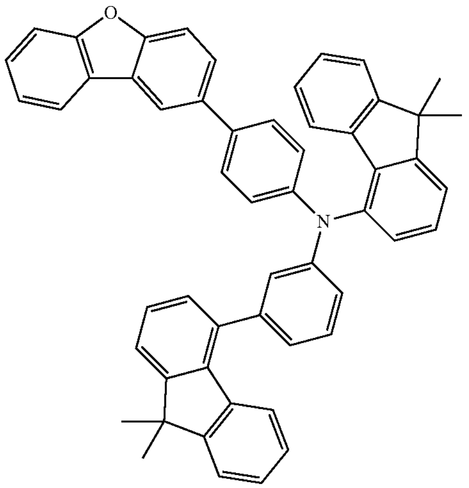
-continued
399
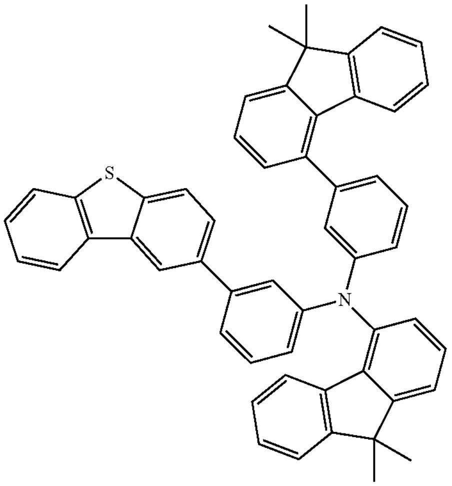
400
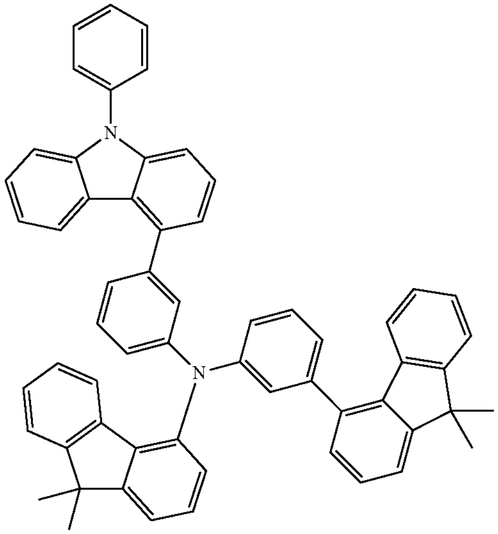
401
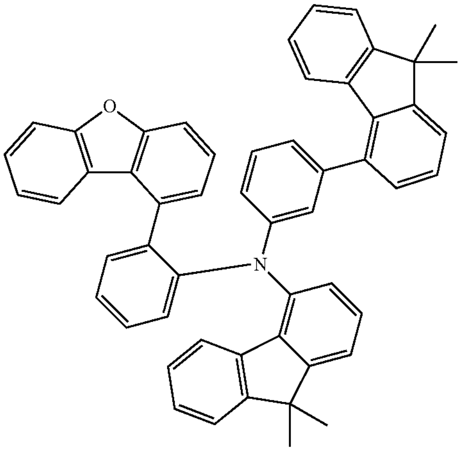

-continued
402
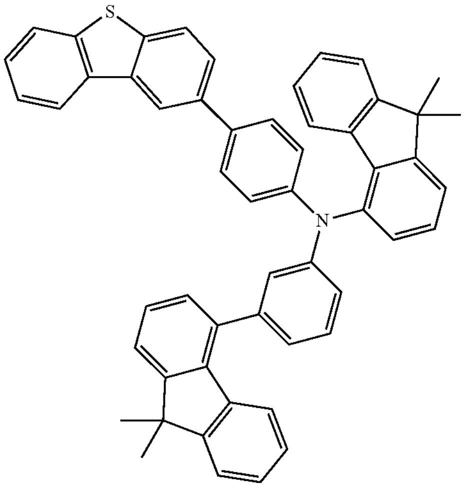
403
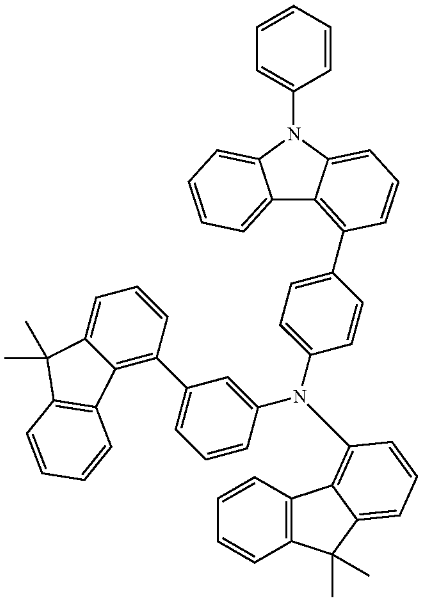
404
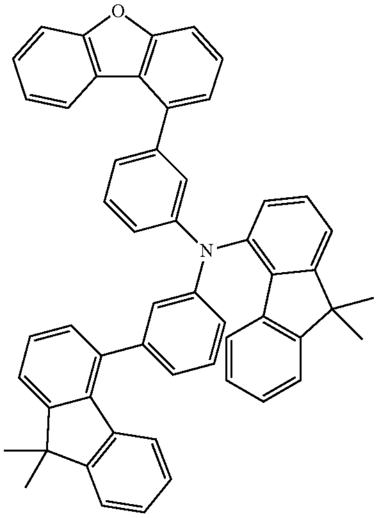
-continued
405
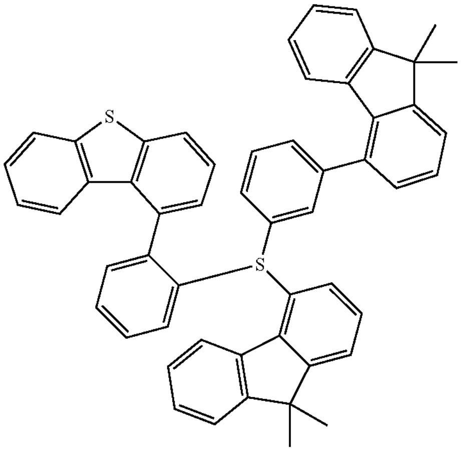
406
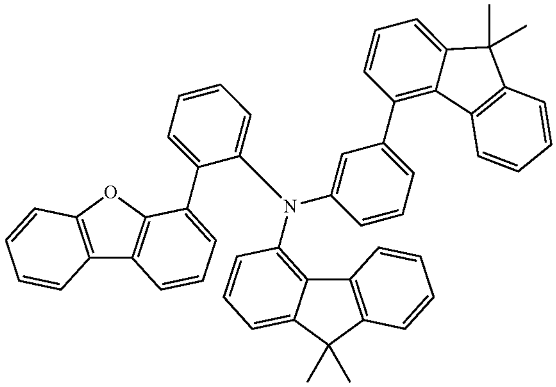
407
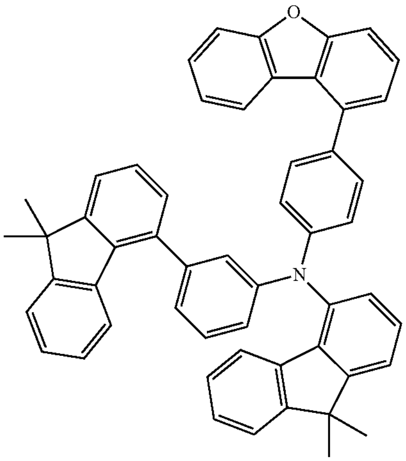

-continued
408
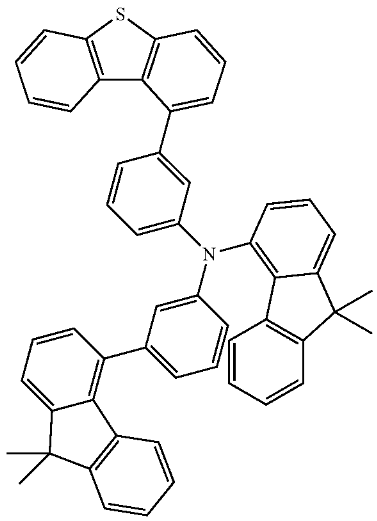
409
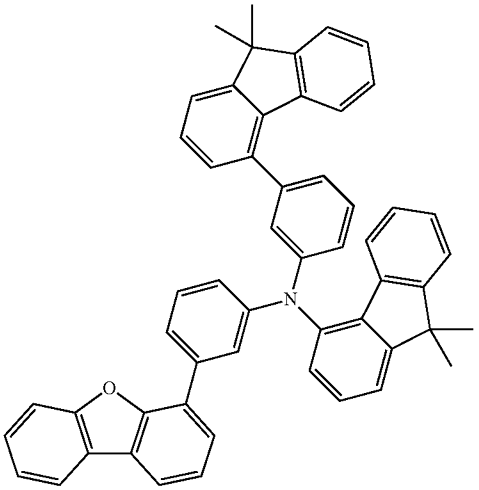
410
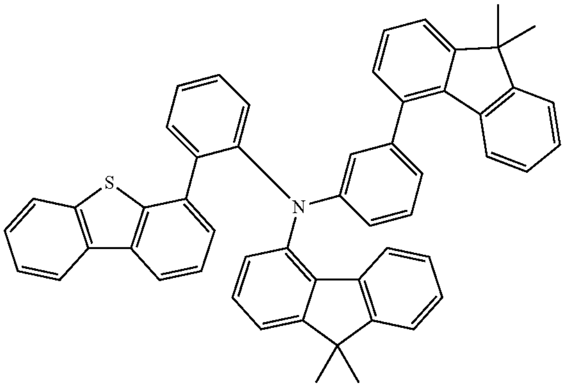
-continued
411
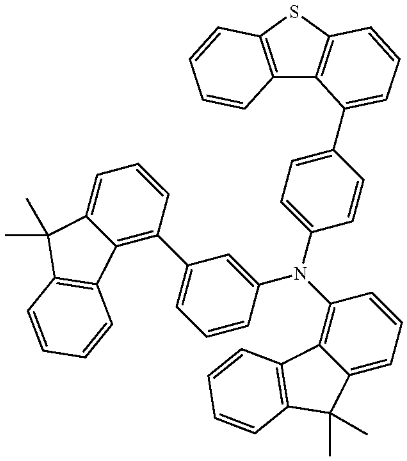
412
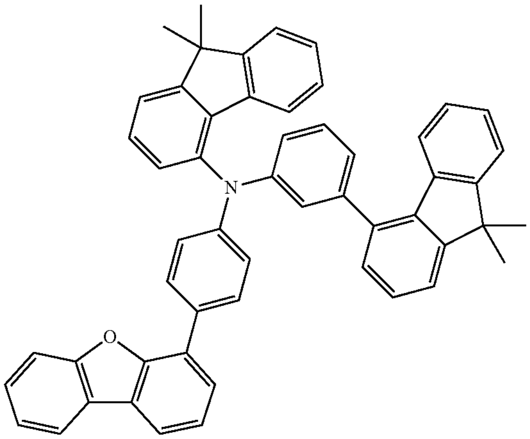
413
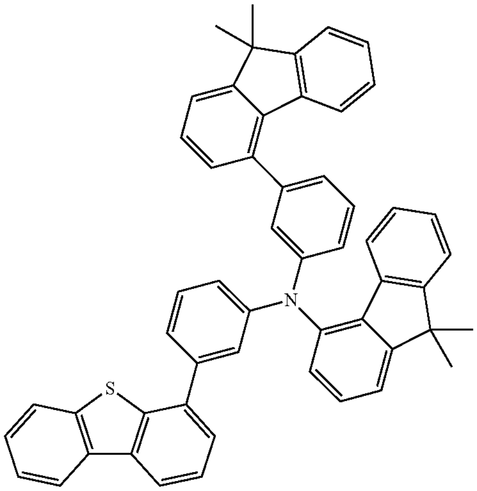

414
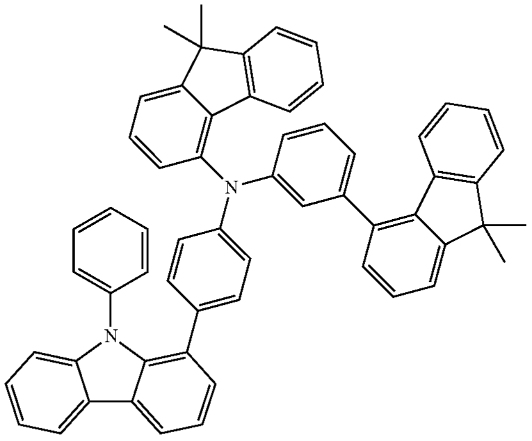
415
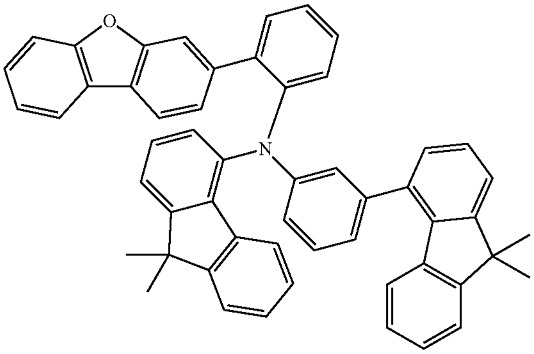
416
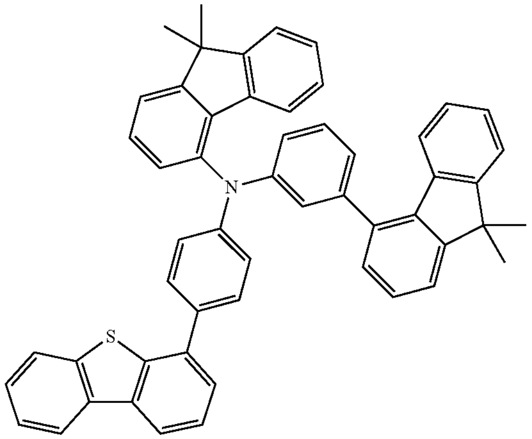
417
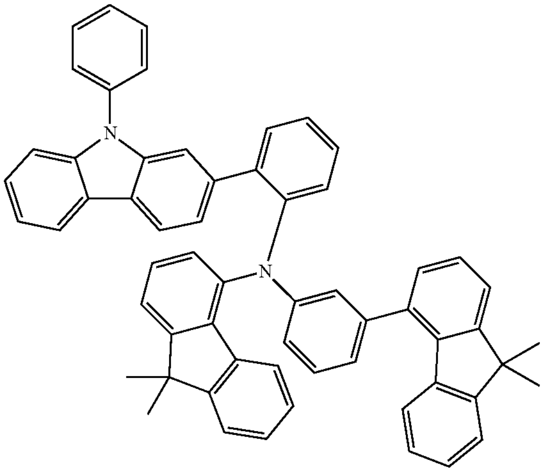
418
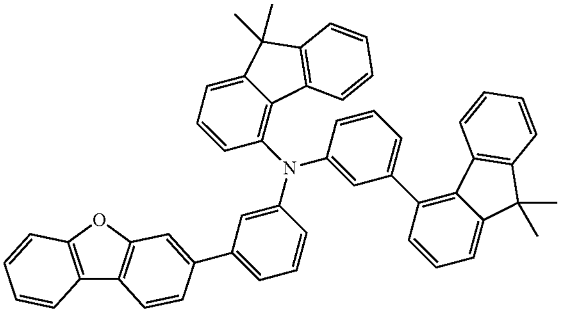
419
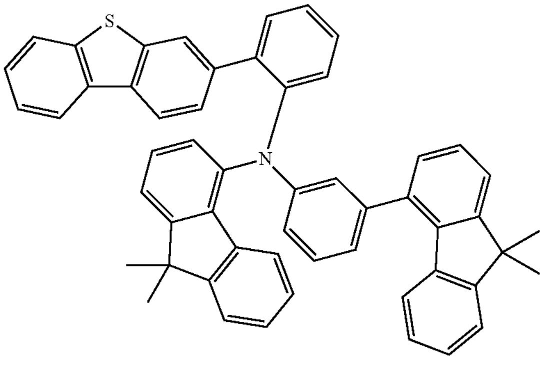

-continued
420
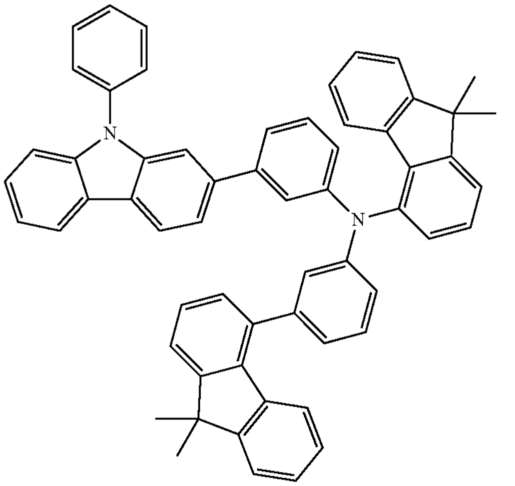
421
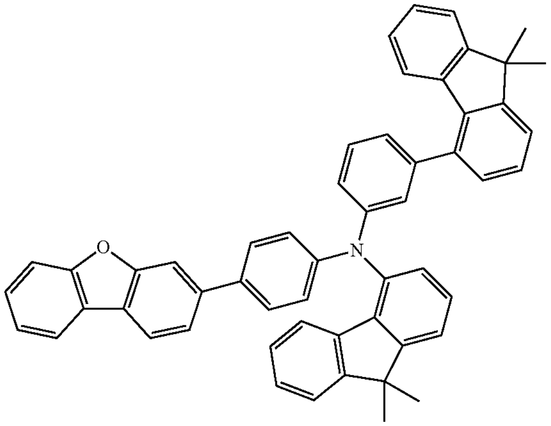
422
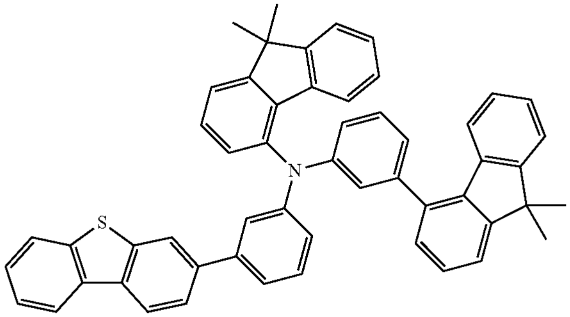
-continued
423
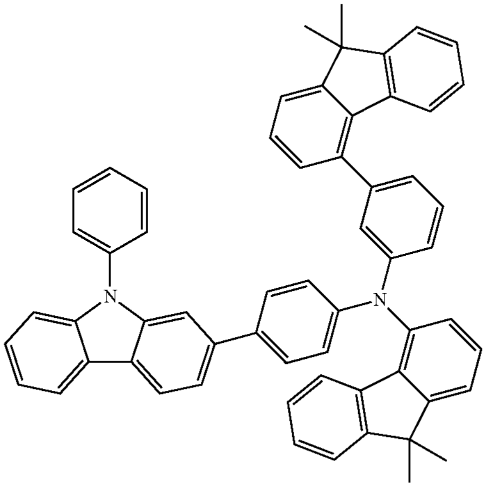
424
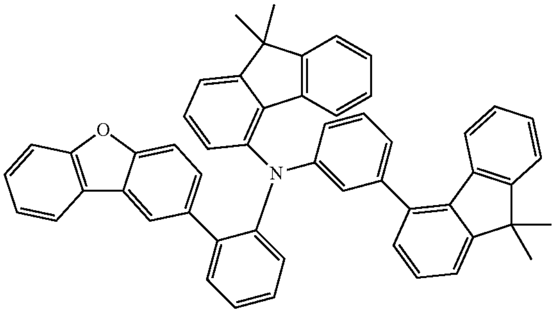
425
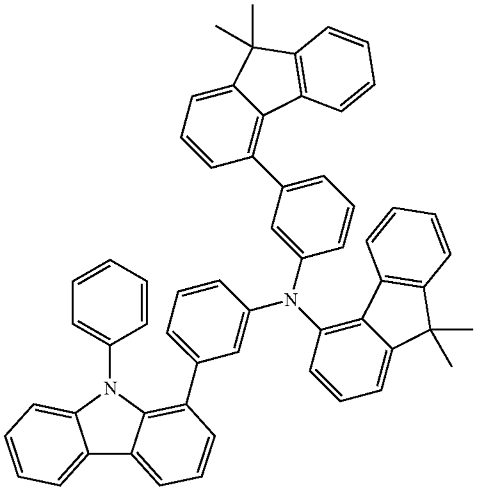

-continued
426
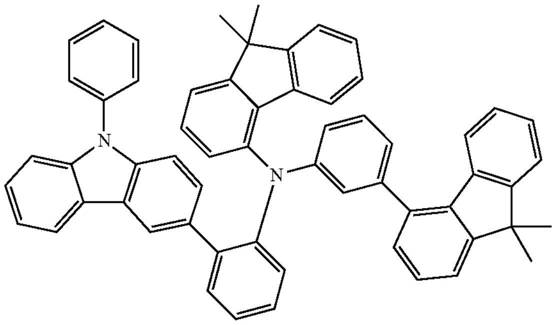
427
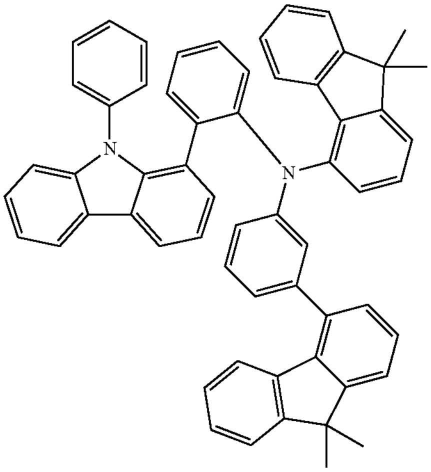
428
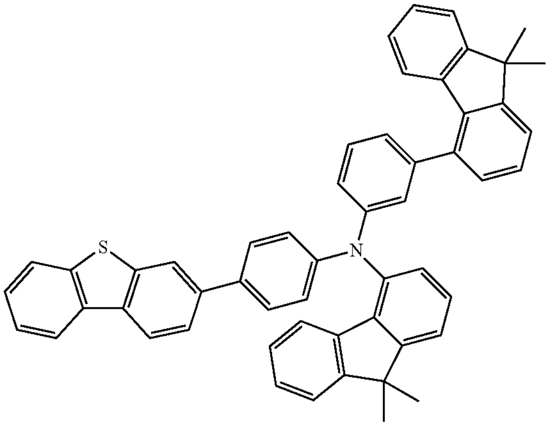
-continued
429
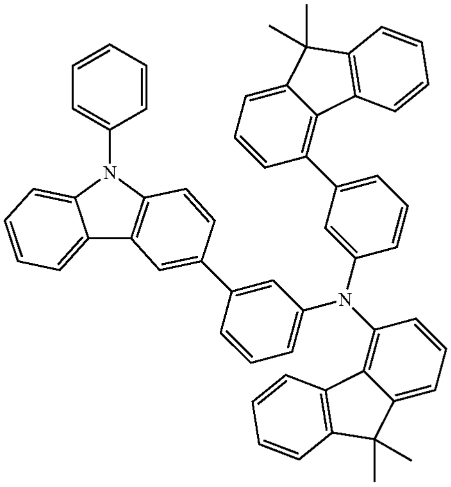
430
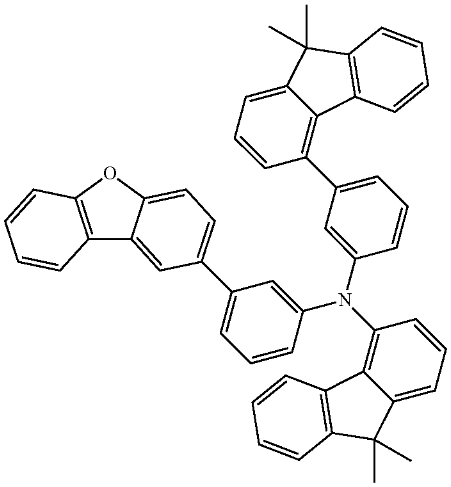
431
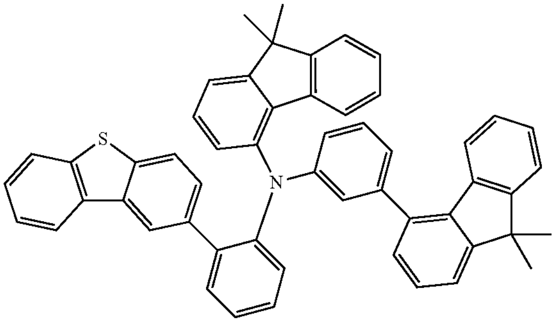

-continued
432
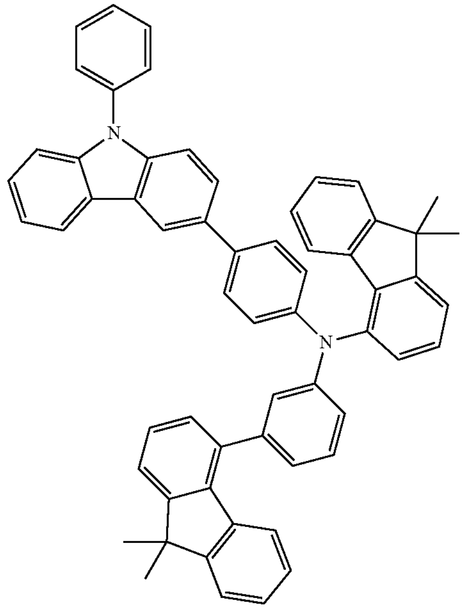
433
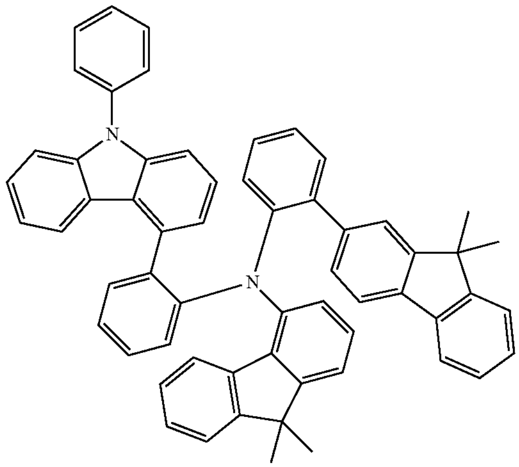
434
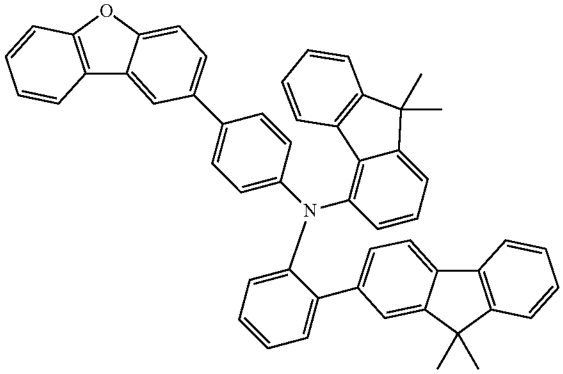
-continued
435
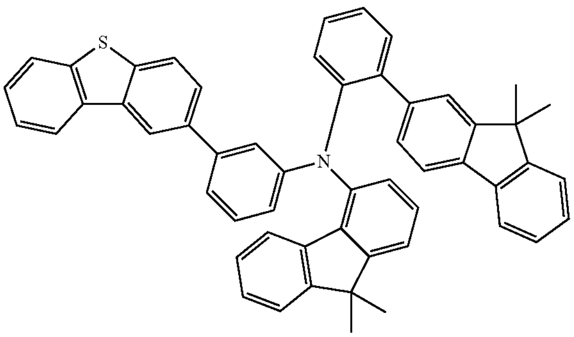
436
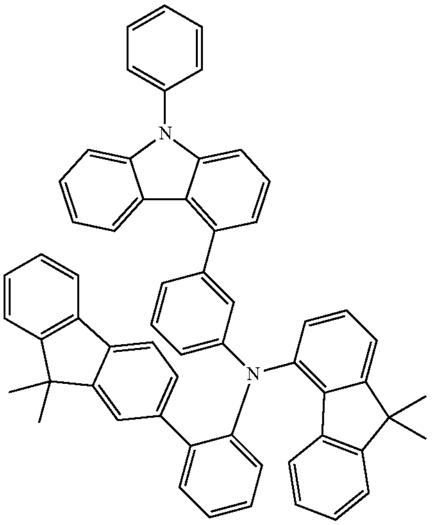
437
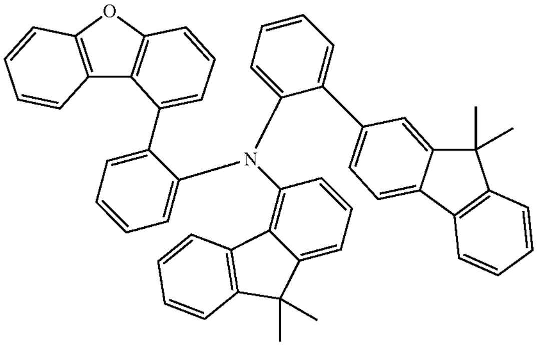
438
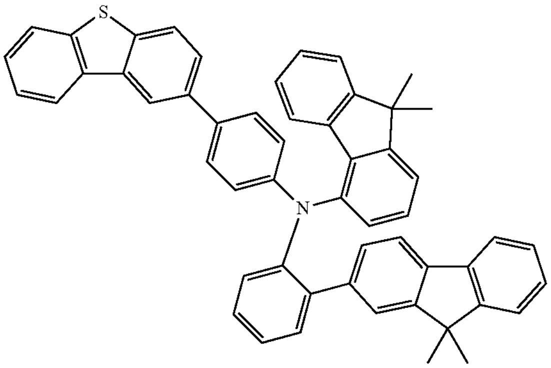

-continued
439
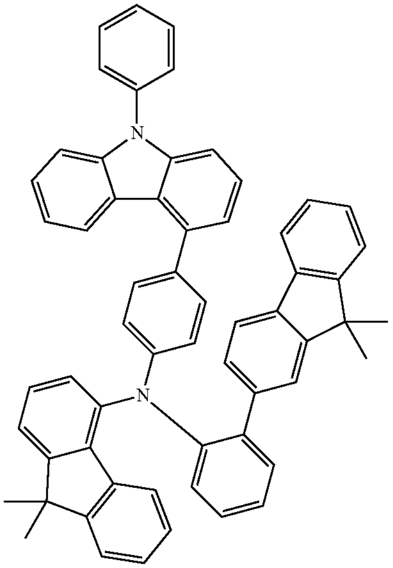
440
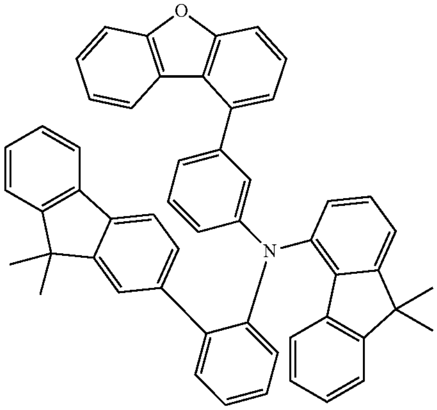
441
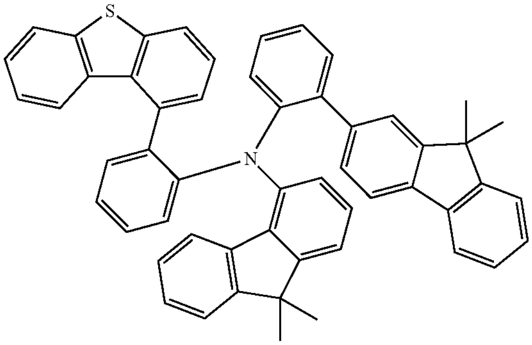
-continued
442
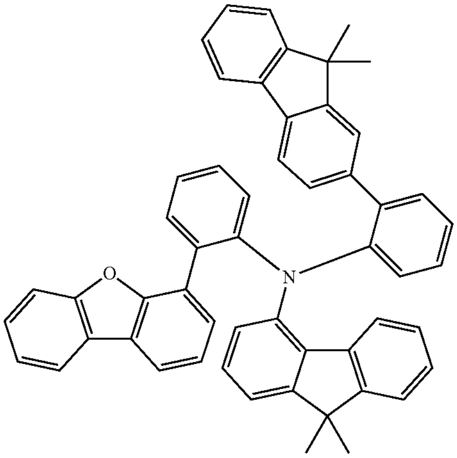
443
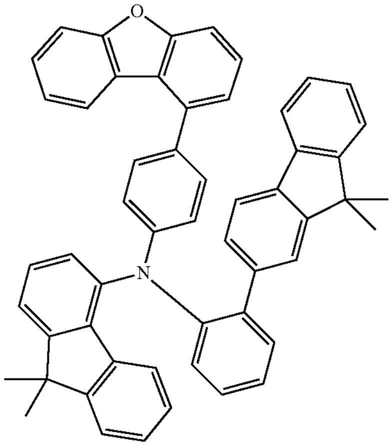
444
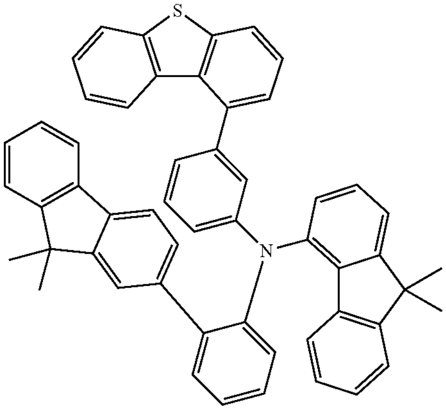

-continued
445
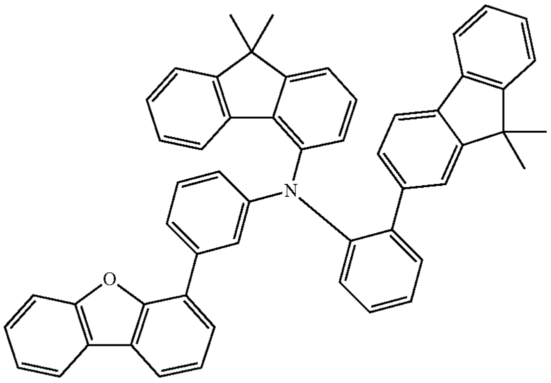
446
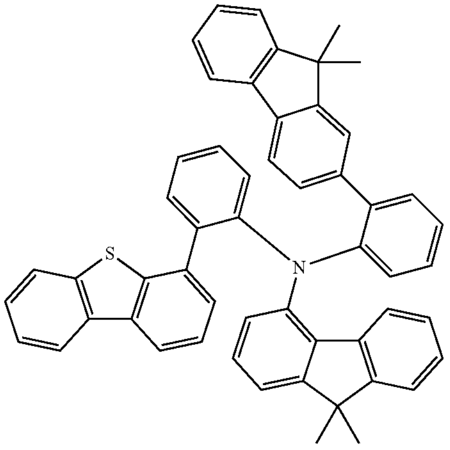
447
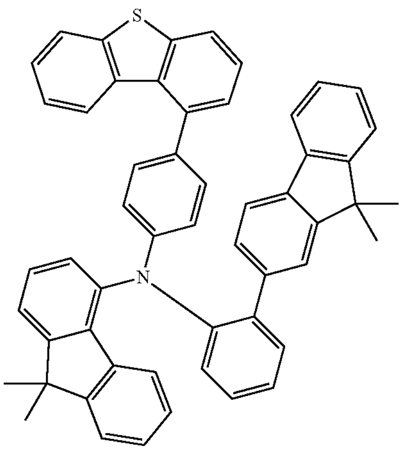
-continued
448
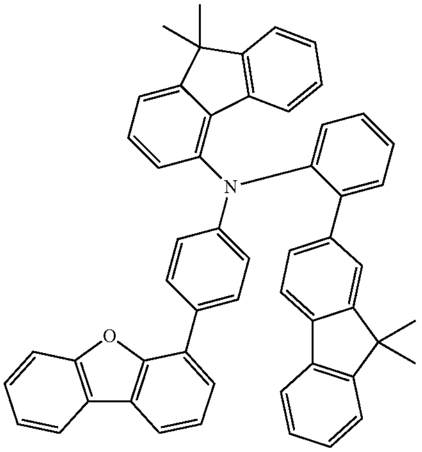
449
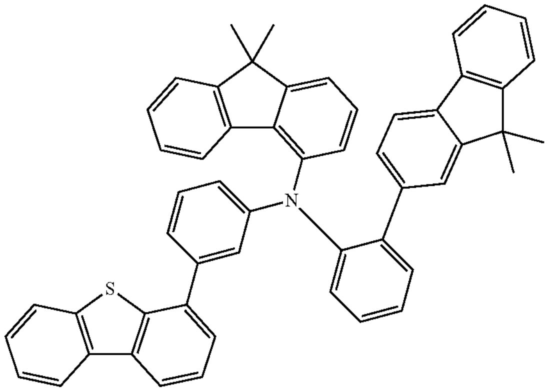
450
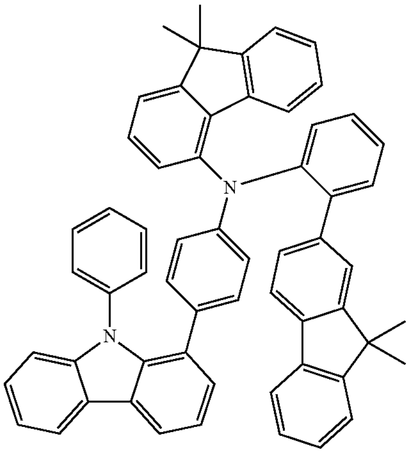

451
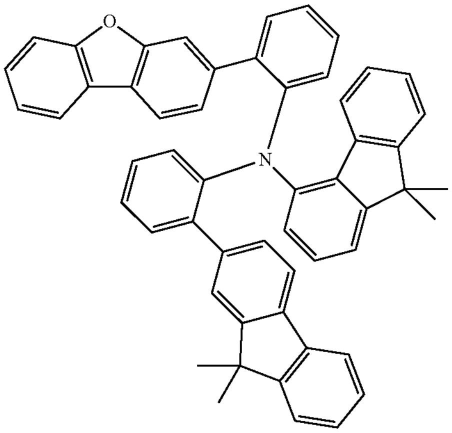
452
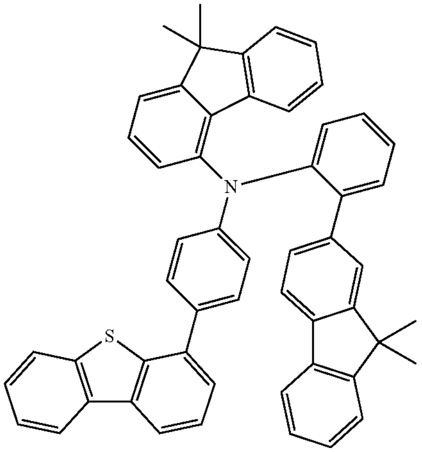
453
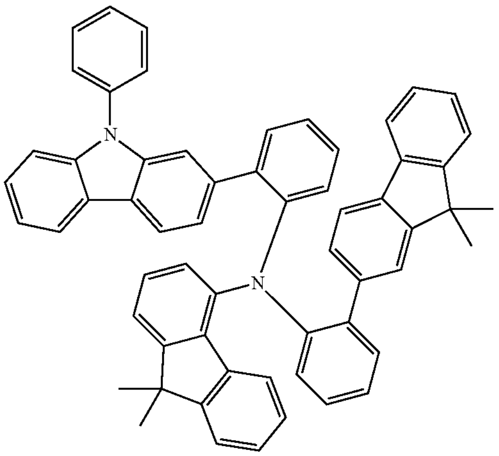
454
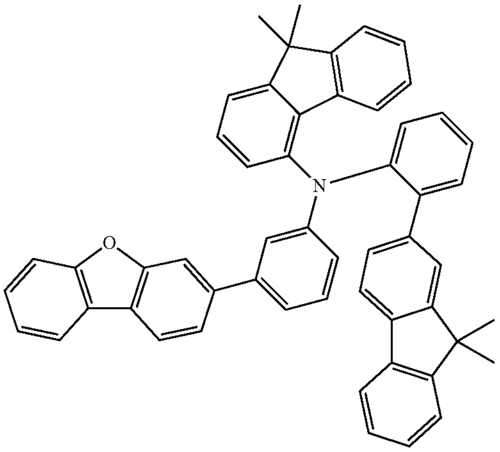
455
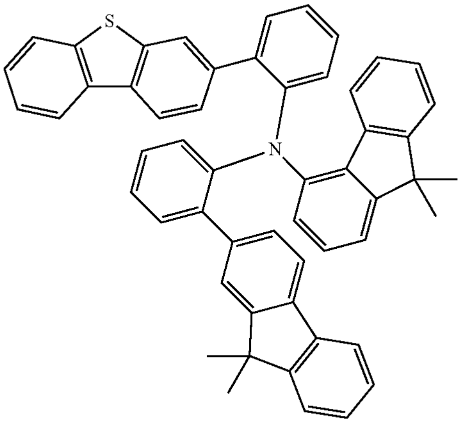
456
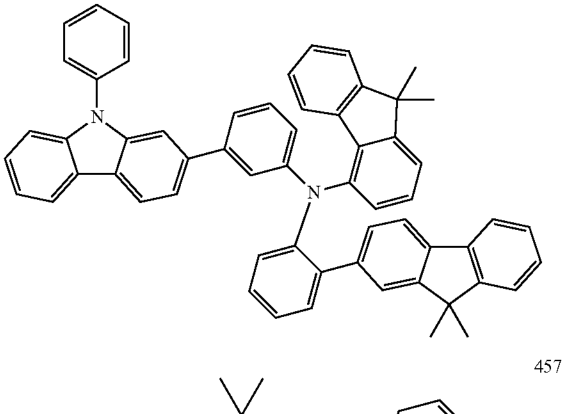
457
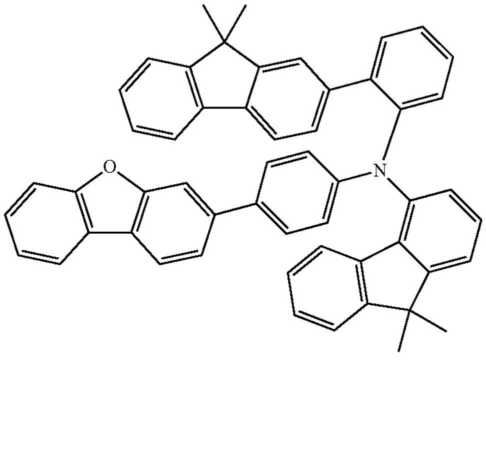

-continued
458
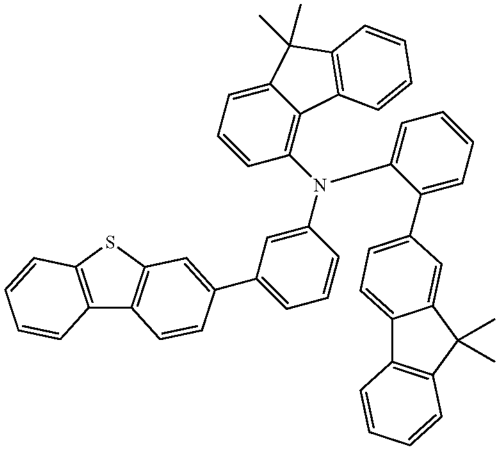
459
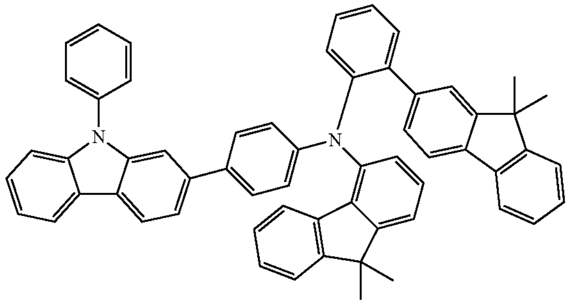
460
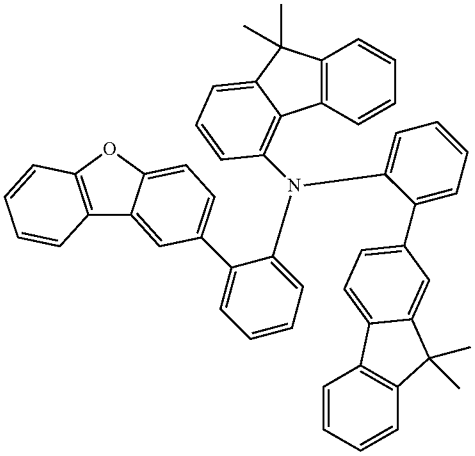
461
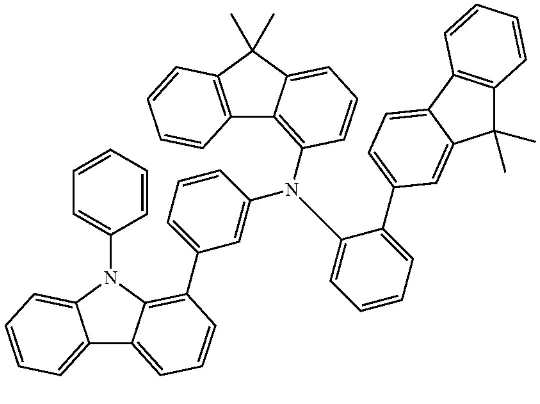
-continued
462
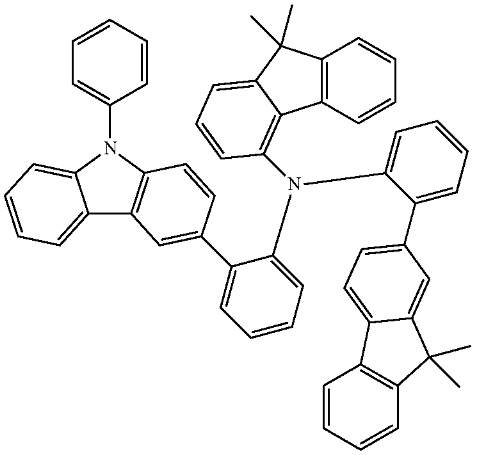
463
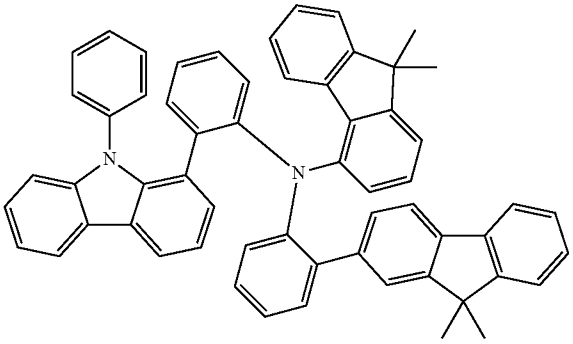
464
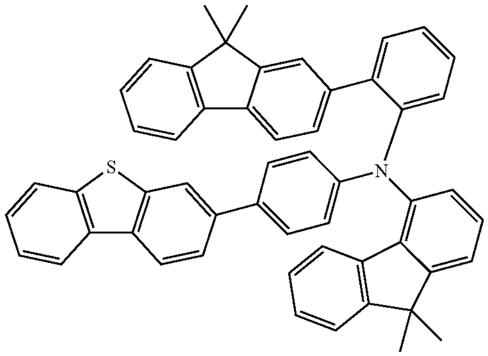
465
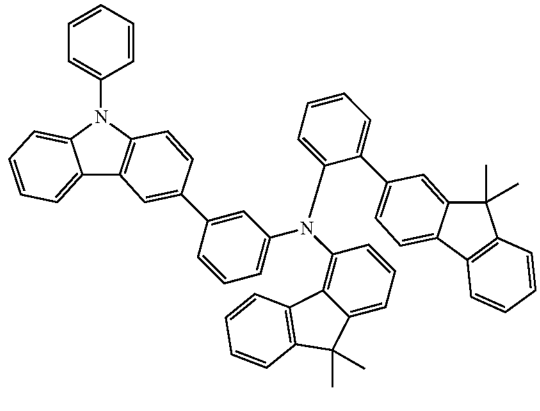

466
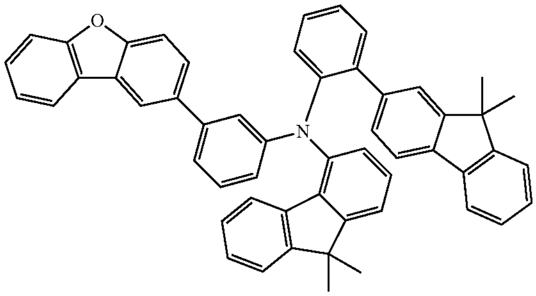
467
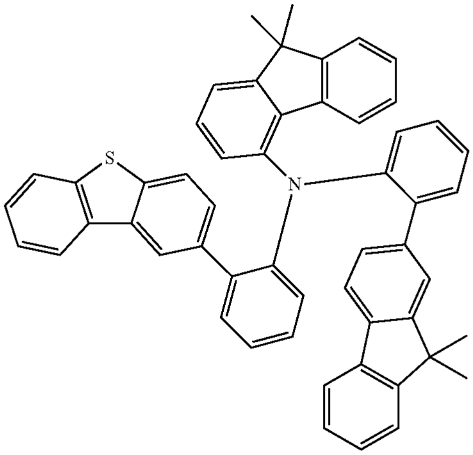
468
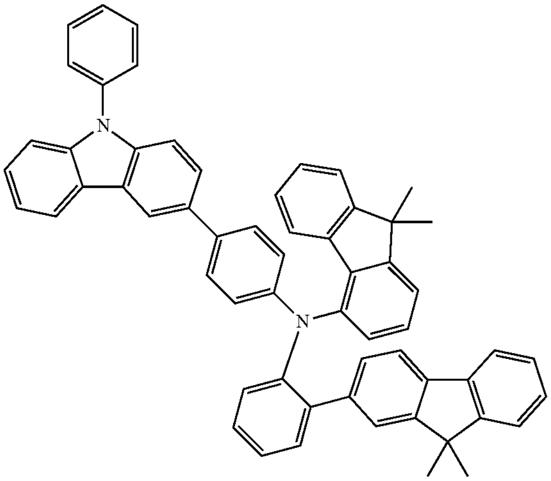
469
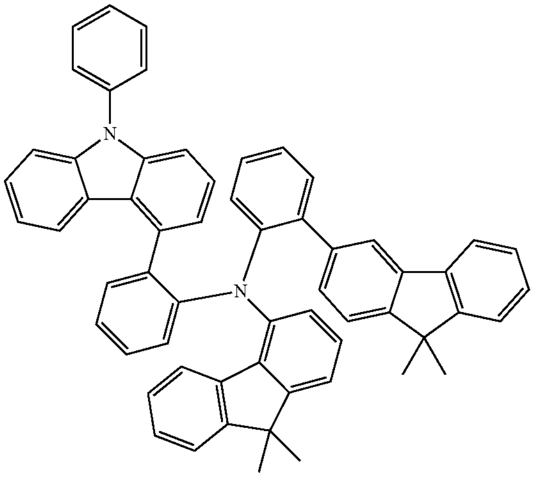
470
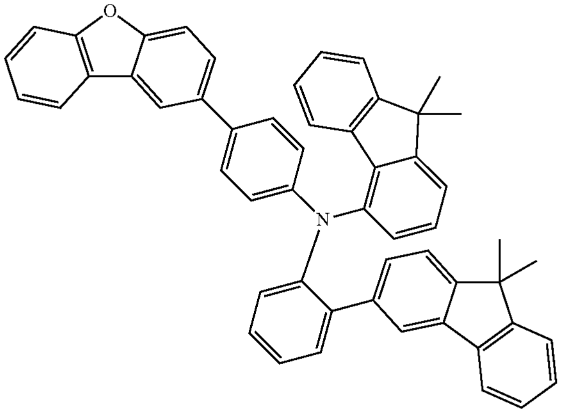
471
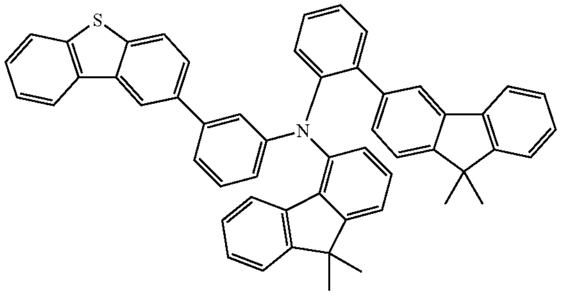

-continued
472
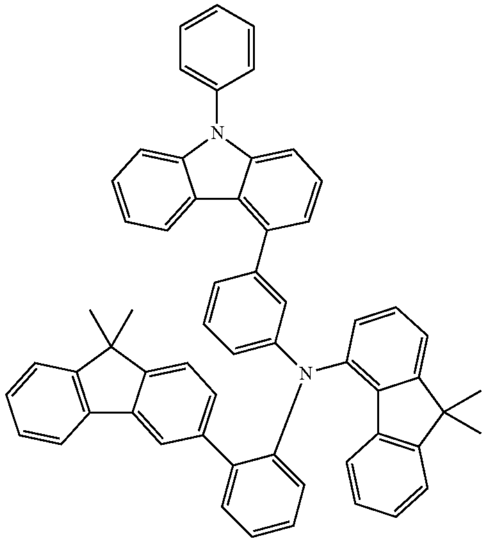
473
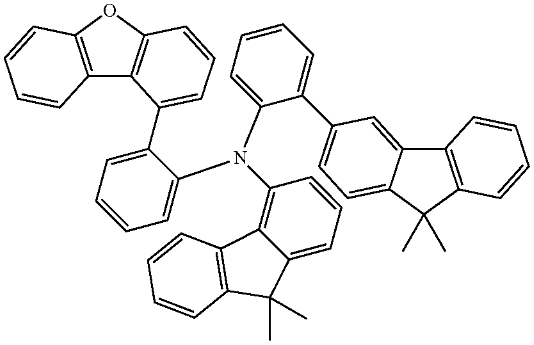
474
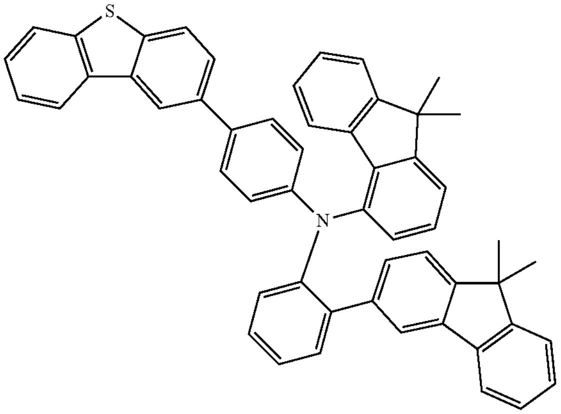
-continued
475
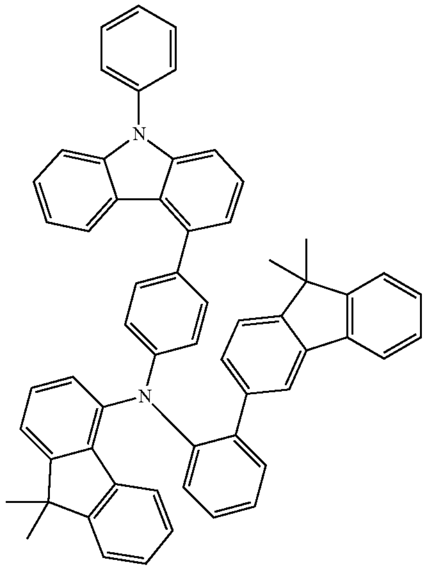
476
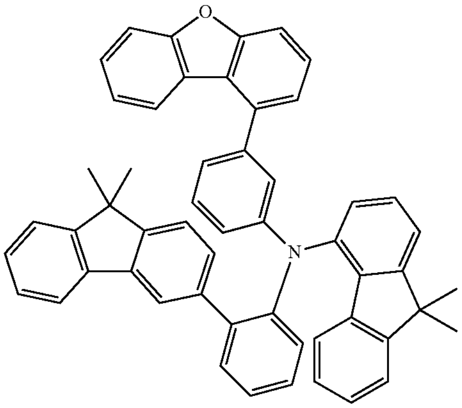
477
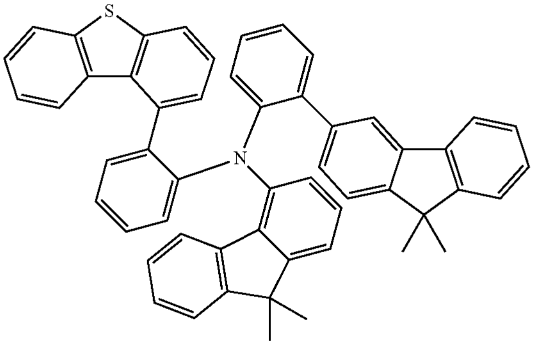

-continued
478
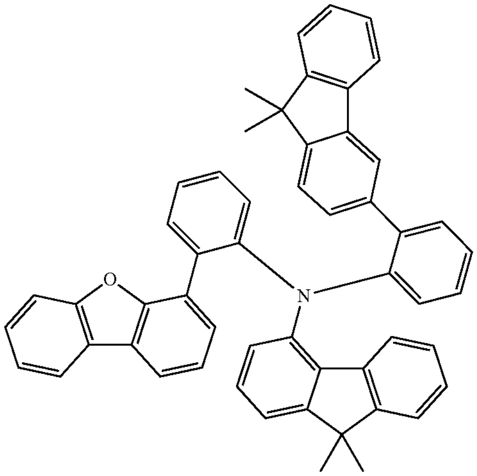
479
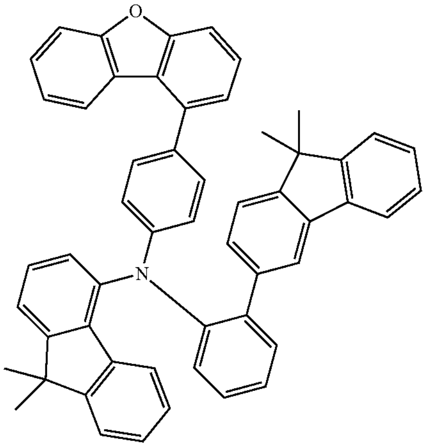
480
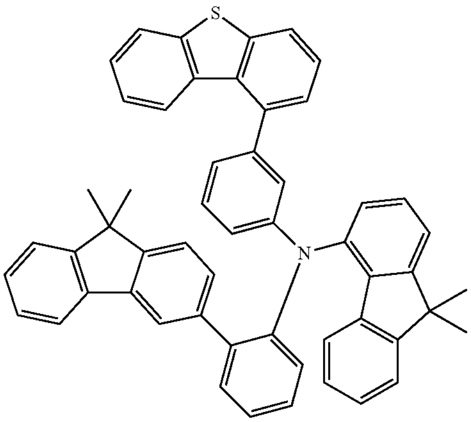
-continued
481
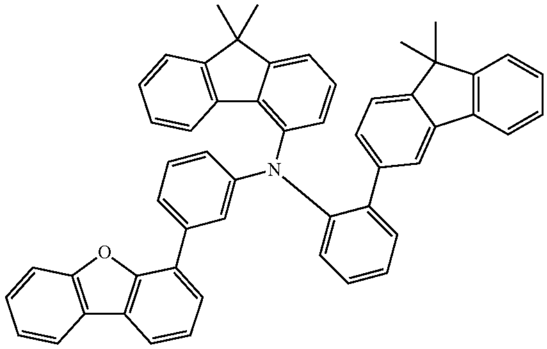
482
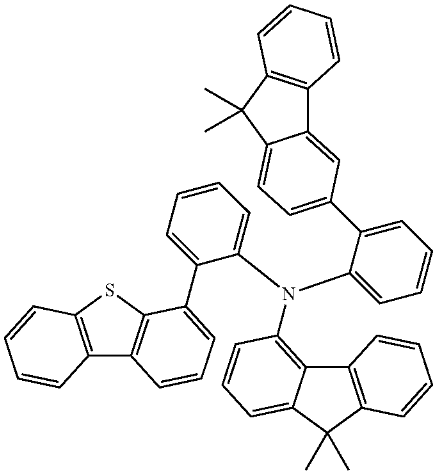
483
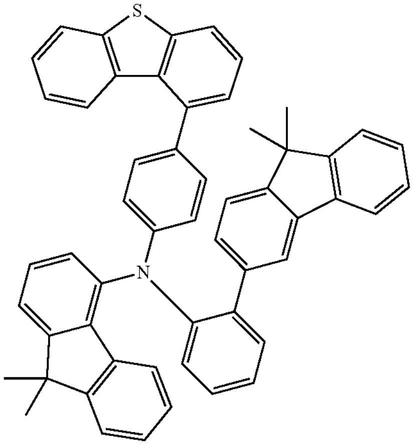

-continued
484
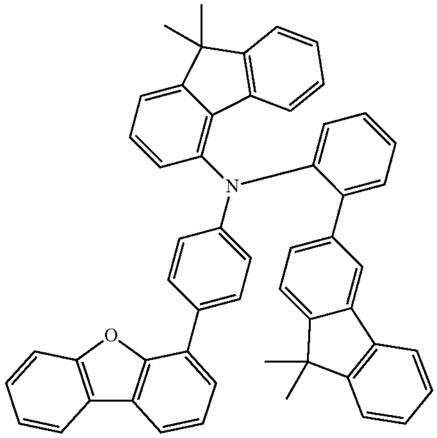
485
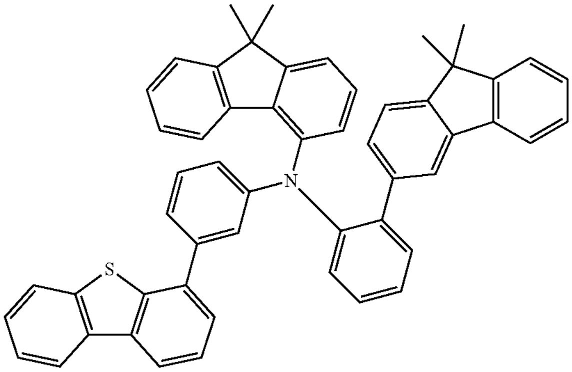
486
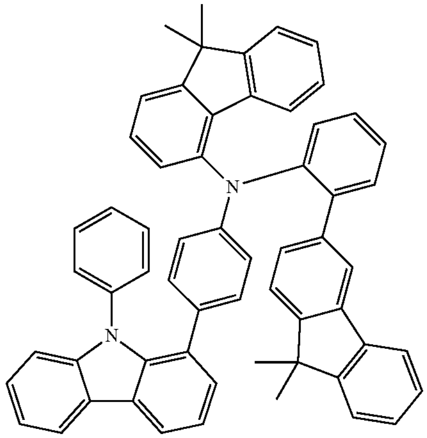
-continued
487
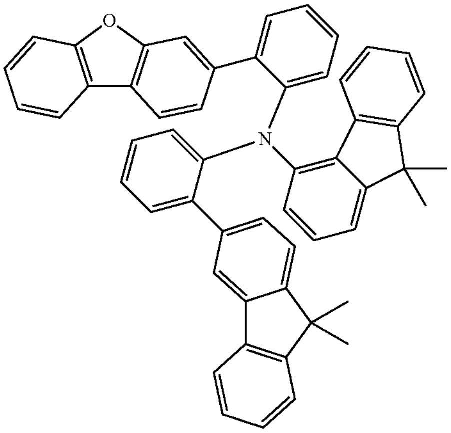
488
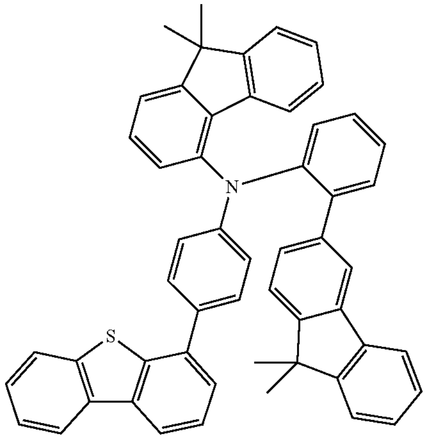
489
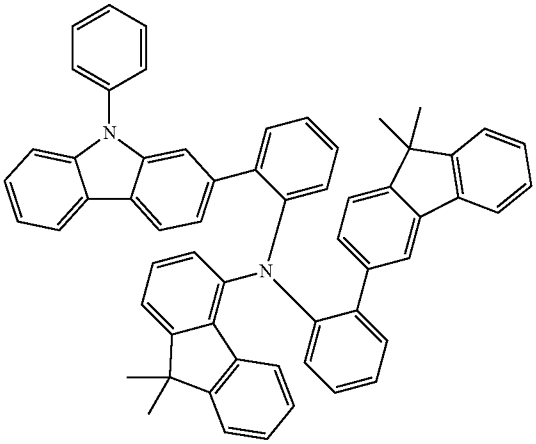

-continued
490
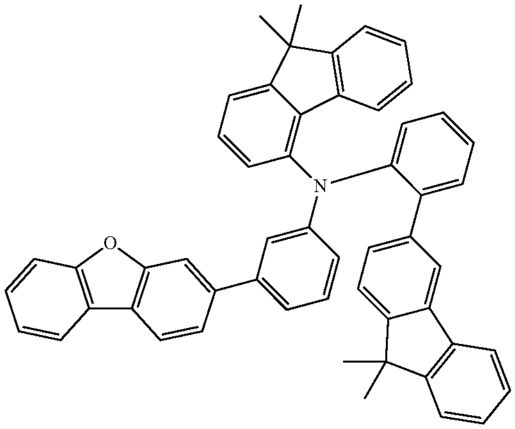
491
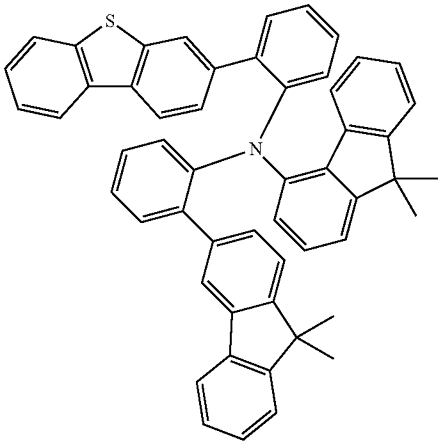
492
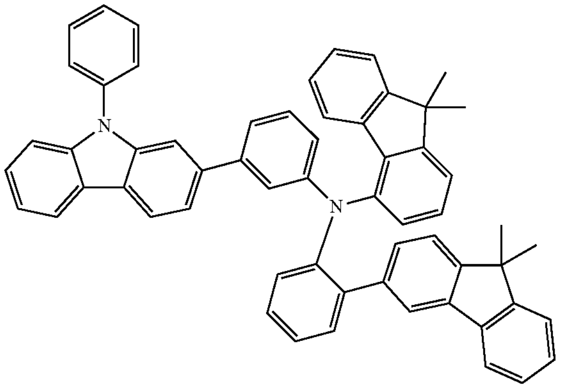
-continued
493
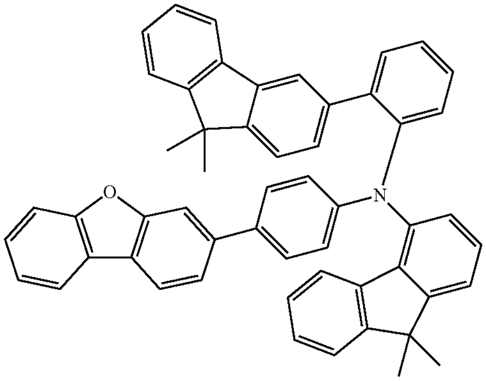
494
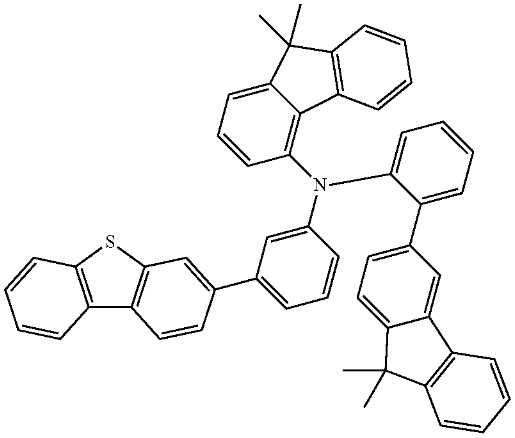
495
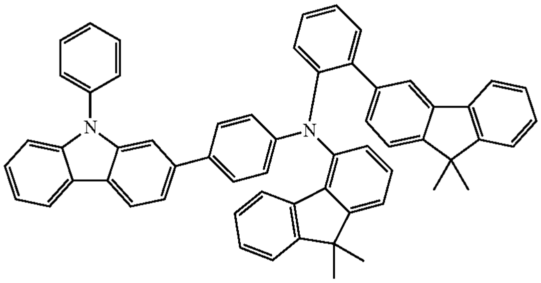
496
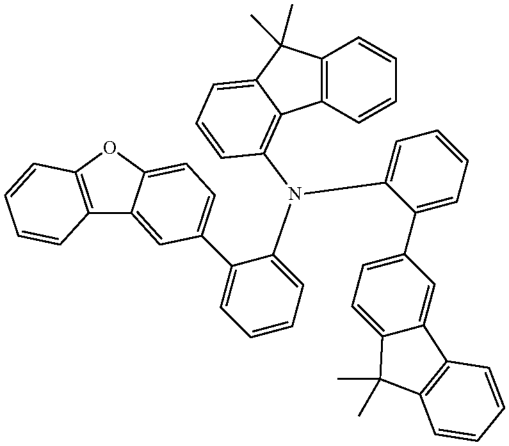

-continued
497
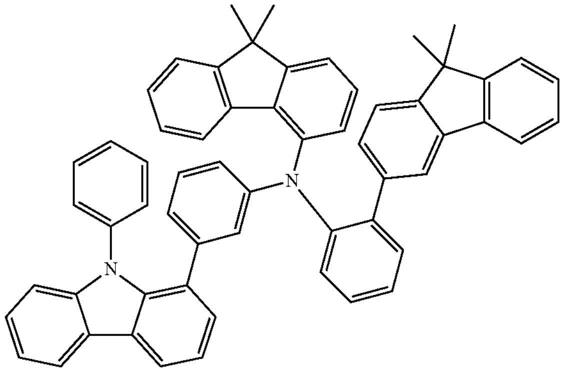
498
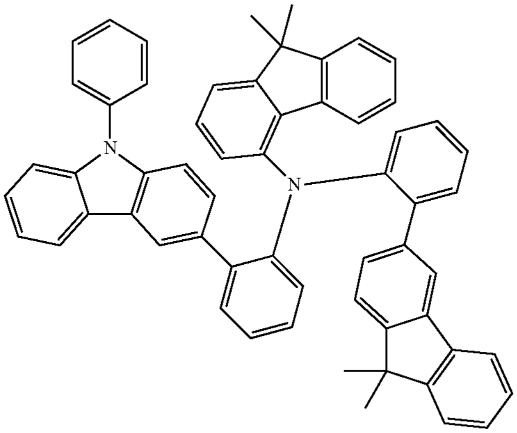
499
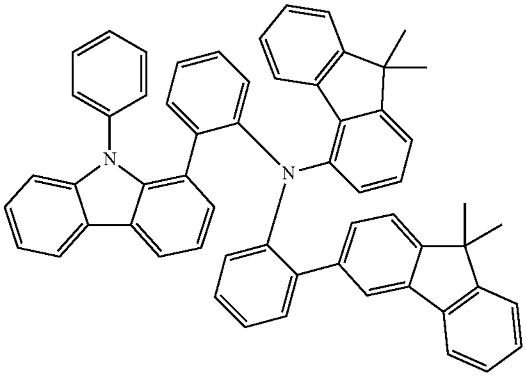
500
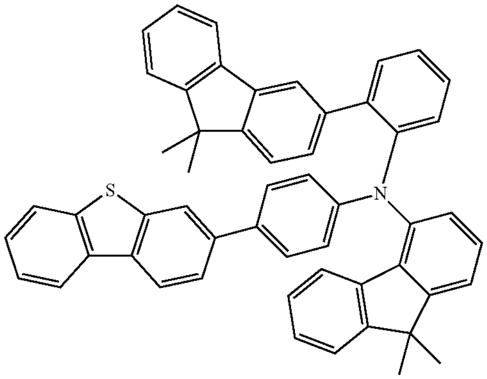
-continued
501
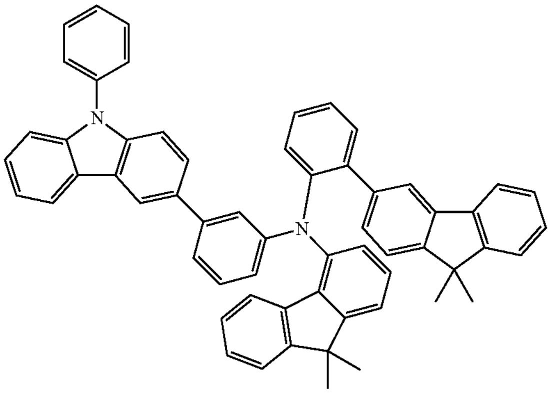
502
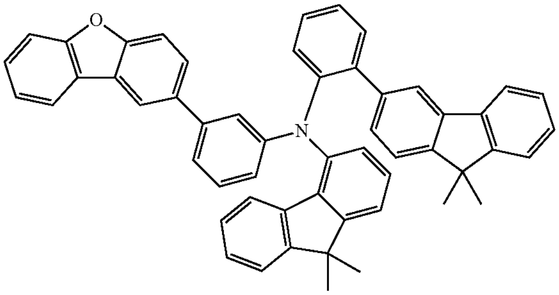
503
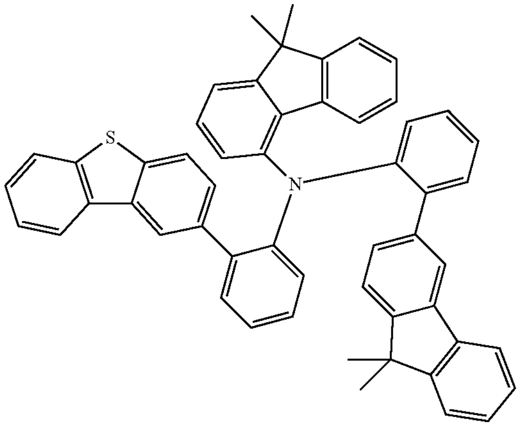

-continued
504
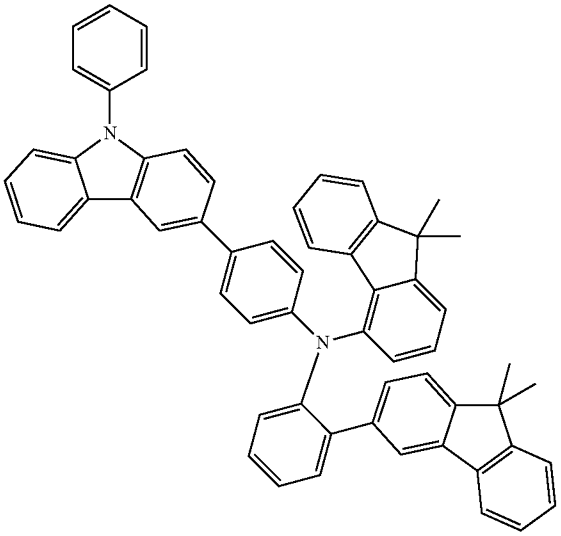
505
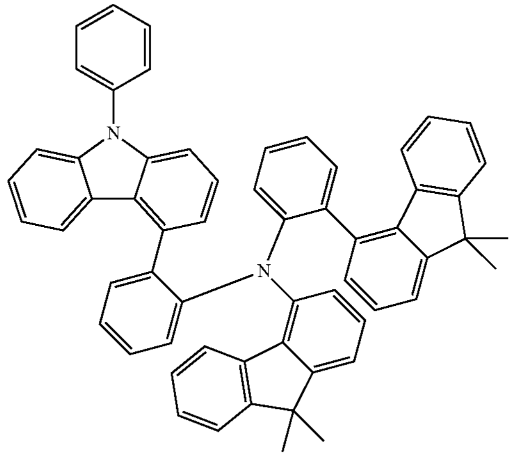
506
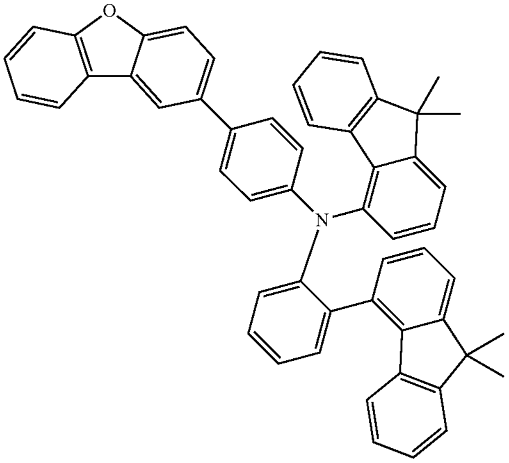
-continued
507
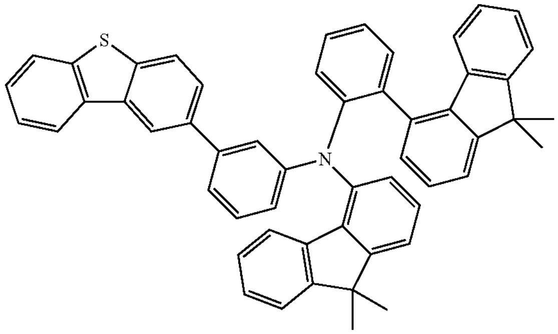
508
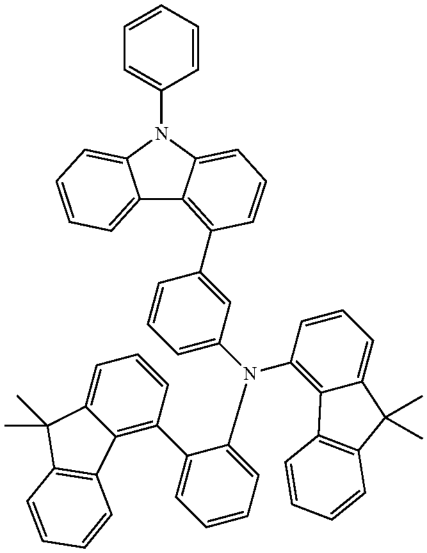
509
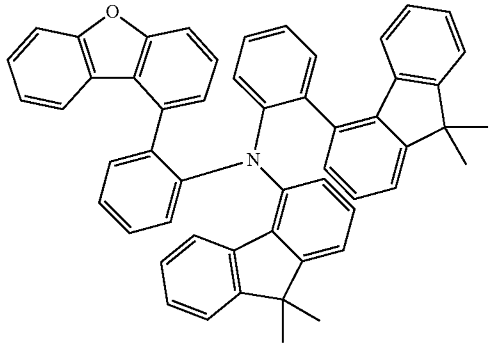

-continued
510
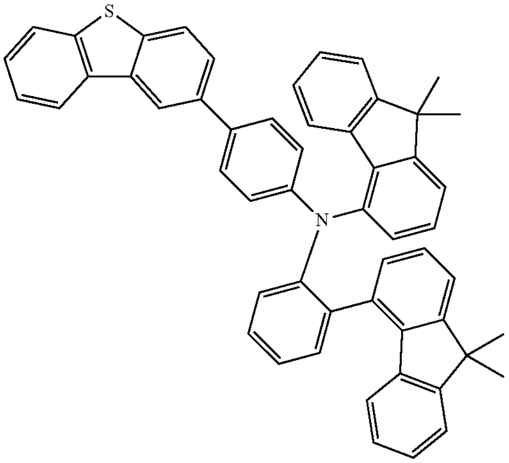
511
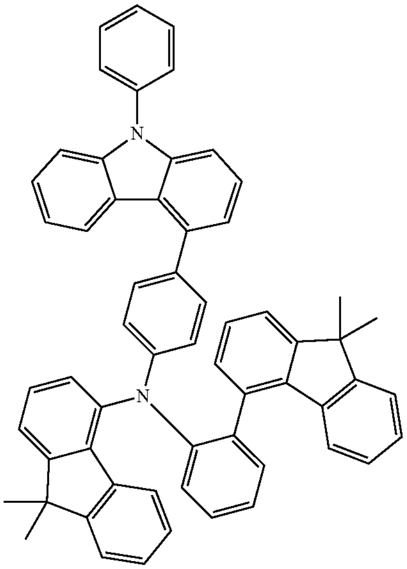
512
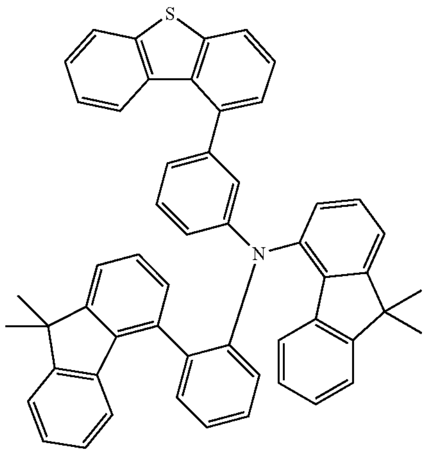
-continued
513
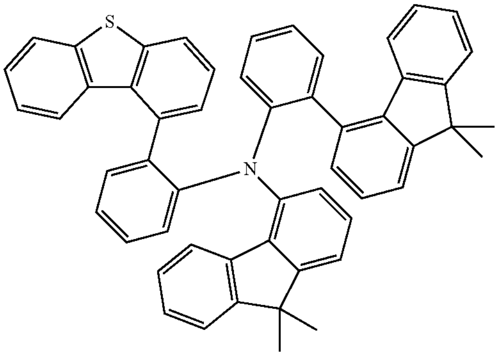
514
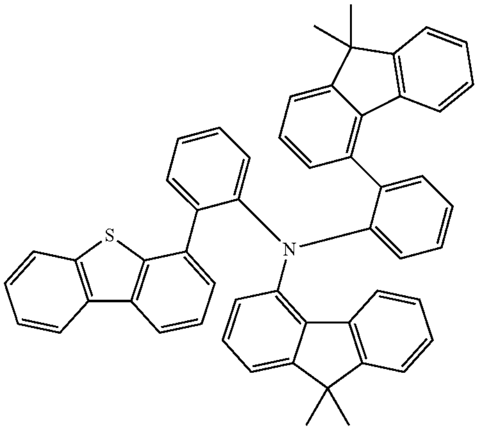
515
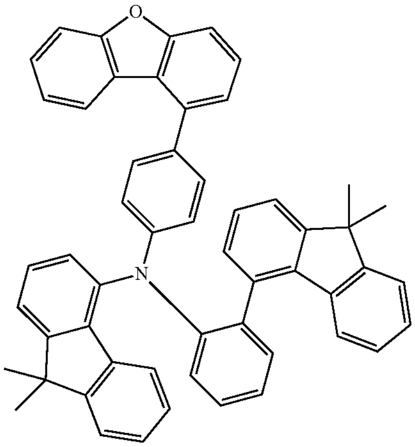

-continued
516
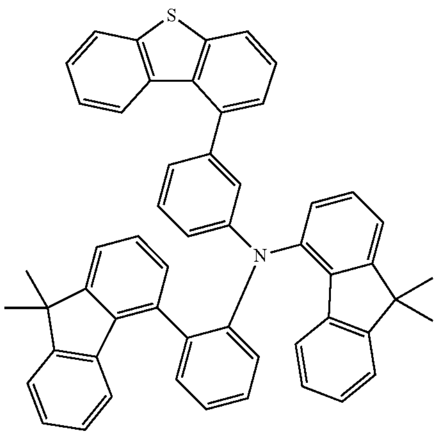
517
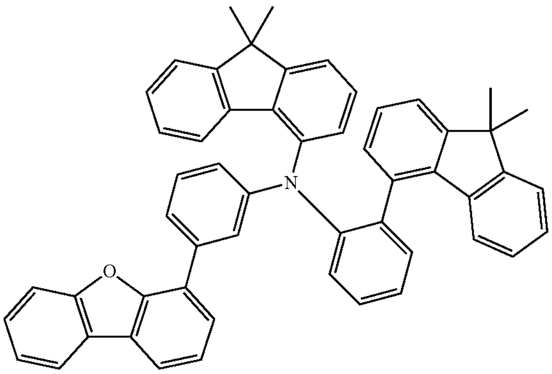
518
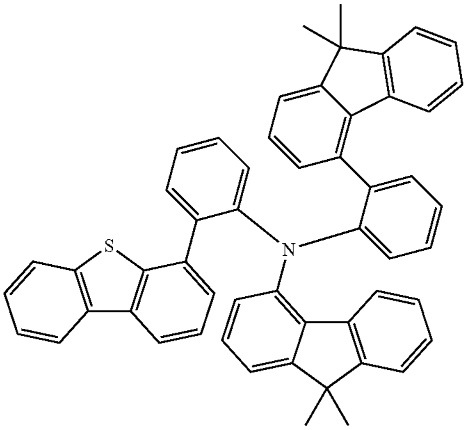
-continued
519
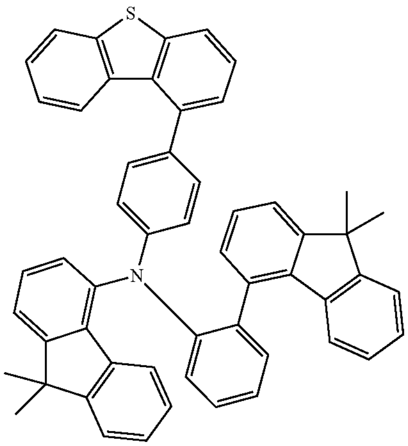
520
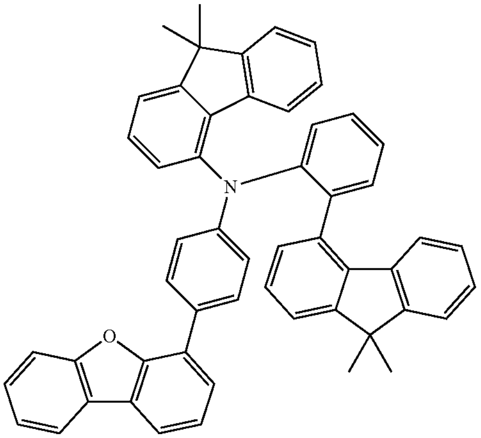
521
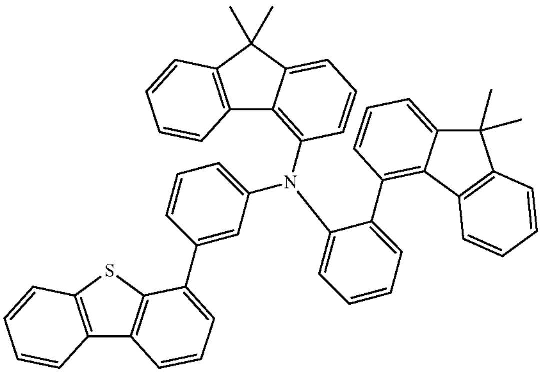

-continued
522
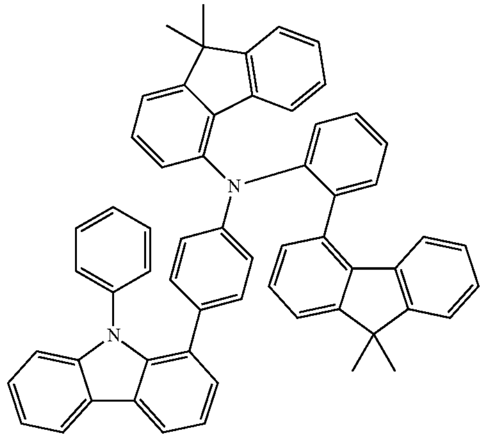
523
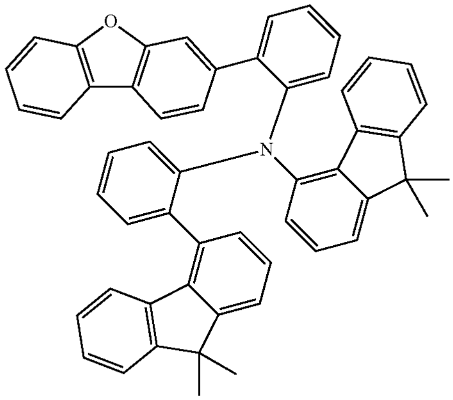
524
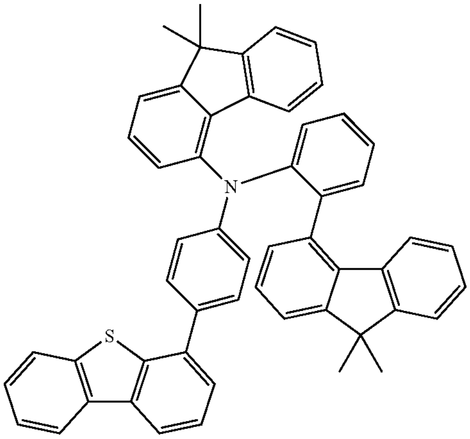
-continued
525
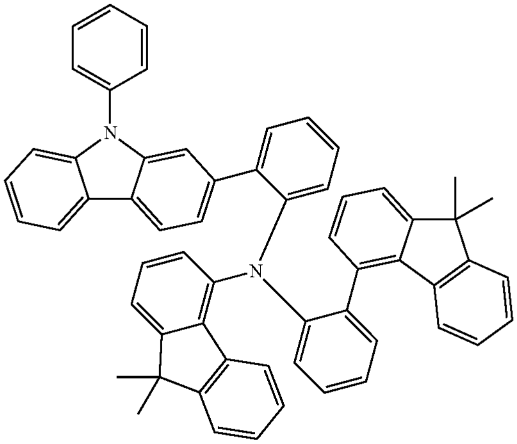
526
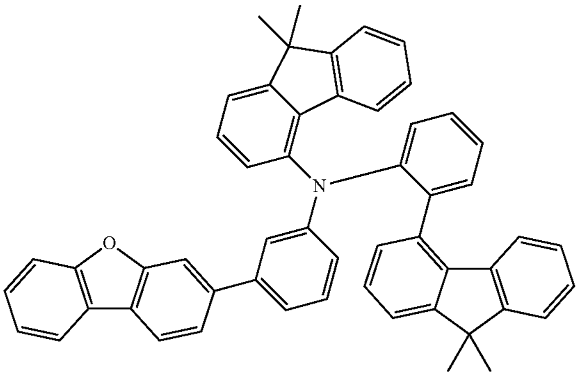
527
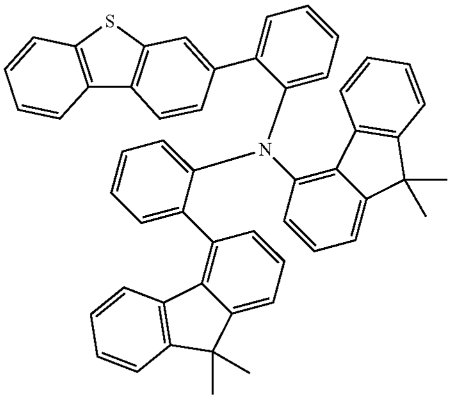

-continued
528
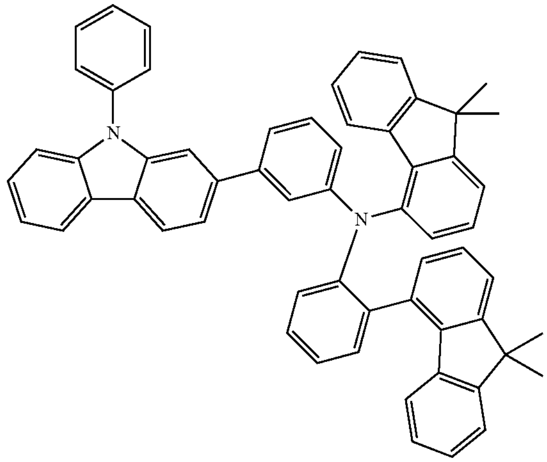
529
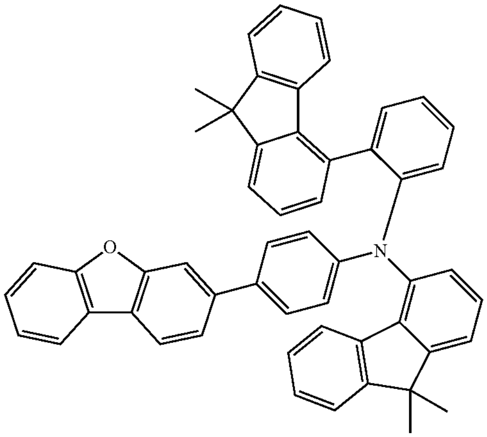
530
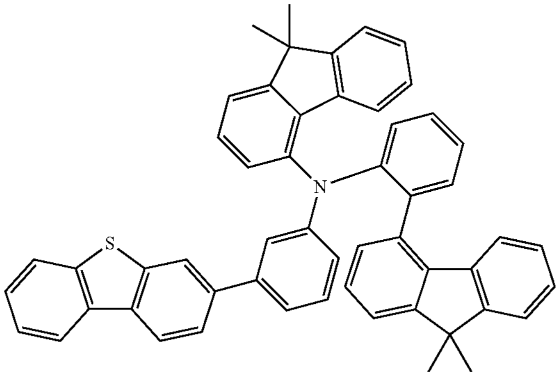
531
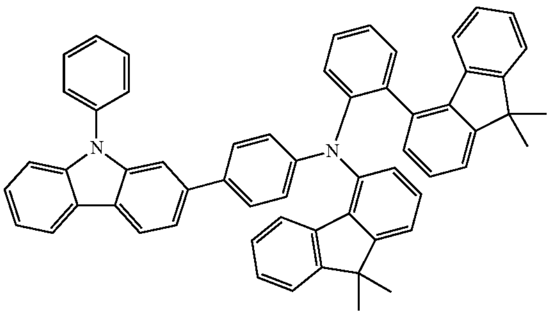
-continued
532
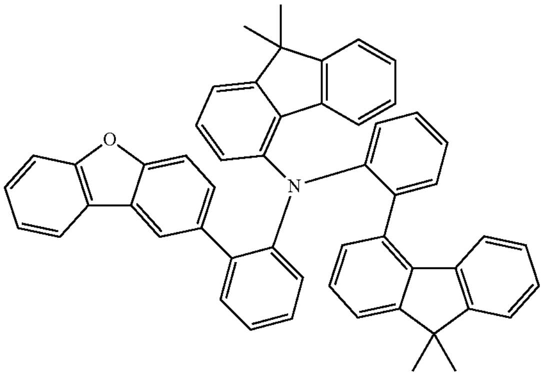
533
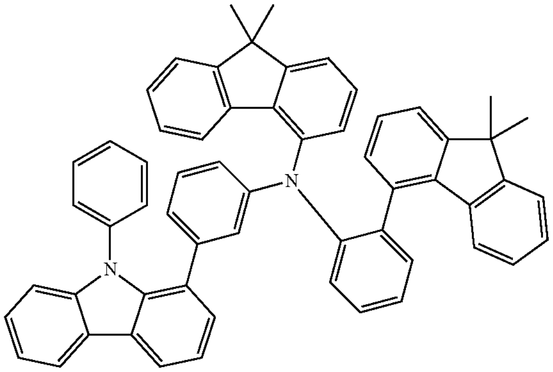
534
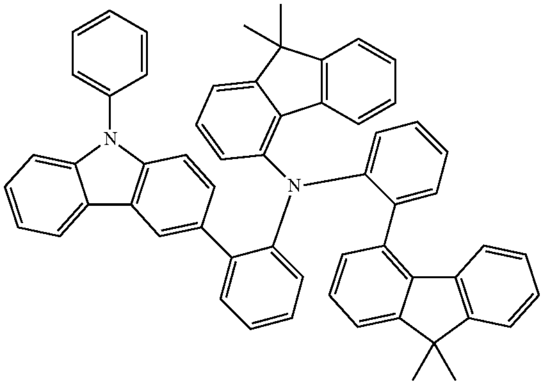
535
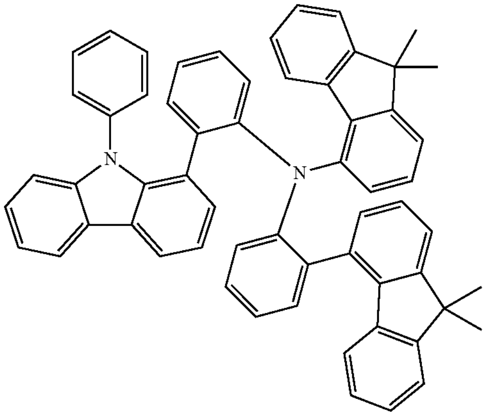

-continued
536
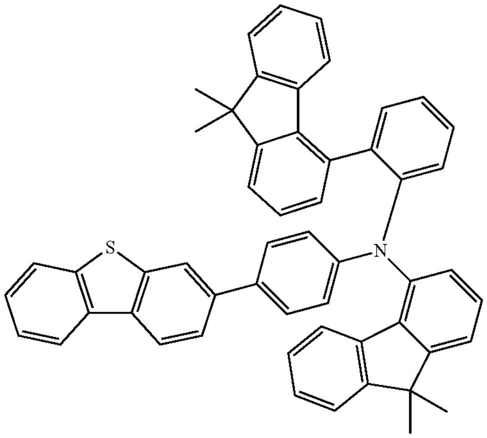
537
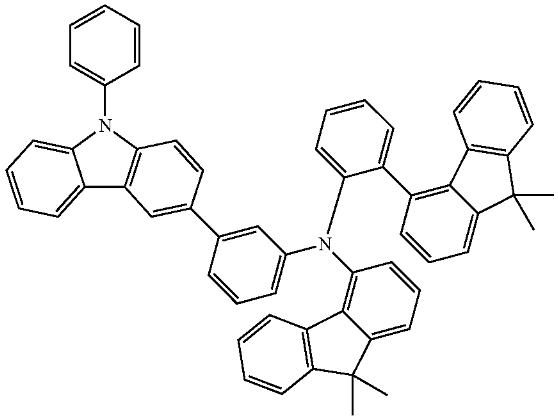
538
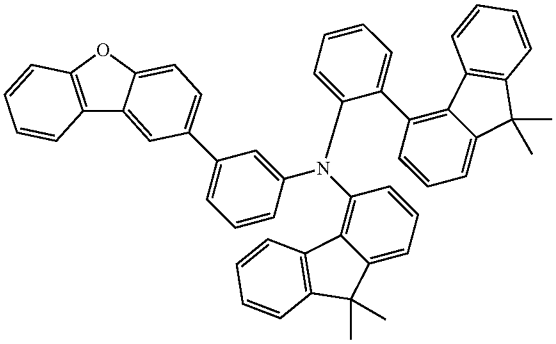
539
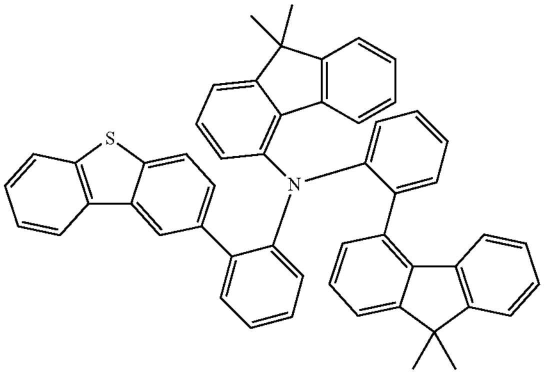
-continued
540
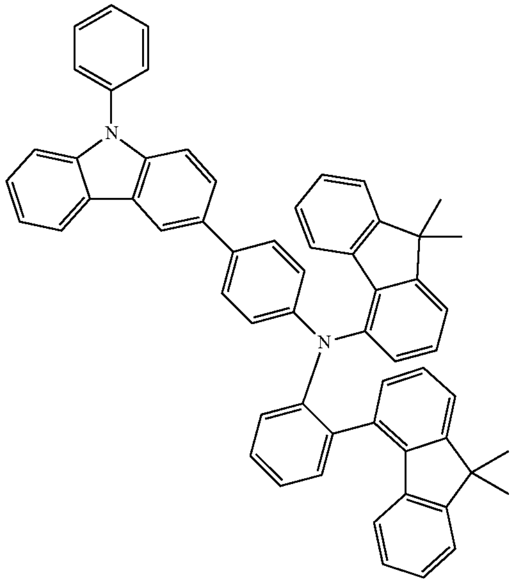
541
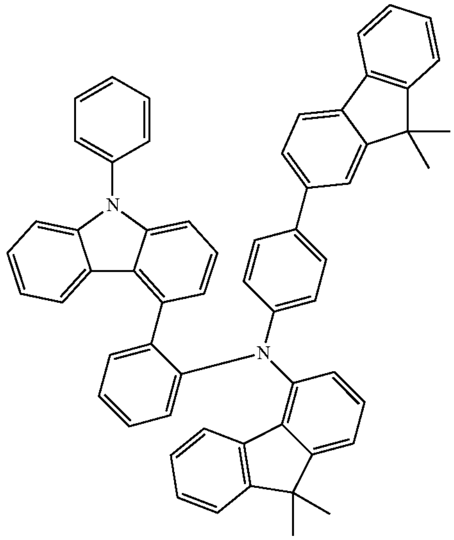

-continued
542
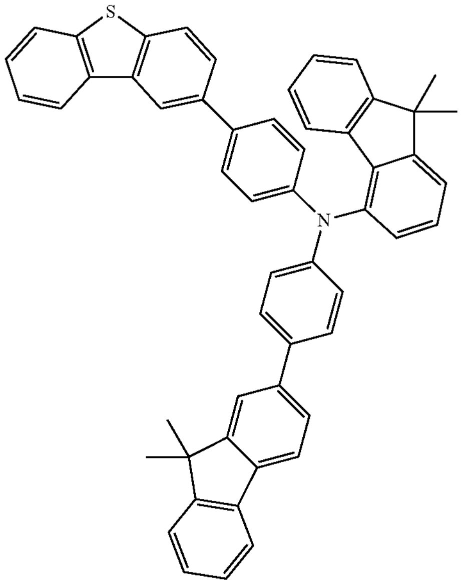
543
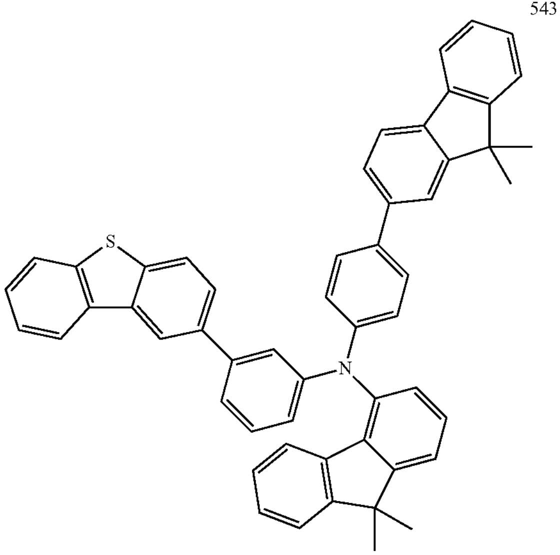
-continued
544
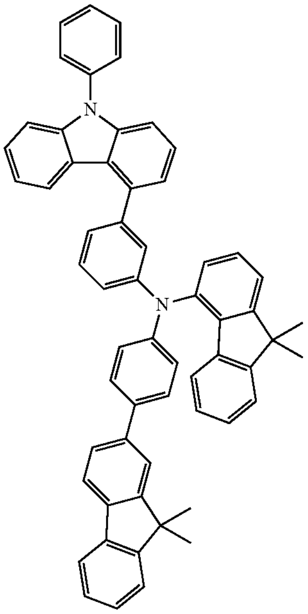
545
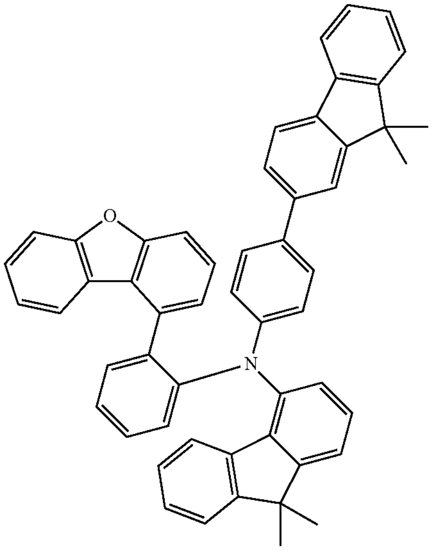

-continued
546
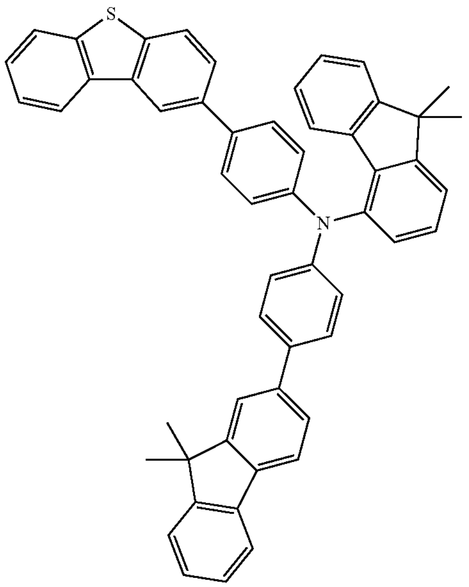
547
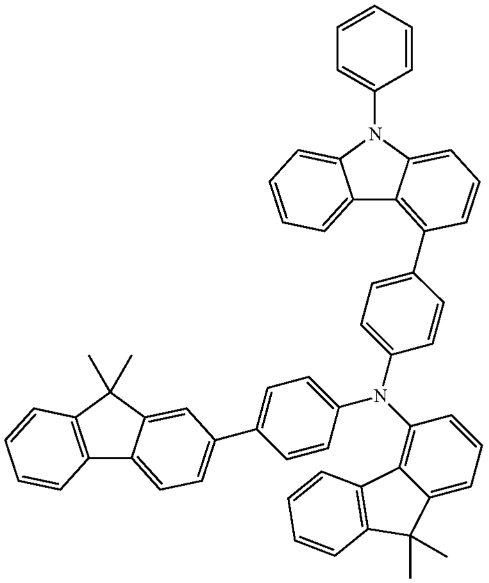
-continued
548
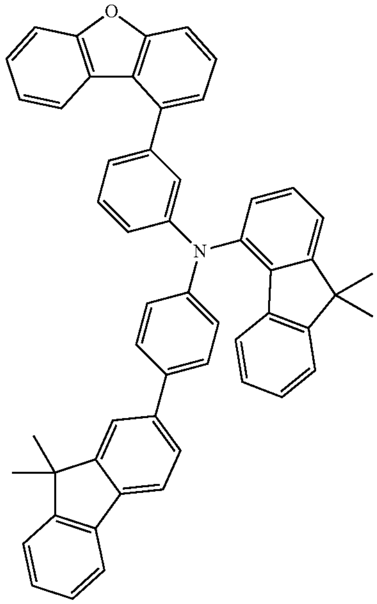
549
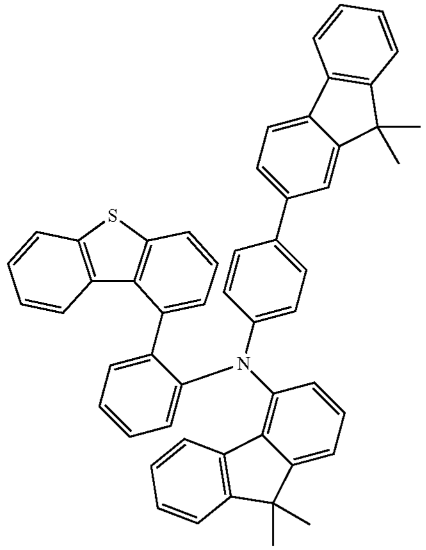
550
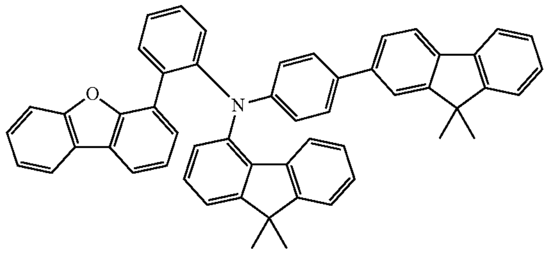

-continued
551
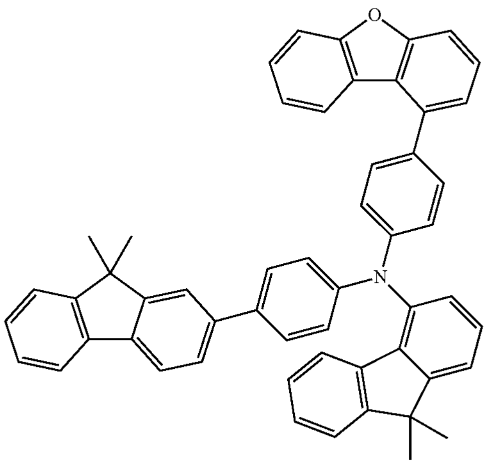
552
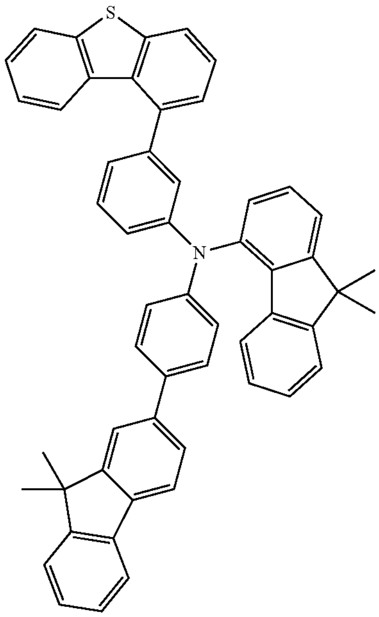
553
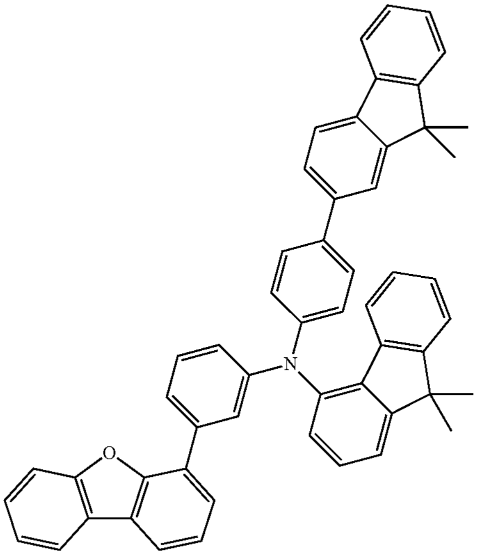
-continued
554
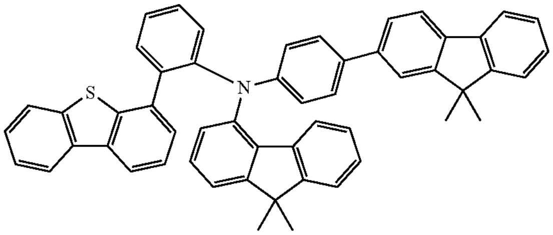
555
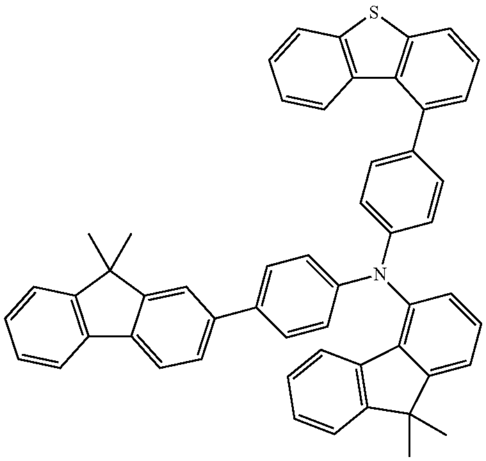
556
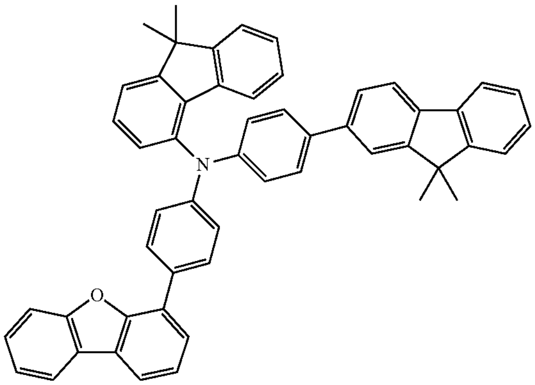

-continued
557
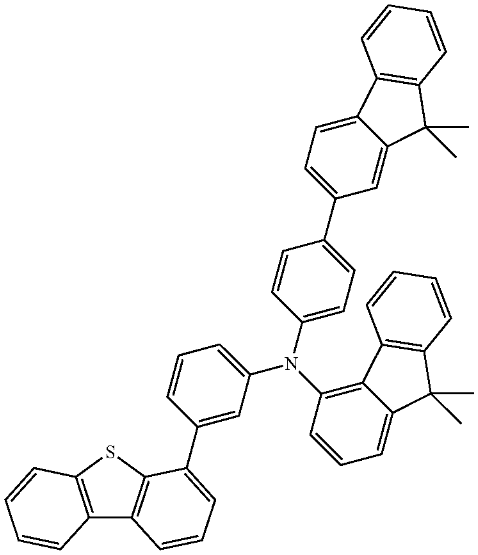
558
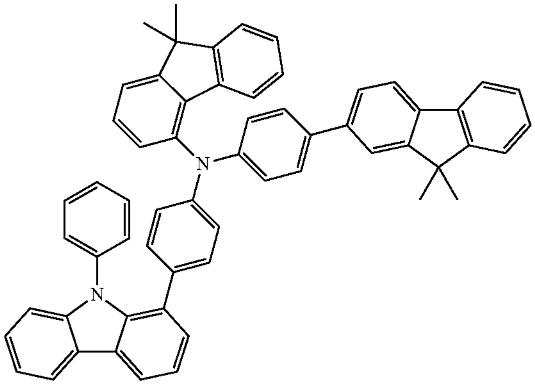
559
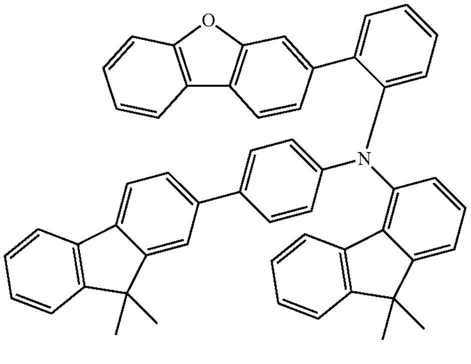
-continued
560
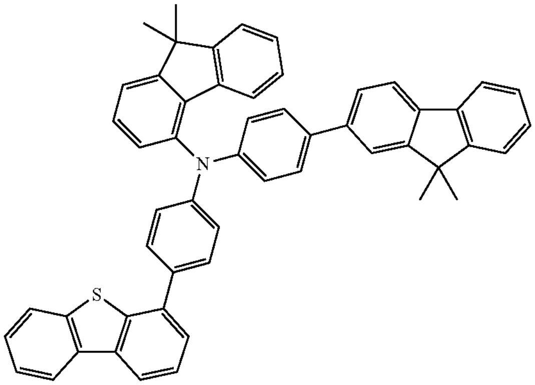
561
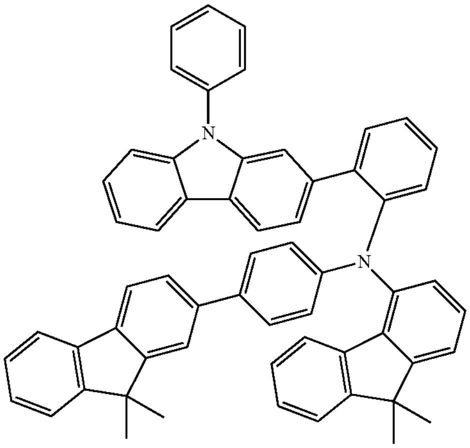
562
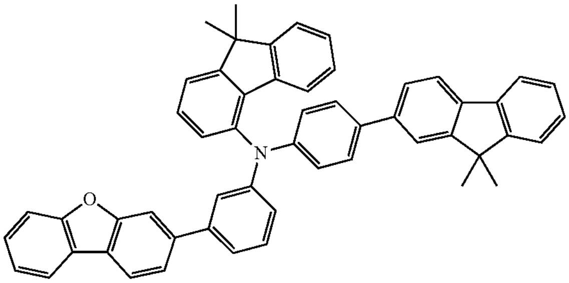
563
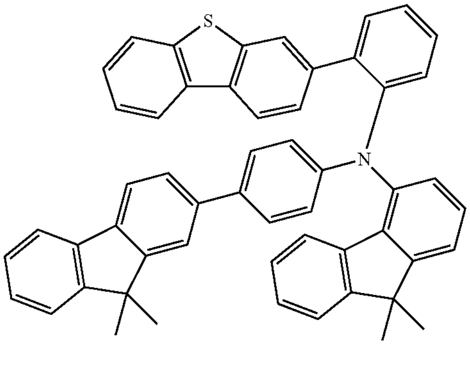

-continued
564
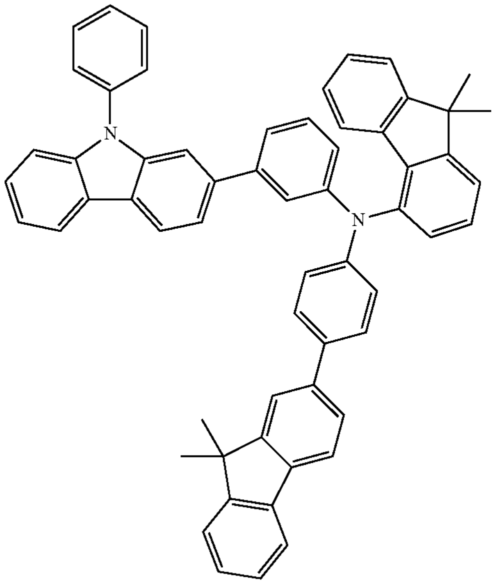
565
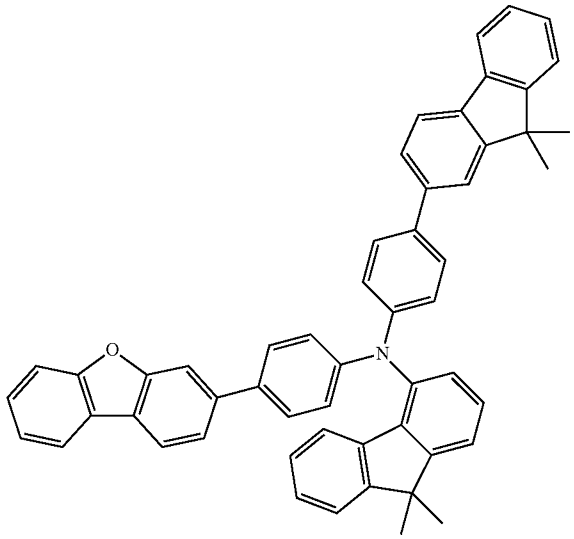
566
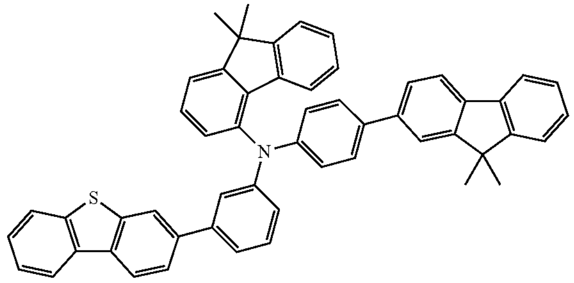
-continued
567
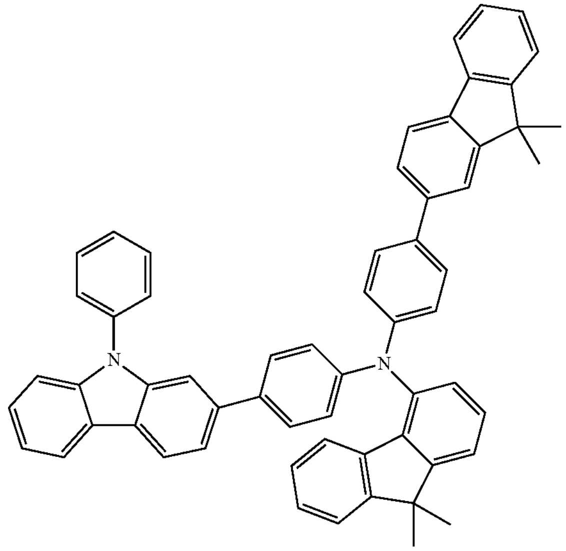
568
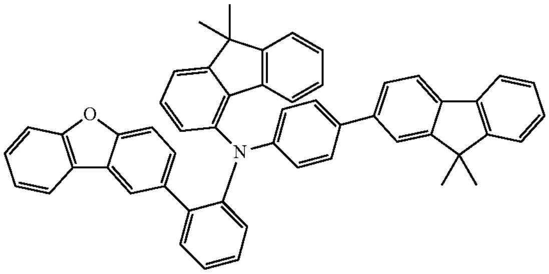
569
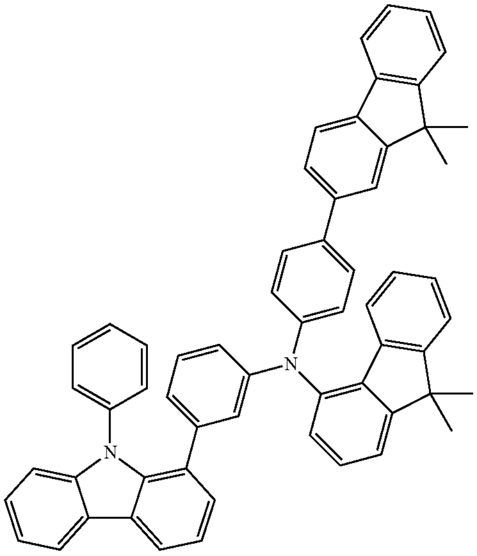

-continued
570
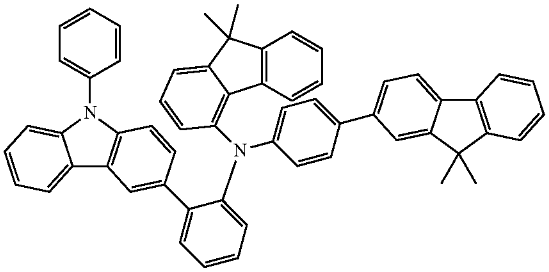
571
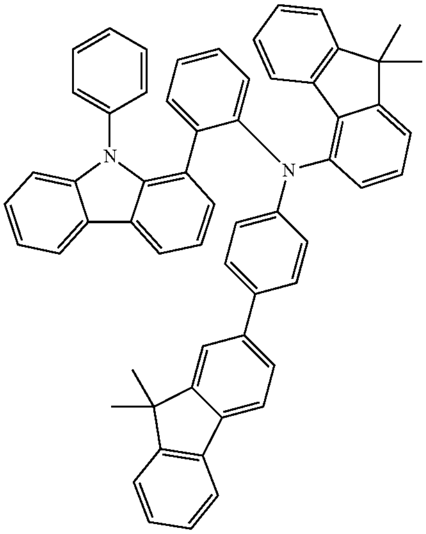
572
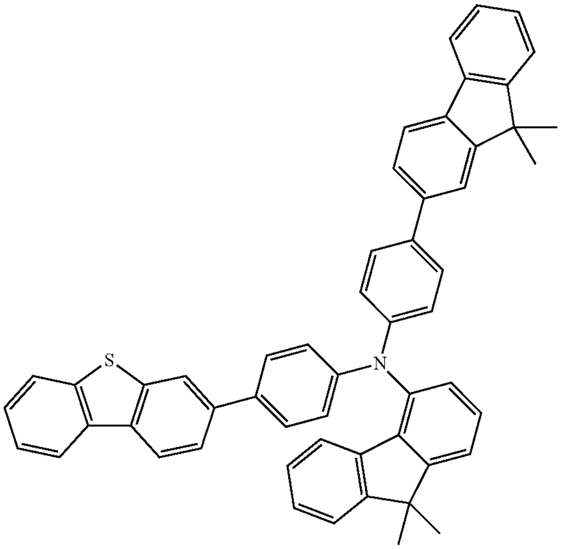
-continued
573
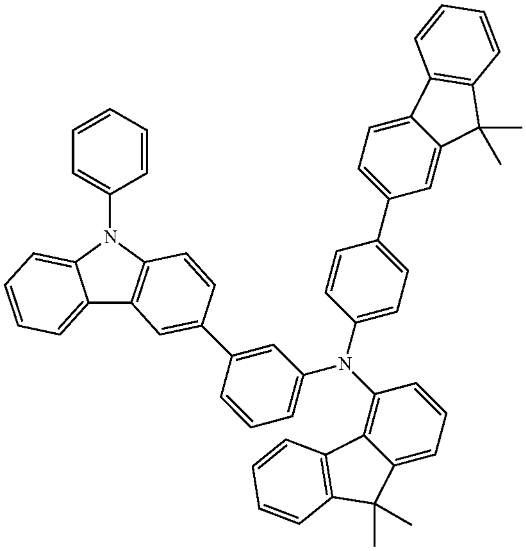
574
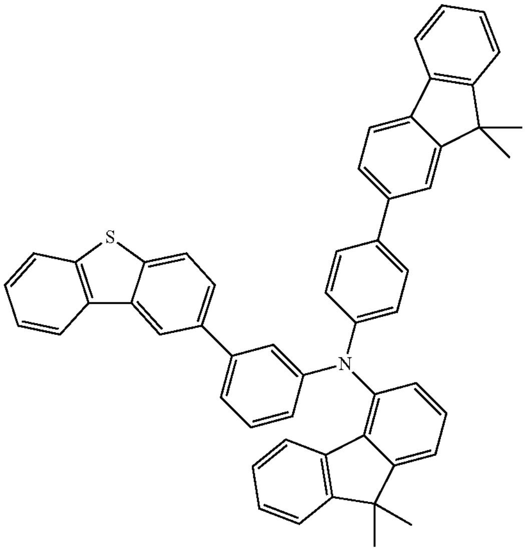
575
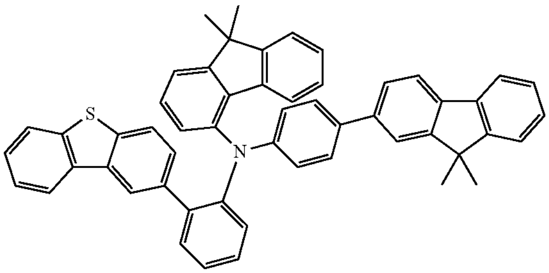

-continued
576
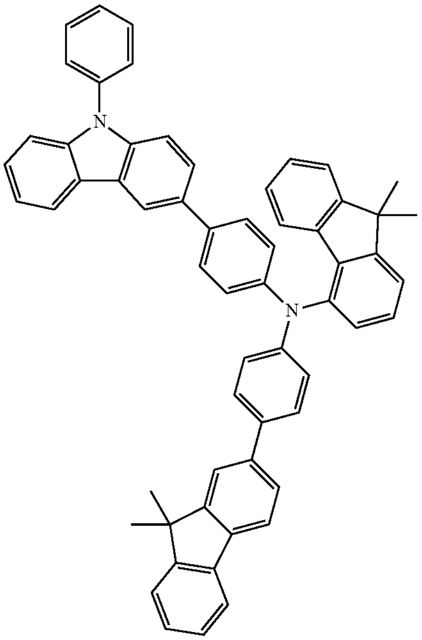
577
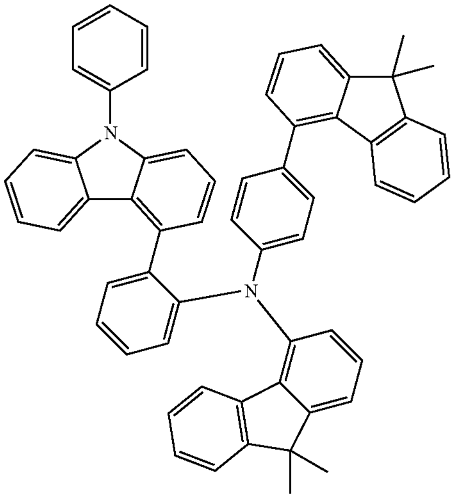
578
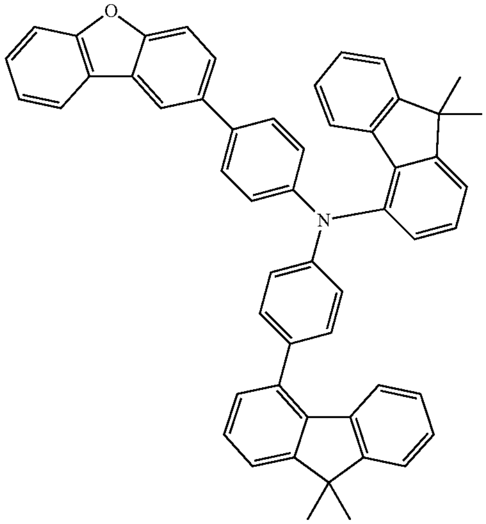
-continued
579
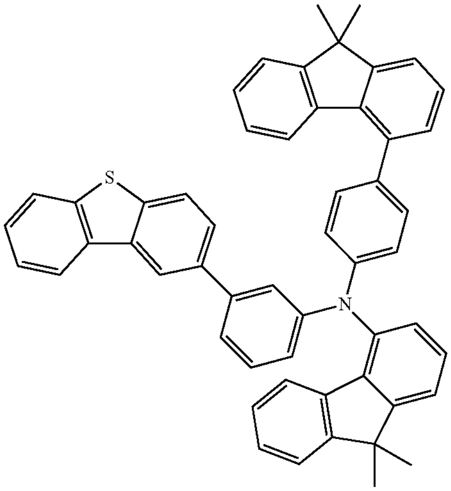
580
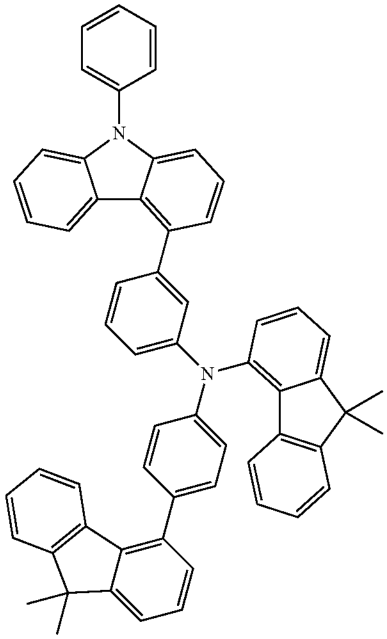
581
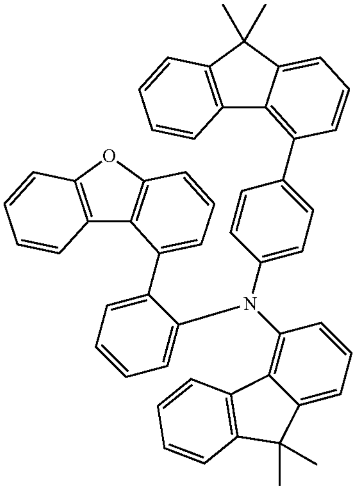

-continued
582
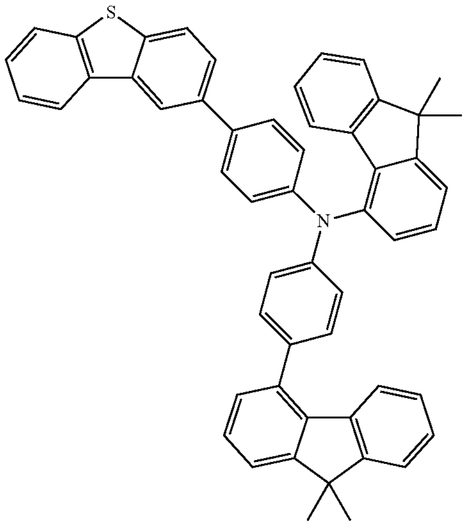
583
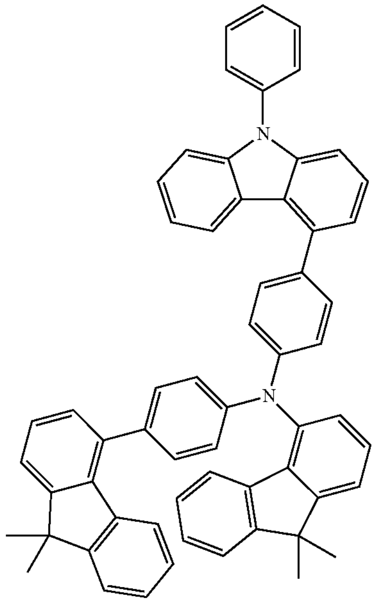
-continued
584
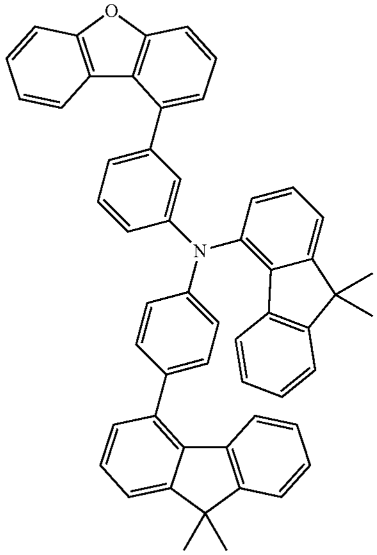
585
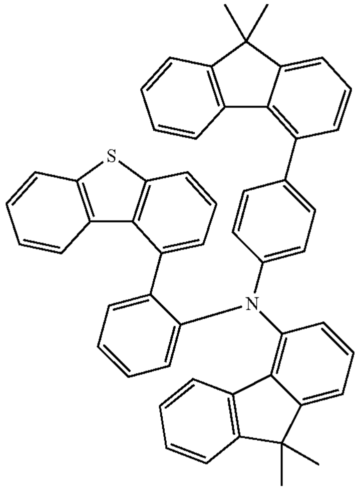
586
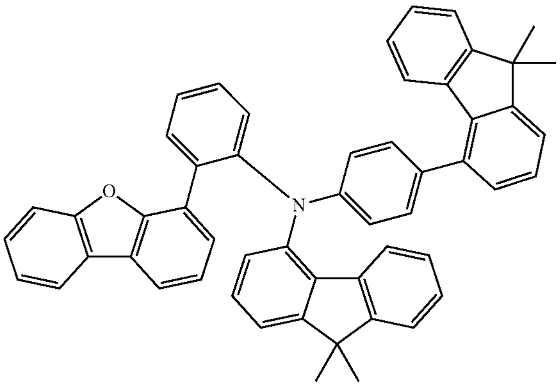

-continued
587
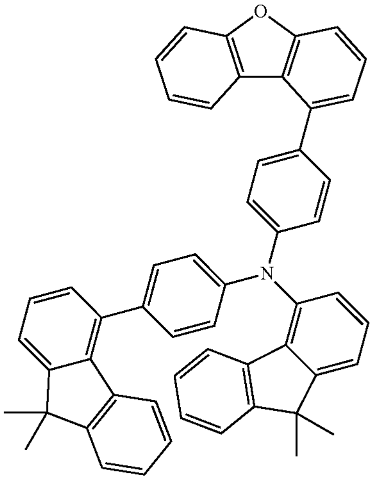
588
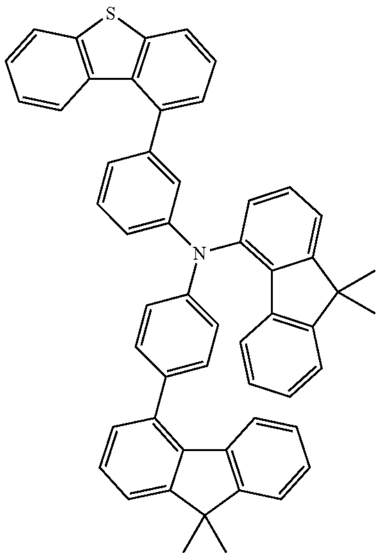
589
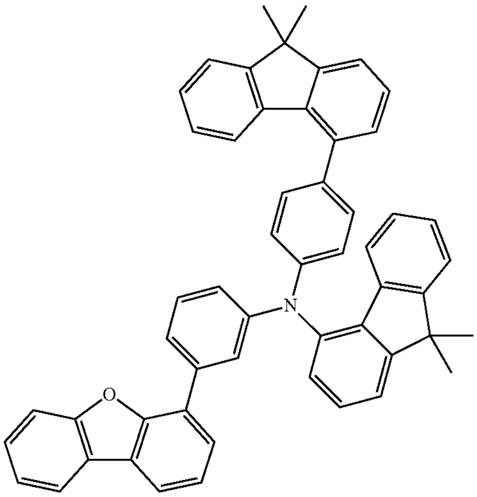
-continued
590
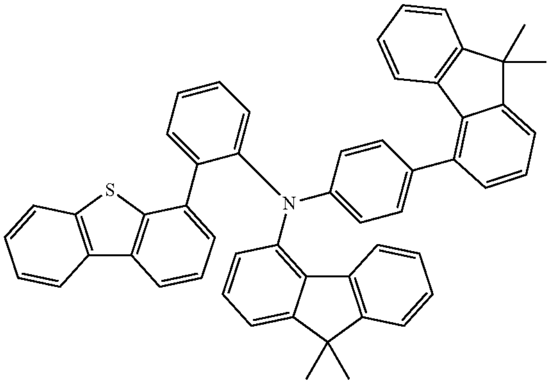
591
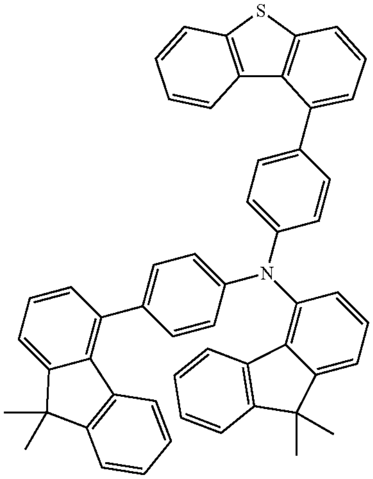
592
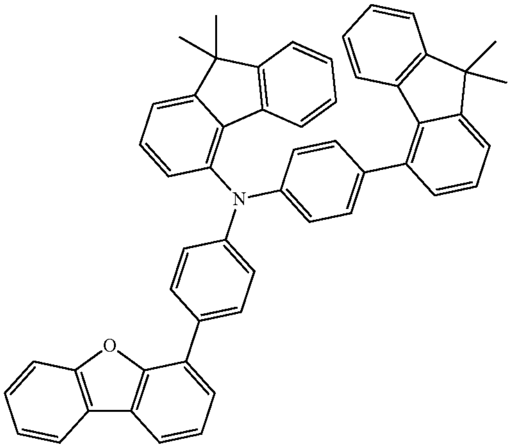

-continued
593
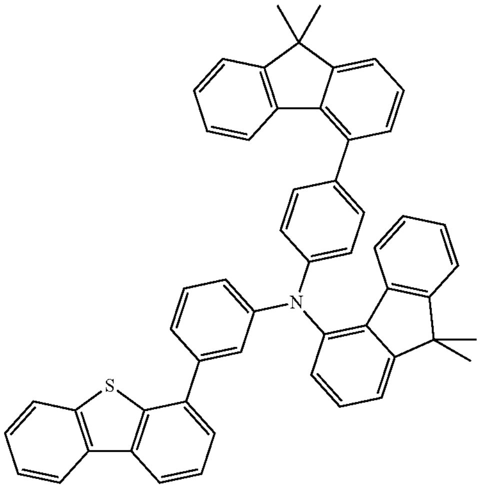
594
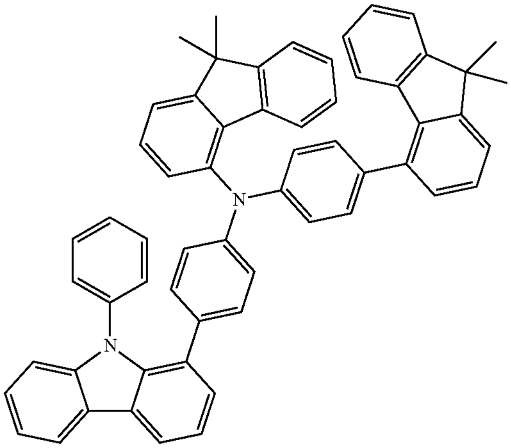
595
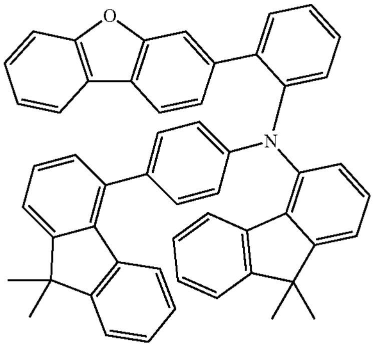
-continued
596
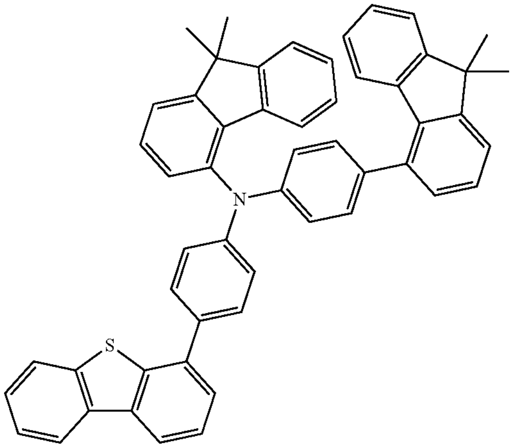
597
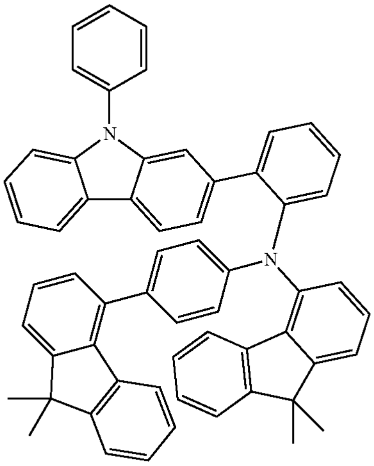
598
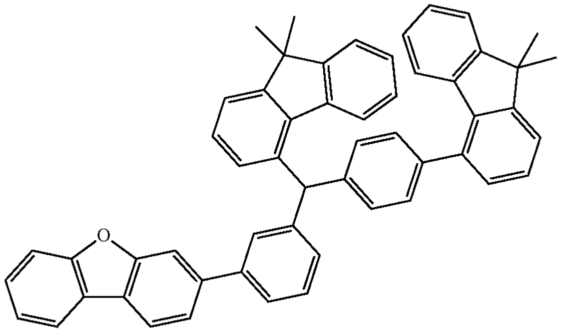
599
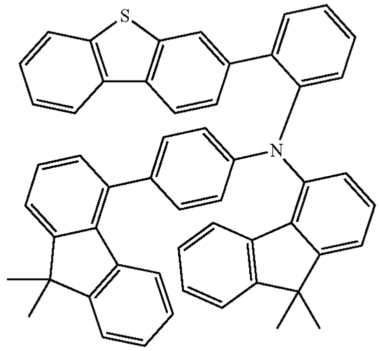

-continued
600
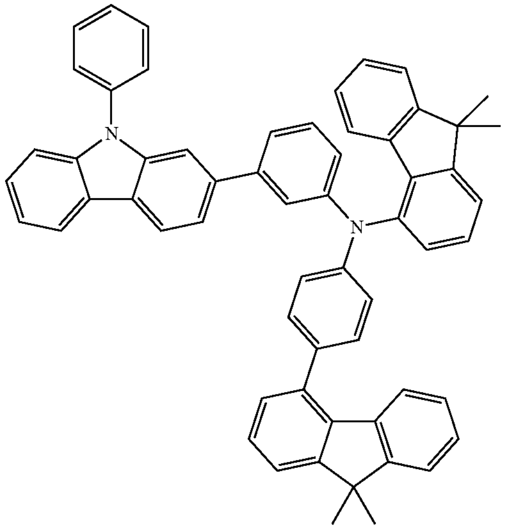
601
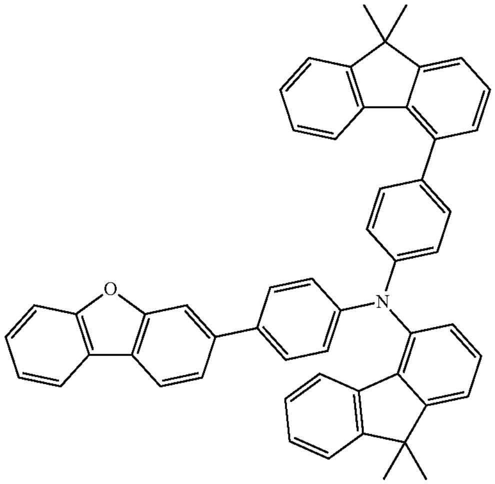
602
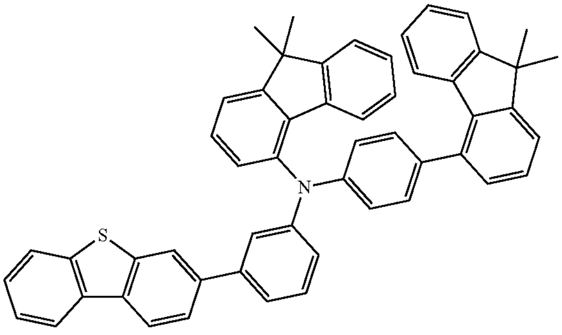
-continued
603
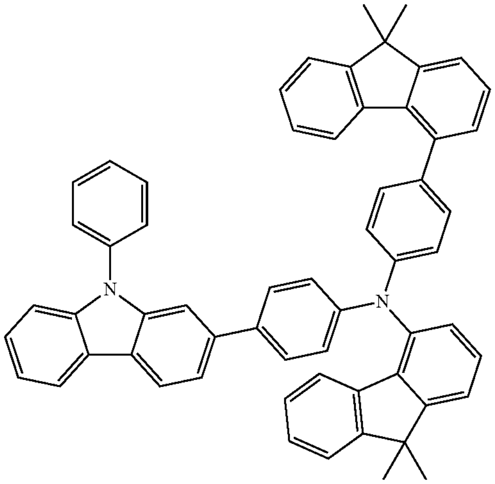
604
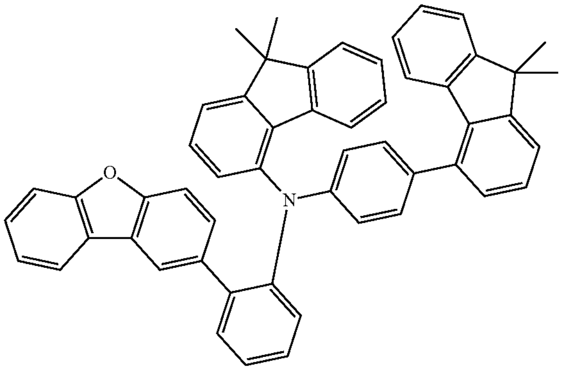
605
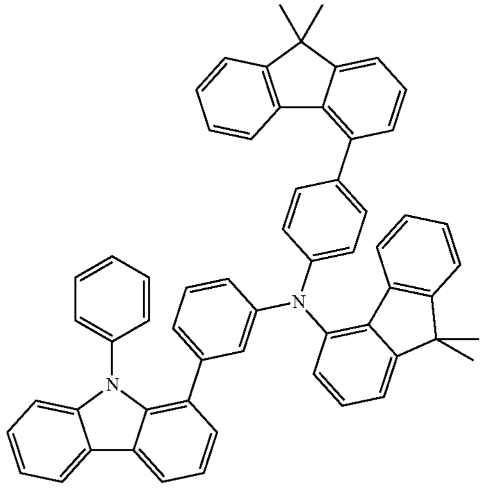

-continued
606
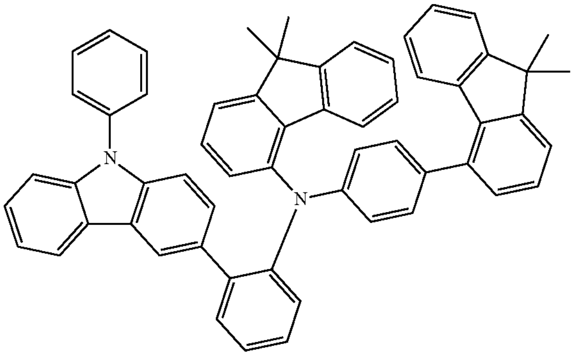
607
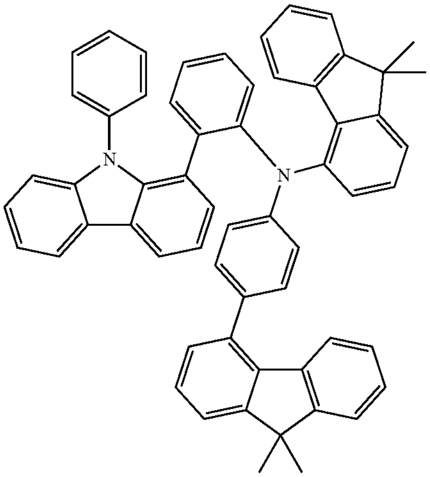
608
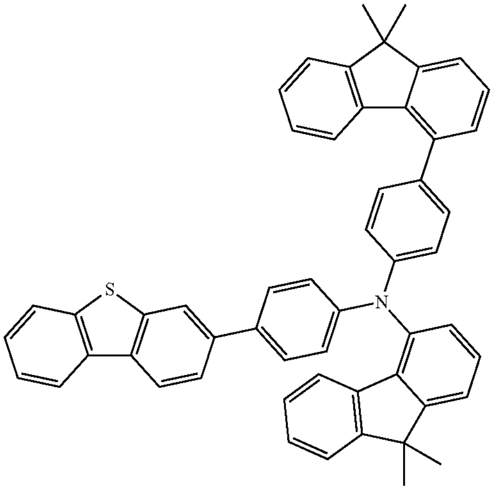
-continued
609
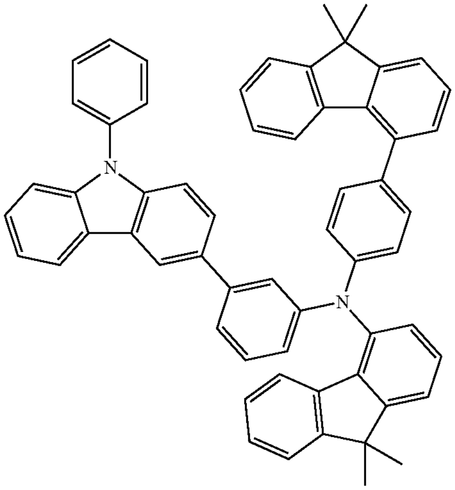
610
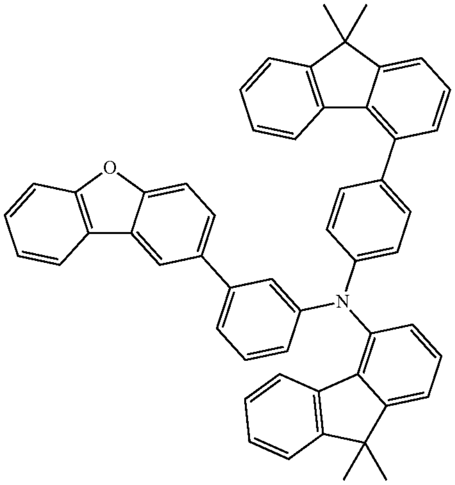
611
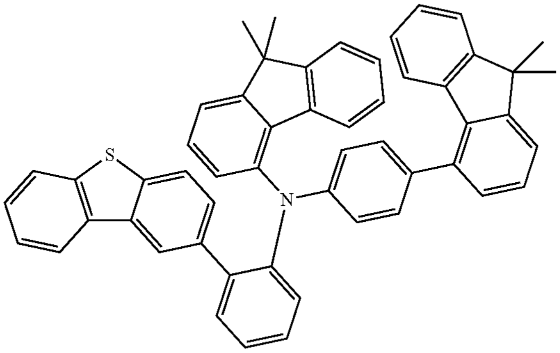

-continued
612
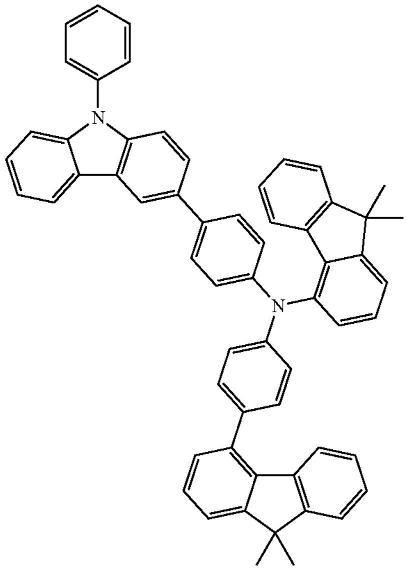
613
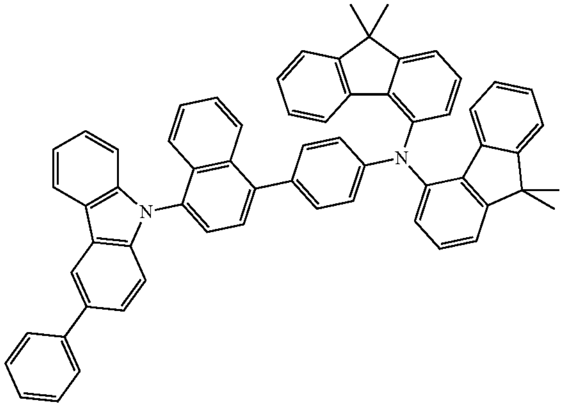
614
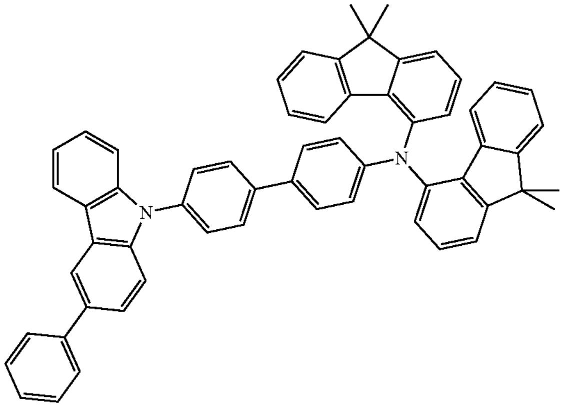
-continued
615
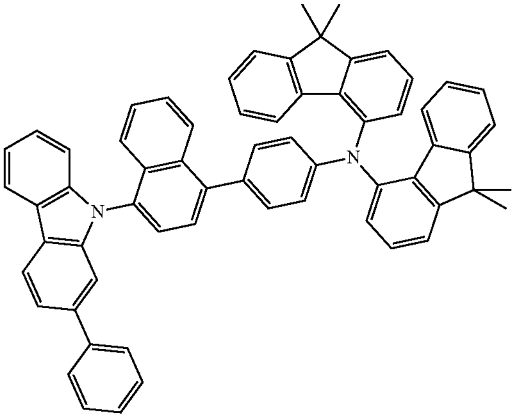
616
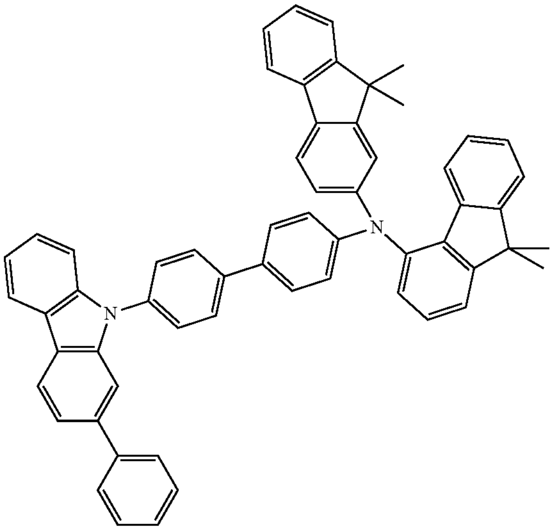
617
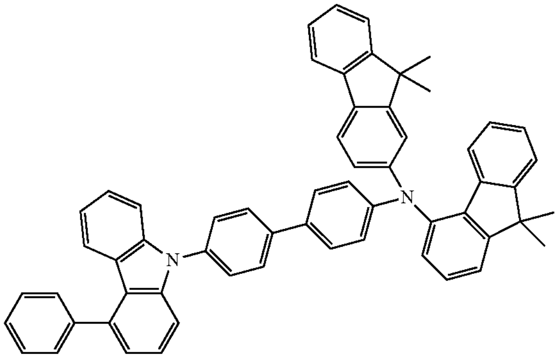

-continued
618
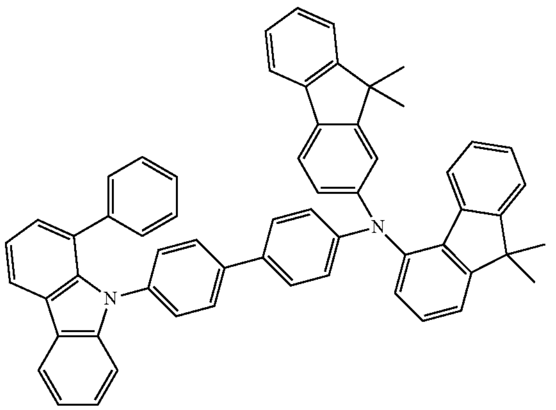
619
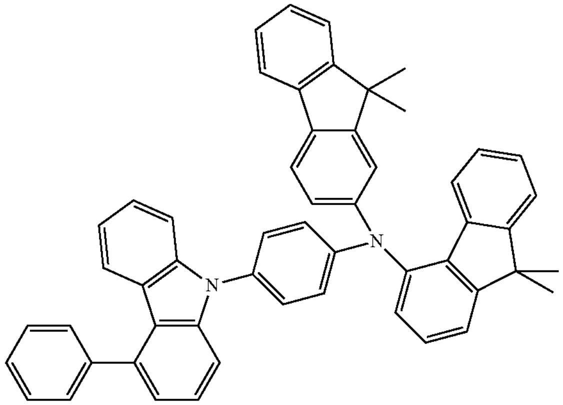
620
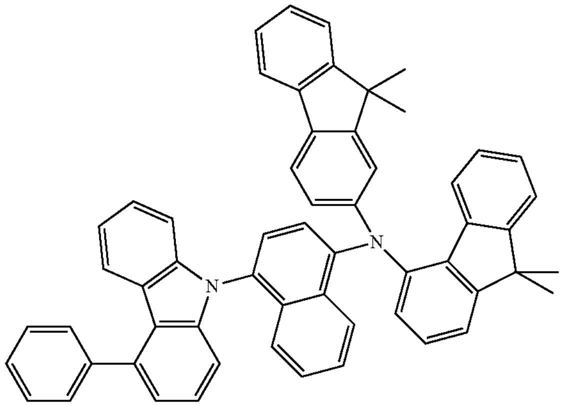
621
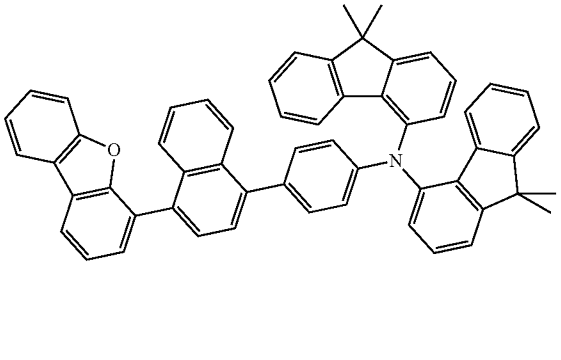
-continued
622
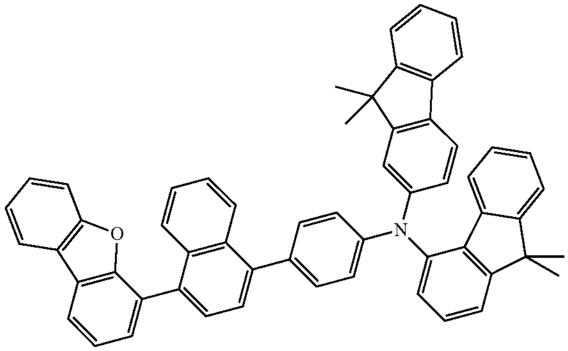
623
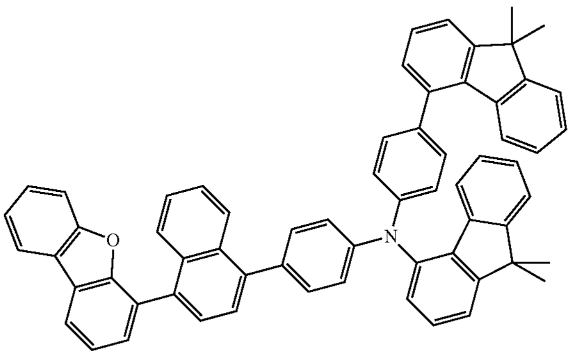
624
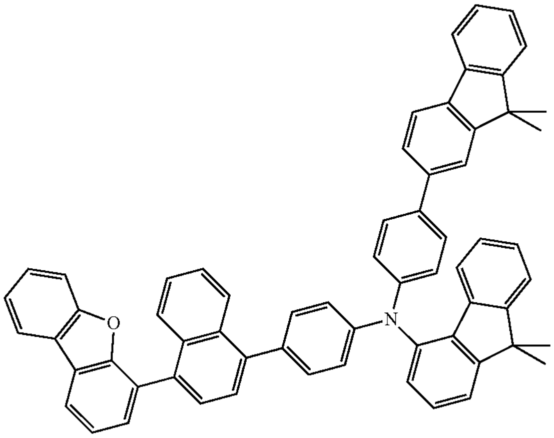

-continued
625
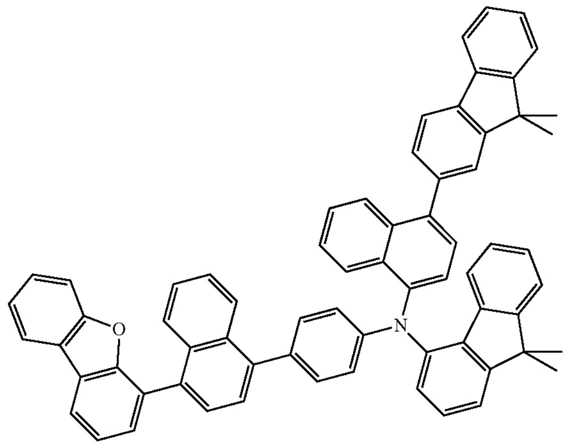
626
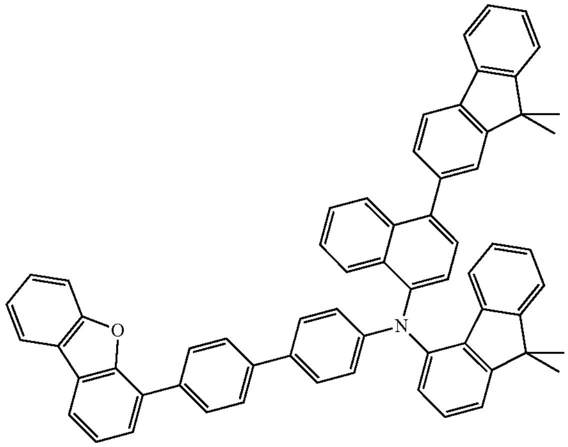
627
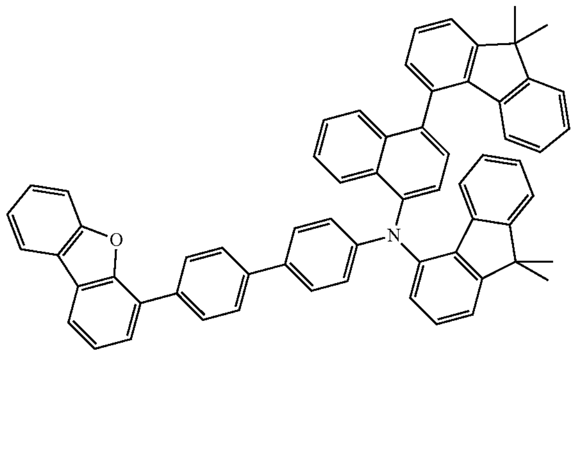
-continued
628
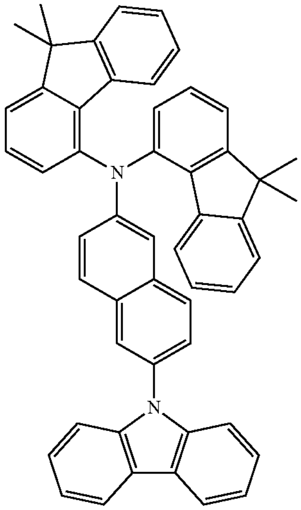
629
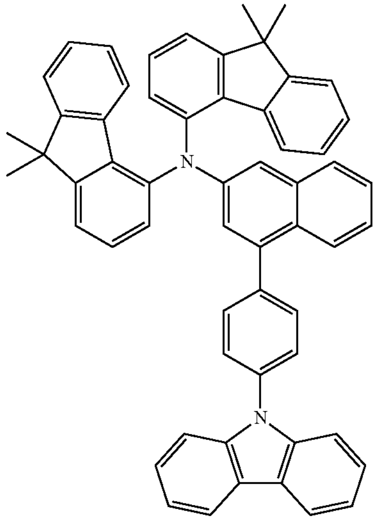
630
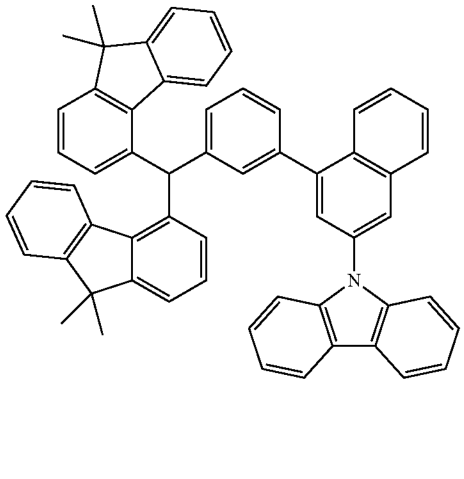

-continued
631
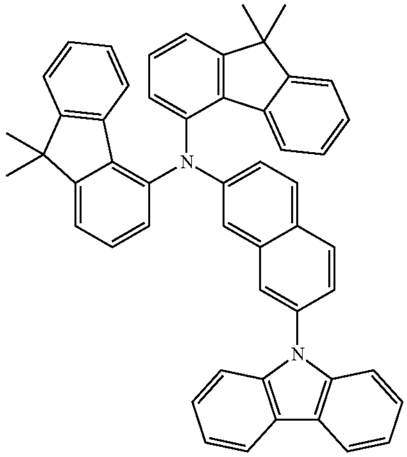
632
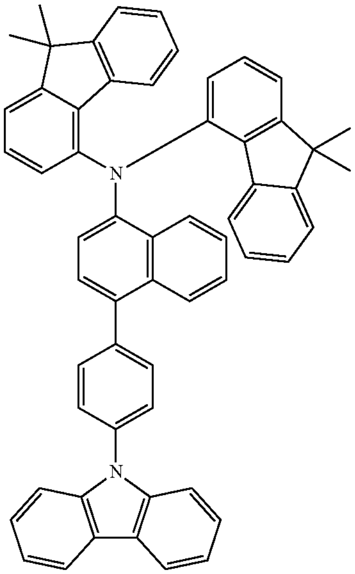
633
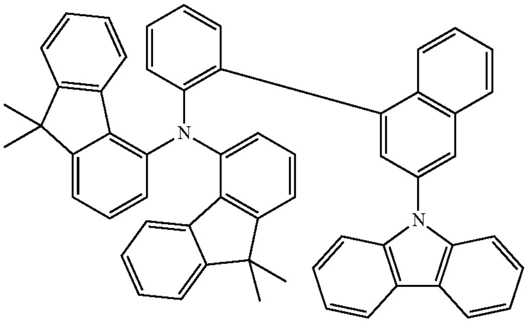
634
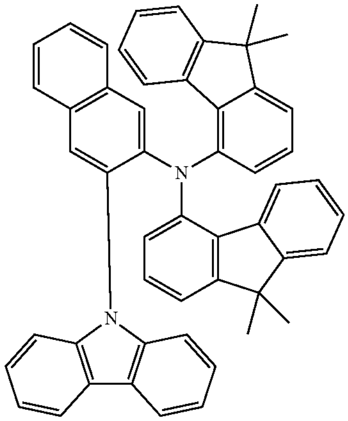
635
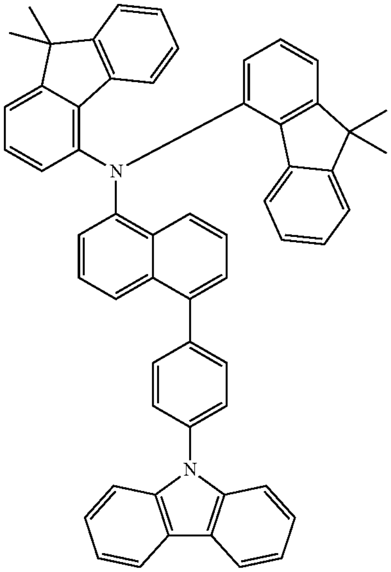
636
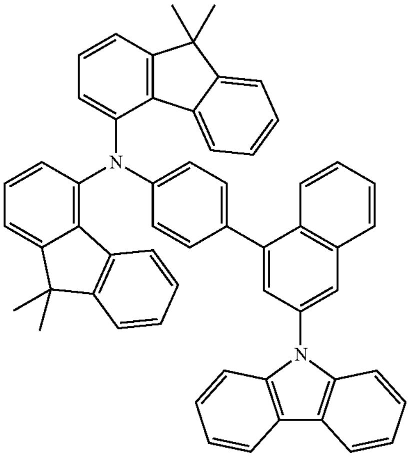

-continued
637
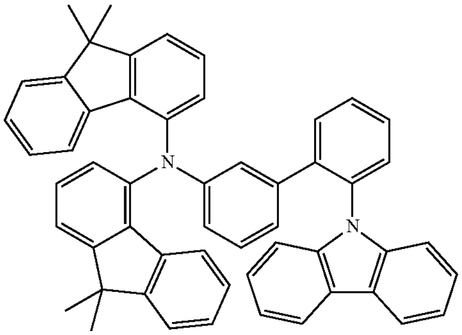
638
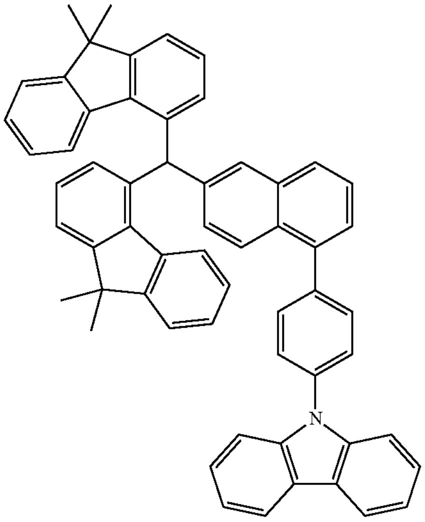
639
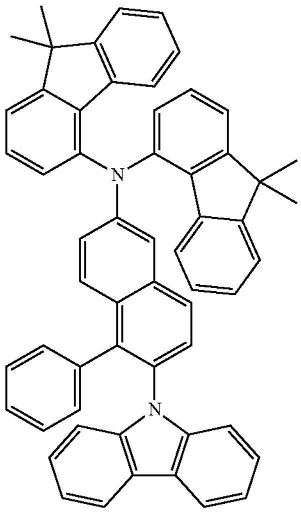
-continued
640
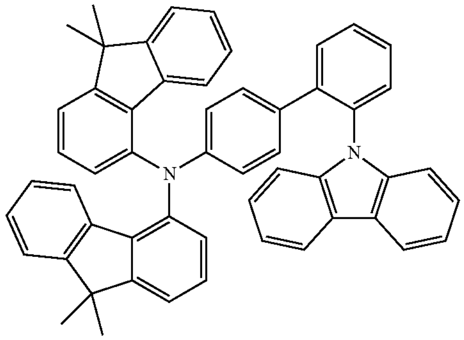
641
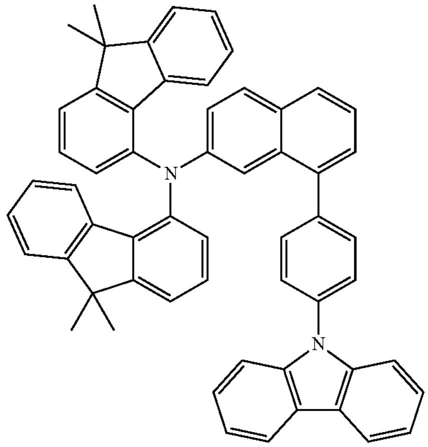
642
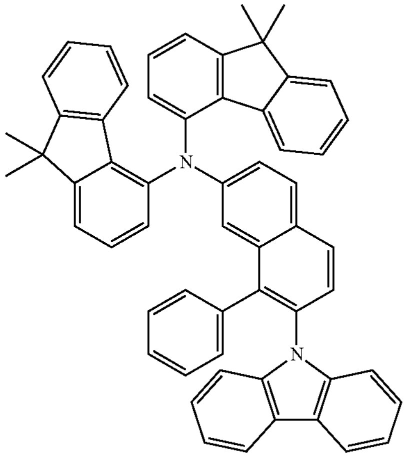

-continued
643
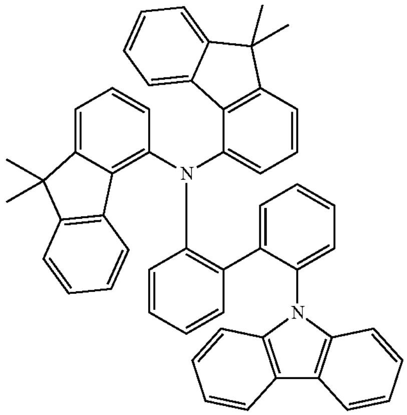
644
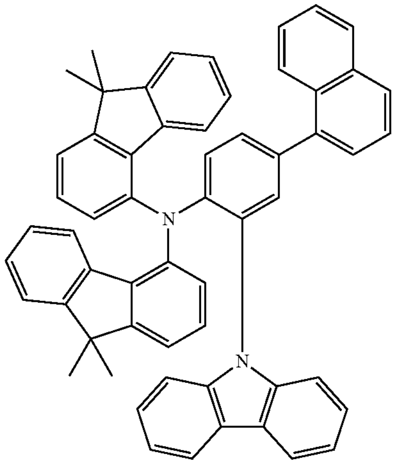
645
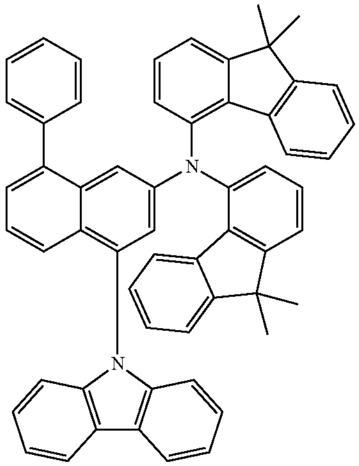
-continued
646
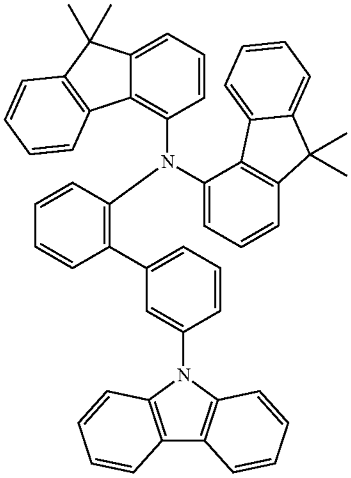
647
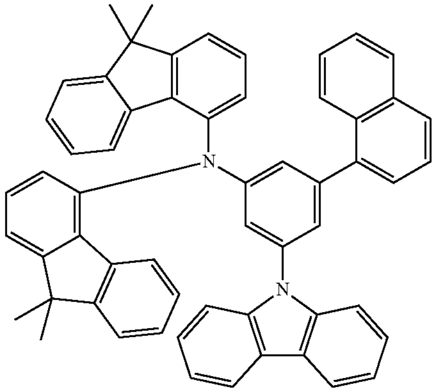
648
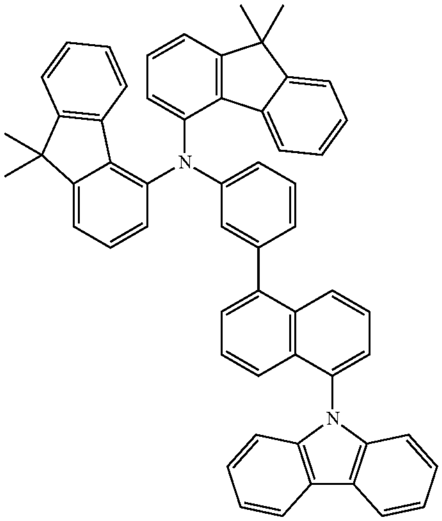

-continued
649
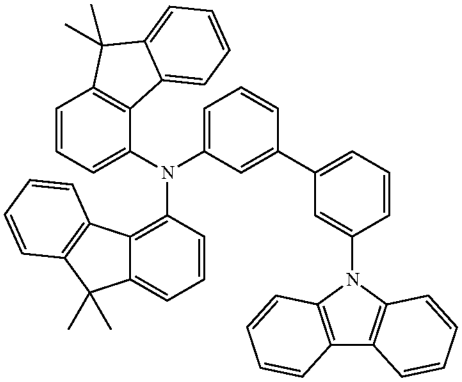
650
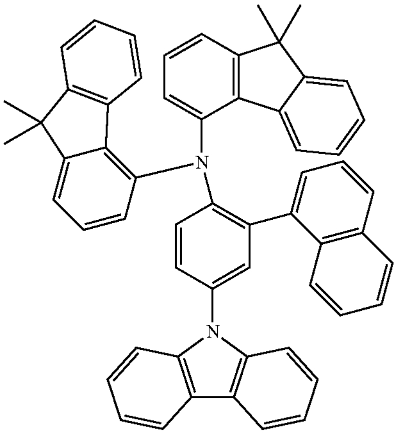
651
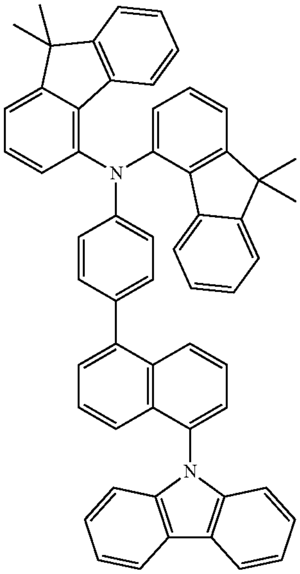
-continued
652
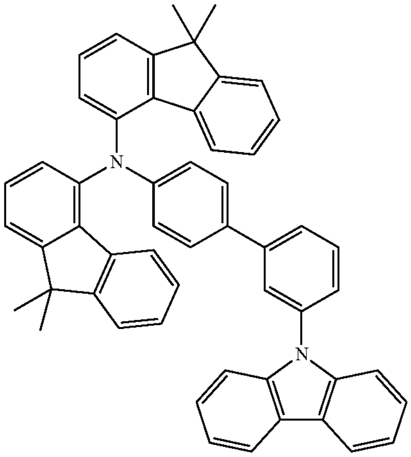
653
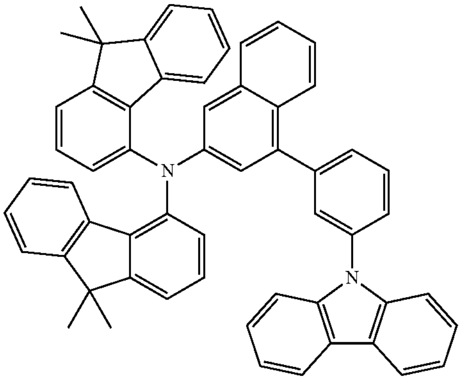
654
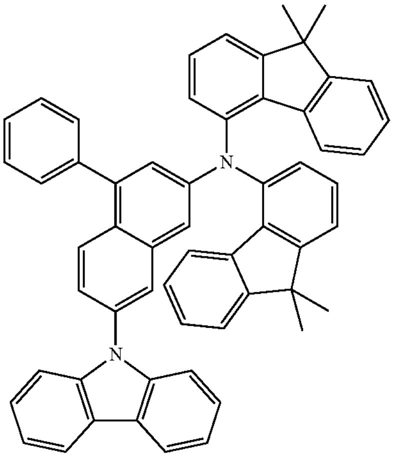

655
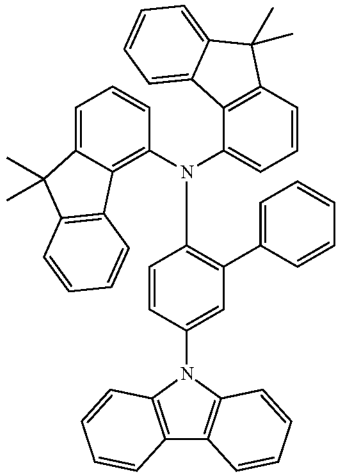
656
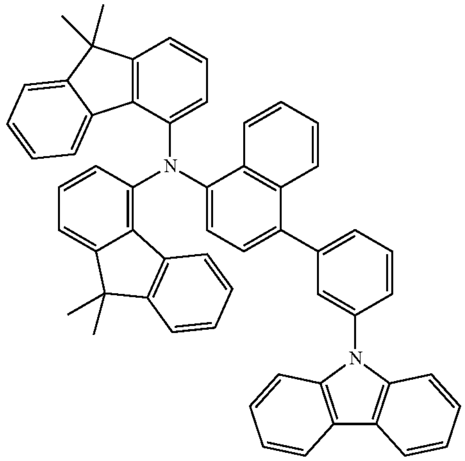
657
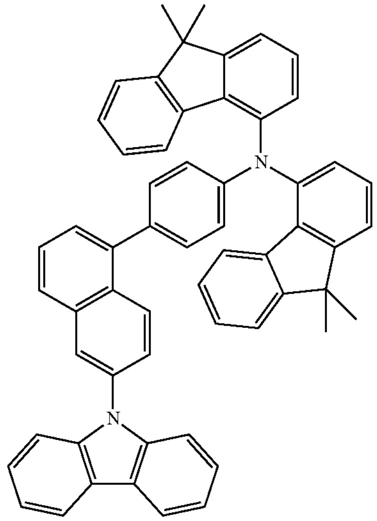
658
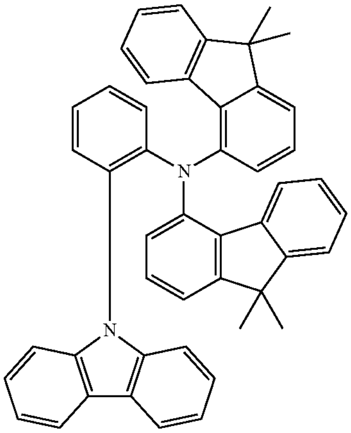
659
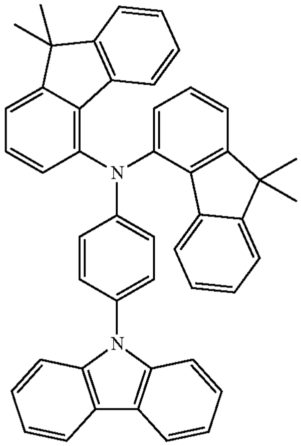
660
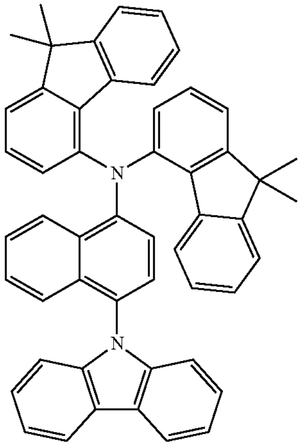

-continued
661
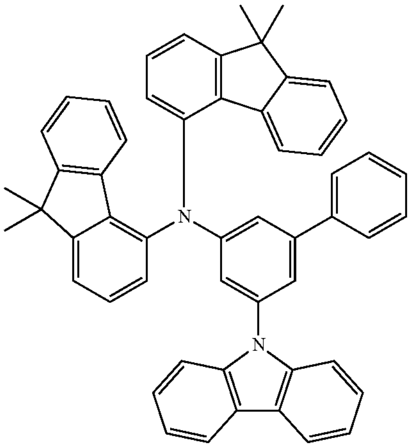
662
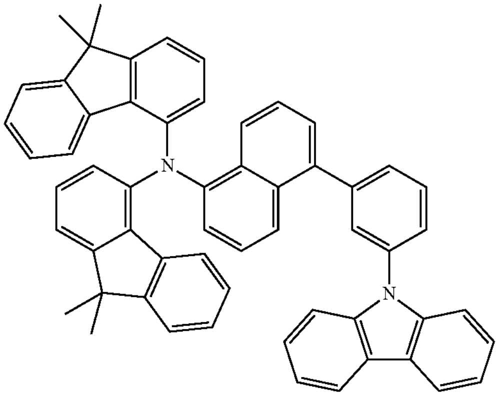
663
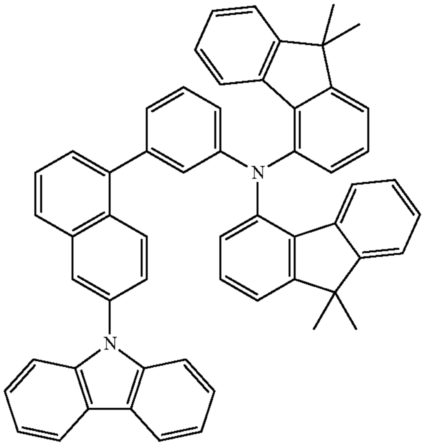
-continued
664
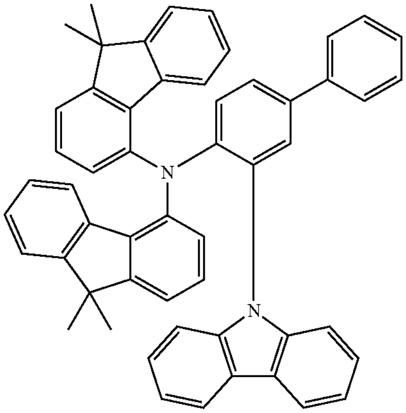
665
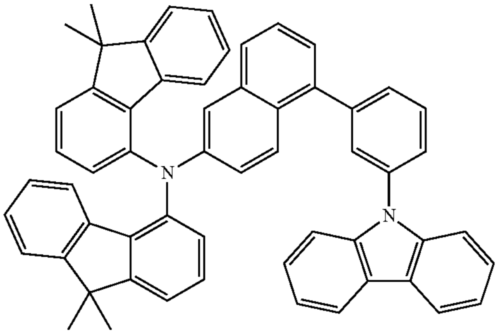
666
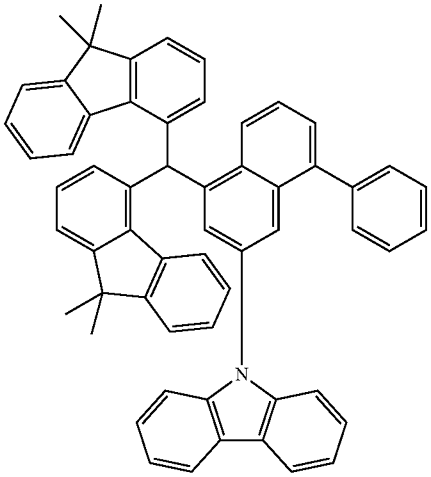

-continued
667
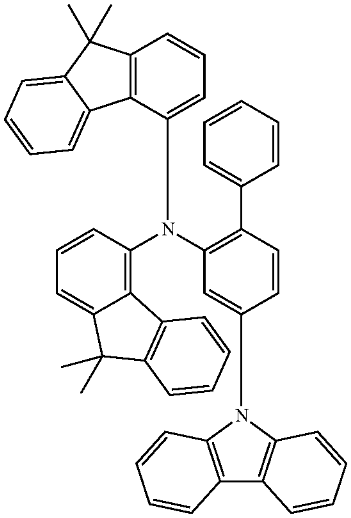
668
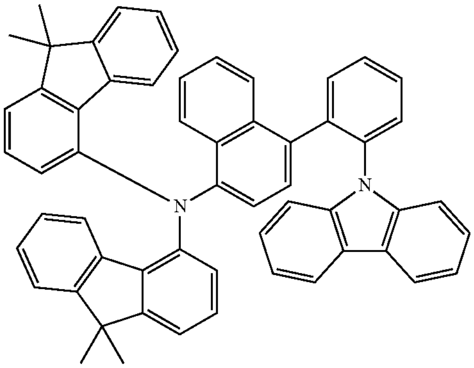
669
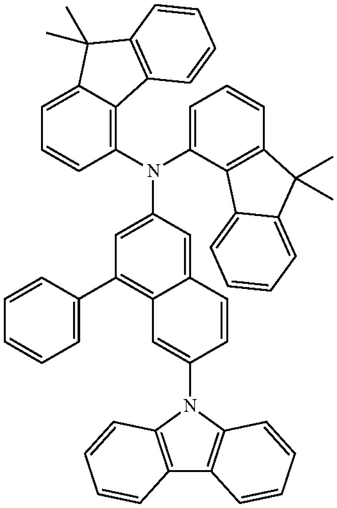
-continued
670
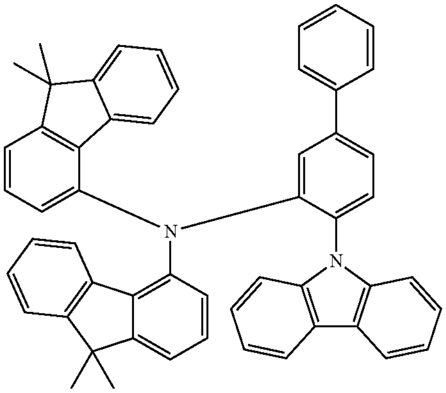
671
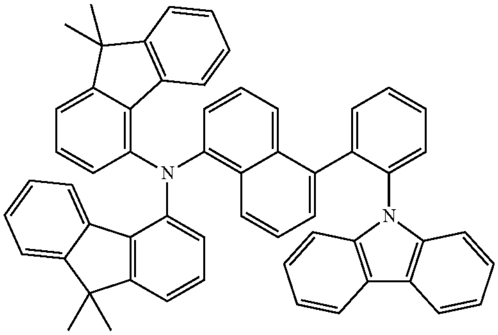
672
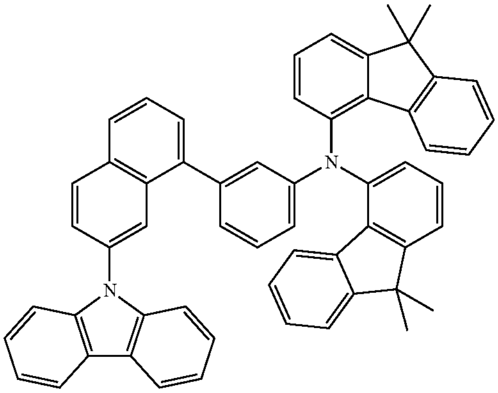
673
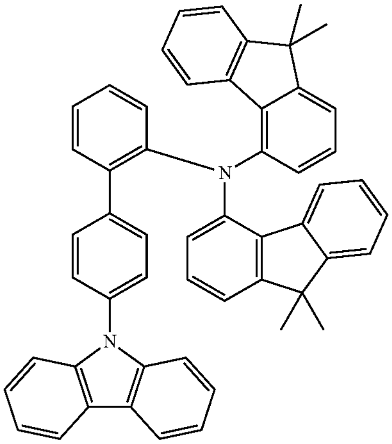

-continued
674
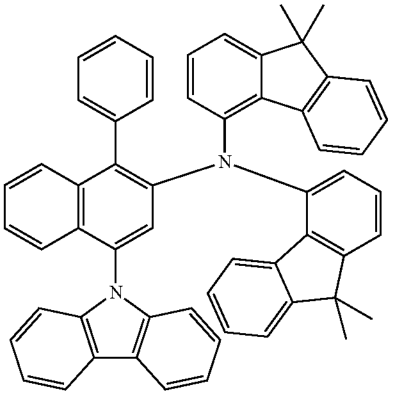
675
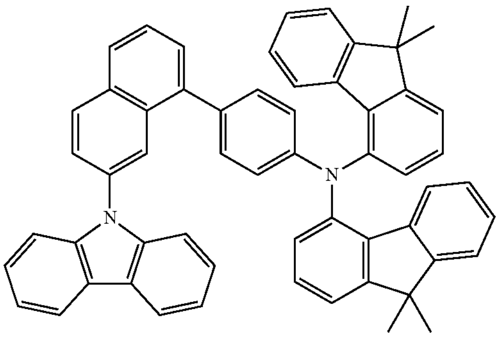
676
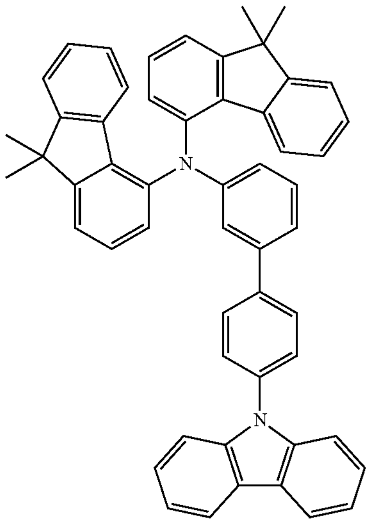
-continued
677
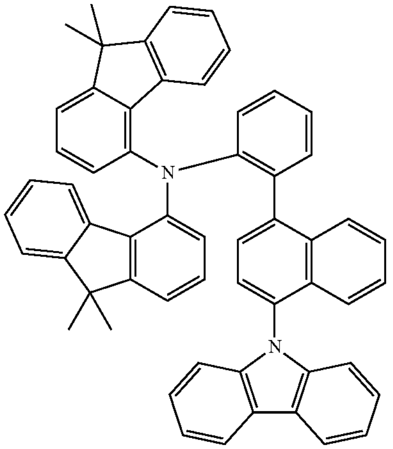
678
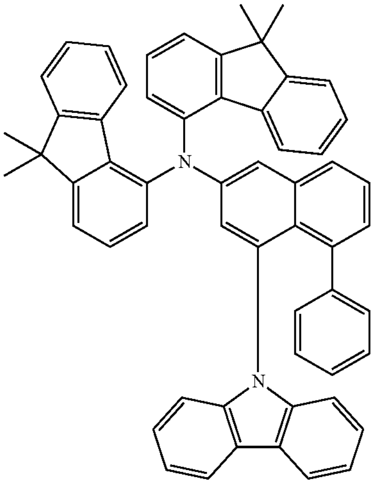
679
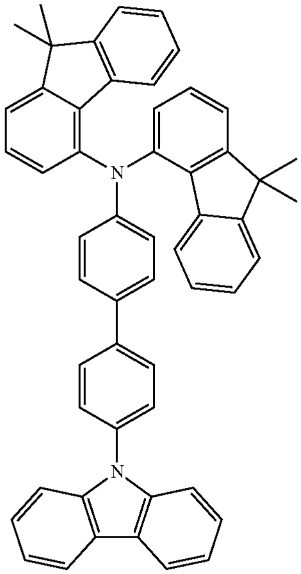

-continued
680
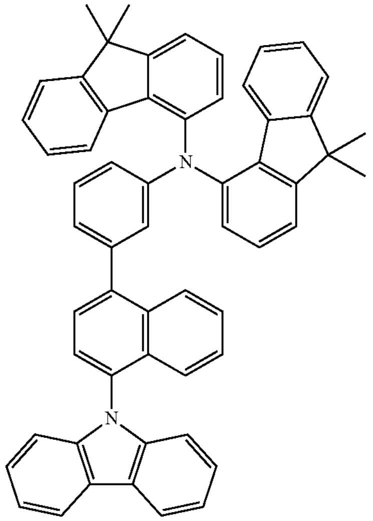
681
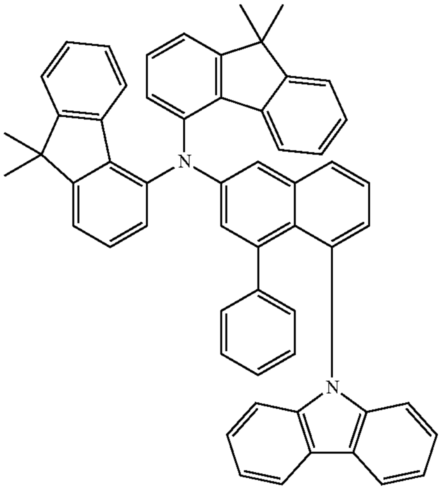
682
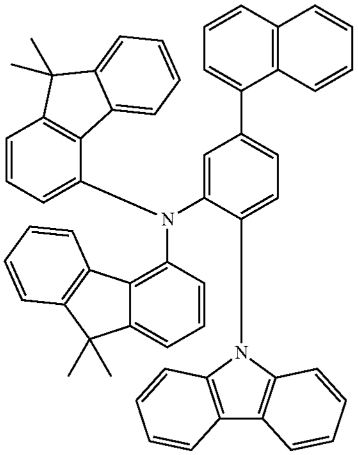
-continued
683
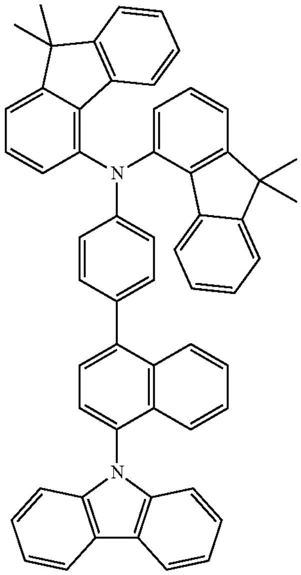
684
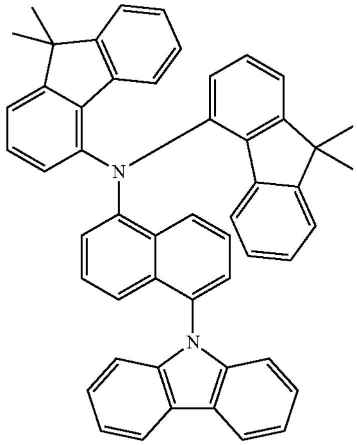
685
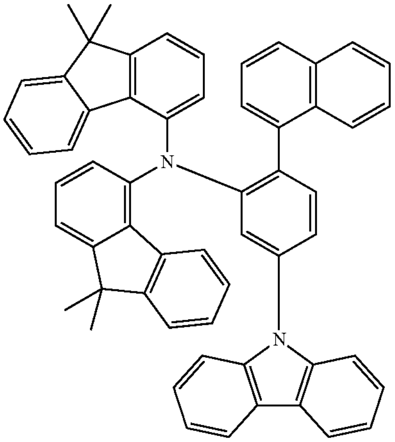

-continued
686
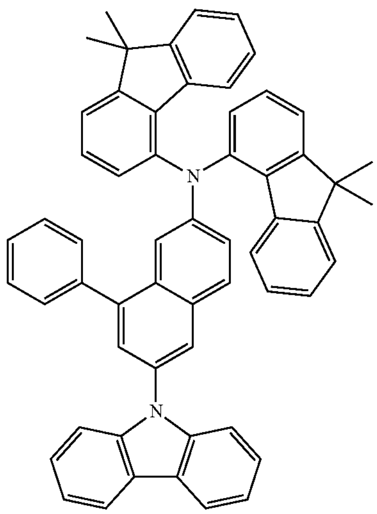
687
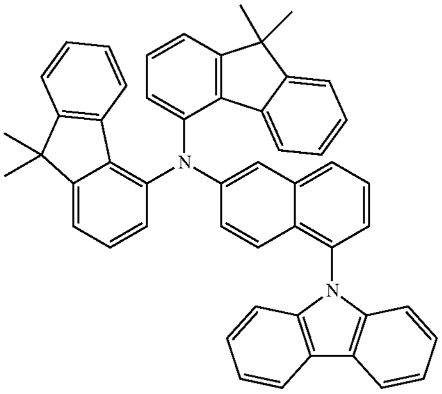
688
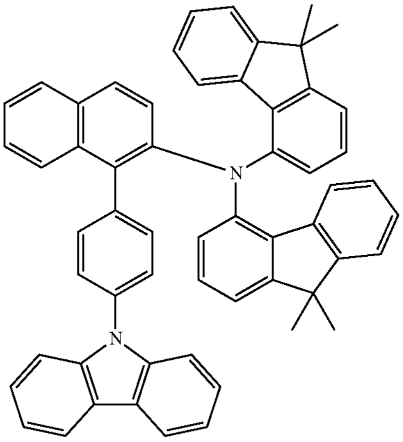
-continued
689
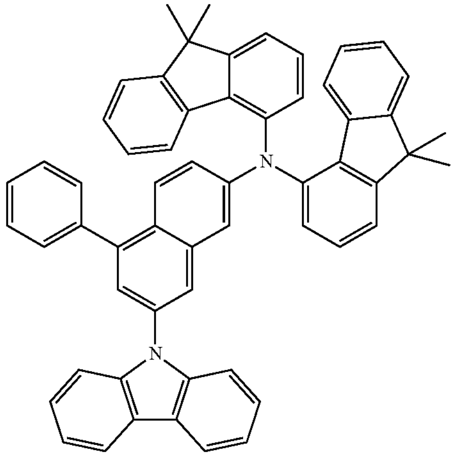
690
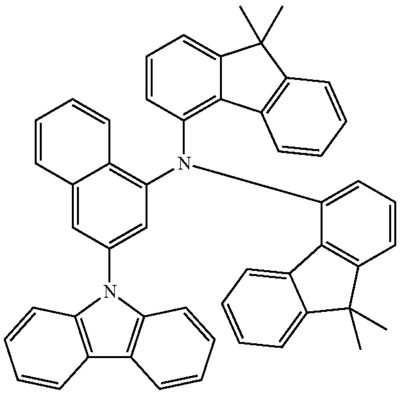
691
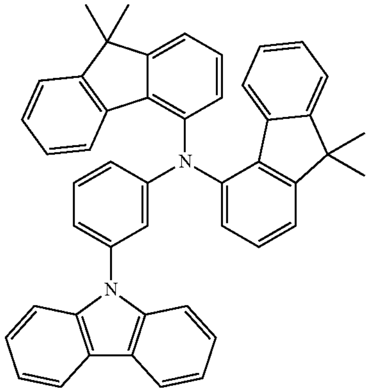
692
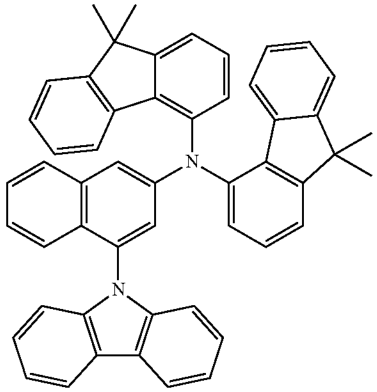

-continued
693
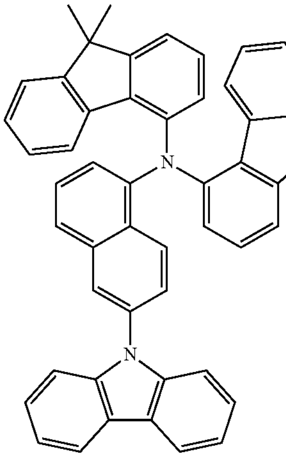
694
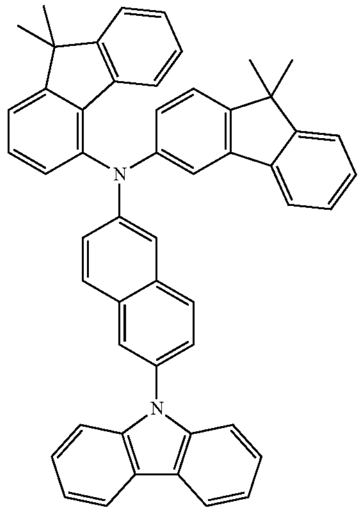
695
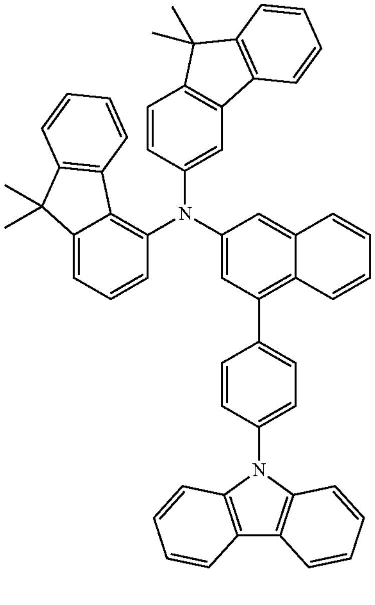
-continued
696
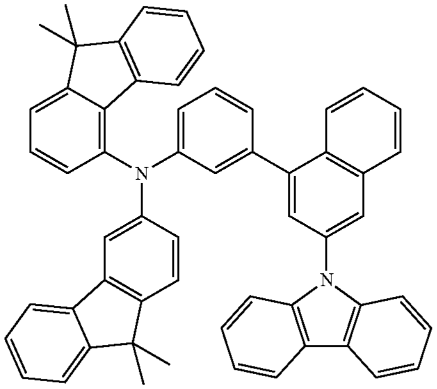
697
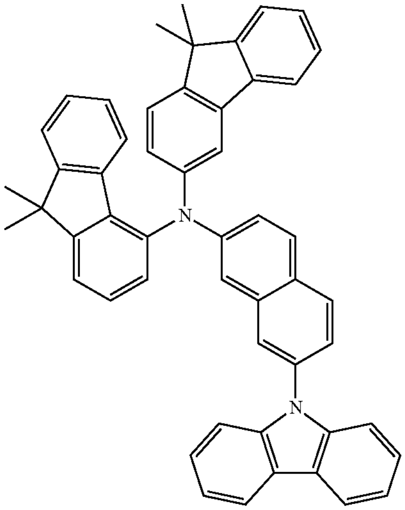
698
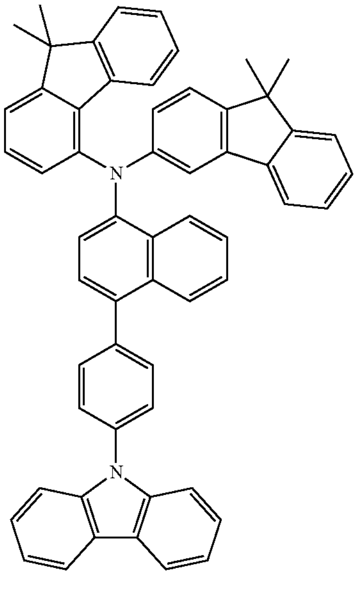

-continued
699
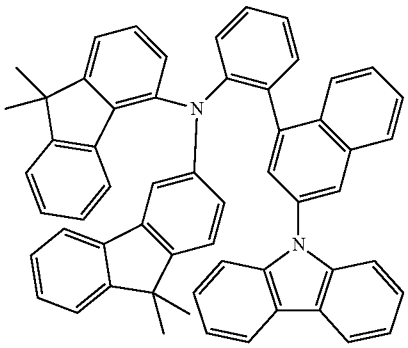
700
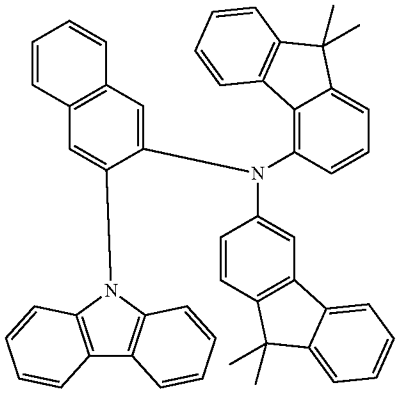
701
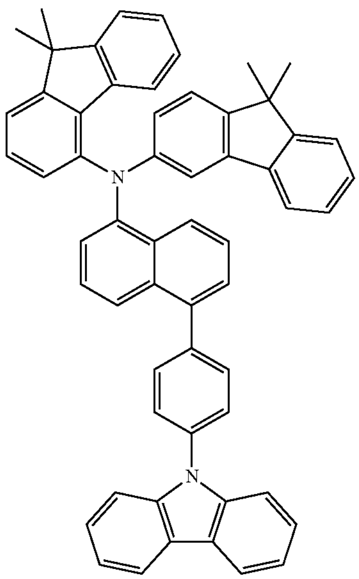
-continued
702
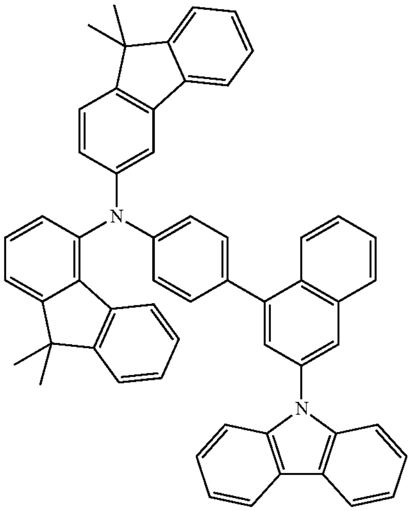
703
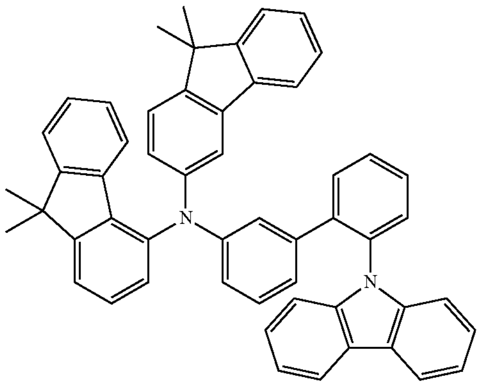
704
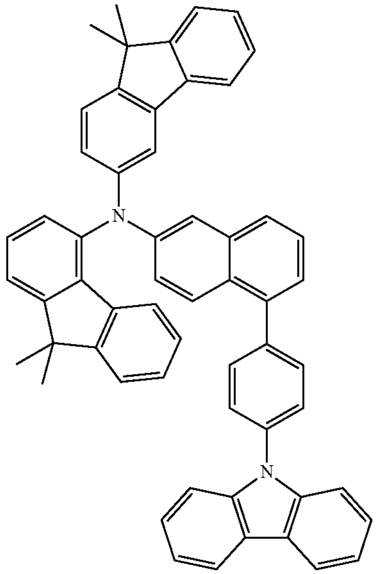

-continued
705
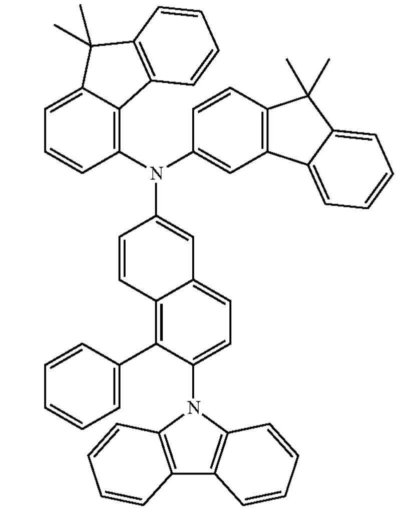
706
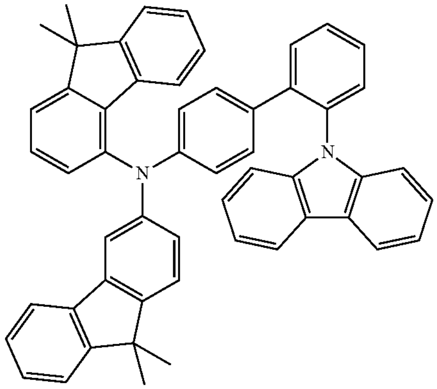
707
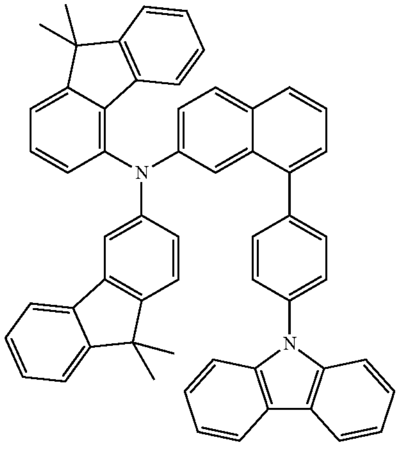
-continued
708
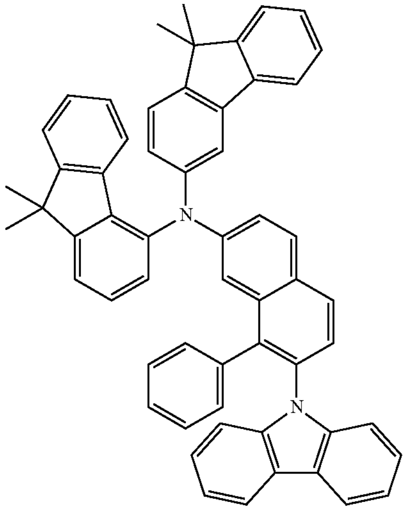
709
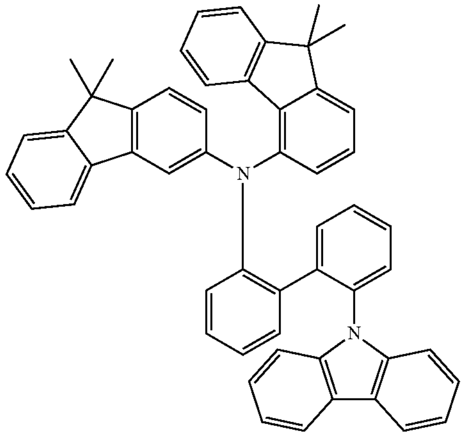
710
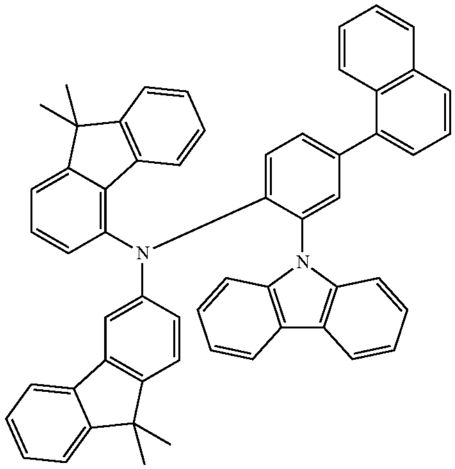

-continued
711
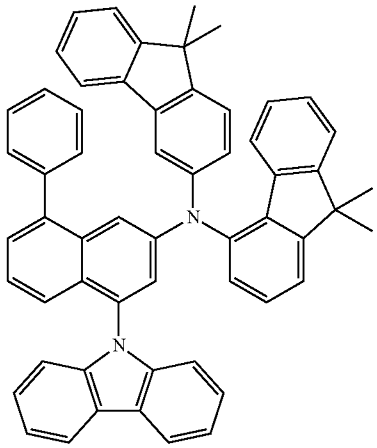
712
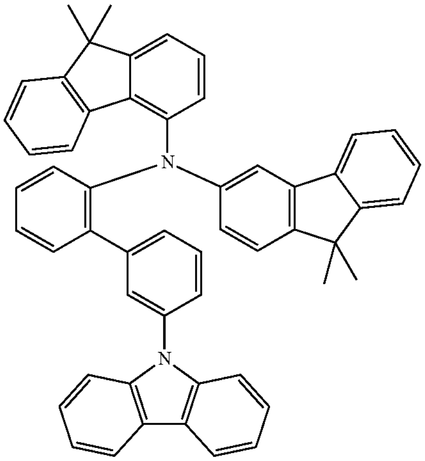
713
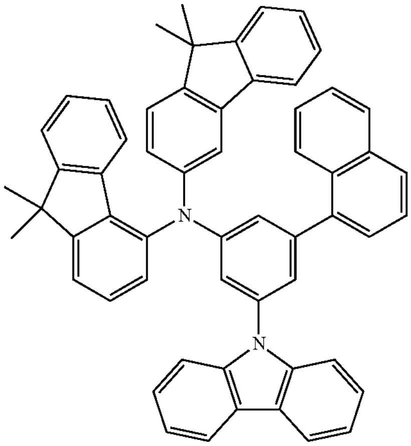
-continued
714
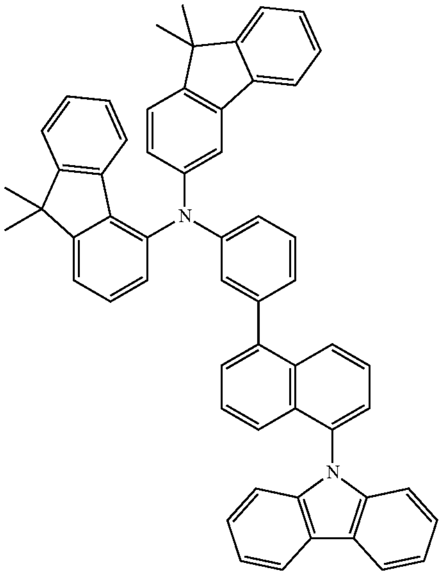
715
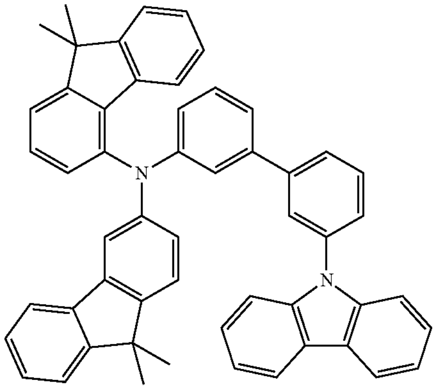
716
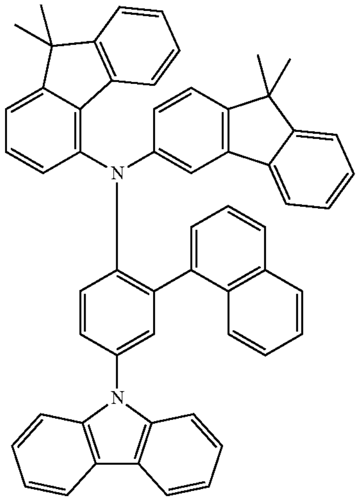

-continued
717
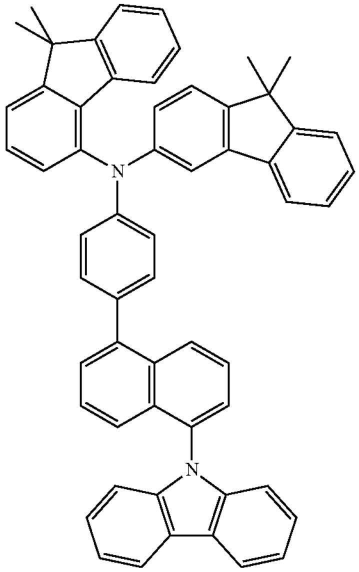
718
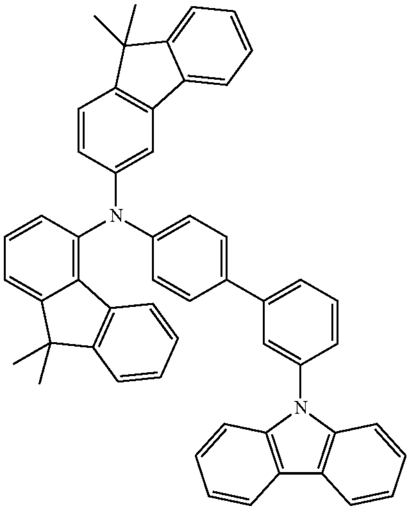
719
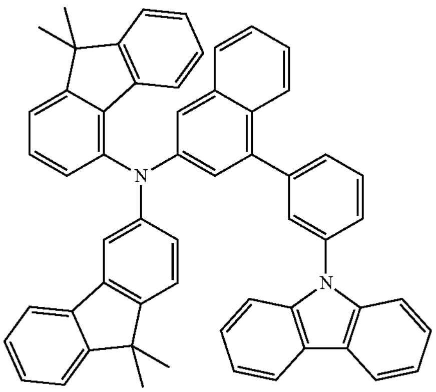
-continued
720
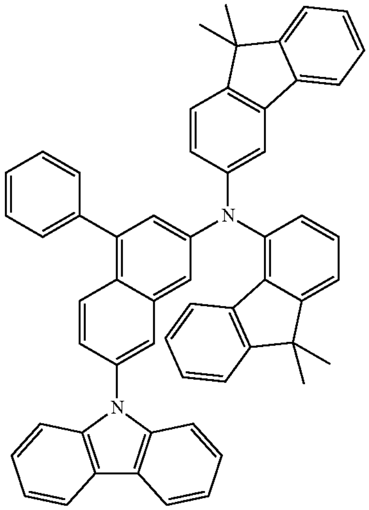
721
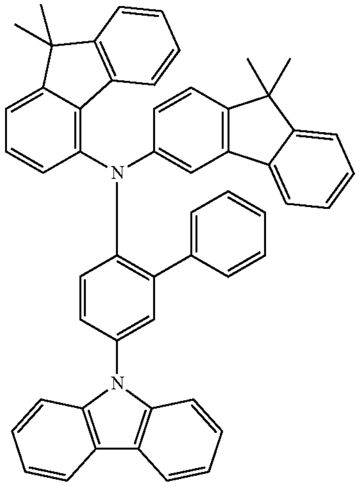
722
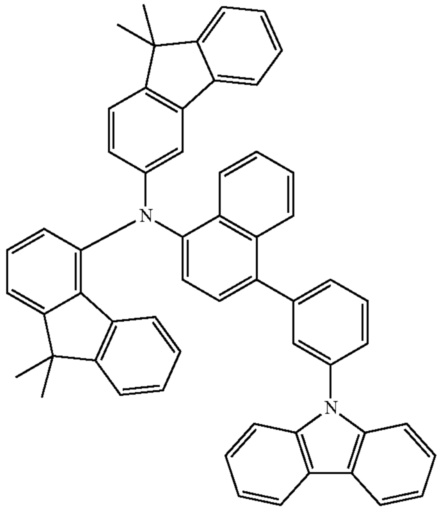

-continued
723
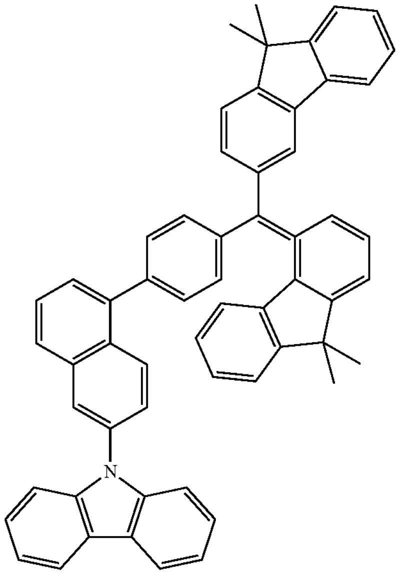
724
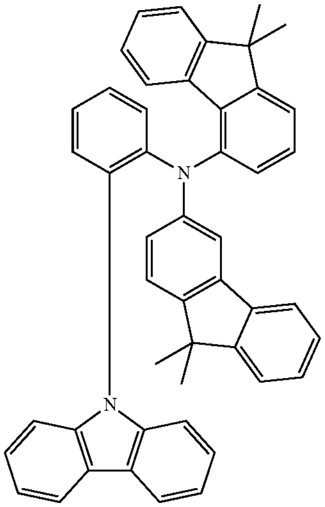
725
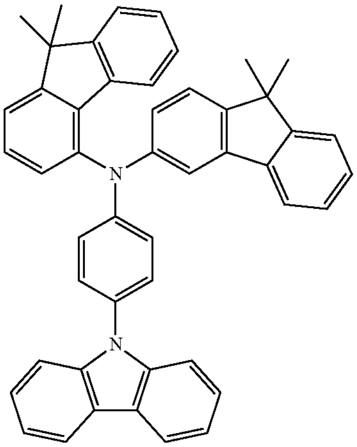
-continued
726
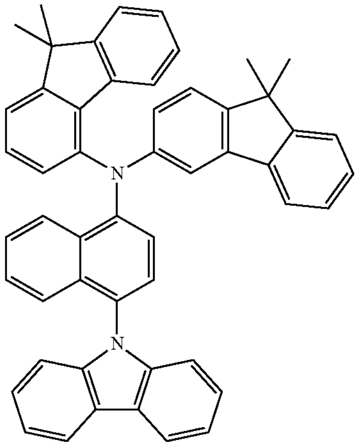
727
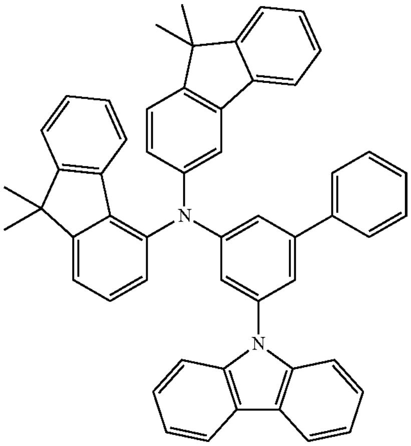
728
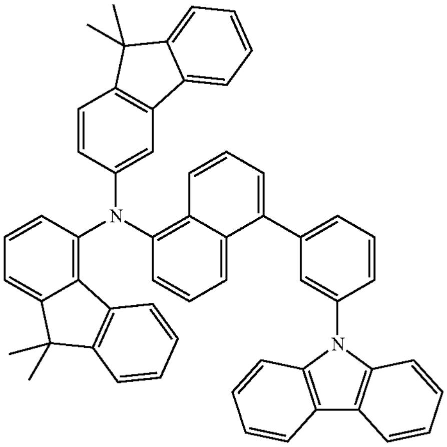

729
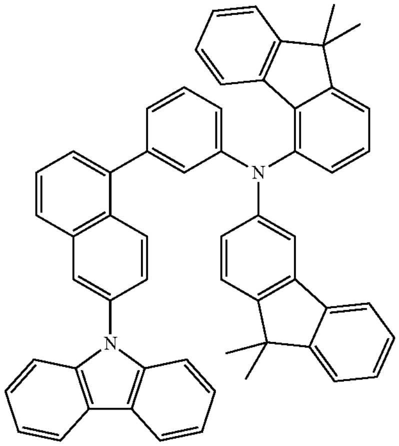
730
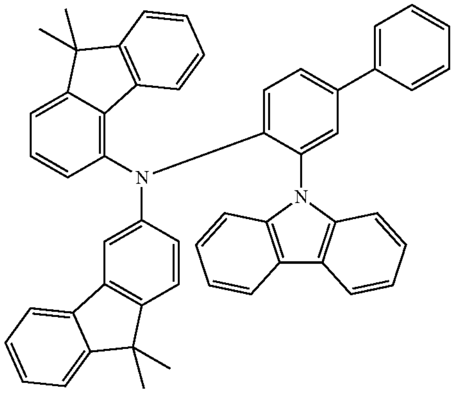
731
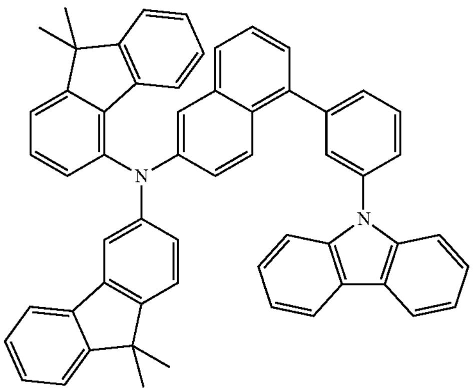
732
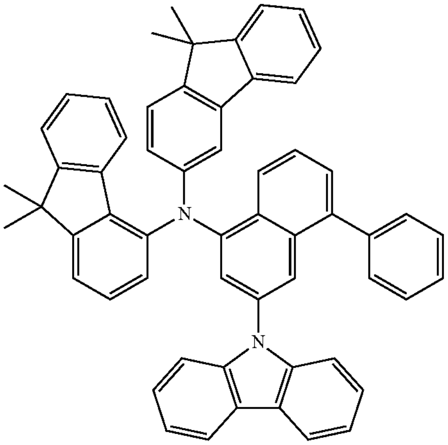
733
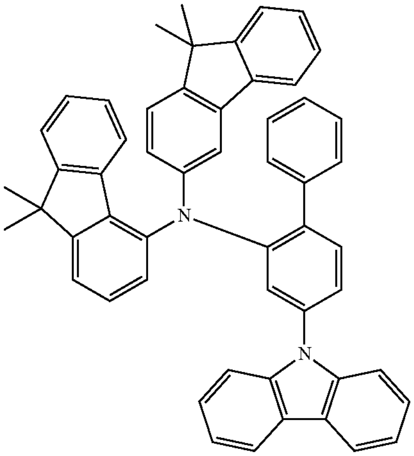
734
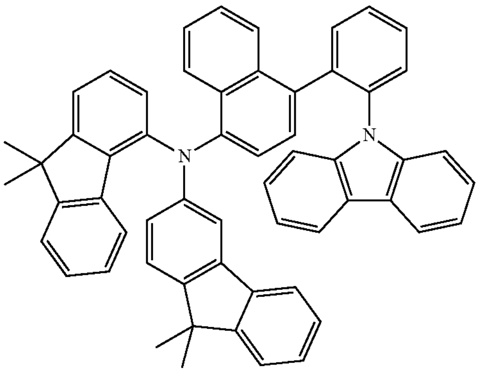

-continued
735
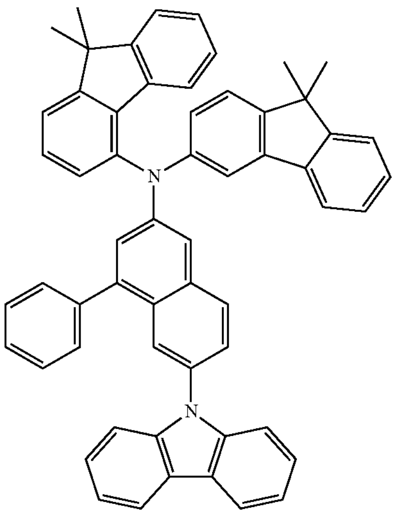
736
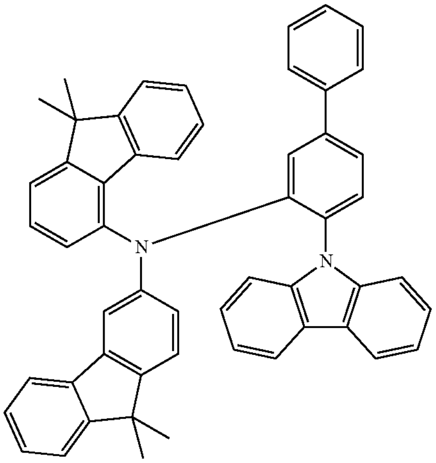
737
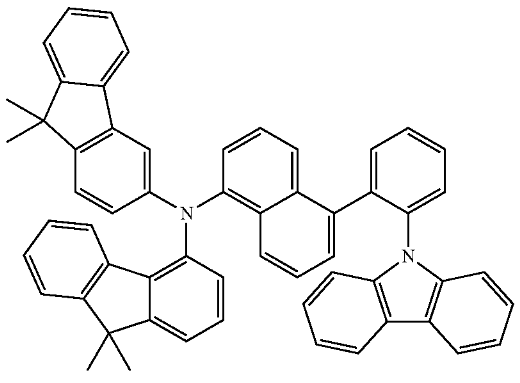
-continued
738
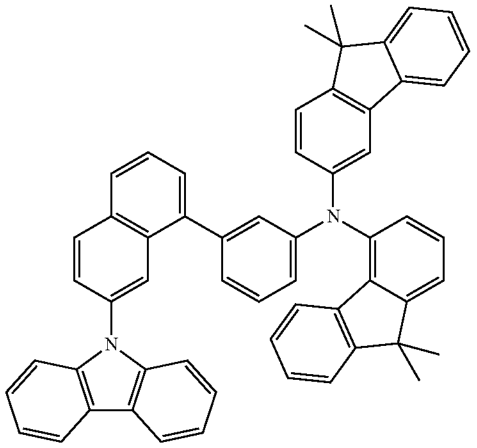
739
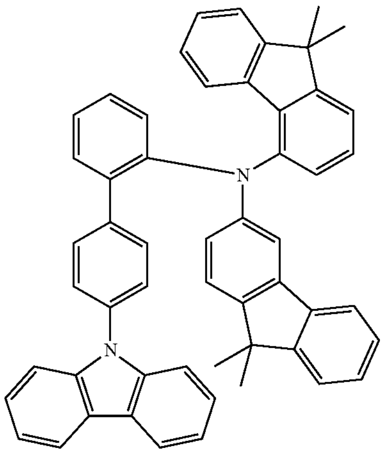
740
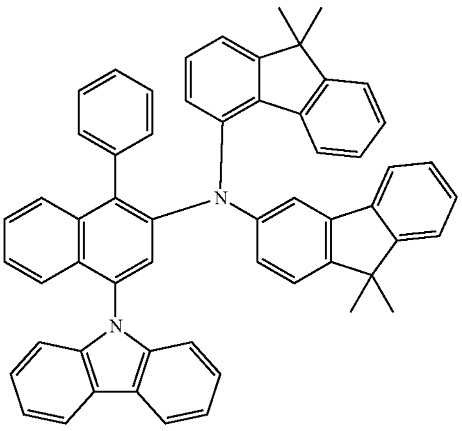

-continued
741
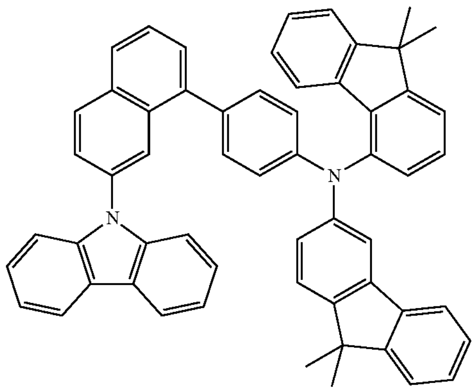
742
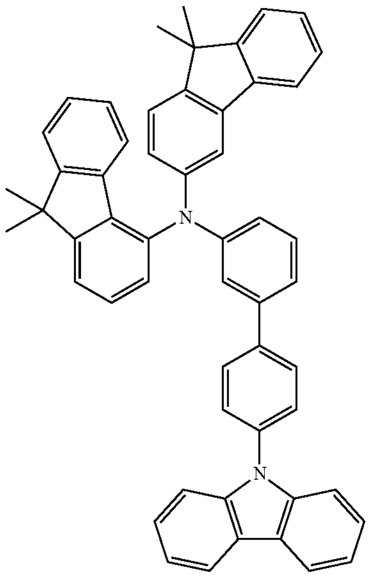
743
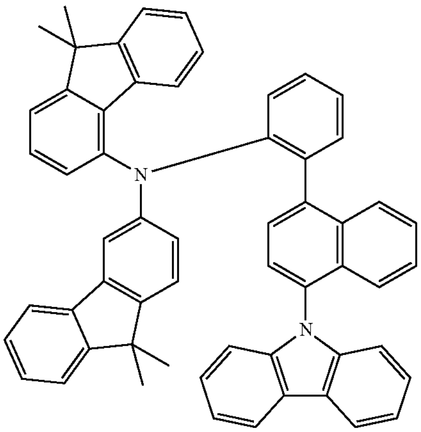
-continued
744
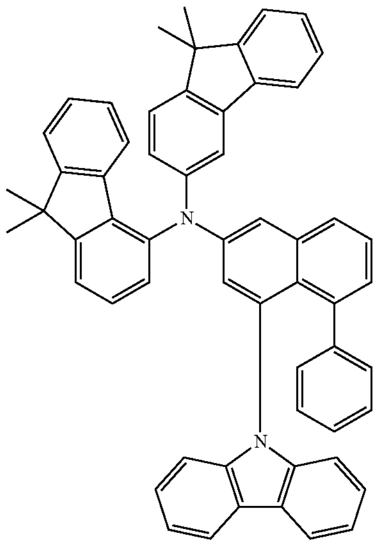
745
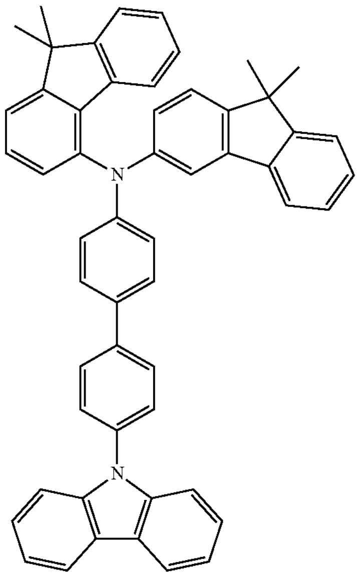

-continued
746
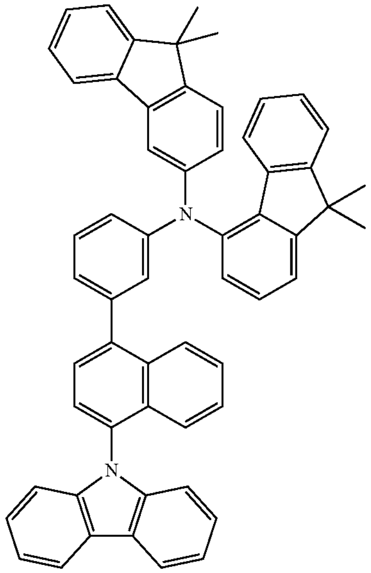
747
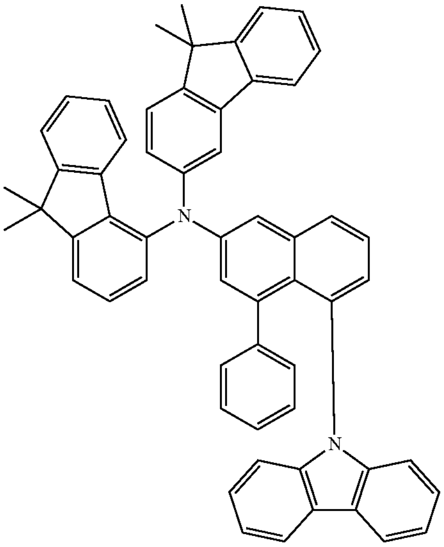
748
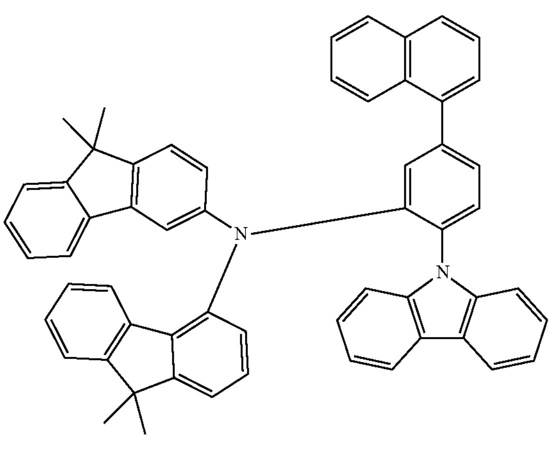
-continued
749
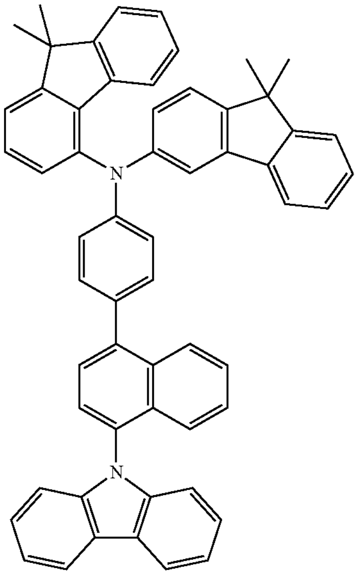
750
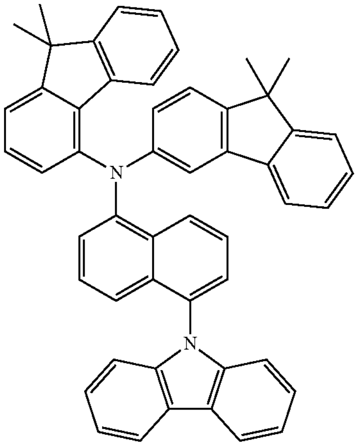
751
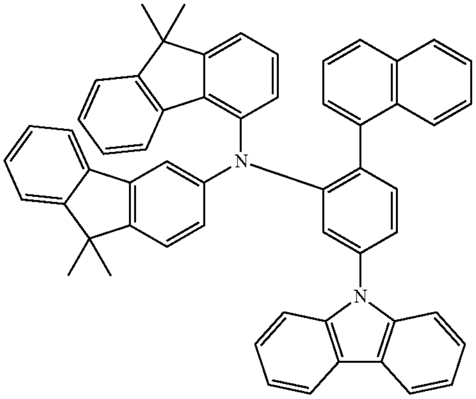

-continued
752
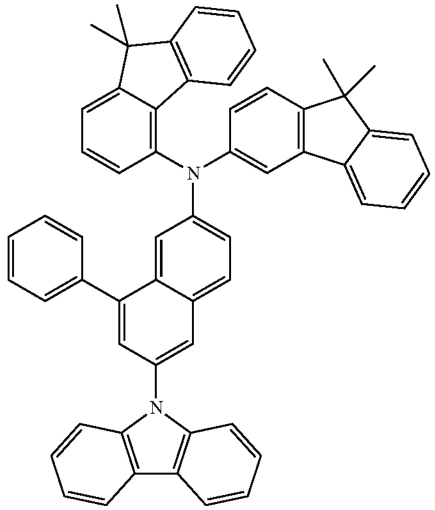
753
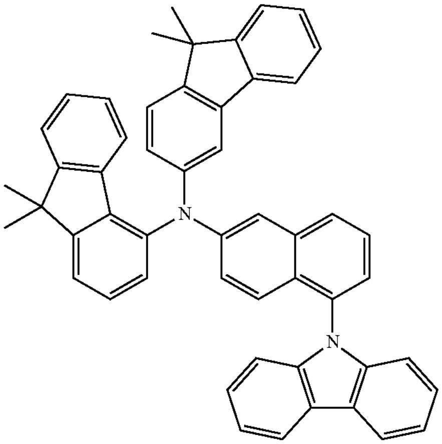
754
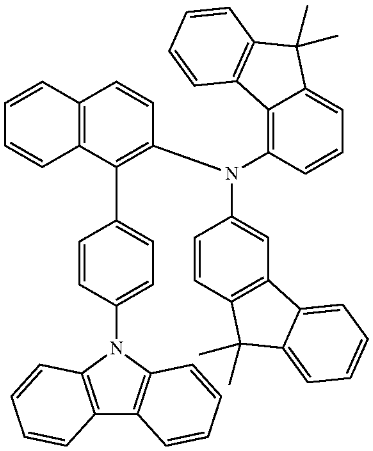
-continued
755
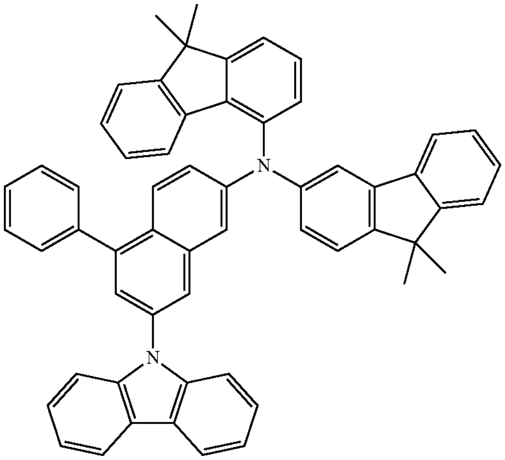
756
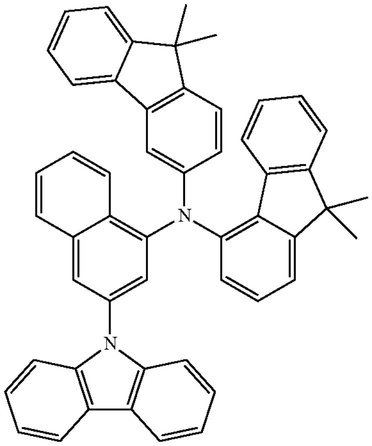
757
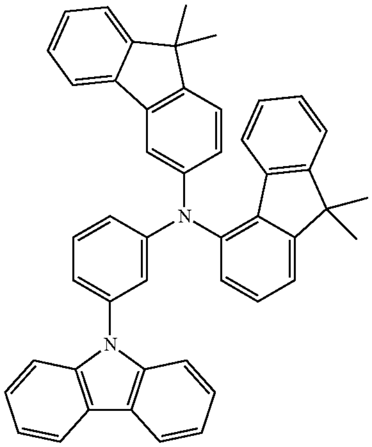

-continued
758
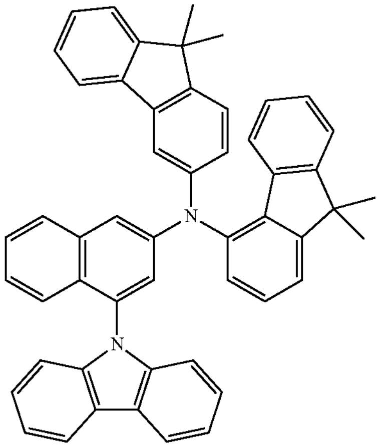
759
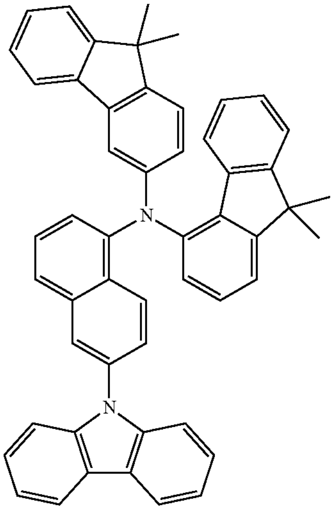
760
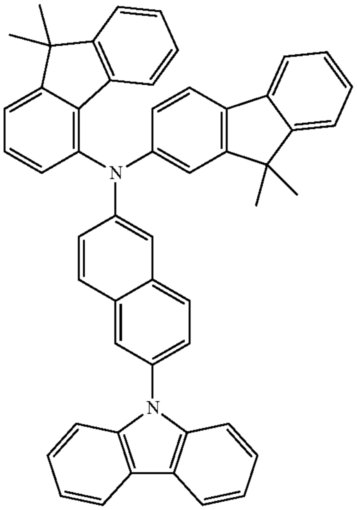
-continued
761
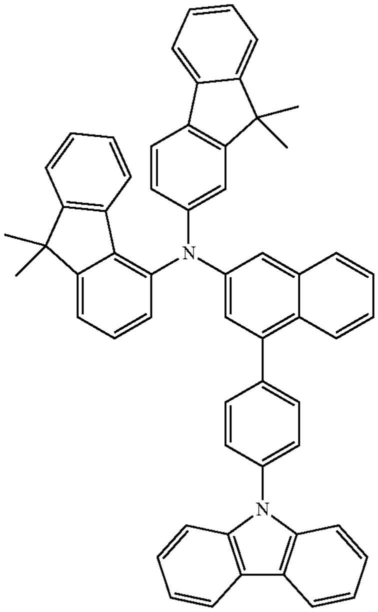
762
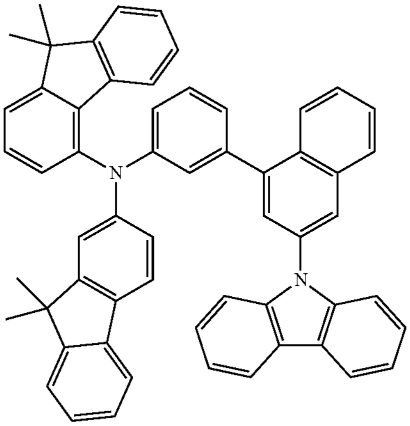
763
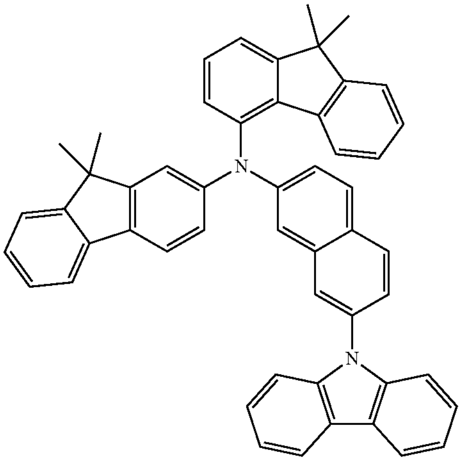

-continued
764
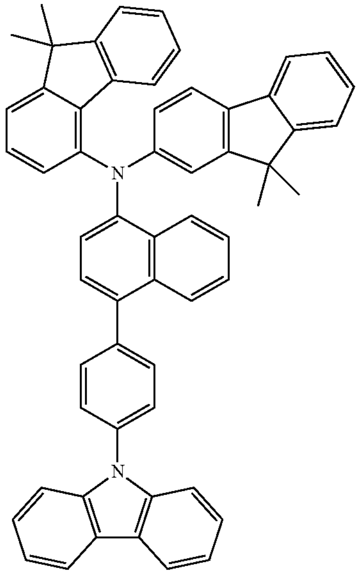
765
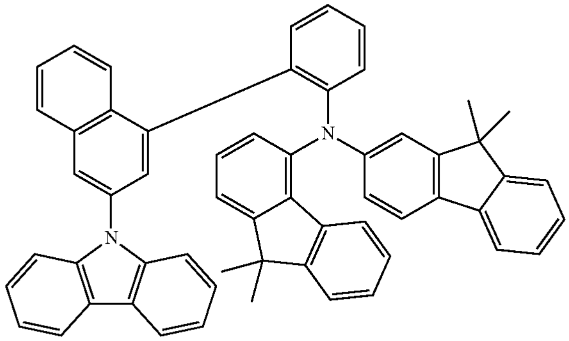
766
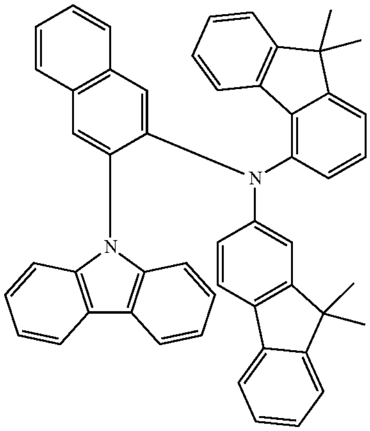
-continued
767
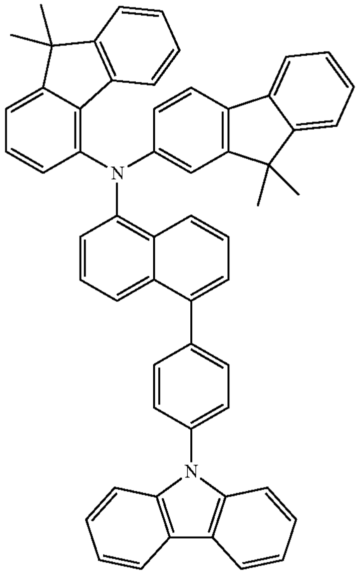
768
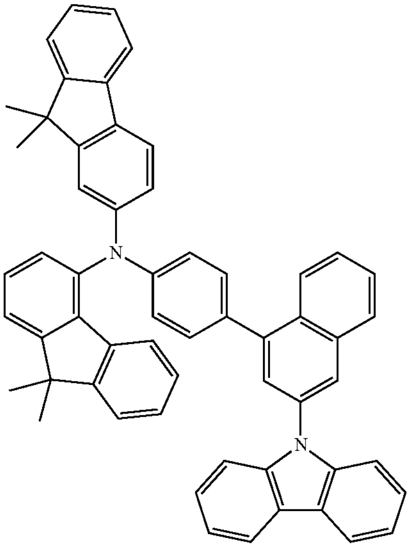
769
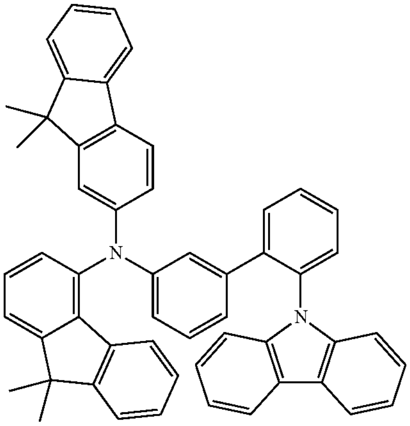

-continued
770
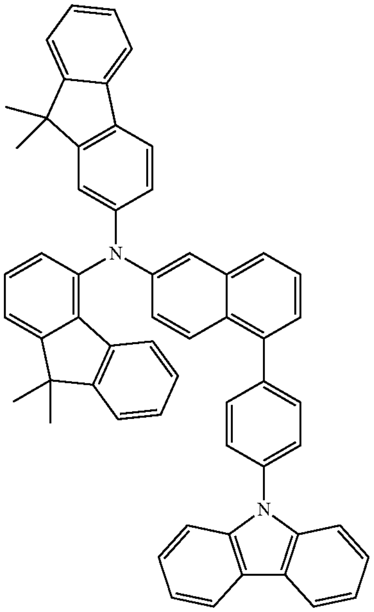
771
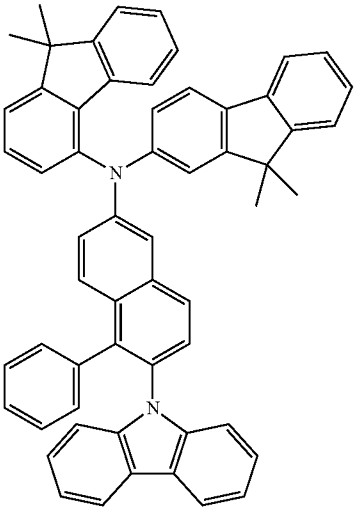
772
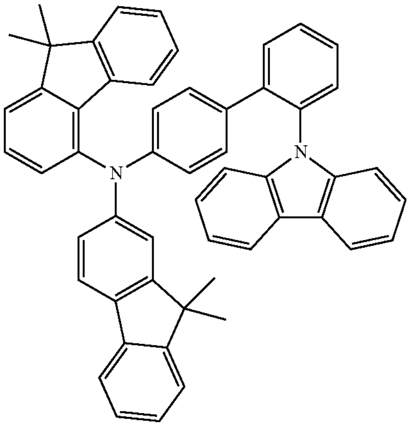
-continued
773
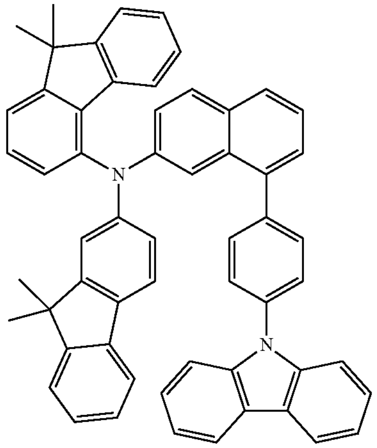
774
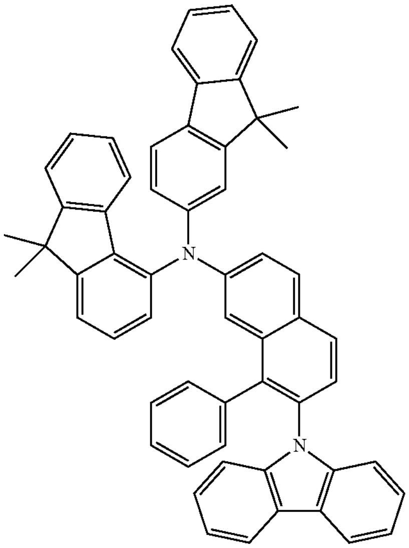
775
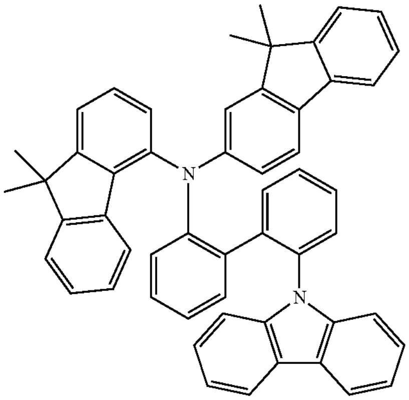

-continued
776
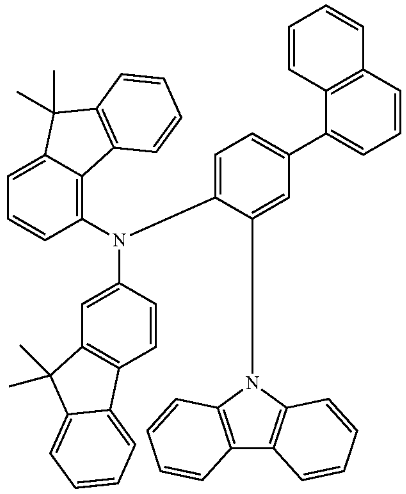
777
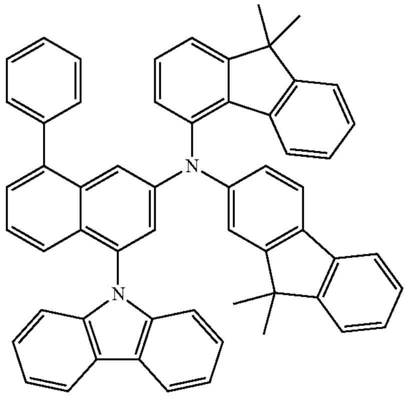
778
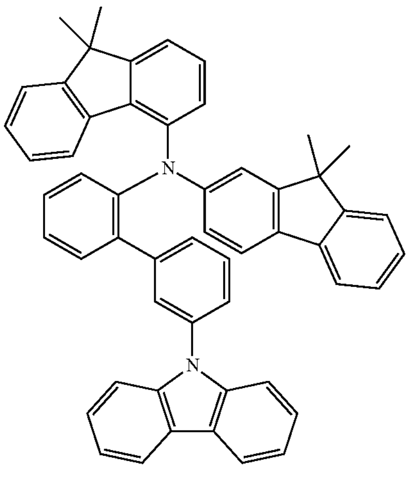
-continued
779
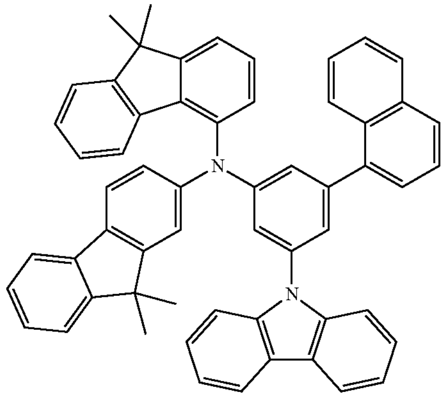
780
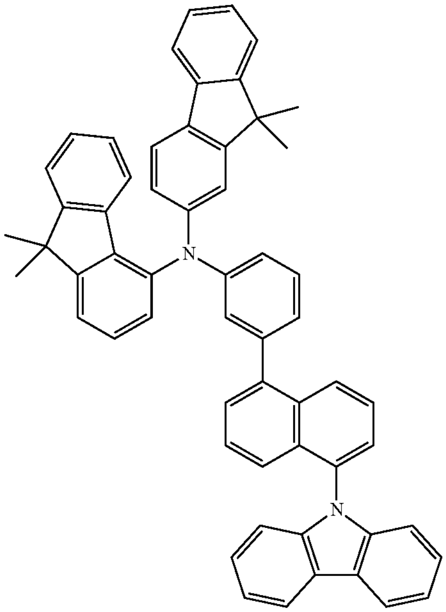
781
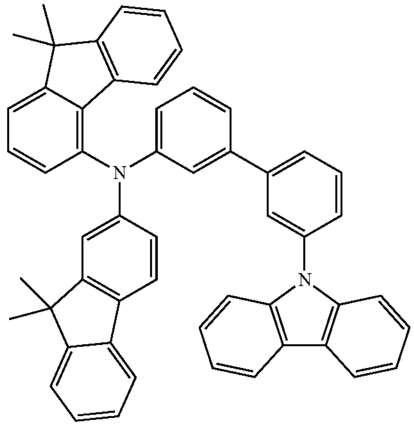

-continued
782
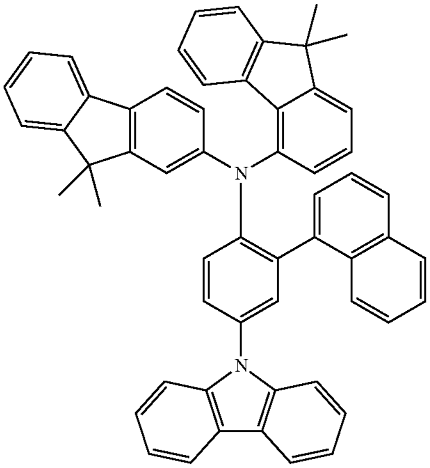
783
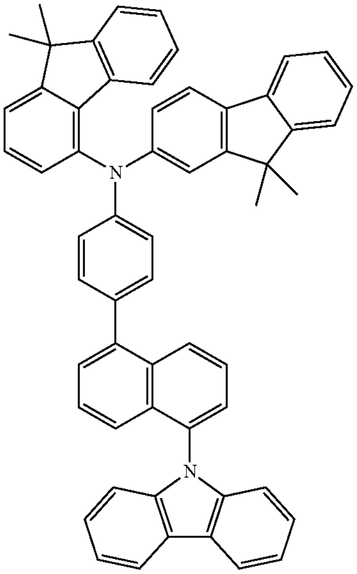
784
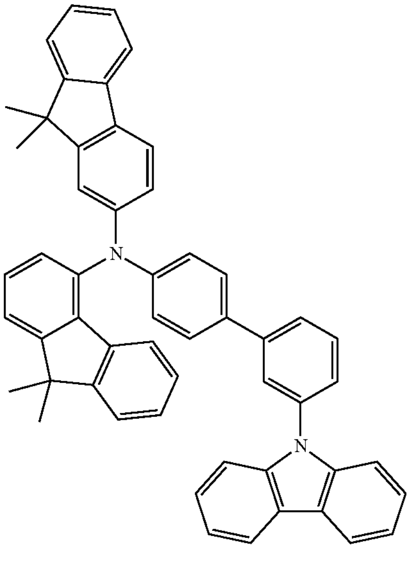
785
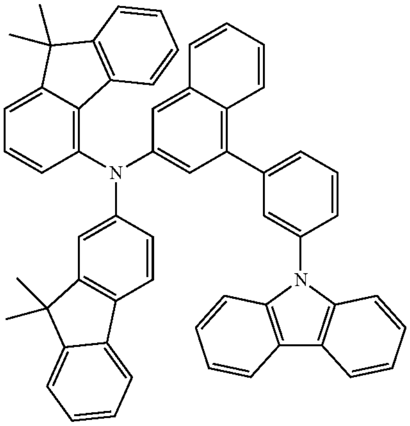
786
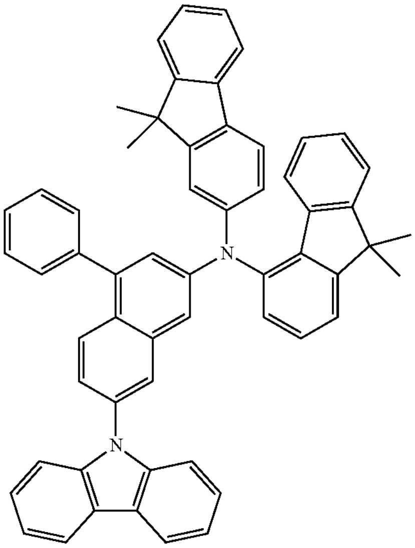
787
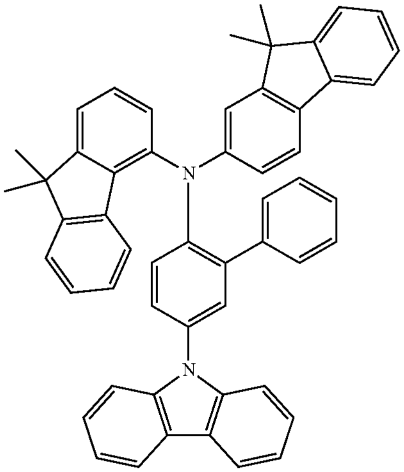

-continued
788
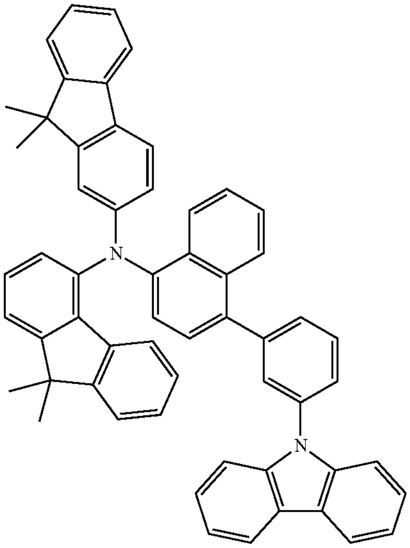
789
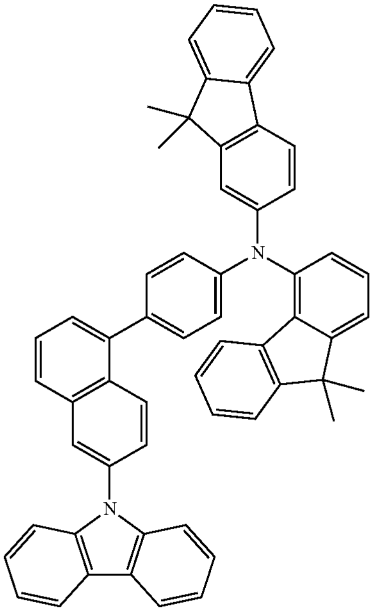
790
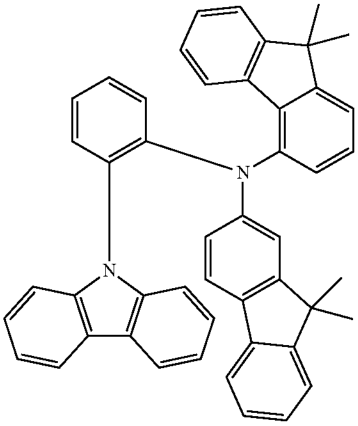
-continued
791
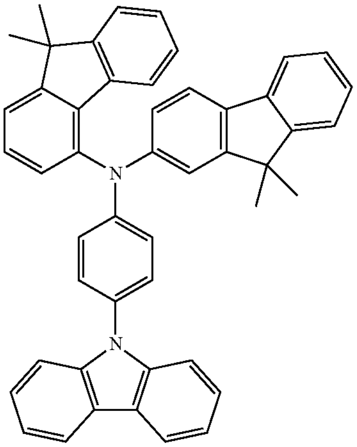
792
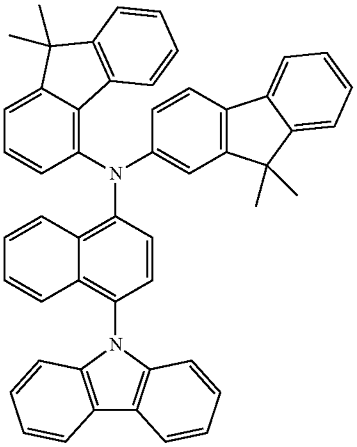
793
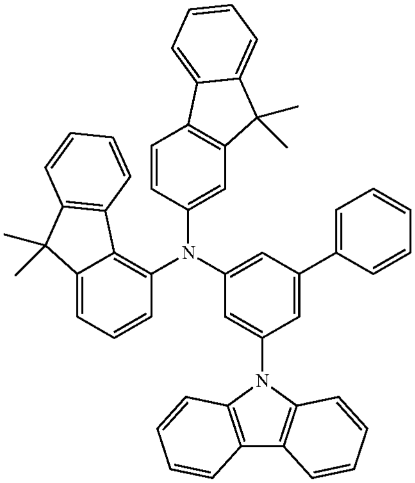

-continued
794
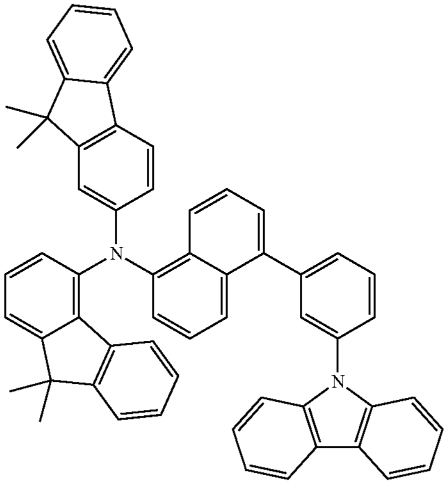
795
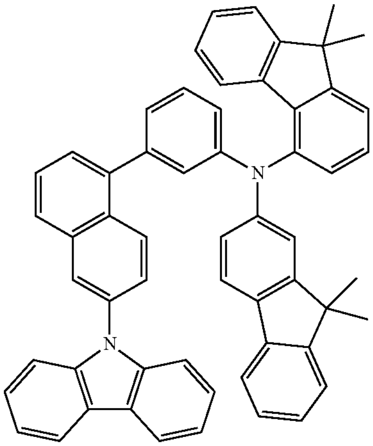
796
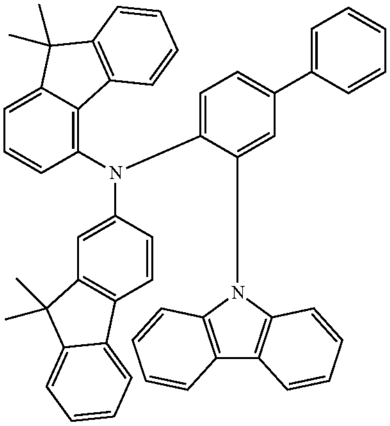
-continued
797
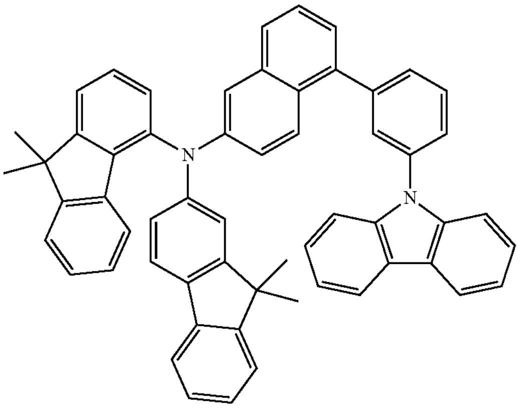
798
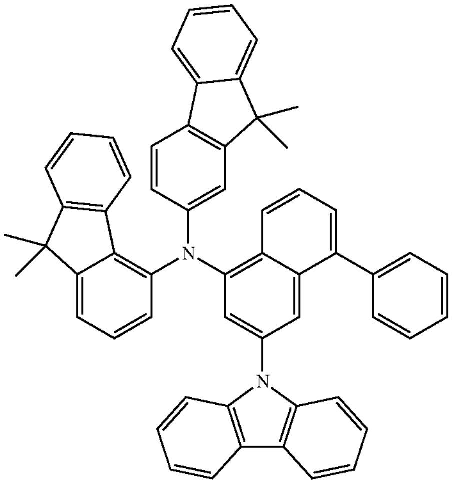
799
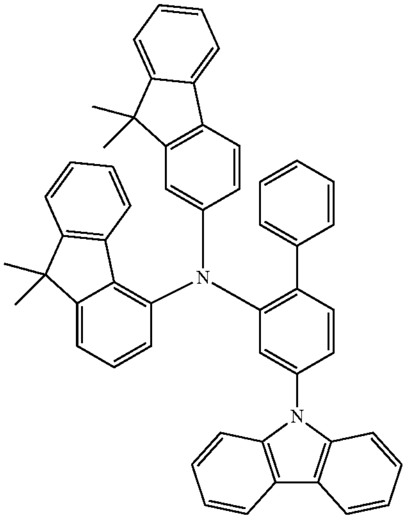

-continued
800
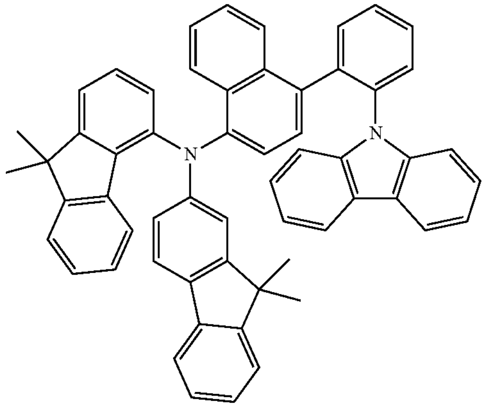
801
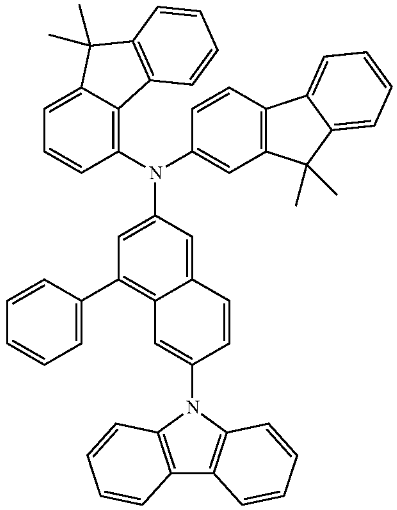
802
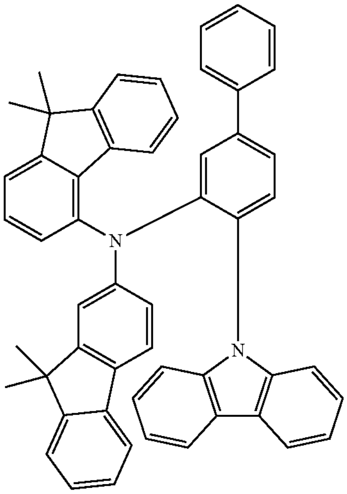
-continued
803
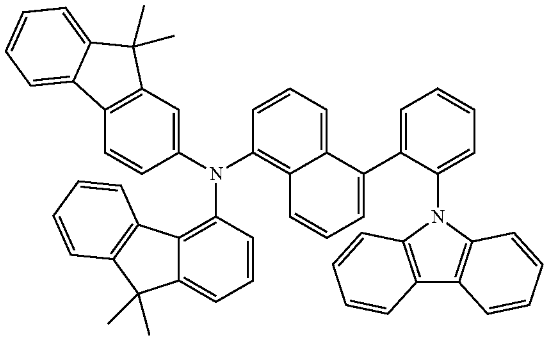
804
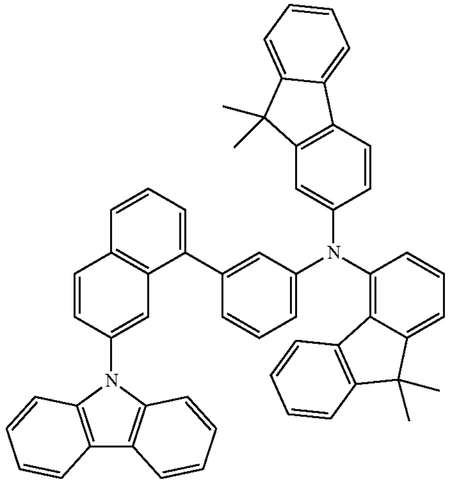
805
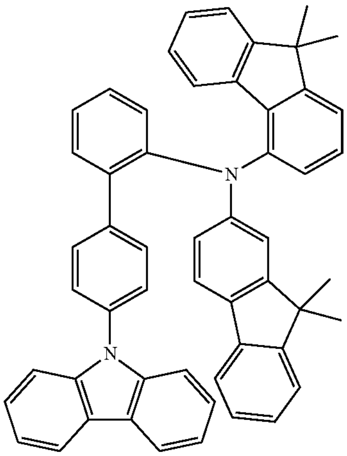

-continued
806
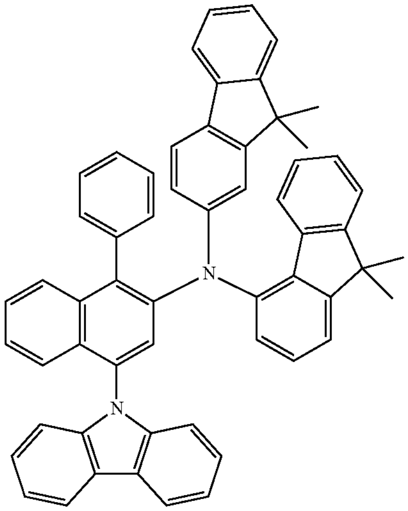
807
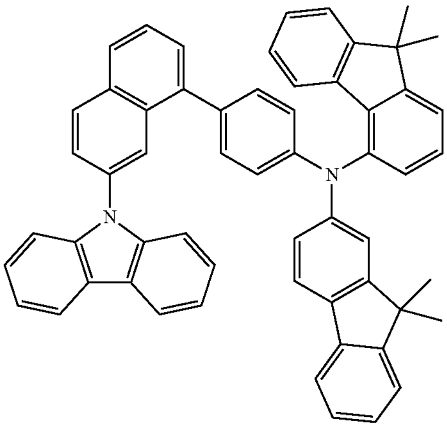
808
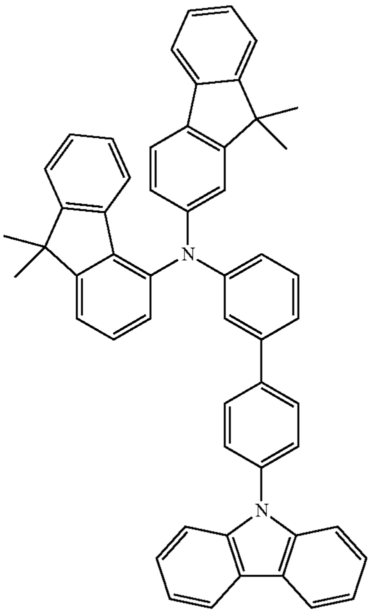
-continued
809
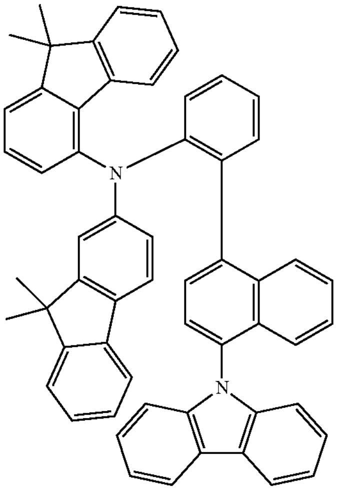
810
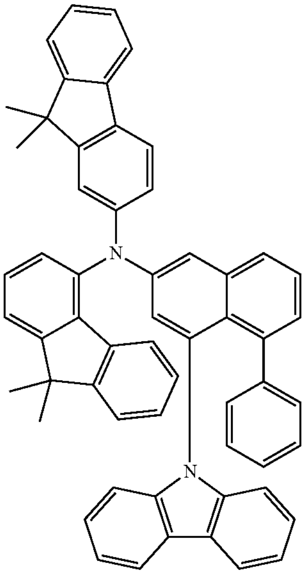
811
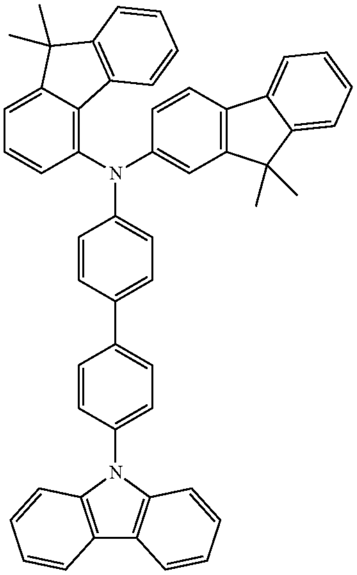

-continued
812
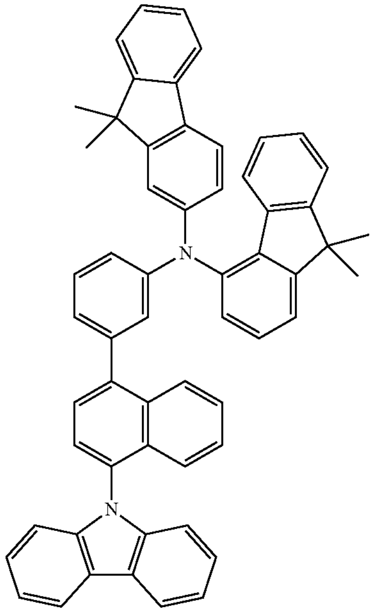
813
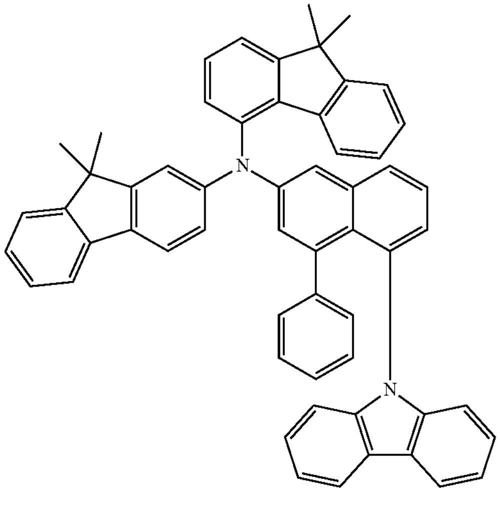
814
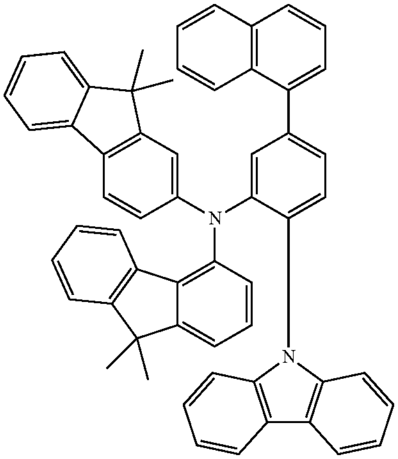
-continued
815
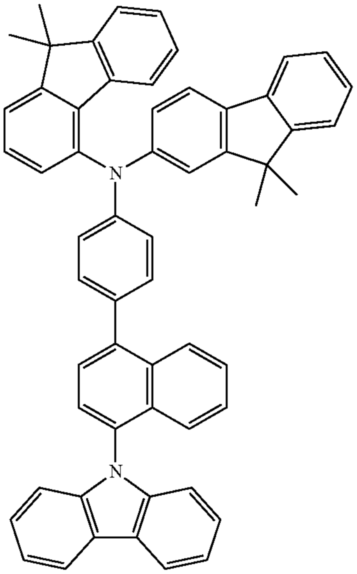
816
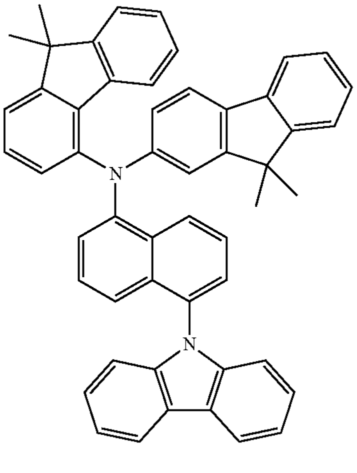
817
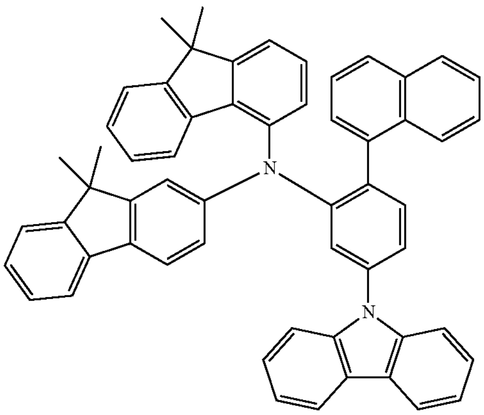

-continued
818
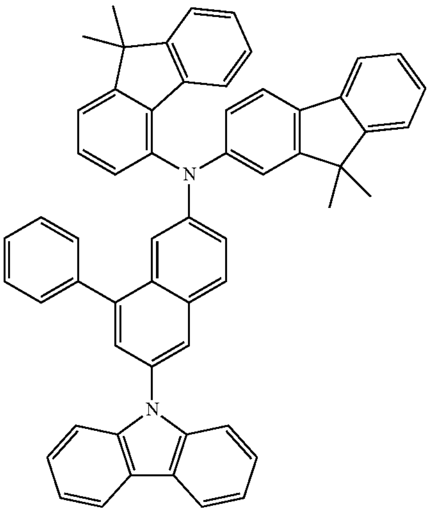
819
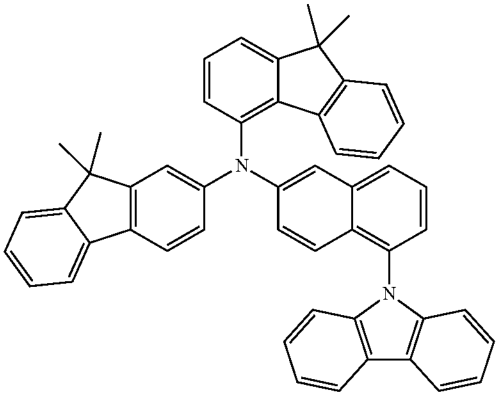
820
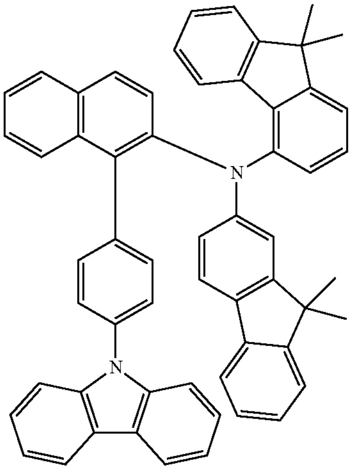
-continued
821
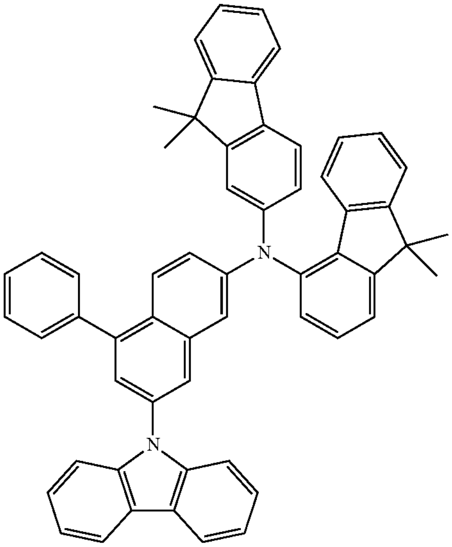
822
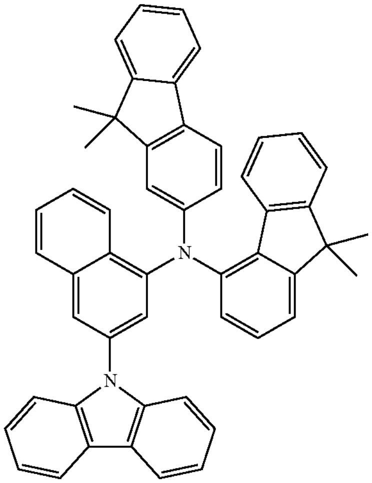
823
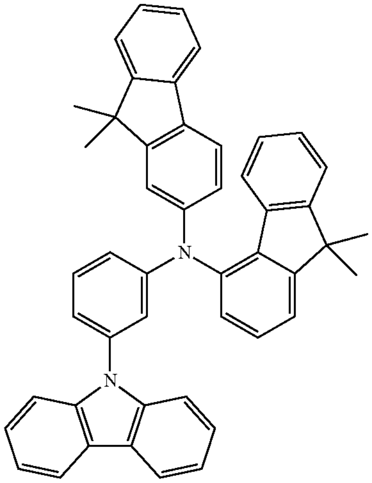

-continued
824
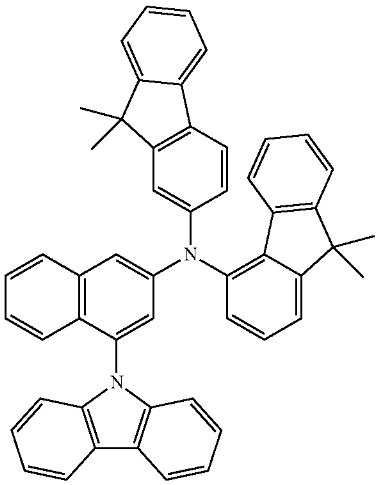
825
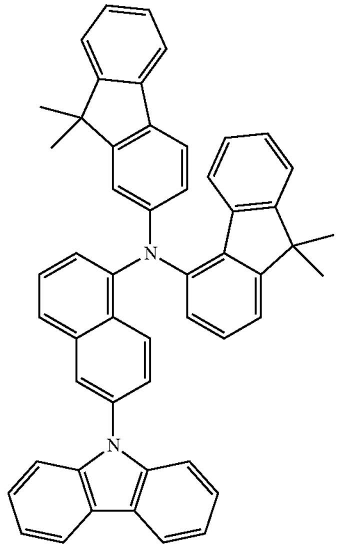
826
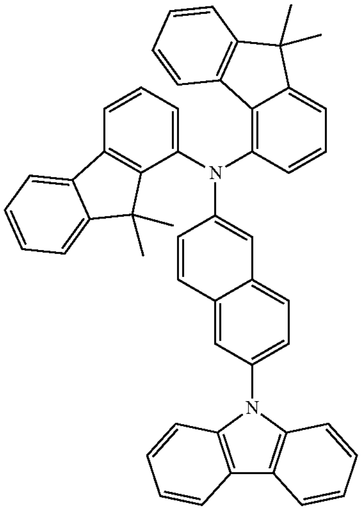
-continued
827
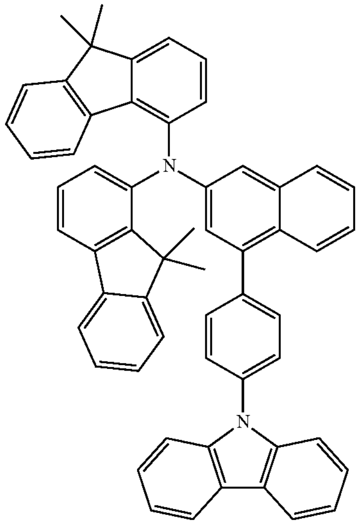
828
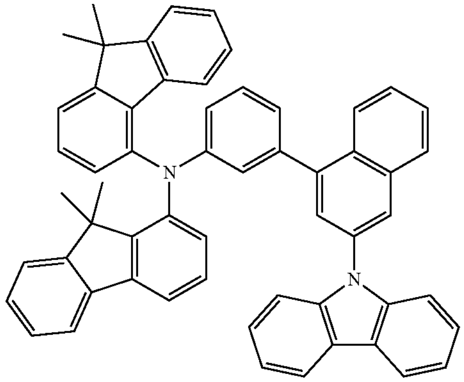
829
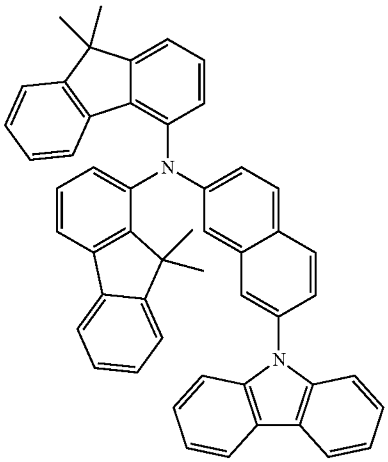

-continued
830
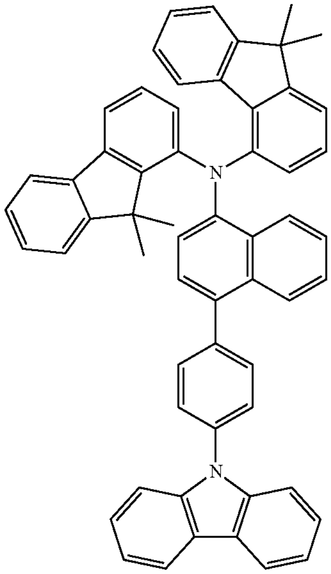
831
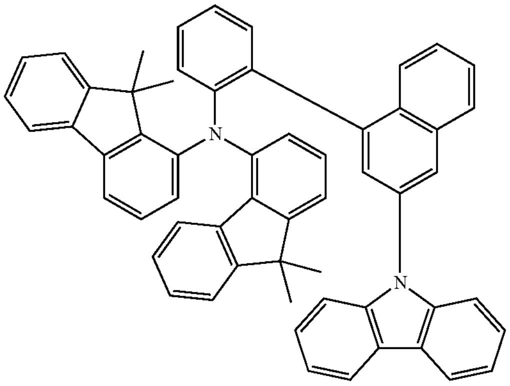
832
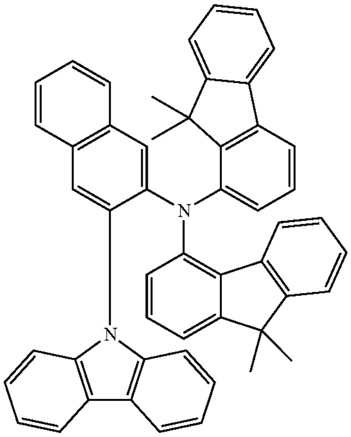
-continued
833
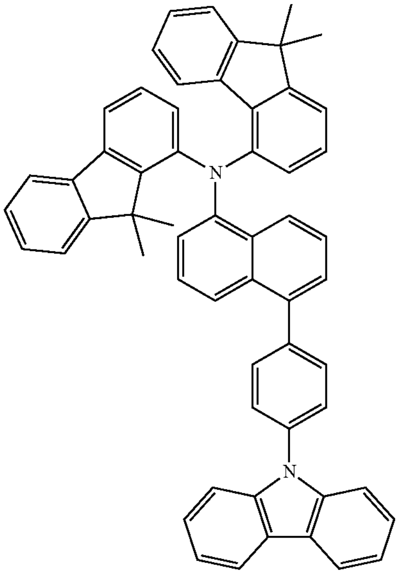
834
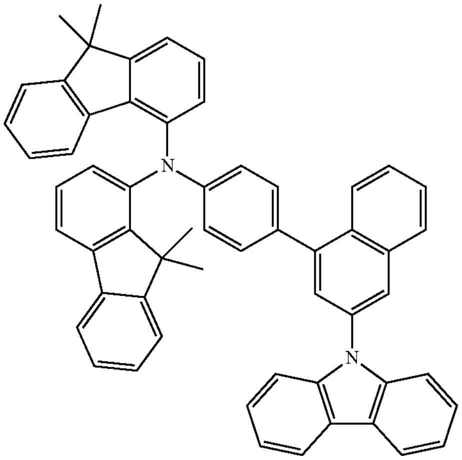
835
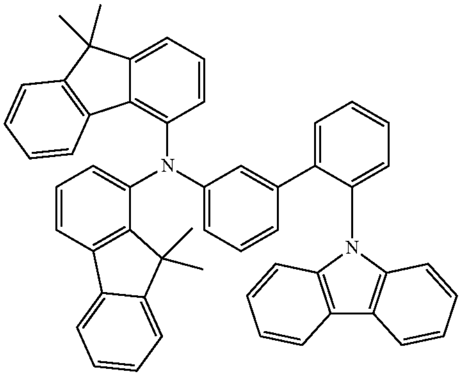

-continued
836
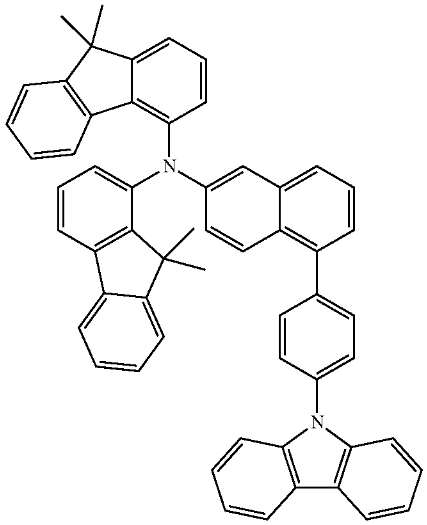
837
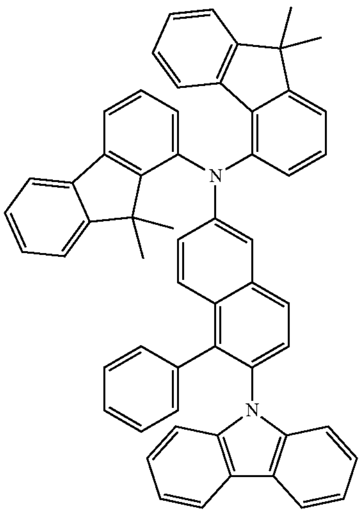
838
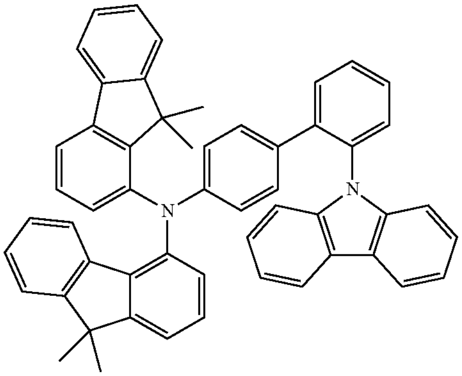
-continued
839
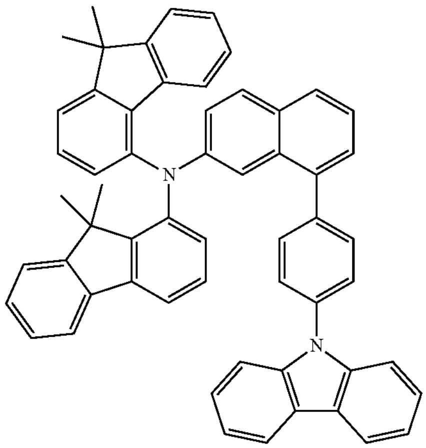
840
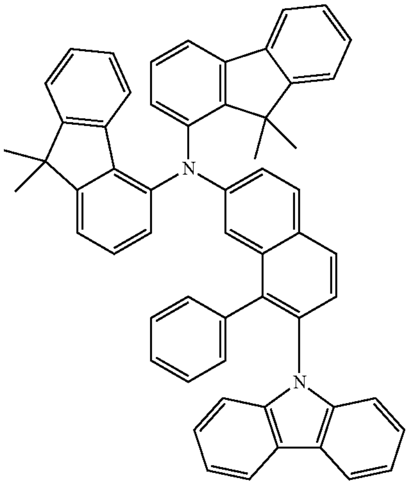
841
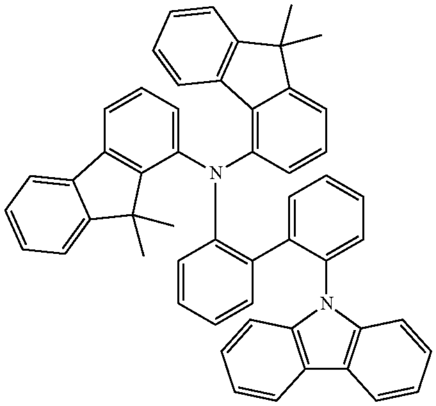

-continued
842
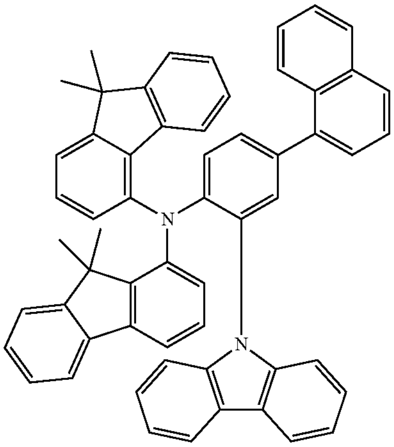
843
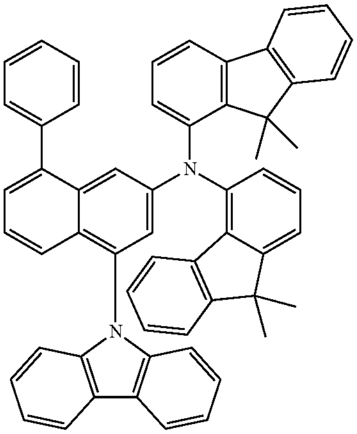
844
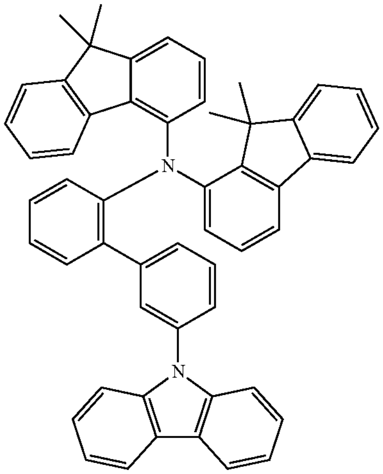
-continued
845
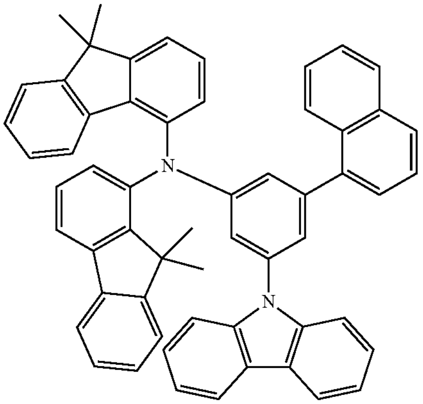
846
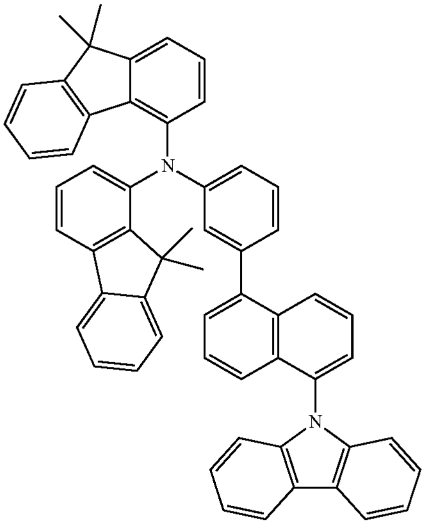
847
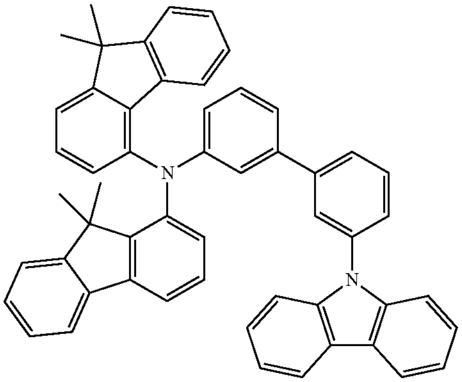

-continued
848
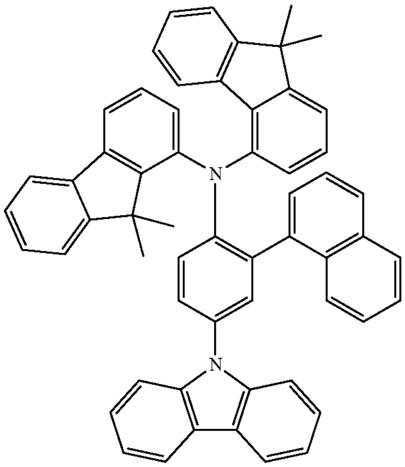
849
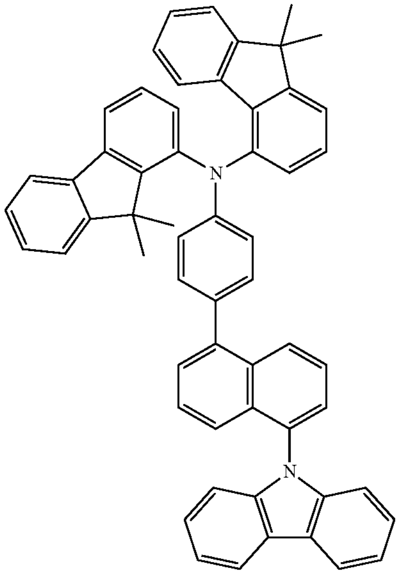
850
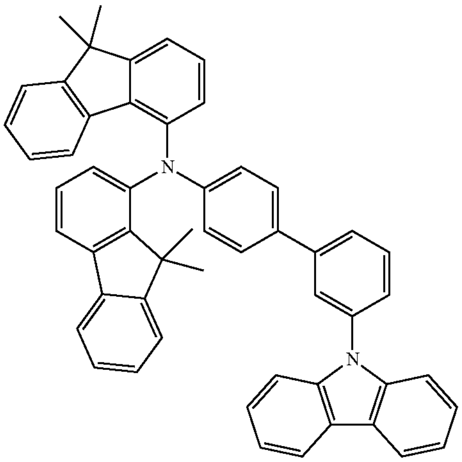
-continued
851
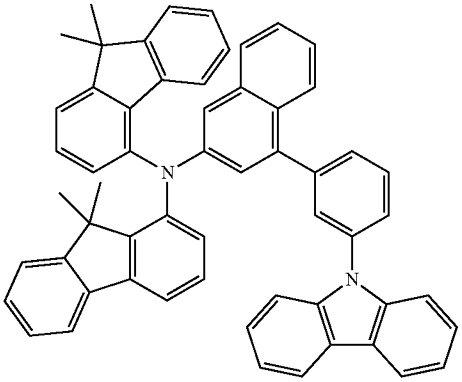
852
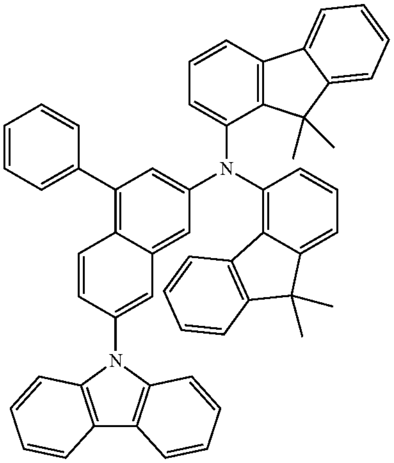
853
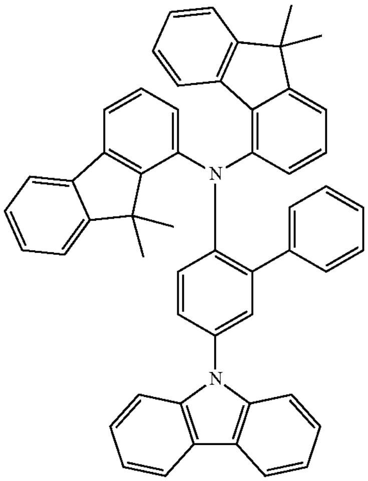

-continued
854
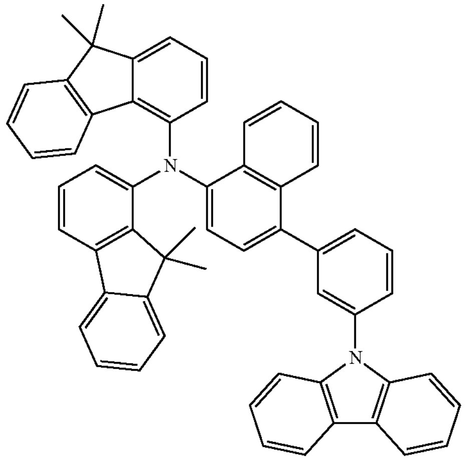
855
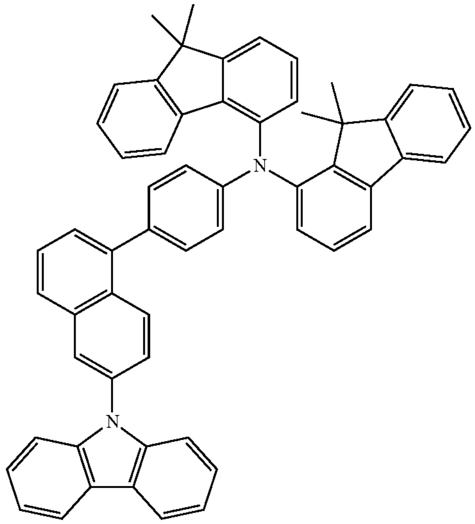
856
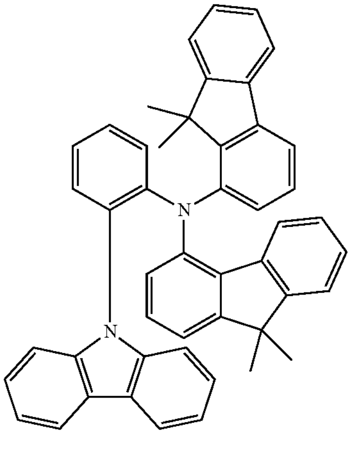
-continued
857
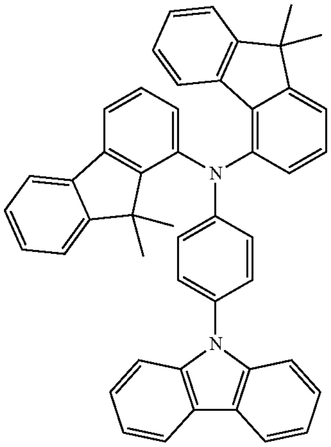
858
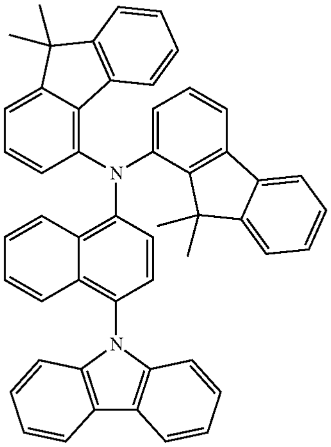
859
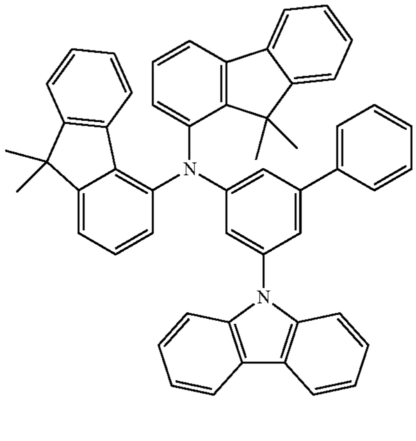

-continued
860
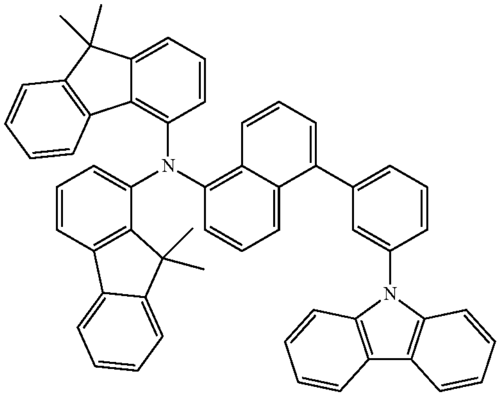
861
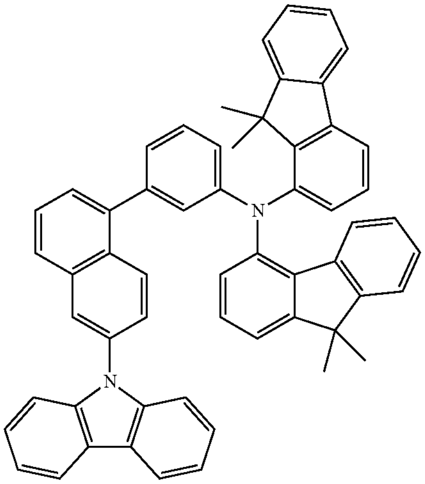
862
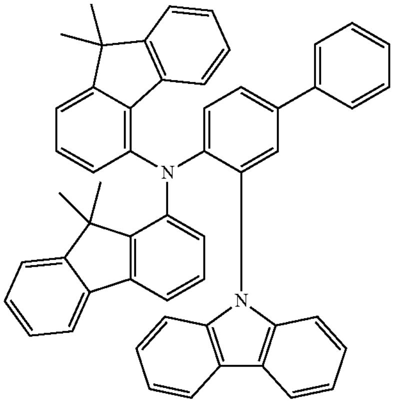
863
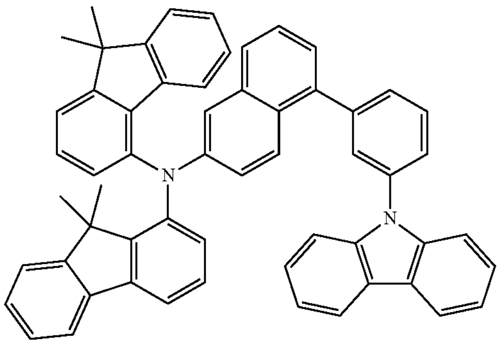
-continued
864
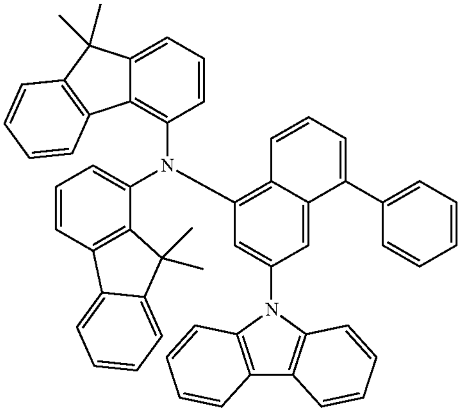
865
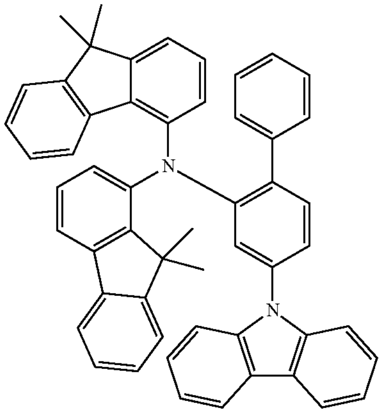
866
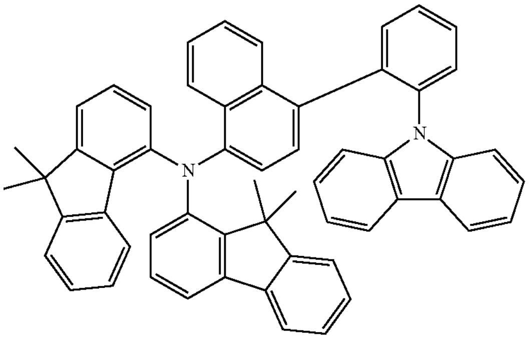

-continued
867
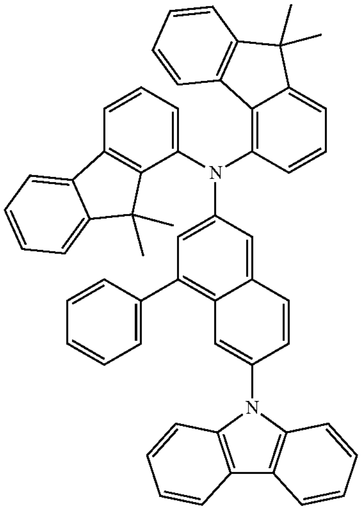
868
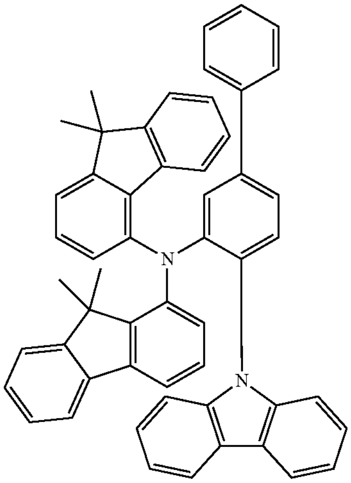
869
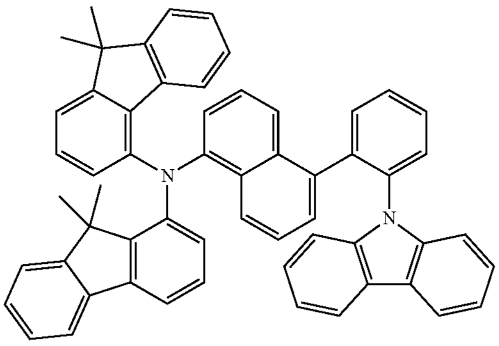
-continued
870
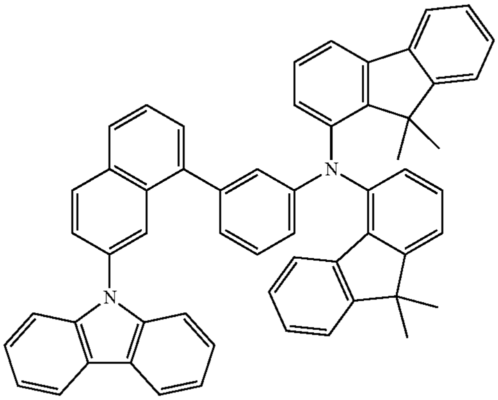
871
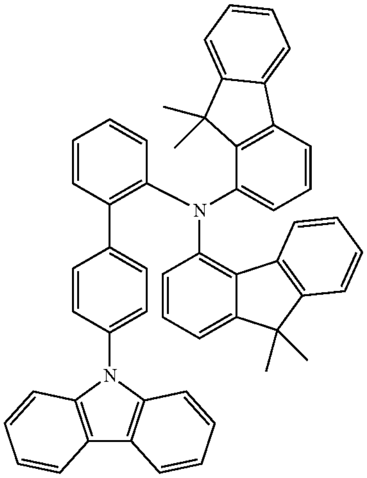
872
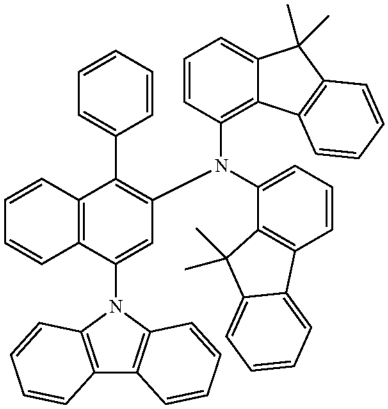

-continued
873
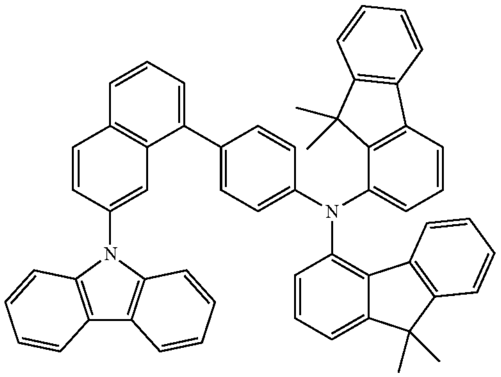
874
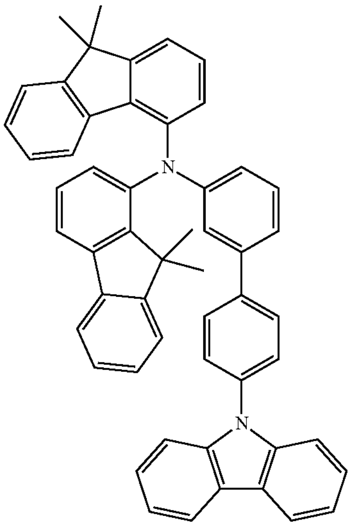
875
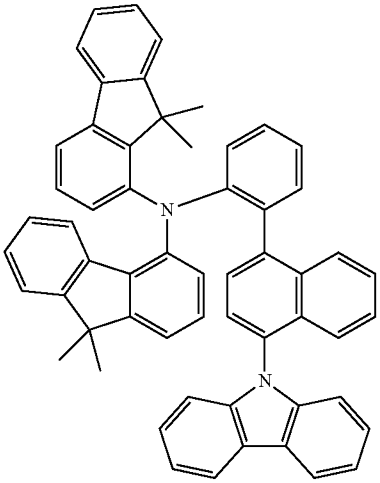
-continued
876
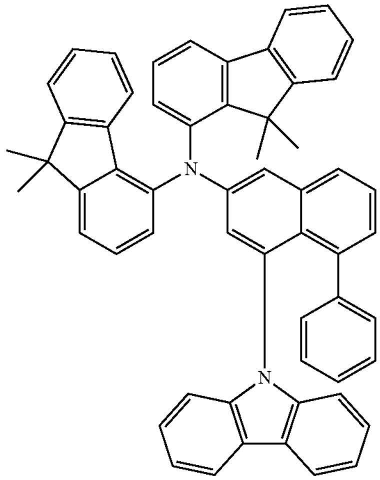
877
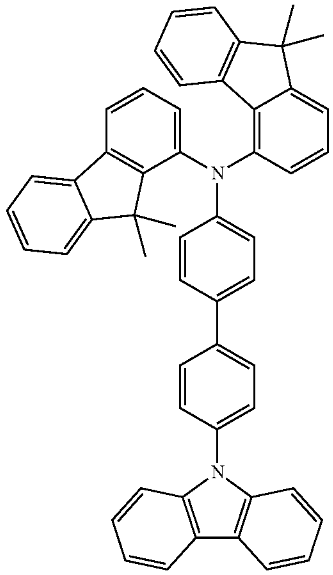
878
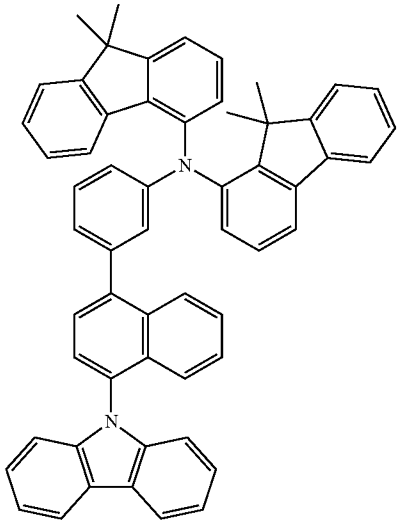

-continued
879
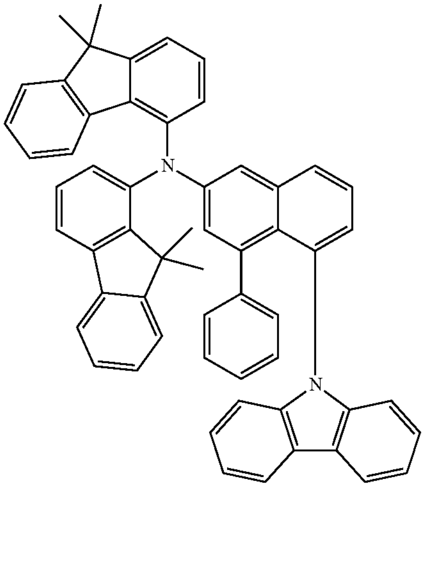
880
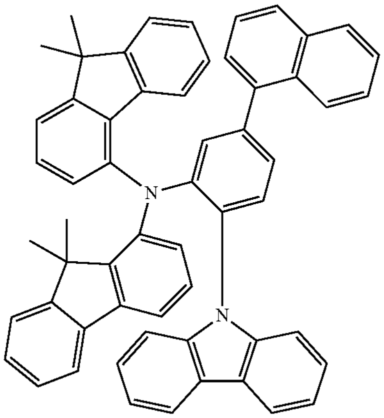
881
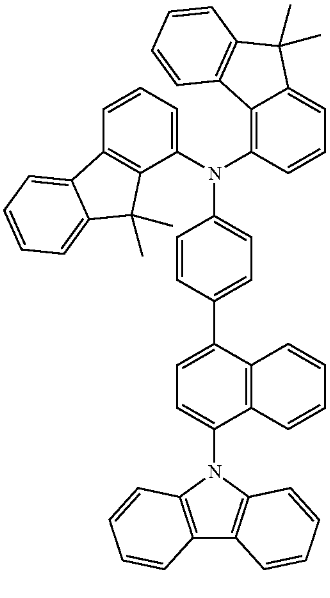
-continued
882
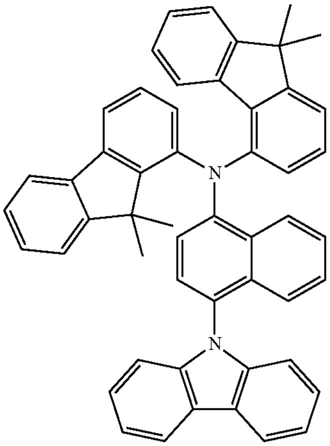
883
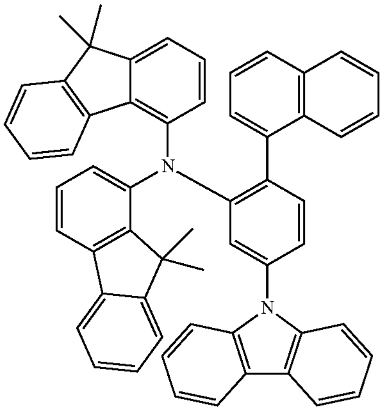
884
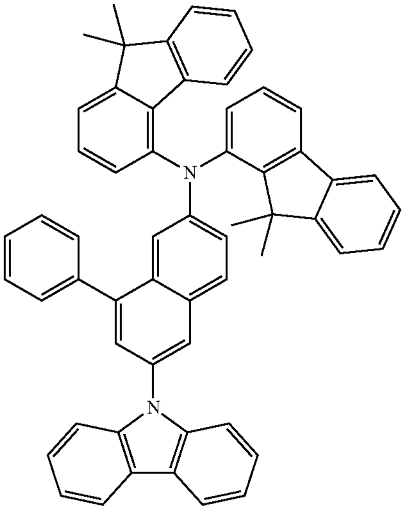

-continued
885
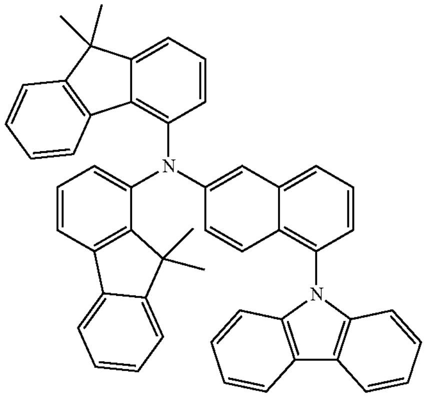
886
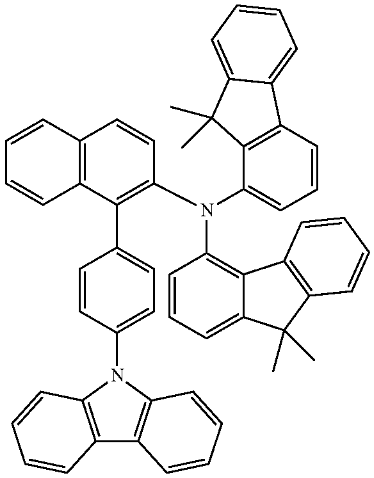
887
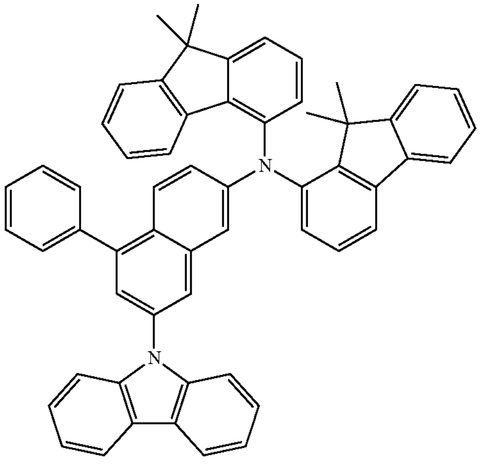
-continued
888
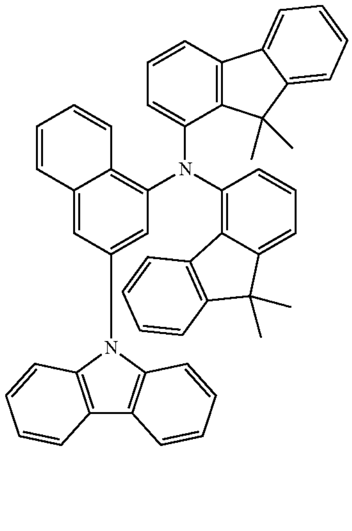
889
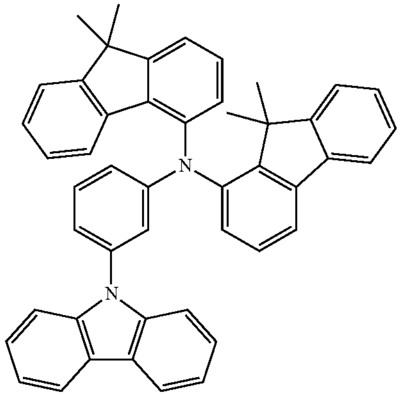
890
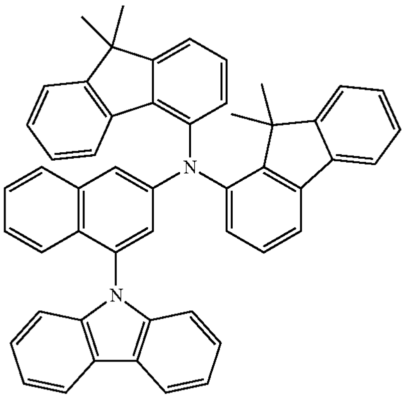

-continued

891

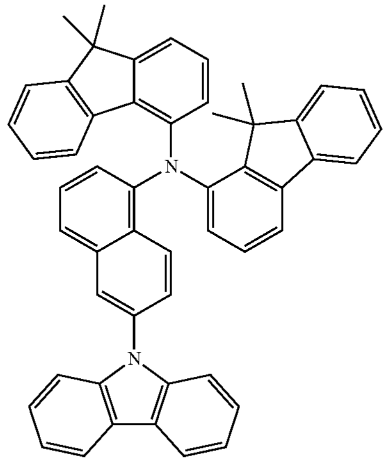

The compounds of the formula (I) can be prepared by means of known reactions in organic chemistry, especially by means of Buchwald coupling reactions.

A preferred synthesis route for preparation of compounds of the formula (I) is shown in Scheme 1 below.

Scheme 1

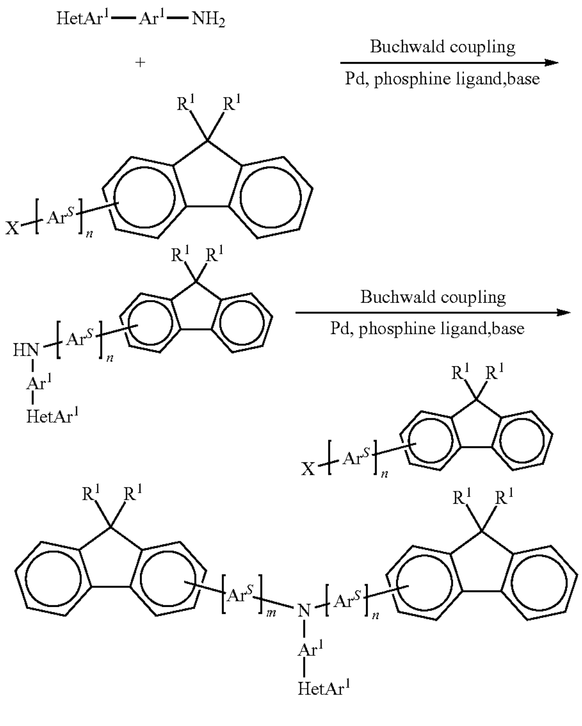

The variables that occur here are as defined for formula (I), and X is selected from reactive groups, preferably from Cl, Br and I.

In Scheme 1, the primary amine of the formula $HetAr^1$—$Ar^1$—$NH_2$ is used as starting material. In many cases, the synthesis thereof is known in the prior art. In the other cases, it can be prepared by means of known synthesis methods. The primary amine mentioned is reacted in a Buchwald coupling reaction with a fluorenyl derivative bearing a reactive X group. The intermediate obtained, a secondary amine, is reacted with another fluorenyl derivative in a second Buchwald coupling reaction. This affords the compound of the formula (I).

An alternative, likewise preferred method for preparation of compounds of the formula (I) is shown in Scheme 2 below. In this method, the primary amine $HetAr^1$—$Ar^1$—$NH_2$ is converted in a single Buchwald coupling reaction to a compound of the formula (I). This uses more equivalents of the fluorenyl derivative that bears a reactive group, and so the tertiary amine is obtained directly from the primary amine in one step.

Scheme 2

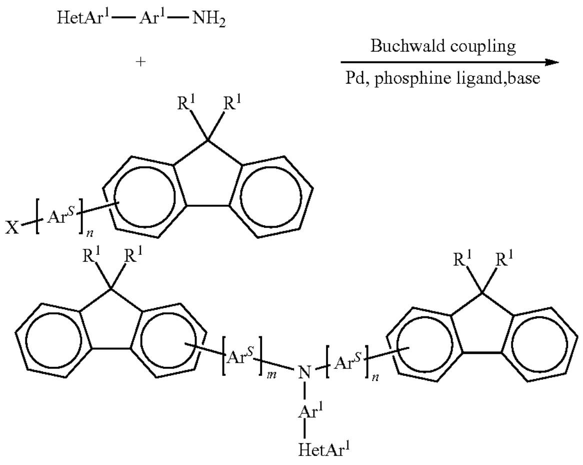

The present application provides a process for preparing a compound of the formula (I), characterized in that a compound $HetAr^1$—$Ar^1$—$NH_2$ where the variables that occur are as defined for formula (I) is reacted with a fluorene having a reactive X group in a Buchwald coupling reaction.

Preferably, the reactive group X is selected from Cl, Br and I. In a preferred embodiment, the compound of the formula (I) is obtained from the compound $HetAr^1$—$Ar^1$—$NH_2$ in a single step by a double coupling reaction in one step. In an alternative preferred embodiment, the compound of the formula (I) is obtained in two successive steps by first reacting the compound $HetAr^1$—$Ar^1$—$NH_2$ with a fluorene bearing a reactive group at one of the two N—H bonds of the primary amine in a first Buchwald coupling reaction. Subsequently, the intermediate obtained, which is a secondary amine, is reacted with a further fluorene bearing a reactive group at the remaining N—H bond in a second Buchwald coupling reaction, giving the compound of the formula (I).

The above-described compounds, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendrimer may be localized at any desired positions substituted by $R^1$, $R^2$, $R^3$, $R^4$ or $R^5$ in formula (I). According to the linkage of the compound, the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (I) to be joined via a trivalent or higher-valency group, for example via a trivalent or higher-valency aromatic or heteroaromatic group, to give a branched or dendritic oligomer or polymer.

For the repeat units of formula (I) in oligomers, dendrimers and polymers, the same preferences apply as described above for compounds of formula (I).

For preparation of the oligomers or polymers, the monomers of the invention are homopolymerized or copolymerized with further monomers. Suitable and preferred comonomers are selected from fluorenes, spirobifluorenes, paraphenylenes, carbazoles, thiophenes, dihydrophenanthrenes, cis- and trans-indenofluorenes, ketones, phenanthrenes or else two or more of these units. The polymers, oligomers and dendrimers typically contain still further units, for example emitting (fluorescent or phosphorescent) units, for example vinyltriarylamines or phosphorescent metal complexes, and/or charge transport units, especially those based on triarylamines.

The polymers and oligomers of the invention are generally prepared by polymerization of one or more monomer types, of which at least one monomer leads to repeat units of the formula (I) in the polymer. Suitable polymerization reactions are known to those skilled in the art and are described in the literature. Particularly suitable and preferred polymerization reactions which lead to formation of C—C or C—N bonds are the Suzuki polymerization, the Yamamoto polymerization, the Stille polymerization and the Hartwig-Buchwald polymerization.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (I) and at least one solvent, preferably an organic solvent. The way in which such solutions can be prepared is known to those skilled in the art. The compounds of the invention are suitable for use in electronic devices, especially in organic electroluminescent devices (OLEDs). Depending on the substitution, the compounds are used in different functions and layers.

The invention therefore further provides for the use of the compound of formula (I) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound of formula (I). This electronic device is preferably selected from the abovementioned devices.

More preferable is an organic electroluminescent device (OLED) comprising anode, cathode and at least one emitting layer, characterized in that at least one organic layer, which may be an emitting layer, a hole-transporting layer or another layer, comprises at least one compound of formula (I).

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers and/or organic or inorganic p/n junctions.

The sequence of the layers of the organic electroluminescent device comprising the compound of the formula (I) is preferably as follows: anode-hole injection layer-hole transport layer-optionally further hole transport layer(s)-optionally electron blocker layer-emitting layer-optionally hole blocker layer-electron transport layer-electron injection layer-cathode. It is additionally possible for further layers to be present in the OLED.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where the three layers show blue, green and orange or red emission. The compounds of the invention are preferably present here in a hole transport layer, hole injection layer, electron blocker layer, and/or emitting layer, more preferably in an emitting layer as matrix material, and/or in an electron blocker layer.

It is preferable in accordance with the invention when the compound of formula (I) is used in an electronic device comprising one or more phosphorescent emitting compounds. In this case, the compound may be present in different layers, preferably in a hole transport layer, an electron blocker layer, a hole injection layer and/or an emitting layer. More preferably, it is present in an electron blocker layer or in an emitting layer in combination with a phosphorescent emitting compound. In the latter case, the phosphorescent emitting compound is preferably selected from red- or green-phosphorescent emitting compounds. It is most preferably present in an electron blocker layer.

The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds.

In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds of formula (I) in organic electroluminescent devices. Further examples are listed in the following table:

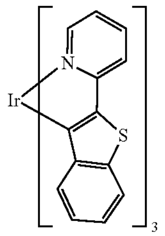

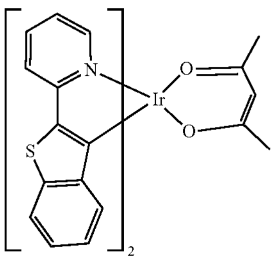

-continued

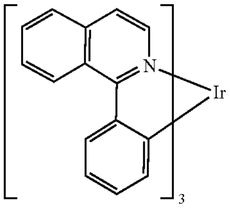

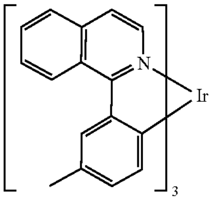

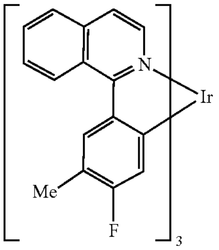

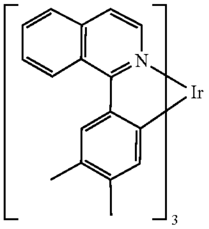

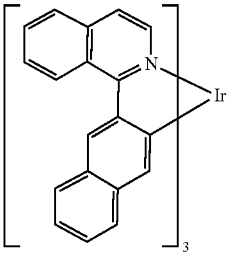

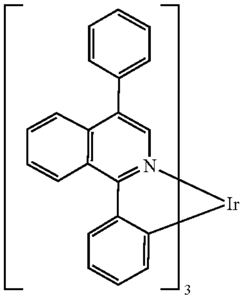

-continued
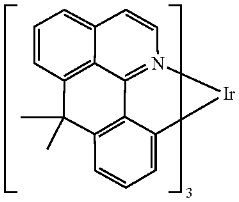
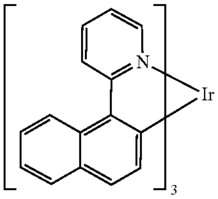
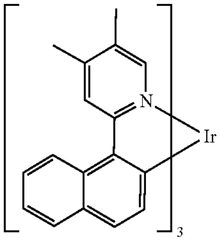
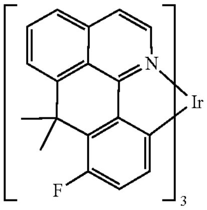
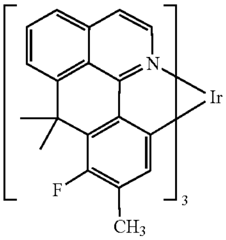
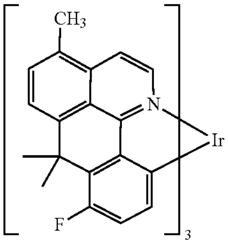
-continued
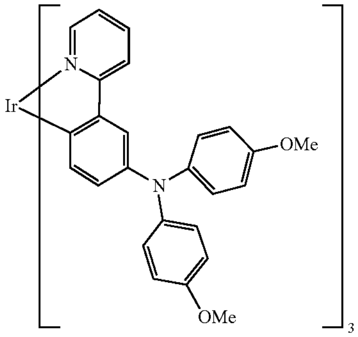
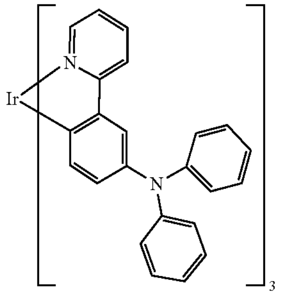
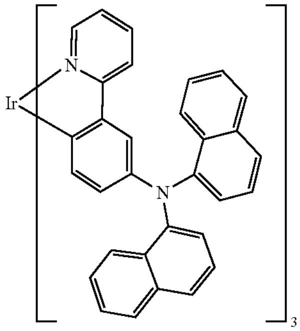
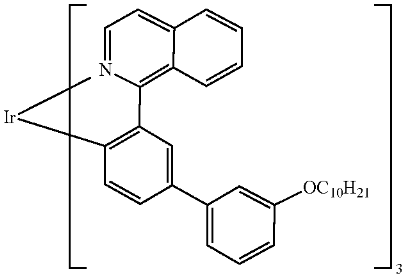
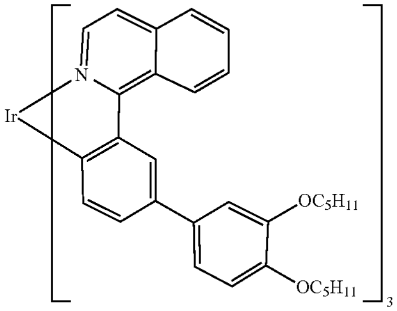

-continued
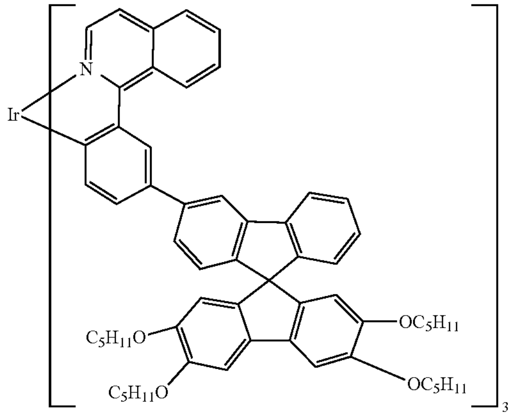
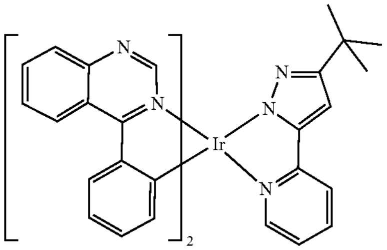
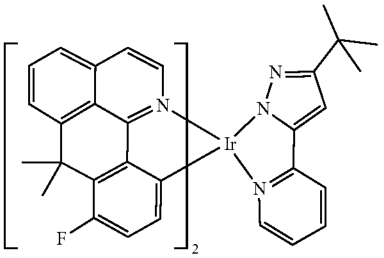
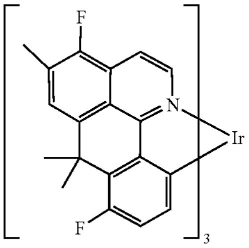
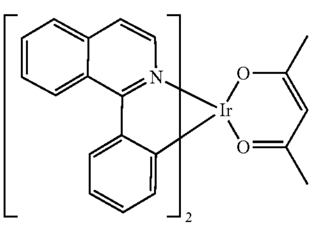
-continued
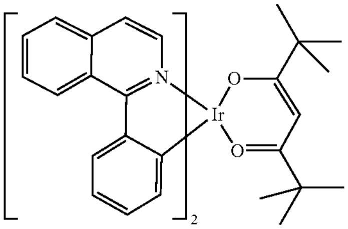
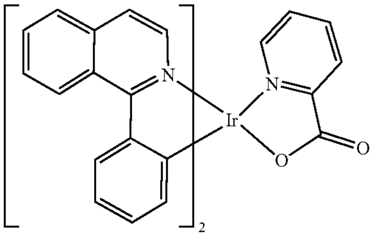
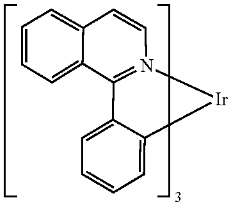
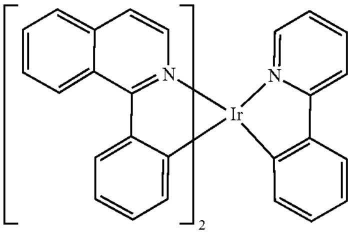
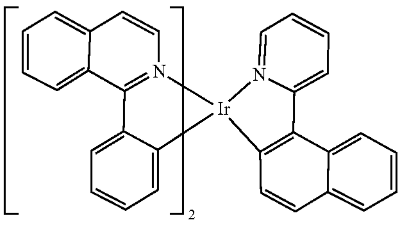
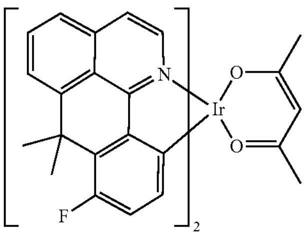

-continued
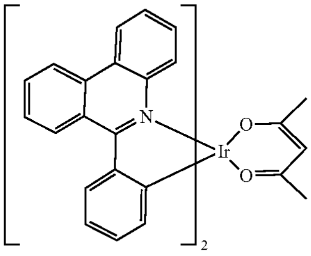
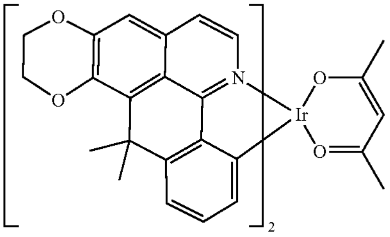
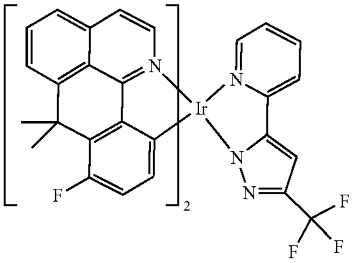
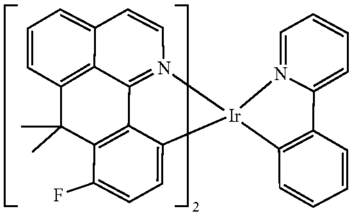
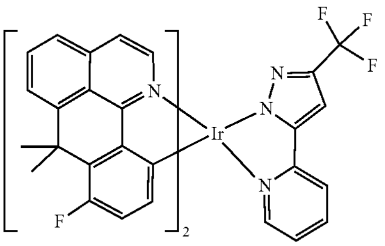
-continued
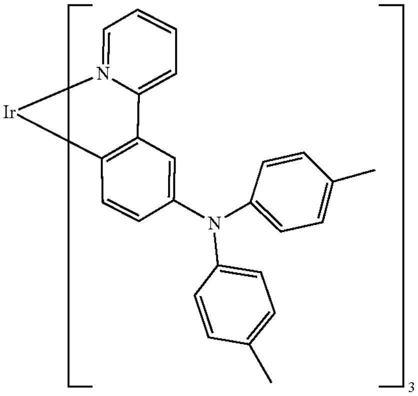
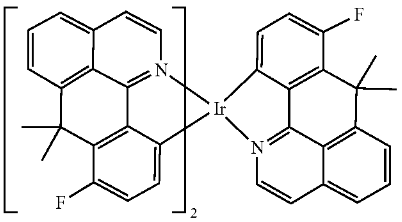
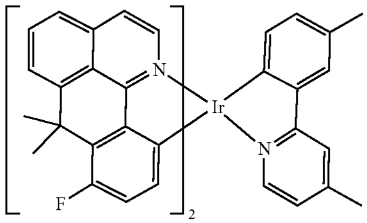
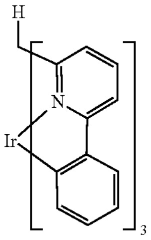
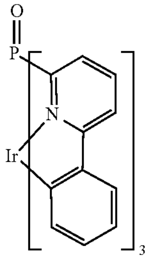
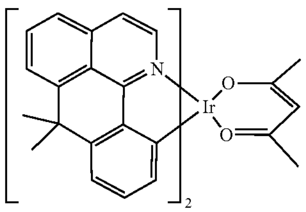

-continued
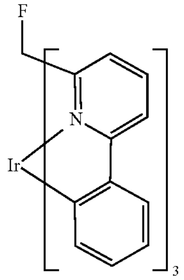
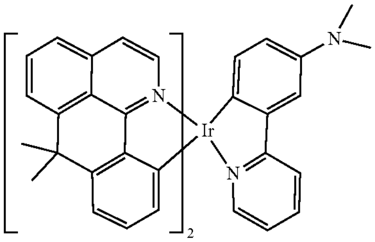
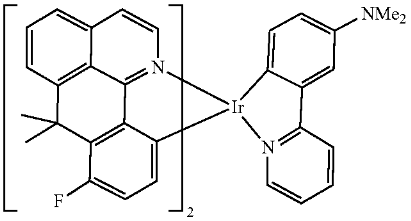
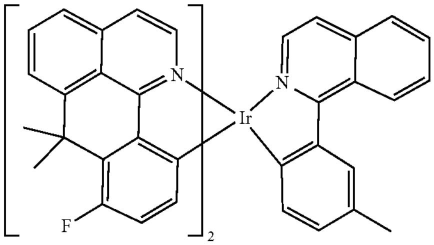
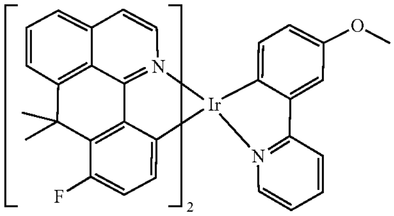
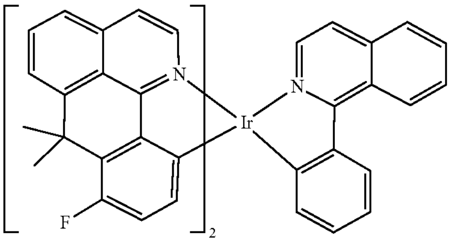
-continued
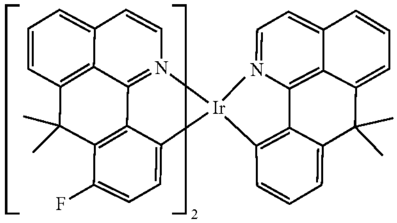
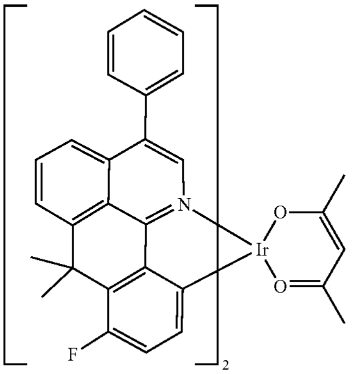
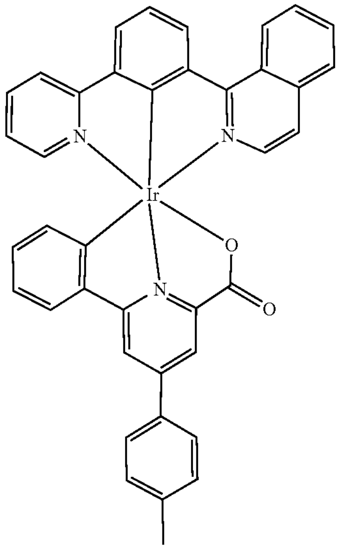
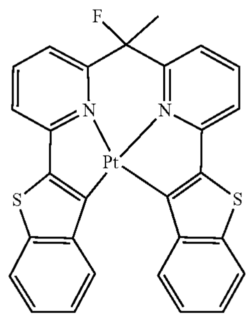

-continued
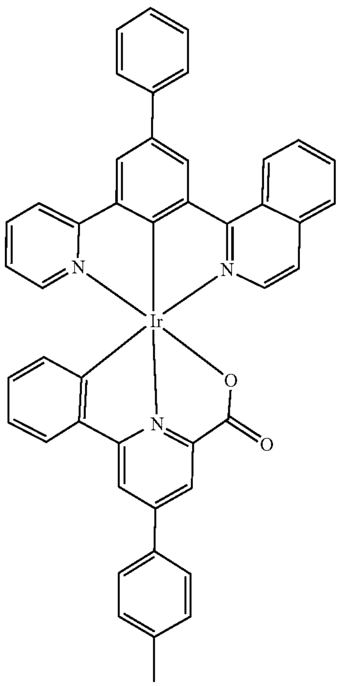
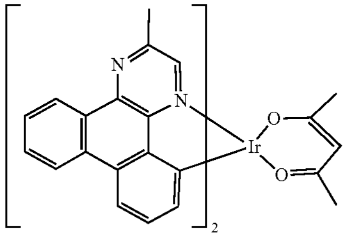
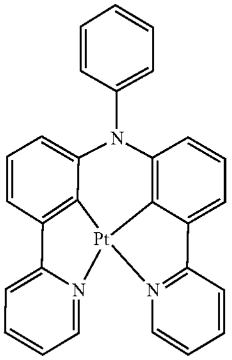
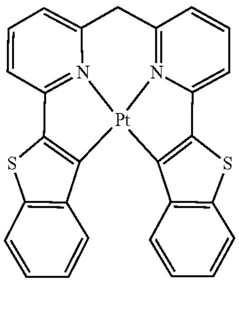
-continued
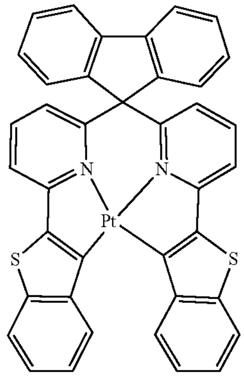
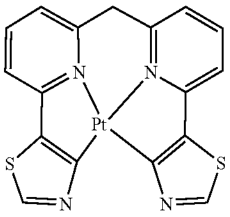
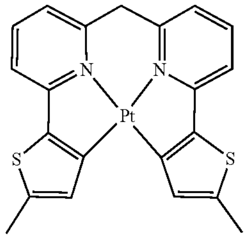
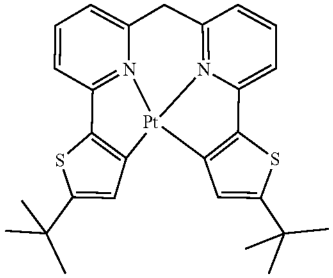
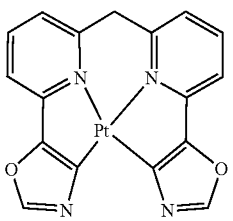
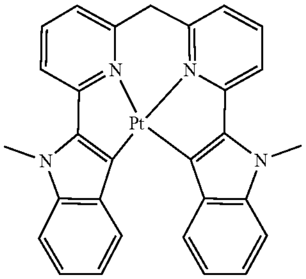

-continued
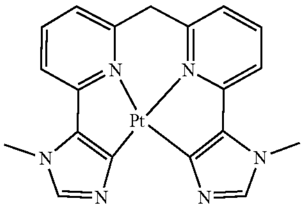
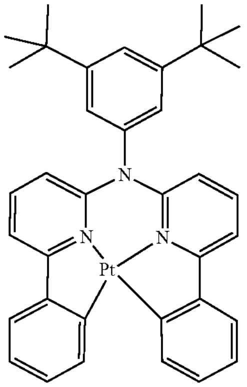
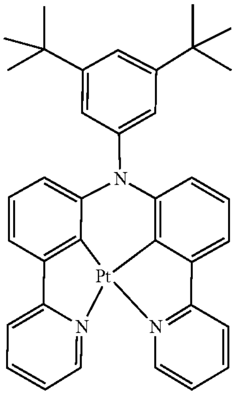
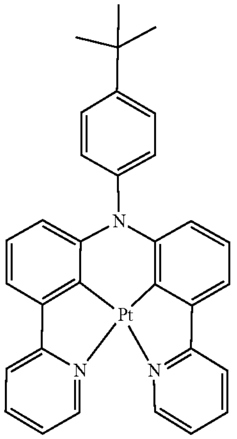
-continued
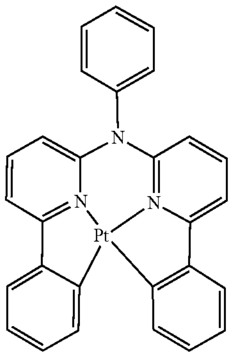
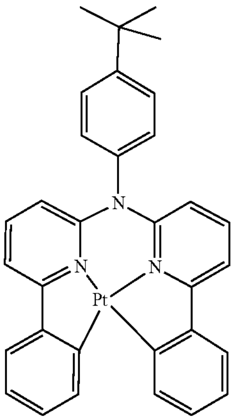
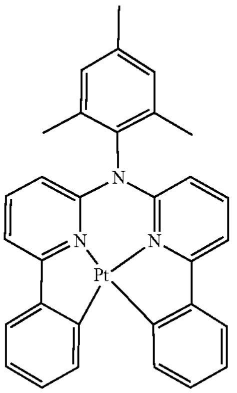
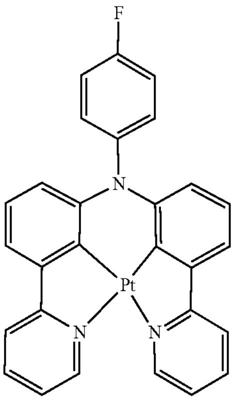

-continued
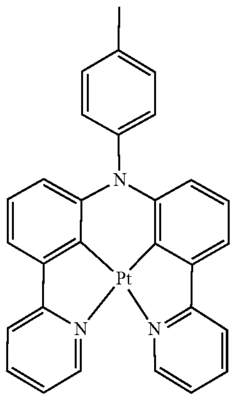
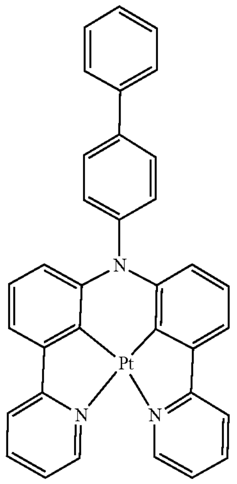
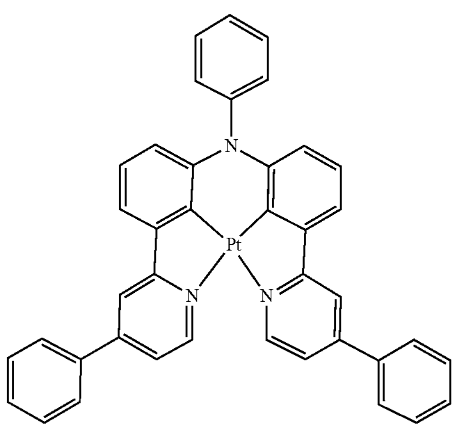
-continued
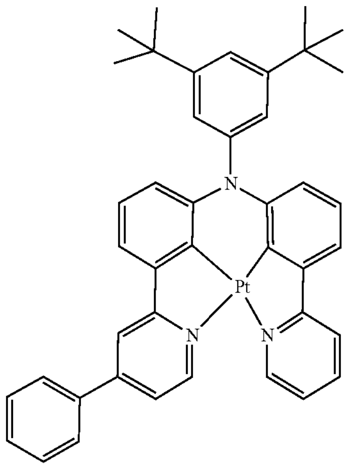
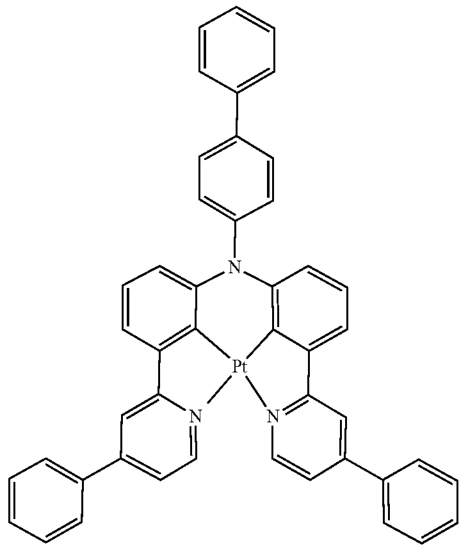
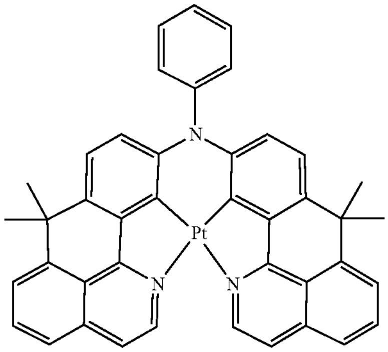

-continued
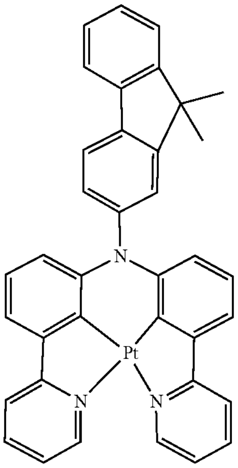
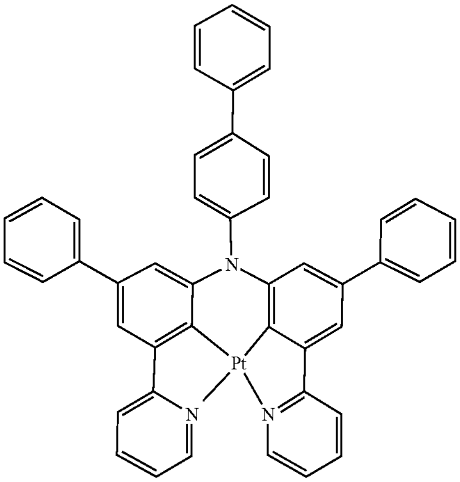
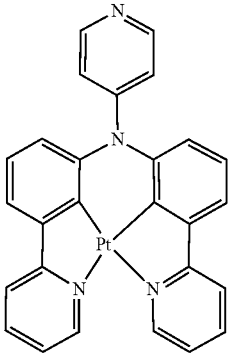
-continued
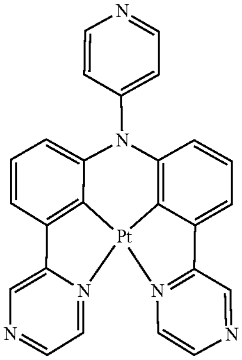
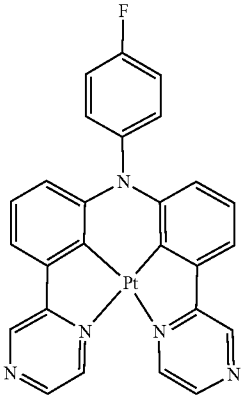
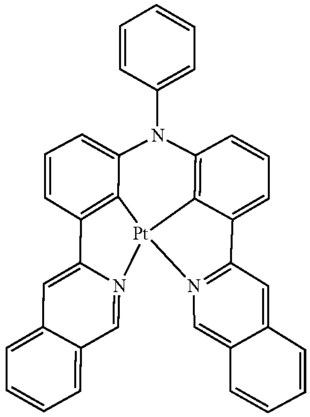
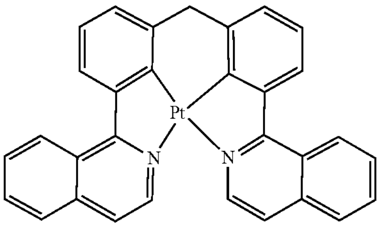

-continued
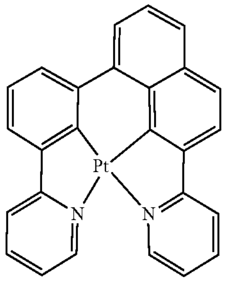
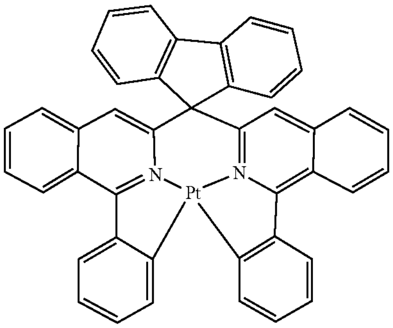
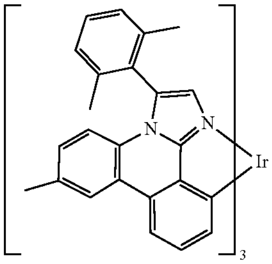
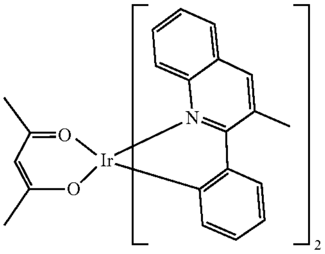
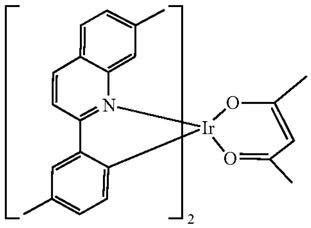
-continued
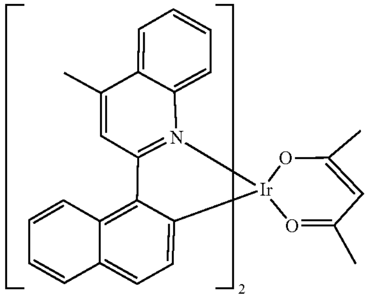
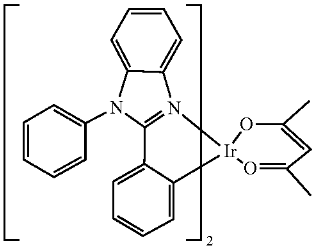
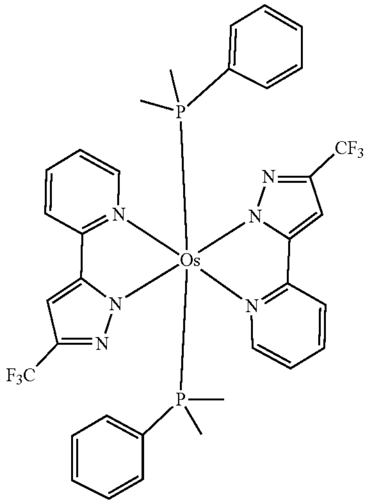
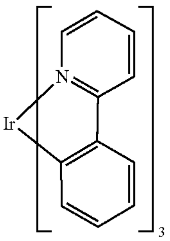
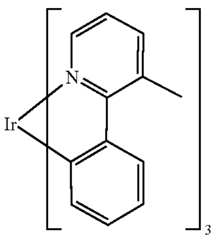

-continued
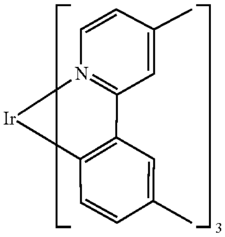
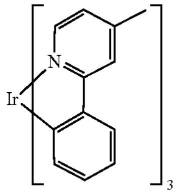
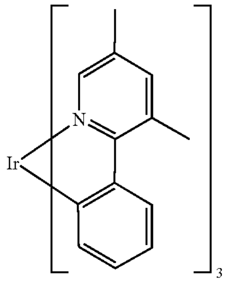
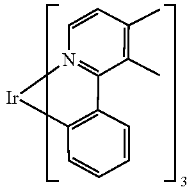
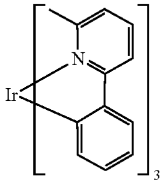
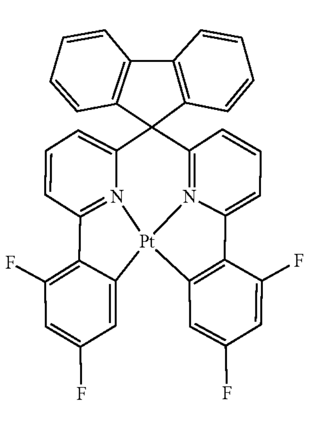
-continued
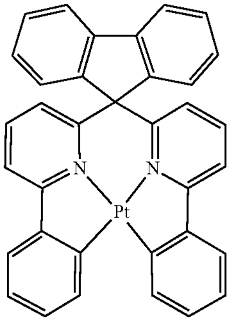
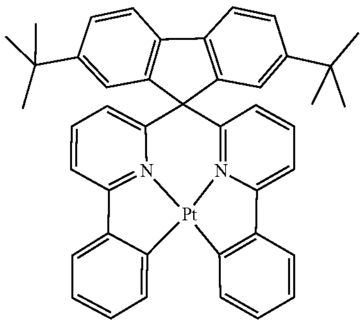
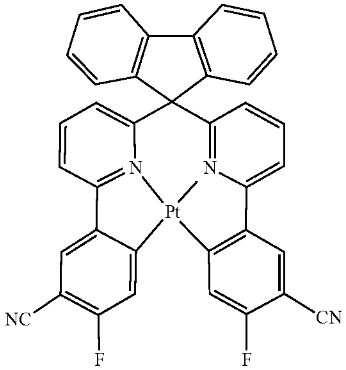
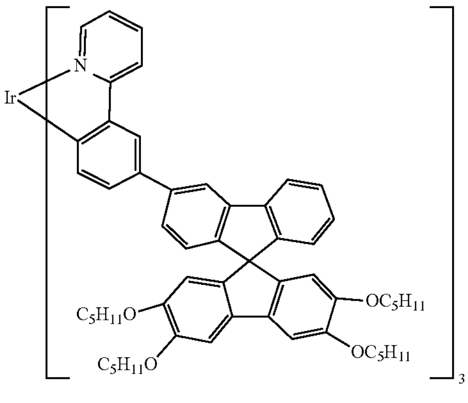

-continued
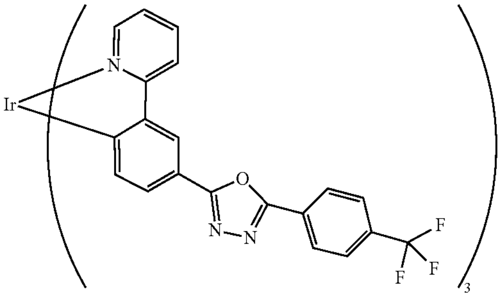
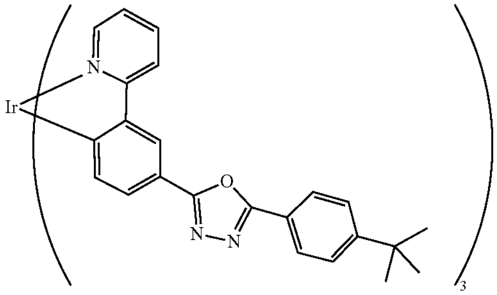
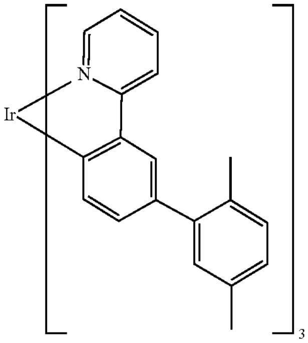
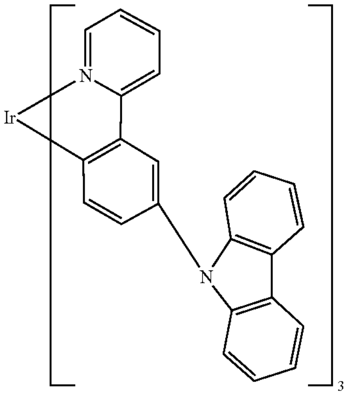
-continued
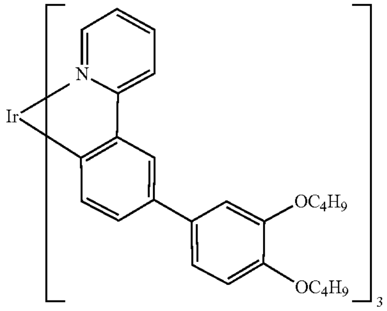
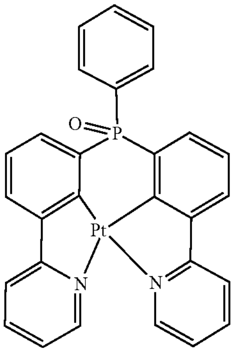
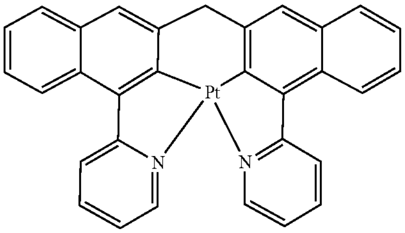
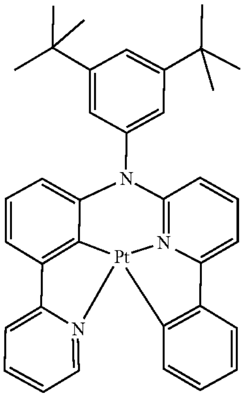
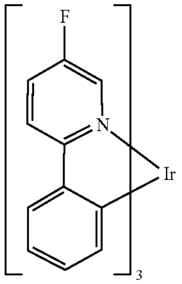

-continued
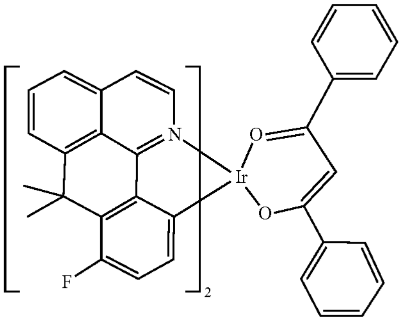
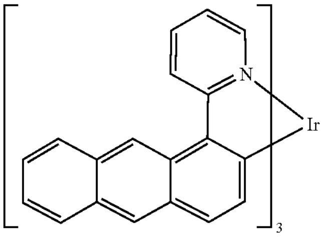
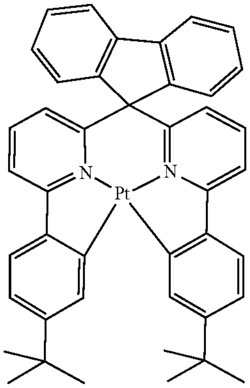
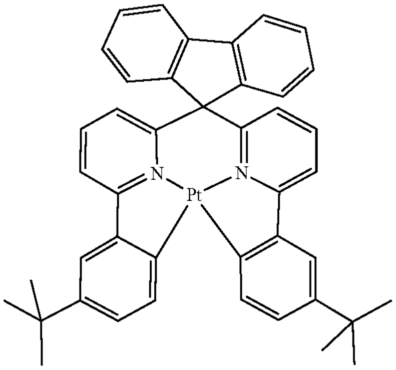
-continued
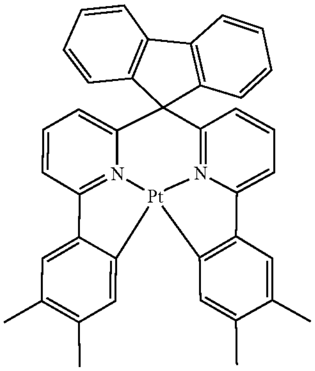
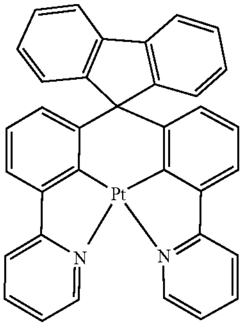
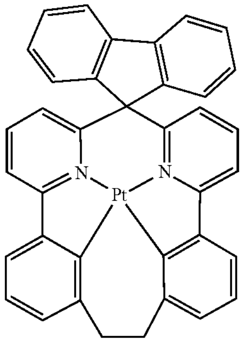
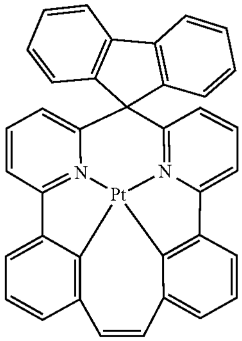

-continued
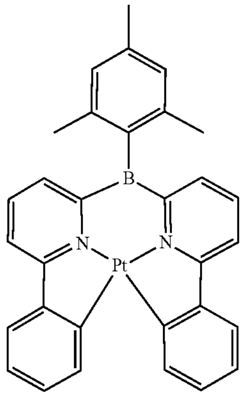
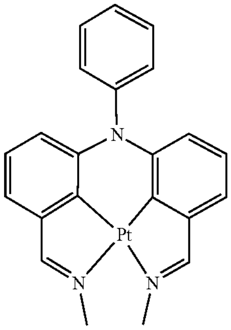
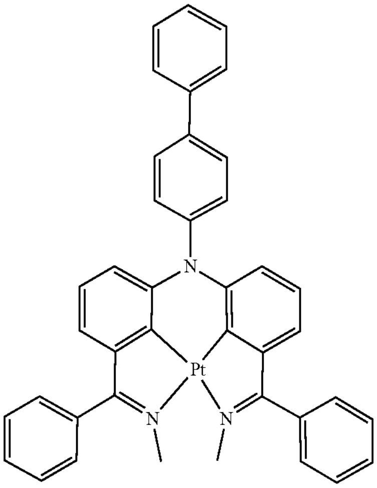
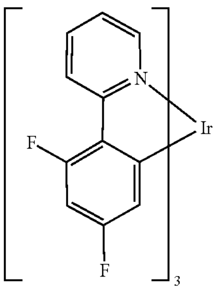
-continued
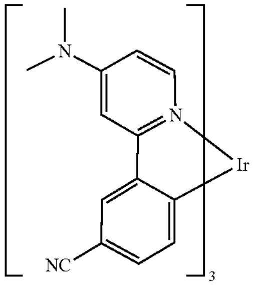
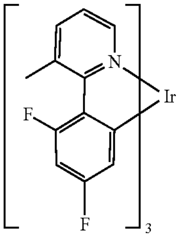
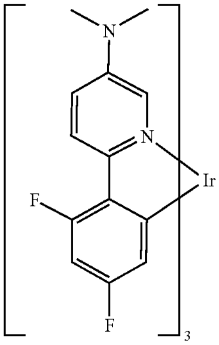
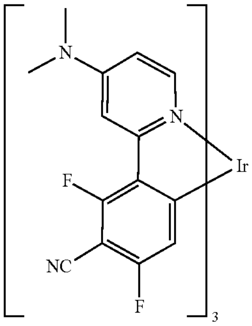
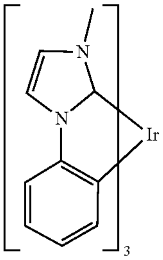

-continued
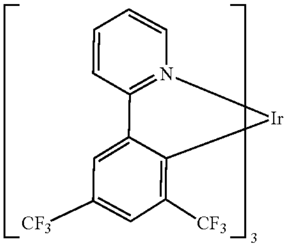
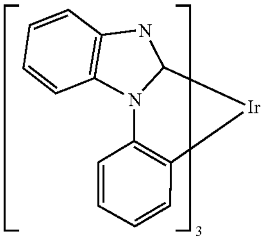
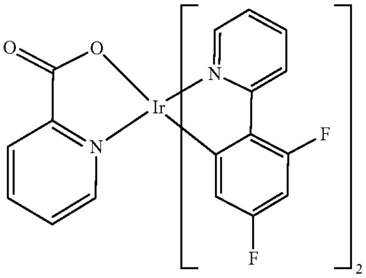
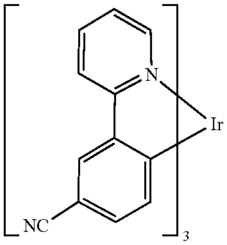
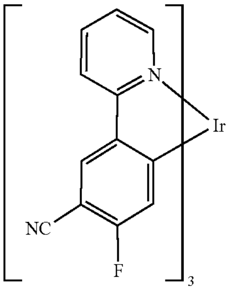
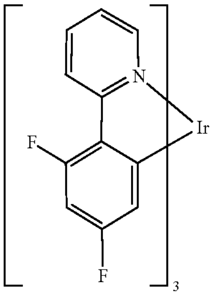
-continued
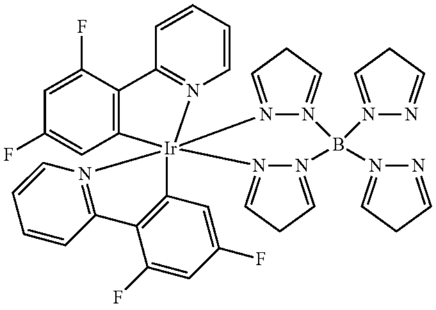
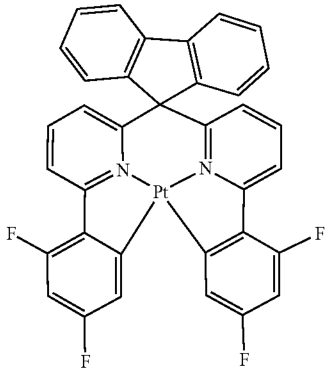
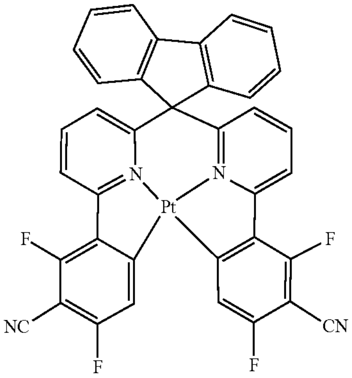
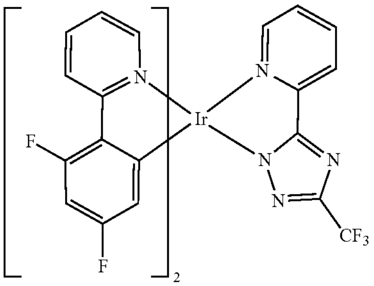

-continued
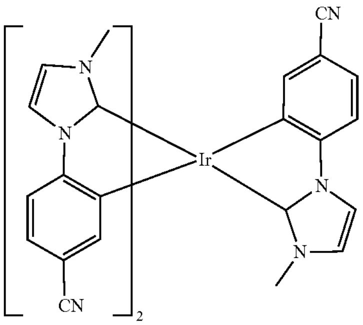
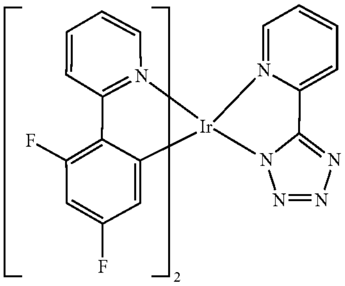
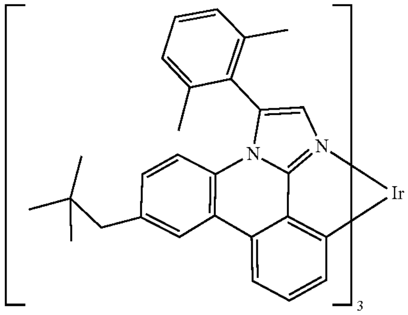
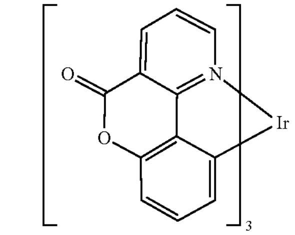
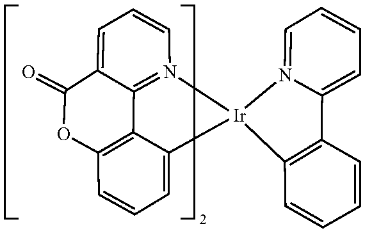
-continued
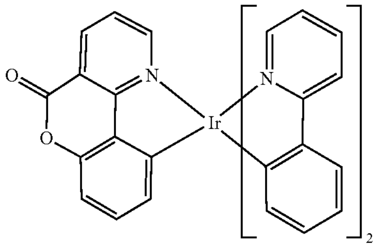
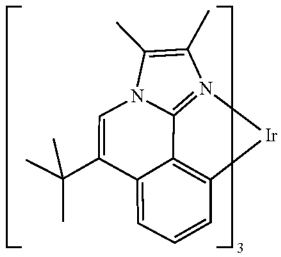
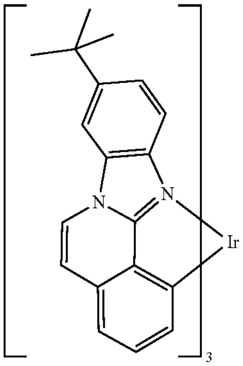
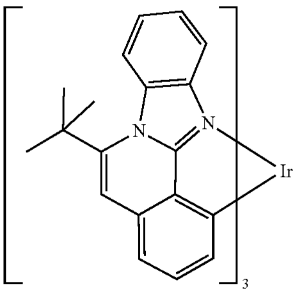
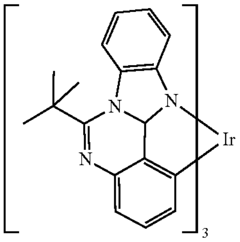

-continued
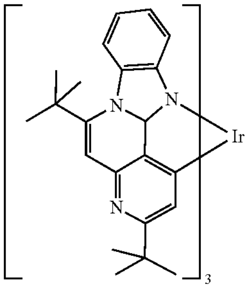
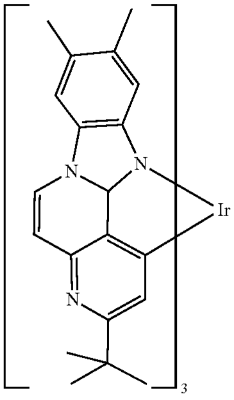
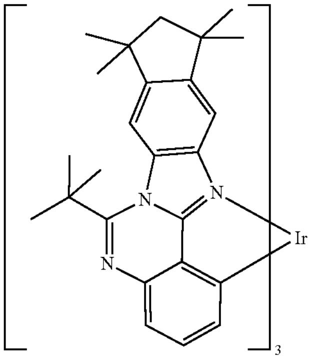
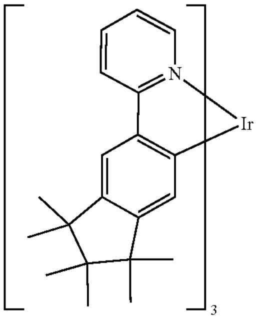
-continued
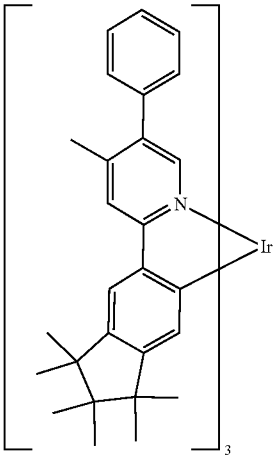
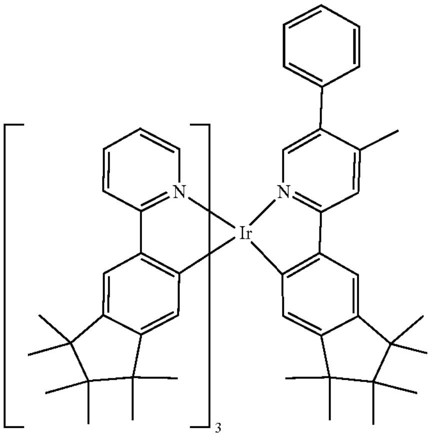
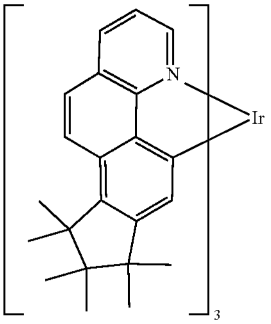
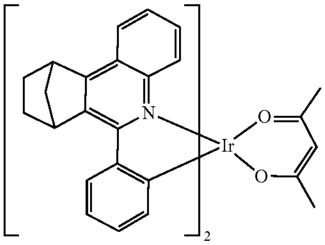

-continued
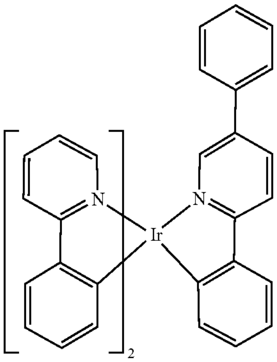
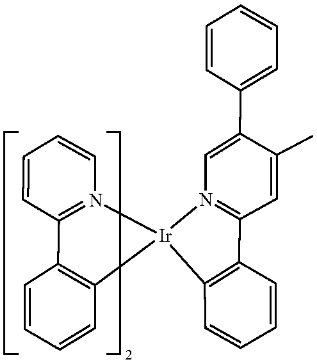
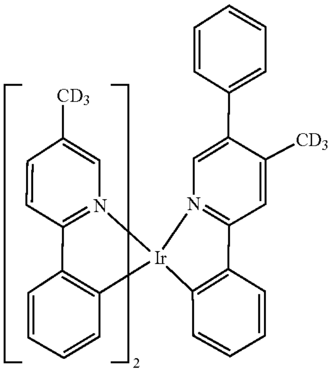
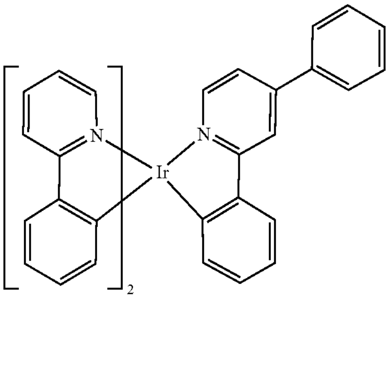
-continued
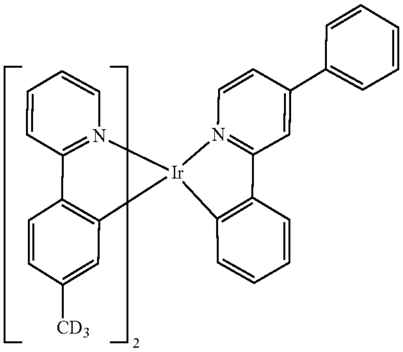
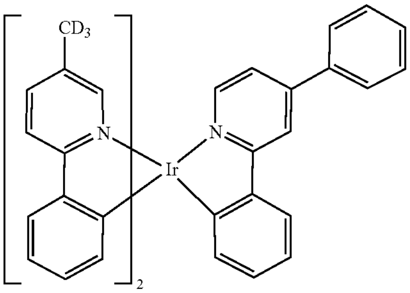
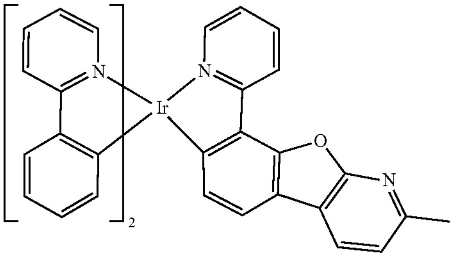
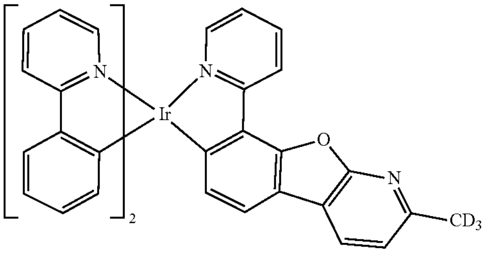
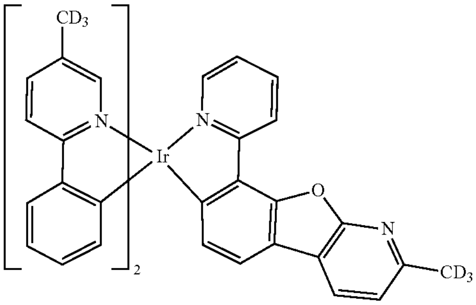

-continued
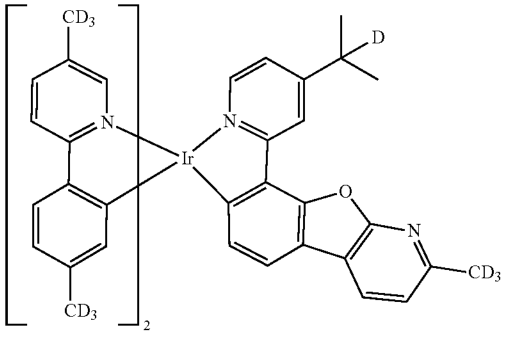
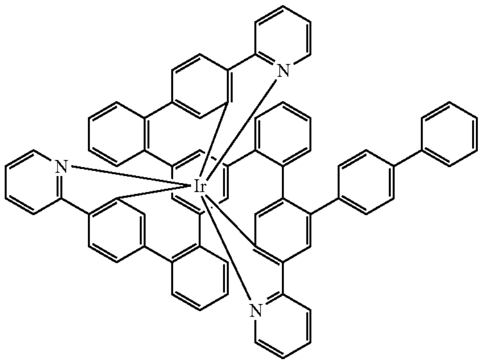
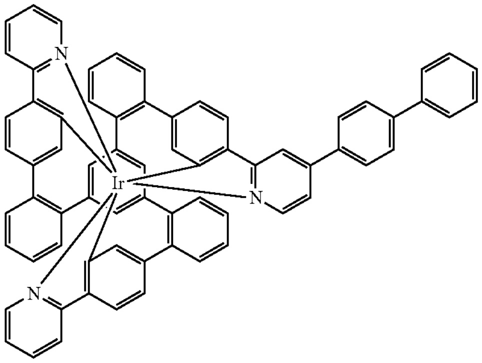
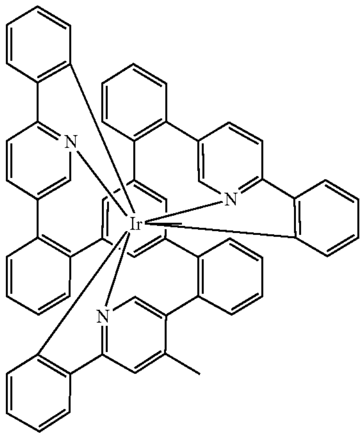
-continued
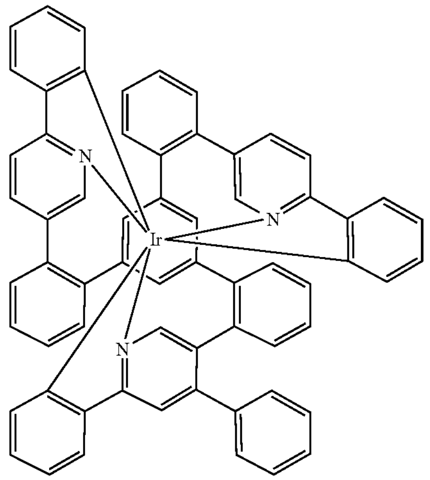
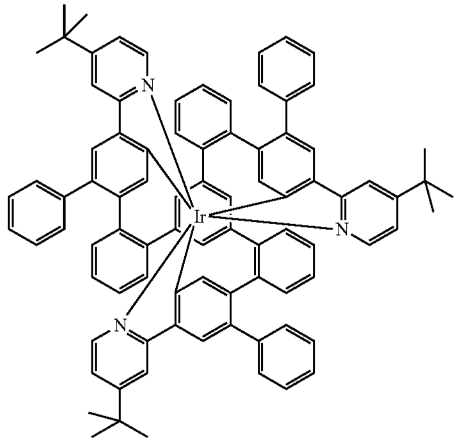
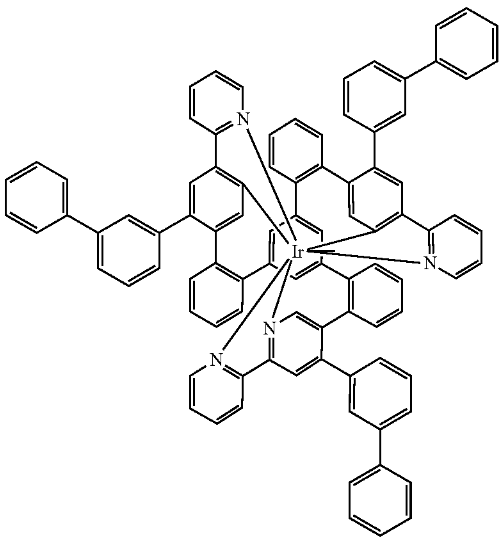

-continued

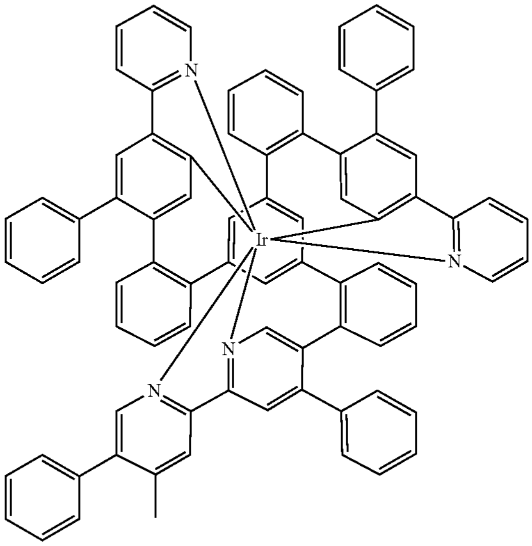

-continued

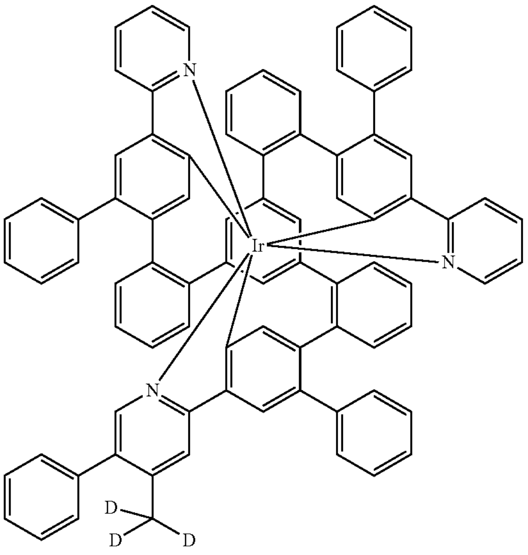

In addition, it is possible to use the following:

| | | | |
|---|---|---|---|
| CAS-1269508-30-6 | CAS-1989601-68-4 | CAS-1989602-19-8 | CAS-1989602-70-1 |
| CAS-1215692-34-4 | CAS-1989601-69-5 | CAS-1989602-20-1 | CAS-1989602-71-2 |
| CAS-1370364-40-1 | CAS-1989601-70-8 | CAS-1989602-21-2 | CAS-1989602-72-3 |
| CAS-1370364-42-3 | CAS-1989601-71-9 | CAS-1989602-22-3 | CAS-1989602-73-4 |
| CAS-1989600-74-9 | CAS-1989601-72-0 | CAS-1989602-23-4 | CAS-1989602-74-5 |
| CAS-1989600-75-0 | CAS-1989601-73-1 | CAS-1989602-24-5 | CAS-1989602-75-6 |
| CAS-1989600-77-2 | CAS-1989601-74-2 | CAS-1989602-25-6 | CAS-1989602-76-7 |
| CAS-1989600-78-3 | CAS-1989601-75-3 | CAS-1989602-26-7 | CAS-1989602-77-8 |
| CAS-1989600-79-4 | CAS-1989601-76-4 | CAS-1989602-27-8 | CAS-1989602-78-9 |
| CAS-1989600-82-9 | CAS-1989601-77-5 | CAS-1989602-28-9 | CAS-1989602-79-0 |
| CAS-1989600-83-0 | CAS-1989601-78-6 | CAS-1989602-29-0 | CAS-1989602-80-3 |
| CAS-1989600-84-1 | CAS-1989601-79-7 | CAS-1989602-30-3 | CAS-1989602-82-5 |
| CAS-1989600-85-2 | CAS-1989601-80-0 | CAS-1989602-31-4 | CAS-1989602-84-7 |
| CAS-1989600-86-3 | CAS-1989601-81-1 | CAS-1989602-32-5 | CAS-1989602-85-8 |
| CAS-1989600-87-4 | CAS-1989601-82-2 | CAS-1989602-33-6 | CAS-1989602-86-9 |
| CAS-1989600-88-5 | CAS-1989601-83-3 | CAS-1989602-34-7 | CAS-1989602-87-0 |
| CAS-1989600-89-6 | CAS-1989601-84-4 | CAS-1989602-35-8 | CAS-1989602-88-1 |
| CAS-1989601-11-7 | CAS-1989601-85-5 | CAS-1989602-36-9 | CAS-1989604-00-3 |
| CAS-1989601-23-1 | CAS-1989601-86-6 | CAS-1989602-37-0 | CAS-1989604-01-4 |
| CAS-1989601-26-4 | CAS-1989601-87-7 | CAS-1989602-38-1 | CAS-1989604-02-5 |
| CAS-1989601-28-6 | CAS-1989601-88-8 | CAS-1989602-39-2 | CAS-1989604-03-6 |
| CAS-1989601-29-7 | CAS-1989601-89-9 | CAS-1989602-40-5 | CAS-1989604-04-7 |
| CAS-1989601-33-3 | CAS-1989601-90-2 | CAS-1989602-41-6 | CAS-1989604-05-8 |
| CAS-1989601-40-2 | CAS-1989601-91-3 | CAS-1989602-42-7 | CAS-1989604-06-9 |
| CAS-1989601-41-3 | CAS-1989601-92-4 | CAS-1989602-43-8 | CAS-1989604-07-0 |
| CAS-1989601-42-4 | CAS-1989601-93-5 | CAS-1989602-44-9 | CAS-1989604-08-1 |
| CAS-1989601-43-5 | CAS-1989601-94-6 | CAS-1989602-45-0 | CAS-1989604-09-2 |
| CAS-1989601-44-6 | CAS-1989601-95-7 | CAS-1989602-46-1 | CAS-1989604-10-5 |
| CAS-1989601-45-7 | CAS-1989601-96-8 | CAS-1989602-47-2 | CAS-1989604-11-6 |
| CAS-1989601-46-8 | CAS-1989601-97-9 | CAS-1989602-48-3 | CAS-1989604-13-8 |
| CAS-1989601-47-9 | CAS-1989601-98-0 | CAS-1989602-49-4 | CAS-1989604-14-9 |
| CAS-1989601-48-0 | CAS-1989601-99-1 | CAS-1989602-50-7 | CAS-1989604-15-0 |
| CAS-1989601-49-1 | CAS-1989602-00-7 | CAS-1989602-51-8 | CAS-1989604-16-1 |
| CAS-1989601-50-4 | CAS-1989602-01-8 | CAS-1989602-52-9 | CAS-1989604-17-2 |
| CAS-1989601-51-5 | CAS-1989602-02-9 | CAS-1989602-53-0 | CAS-1989604-18-3 |
| CAS-1989601-52-6 | CAS-1989602-03-0 | CAS-1989602-54-1 | CAS-1989604-19-4 |
| CAS-1989601-53-7 | CAS-1989602-04-1 | CAS-1989602-55-2 | CAS-1989604-20-7 |
| CAS-1989601-54-8 | CAS-1989602-05-2 | CAS-1989602-56-3 | CAS-1989604-21-8 |
| CAS-1989601-55-9 | CAS-1989602-06-3 | CAS-1989602-57-4 | CAS-1989604-22-9 |
| CAS-1989601-56-0 | CAS-1989602-07-4 | CAS-1989602-58-5 | CAS-1989604-23-0 |
| CAS-1989601-57-1 | CAS-1989602-08-5 | CAS-1989602-59-6 | CAS-1989604-24-1 |
| CAS-1989601-58-2 | CAS-1989602-09-6 | CAS-1989602-60-9 | CAS-1989604-25-2 |
| CAS-1989601-59-3 | CAS-1989602-10-9 | CAS-1989602-61-0 | CAS-1989604-26-3 |
| CAS-1989601-60-6 | CAS-1989602-11-0 | CAS-1989602-62-1 | CAS-1989604-27-4 |
| CAS-1989601-61-7 | CAS-1989602-12-1 | CAS-1989602-63-2 | CAS-1989604-28-5 |
| CAS-1989601-62-8 | CAS-1989602-13-2 | CAS-1989602-64-3 | CAS-1989604-29-6 |
| CAS-1989601-63-9 | CAS-1989602-14-3 | CAS-1989602-65-4 | CAS-1989604-30-9 |
| CAS-1989601-64-0 | CAS-1989602-15-4 | CAS-1989602-66-5 | CAS-1989604-31-0 |

-continued

| | | | |
|---|---|---|---|
| CAS-1989601-65-1 | CAS-1989602-16-5 | CAS-1989602-67-6 | CAS-1989604-32-1 |
| CAS-1989601-66-2 | CAS-1989602-17-6 | CAS-1989602-68-7 | CAS-1989604-33-2 |
| CAS-1989601-67-3 | CAS-1989602-18-7 | CAS-1989602-69-8 | CAS-1989604-34-3 |
| CAS-1989604-35-4 | CAS-1989604-88-7 | CAS-1989605-52-8 | CAS-1989606-07-6 |
| CAS-1989604-36-5 | CAS-1989604-89-8 | CAS-1989605-53-9 | CAS-1989606-08-7 |
| CAS-1989604-37-6 | CAS-1989604-90-1 | CAS-1989605-54-0 | CAS-1989606-09-8 |
| CAS-1989604-38-7 | CAS-1989604-92-3 | CAS-1989605-55-1 | CAS-1989606-10-1 |
| CAS-1989604-39-8 | CAS-1989604-93-4 | CAS-1989605-56-2 | CAS-1989606-11-2 |
| CAS-1989604-40-1 | CAS-1989604-94-5 | CAS-1989605-57-3 | CAS-1989606-12-3 |
| CAS-1989604-41-2 | CAS-1989604-95-6 | CAS-1989605-58-4 | CAS-1989606-13-4 |
| CAS-1989604-42-3 | CAS-1989604-96-7 | CAS-1989605-59-5 | CAS-1989606-14-5 |
| CAS-1989604-43-4 | CAS-1989604-97-8 | CAS-1989605-61-9 | CAS-1989606-15-6 |
| CAS-1989604-45-6 | CAS-1989605-09-5 | CAS-1989605-62-0 | CAS-1989606-16-7 |
| CAS-1989604-46-7 | CAS-1989605-10-8 | CAS-1989605-63-1 | CAS-1989606-17-8 |
| CAS-1989604-47-8 | CAS-1989605-11-9 | CAS-1989605-64-2 | CAS-1989606-18-9 |
| CAS-1989604-48-9 | CAS-1989605-13-1 | CAS-1989605-65-3 | CAS-1989606-19-0 |
| CAS-1989604-49-0 | CAS-1989605-14-2 | CAS-1989605-66-4 | CAS-1989606-20-3 |
| CAS-1989604-50-3 | CAS-1989605-15-3 | CAS-1989605-67-5 | CAS-1989606-21-4 |
| CAS-1989604-52-5 | CAS-1989605-16-4 | CAS-1989605-68-6 | CAS-1989606-22-5 |
| CAS-1989604-53-6 | CAS-1989605-17-5 | CAS-1989605-69-7 | CAS-1989606-23-6 |
| CAS-1989604-54-7 | CAS-1989605-18-6 | CAS-1989605-70-0 | CAS-1989606-24-7 |
| CAS-1989604-55-8 | CAS-1989605-19-7 | CAS-1989605-71-1 | CAS-1989606-26-9 |
| CAS-1989604-56-9 | CAS-1989605-20-0 | CAS-1989605-72-2 | CAS-1989606-27-0 |
| CAS-1989604-57-0 | CAS-1989605-21-1 | CAS-1989605-73-3 | CAS-1989606-28-1 |
| CAS-1989604-58-1 | CAS-1989605-22-2 | CAS-1989605-74-4 | CAS-1989606-29-2 |
| CAS-1989604-59-2 | CAS-1989605-23-3 | CAS-1989605-75-5 | CAS-1989606-30-5 |
| CAS-1989604-60-5 | CAS-1989605-24-4 | CAS-1989605-76-6 | CAS-1989606-31-6 |
| CAS-1989604-61-6 | CAS-1989605-25-5 | CAS-1989605-77-7 | CAS-1989606-32-7 |
| CAS-1989604-62-7 | CAS-1989605-26-6 | CAS-1989605-78-8 | CAS-1989606-33-8 |
| CAS-1989604-63-8 | CAS-1989605-27-7 | CAS-1989605-79-9 | CAS-1989606-34-9 |
| CAS-1989604-64-9 | CAS-1989605-28-8 | CAS-1989605-81-3 | CAS-1989606-35-0 |
| CAS-1989604-65-0 | CAS-1989605-29-9 | CAS-1989605-82-4 | CAS-1989606-36-1 |
| CAS-1989604-66-1 | CAS-1989605-30-2 | CAS-1989605-83-5 | CAS-1989606-37-2 |
| CAS-1989604-67-2 | CAS-1989605-31-3 | CAS-1989605-84-6 | CAS-1989606-38-3 |
| CAS-1989604-68-3 | CAS-1989605-32-4 | CAS-1989605-85-7 | CAS-1989606-39-4 |
| CAS-1989604-69-4 | CAS-1989605-33-5 | CAS-1989605-86-8 | CAS-1989606-40-7 |
| CAS-1989604-70-7 | CAS-1989605-34-6 | CAS-1989605-87-9 | CAS-1989606-41-8 |
| CAS-1989604-71-8 | CAS-1989605-35-7 | CAS-1989605-88-0 | CAS-1989606-42-9 |
| CAS-1989604-72-9 | CAS-1989605-36-8 | CAS-1989605-89-1 | CAS-1989606-43-0 |
| CAS-1989604-73-0 | CAS-1989605-37-9 | CAS-1989605-90-4 | CAS-1989606-44-1 |
| CAS-1989604-74-1 | CAS-1989605-38-0 | CAS-1989605-91-5 | CAS-1989606-45-2 |
| CAS-1989604-75-2 | CAS-1989605-39-1 | CAS-1989605-92-6 | CAS-1989606-46-3 |
| CAS-1989604-76-3 | CAS-1989605-40-4 | CAS-1989605-93-7 | CAS-1989606-48-5 |
| CAS-1989604-77-4 | CAS-1989605-41-5 | CAS-1989605-94-8 | CAS-1989606-49-6 |
| CAS-1989604-78-5 | CAS-1989605-42-6 | CAS-1989605-95-9 | CAS-1989606-53-2 |
| CAS-1989604-79-6 | CAS-1989605-43-7 | CAS-1989605-96-0 | CAS-1989606-55-4 |
| CAS-1989604-80-9 | CAS-1989605-44-8 | CAS-1989605-97-1 | CAS-1989606-56-5 |
| CAS-1989604-81-0 | CAS-1989605-45-9 | CAS-1989605-98-2 | CAS-1989606-61-2 |
| CAS-1989604-82-1 | CAS-1989605-46-0 | CAS-1989605-99-3 | CAS-1989606-62-3 |
| CAS-1989604-83-2 | CAS-1989605-47-1 | CAS-1989606-00-9 | CAS-1989606-63-4 |
| CAS-1989604-84-3 | CAS-1989605-48-2 | CAS-1989606-01-0 | CAS-1989606-67-8 |
| CAS-1989604-85-4 | CAS-1989605-49-3 | CAS-1989606-04-3 | CAS-1989606-69-0 |
| CAS-1989604-86-5 | CAS-1989605-50-6 | CAS-1989606-05-4 | CAS-1989606-70-3 |
| CAS-1989604-87-6 | CAS-1989605-51-7 | CAS-1989606-06-5 | CAS-1989606-74-7 |
| CAS-1989658-39-0 | CAS-2088184-56-7 | CAS-2088185-07-1 | CAS-2088185-66-2 |
| CAS-1989658-41-4 | CAS-2088184-57-8 | CAS-2088185-08-2 | CAS-2088185-67-3 |
| CAS-1989658-43-6 | CAS-2088184-58-9 | CAS-2088185-09-3 | CAS-2088185-68-4 |
| CAS-1989658-47-0 | CAS-2088184-59-0 | CAS-2088185-10-6 | CAS-2088185-69-5 |
| CAS-1989658-49-2 | CAS-2088184-60-3 | CAS-2088185-11-7 | CAS-2088185-70-8 |
| CAS-2088184-07-8 | CAS-2088184-61-4 | CAS-2088185-12-8 | CAS-2088185-71-9 |
| CAS-2088184-08-9 | CAS-2088184-62-5 | CAS-2088185-13-9 | CAS-2088185-72-0 |
| CAS-2088184-09-0 | CAS-2088184-63-6 | CAS-2088185-14-0 | CAS-2088185-73-1 |
| CAS-2088184-10-3 | CAS-2088184-64-7 | CAS-2088185-15-1 | CAS-2088185-74-2 |
| CAS-2088184-11-4 | CAS-2088184-65-8 | CAS-2088185-16-2 | CAS-2088185-75-3 |
| CAS-2088184-13-6 | CAS-2088184-66-9 | CAS-2088185-17-3 | CAS-2088185-76-4 |
| CAS-2088184-14-7 | CAS-2088184-67-0 | CAS-2088185-18-4 | CAS-2088185-77-5 |
| CAS-2088184-15-8 | CAS-2088184-68-1 | CAS-2088185-19-5 | CAS-2088185-78-6 |
| CAS-2088184-16-9 | CAS-2088184-69-2 | CAS-2088185-20-8 | CAS-2088185-79-7 |
| CAS-2088184-17-0 | CAS-2088184-70-5 | CAS-2088185-21-9 | CAS-2088185-80-0 |
| CAS-2088184-18-1 | CAS-2088184-71-6 | CAS-2088185-22-0 | CAS-2088185-81-1 |
| CAS-2088184-19-2 | CAS-2088184-72-7 | CAS-2088185-23-1 | CAS-2088185-82-2 |
| CAS-2088184-20-5 | CAS-2088184-73-8 | CAS-2088185-32-2 | CAS-2088185-83-3 |
| CAS-2088184-21-6 | CAS-2088184-74-9 | CAS-2088185-33-3 | CAS-2088185-84-4 |
| CAS-2088184-22-7 | CAS-2088184-75-0 | CAS-2088185-34-4 | CAS-2088185-85-5 |
| CAS-2088184-23-8 | CAS-2088184-76-1 | CAS-2088185-35-5 | CAS-2088185-86-6 |
| CAS-2088184-24-9 | CAS-2088184-77-2 | CAS-2088185-36-6 | CAS-2088185-87-7 |
| CAS-2088184-25-0 | CAS-2088184-78-3 | CAS-2088185-37-7 | CAS-2088185-88-8 |
| CAS-2088184-26-1 | CAS-2088184-79-4 | CAS-2088185-38-8 | CAS-2088185-89-9 |
| CAS-2088184-27-2 | CAS-2088184-80-7 | CAS-2088185-39-9 | CAS-2088185-90-2 |

-continued

| | | | |
|---|---|---|---|
| CAS-2088184-28-3 | CAS-2088184-81-8 | CAS-2088185-40-2 | CAS-2088185-91-3 |
| CAS-2088184-29-4 | CAS-2088184-82-9 | CAS-2088185-41-3 | CAS-2088185-92-4 |
| CAS-2088184-30-7 | CAS-2088184-83-0 | CAS-2088185-42-4 | CAS-2088185-93-5 |
| CAS-2088184-32-9 | CAS-2088184-84-1 | CAS-2088185-43-5 | CAS-2088185-94-6 |
| CAS-2088184-34-1 | CAS-2088184-85-2 | CAS-2088185-44-6 | CAS-2088185-95-7 |
| CAS-2088184-35-2 | CAS-2088184-86-3 | CAS-2088185-45-7 | CAS-2088185-96-8 |
| CAS-2088184-36-3 | CAS-2088184-87-4 | CAS-2088185-46-8 | CAS-2088185-97-9 |
| CAS-2088184-37-4 | CAS-2088184-88-5 | CAS-2088185-47-9 | CAS-2088185-98-0 |
| CAS-2088184-38-5 | CAS-2088184-89-6 | CAS-2088185-48-0 | CAS-2088185-99-1 |
| CAS-2088184-39-6 | CAS-2088184-90-9 | CAS-2088185-49-1 | CAS-2088186-00-7 |
| CAS-2088184-40-9 | CAS-2088184-91-0 | CAS-2088185-50-4 | CAS-2088186-01-8 |
| CAS-2088184-41-0 | CAS-2088184-92-1 | CAS-2088185-51-5 | CAS-2088186-02-9 |
| CAS-2088184-42-1 | CAS-2088184-93-2 | CAS-2088185-52-6 | CAS-2088195-88-2 |
| CAS-2088184-43-2 | CAS-2088184-94-3 | CAS-2088185-53-7 | CAS-2088195-89-3 |
| CAS-2088184-44-3 | CAS-2088184-95-4 | CAS-2088185-54-8 | CAS-2088195-90-6 |
| CAS-2088184-45-4 | CAS-2088184-96-5 | CAS-2088185-55-9 | CAS-2088195-91-7 |
| CAS-2088184-46-5 | CAS-2088184-97-6 | CAS-2088185-56-0 | CAS-861806-70-4 |
| CAS-2088184-47-6 | CAS-2088184-98-7 | CAS-2088185-57-1 | CAS-1269508-30-6 |
| CAS-2088184-48-7 | CAS-2088184-99-8 | CAS-2088185-58-2 | |
| CAS-2088184-49-8 | CAS-2088185-00-4 | CAS-2088185-59-3 | |
| CAS-2088184-50-1 | CAS-2088185-01-5 | CAS-2088185-60-6 | |
| CAS-2088184-51-2 | CAS-2088185-02-6 | CAS-2088185-61-7 | |
| CAS-2088184-52-3 | CAS-2088185-03-7 | CAS-2088185-62-8 | |
| CAS-2088184-53-4 | CAS-2088185-04-8 | CAS-2088185-63-9 | |
| CAS-2088184-54-5 | CAS-2088185-05-9 | CAS-2088185-64-0 | |
| CAS-2088184-55-6 | CAS-2088185-06-0 | CAS-2088185-65-1 | |

In a preferred embodiment of the invention, the compounds of formula (I) are used as hole-transporting material. The compounds are then preferably in a hole-transporting layer. Preferred embodiments of hole-transporting layers are hole transport layers, electron blocker layers and hole injection layers. When the compound of the formula (I) is present in a hole-transporting layer, the latter is preferably an electron-blocking layer. This preferably directly adjoins the emitting layer on the anode side.

A hole transport layer according to the present application is a layer having a hole-transporting function between the anode and emitting layer. More particularly, it is a hole-transporting layer which is not a hole injection layer and not an electron blocker layer.

Hole injection layers and electron blocker layers are understood in the context of the present application to be specific embodiments of hole-transporting layers. A hole injection layer, in the case of a plurality of hole-transporting layers between the anode and emitting layer, is a hole-transporting layer which directly adjoins the anode or is separated therefrom only by a single coating of the anode. An electron blocker layer, in the case of a plurality of hole-transporting layers between the anode and emitting layer, is that hole-transporting layer which directly adjoins the emitting layer on the anode side. Preferably, the OLED of the invention comprises two, three or four hole-transporting layers between the anode and emitting layer, at least one of which preferably contains a compound of formula (I), and more preferably exactly one or two contain a compound of formula (I).

If the compound of formula (I) is used as hole transport material in a hole transport layer, a hole injection layer or an electron blocker layer, the compound can be used as pure material, i.e. in a proportion of 100%, in the hole transport layer, or it can be used in combination with one or more further compounds. In a preferred embodiment, the organic layer comprising the compound of the formula (I) then additionally contains one or more p-dopants. p-Dopants used according to the present invention are preferably those organic electron acceptor compounds capable of oxidizing one or more of the other compounds in the mixture.

Particularly preferred as p-dopants are quinodimethane compounds, azaindenofluorenediones, azaphenalenes, azatriphenylenes, $I_2$, metal halides, preferably transition metal halides, metal oxides, preferably metal oxides comprising at least one transition metal or a metal from main group 3, and transition metal complexes, preferably complexes of Cu, Co, Ni, Pd and Pt with ligands containing at least one oxygen atom as binding site. Preference is further given to transition metal oxides as dopants, preferably oxides of rhenium, molybdenum and tungsten, more preferably $Re_2O_7$, $MoO_3$, $WO_3$ and $ReO_3$.

The p-dopants are preferably in substantially homogeneous distribution in the p-doped layers. This can be achieved, for example, by coevaporation of the p-dopant and the hole transport material matrix.

Preferred p-dopants are especially the following compounds:

(D-1)

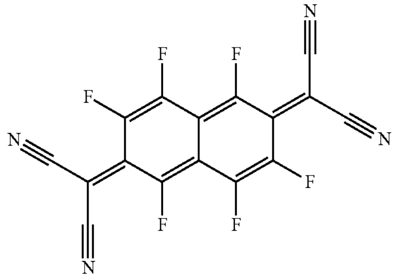

(D-2)

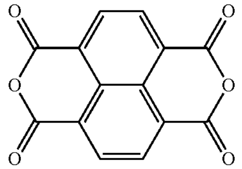

-continued
(D-3)
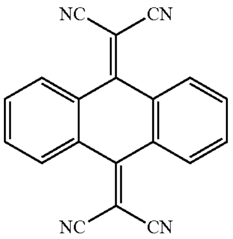
(D-4)
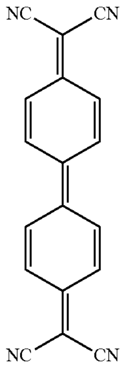
(D-5)
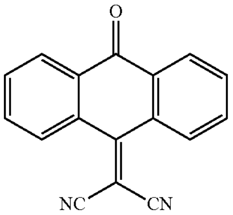
(D-6)
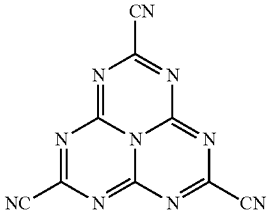
(D-7)
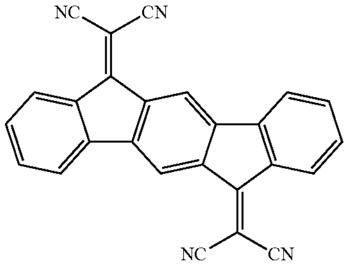
(D-8)
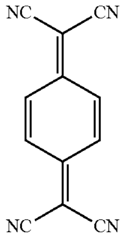
-continued
(D-9)
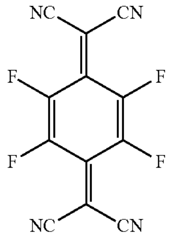
(D-10)
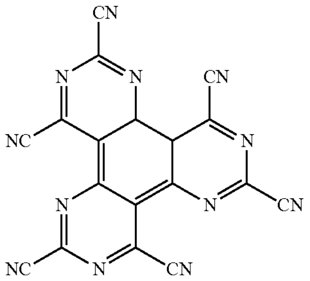
(D-11)
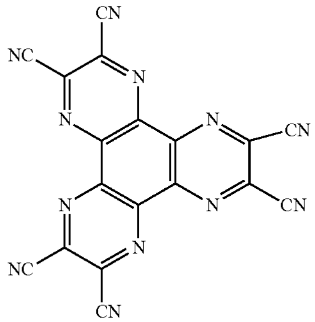
(D-12)
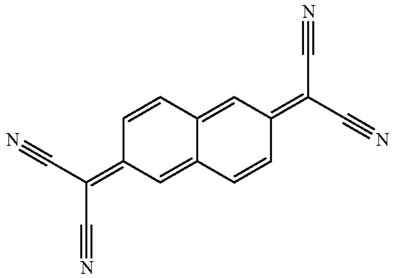
(D-13)
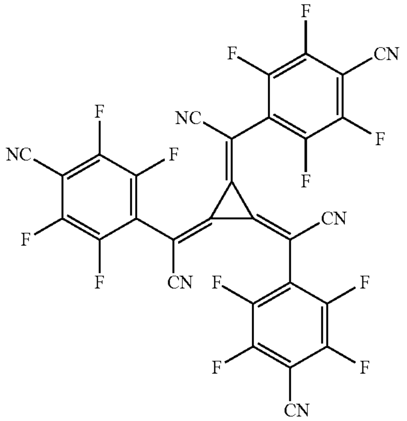

-continued (D-14)

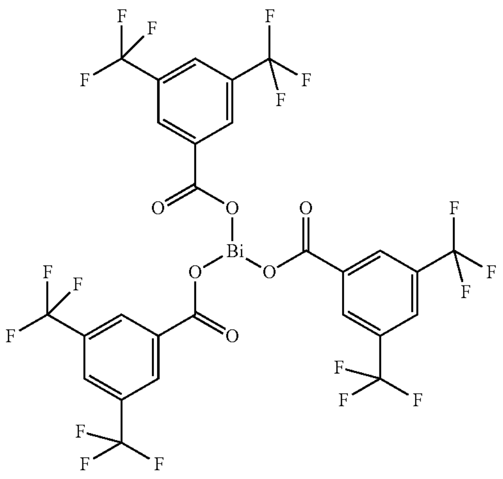

In a further preferred embodiment of the invention, the compound of formula (I) is used as hole transport material in combination with a hexaazatriphenylene derivative in an OLED. Particular preference is given here to using the hexaazatriphenylene derivative in a separate layer.

In a preferred embodiment of the present invention, the compound of the formula (I) is used in an emitting layer as matrix material in combination with one or more emitting compounds, preferably phosphorescent emitting compounds. The phosphorescent emitting compounds here are preferably selected from red-phosphorescent and green-phosphorescent compounds.

The proportion of the matrix material in the emitting layer in this case is between 50.0% and 99.9% by volume, preferably between 80.0% and 99.5% by volume, and more preferably between 85.0% and 97.0% by volume.

Correspondingly, the proportion of the emitting compound is between 0.1% and 50.0% by volume, preferably between 0.5% and 20.0% by volume, and more preferably between 3.0% and 15.0% by volume.

An emitting layer of an organic electroluminescent device may also contain systems comprising a plurality of matrix materials (mixed matrix systems) and/or a plurality of emitting compounds. In this case too, the emitting compounds are generally those compounds having the smaller proportion in the system and the matrix materials are those compounds having the greater proportion in the system. In individual cases, however, the proportion of a single matrix material in the system may be less than the proportion of a single emitting compound.

It is preferable that the compounds of formula (I) are used as a component of mixed matrix systems, preferably for phosphorescent emitters. The mixed matrix systems preferably comprise two or three different matrix materials, more preferably two different matrix materials. Preferably, in this case, one of the two materials is a material having hole-transporting properties and the other material is a material having electron-transporting properties. The compound of the formula (I) is preferably the matrix material having hole-transporting properties. Correspondingly, when the compound of the formula (I) is used as matrix material for a phosphorescent emitter in the emitting layer of an OLED, a second matrix compound having electron-transporting properties is present in the emitting layer. The two different matrix materials may be present in a ratio of 1:50 to 1:1, preferably 1:20 to 1:1, more preferably 1:10 to 1:1 and most preferably 1:4 to 1:1.

The desired electron-transporting and hole-transporting properties of the mixed matrix components may, however, also be combined mainly or entirely in a single mixed matrix component, in which case the further mixed matrix component(s) fulfil(s) other functions.

The mixed matrix systems may comprise one or more emitting compounds, preferably one or more phosphorescent emitting compounds. In general, mixed matrix systems are preferably used in phosphorescent organic electroluminescent devices.

Particularly suitable matrix materials which can be used in combination with the inventive compounds as matrix components of a mixed matrix system are selected from the preferred matrix materials specified below for phosphorescent emitting compounds, and among these especially from those having electron-transporting properties. Particularly preferred matrix materials that may be used in combination with the compounds of the invention as matrix components of a mixed matrix system are the following materials.

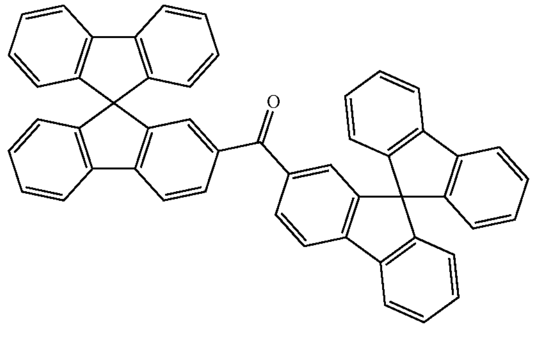

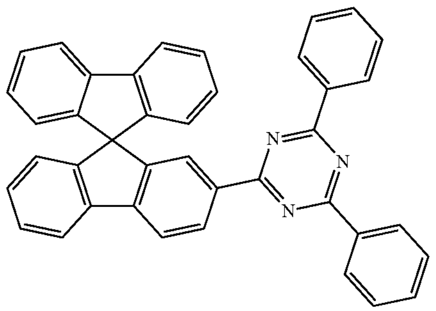

-continued
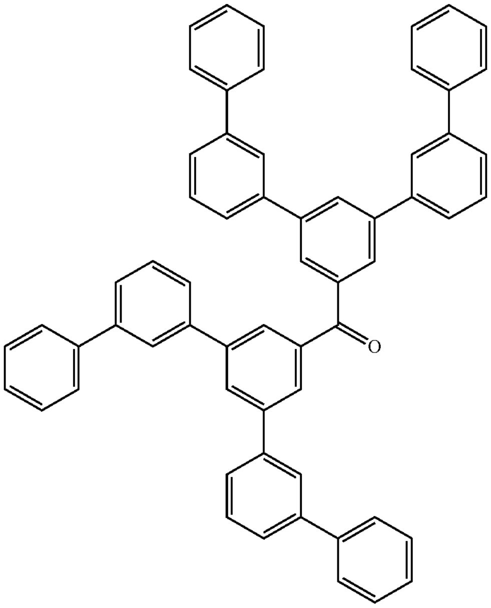
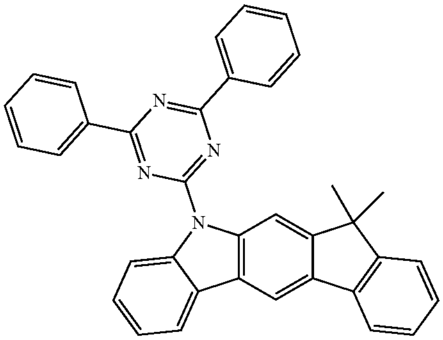
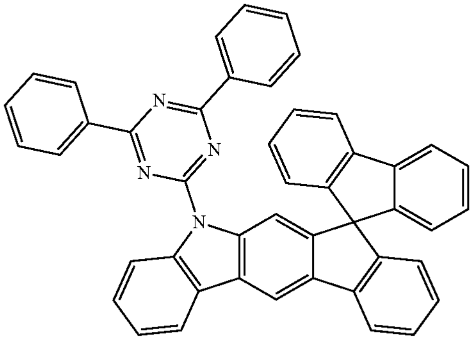
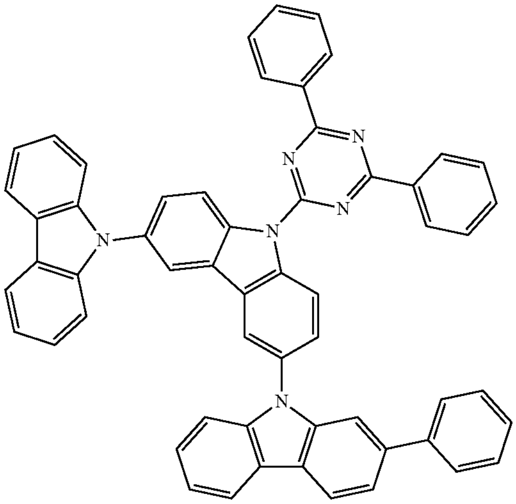
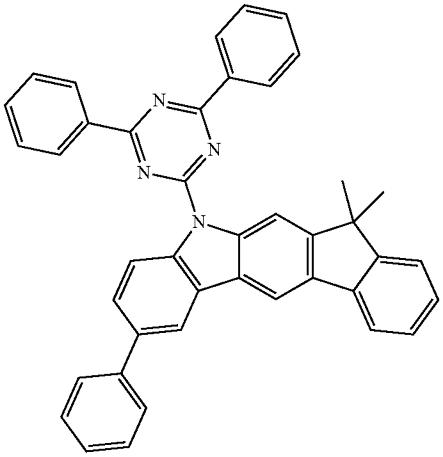
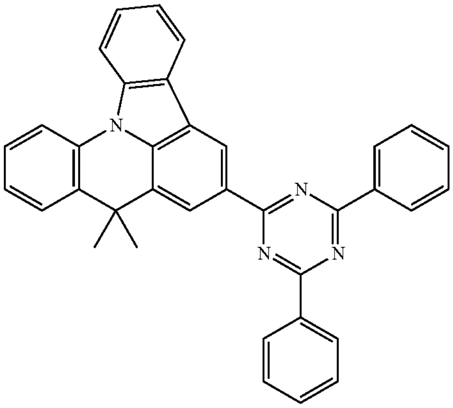

-continued
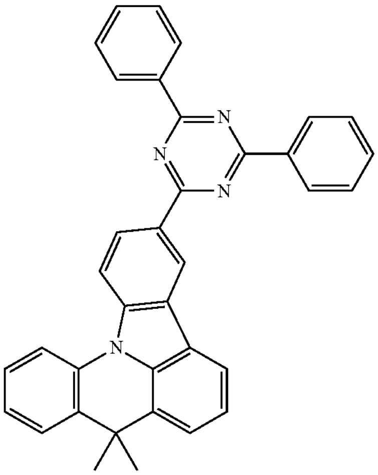
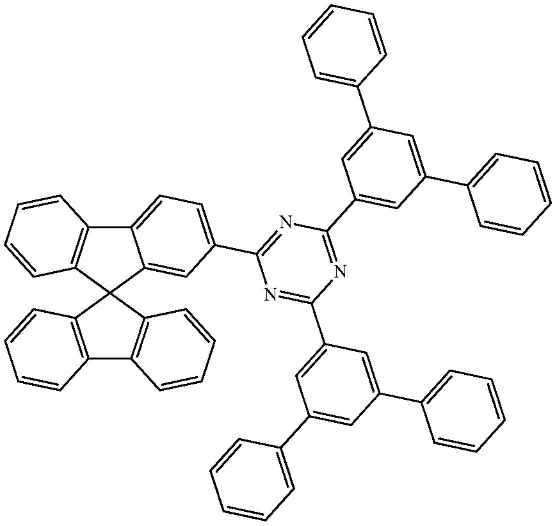
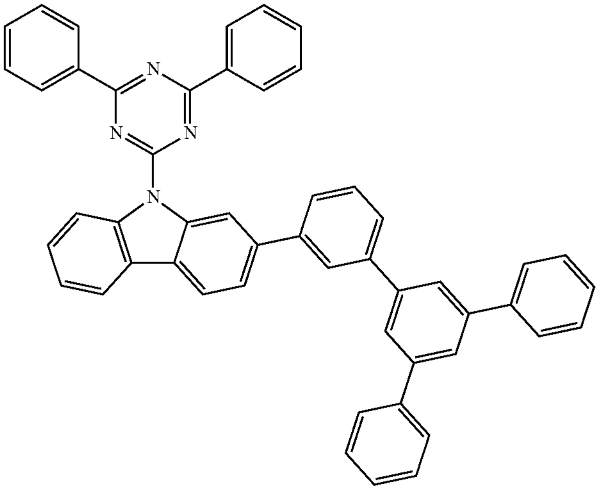
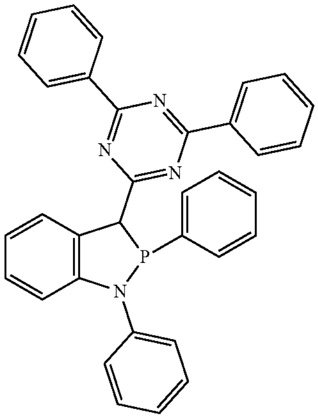
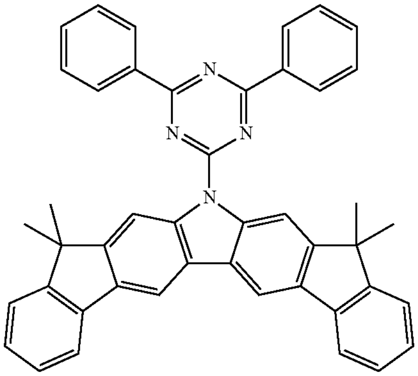
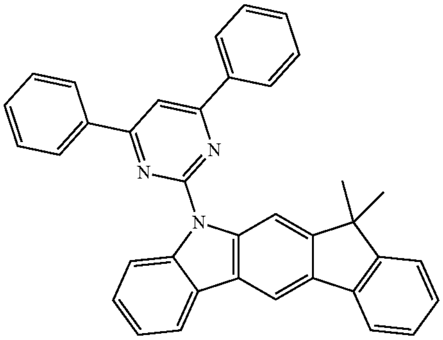

-continued
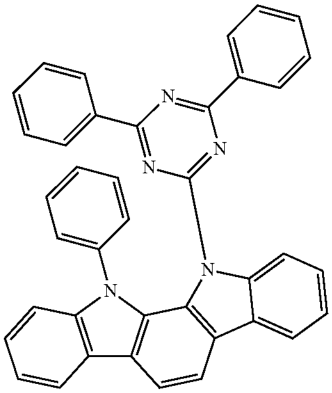
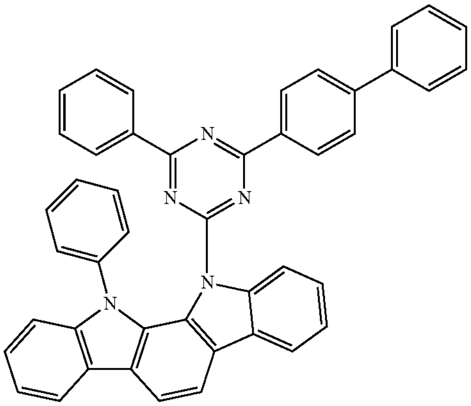
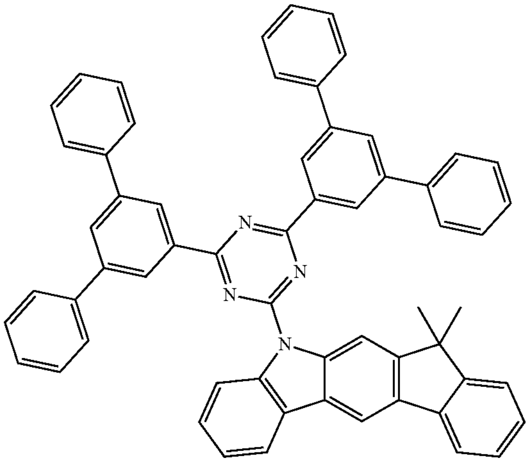
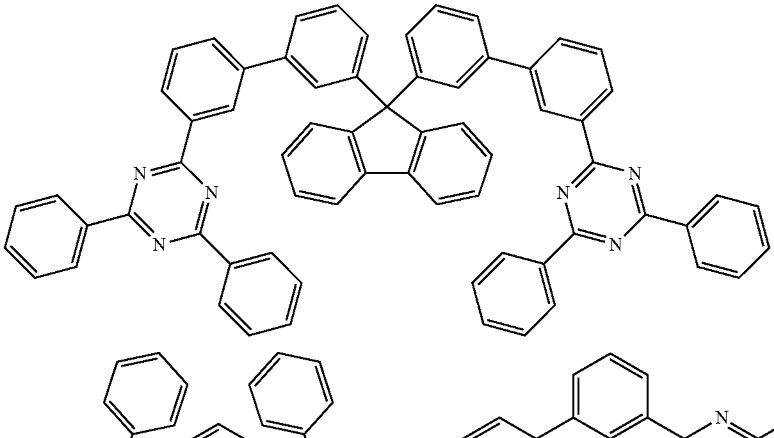
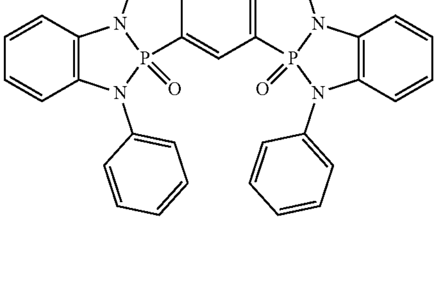
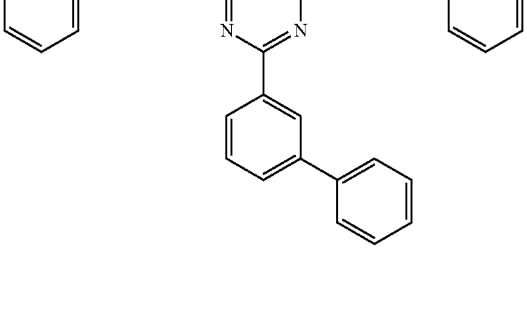

-continued
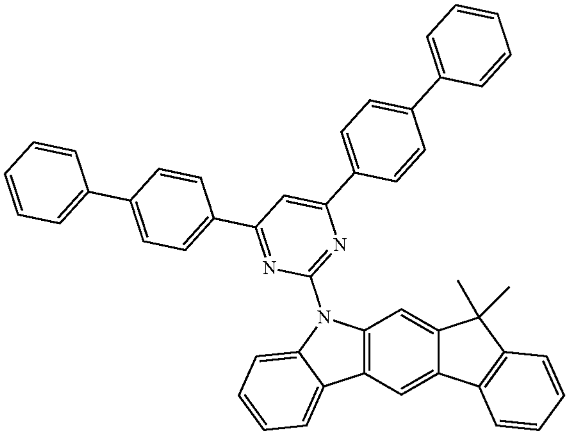
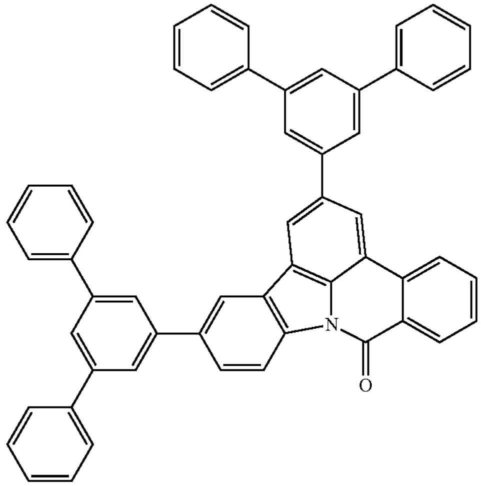
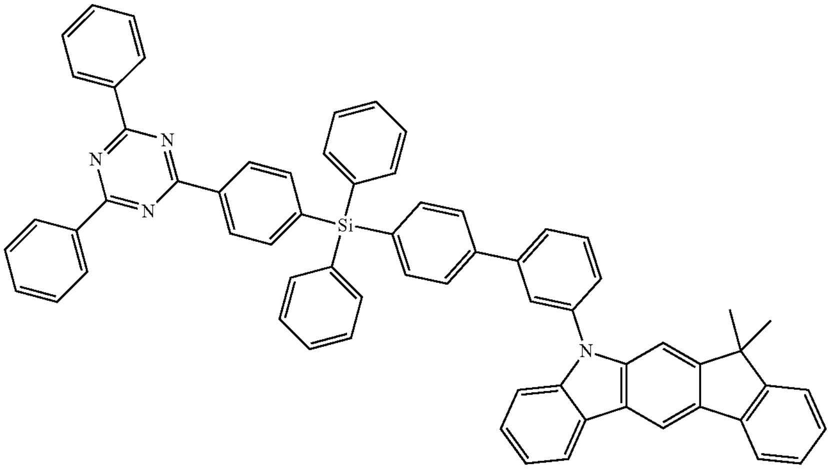
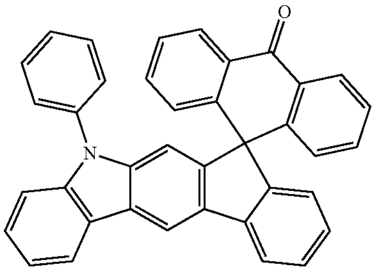
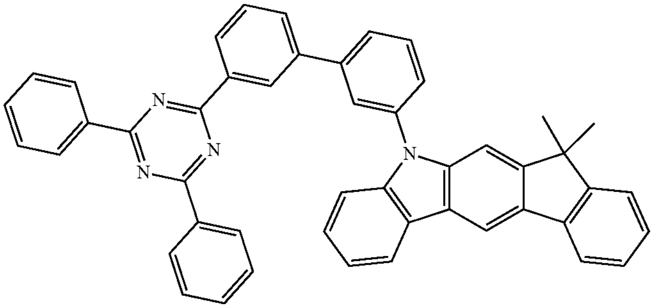
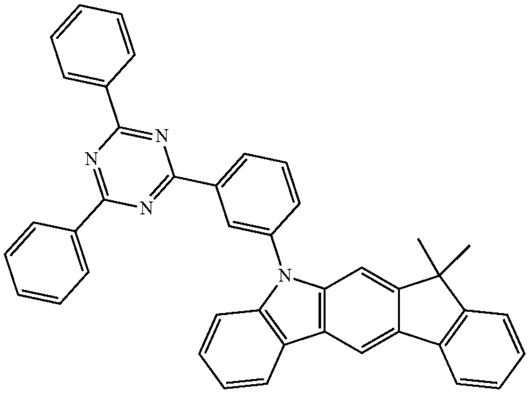
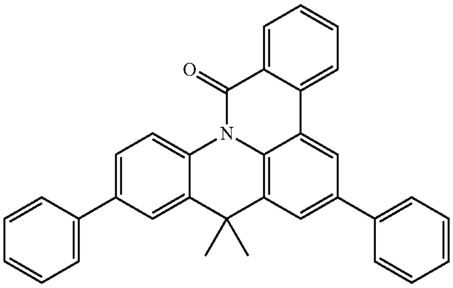

-continued
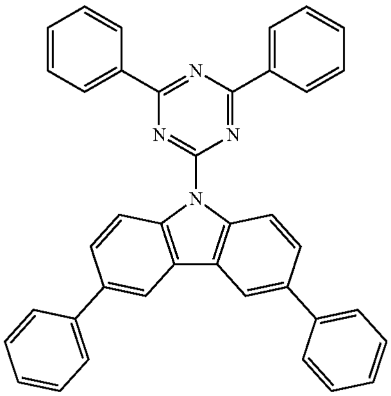
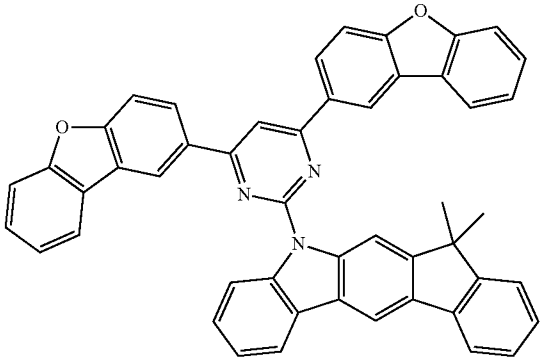
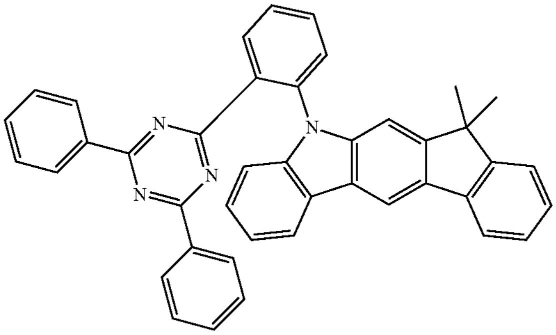
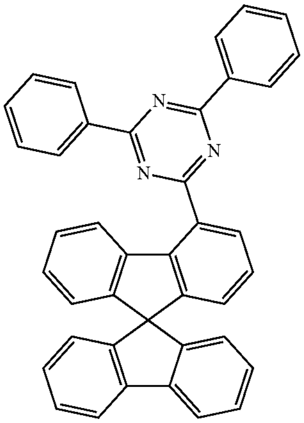
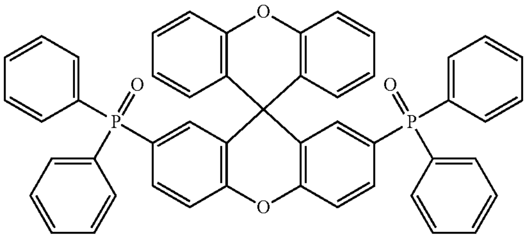
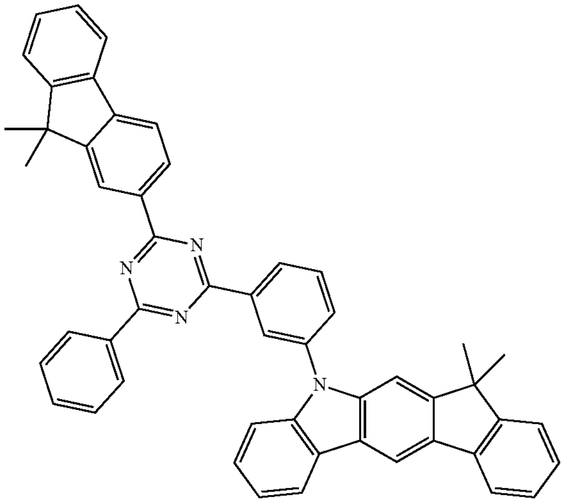

-continued
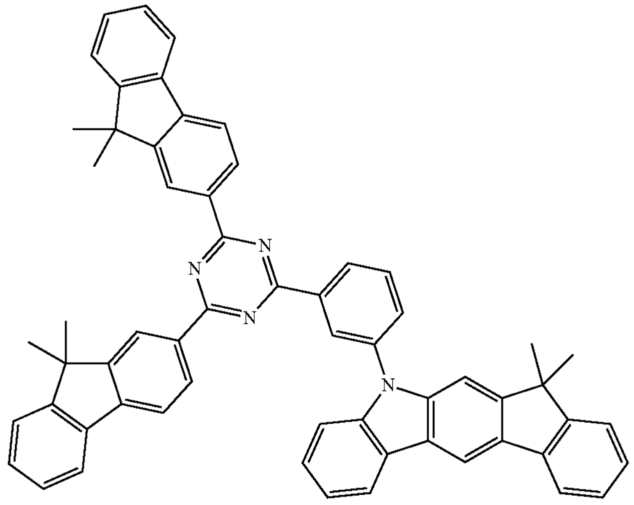
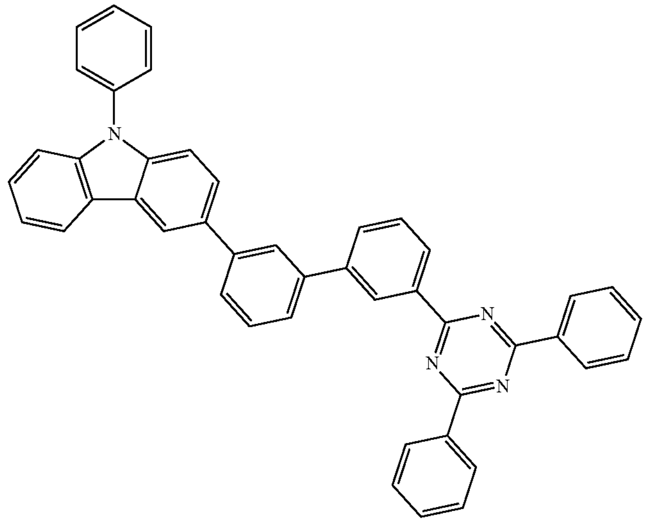
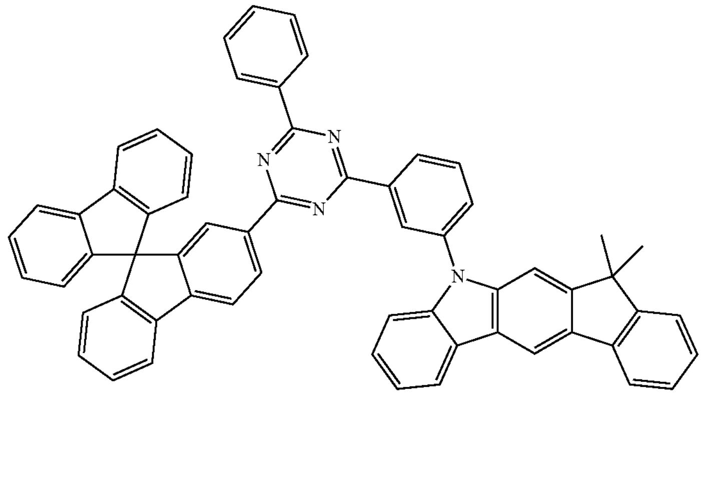

-continued
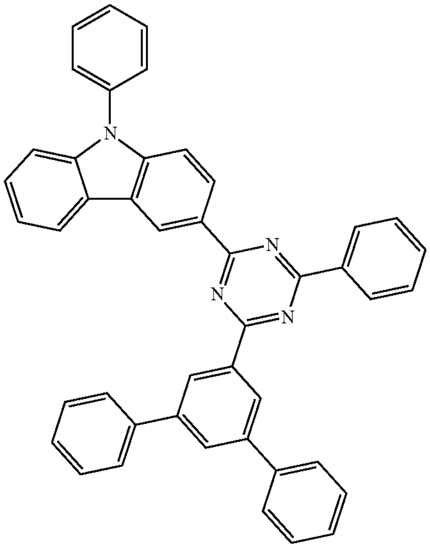
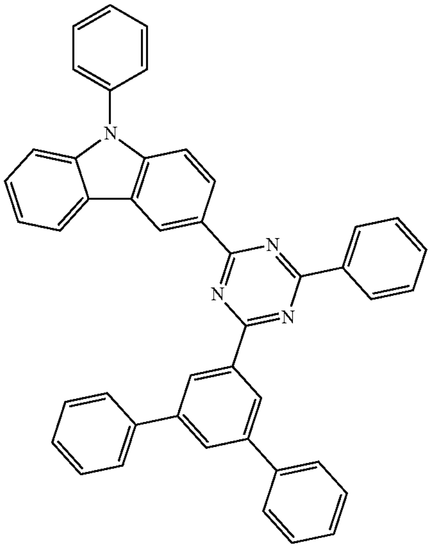
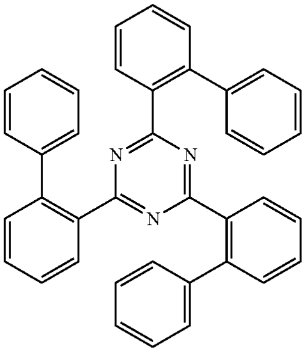
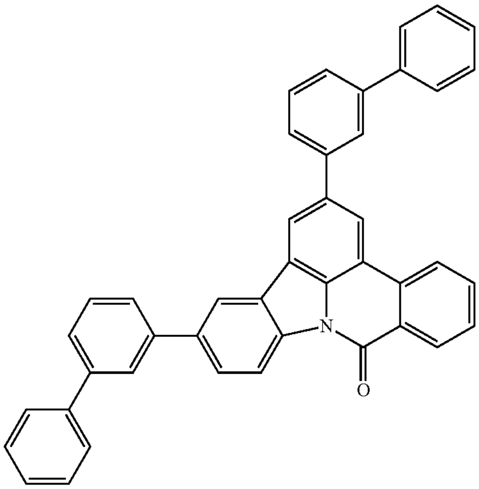
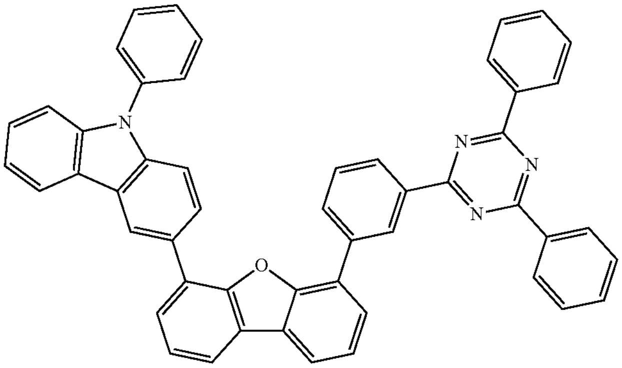

-continued
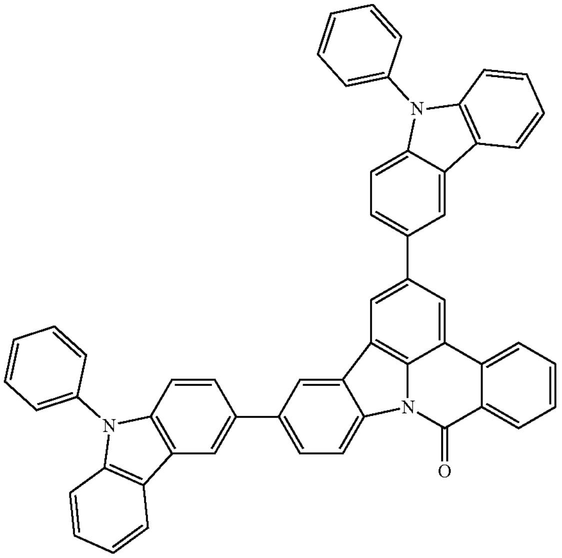
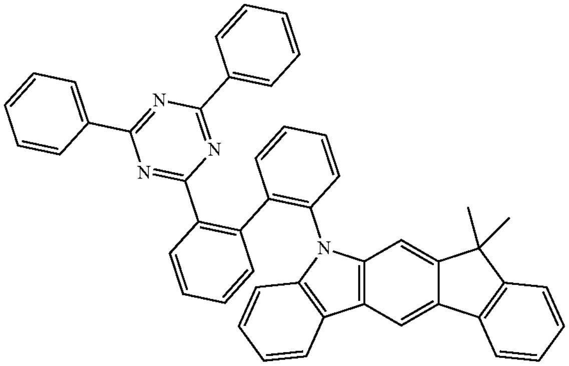
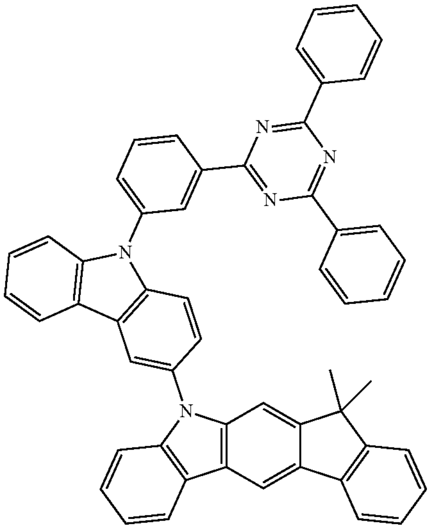
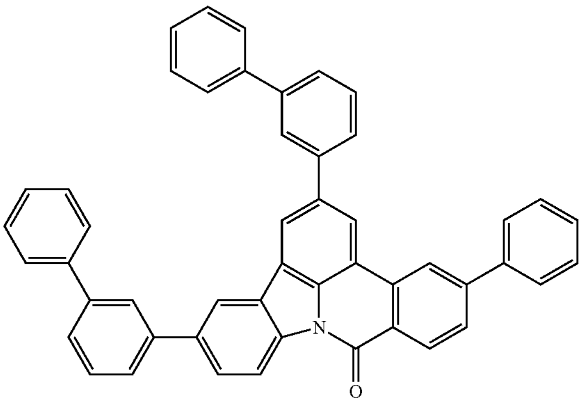
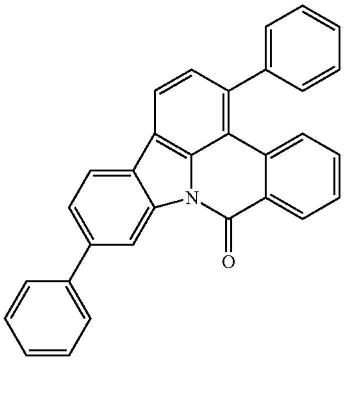
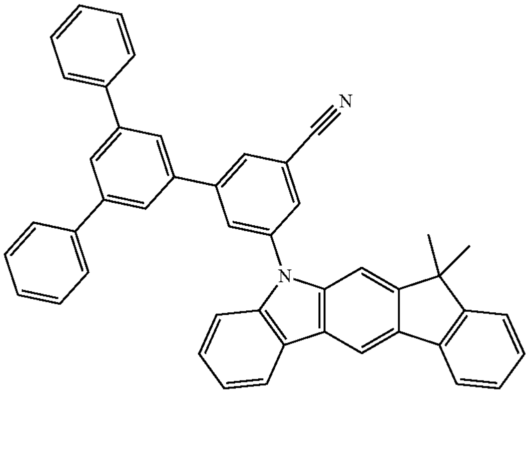

-continued
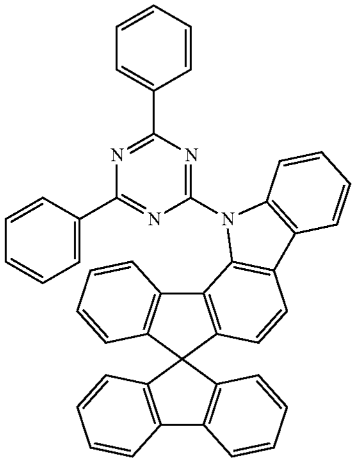
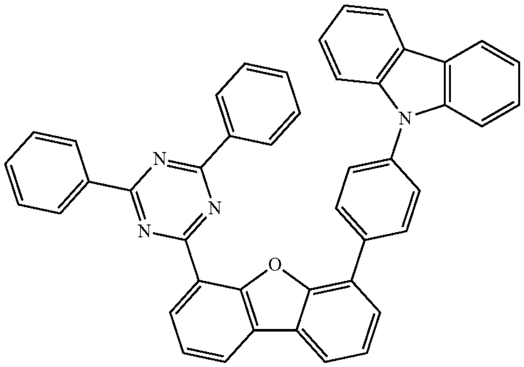
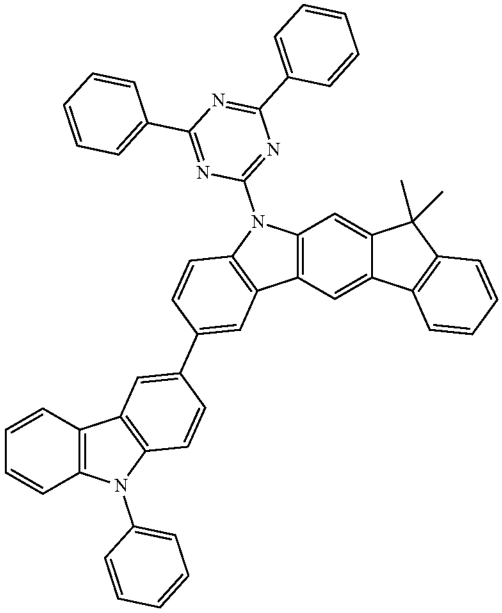
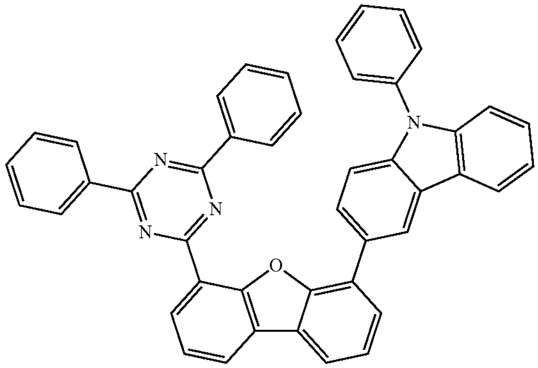
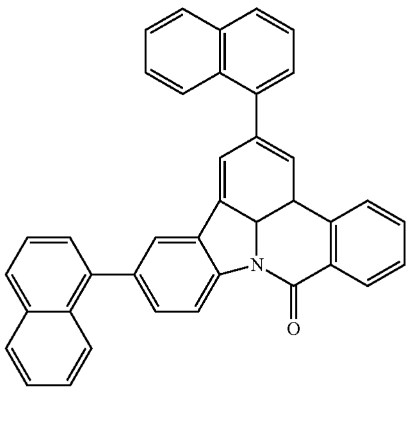
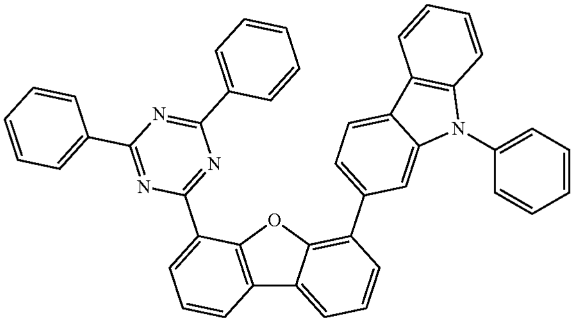

-continued
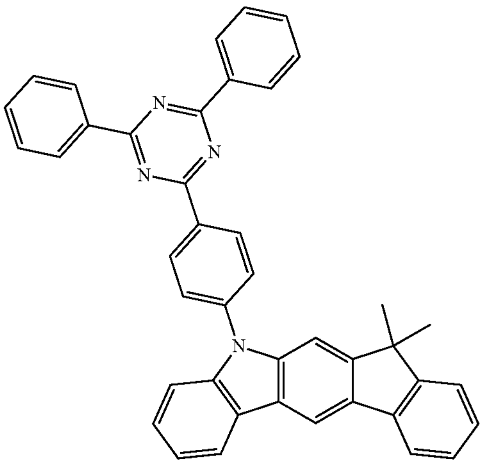
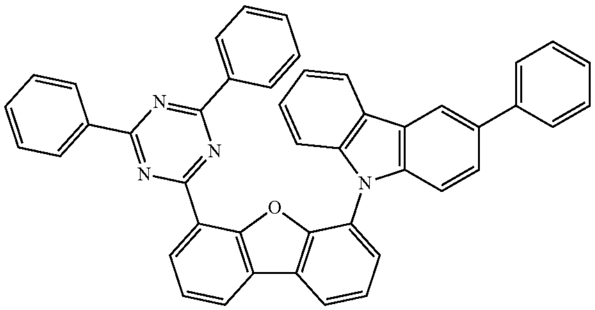
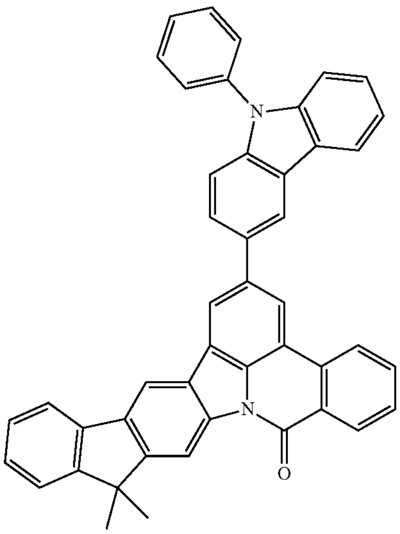
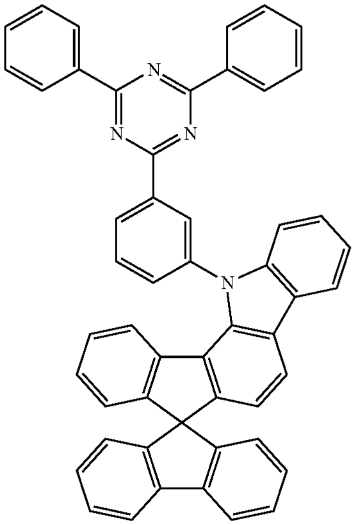
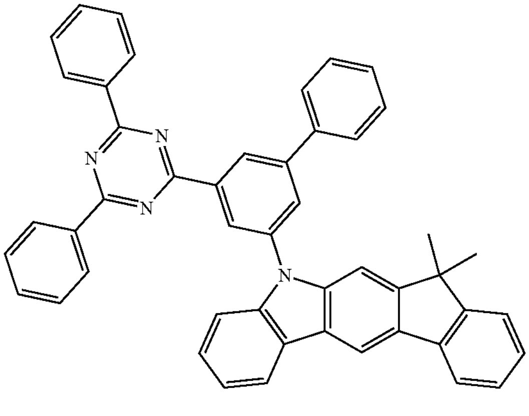
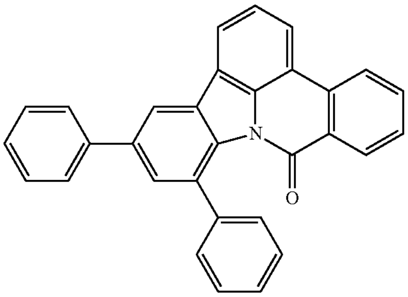

-continued
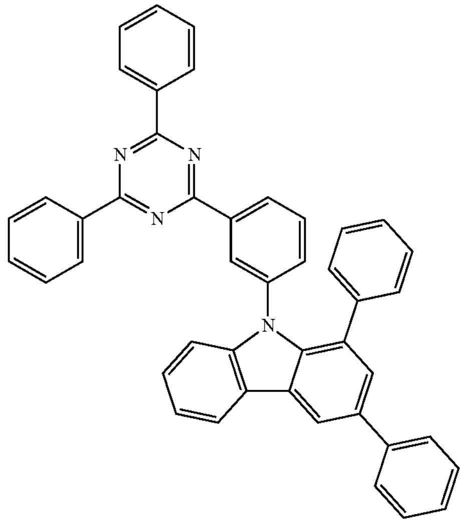
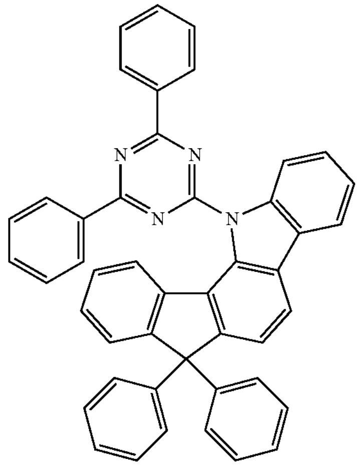
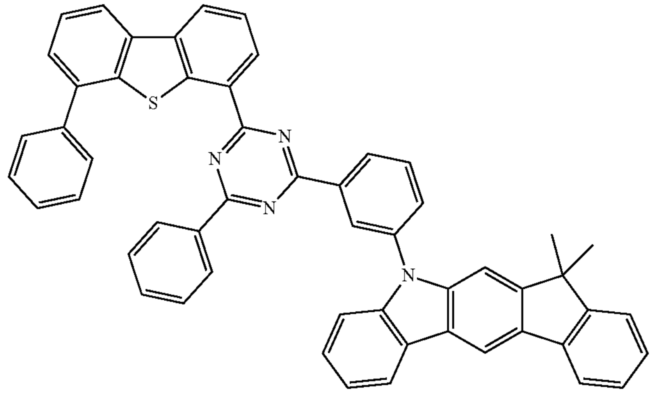
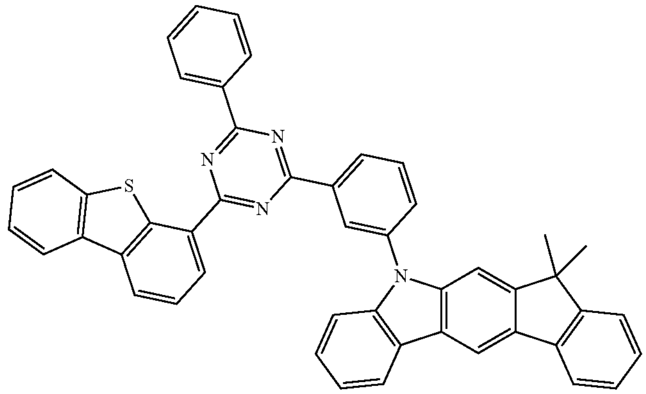

-continued
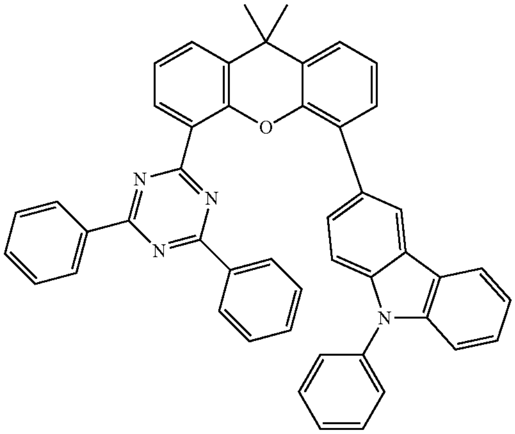
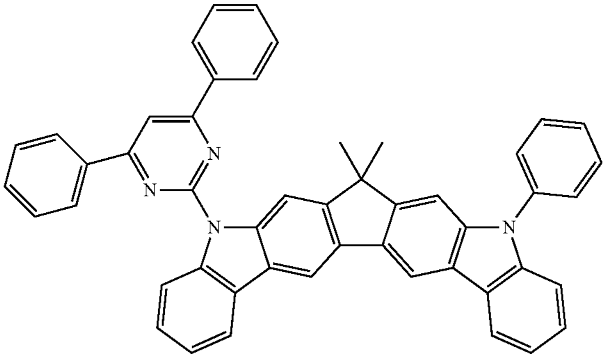
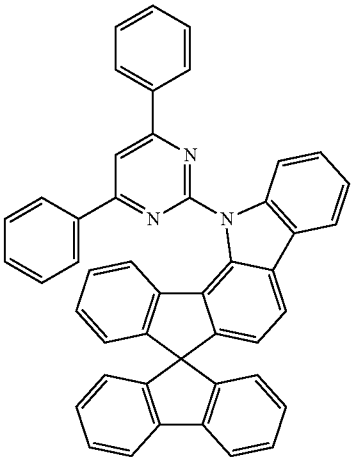
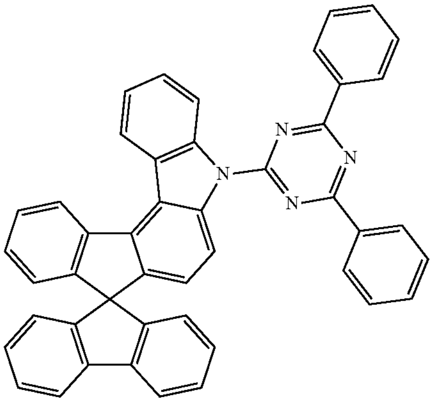
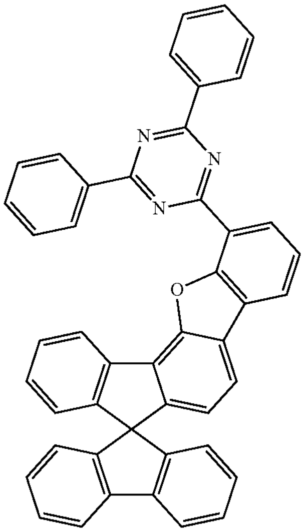
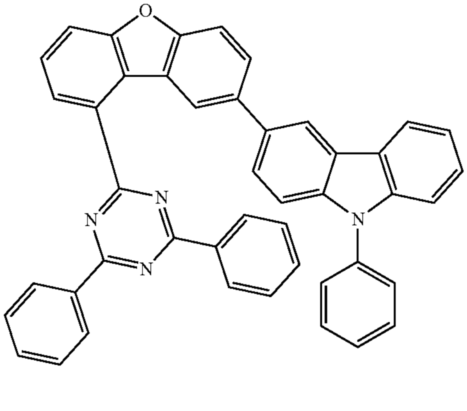
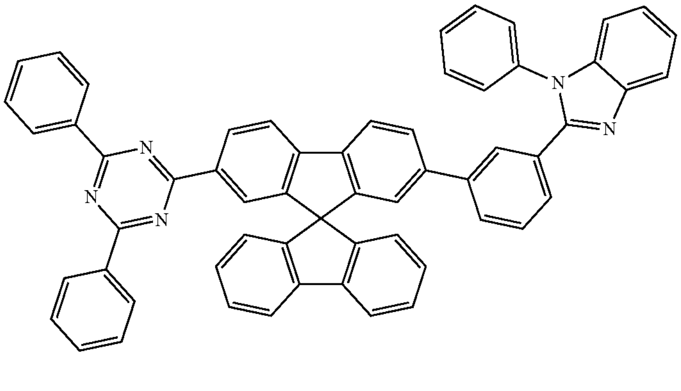

-continued
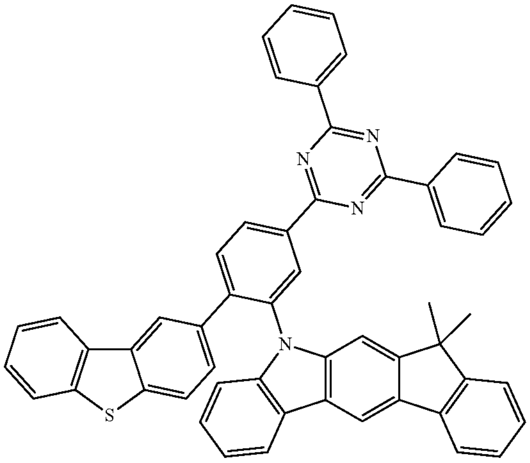
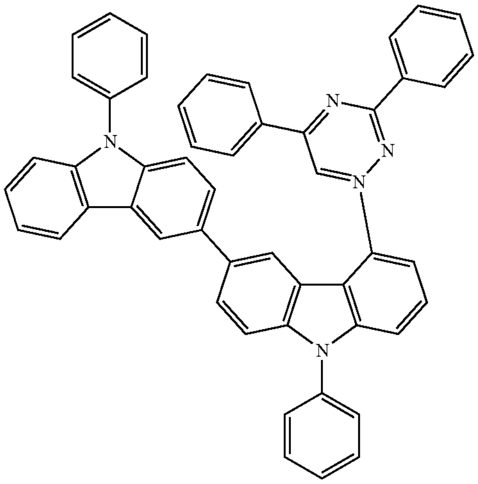
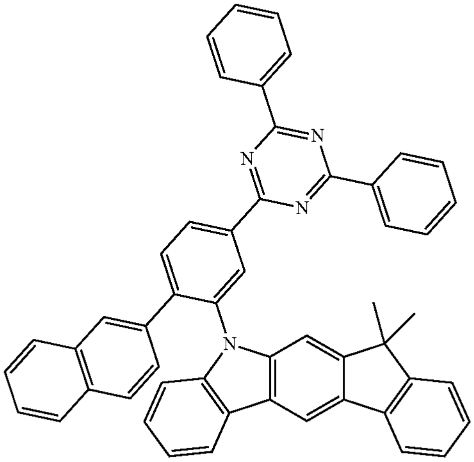
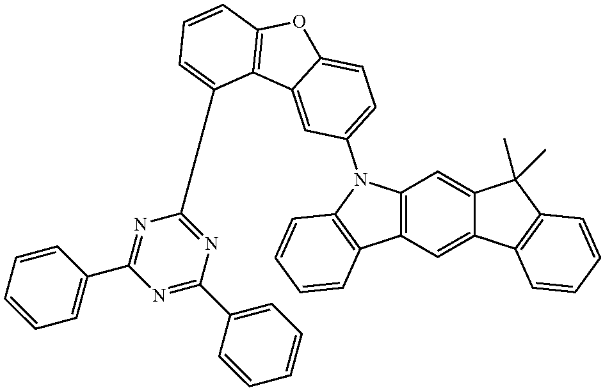
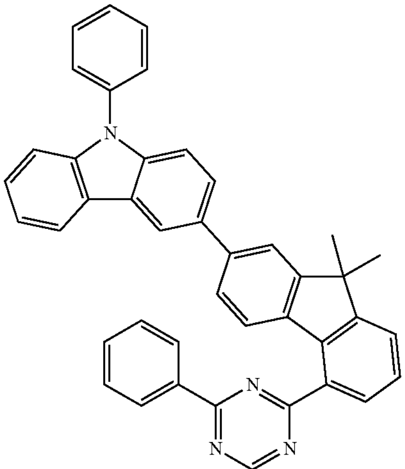
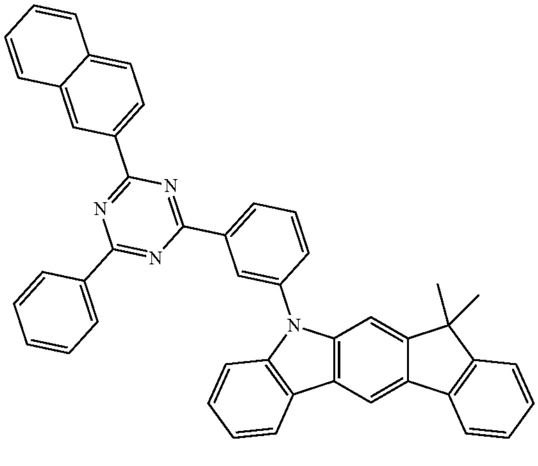

-continued
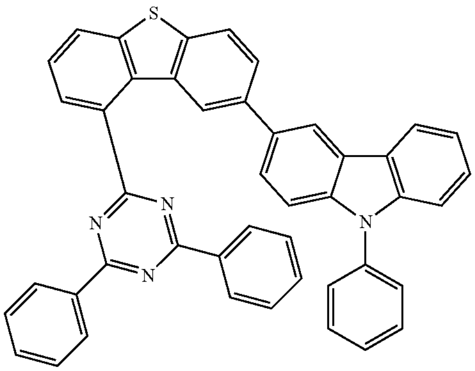
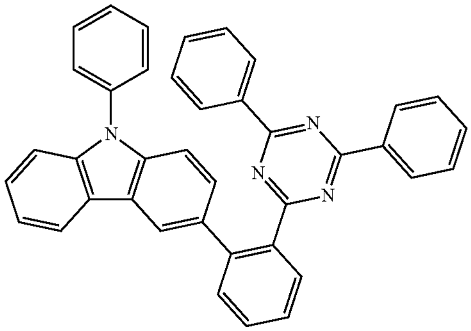
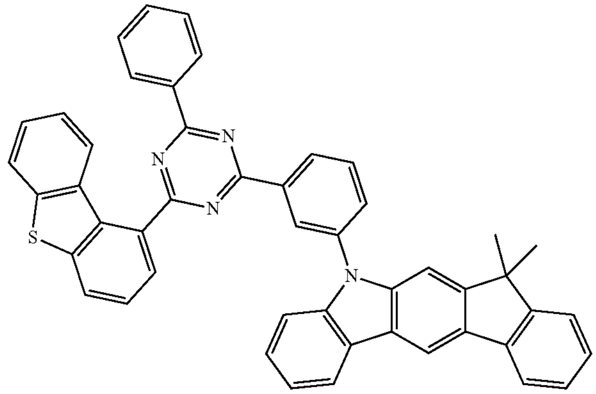
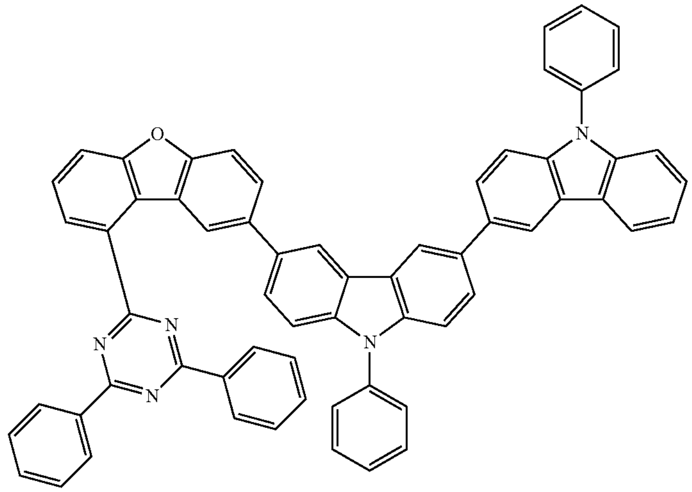
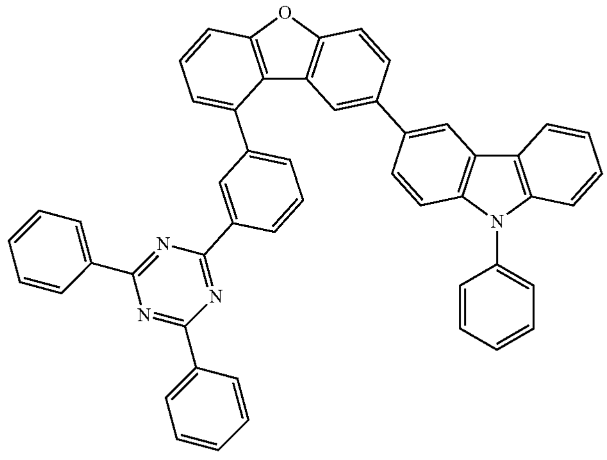
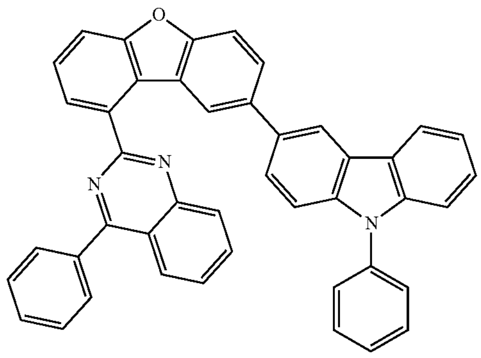

-continued
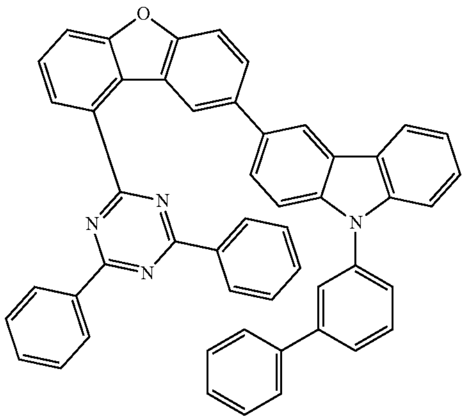
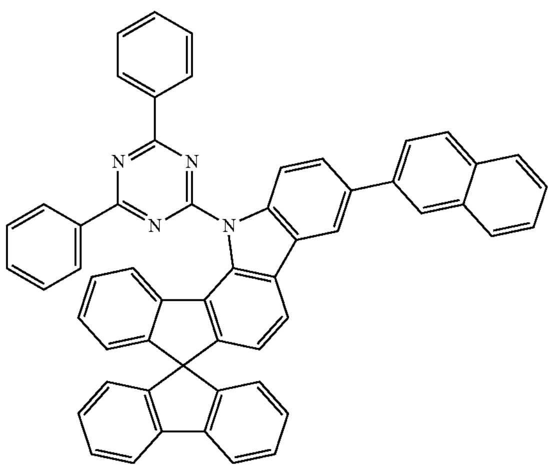
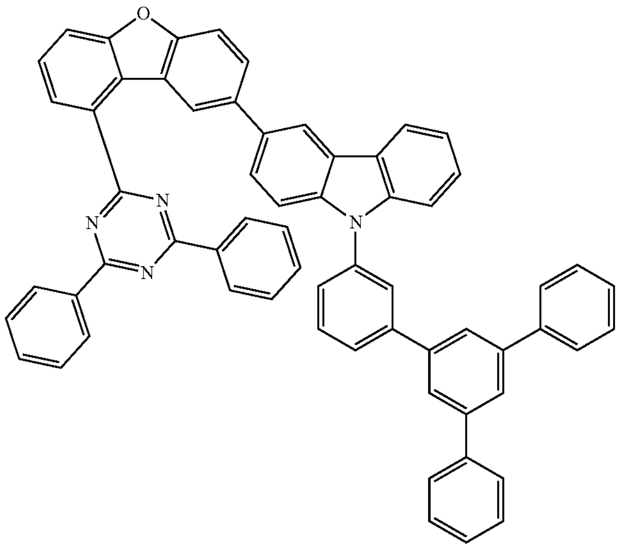
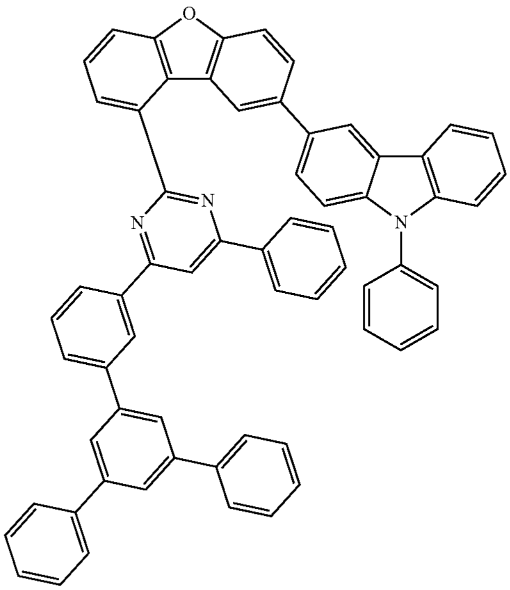
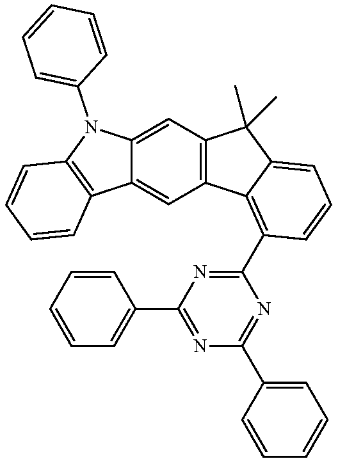
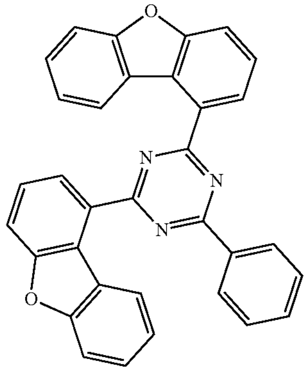

-continued
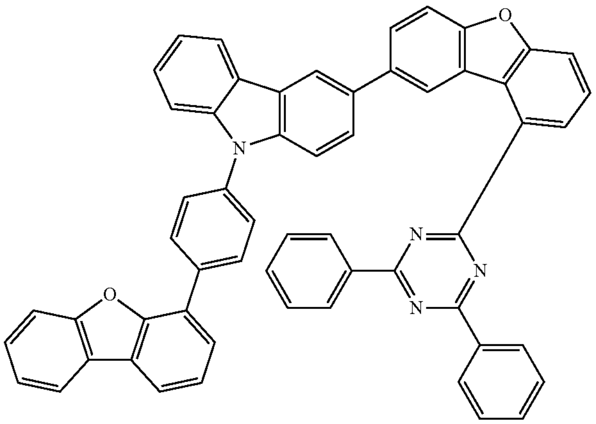
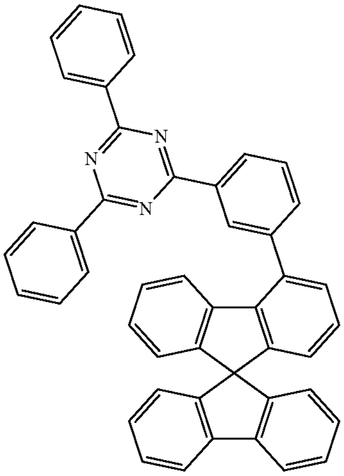
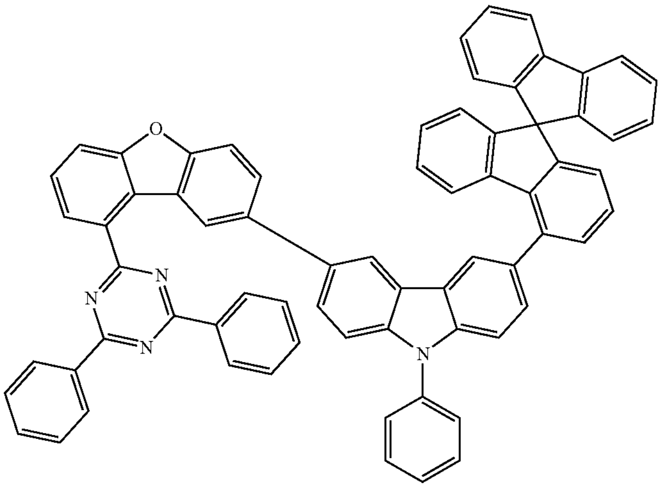
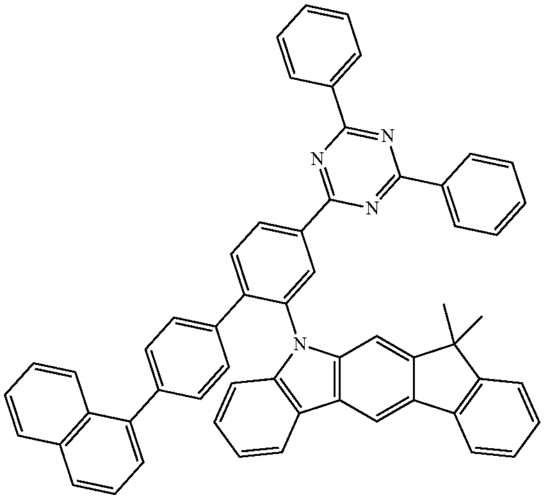
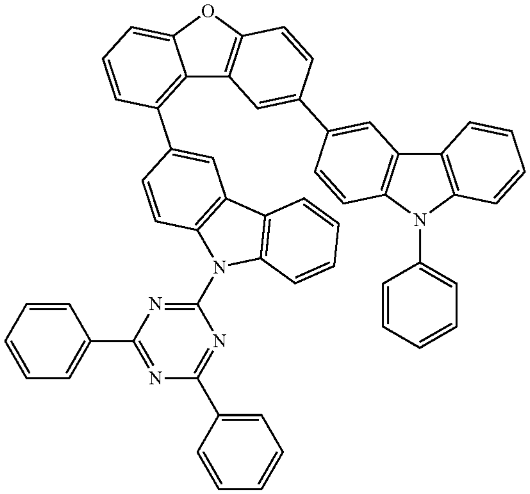

-continued
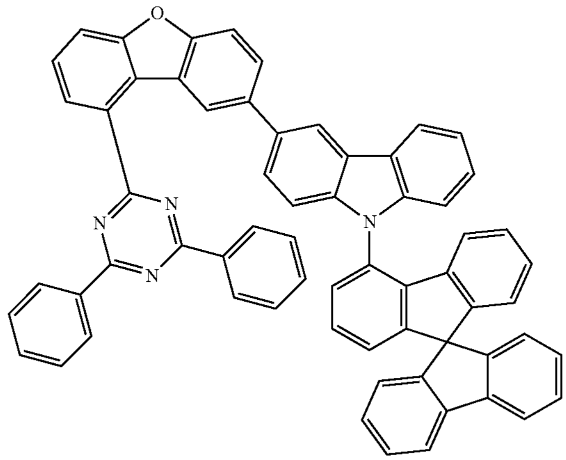
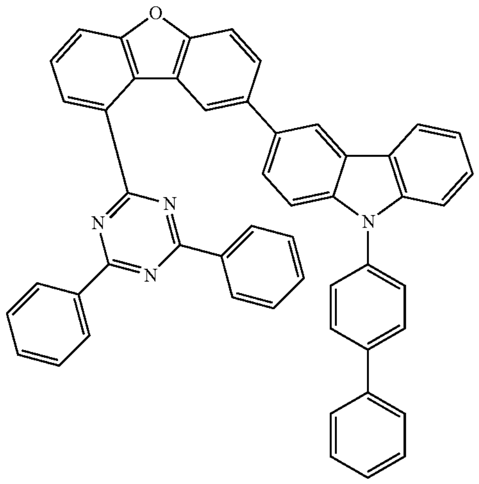
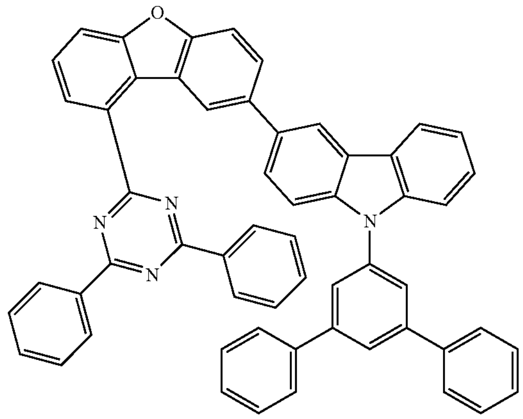
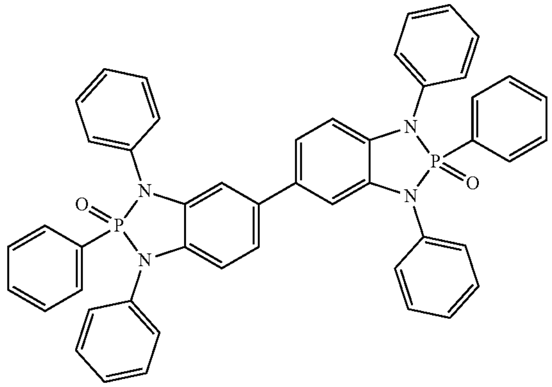
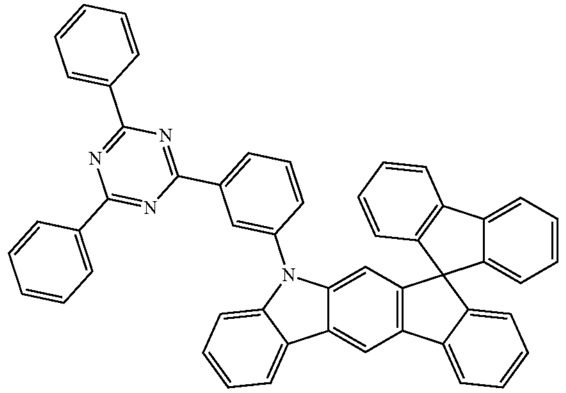

-continued
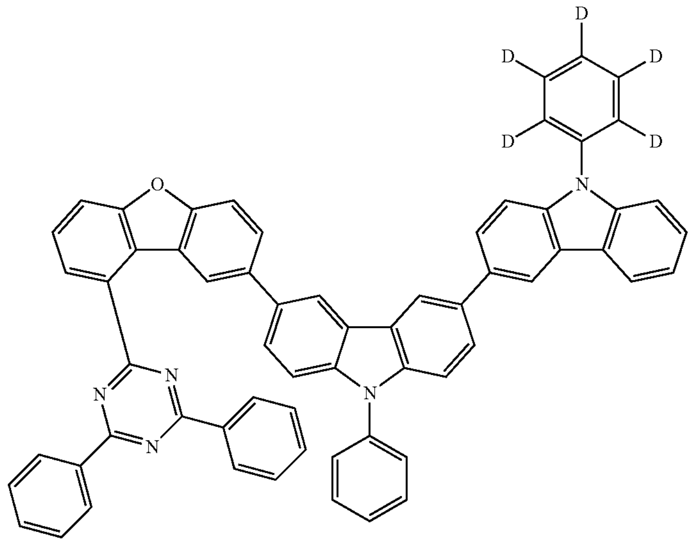
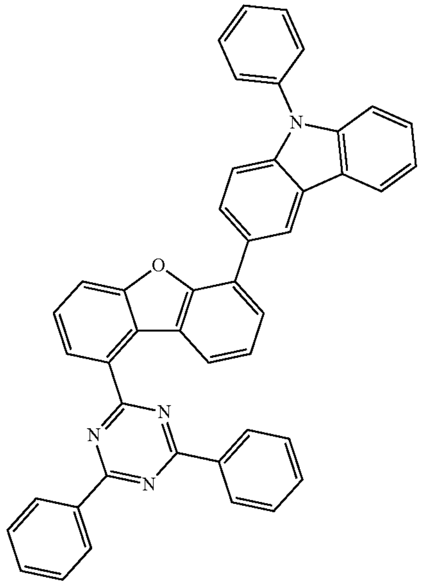
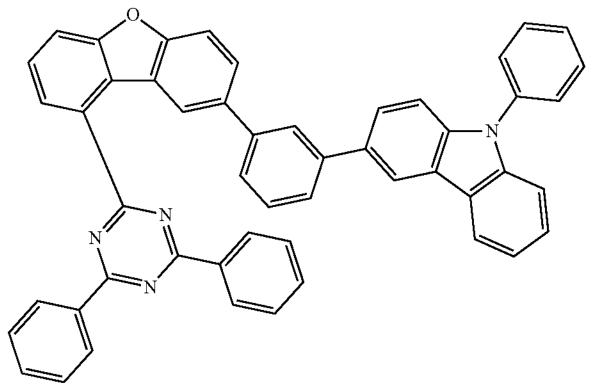
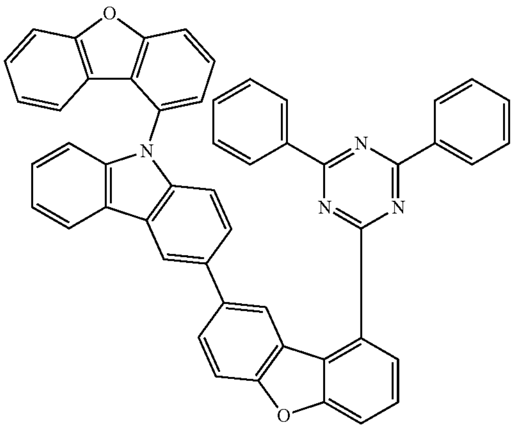
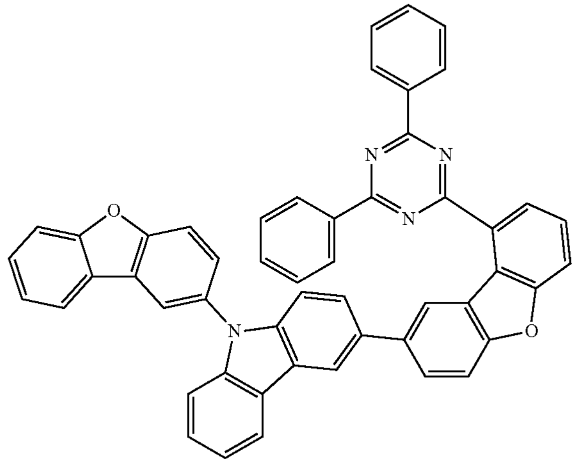
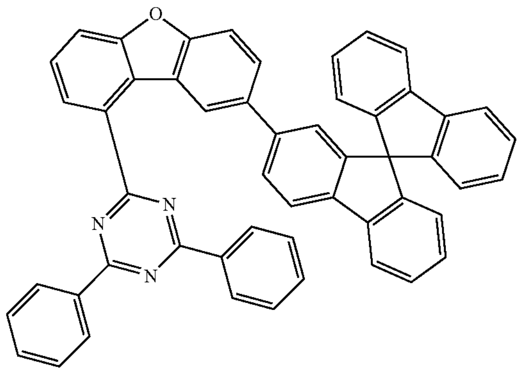

-continued
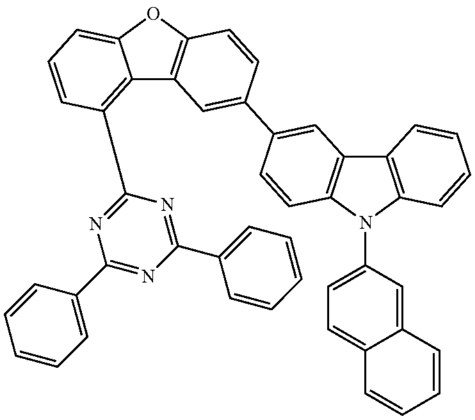
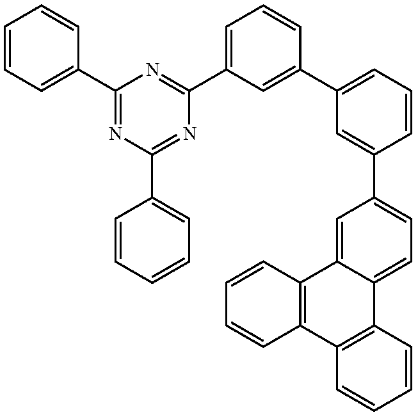
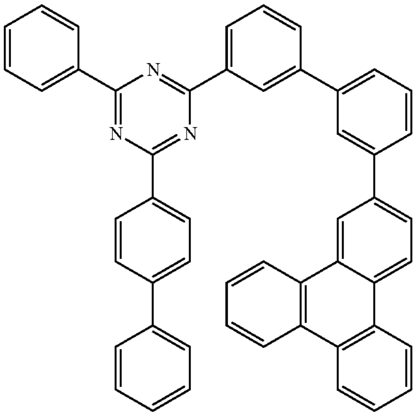
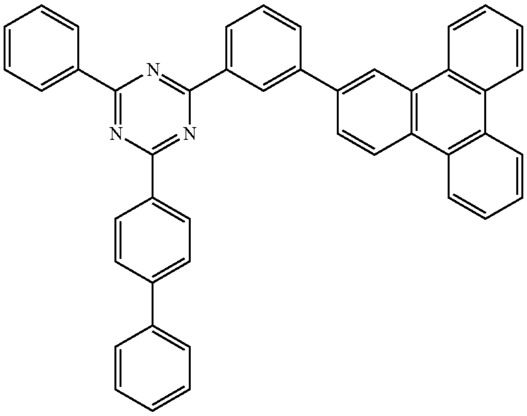
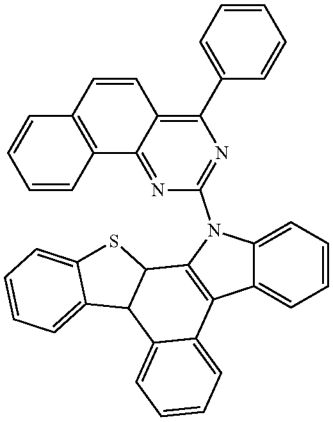
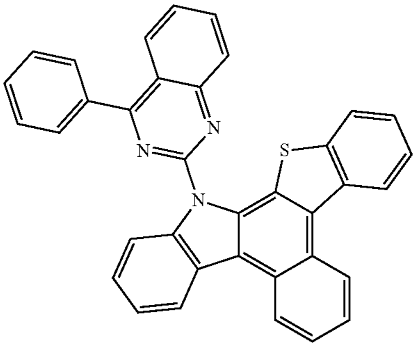

-continued
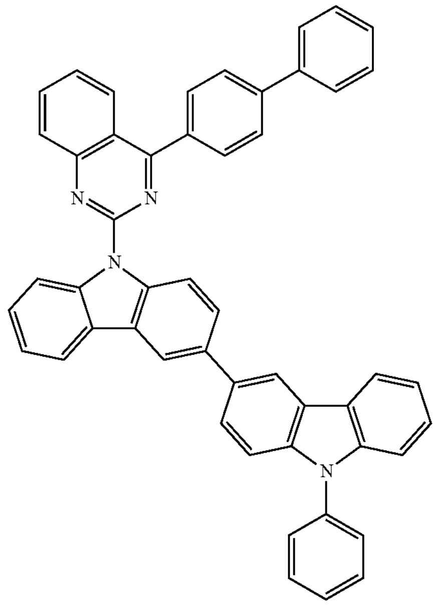
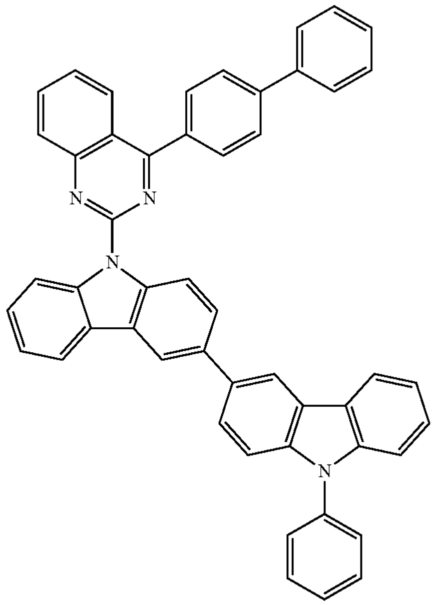
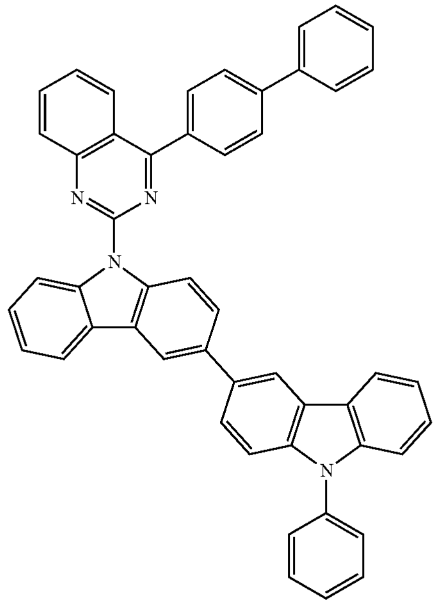
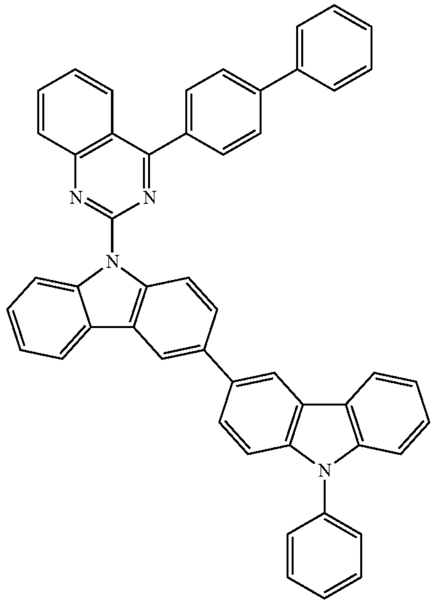

-continued

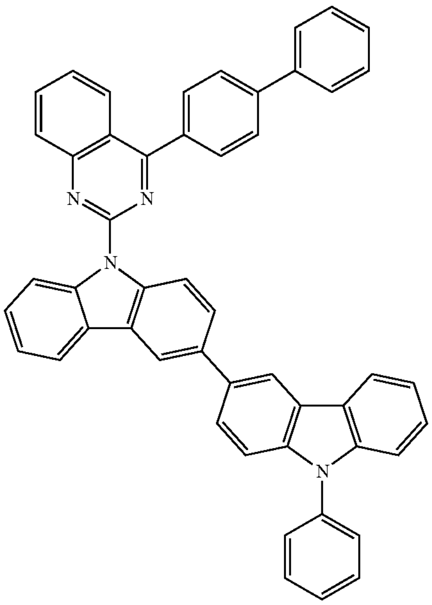

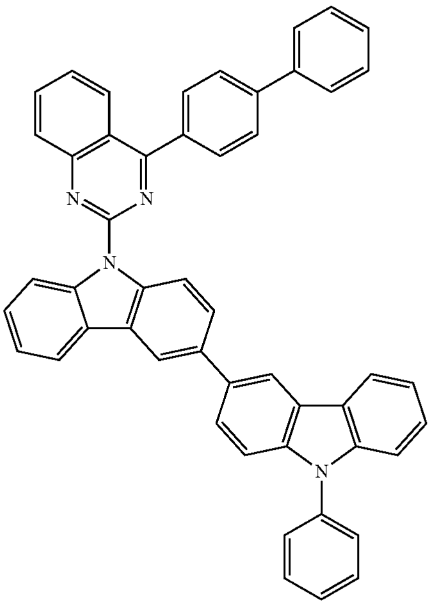

Preferred embodiments of the different functional materials in the electronic device are listed hereinafter.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups are bonded to the pyrene preferably in the 1 position or 1,6 positions. Further preferred emitting compounds are indenofluoreneamines or -diamines, benzoindenofluoreneamines or -diamines, and dibenzoindenofluoreneamines or -diamines, and indenofluorene derivatives having fused aryl groups. Likewise preferred are pyrenearylamines, benzoindenofluoreneamines, benzofluoreneamines, extended benzoindenofluorenes, phenoxazines, and fluorene derivatives substituted by furan units or by thiophene units.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene or dinaphthylanthracene), especially the oligoarylenes containing fused aromatic groups, the oligoarylenevinylenes (e.g. DPVBi or spiro-DPVBi), the polypodal metal complexes, the hole-conducting compounds, the electron-conducting compounds, especially ketones, phosphine oxides and sulfur oxides, the atropisomers, the boronic acid derivatives or the benzanthracenes. Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another.

Preferred matrix materials for phosphorescent emitting compounds are, as well as the compounds of the formula (I), aromatic ketones, aromatic phosphine oxides or aromatic sulfoxides or sulfones, triarylamines, carbazole derivatives, indolocarbazole derivatives, indenocarbazole derivatives, azacarbazole derivatives, bipolar matrix materials, silanes, azaboroles or boronic esters, triazine derivatives, zinc complexes, diazasilole or tetraazasilole derivatives, diazaphosphole derivatives, bridged carbazole derivatives, triphenylene derivatives and lactams.

Suitable charge transport materials as usable in the hole injection or hole transport layer or electron blocker layer or in the electron transport layer of the electronic device of the invention are, as well as the compounds of the formula (I), for example, the compounds disclosed in Y. Shirota et al., Chem. Rev. 2007, 107(4), 953-1010, or other materials as used in these layers according to the prior art.

Preferred materials for hole-transporting layers of the OLEDs are the following materials:

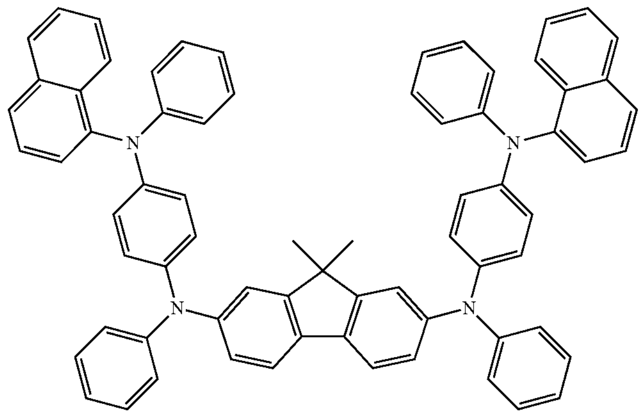
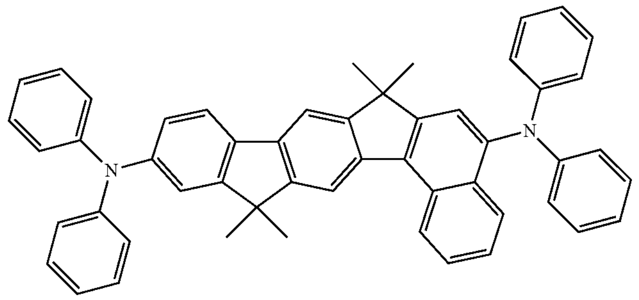
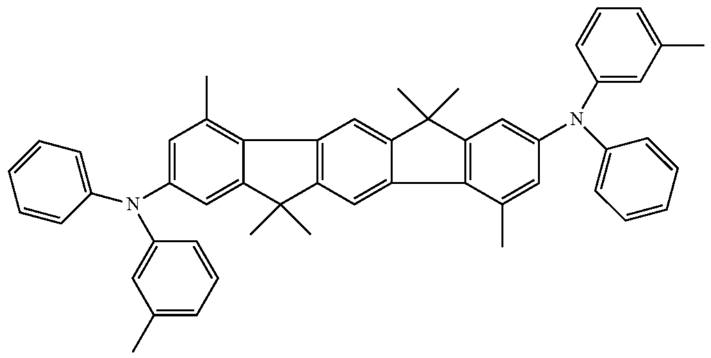
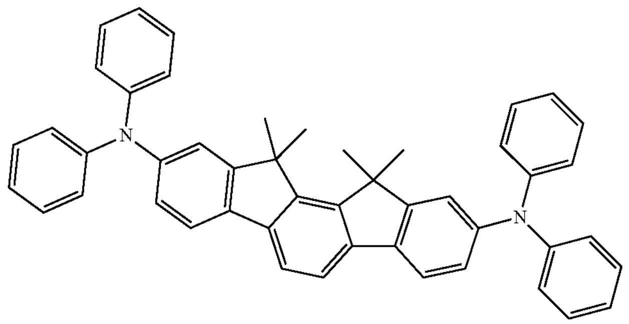
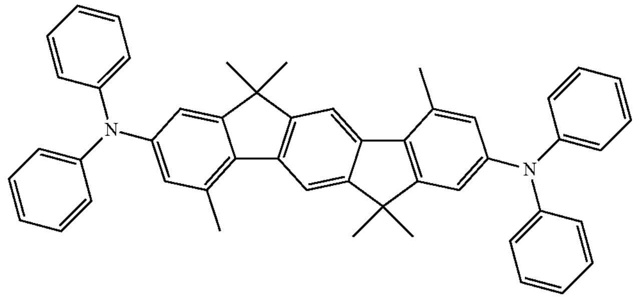

-continued
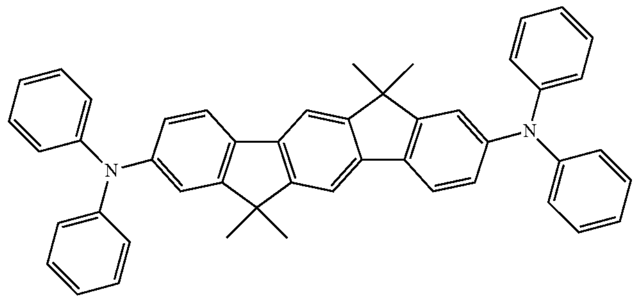
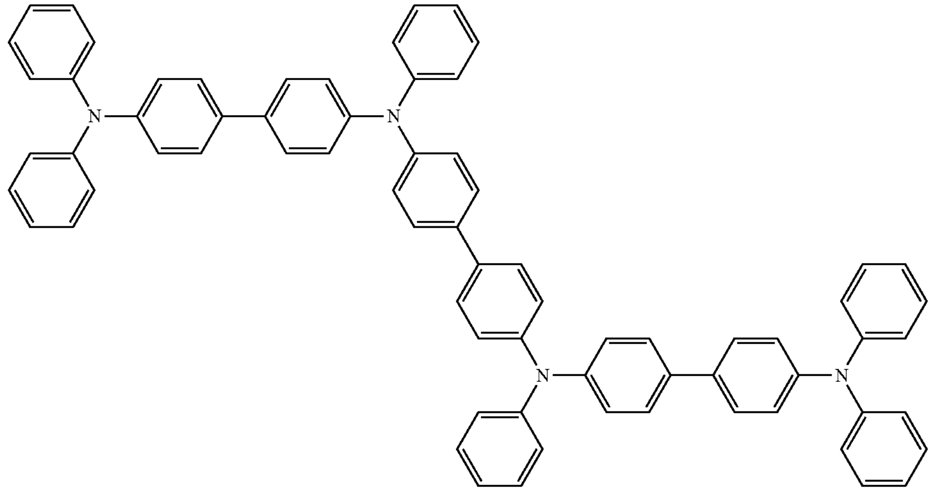
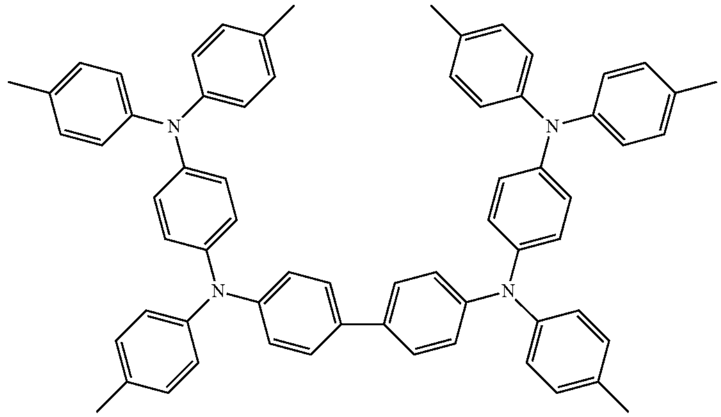

-continued
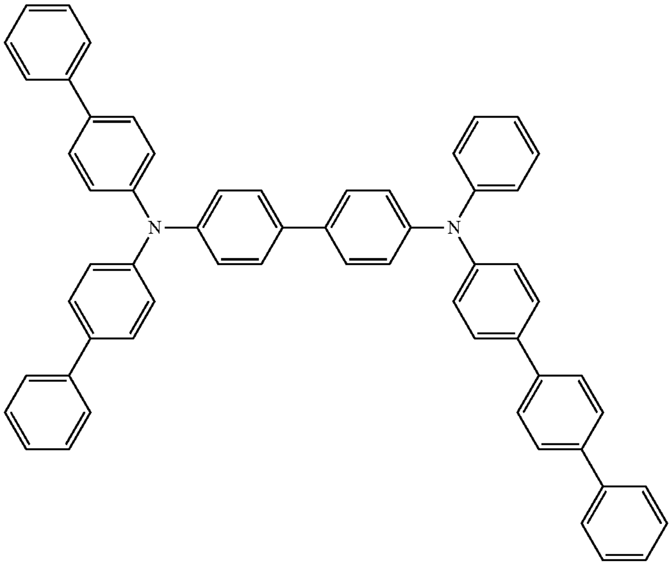
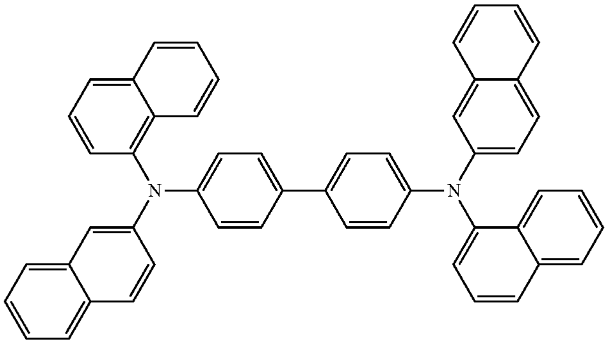
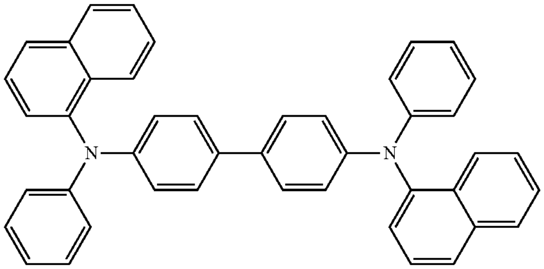
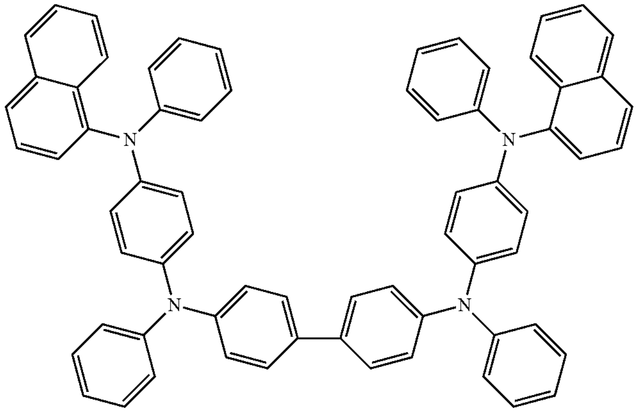

-continued
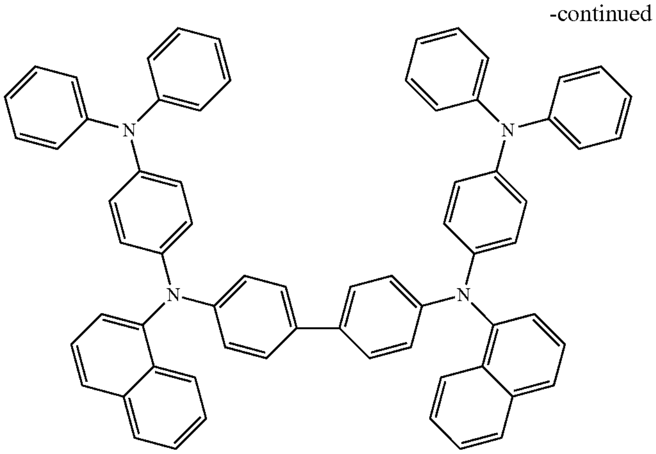
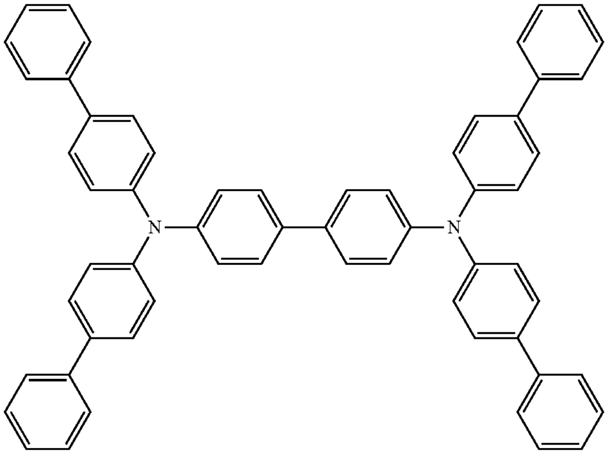
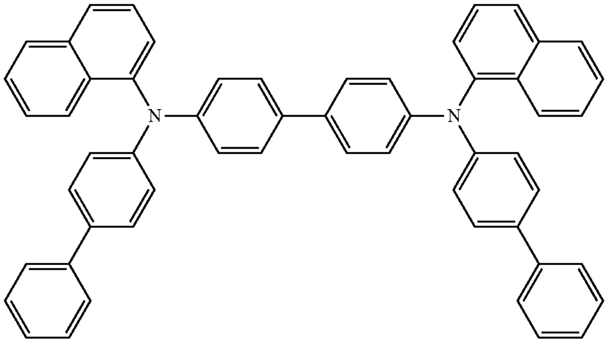
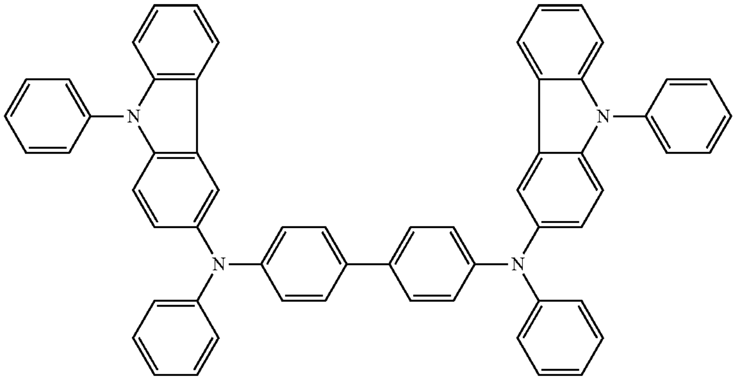

-continued
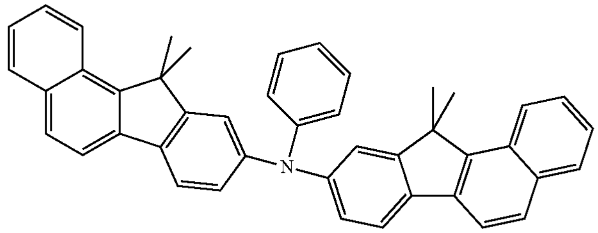
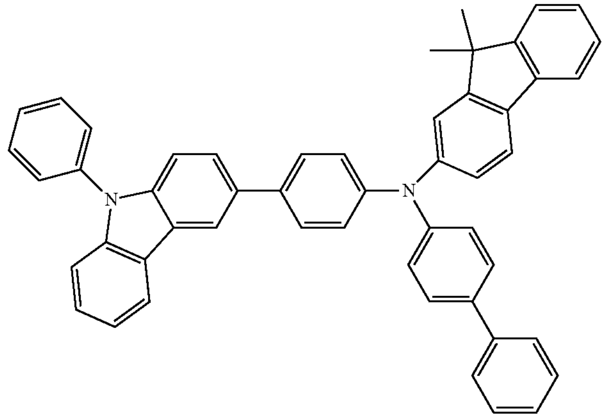
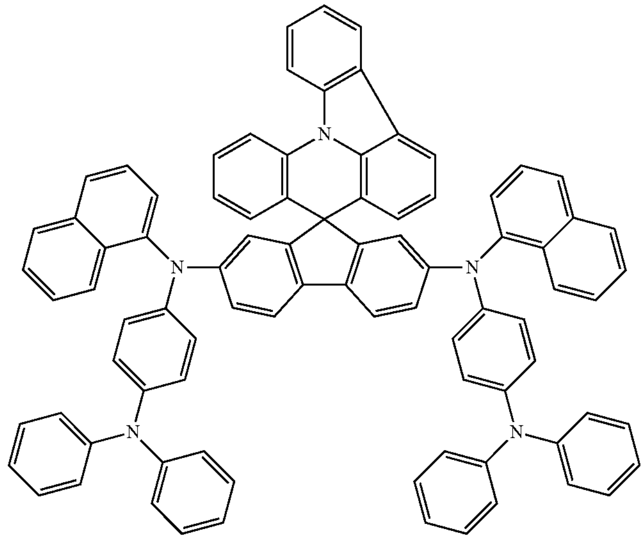
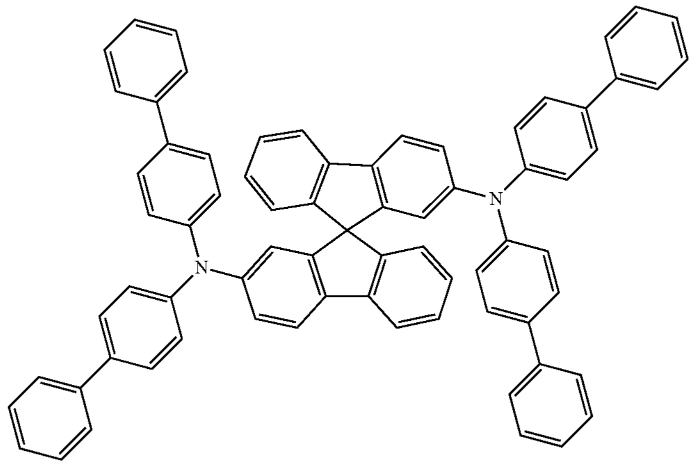

-continued

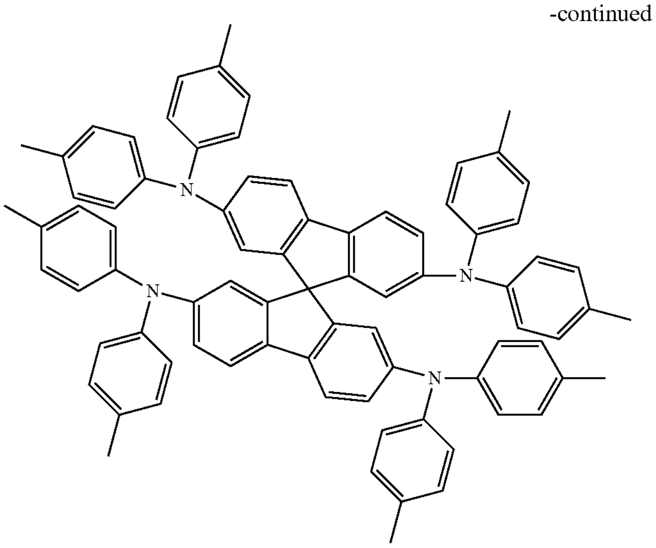

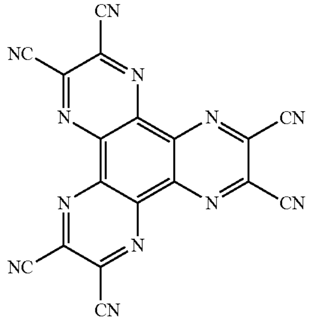

Preferably, the inventive OLED comprises two or more different hole-transporting layers. The compound of the formula (I) may be used here in one or in more of or in all the hole-transporting layers. In a preferred embodiment, the compound of the formula (I) is used in exactly one or exactly two hole-transporting layers, and other compounds, preferably aromatic amine compounds, are used in the further hole-transporting layers present. Further compounds which, as well as the compounds of the formula (I), are preferably used in hole-transporting layers of the OLEDs of the invention are especially indenofluoreneamine derivatives, amine derivatives, hexaazatriphenylene derivatives, amine derivatives with fused aromatic systems, monobenzoindenofluoreneamines, dibenzoindenofluoreneamines, spirobifluoreneamines, fluoreneamines, spirodibenzopyranamines, dihydroacridine derivatives, spirodibenzofurans and spirodibenzothiophenes, phenanthrenediarylamines, spirotribenzotropolones, spirobifluorenes having meta-phenyldiamine groups, spirobisacridines, xanthenediarylamines, and 9,10-dihydroanthracene spiro compounds having diarylamino groups.

Materials used for the electron transport layer may be any materials as used according to the prior art as electron transport materials in the electron transport layer. Especially suitable are aluminium complexes, for example $Alq_3$, zirconium complexes, for example $Zrq_4$, lithium complexes, for example Liq, benzimidazole derivatives, triazine derivatives, pyrimidine derivatives, pyridinederivatives, pyrazine derivatives, quinoxaline derivatives, quinoline derivatives, oxadiazole derivatives, aromatic ketones, lactams, boranes, diazaphosphole derivatives and phosphine oxide derivatives. Particular preference is given to the compounds shown in the following table:

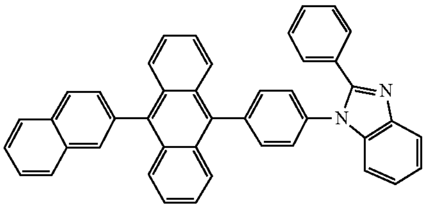 [SMILES: c1ccc(-c2nc3ccccc3n2-c2ccc(-c3c4ccccc4c(-c4ccc5ccccc5c4)c4ccccc34)cc2)cc1]

-continued

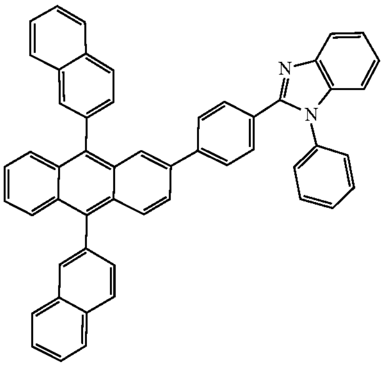 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

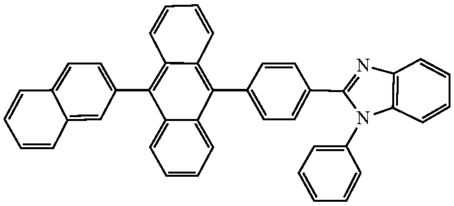 [SMILES: c1ccc(-n2c(-c3ccc(-c4c5ccccc5c(-c5ccc6ccccc6c5)c5ccccc45)cc3)nc3ccccc32)cc1]

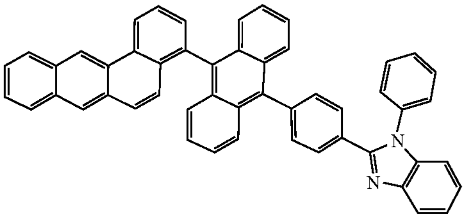 [SMILES: c1ccc(-n2c(-c3ccc(-c4c5ccccc5c(-c5cccc6c5ccc5cc7ccccc7cc56)c5ccccc45)cc3)nc3ccccc32)cc1]

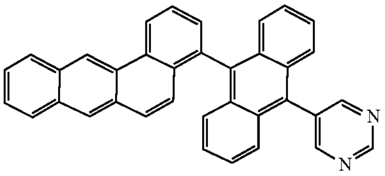 [SMILES: c1ccc2cc3c(ccc4c(-c5c6ccccc6c(-c6cncnc6)c6ccccc56)cccc43)cc2c1]

-continued
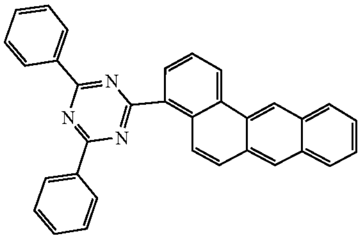 [SMILES: c1ccc(-c2nc(-c3ccccc3)nc(-c3cccc4c3ccc3cc5ccccc5cc34)n2)cc1]
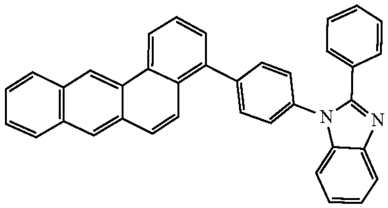 [SMILES: c1ccc(-c2nc3ccccc3n2-c2ccc(-c3cccc4c3ccc3cc5ccccc5cc34)cc2)cc1]
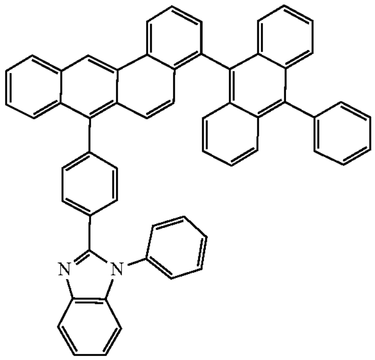 [SMILES: c1ccc(-c2c3ccccc3c(-c3cccc4c3ccc3c(-c5ccc(-c6nc7ccccc7n6-c6ccccc6)cc5)c5ccccc5cc34)c3ccccc23)cc1]
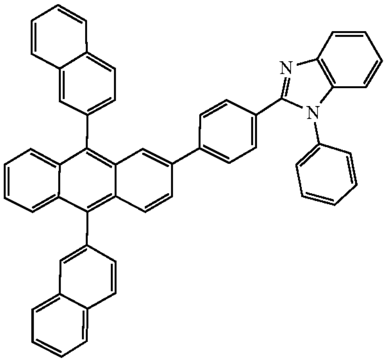 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]
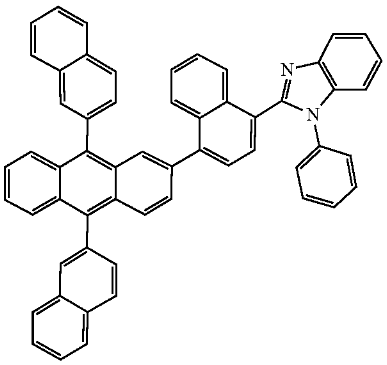 [SMILES: c1ccc(-n2c(-c3ccc(-c4ccc5c(-c6ccc7ccccc7c6)c6ccccc6c(-c6ccc7ccccc7c6)c5c4)c4ccccc34)nc3ccccc32)cc1]
-continued
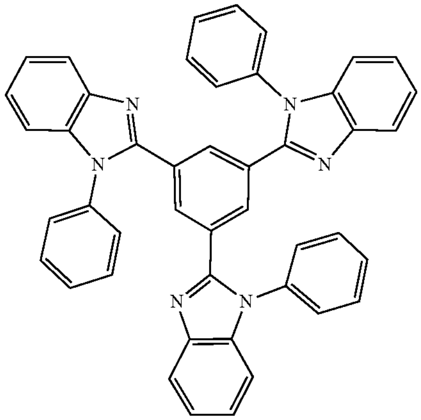 [SMILES: c1ccc(-n2c(-c3cc(-c4nc5ccccc5n4-c4ccccc4)cc(-c4nc5ccccc5n4-c4ccccc4)c3)nc3ccccc32)cc1]
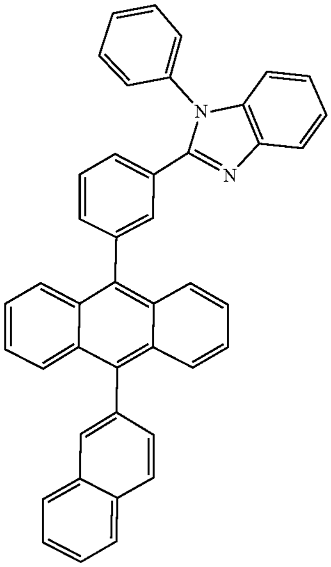 [SMILES: c1ccc(-n2c(-c3cccc(-c4c5ccccc5c(-c5ccc6ccccc6c5)c5ccccc45)c3)nc3ccccc32)cc1]
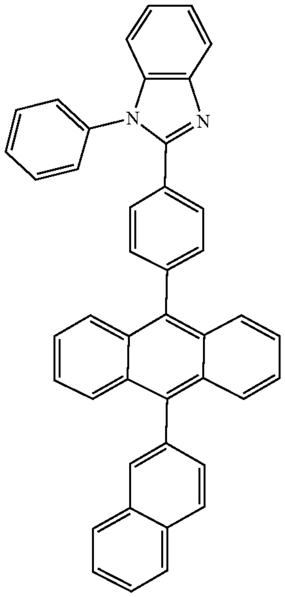 [SMILES: c1ccc(-n2c(-c3ccc(-c4c5ccccc5c(-c5ccc6ccccc6c5)c5ccccc45)cc3)nc3ccccc32)cc1]

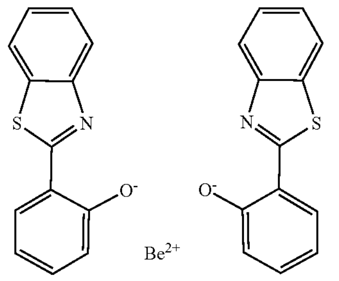
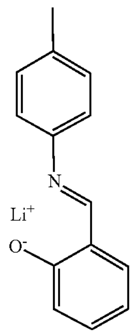 [SMILES: [Li+] ; Cc1ccc(/N=C/c2ccccc2[O-])cc1]
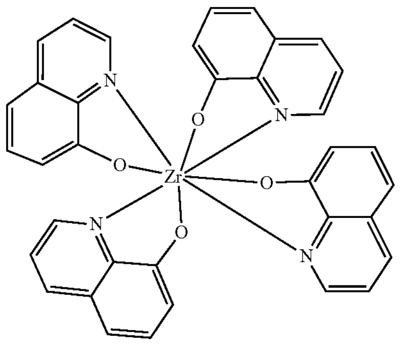
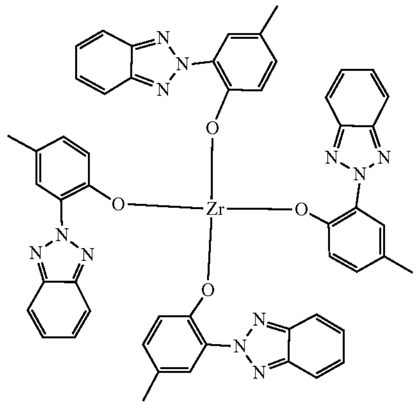
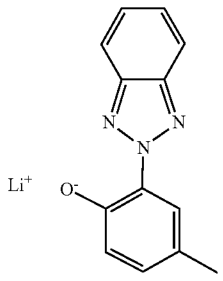 [SMILES: [Li+] ; Cc1ccc([O-])c(-n2nc3ccccc3n2)c1]
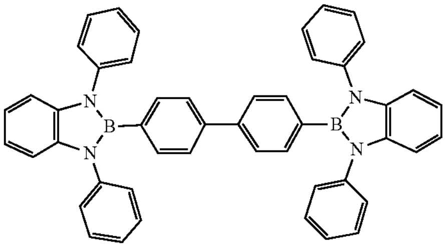 [SMILES: c1ccc(N2B(c3ccc(-c4ccc(B5N(c6ccccc6)c6ccccc6N5c5ccccc5)cc4)cc3)N(c3ccccc3)c3ccccc32)cc1]
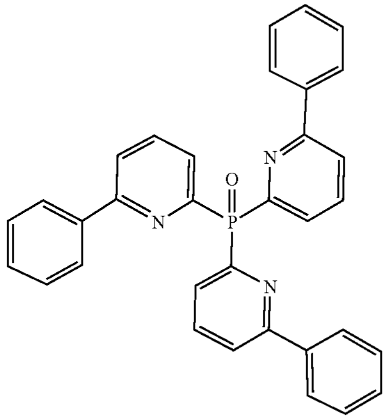 [SMILES: O=P(c1cccc(-c2ccccc2)n1)(c1cccc(-c2ccccc2)n1)c1cccc(-c2ccccc2)n1]
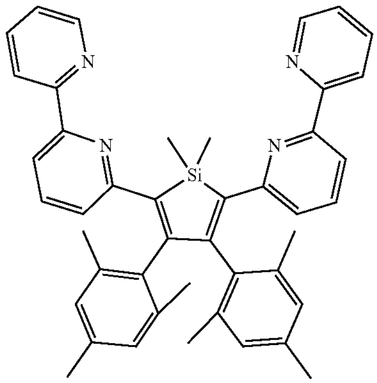 [SMILES: Cc1cc(C)c(C2=C(c3cccc(-c4ccccn4)n3)[Si](C)(C)C(c3cccc(-c4ccccn4)n3)=C2c2c(C)cc(C)cc2C)c(C)c1]

-continued

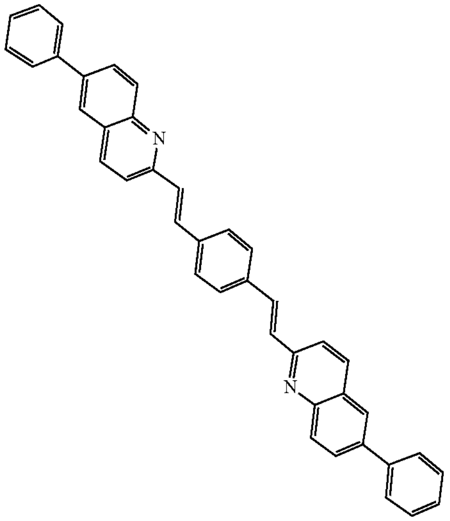 [SMILES: C(=C\c1ccc2cc(-c3ccccc3)ccc2n1)/c1ccc(/C=C/c2ccc3cc(-c4ccccc4)ccc3n2)cc1]

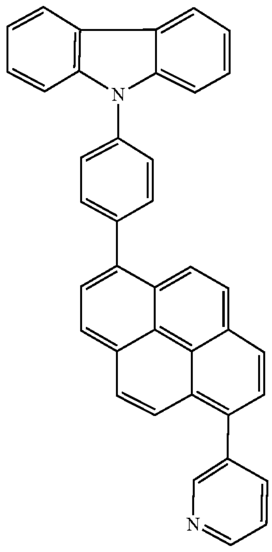 [SMILES: c1cncc(-c2ccc3ccc4c(-c5ccc(-n6c7ccccc7c7ccccc76)cc5)ccc5ccc2c3c54)c1]

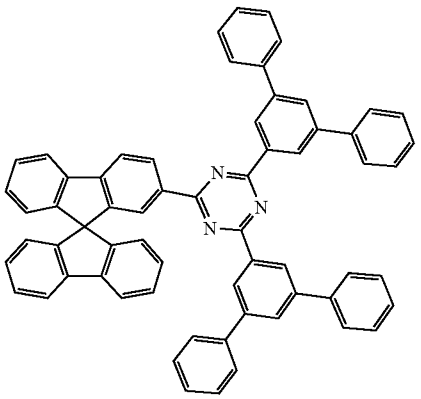 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

-continued

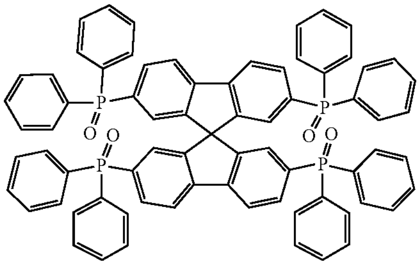 [SMILES: O=P(c1ccccc1)(c1ccccc1)c1ccc2c(c1)C1(c3cc(P(=O)(c4ccccc4)c4ccccc4)ccc3-2)c2cc(P(=O)(c3ccccc3)c3ccccc3)ccc2-c2ccc(P(=O)(c3ccccc3)c3ccccc3)cc21]

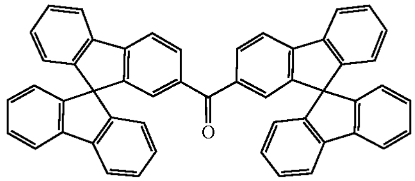 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2]

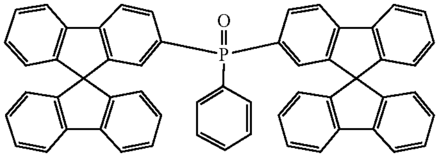 [SMILES: O=P(c1ccccc1)(c1ccc2c(c1)C1(c3ccccc3-c3ccccc31)c1ccccc1-2)c1ccc2c(c1)C1(c3ccccc3-c3ccccc31)c1ccccc1-2]

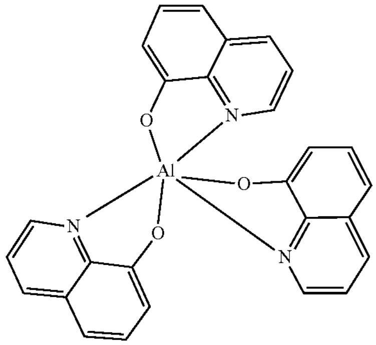

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects of water and air.

In a preferred embodiment, the electronic device is characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an electronic device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I) are needed. High solubility can be achieved by suitable substitution of the compounds.

It is further preferable that an electronic device of the invention is produced by applying one or more layers from solution and one or more layers by a sublimation method.

According to the invention, the electronic devices comprising one or more compounds of formula (I) can be used in displays, as light sources in lighting applications and as light sources in medical and/or cosmetic applications.

EXAMPLES

A) Synthesis Examples

The syntheses which follow, unless stated otherwise, are conducted under a protective gas atmosphere in dried solvents. The solvents and reagents can be purchased, for example, from Sigma-ALDRICH or ABCR. The respective figures in square brackets or the numbers quoted for individual compounds relate to the CAS numbers of the compounds known from the literature.

A-1) Preparation of the Synthons:

S1:

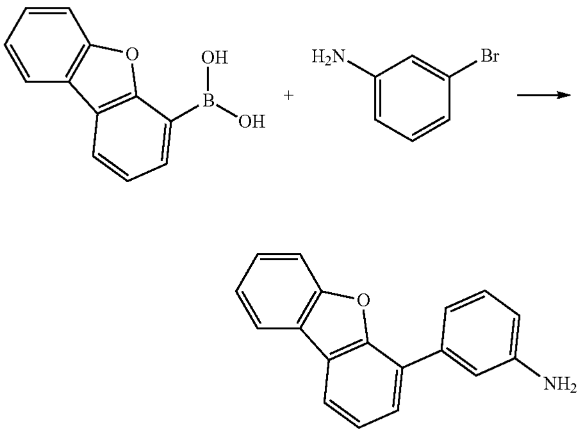

4-Dibenzofuranboronic acid [CAS-100124-06-9] (70.10 g; 330.7 mmol), 3-bromoaniline [CAS-591-19-5] (52.00 g; 302.2 mmol) and 20% w/w sodium hydroxide solution (180 ml; 1.37 mol) are initially charged in tetrahydrofuran (750 ml) and water (100 ml) and saturated with argon for 45 min. Thereafter, tris(dibenzylideneacetone)dipalladium(0) [CAS-51364-51-3] (276 mg; 0.30 mmol) and tri-o-tolylphosphine (920 mg; 3.02 mmol) are introduced and the reaction mixture is stirred under reflux for 10 h. After cooling the mixture, it is adjusted to pH 7 with glacial acetic acid, and the organic phase is separated off in a separating funnel and isolated. Subsequently, the organic phase is filtered through a frit with silica gel in the form of an ethyl acetate slurry. The silica gel is washed through twice with ethyl acetate (150 ml each time), and the filtrate is dried over $Na_2SO_4$ and then concentrated to dryness. The crude product is recrystallized from ethyl acetate. Yield: 66.5 g (244 mmol), 81%; purity: >95% by $^1H$ NMR.

S15:

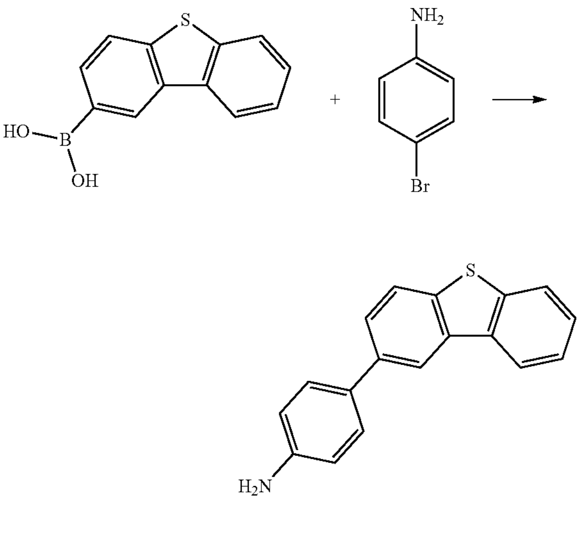

Procedure analogous to the experimental description for S1, except that 2-dibenzothiopheneboronic acid [CAS-668983-97-9] is used rather than 4-dibenzofuranboronic acid, and 4-bromoaniline [CAS-106-40-1] rather than 3-bromoaniline. The workup is analogous. The crude product is recrystallized from n-butanol. Yield 73.5 g (267 mmol, 88%); purity >97% by $^{1}$H NMR.

S23:

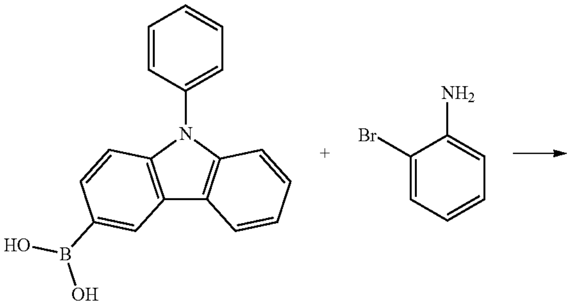

-continued

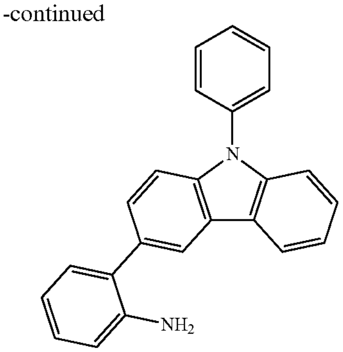

Procedure analogous to the experimental description for S1, except that 3-N-phenylcarbazoleboronic acid [CAS-854952-58-2] is used rather than 4-dibenzofuranboronic acid, and 2-bromoaniline [CAS-615-36-1] rather than 3-bromoaniline. The workup is analogous. The crude product is purified via column chromatography. Yield 48.0 g (144 mmol, 47%); purity >95% by $^{1}$H NMR.

The compounds which follow can be prepared in an analogous manner. In this case, purification can also be effected using column chromatography, or recrystallization or hot extraction using other standard solvents such as ethanol, butanol, acetone, ethyl acetate, acetonitrile, toluene, xylene, dichiloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone etc. The yields are typically in the range between 40% and 90%.

| Reactant 1 | Reactant 2 | Product |
|---|---|---|
| 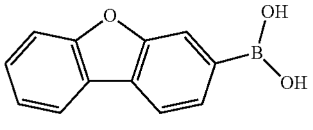 CAS-395087-89-5 | 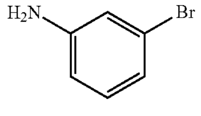 CAS-591-19-5 | 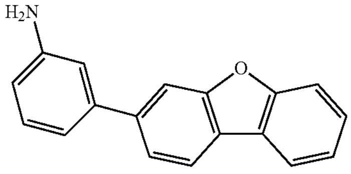 S2 |
| 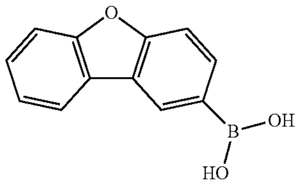 CAS-402936-15-6 | 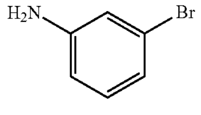 CAS-591-19-5 | 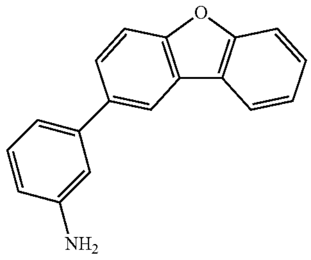 S3 |
| 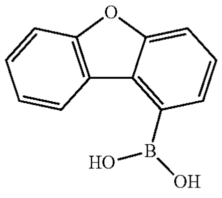 CAS-162607-19-4 | 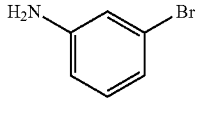 CAS-591-19-5 | 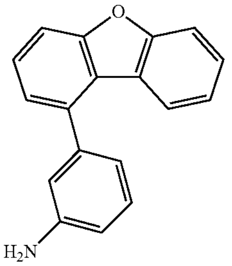 S4 |

-continued
| Reactant 1 | Reactant 2 | Product |
|---|---|---|
| 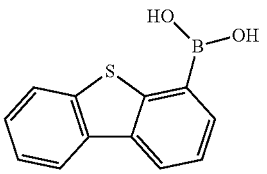<br>CAS-108847-20-7 | 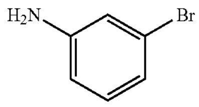<br>CAS-591-19-5 | 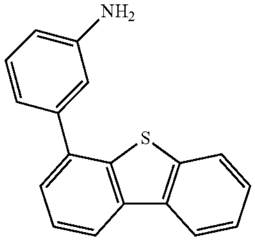<br>S5 |
| 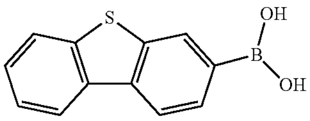<br>CAS-108847-24-1 | 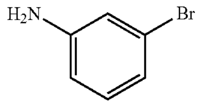<br>CAS-591-19-5 | 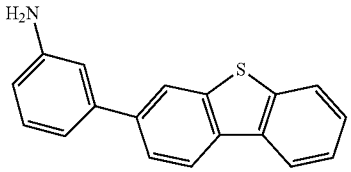<br>S6 |
| 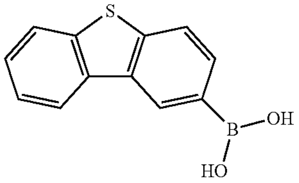<br>CAS-668983-97-9 | 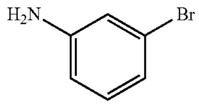<br>CAS-591-19-5 | 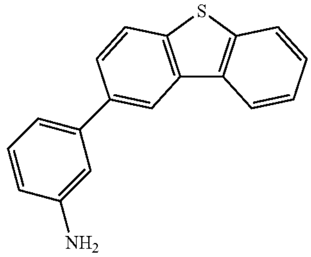<br>S7 |
| 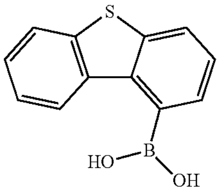<br>CAS-1245943-60-5 | 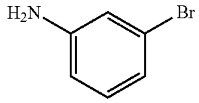<br>CAS-591-19-5 | 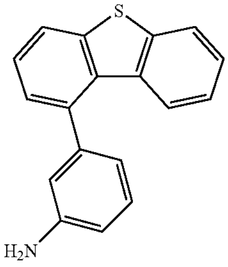<br>S8 |
| 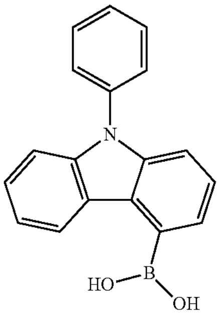<br>CAS-1370555-65-9 | 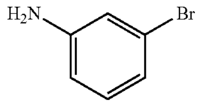<br>CAS-591-19-5 | 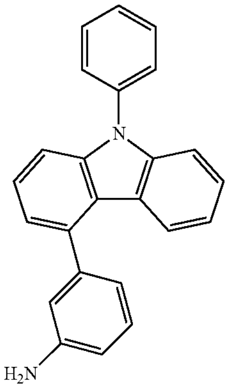<br>S9 |

-continued
| Reactant 1 | Reactant 2 | Product |
|---|---|---|
| 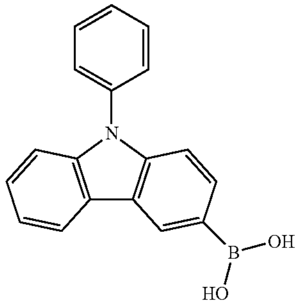 CAS-854952-58-2 | 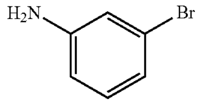 CAS-591-19-5 | 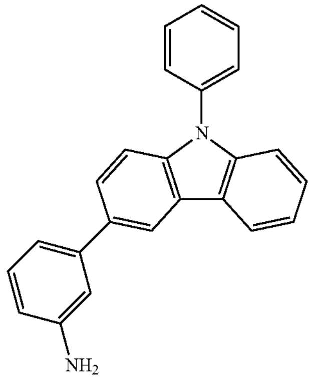 S10 |
| 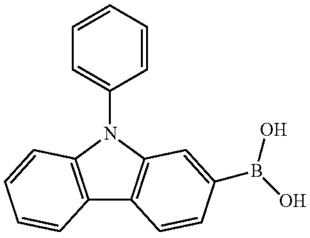 CAS-1001911-63-2 | 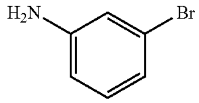 CAS-591-19-5 | 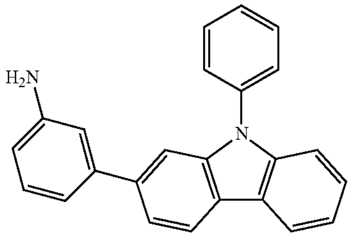 S11 |
| 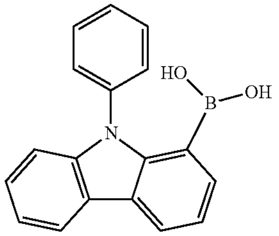 CAS-1333002-41-7 | 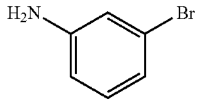 CAS-591-19-5 | 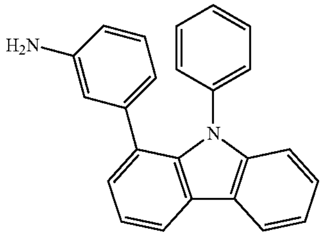 S12 |
| 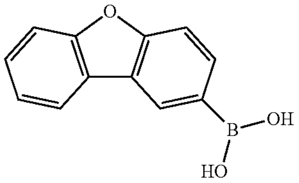 CAS-402936-15-6 | 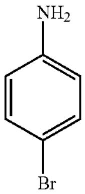 CAS-106-40-1 | 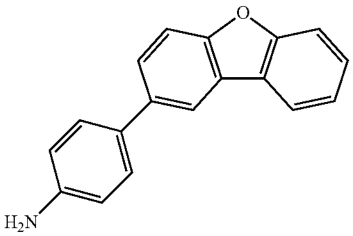 S13 |
| 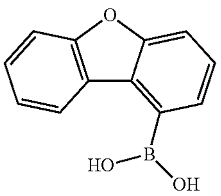 CAS-162607-19-4 | 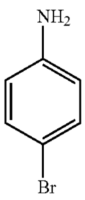 CAS-106-40-1 | 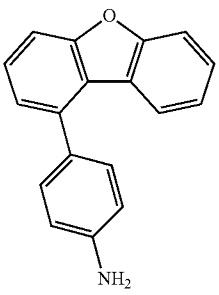 S14 |

-continued
| Reactant 1 | Reactant 2 | Product |
| --- | --- | --- |
| 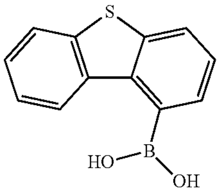 CAS-1245943-60-5 | 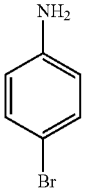 CAS-106-40-1 | 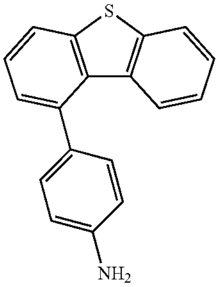 S16 |
| 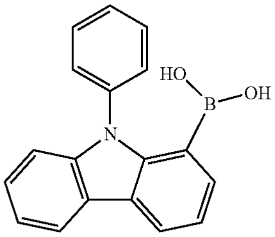 CAS-1333002-41-7 | 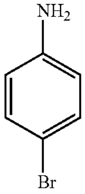 CAS-106-40-1 | 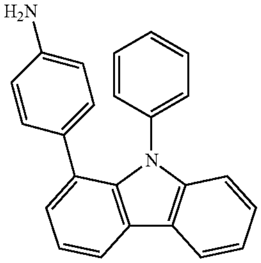 S17 |
| 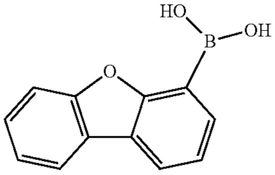 CAS-100124-06-9 | 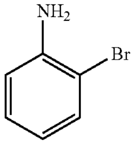 CAS-615-36-1 | 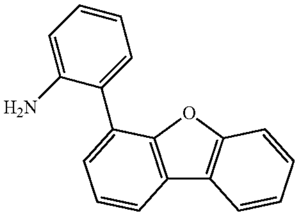 S18 |
| 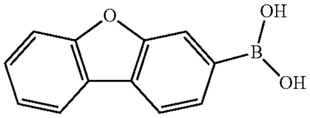 CAS-395087-89-5 | 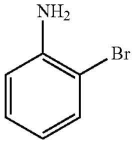 CAS-615-36-1 | 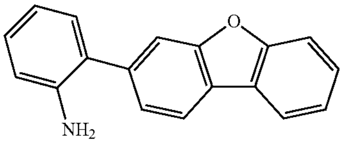 S19 |
| 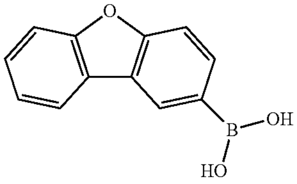 CAS-402936-15-6 | 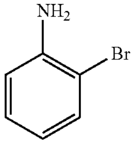 CAS-615-36-1 | 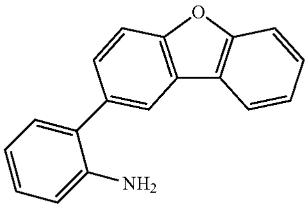 S20 |
| 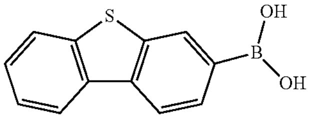 CAS-108847-24-1 | 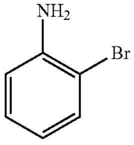 CAS-615-36-1 | 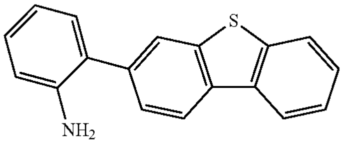 S21 |

-continued
| Reactant 1 | Reactant 2 | Product |
|---|---|---|
| 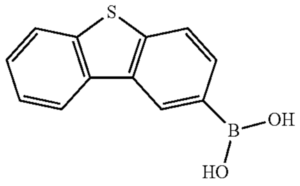 CAS-668983-97-9 | 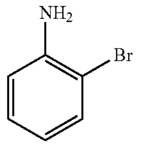 CAS-615-36-1 | 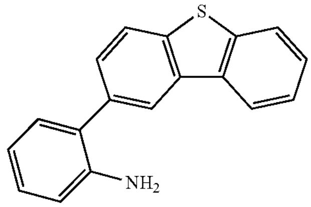 S22 |
| 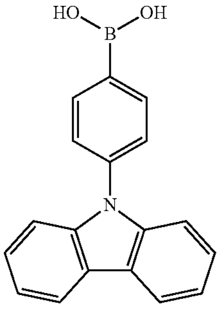 CAS-419536-33-7 | 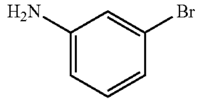 CAS-591-19-5 | 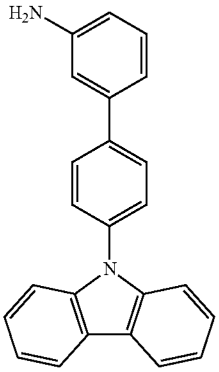 S24 |
| 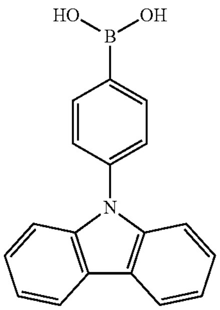 CAS-419536-33-7 | 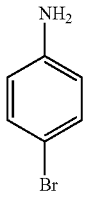 CAS-106-40-1 | 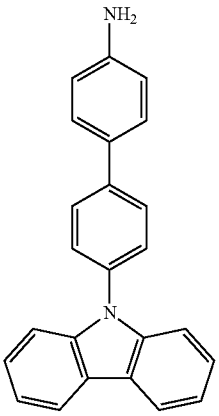 S25 |
| 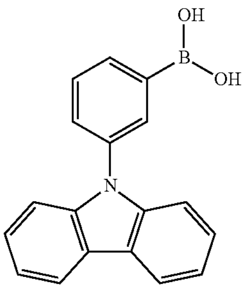 CAS-864377-33-3 | 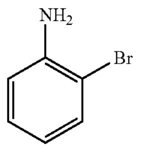 CAS-615-36-1 | 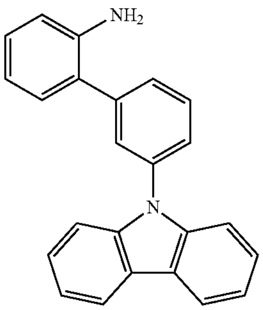 S26 |

-continued
| Reactant 1 | Reactant 2 | Product |
|---|---|---|
| 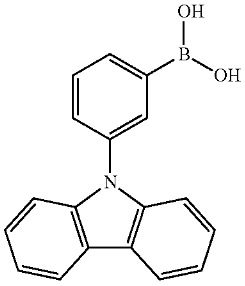 CAS-864377-33-3 | 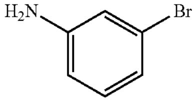 CAS-591-19-5 | 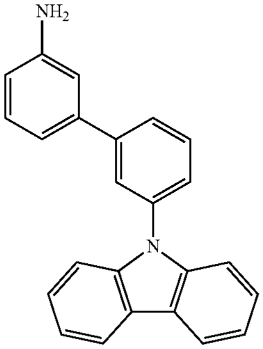 S27 |
| 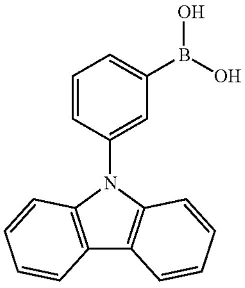 CAS-864377-33-3 | 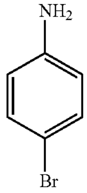 CAS-106-40-1 | 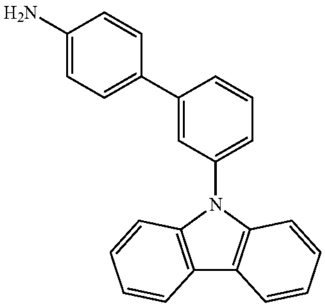 S28 |
| 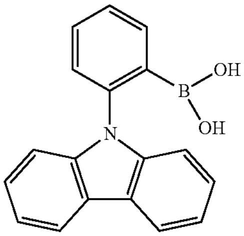 CAS-1189047-28-6 | 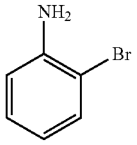 CAS-615-36-1 | 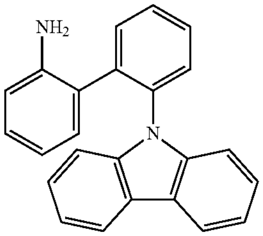 S29 |
| 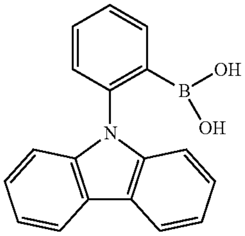 CAS-1189047-28-6 | 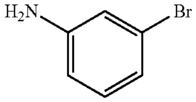 CAS-591-19-5 | 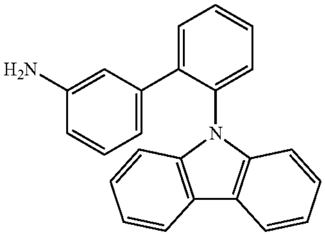 S30 |
| 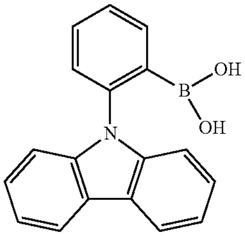 CAS-1189047-28-6 | 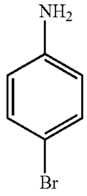 CAS-106-40-1 | 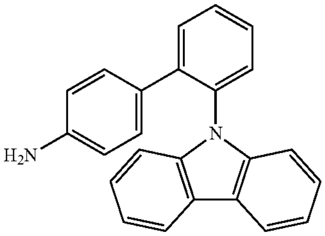 S31 |

-continued
| Reactant 1 | Reactant 2 | Product |
|---|---|---|
| 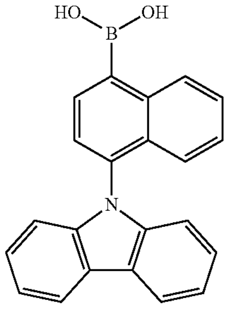 CAS-1246021-50-0 | 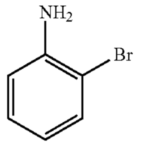 CAS-615-36-1 | 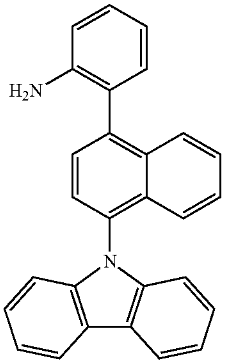 S32 |
| 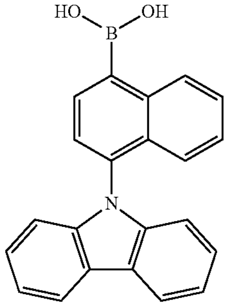 CAS-1246021-50-0 | 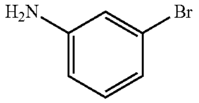 CAS-591-19-5 | 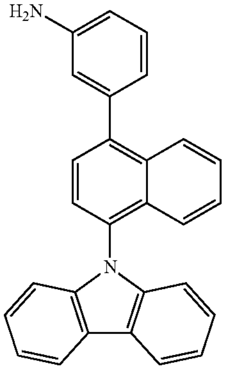 S33 |
| 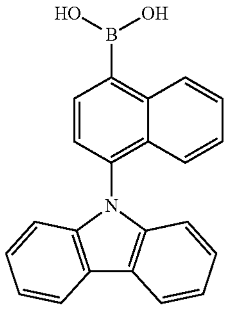 CAS-1246021-50-0 | 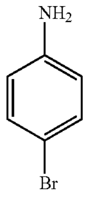 CAS-106-40-1 | 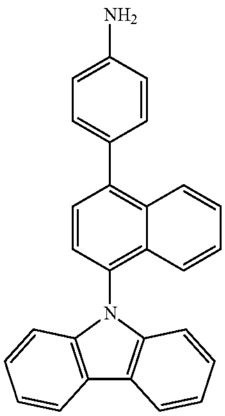 S34 |
| 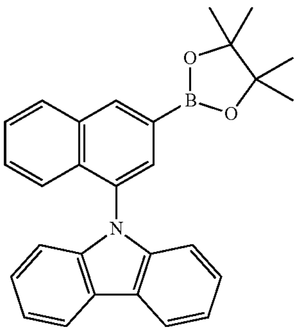 CAS-1819346-26-3 | 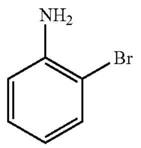 CAS-615-36-1 | 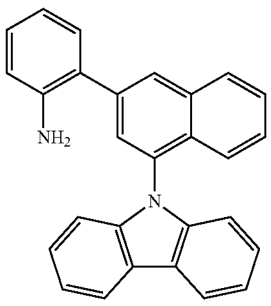 S35 |

-continued
| Reactant 1 | Reactant 2 | Product |
|---|---|---|
| 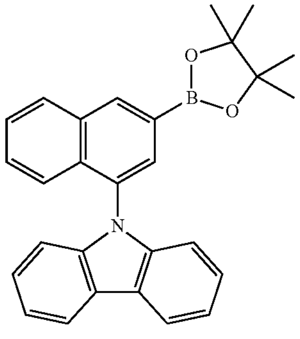<br>CAS-1819346-26-3 | 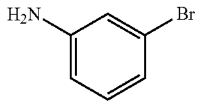<br>CAS-591-19-5 | 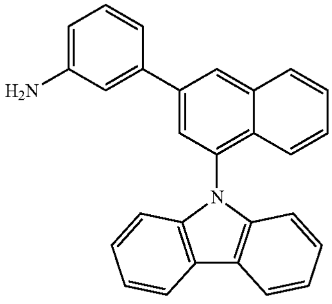<br>S36 |
| 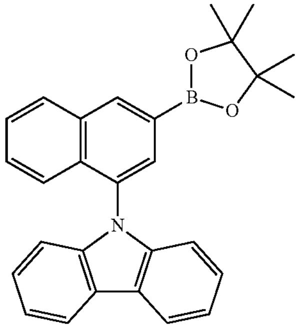<br>CAS-1819346-26-3 | 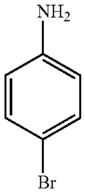<br>CAS-106-40-1 | 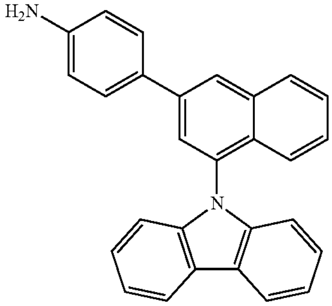<br>S37 |
| 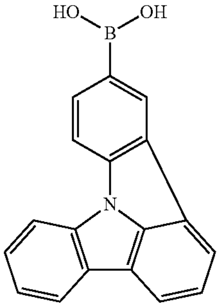<br>CAS-1174032-92-8 | 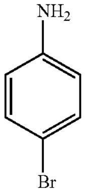<br>CAS-106-40-1 | 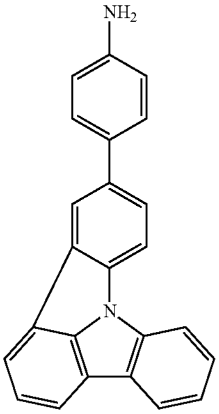<br>S38 |
| 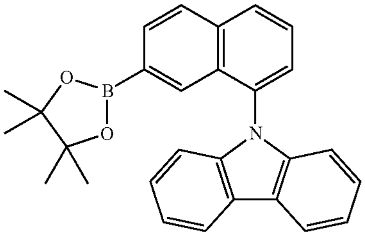<br>CAS-1221685-92-2 | 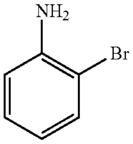<br>CAS-615-36-1 | 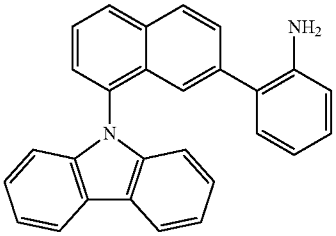<br>S39 |

-continued
| Reactant 1 | Reactant 2 | Product |
| --- | --- | --- |
| 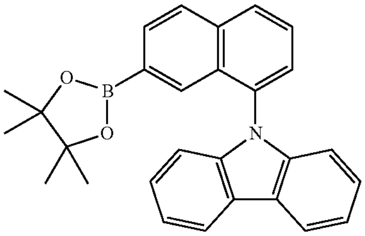 CAS-1221685-92-2 | 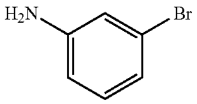 CAS-591-19-5 | 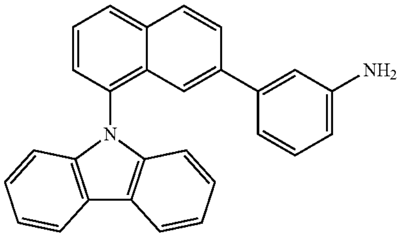 S40 |
| 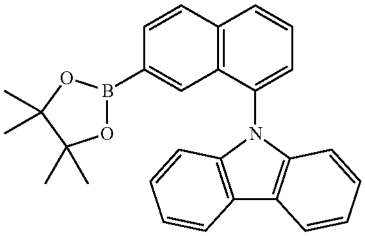 CAS-1221685-92-2 | 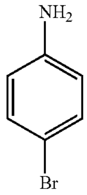 CAS-106-40-1 | 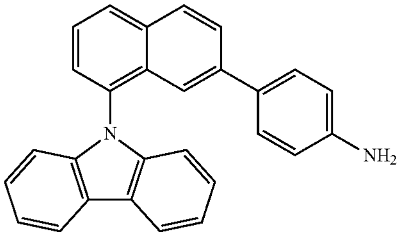 S41 |
| 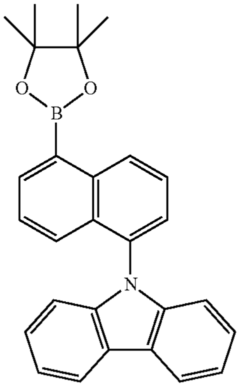 [SMILES: CC1(C)OB(c2cccc3c(-n4c5ccccc5c5ccccc54)cccc23)OC1(C)C] CAS-1820789-13-6 | 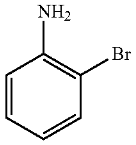 CAS-615-36-1 | 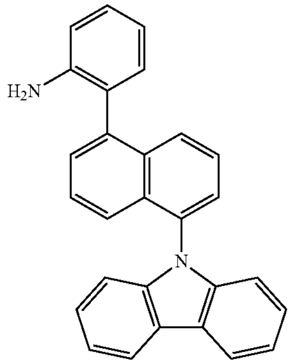 S42 |
| 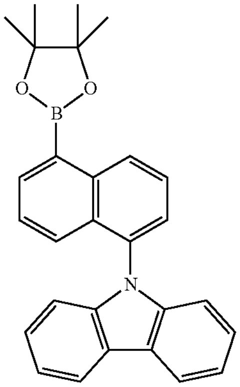 [SMILES: CC1(C)OB(c2cccc3c(-n4c5ccccc5c5ccccc54)cccc23)OC1(C)C] | 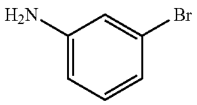 CAS-591-19-5 | 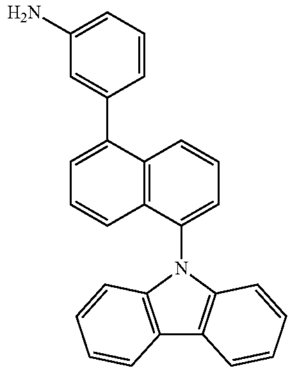 S43 |

-continued

| Reactant 1 | Reactant 2 | Product |
|---|---|---|
| 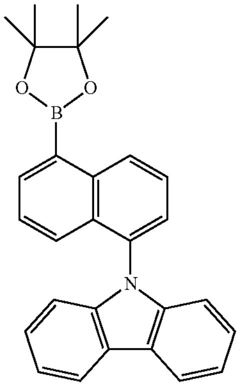 | 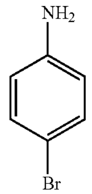<br>CAS-106-40-1 | 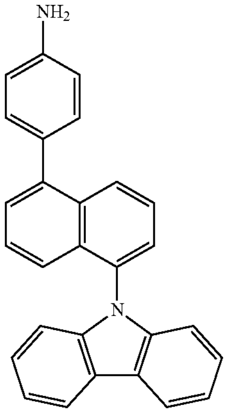<br>S44 |
| 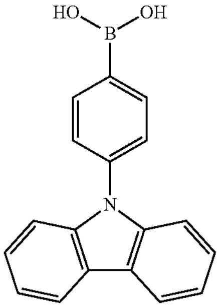<br>CAS-419536-33-7 | 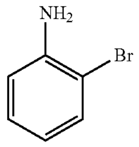<br>CAS-615-36-1 | 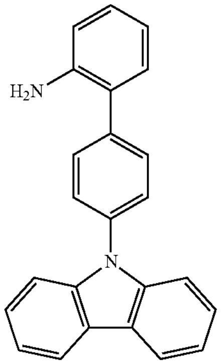<br>S45 |

S100

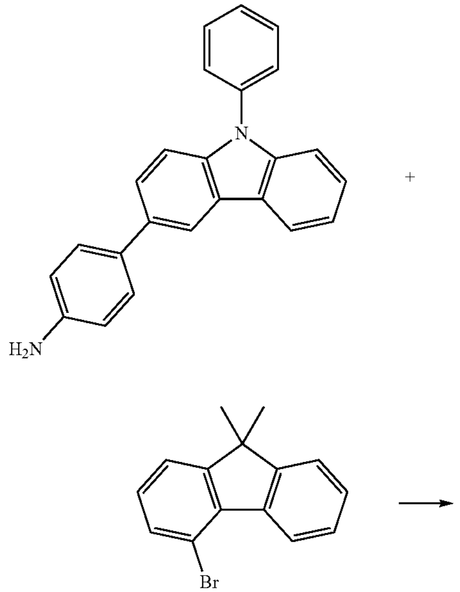

-continued

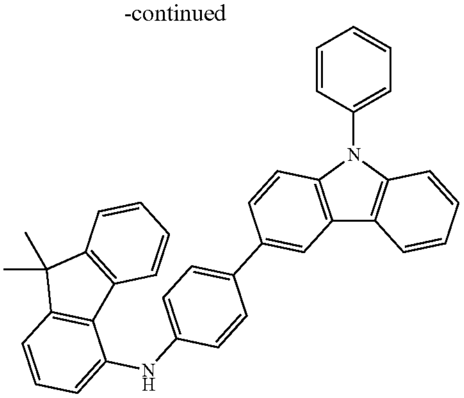

4-(9-Phenylcarbazol-3-yl)aniline [CAS-1370034-59-5] (16.72 g; 50.0 mmol), 4-bromo-9,9-dimethyl-9H-fluorene [CAS-942615-32-9](14.34 g; 52.5 mmol) and caesium carbonate (32.58 g; 100.0 mmol) are initially charged in o-xylene (300 ml) and saturated with argon for 45 min. Thereafter, 1,1-bis(diphenylphosphino)ferrocenedichloropalladium(II) complex with DCM [CAS-95464-05-4] (1.22 g; 1.5 mmol) is introduced and the reaction mixture is stirred under reflux for 24 h. After the mixture has been cooled, it is extended with 400 ml of toluene, and the organic phase is washed with water (2×400 ml). The organic phase is used to form a Celite bed slurry and filtered with toluene, and the filtrate is dried over $Na_2SO_4$ and concentrated to dryness. The residue is recrystallized from cyclohexane. Yield: 20.4 g (38.7 mmol), 77%; purity: >98% by $^1H$ NMR.

S101:

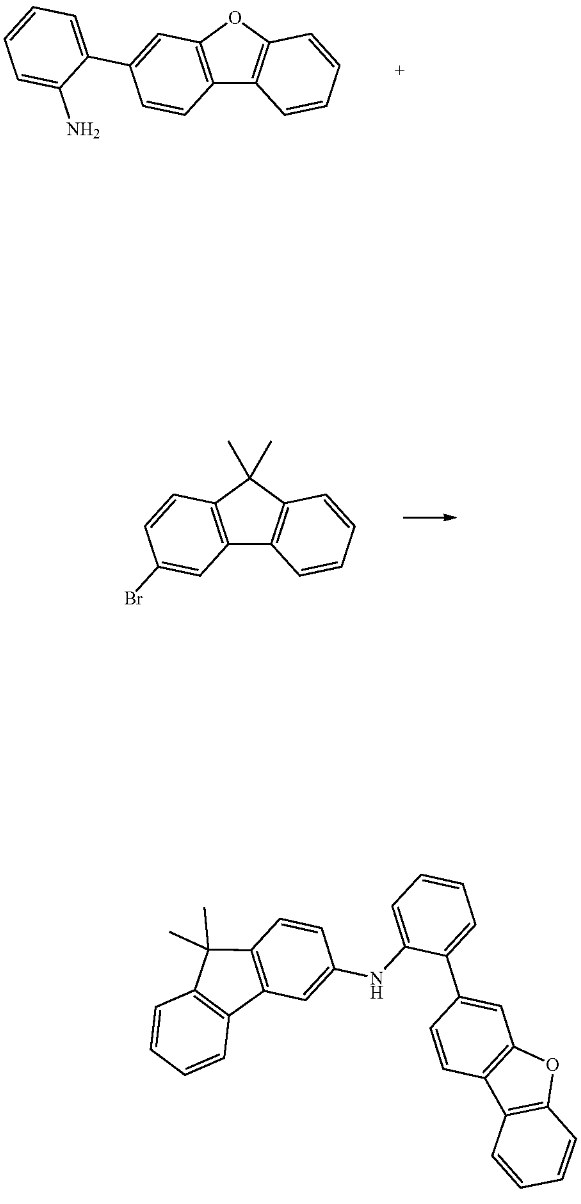

Procedure analogous to the experimental description for S100, except that S19 is used rather than 4-(9-phenylcarbazol-3-yl)aniline and 3-bromo-9,9-dimethyl-9H-fluorene [CAS-1190360-23-6] rather than 4-bromo-9,9-dimethyl-9H-fluorene. The crude product is purified via column chromatography. Yield: 10.9 g (24.2 mmol), 48%; purity: >97% by $^1H$ NMR.

S102

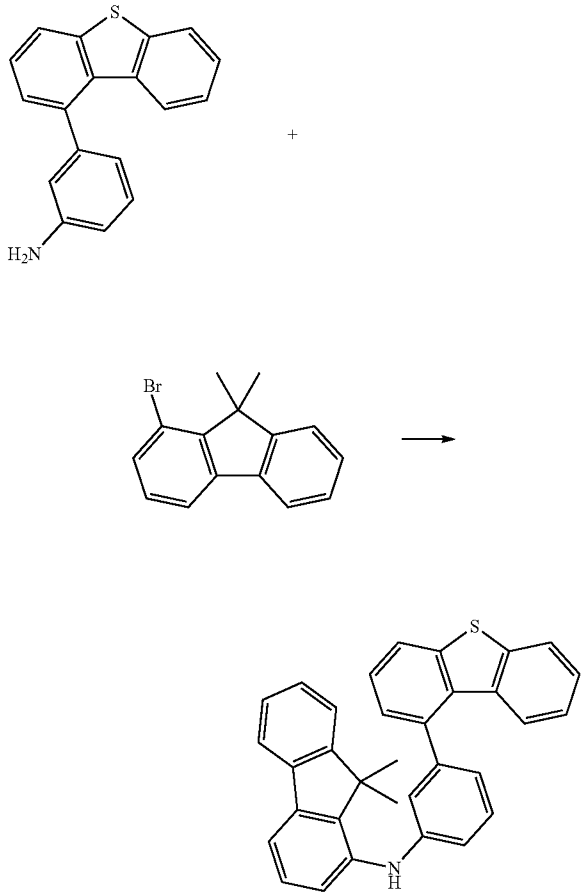

Procedure analogous to the experimental description for S100, except that S8 is used rather than 4-(9-phenylcarbazol-3-yl)aniline and 1-bromo-9,9-dimethyl-9H-fluorene [CAS-1225053-54-2] rather than 4-bromo-9,9-dimethyl-9H-fluorene. The crude product is recrystallized from acetonitrile. Yield: 15.9 g (33.9 mmol), 68%; purity: >97% by $^1H$ NMR.

In an analogous manner, it is possible to prepare the following compounds: In this case, the catalyst system used may also be tris(dibenzylideneacetone)dipalladium(0) [CAS-51364-51-3] (0.02 equiv.) and S-Phos [CAS-657408-07-6] (0.04 equiv) rather than 1,1-bis(diphenylphosphino) ferrocenedichloropalladium(II) complex with DCM [CAS-95464-05-4]. In this case, purification can also be effected using column chromatography, or recrystallization or hot extraction using other standard solvents such as ethanol, butanol, acetone, ethyl acetate, acetonitrile, toluene, xylene, dichloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone etc. The yields are typically in the range between 40% and 85%.

| Reactant 1 | Reactant 2 | Product |
|---|---|---|
| 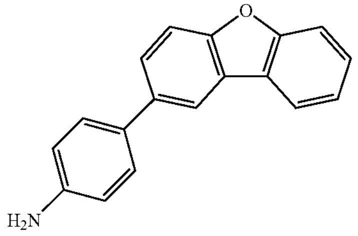 CAS-1178274-17-3 | 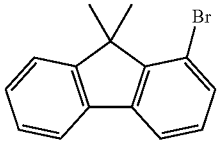 CAS-1225053-54-2 | 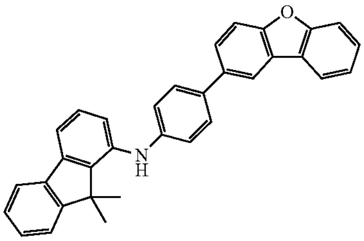 S103 |
| 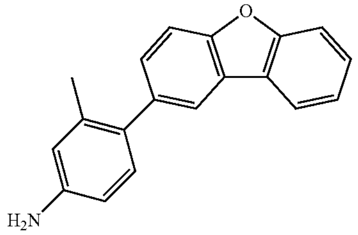 CAS-1184428-04-3 | 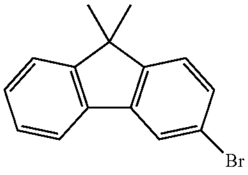 CAS-1190360-23-6 | 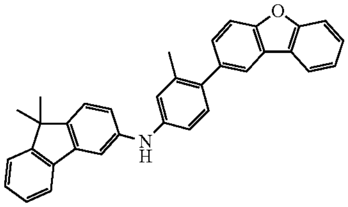 S104 |
| 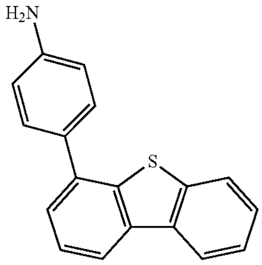 CAS-1370034-50-6 | 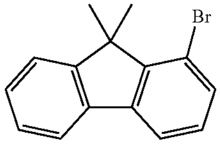 CAS-1225053-54-2 | 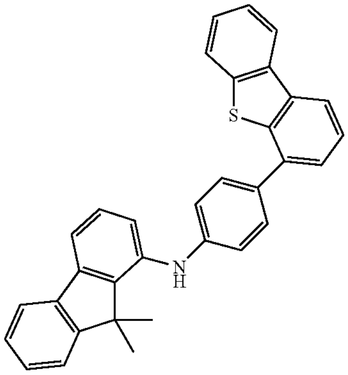 S105 |
| 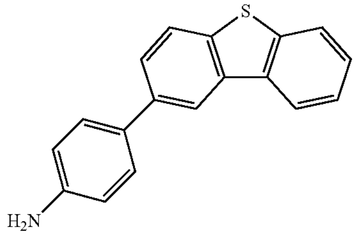 CAS-1574121-68-8 | 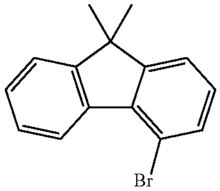 CAS-942615-32-9 | 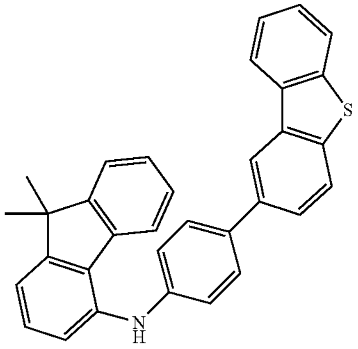 S106 |

-continued
| Reactant 1 | Reactant 2 | Product |
|---|---|---|
| 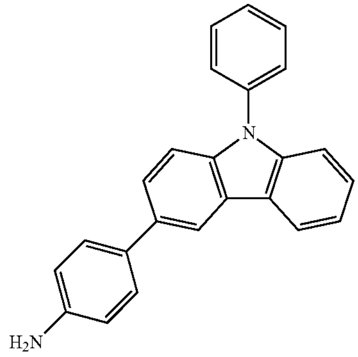 CAS-1370034-59-5 | 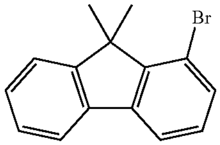 CAS-1225053-54-2 | 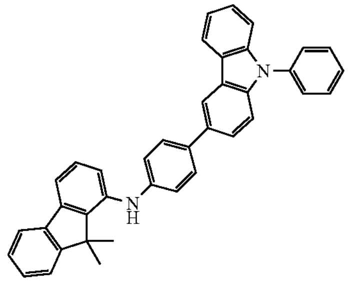 S107 |
| 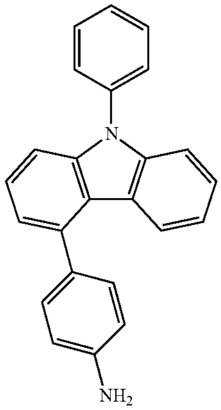 CAS-1629995-08-9 | 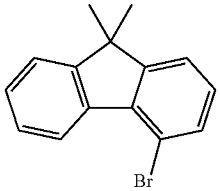 CAS-942615-32-9 | 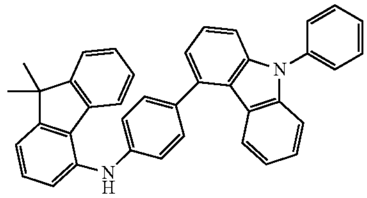 S108 |
| 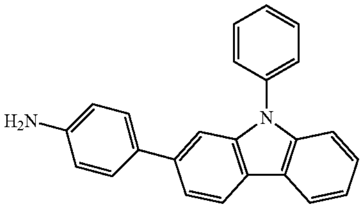 CAS-1911626-45-3 | 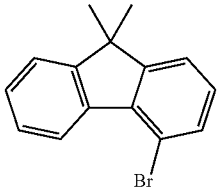 CAS-942615-32-9 | 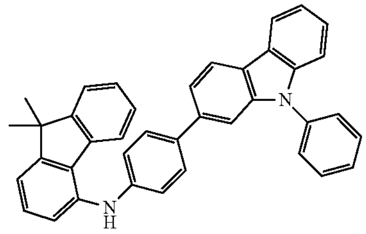 S108 |
| 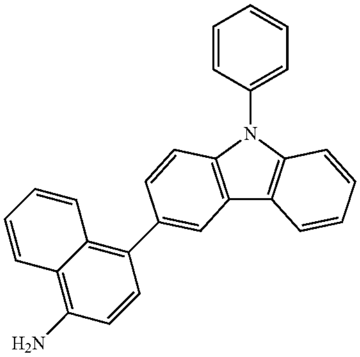 CAS-1699765-82-6 | 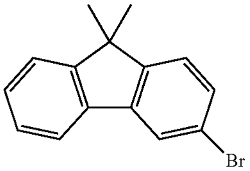 CAS-1190360-23-6 | 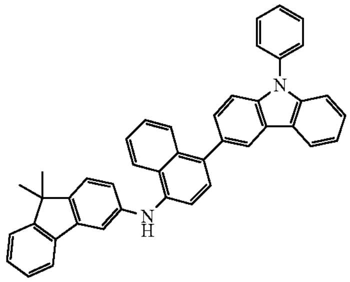 S110 |

-continued
| Reactant 1 | Reactant 2 | Product |
| --- | --- | --- |
| 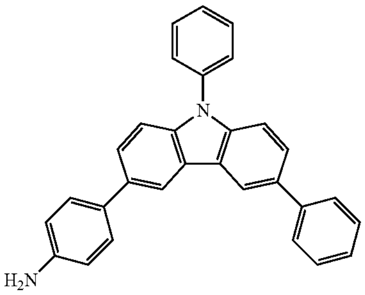 CAS-1458611-14-7 | 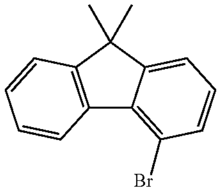 CAS-942615-32-9 | 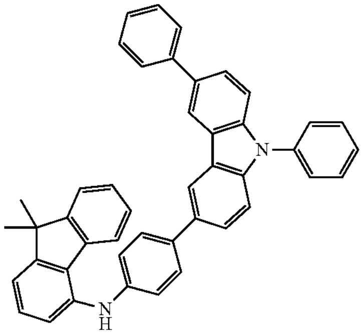 S111 |
| 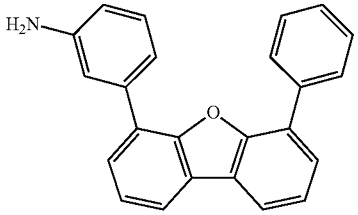 CAS-1458611-14-7 | 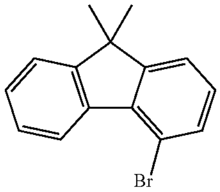 CAS-942615-32-9 | 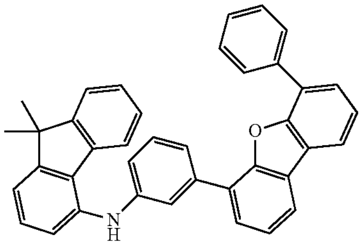 S112 |
| 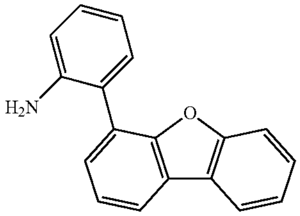 CAS-1559070-70-0 | 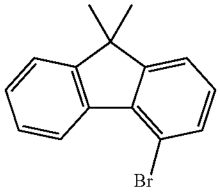 CAS-942615-32-9 | 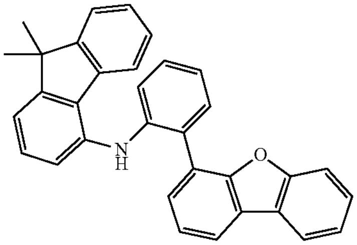 S113 |
| 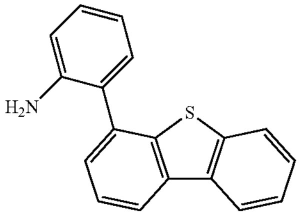 CAS-530403-06-6 | 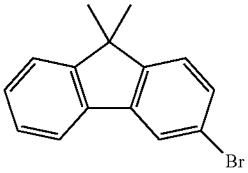 CAS-1190360-23-6 | 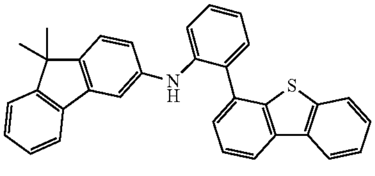 S114 |
| 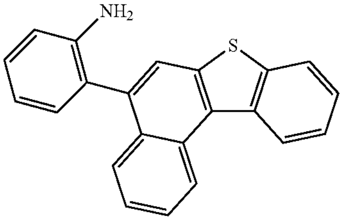 CAS-2044846-62-8 | 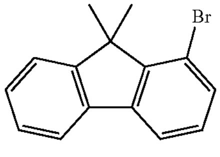 CAS-1225053-54-2 | 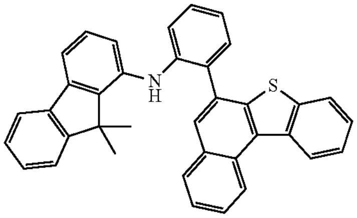 S115 |

-continued
| Reactant 1 | Reactant 2 | Product |
|---|---|---|
| 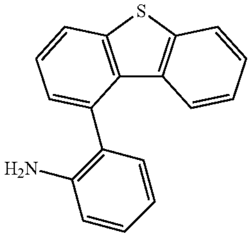 CAS-1850406-53-9 | 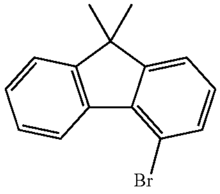 CAS-942615-32- | 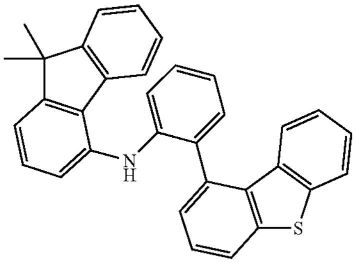 S116 |
| 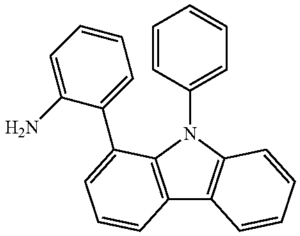 CAS-1850406-99-3 | 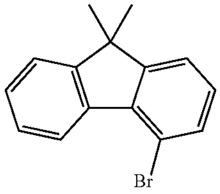 CAS-942615-32- | 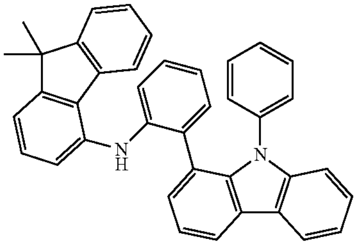 S117 |
| 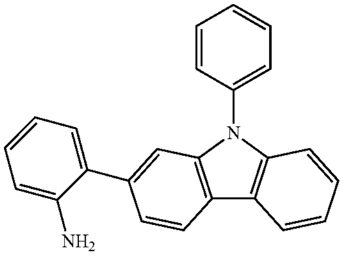 CAS1850406-91-5 | 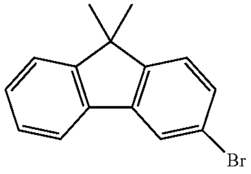 CAS-1190360-23-6 | 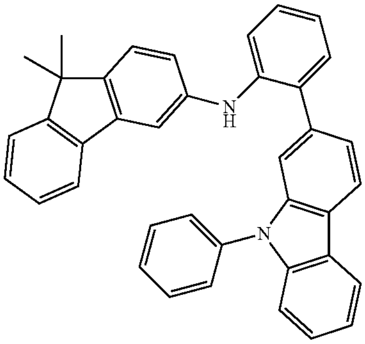 S118 |
| 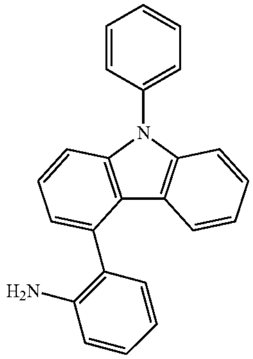 CAS-1850406-35-7 | 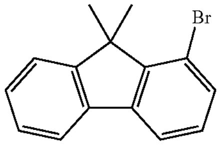 CAS-1225053-54-2 | 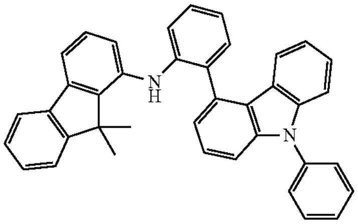 S119 |
| 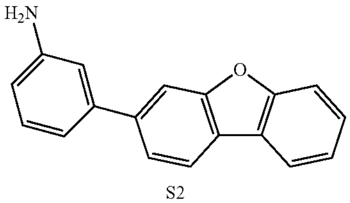 S2 | 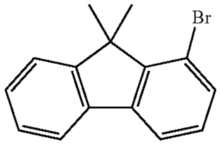 CAS-1225053-54-2 | 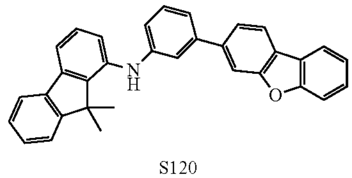 S120 |

-continued
| Reactant 1 | Reactant 2 | Product |
|---|---|---|
| 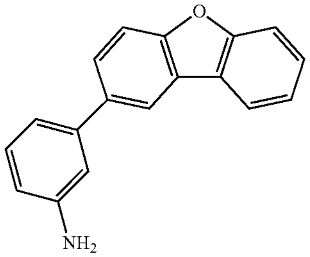 S3 | 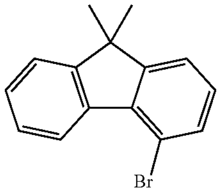 CAS-942615-32- | 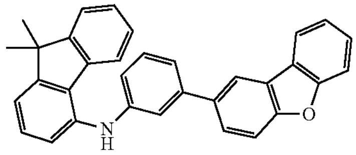 S121 |
| 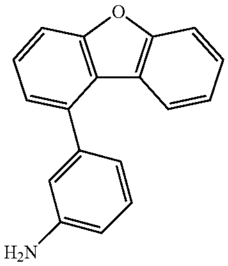 S4 | 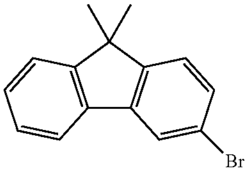 CAS-1190360-23-6 | 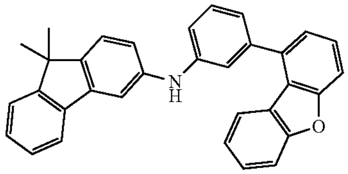 S122 |
| 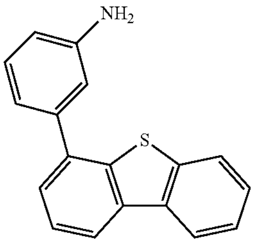 S5 | 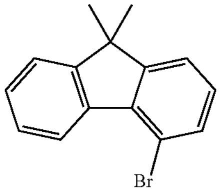 CAS-942615-32 | 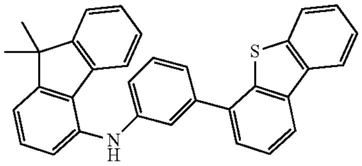 S123 |
| 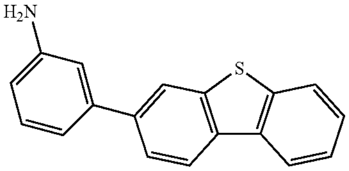 S6 | 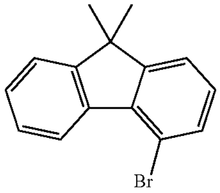 CAS-942615-32 | 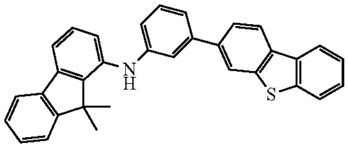 S124 |
| 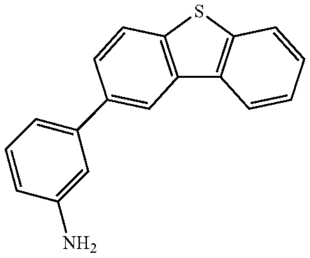 S7 | 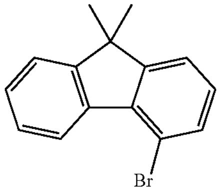 CAS-942615-32 | 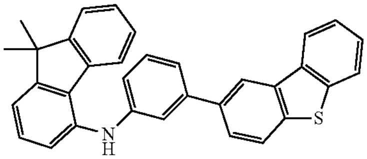 S125 |

-continued
| Reactant 1 | Reactant 2 | Product |
| --- | --- | --- |
| 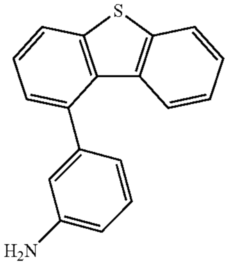 S8 | 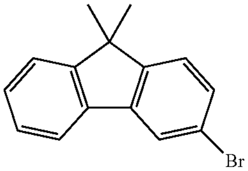 CAS-1190360-23-6 | 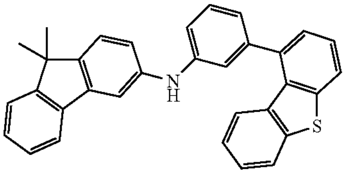 S126 |
| 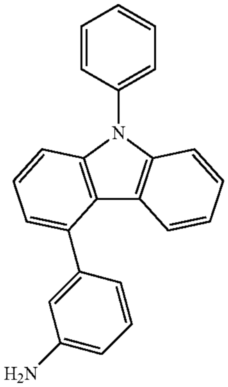 S9 | 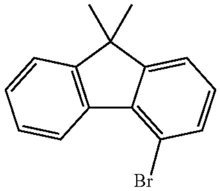 CAS-942615-32 | 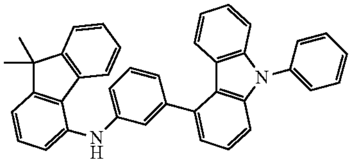 S127 |
| 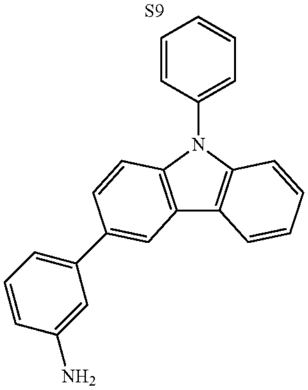 S10 | 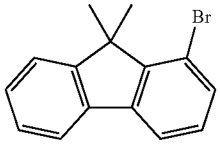 [SMILES: CC1(C)c2ccccc2-c2cccc(Br)c21] CAS-1225053-54-2 | 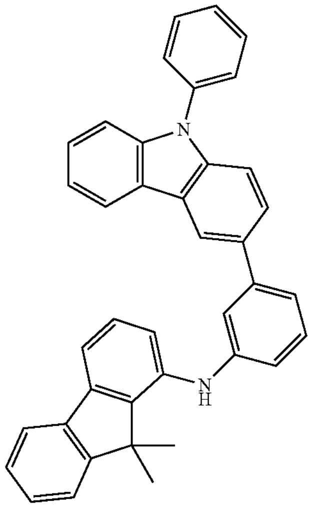 S128 |
| 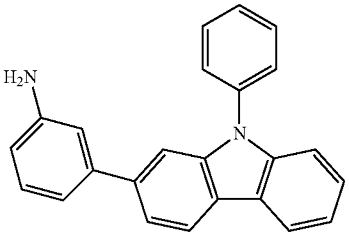 S11 | 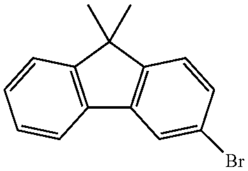 CAS-1190360-23-6 | 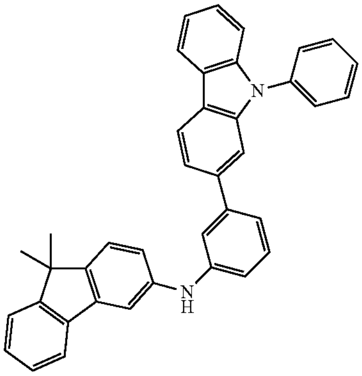 S129 |

-continued
| Reactant 1 | Reactant 2 | Product |
| --- | --- | --- |
| 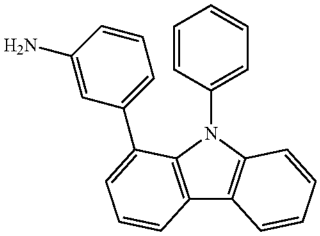 S12 | 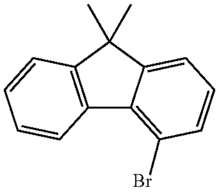 CAS-942615-32 | 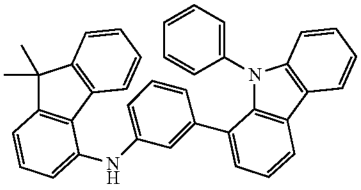 S130 |
| 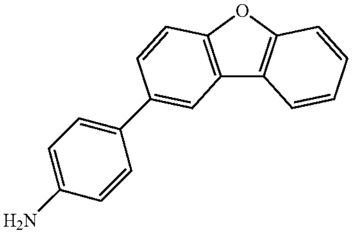 S13 | 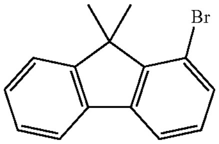 CAS-1225053-54-2 | 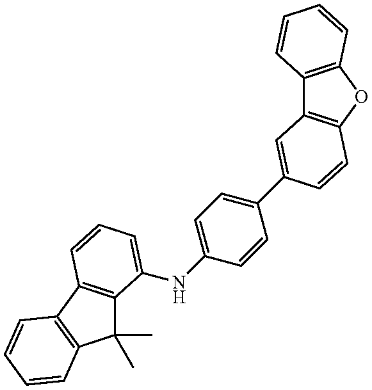 S131 |
| 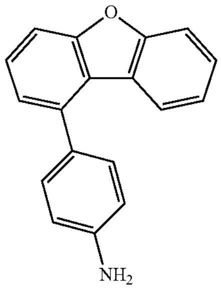 S14 | 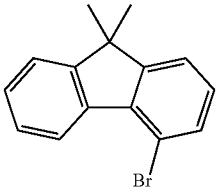 CAS-942615-32 | 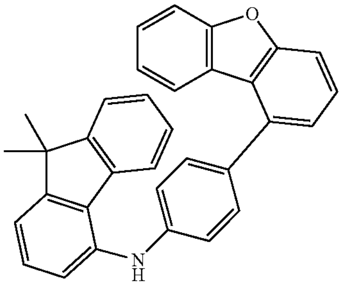 S132 |
| 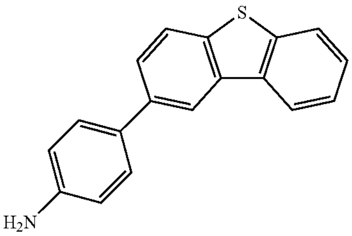 S15 | 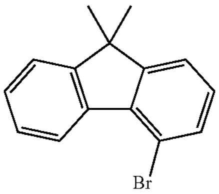 CAS-942615-32 | 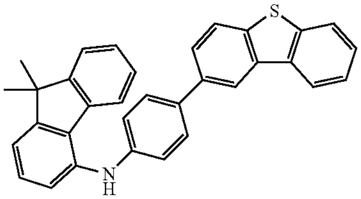 S133 |

-continued
| Reactant 1 | Reactant 2 | Product |
| --- | --- | --- |
| 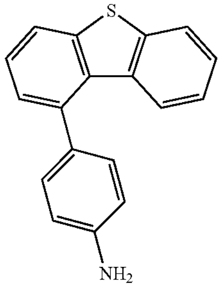 S16 | 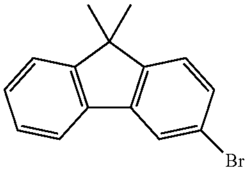 CAS-1190360-23-6 | 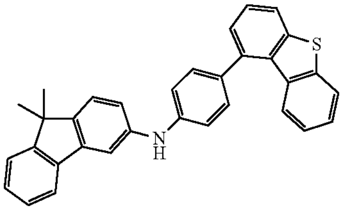 S134 |
| 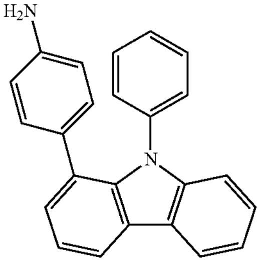 S17 | 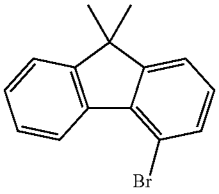 CAS-942615-32 | 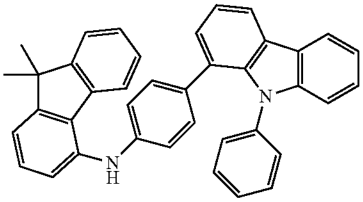 S135 |
| 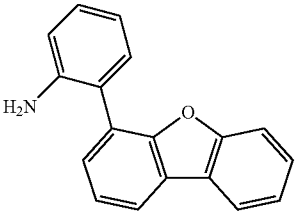 S18 | 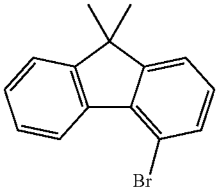 CAS-942615-32 | 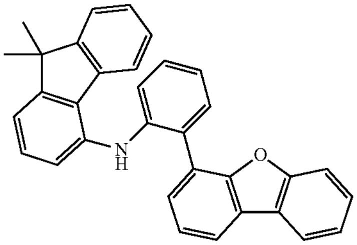 S136 |
| 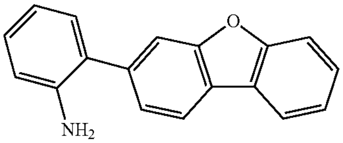 S19 | 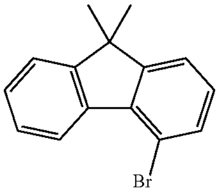 CAS-942615-32 | 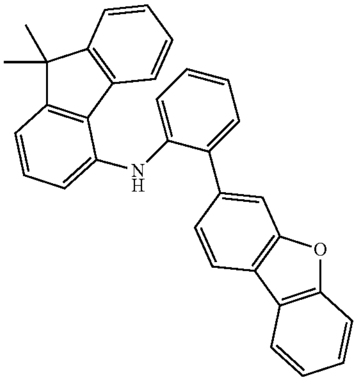 S137 |
| 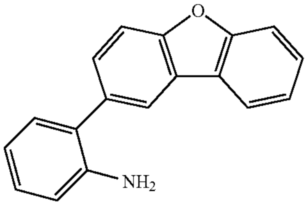 S20 | 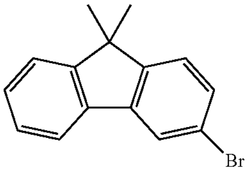 CAS-1190360-23-6 | 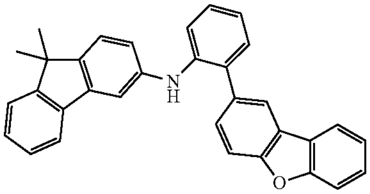 S138 |

-continued
| Reactant 1 | Reactant 2 | Product |
| --- | --- | --- |
| 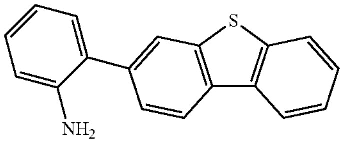 S21 | 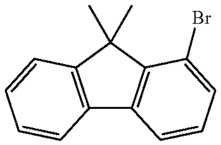 CAS-1225053-54-2 | 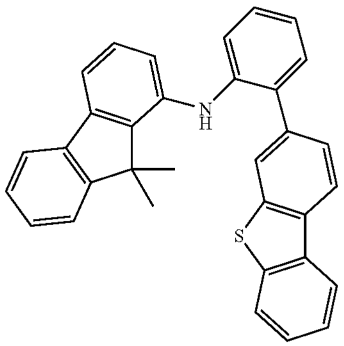 S139 |
| 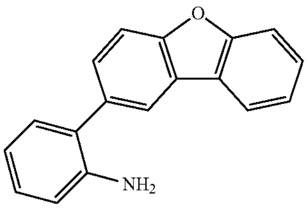 S22 | 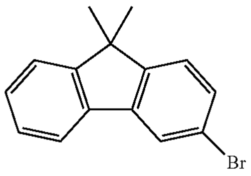 CAS-1190360-23-6 | 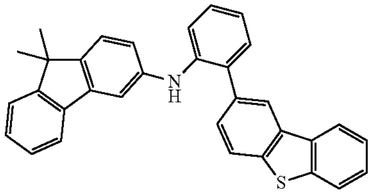 S140 |
| 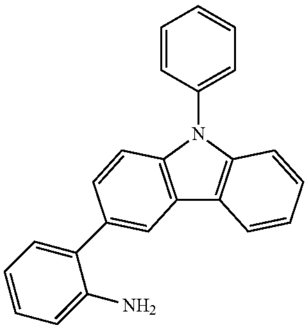 S23 | 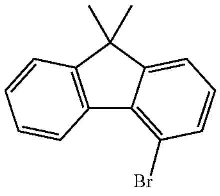 CAS-942615-32 | 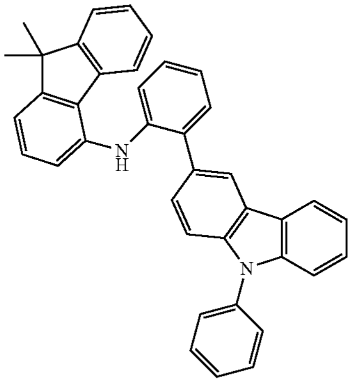 S141 |
| 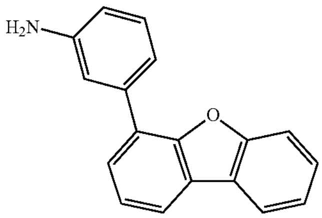 S1 | 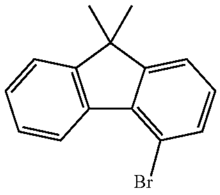 CAS-942615-32 | 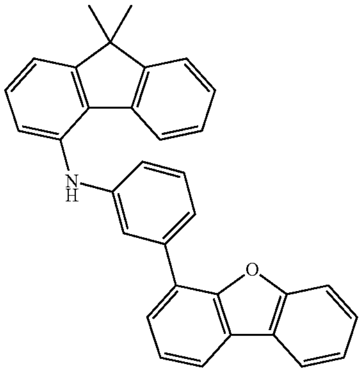 S142 |

-continued
| Reactant 1 | Reactant 2 | Product |
| --- | --- | --- |
| 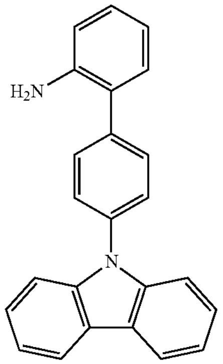 S45 | 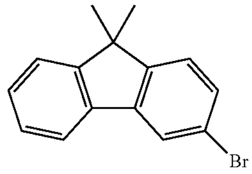 CAS-1190360-23-6 | 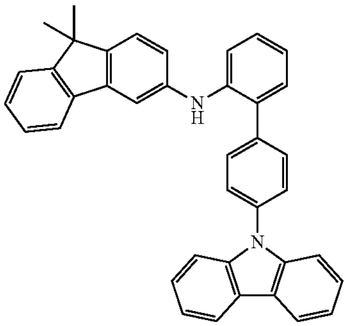 S143 |
| 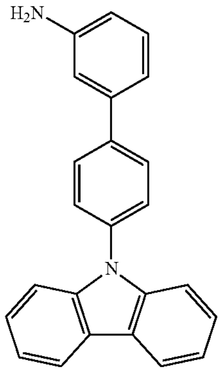 S24 | 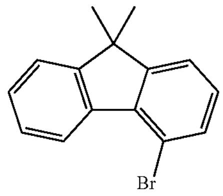 CAS-942615-32 | 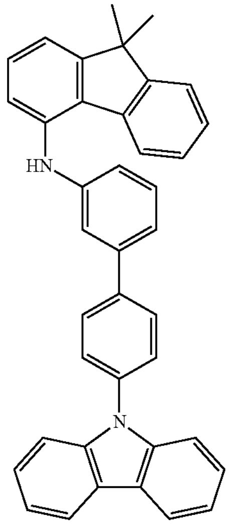 S144 |
| 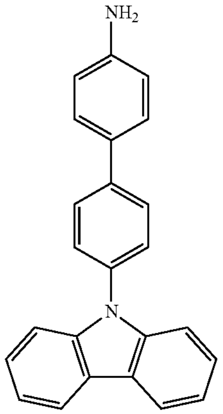 S25 | 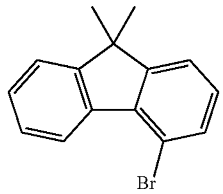 CAS-942615-32 | 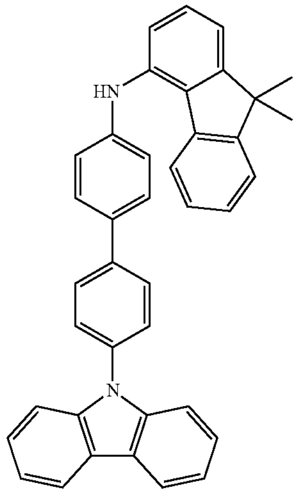 S145 |

-continued
| Reactant 1 | Reactant 2 | Product |
| --- | --- | --- |
| 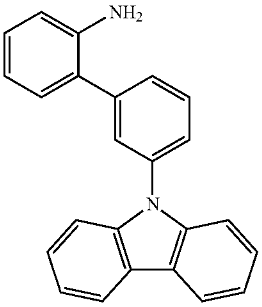 S26 | 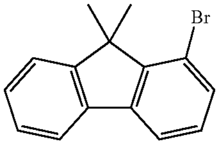 CAS-1225053-54-2 | 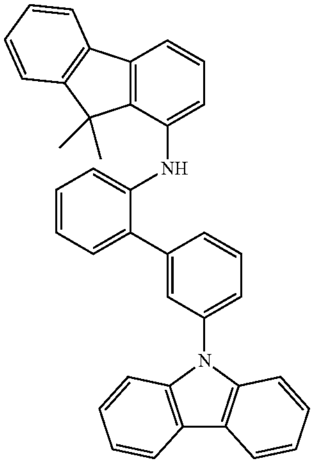 S146 |
| 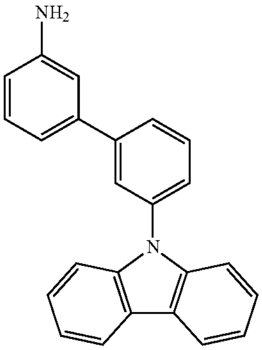 S27 | 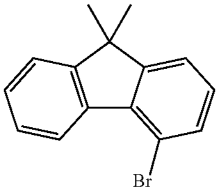 CAS-942615-32 | 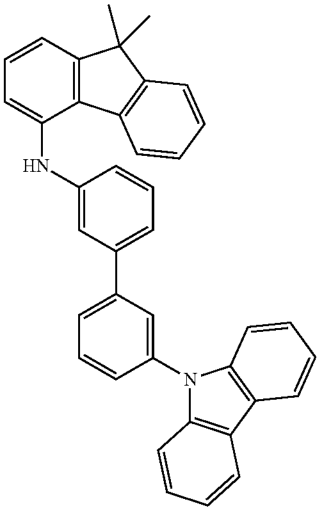 S147 |
| 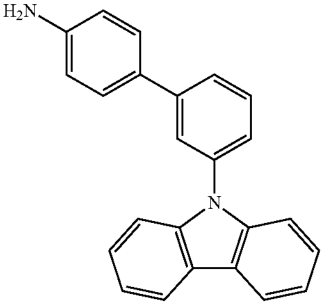 S28 | 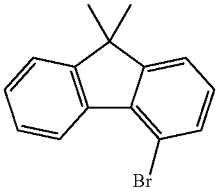 CAS-942615-32 | 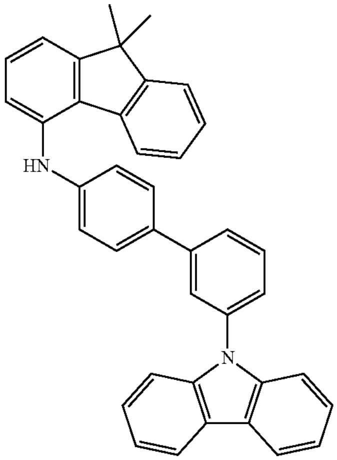 S148 |

-continued
| Reactant 1 | Reactant 2 | Product |
|---|---|---|
| 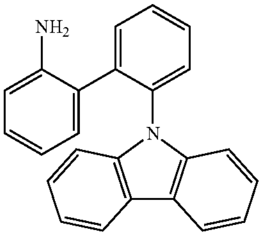 S29 | 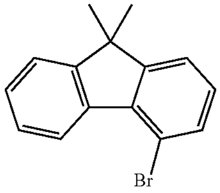 CAS-942615-32 | 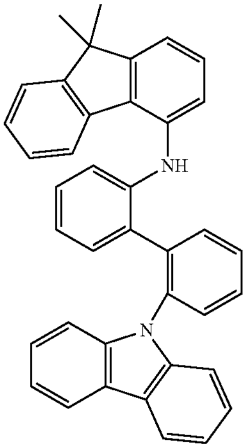 S149 |
| 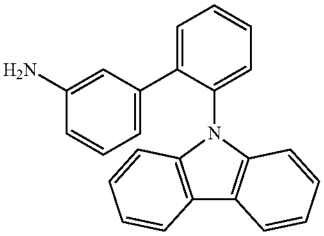 S30 | 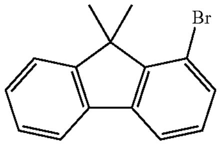 | 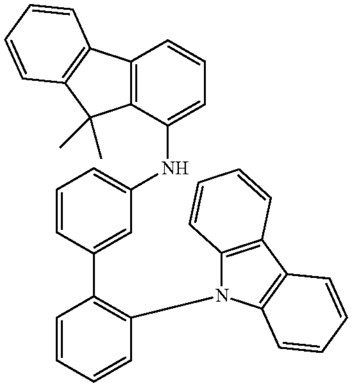 S150 |
| 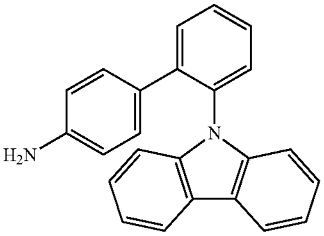 S31 | 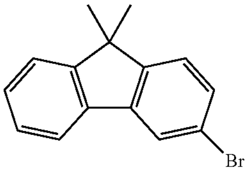 CAS-1190360-23-6 | 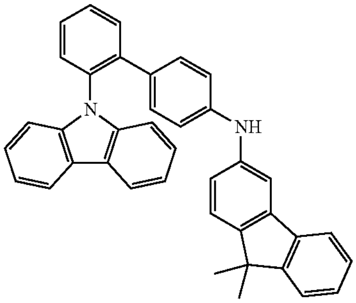 S151 |

-continued
| Reactant 1 | Reactant 2 | Product |
|---|---|---|
| 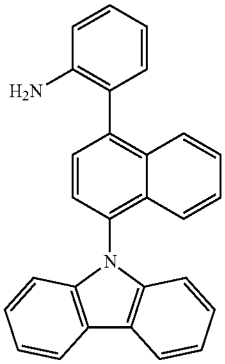 S32 | 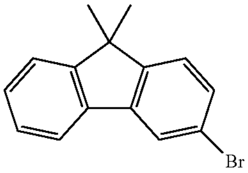 CAS-1190360-23-6 | 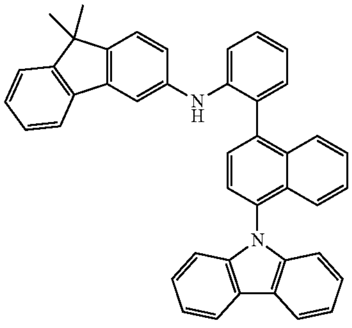 S152 |
| 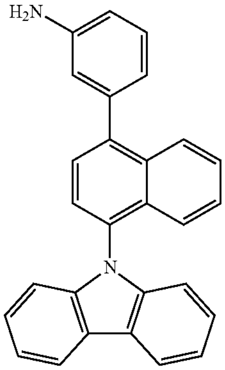 S33 | 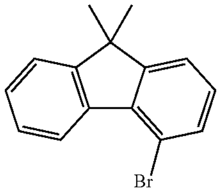 CAS-942615-32 | 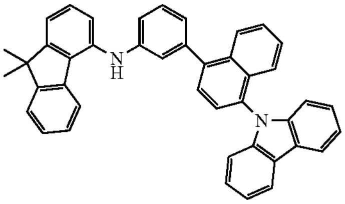 S153 |
| 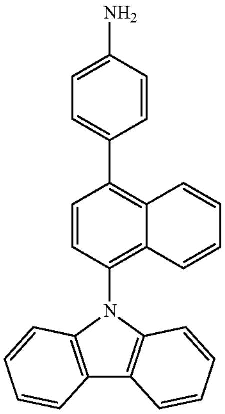 S34 | 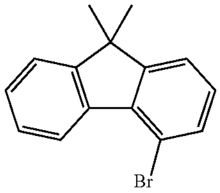 CAS-942615-32 | 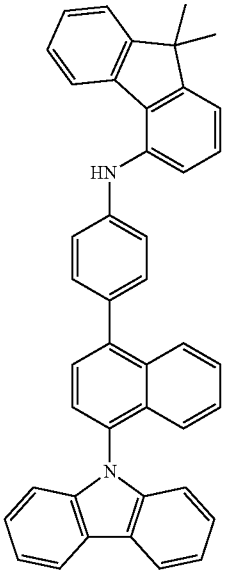 S154 |

-continued
| Reactant 1 | Reactant 2 | Product |
| --- | --- | --- |
| 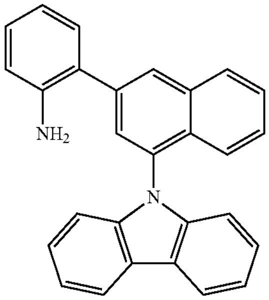 S35 | 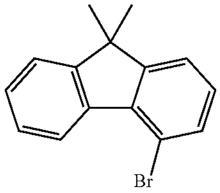 CAS-942615-32 | 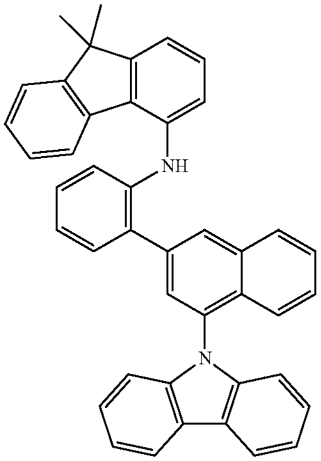 S155 |
| 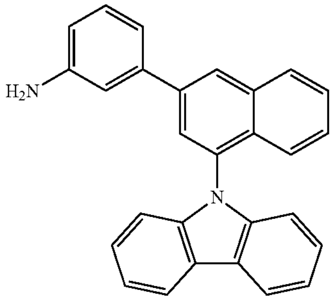 S36 | 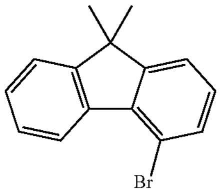 CAS-942615-32 | 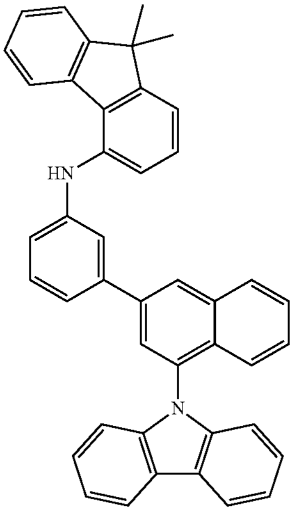 S156 |
| 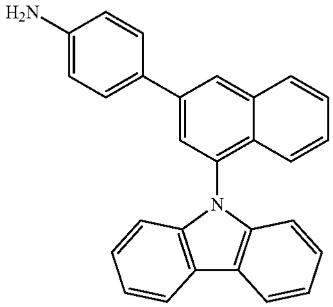 S37 | 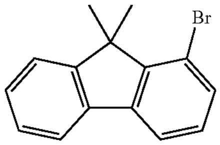 CAS-1225053-54-2 | 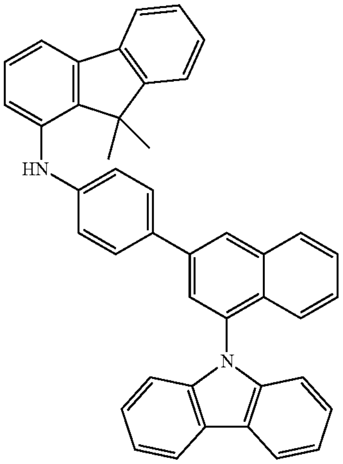 S157 |

-continued
| Reactant 1 | Reactant 2 | Product |
| --- | --- | --- |
| 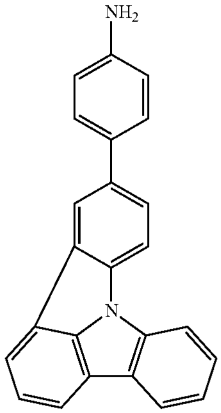 S38 | 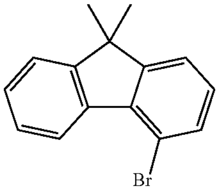 CAS-942615-32 | 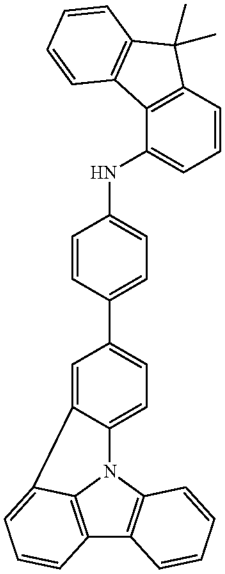 S158 |
| 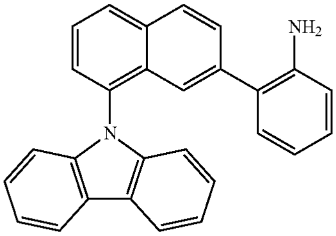 S39 | 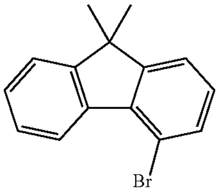 CAS-942615-32 | 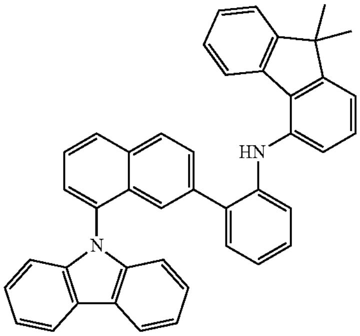 S159 |
| 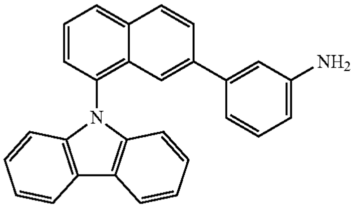 S40 | 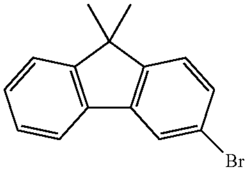 CAS-1190360-23-6 | 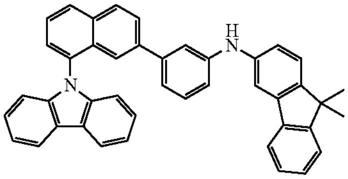 S160 |
| 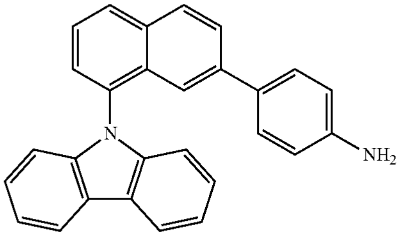 S41 | 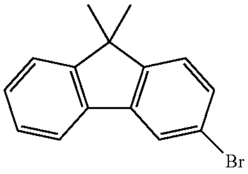 CAS-1190360-23-6 | 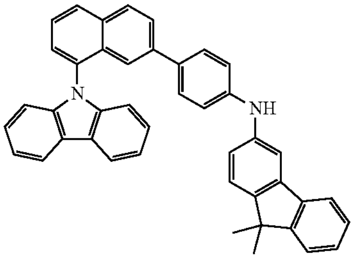 S161 |

-continued
| Reactant 1 | Reactant 2 | Product |
|---|---|---|
| 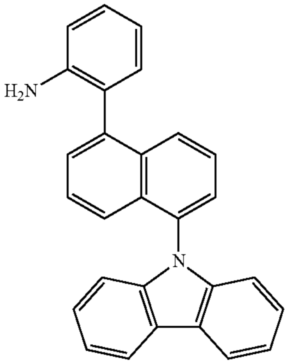 S42 | 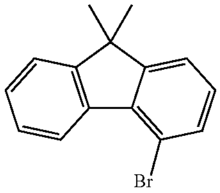 CAS-942615-32 | 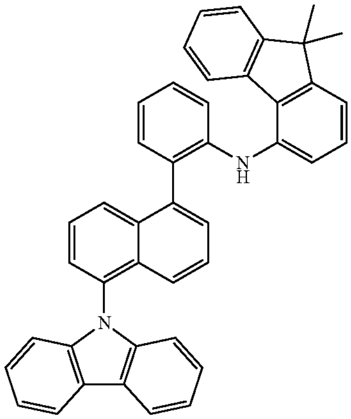 S162 |
| 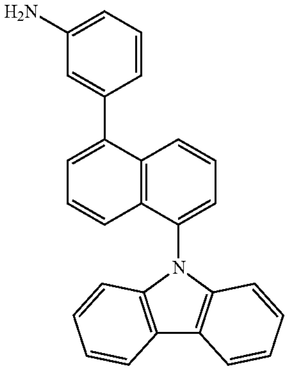 S43 | 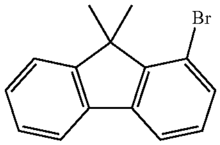 CAS-1225053-54-2 | 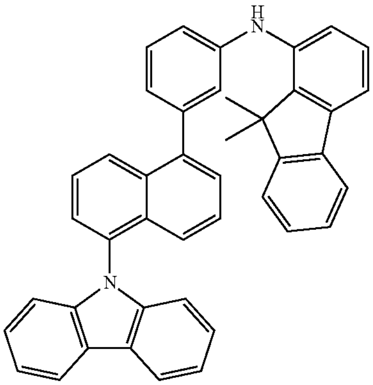 S166 |
| 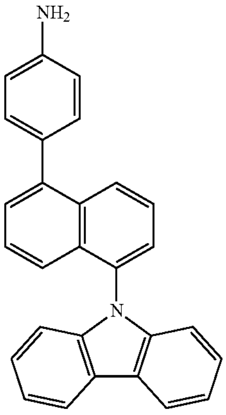 S44 | 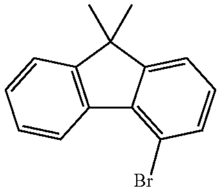 CAS-942615-32 | 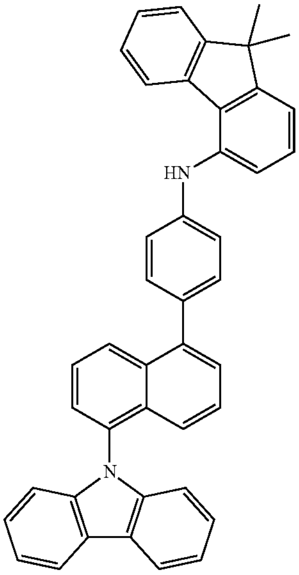 S164 |

-continued
| Reactant 1 | Reactant 2 | Product |
| --- | --- | --- |
| 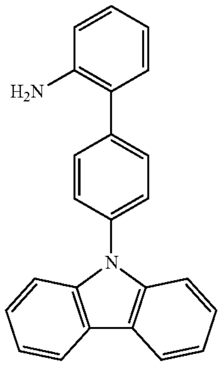 S45 | 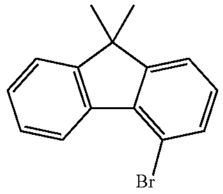 CAS-942615-32 | 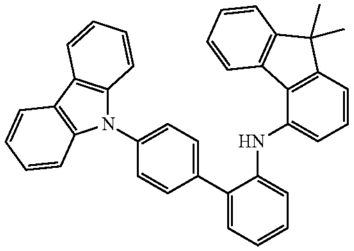 S165 |
| 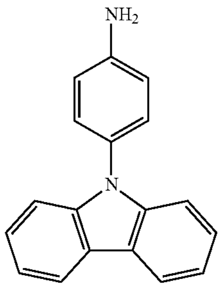 CAS-52708-37-9 | 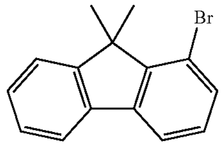 CAS-1225053-54-2 | 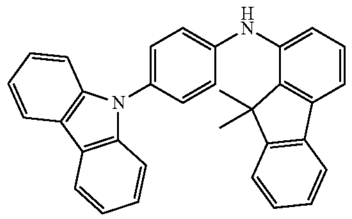 S166 |
| 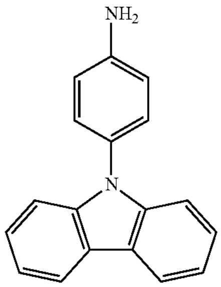 CAS-52708-37-9 | 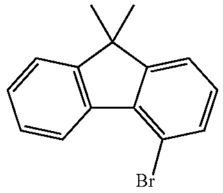 CAS-942615-32 | 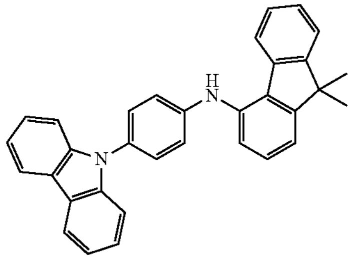 S167 |
| 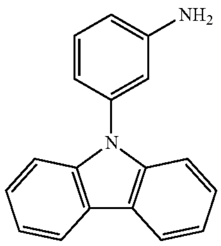 CAS-1023659-21-3 | 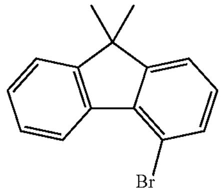 CAS-942615-32 | 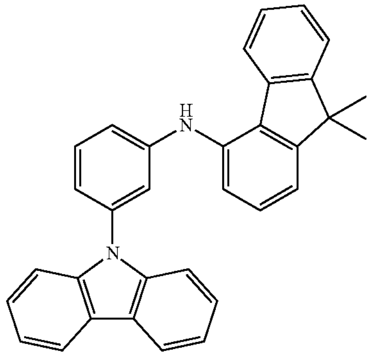 S168 |

-continued
| Reactant 1 | Reactant 2 | Product |
| --- | --- | --- |
| 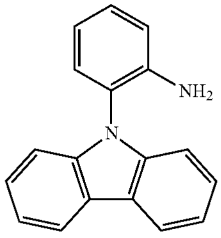 CAS-101716-43-2 | 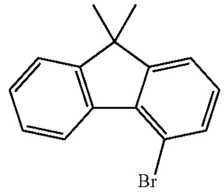 CAS-942615-32 | 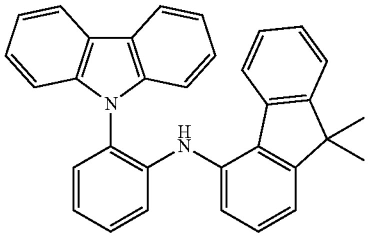 S169 |
| 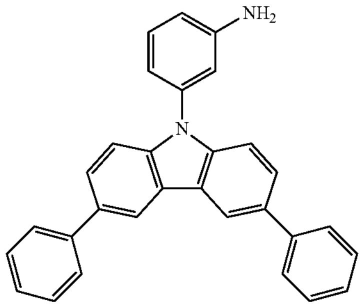 CAS-1708110-65-9 | 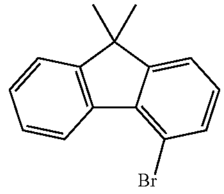 CAS-942615-32 | 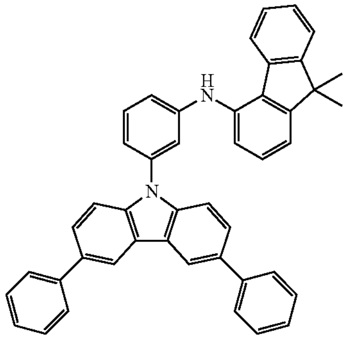 S170 |
| 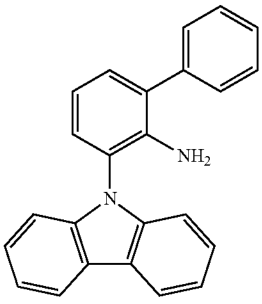 CAS-1673542-71-6 | 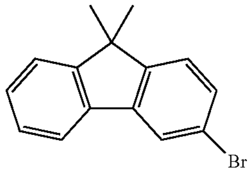 CAS-1190360-23-6 | 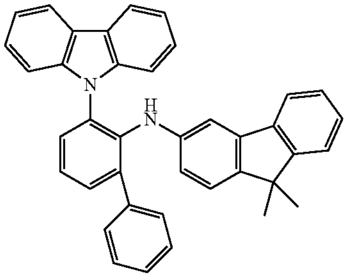 S171 |
A-2) Preparation of the End Products
P1:
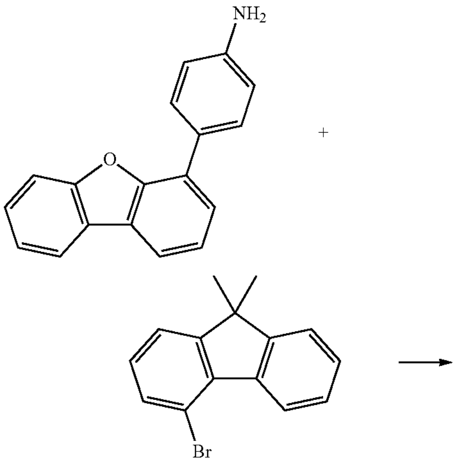
-continued
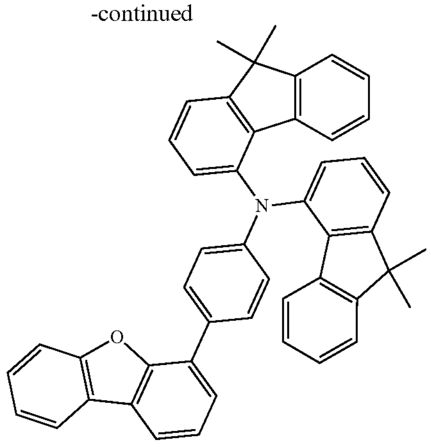
4-Dibenzofuran-4-ylphenylamine [CAS578027-21-1] (12.00 g; 46.26 mmol), 4-bromo-9,9-dimethyl-9H-fluorene [CAS-942615-32-9](26.55 g; 97.2 mmol) and sodium tert-butoxide (13.34 g; 138.83 mmol) are initially charged in toluene (500 ml) and saturated with argon for 45 min.

Thereafter, palladium(II) acetate [3375-31-3] (519 mg; 2.31 mmol) and 1.0 M tri-tert-butylphosphine solution in toluene [13716-12-6] (4.63 ml; 4.63 mmol) are introduced and the mixture is stirred under reflux for 16 h. After this mixture has been cooled, it is extended with 200 ml of n-heptane, the precipitated solids are filtered off with suction and stirred with 500 ml of water, and the solids are filtered off again and washed with ethanol (4×50 ml). The crude product is subjected to basic hot extraction twice with toluene/n-heptane over aluminium oxide, then recrystallized twice from o-xylene and finally sublimed under high vacuum.

Yield: 16.0 g (24.9 mmol), 54%; purity: >99.9% by HPLC.

Comp. 1

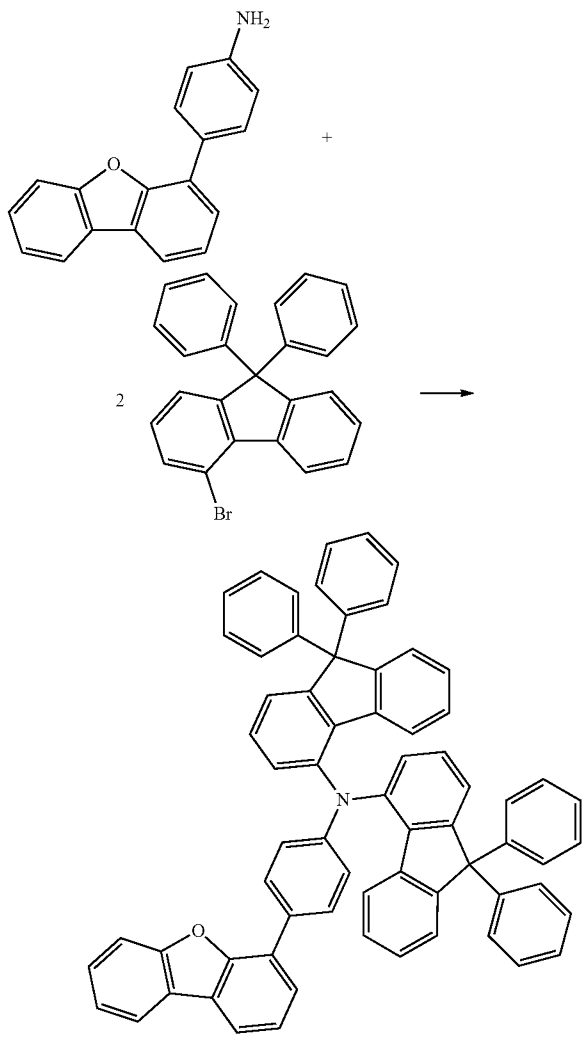

Procedure analogous to the experimental description for P1, except that 4-bromo-9,9-diphenyl-9H-fluorene [CAS-713125-22-5] is used rather than 4-bromo-9,9-dimethyl-9H-fluorene. Purification is effected by basic hot extraction twice with toluene over aluminium oxide, recrystallization once from o-xylene and final sublimation under high vacuum. Yield: 26.4 g (29.6 mmol, 64%); purity: >99.9% by HPLC

P2

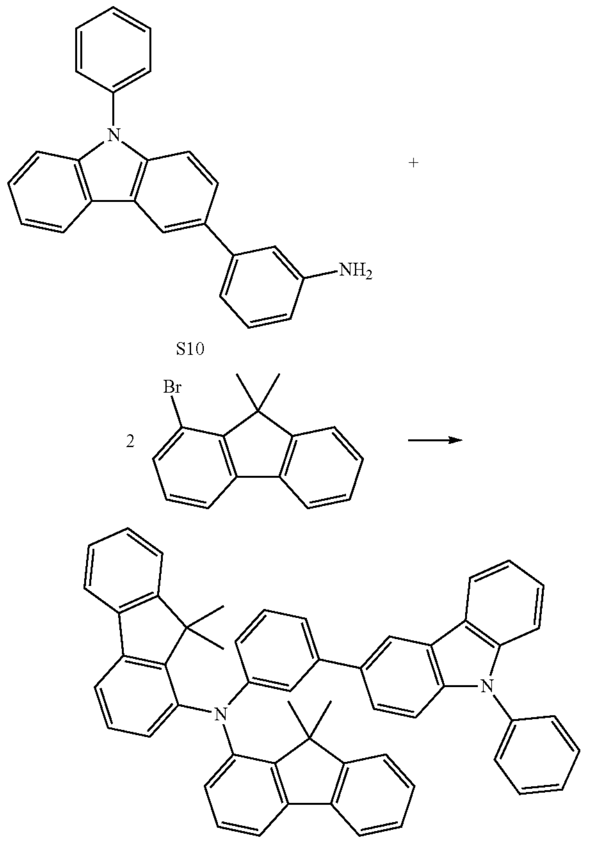

Procedure analogous to the experimental description for P1, except that S10 (46.26 mmol) is used rather than 4-dibenzofuran-4-ylphenylamine and 1-bromo-9,9-dimethyl-9H-fluorene [CAS-1225053-54-2] rather than 4-bromo-9,9-dimethyl-9H-fluorene. Purification is effected by basic hot extraction twice with toluene/n-heptane over aluminium oxide, recrystallization twice from n-butyl acetate and final sublimation under high vacuum. Yield: 6.6 g (9.1 mmol, 20%); purity: >99.9% by HPLC

P3

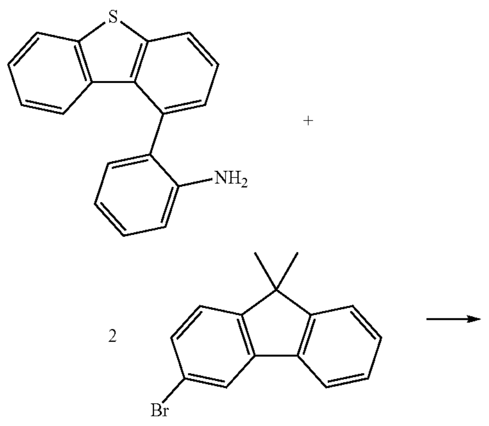

-continued

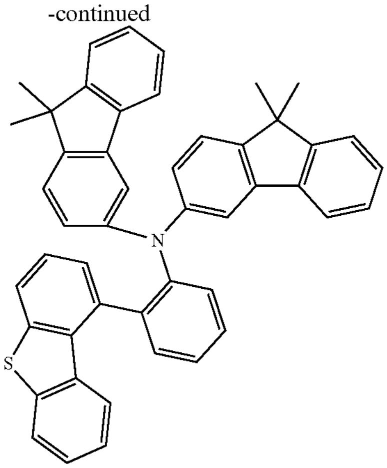

Procedure analogous to the experimental description for P1, except that 1-dibenzothiophen-2-ylphenylamine [CAS-1850406-53-9] (46.26 mmol) is used rather than 4-dibenzofuran-4-ylphenylamine and 3-bromo-9,9-dimethyl-9H-fluorene [CAS-1190360-23-6] rather than 4-bromo-9,9-dimethyl-9H-fluorene. The catalyst system used is tris(dibenzylideneacetone)dipalladium(0) [CAS-51364-51-3] (0.01 equiv) and S-Phos [CAS-657408-07-6] (0.03 equiv) rather than palladium(II) acetate and tri-tert-butylphosphine. Purification is effected by basic hot extraction twice with toluene/n-heptane over aluminium oxide, recrystallization once from toluene and final sublimation under high vacuum. Yield: 10.1 g (15.3 mmol, 33%); purity: >99.9% by HPLC In an analogous manner, it is possible to prepare the following compounds: In this case, purification can also be effected using column chromatography, or recrystallization or hot extraction using other standard solvents such as ethanol, butanol, acetone, ethyl acetate, acetonitrile, toluene, xylene, dichloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone etc. The yields are typically in the range between 15% and 75%.

| Reactant 1 | Reactant 2 | Product |
|---|---|---|
| 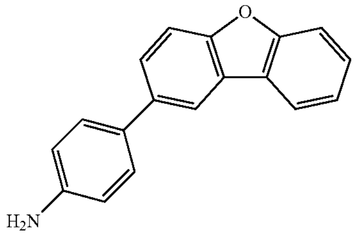 CAS-1178274-17-3 | 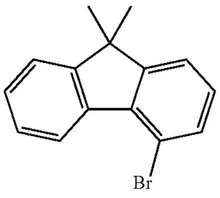 CAS-942615-32-9 | 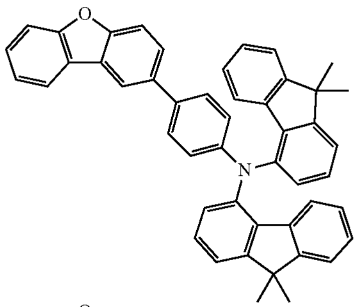 P4 |
| 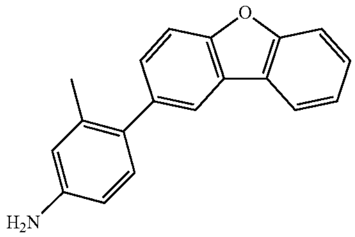 CAS-1184428-04-3 | 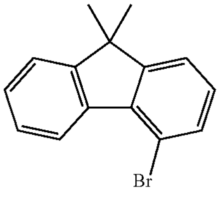 CAS-942615-32-9 | 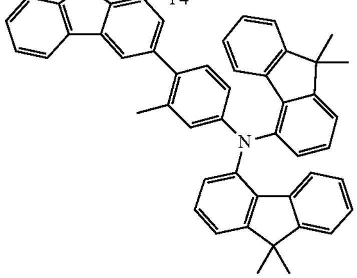 P5 |
| 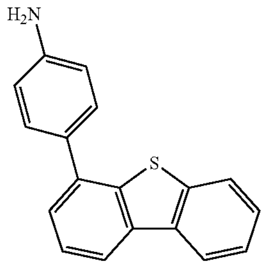 CAS-1370034-50-6 | 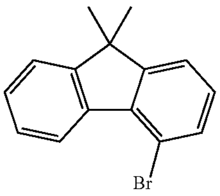 CAS-942615-32-9 | 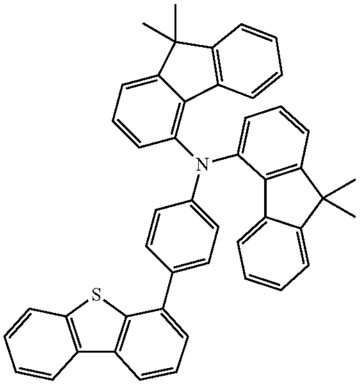 P6 |

-continued
| Reactant 1 | Reactant 2 | Product |
|---|---|---|
| 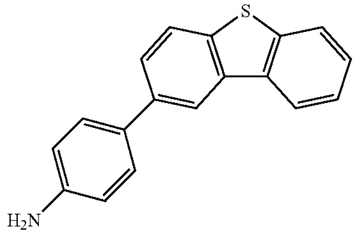 CAS-1574121-68-8 | 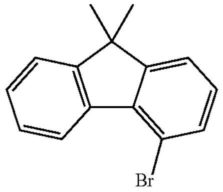 CAS-942615-32-9 | 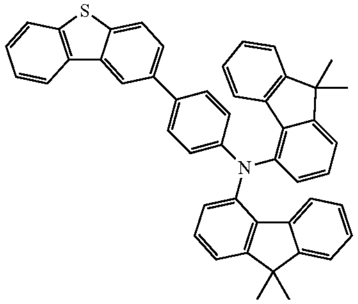 P7 |
| 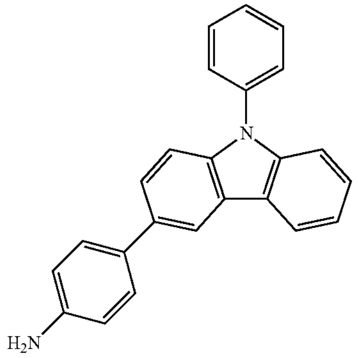 CAS-1370034-59-5 | 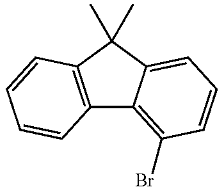 CAS-942615-32-9 | 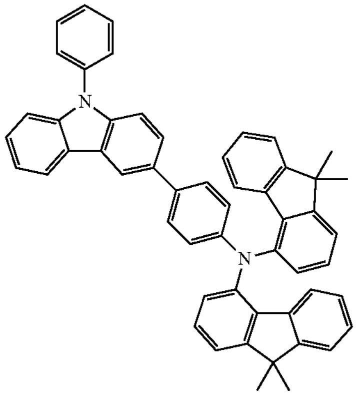 P8 |
| 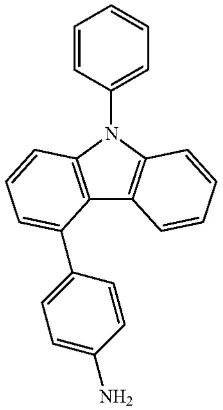 CAS-1629995-08-9 | 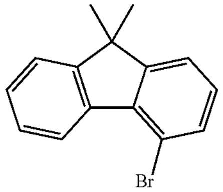 CAS-942615-32-9 | 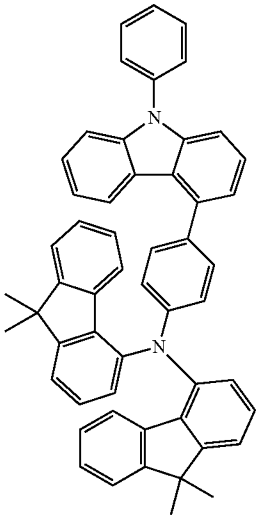 P9 |
| 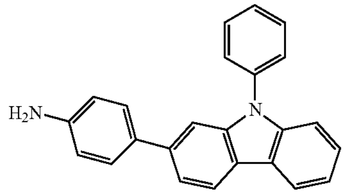 CAS-1911626-45-3 | 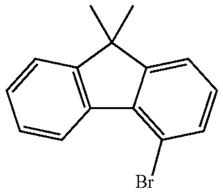 CAS-942615-32-9 | 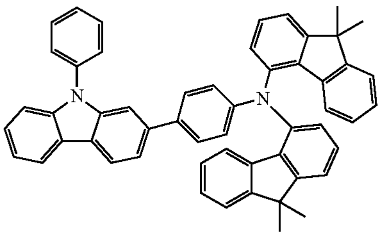 P10 |

-continued
| Reactant 1 | Reactant 2 | Product |
| --- | --- | --- |
| 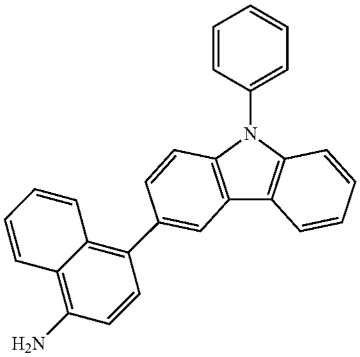 CAS-1699765-82-6 | 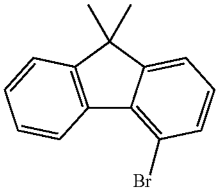 CAS-942615-32-9 | 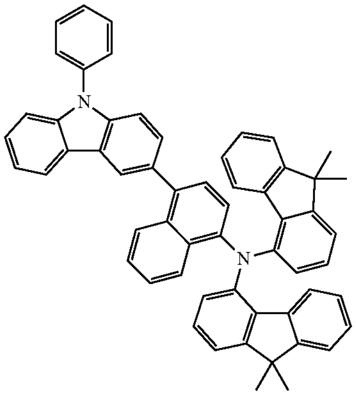 P11 |
| 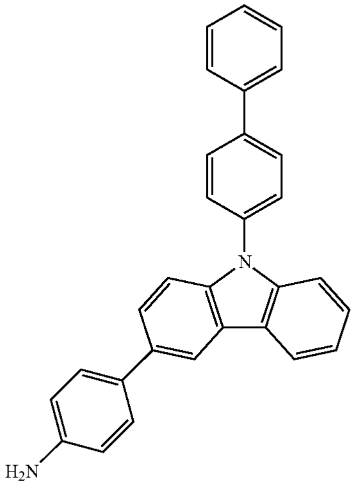 CAS-1401003-448 | 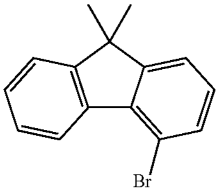 CAS-942615-32-9 | 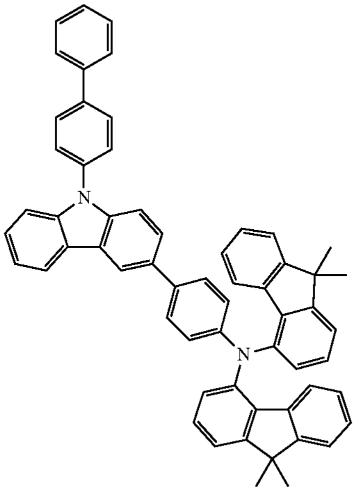 P12 |
| 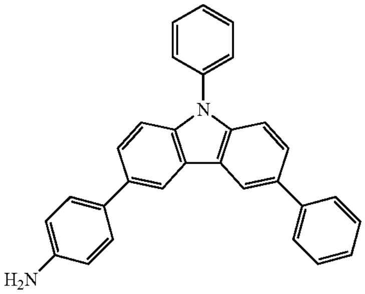 CAS-1458611-14-7 | 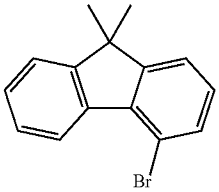 CAS-942615-32-9 | 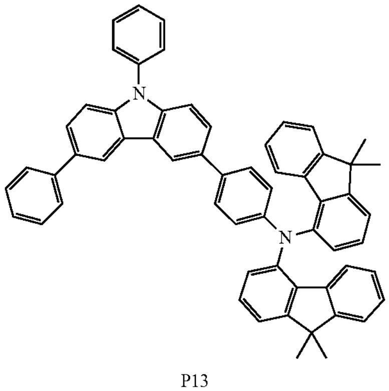 P13 |

-continued
| Reactant 1 | Reactant 2 | Product |
| --- | --- | --- |
| 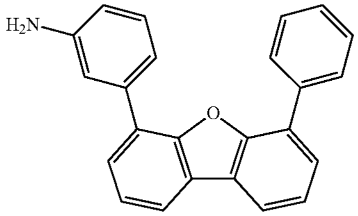 CAS-2101611-03-2 | 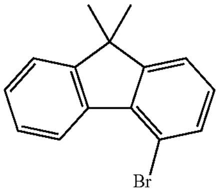 CAS-942615-32-9 | 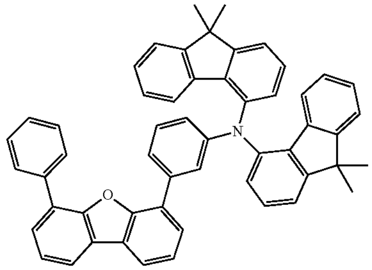 P14 |
| 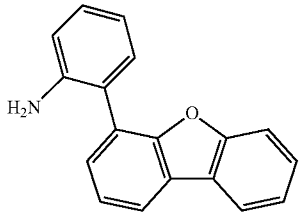 CAS-1559070-70-0 | 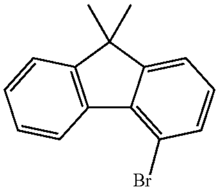 CAS-942615-32-9 | 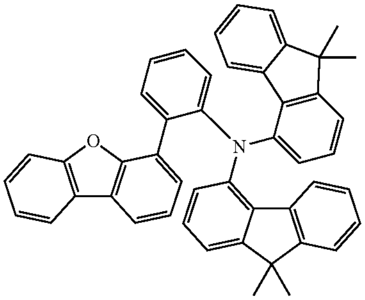 P15 |
| 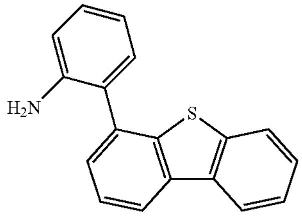 CAS-530403-06-6 | 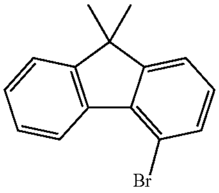 CAS-942615-32-9 | 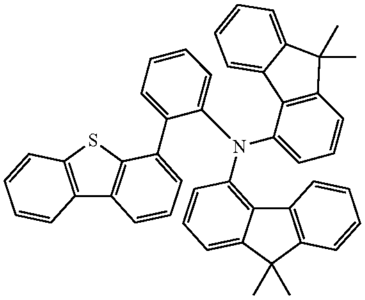 P16 |
| 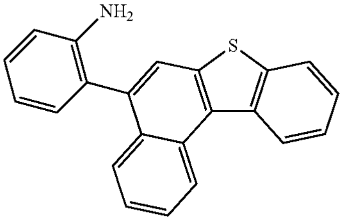 CAS-2044846-62-8 | 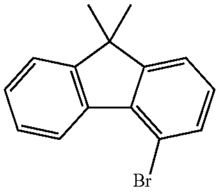 CAS-942615-32-9 | 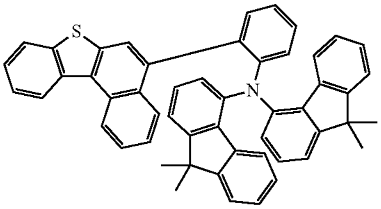 P17 |
| 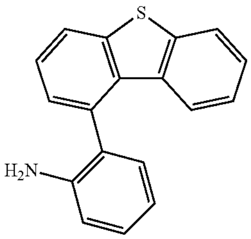 CAS-1850406-53-9 | 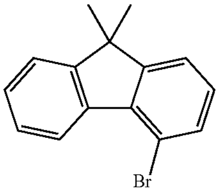 CAS-942615-32-9 | 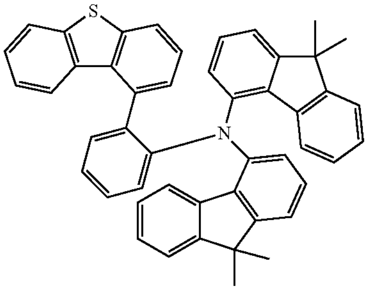 P18 |

-continued
| Reactant 1 | Reactant 2 | Product |
|---|---|---|
| 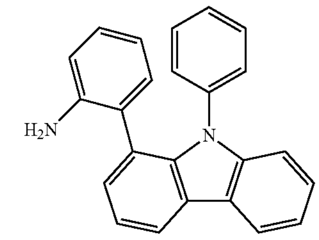 CAS-1850406-99-3 | 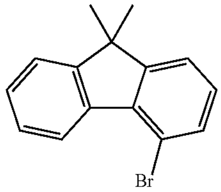 CAS-942615-32-9 | 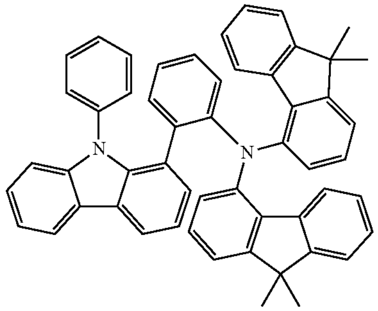 P19 |
| 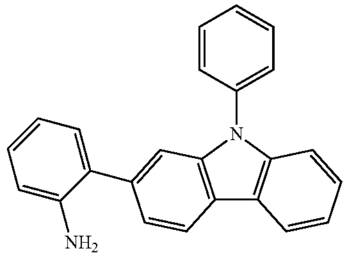 CAS1850406-91-5 | 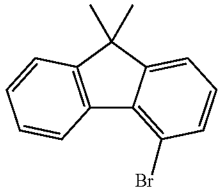 CAS-942615-32-9 | 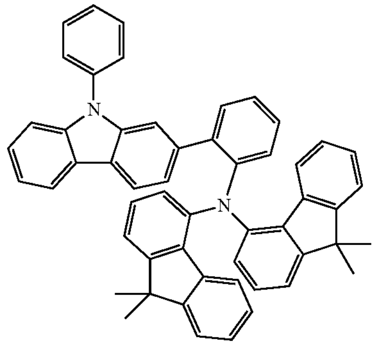 P20 |
| 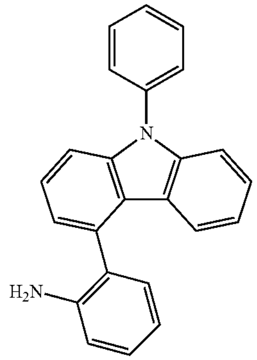 CAS-1850406-35-7 | 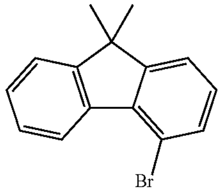 CAS-942615-32-9 | 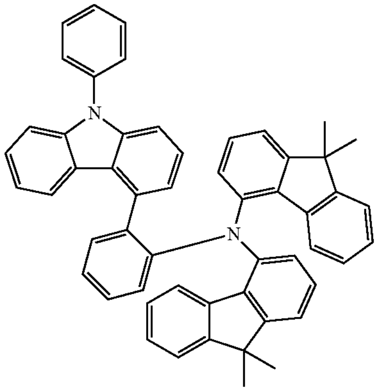 P21 |
| 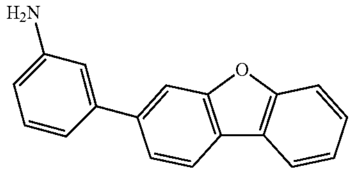 S2 | 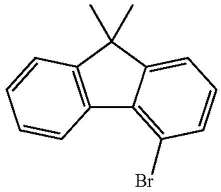 CAS-942615-32-9 | 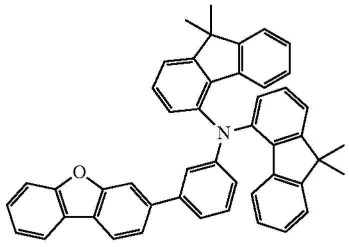 P22 |

-continued
| Reactant 1 | Reactant 2 | Product |
| --- | --- | --- |
| 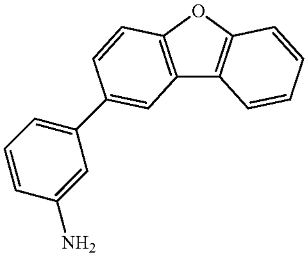 S3 | 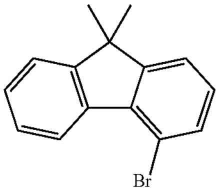 CAS-942615-32-9 | 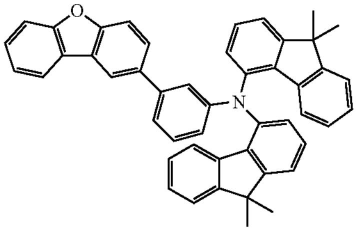 P23 |
| 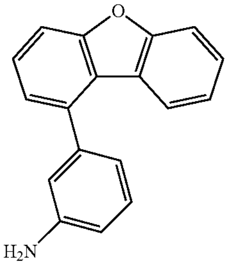 S4 | 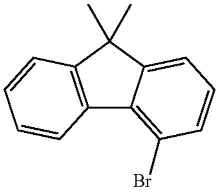 CAS-942615-32-9 | 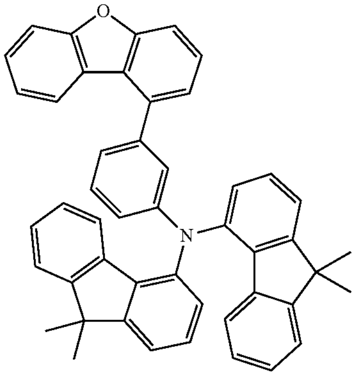 P24 |
| 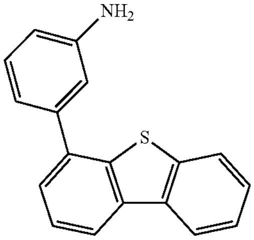 S5 | 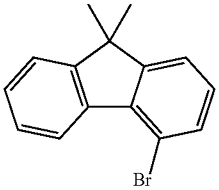 CAS-942615-32-9 | 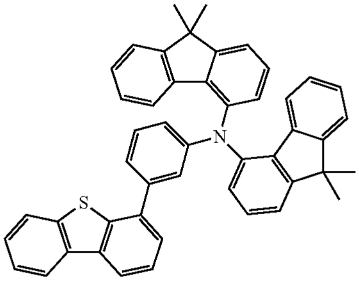 P25 |
| 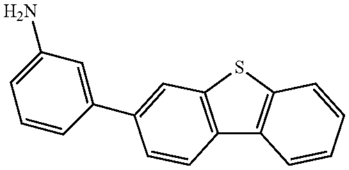 S6 | 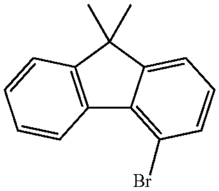 CAS-942615-32-9 | 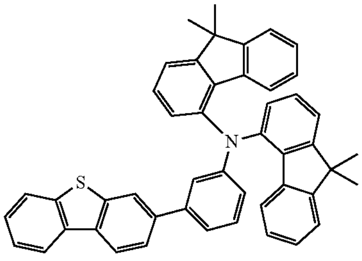 P26 |
| 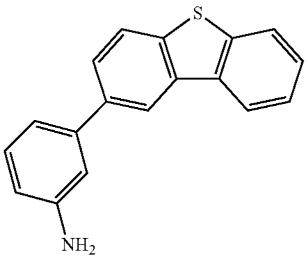 S7 | 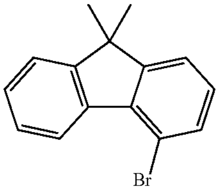 CAS-942615-32-9 | 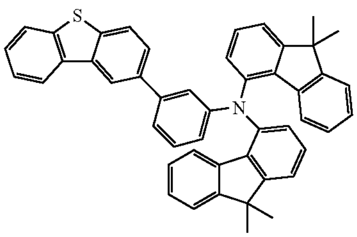 P27 |

-continued
| Reactant 1 | Reactant 2 | Product |
| --- | --- | --- |
| 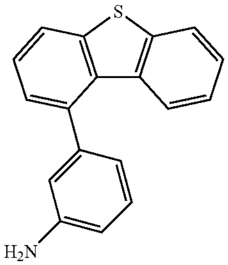 S8 | 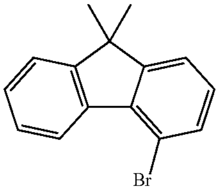 CAS-942615-32-9 | 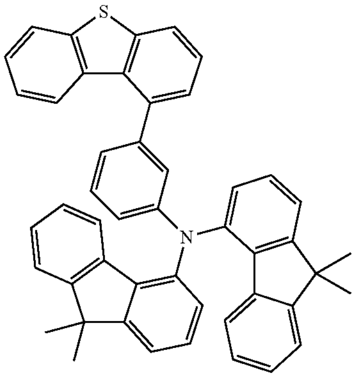 P28 |
| 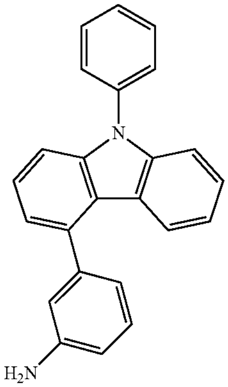 S9 | 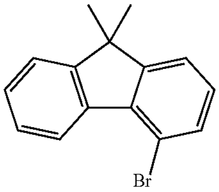 CAS-942615-32-9 | 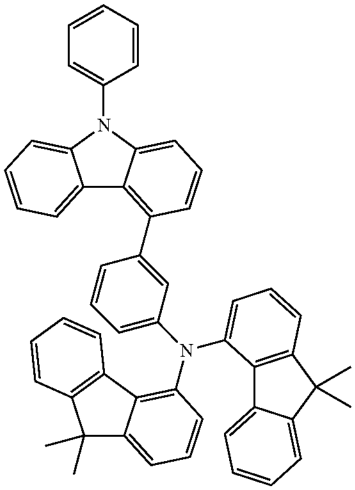 P29 |
| 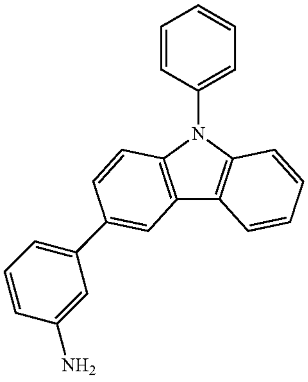 S10 | 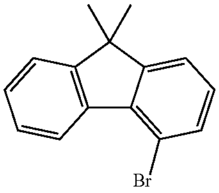 CAS-942615-32-9 | 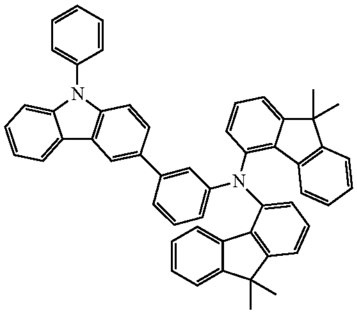 P30 |

-continued
| Reactant 1 | Reactant 2 | Product |
| --- | --- | --- |
| 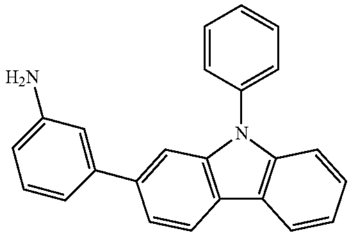 S11 | 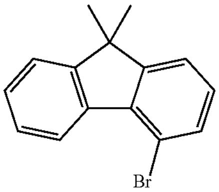 CAS-942615-32-9 | 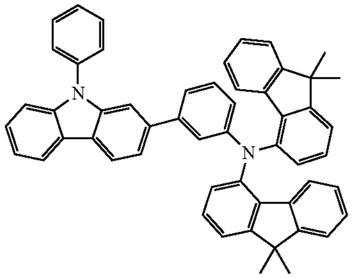 P31 |
| 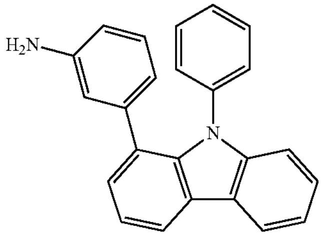 S12 | 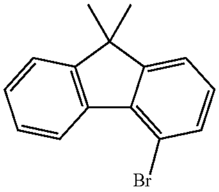 CAS-942615-32-9 | 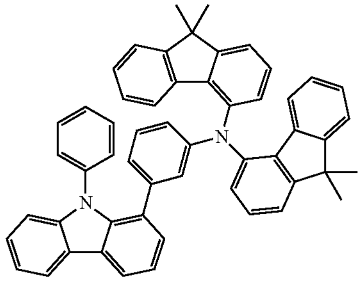 P32 |
| 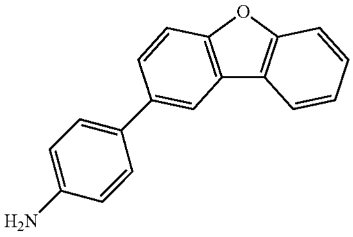 S13 | 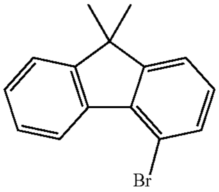 CAS-942615-32-9 | 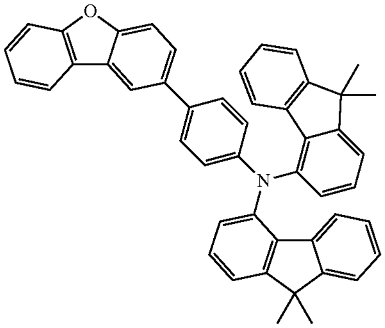 P33 |
| 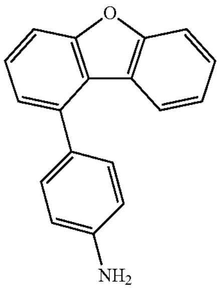 S14 | 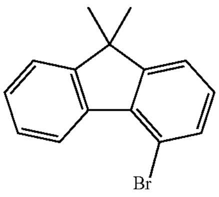 CAS-942615-32-9 | 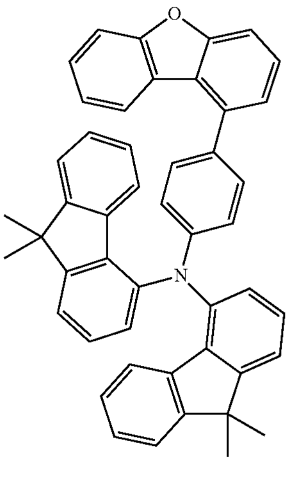 P34 |

-continued
| Reactant 1 | Reactant 2 | Product |
|---|---|---|
| 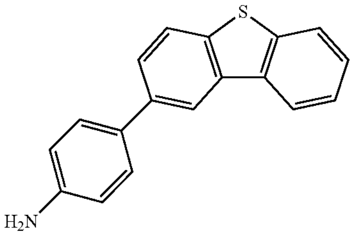 S15 | 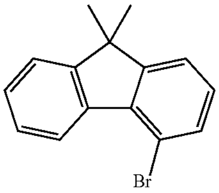 CAS-942615-32-9 | 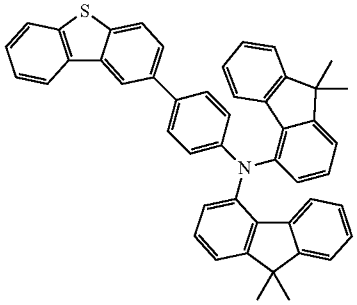 P35 |
| 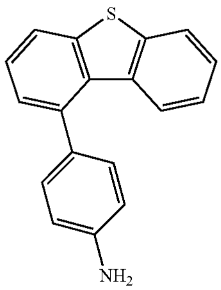 S16 | 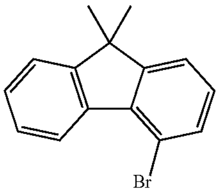 CAS-942615-32-9 | 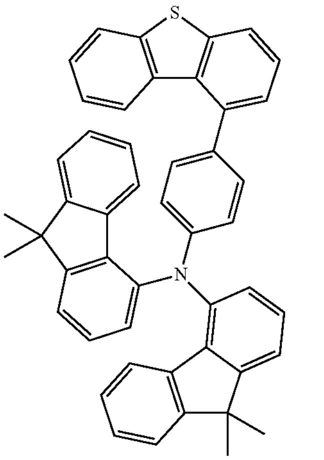 P36 |
| 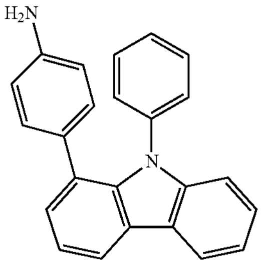 S17 | 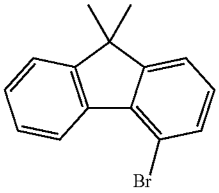 CAS-942615-32-9 | 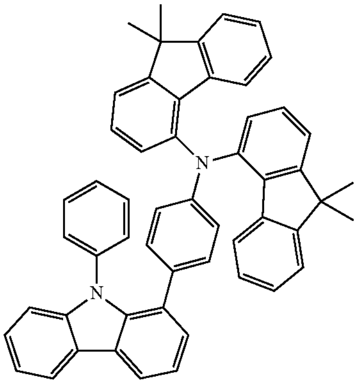 P37 |
| 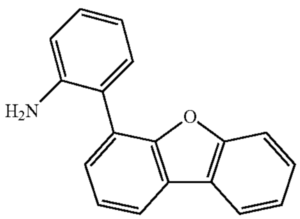 S18 | 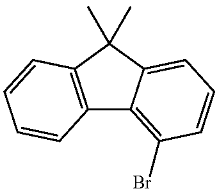 CAS-942615-32-9 | 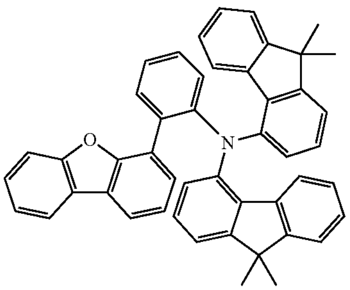 P38 |

-continued
| Reactant 1 | Reactant 2 | Product |
| --- | --- | --- |
| 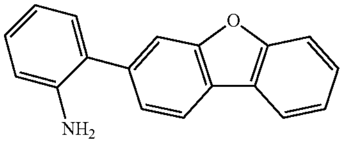 S19 | 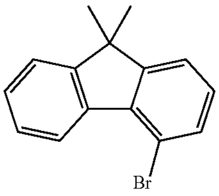 CAS-942615-32-9 | 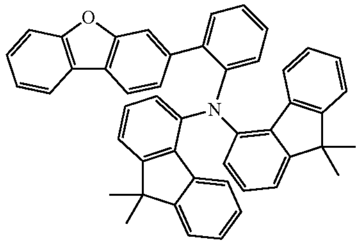 P39 |
| 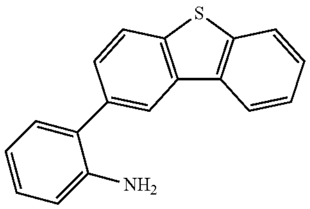 S20 | 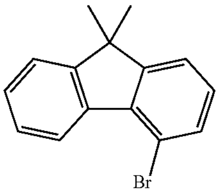 CAS-942615-32-9 | 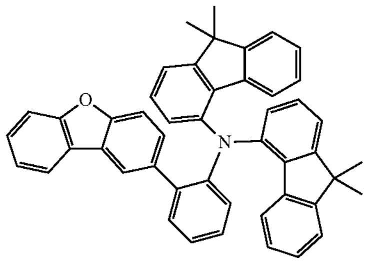 P40 |
| 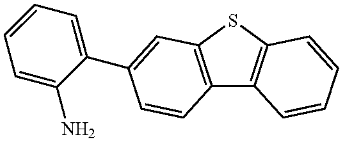 S21 | 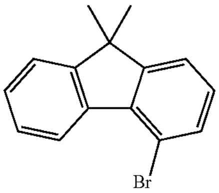 CAS-942615-32-9 | 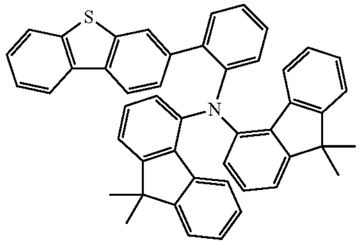 P41 |
| 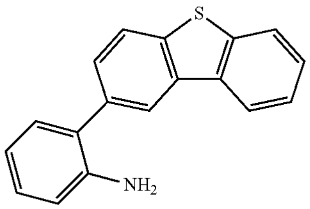 S22 | 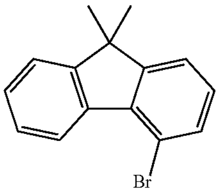 CAS-942615-32-9 | 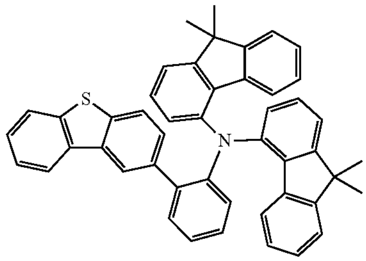 P42 |
| 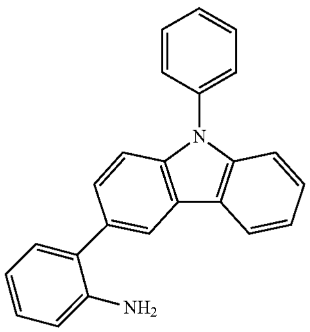 S23 | 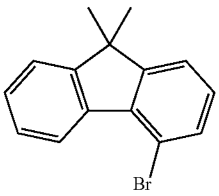 CAS-942615-32-9 | 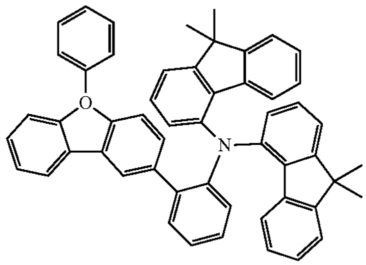 P40 |

-continued
| Reactant 1 | Reactant 2 | Product |
| --- | --- | --- |
| 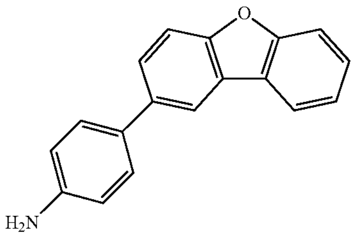 CAS-1178274-17-3 | 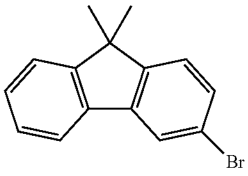 CAS-1190360-23-6 | 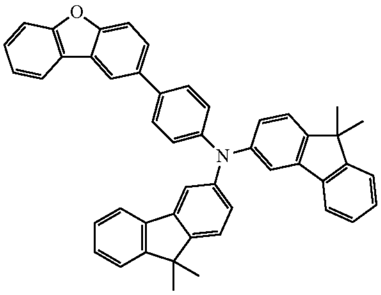 P44 |
| 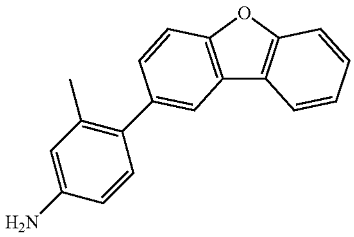 CAS-1184428-04-3 | 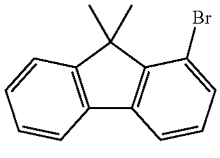 CAS-1225053-54-2 | 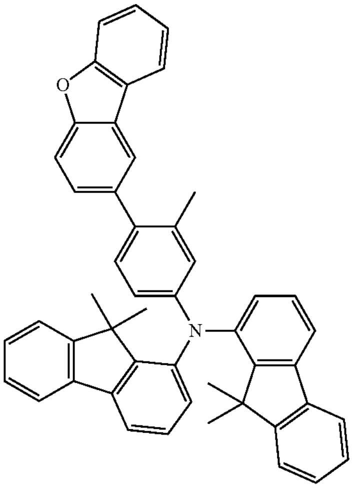 P45 |
| 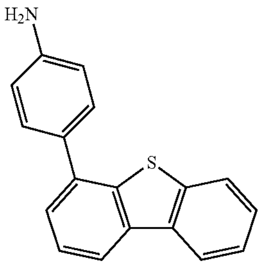 CAS-1370034-50-6 | 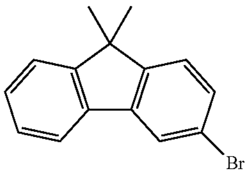 CAS-1190360-23-6 | 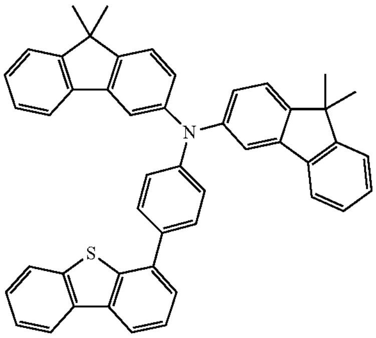 P46 |

-continued
| Reactant 1 | Reactant 2 | Product |
|---|---|---|
| 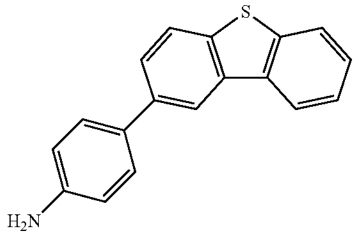 CAS-1574121-68-8 | 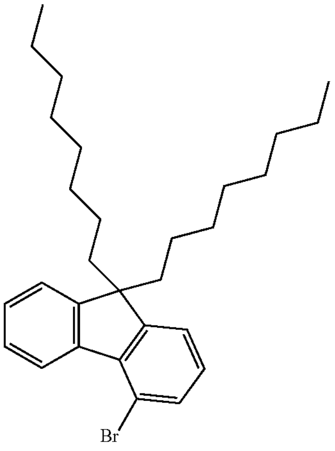 CAS-1469898-60-9 | 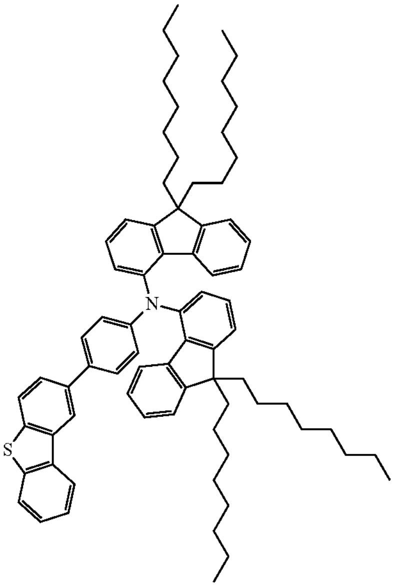 P47 |
| 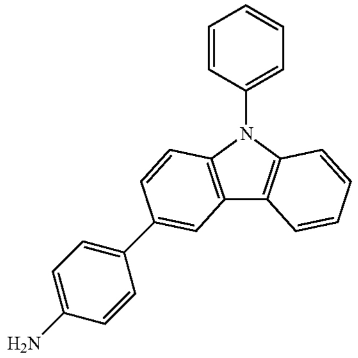 CAS-1370034-59-5 | 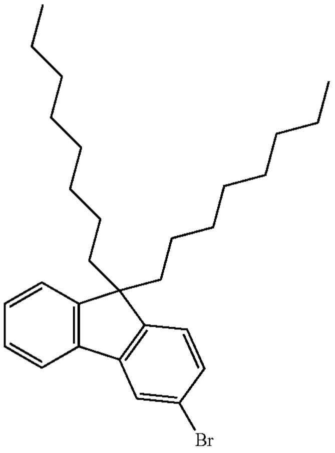 CAS-1609186-23-3 | 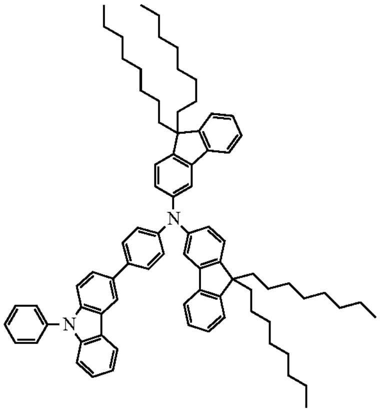 P48 |
| 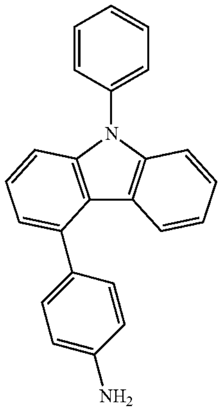 CAS-1629995-08-9 | 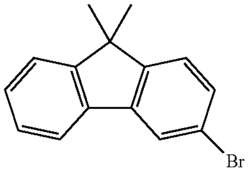 CAS-1190360-23-6 | 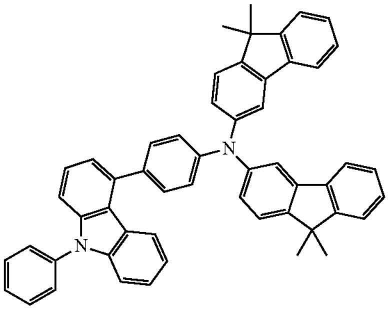 P49 |

-continued
| Reactant 1 | Reactant 2 | Product |
| --- | --- | --- |
| 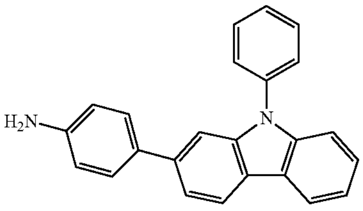 CAS-1911626-45-3 | 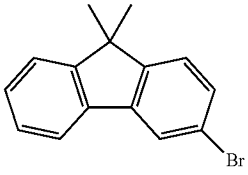 CAS-1190360-23-6 | 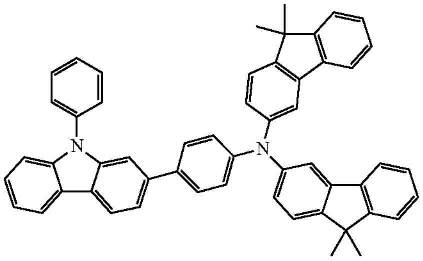 P50 |
| 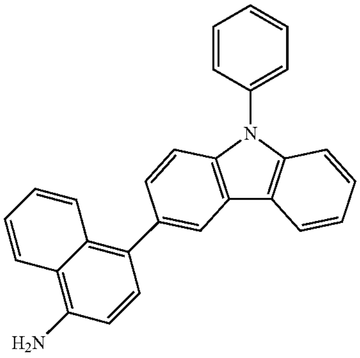 CAS-1699765-82-6 | 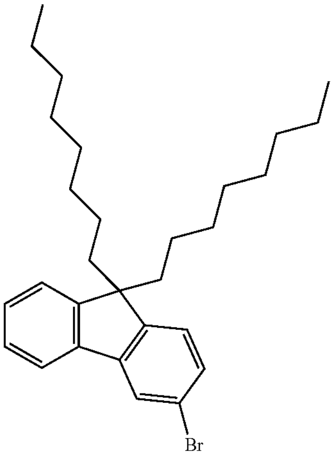 CAS-1609186-23-3 | 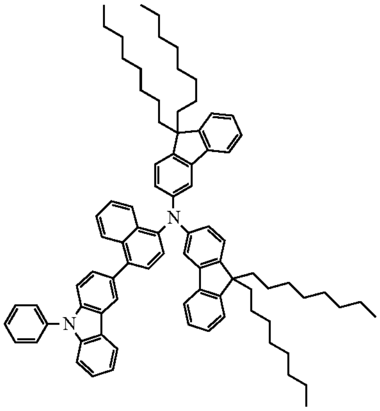 P51 |
| 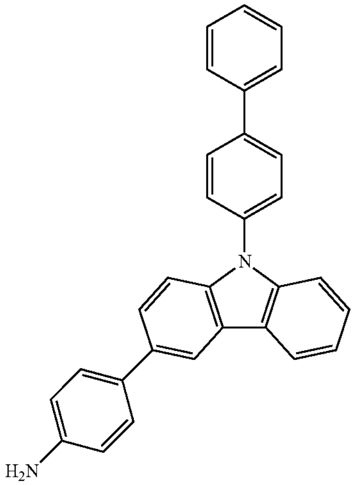 CAS-1401003-44-8 | 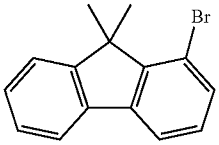 CAS-12255053-54-2 | 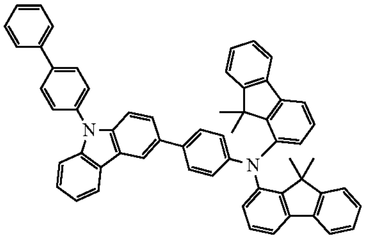 P52 |

-continued
| Reactant 1 | Reactant 2 | Product |
| --- | --- | --- |
| 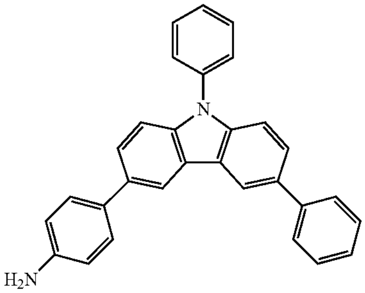 CAS-1458611-14-7 | 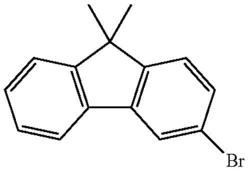 CAS-1190360-23-6 | 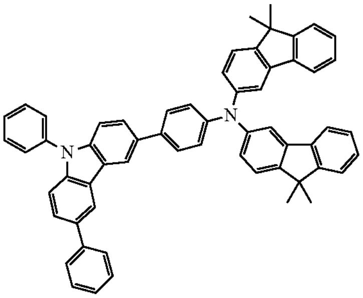 P53 |
| 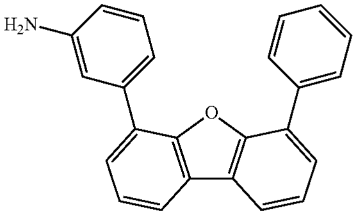 CAS-2101611-03-2 | 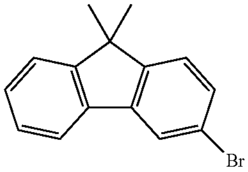 CAS-1190360-23-6 | 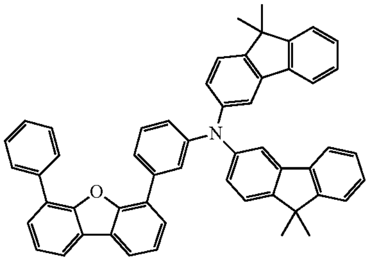 P54 |
| 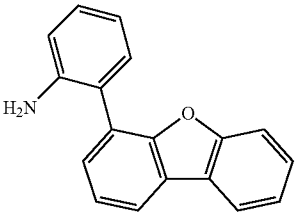 CAS-1559070-70-0 | 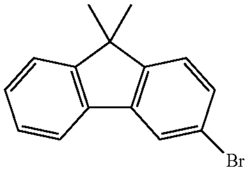 CAS-1190360-23-6 | 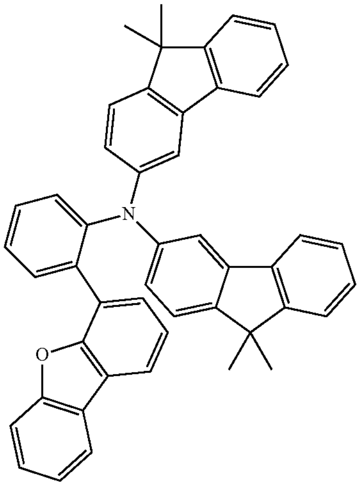 P55 |
| 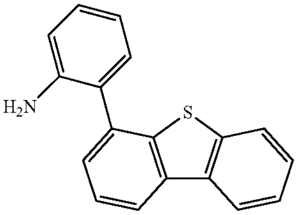 CAS-530403-06-6 | 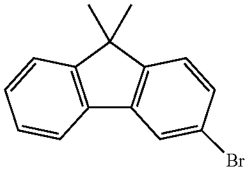 CAS-1190360-23-6 | 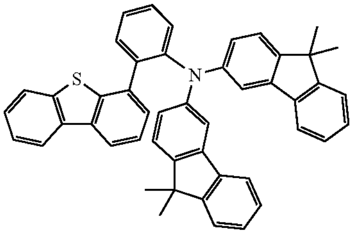 P56 |

-continued
| Reactant 1 | Reactant 2 | Product |
|---|---|---|
| 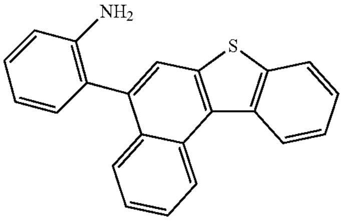 CAS-2044846-62-8 | 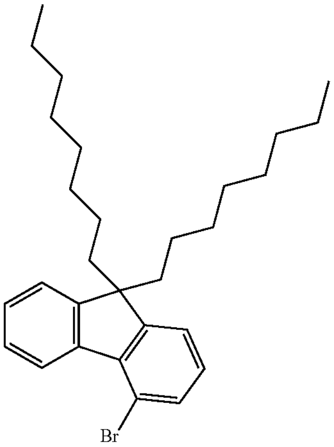 CAS-1469898-60-9 | 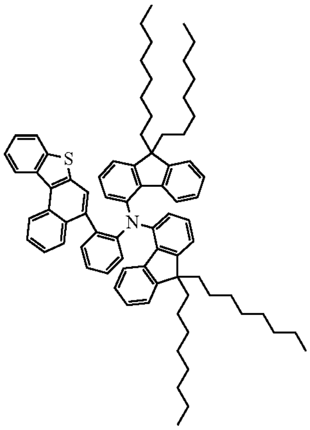 P57 |
| 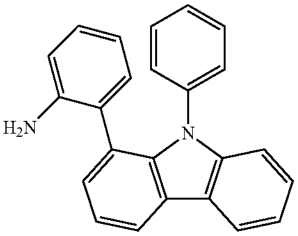 CAS-1850406-99-3 | 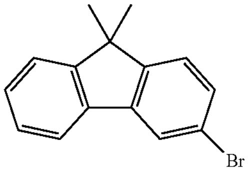 CAS-1190360-23-6 | 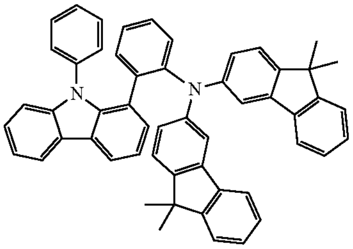 P58 |
| 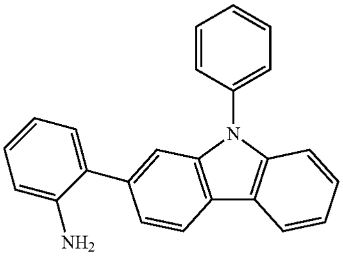 CAS1850406-91-5 | 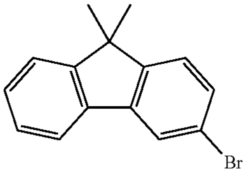 CAS-1190360-23-6 | 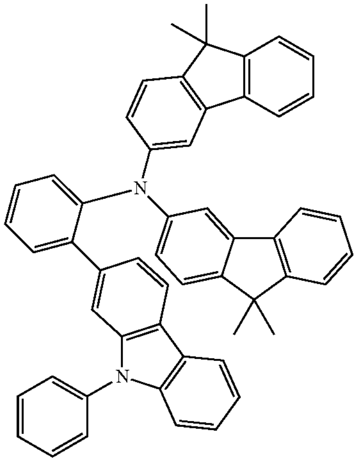 P59 |

-continued
| Reactant 1 | Reactant 2 | Product |
|---|---|---|
| 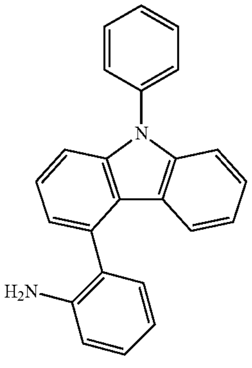 CAS-1850406-35-7 | 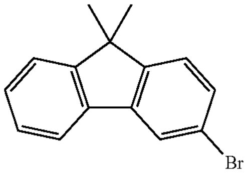 CAS-1190360-23-6 | 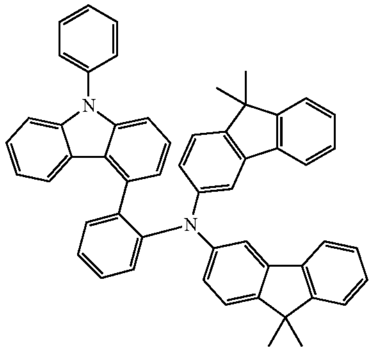 P60 |
| 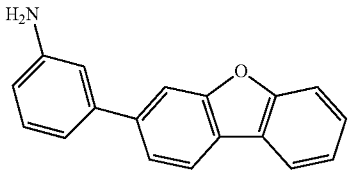 S2 | 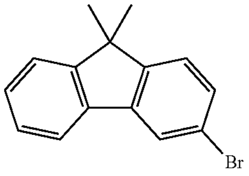 CAS-1190360-23-6 | 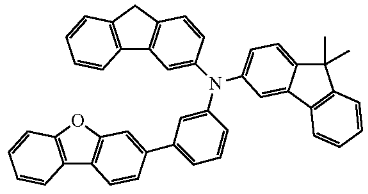 P61 |
| 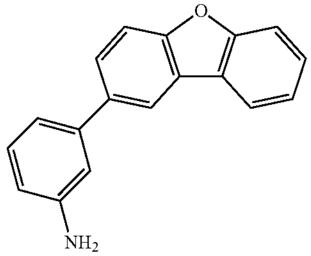 S3 | 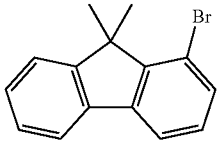 CAS-1225053-54-2 | 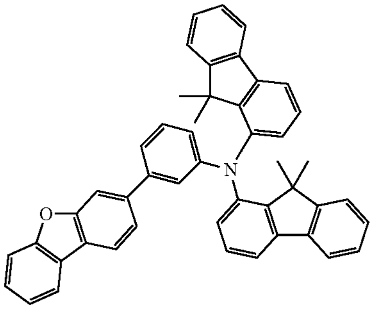 P62 |
| 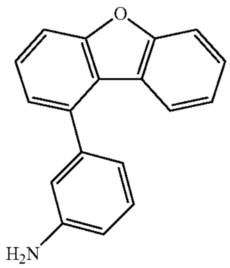 S4 | 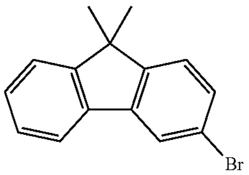 CAS-1190360-23-6 | 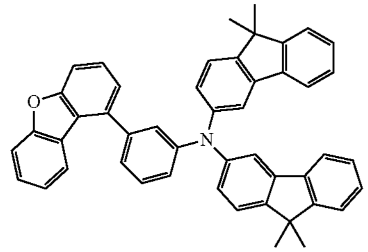 P63 |

-continued
| Reactant 1 | Reactant 2 | Product |
|---|---|---|
| 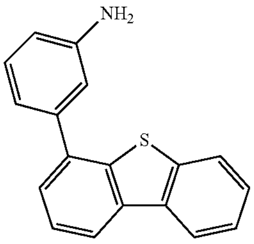 S5 | 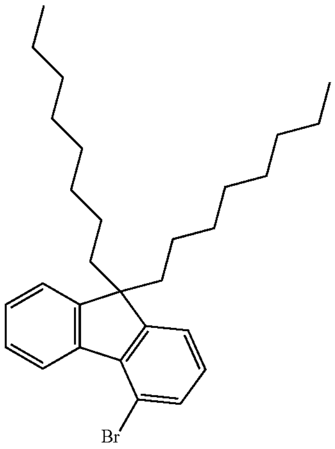 CAS-1609186-23-3 | 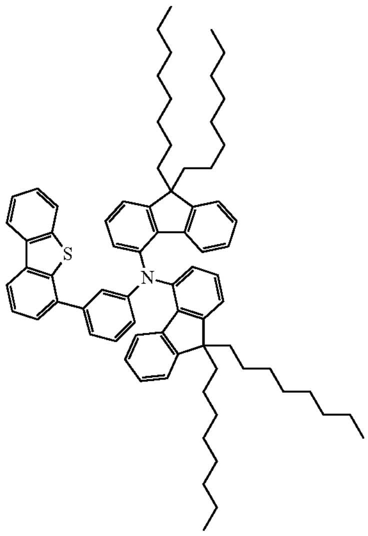 P64 |
| 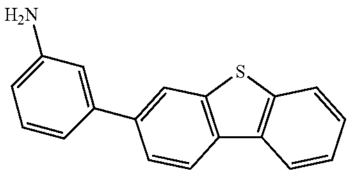 S6 | 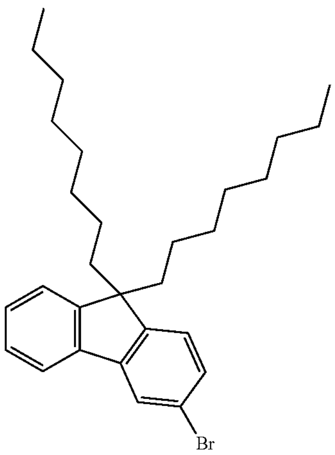 CAS-1609186-23-3 | 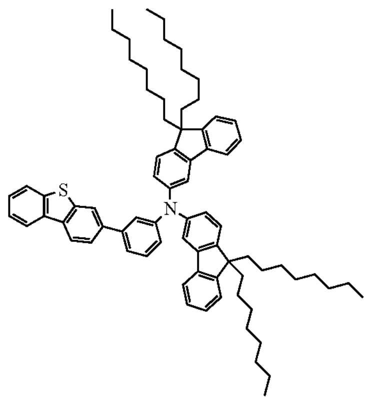 P65 |
| 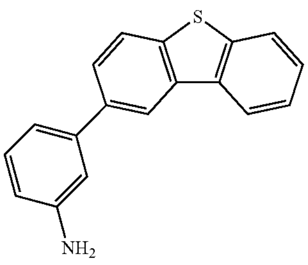 S7 | 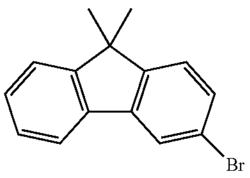 CAS-1190360-23-6 | 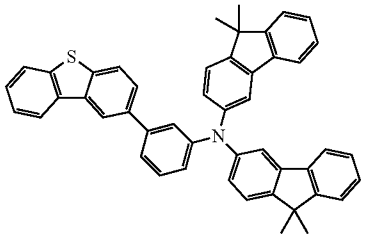 P66 |

-continued
| Reactant 1 | Reactant 2 | Product |
| --- | --- | --- |
| 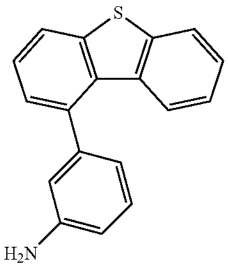 S8 | 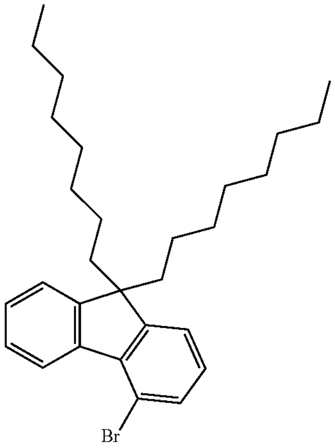 CAS-1469898-60-9 | 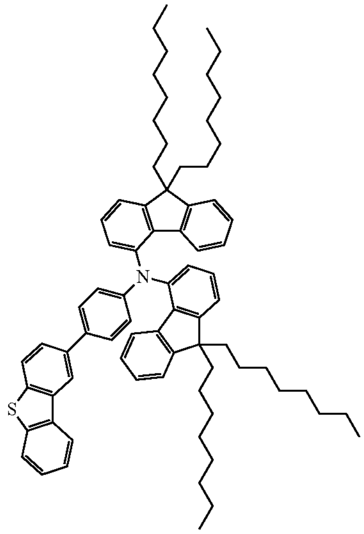 P67 |
| 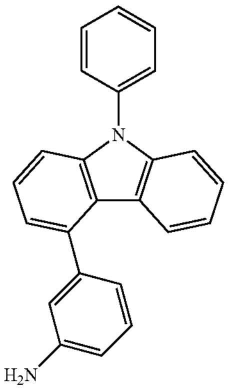 S9 | 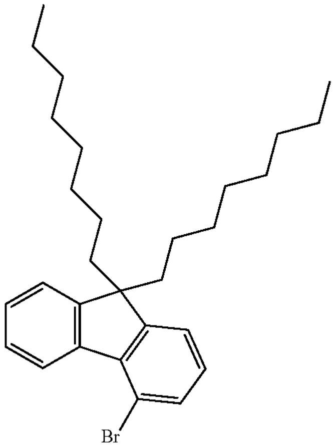 CAS-1469898-60-9 | 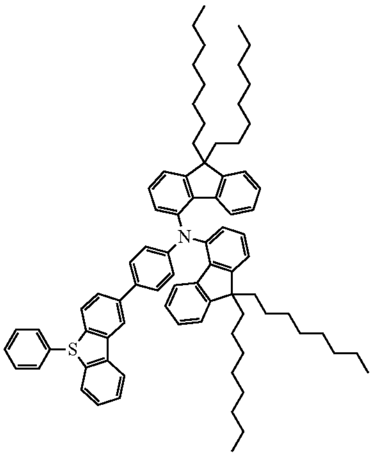 P68 |
| 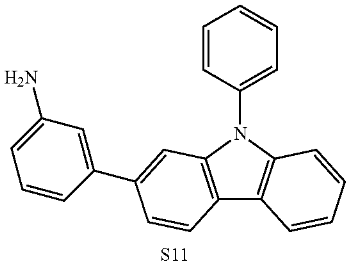 S11 | 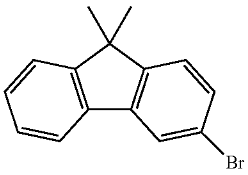 CAS-1190360-23-6 | 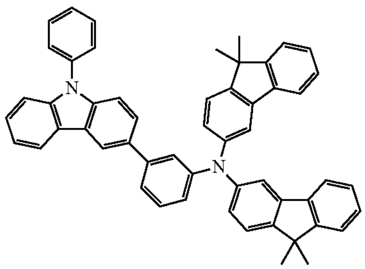 P69 |

-continued
| Reactant 1 | Reactant 2 | Product |
|---|---|---|
| 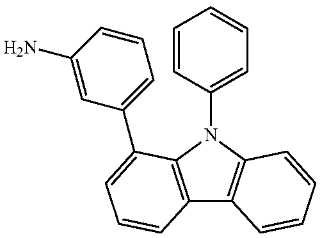 S12 | 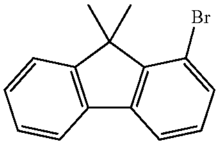 CAS-1225053-54-2 | 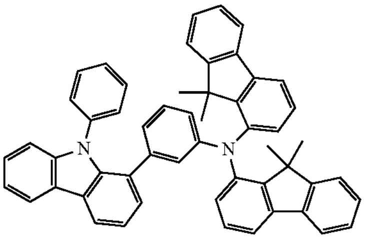 P70 |
| 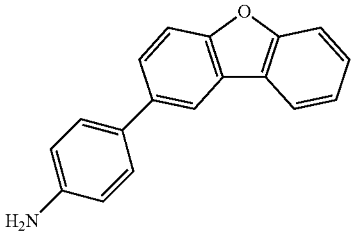 S13 | 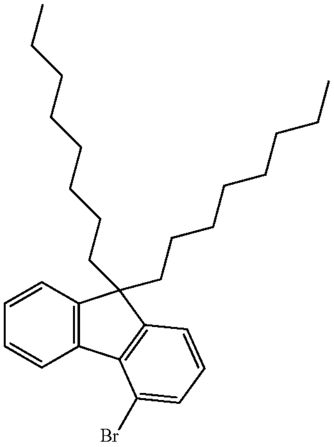 CAS-1469898-60-9 | 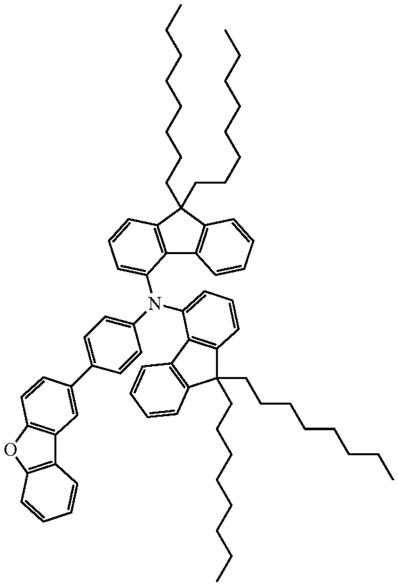 P71 |
| 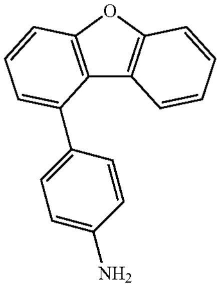 S14 | 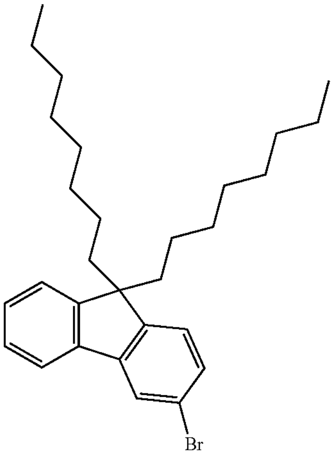 CAS-1609186-23-3 | 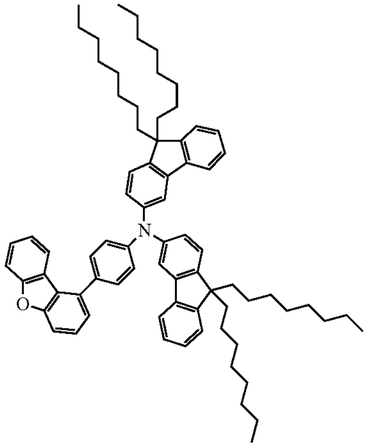 P72 |

-continued
| Reactant 1 | Reactant 2 | Product |
|---|---|---|
| 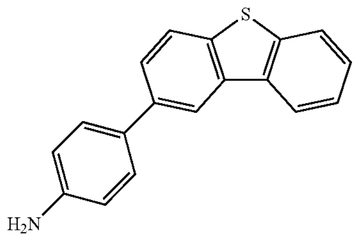 S15 | 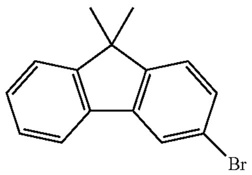 CAS-1190360-23-6 | 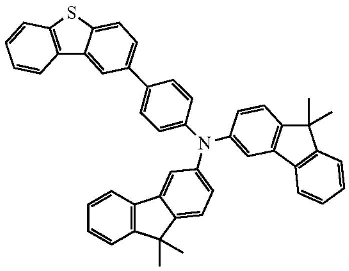 P73 |
| 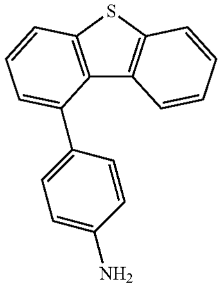 S16 | 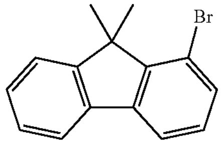 CAS-1225053-54-2 | 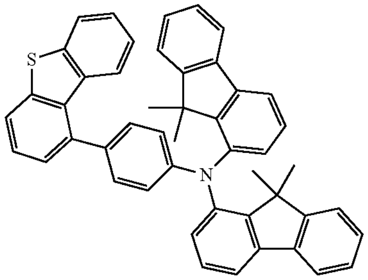 P74 |
| 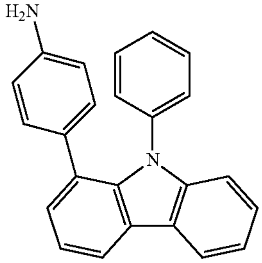 S17 | 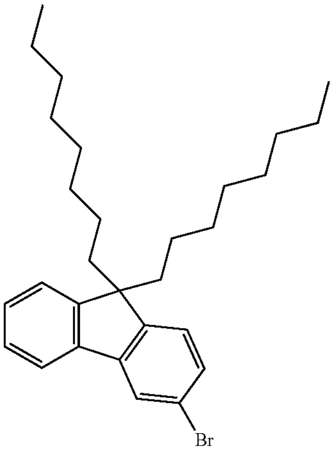 CAS-1609186-23-3 | 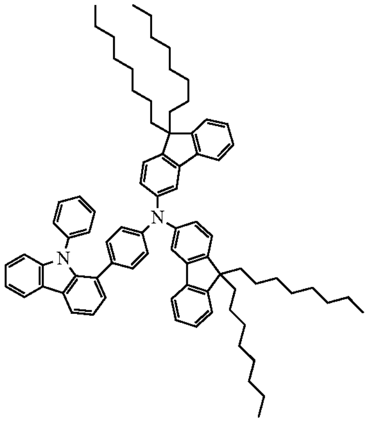 P75 |
| 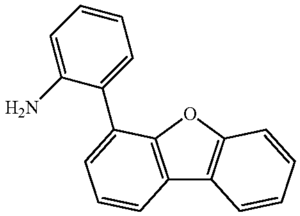 S18 | 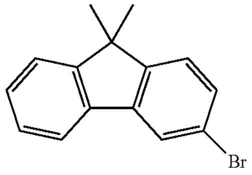 CAS-1190360-23-6 | 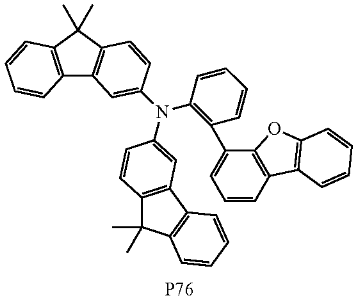 P76 |

-continued
| Reactant 1 | Reactant 2 | Product |
|---|---|---|
| 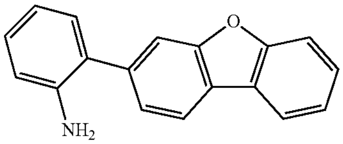 S19 | 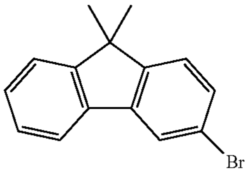 CAS-1190360-23-6 | 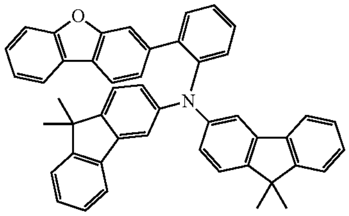 P77 |
| 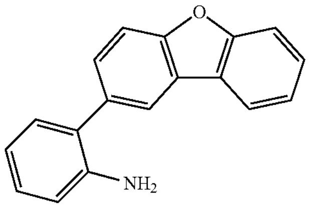 S20 | 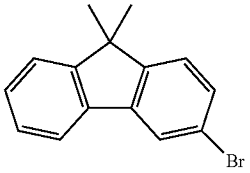 CAS-1190360-23-6 | 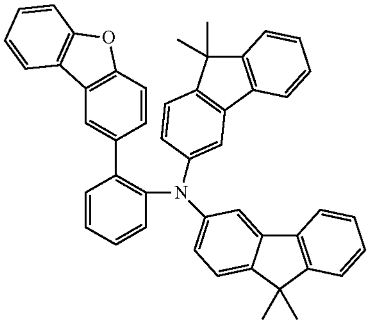 P78 |
| 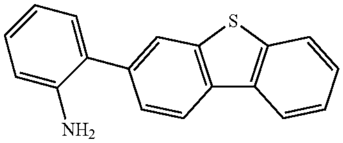 S21 | 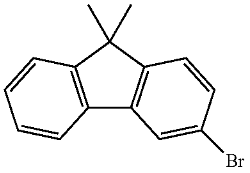 CAS-1190360-23-6 | 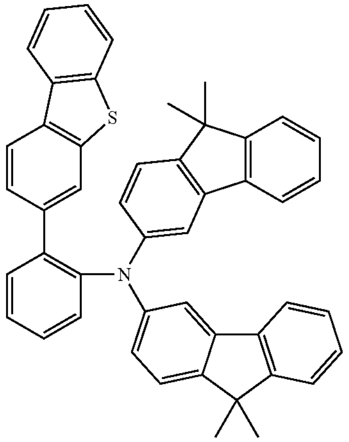 P79 |
| 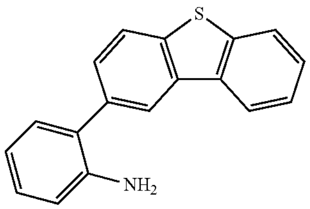 S22 | 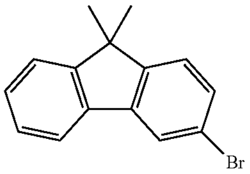 CAS-1190360-23-6 | 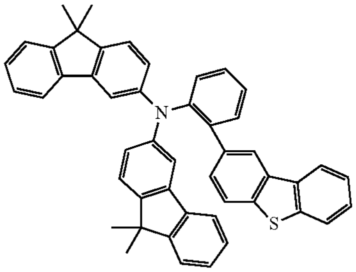 P80 |

-continued
| Reactant 1 | Reactant 2 | Product |
| --- | --- | --- |
| 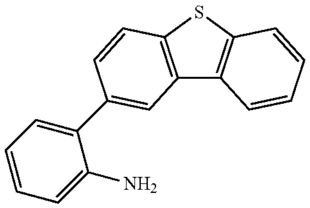 S22 | 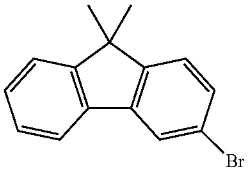 CAS-1190360-23-6 | 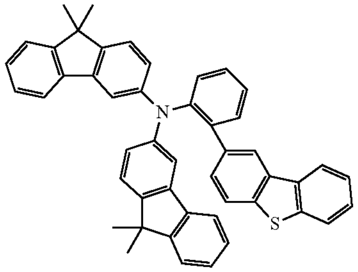 P80 |
| 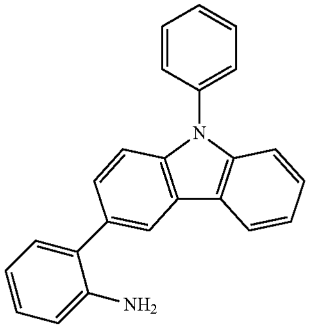 S23 | 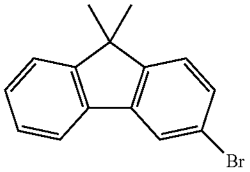 CAS-1190360-23-6 | 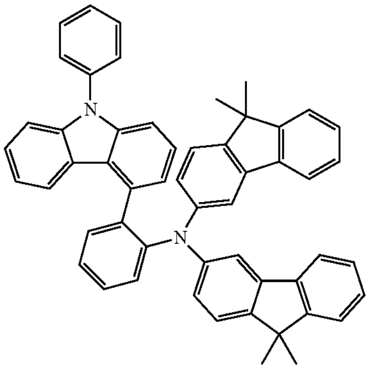 P81 |
| 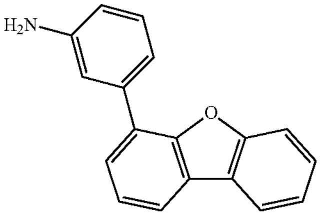 S1 | 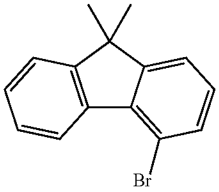 CAS-942615-32-9 | 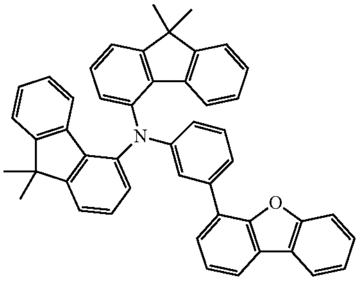 P82 |
| 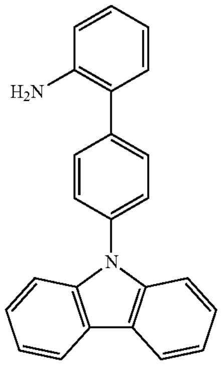 S45 | 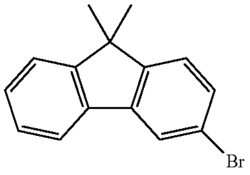 CAS-1190360-23-6 | 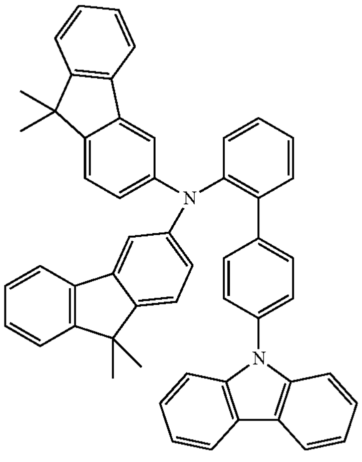 P83 |

-continued
| Reactant 1 | Reactant 2 | Product |
| --- | --- | --- |
| 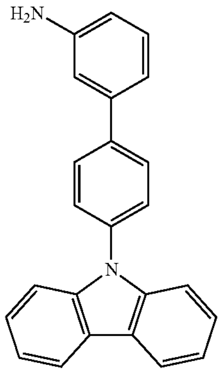 S24 | 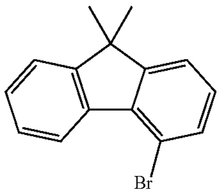 CAS-942615-32 | 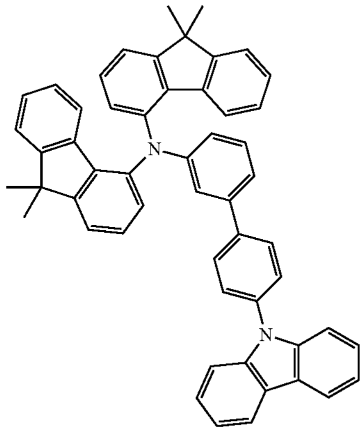 P84 |
| 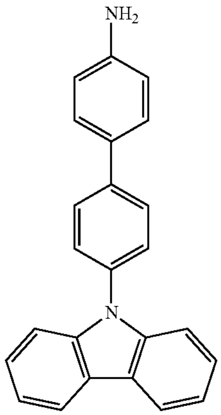 S25 | 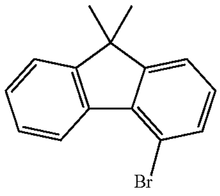 CAS-942615-32 | 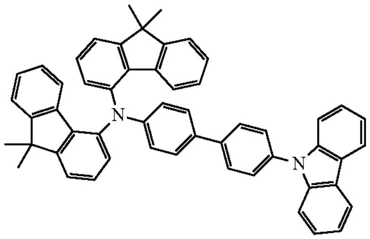 P85 |
| 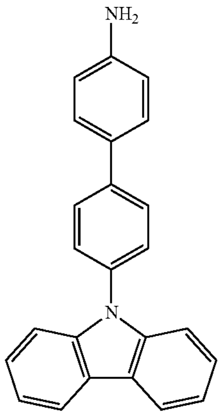 S25 | 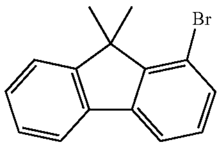 CAS-1225053-54-2 | 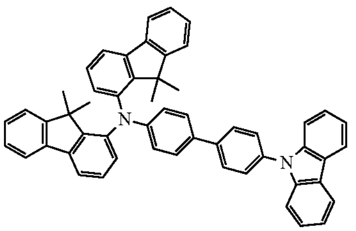 P86 |

-continued
| Reactant 1 | Reactant 2 | Product |
| --- | --- | --- |
| 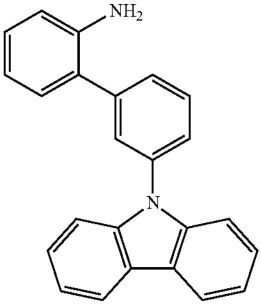 S26 | 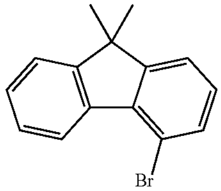 CAS-942615-32 | 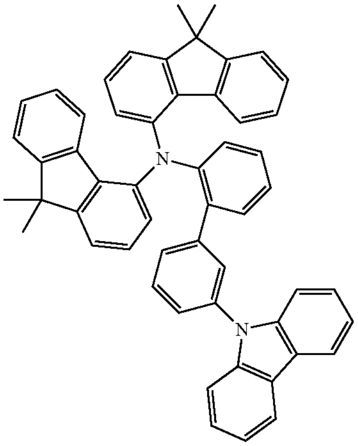 P87 |
| 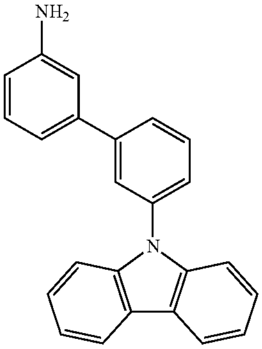 S27 | 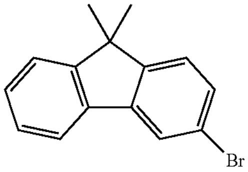 CAS-1190360-23-6 | 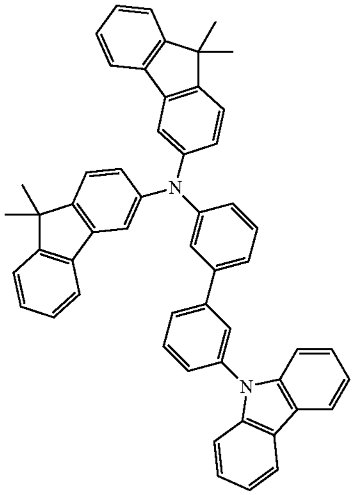 P88 |
| 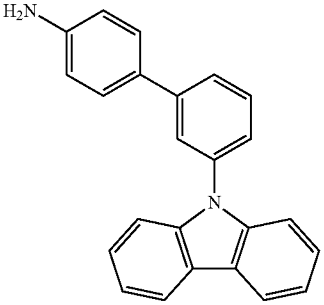 S28 | 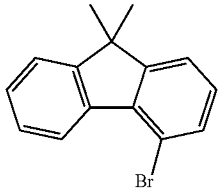 CAS-942615-32 | 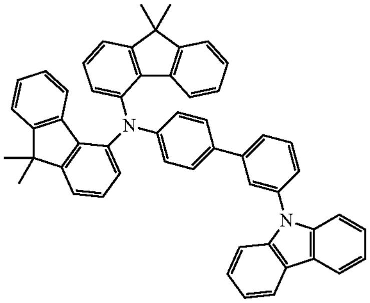 P89 |

-continued
| Reactant 1 | Reactant 2 | Product |
|---|---|---|
| 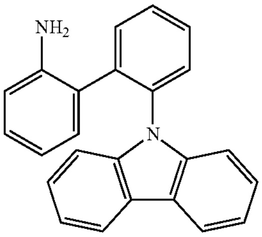 S29 | 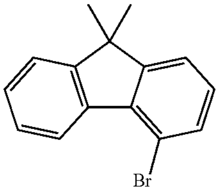 CAS-942615-32 | 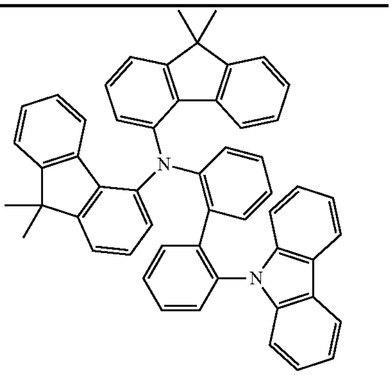 P90 |
| 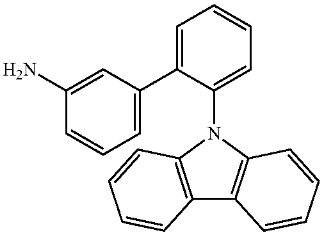 S30 | 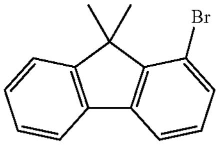 CAS-1225053-54-2 | 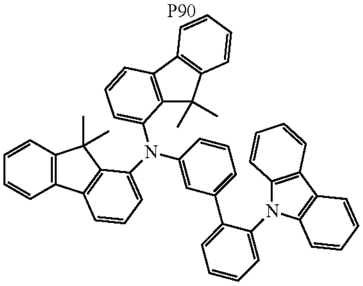 P91 |
| 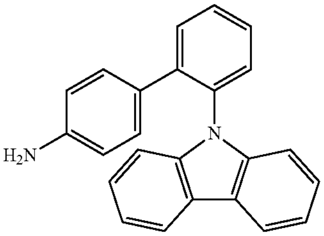 S31 | 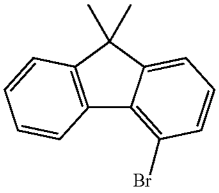 CAS-942615-32 | 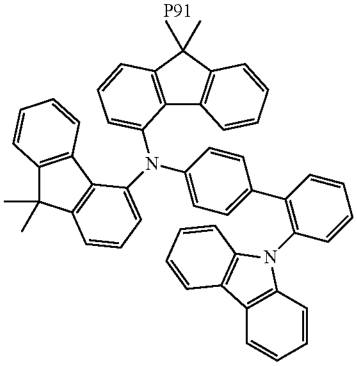 P92 |
| 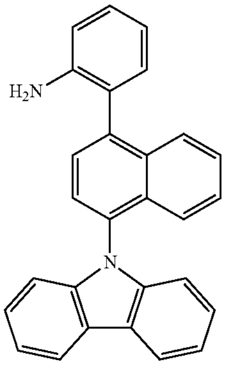 S32 | 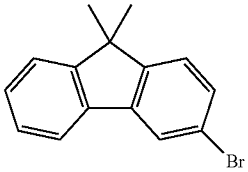 CAS-1190360-23-6 | 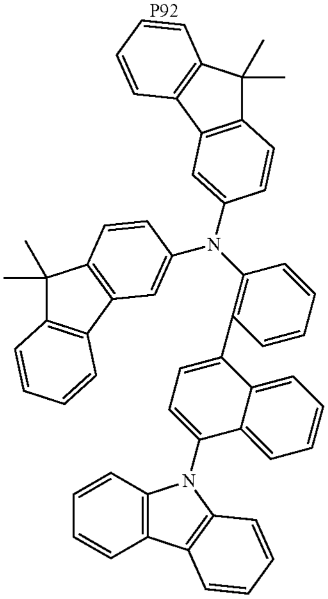 P93 |

-continued
| Reactant 1 | Reactant 2 | Product |
|---|---|---|
| 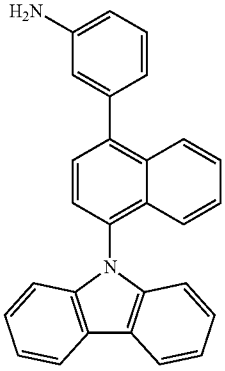 S33 | 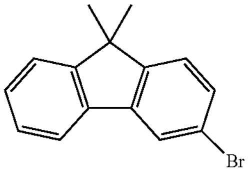 CAS-1190360-23-6 | 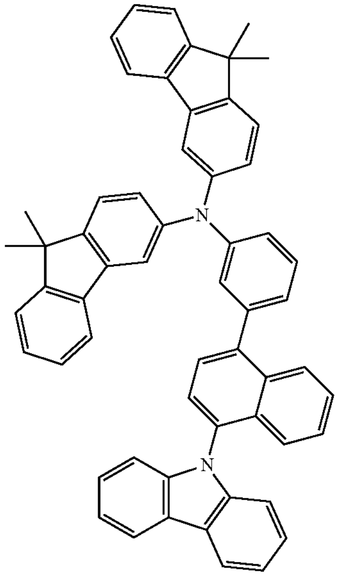 P94 |
| 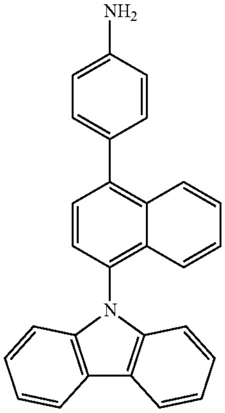 S34 | 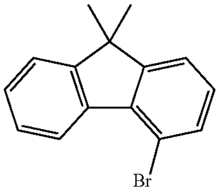 CAS-942615-32 | 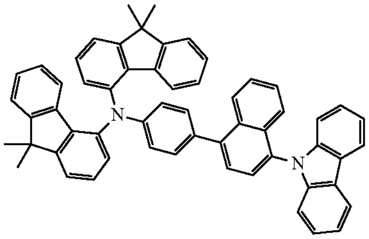 P95 |
| 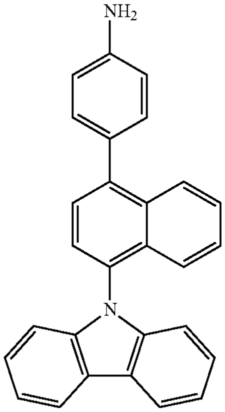 S34 | 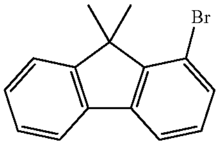 CAS-1225053-54-2 | 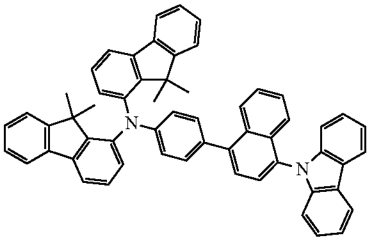 P96 |

-continued
| Reactant 1 | Reactant 2 | Product |
| --- | --- | --- |
| 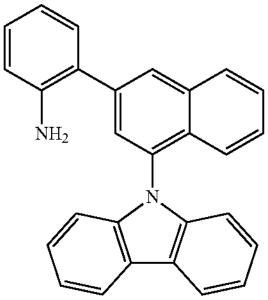 S35 | 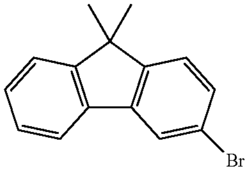 CAS-1190360-23-6 | 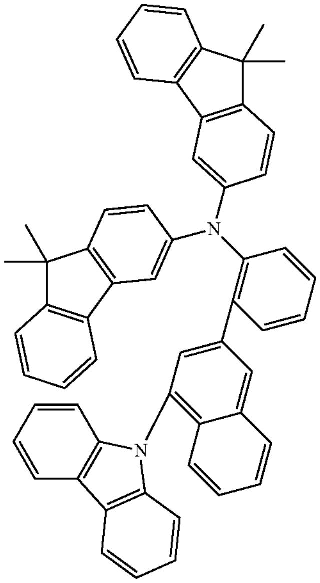 P97 |
| 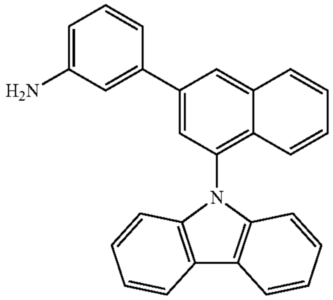 S36 | 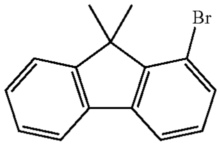 CAS-1225053-54-2 | 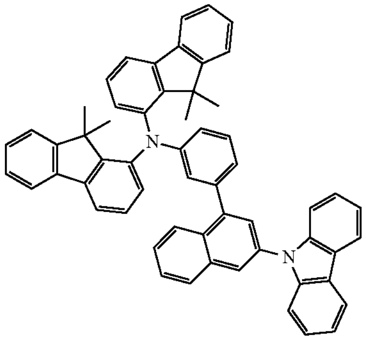 P98 |
| 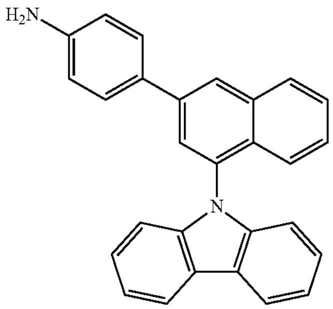 S37 | 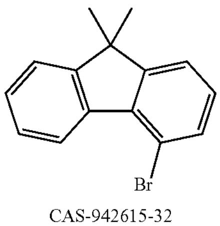 [SMILES: CC1(C)c2ccccc2-c2c(Br)cccc21] CAS-942615-32 | 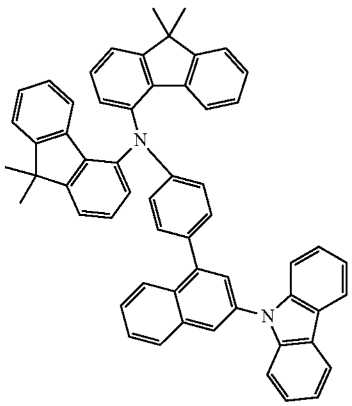 P99 |

-continued
| Reactant 1 | Reactant 2 | Product |
| --- | --- | --- |
| 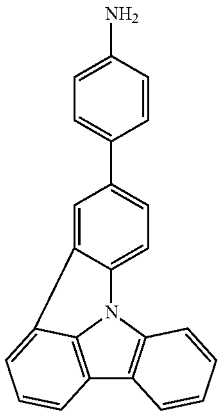 S38 | 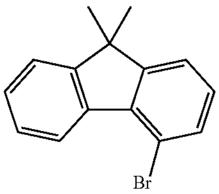 CAS-942615-32 | 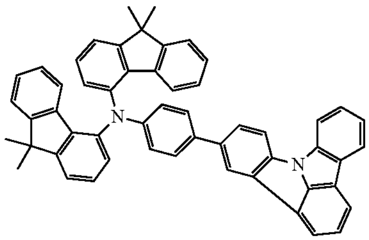 P100 |
| 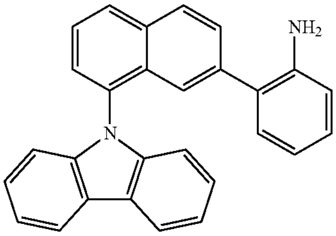 S39 | 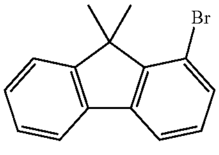 CAS-1225053-54-2 | 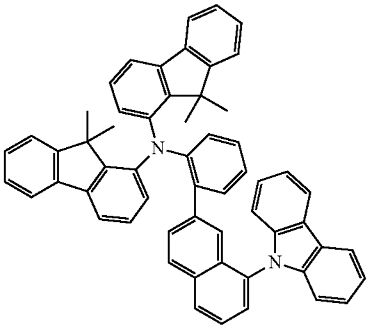 P101 |
| 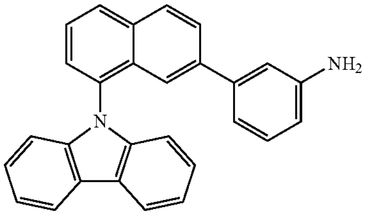 S40 | 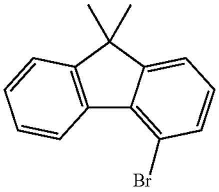 CAS-942615-32 | 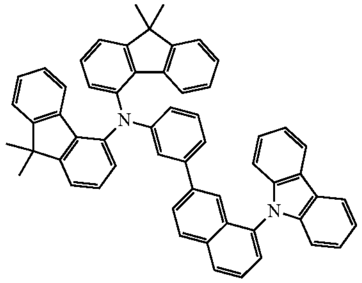 P102 |
| 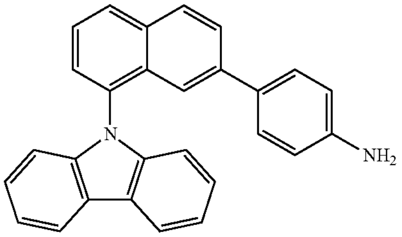 S41 | 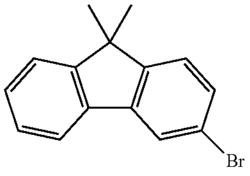 CAS-1190360-23-6 | 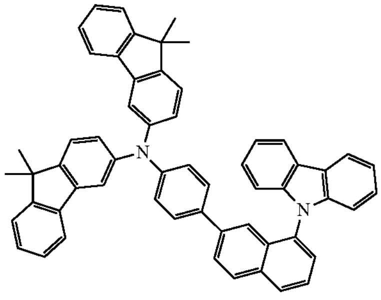 P103 |

-continued
| Reactant 1 | Reactant 2 | Product |
| --- | --- | --- |
| 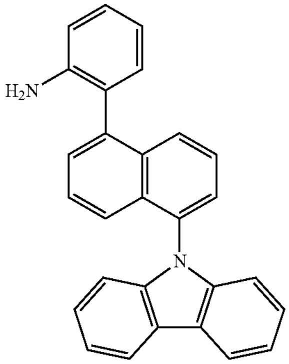 S42 | 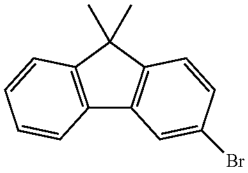 CAS-1190360-23-6 | 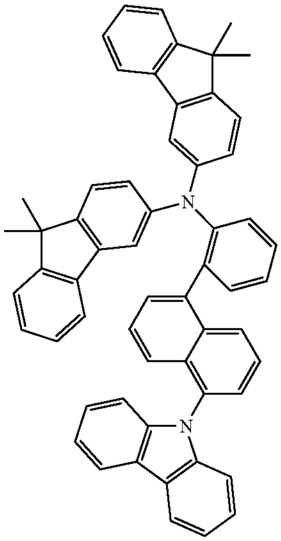 P104 |
| 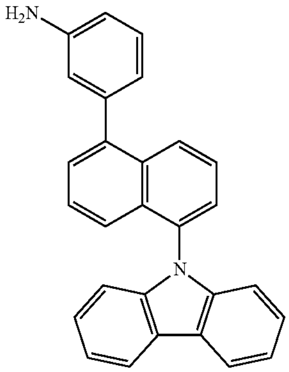 S43 | 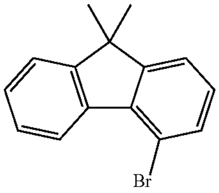 CAS-942615-32 | 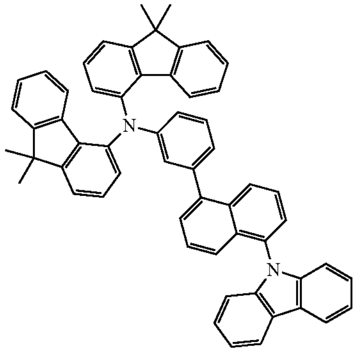 P105 |
| 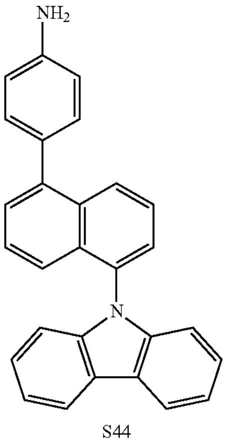 S44 | 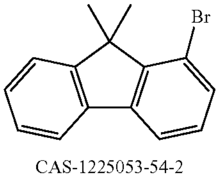 [SMILES: CC1(C)c2ccccc2-c2cccc(Br)c21] CAS-1225053-54-2 | 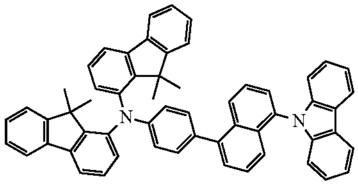 P106 |

-continued
| Reactant 1 | Reactant 2 | Product |
| --- | --- | --- |
| 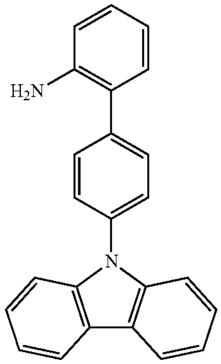 S45 | 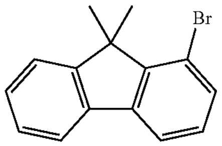 CAS-1225053-54-2 | 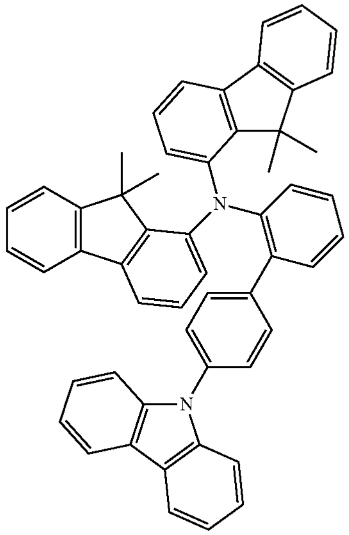 P107 |
| 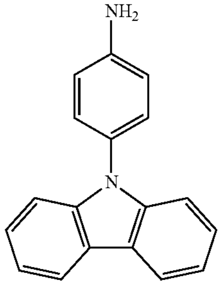 CAS-52708-37-9 | 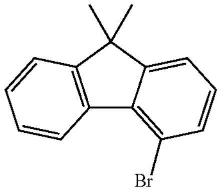 CAS-942615-32 | 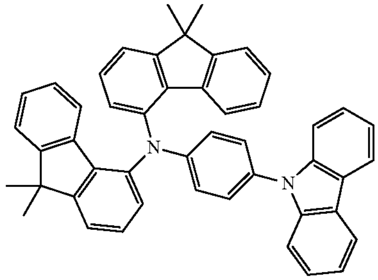 P108 |
| 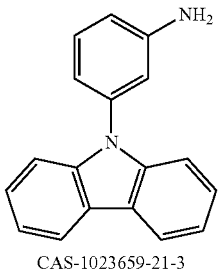 CAS-1023659-21-3 | 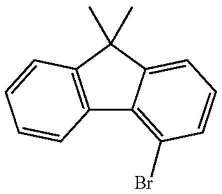 CAS-942615-32 | 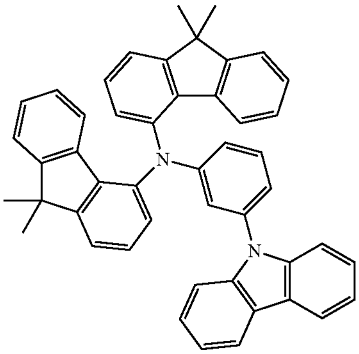 P109 |

-continued
| Reactant 1 | Reactant 2 | Product |
|---|---|---|
| 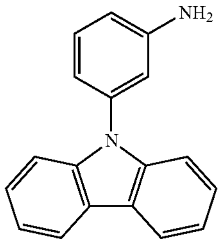 CAS-1023659-21-3 | 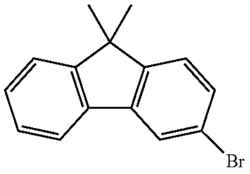 CAS-1190360-23-6 | 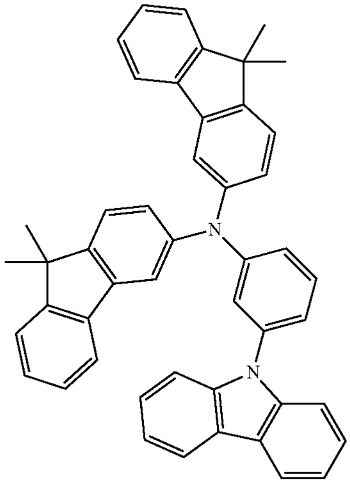 P110 |
| 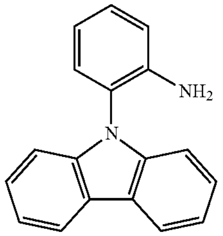 CAS-101716-43-2 | 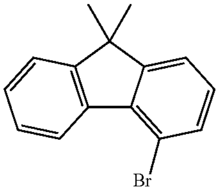 CAS-942615-32 | 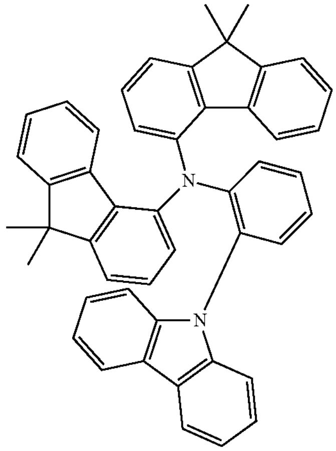 P111 |
| 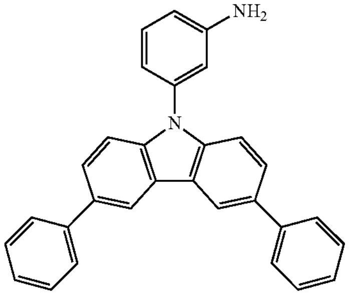 CAS-1708110-65-9 | 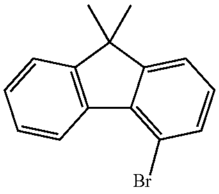 CAS-942615-32 | 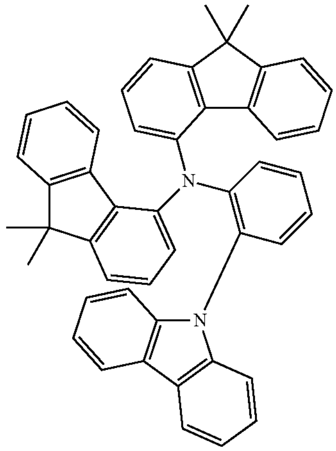 P112 |

-continued

| Reactant 1 | Reactant 2 | Product |
| --- | --- | --- |
| 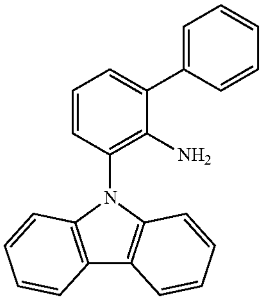 CAS-1673542-71-6 | 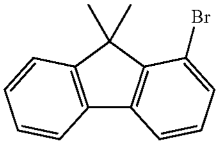 CAS-1225053-54-2 | 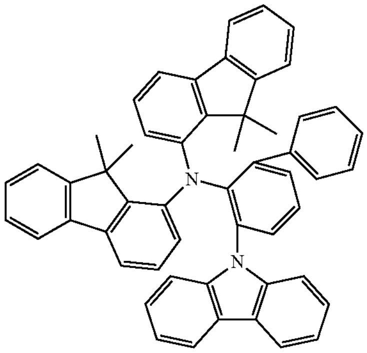 P113 |

P200

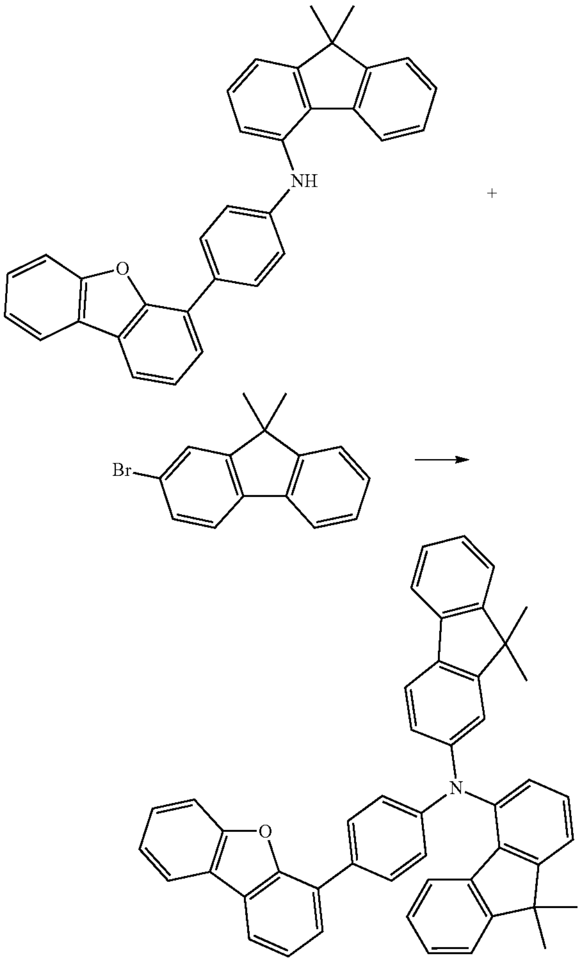

N-(4-(Dibenzo[b,d]furan-4-yl)phenyl)-9,9-dimethyl-9H-fluoren-4-amine [CAS-1933454-49-9] (20.4 g; 45.27 mmol), 2-bromo-9,9-dimethyl-9H-fluorene [CAS-28320-31-2] (14.1 g; 50.0 mmol) and sodium tert-butoxide (6.78 g; 70.55 mmol) are initially charged in toluene (350 ml) and saturated with argon for 45 min. Thereafter, tris(dibenzylideneacetone)dipalladium(0) [CAS-51364-51-3] (831 mg; 0.91 mmol) and S-Phos [CAS-657408-07-6](745 mg; 1.91 mmol) are introduced and the reaction mixture is stirred under reflux for 16 h. After this mixture has been cooled, it is extended with water (300 ml) and worked up by extraction in a separating funnel. The organic phase is washed 2× with water (300 ml each time), dried over $Na_2SO_4$ and concentrated to dryness. The crude product is subjected to basic hot extraction twice with toluene/n-heptane over aluminium oxide, then recrystallized twice from n-butanol and finally sublimed under high vacuum. Yield: 13.6 g (19.6 mmol), 43%; purity: >99.9% by HPLC.

P201

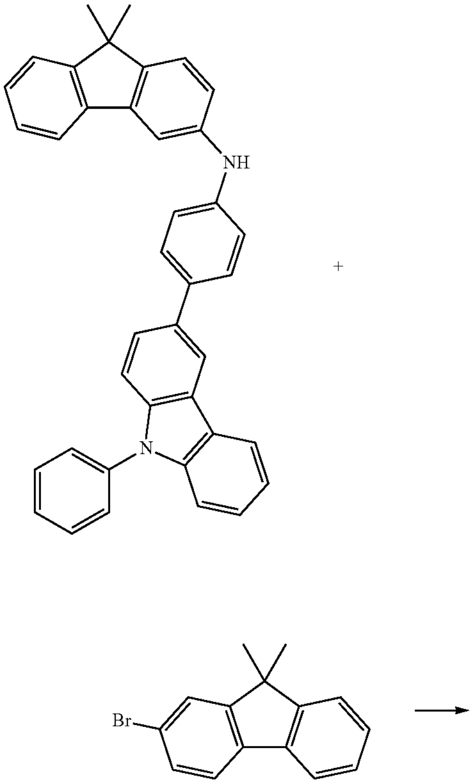

-continued

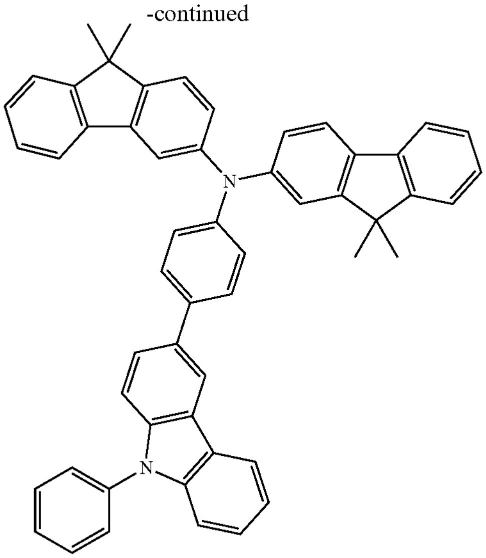

Procedure analogous to the experimental description for P200, except that 9,9-dimethyl-N-[4-(9-phenylcarbazol-3-yl)phenyl]fluoren-3-amine [CAS-2110513-13-6] is used rather than N-(4-(dibenzo[b,d]furan-4-yl)phenyl)-9,9-dimethyl-9H-fluoren-4-amine. The crude product is subjected to basic hot extraction twice with toluene/n-heptane over aluminium oxide, then recrystallized twice from ethyl acetate and finally sublimed under high vacuum. Yield: 12.4 g (17.2 mmol), 38%; purity: >99.9% by HPLC.

P202

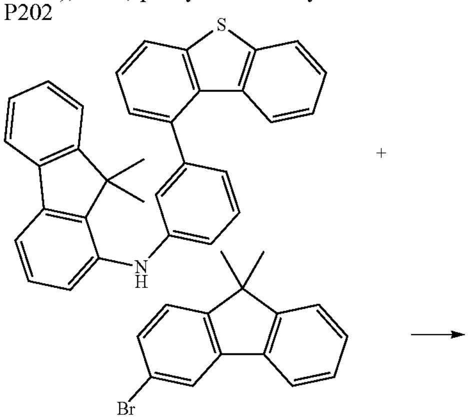

-continued

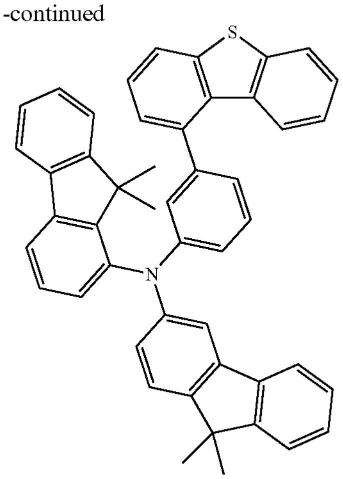

Procedure analogous to the experimental description for P200, except that S102 is used rather than N-(4-(dibenzo[b,d]furan-4-yl)phenyl)-9,9-dimethyl-9H-fluoren-4-amine and 3-bromo-9,9-dimethyl-9H-fluorene [CAS-1190360-23-6] rather than 2-bromo-9,9-dimethyl-9H-fluorene. The crude product is subjected to basic hot extraction twice with toluene/n-heptane over aluminium oxide, then recrystallized twice from n-butyl acetate and finally sublimed under high vacuum. Yield: 14.1 g (21.3 mmol), 47%; purity: >99.9% by HPLC.

In an analogous manner, it is possible to prepare the following compounds: In this case, the catalyst system used may also be palladium(II) acetate [3375-31-3] (0.02 equiv.) and 1.0 M tri-tert-butylphosphine solution in toluene [13716-12-6] (0.05 equiv.) rather than tris(dibenzylideneacetone)dipalladium(0) [CAS-51364-51-3] and S-Phos [CAS-657408-07-6]. In this case, purification can also be effected using column chromatography, or recrystallization or hot extraction using other standard solvents such as ethanol, butanol, acetone, ethyl acetate, acetonitrile, toluene, xylene, dichloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone etc. The yields are typically in the range between 15% and 75%.

| Reactant 1 | Reactant 2 | Product |
|---|---|---|
| 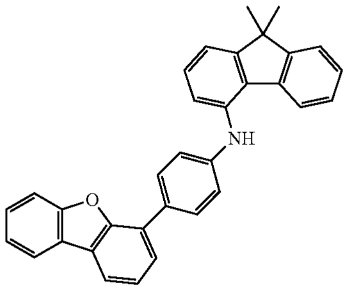 CAS-1933454-49-9 | 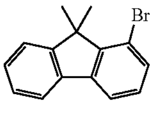 CAS-1225053-54-2 | 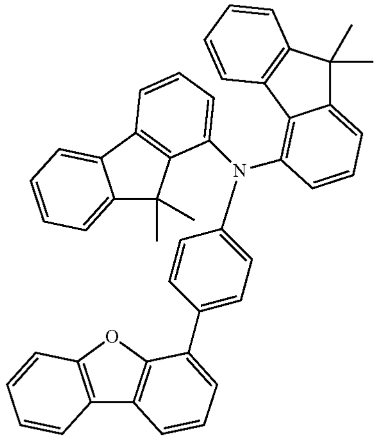 P203 |

-continued
| Reactant 1 | Reactant 2 | Product |
|---|---|---|
| 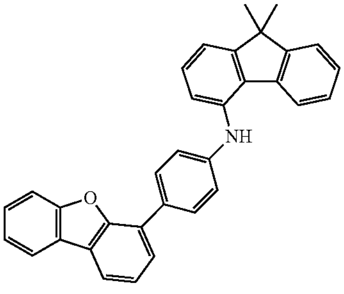 CAS-1933454-49-9 | 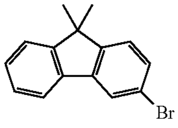 CAS-1190360-23-6 | 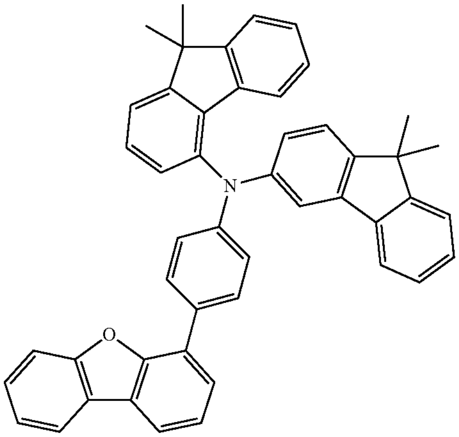 P204 |
| 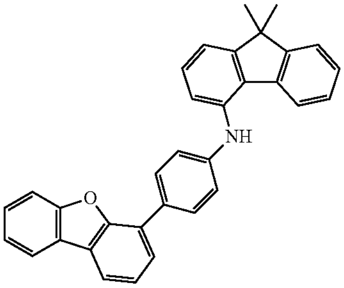 CAS-1933454-49-9 | 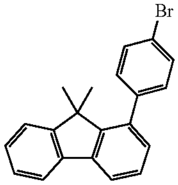 CAS-1786416-87-2 | 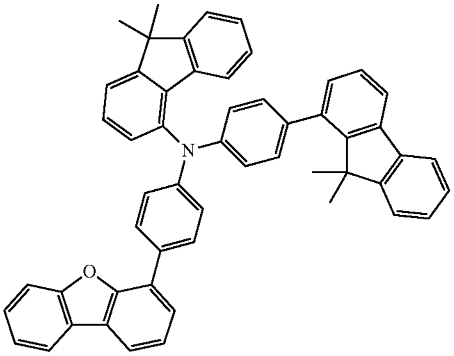 P205 |
| 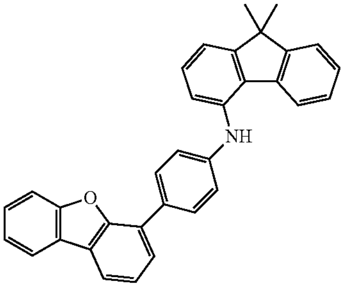 CAS-1933454-49-9 | 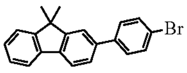 CAS-574750-94-0 | 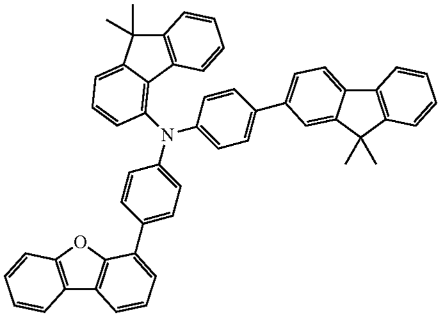 P206 |

-continued
| Reactant 1 | Reactant 2 | Product |
| --- | --- | --- |
| 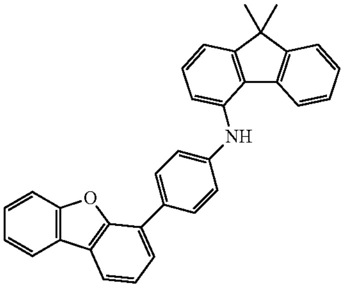 CAS-1933454-49-9 | 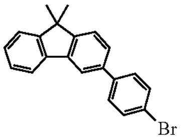 CAS-1421789-06-1 | 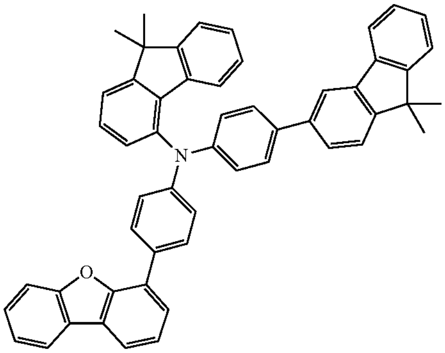 P207 |
| 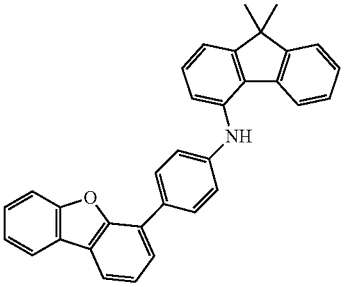 CAS-1933454-49-9 | 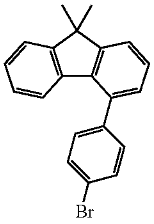 CAS-1860896-38-3 | 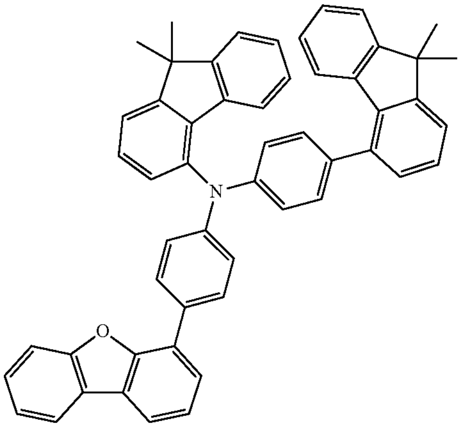 P208 |
| 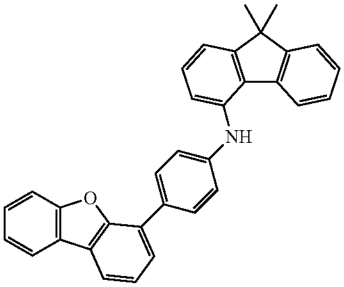 CAS-1933454-49-9 | 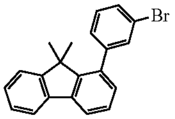 CAS-2035081-41-3 | 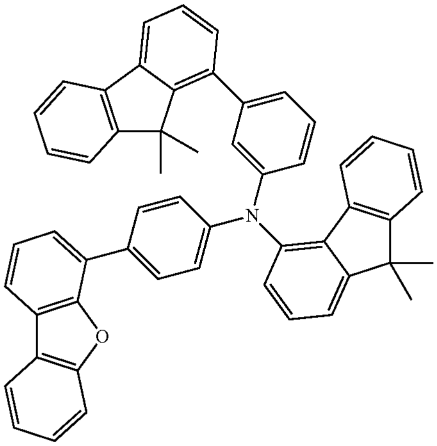 P209 |

-continued
| Reactant 1 | Reactant 2 | Product |
| --- | --- | --- |
| 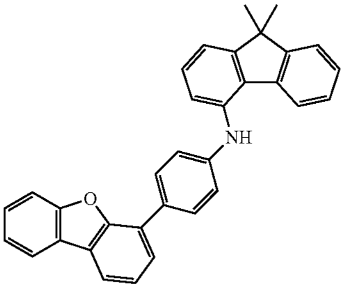 CAS-1933454-49-9 | 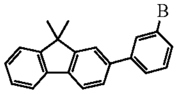 CAS-881912-14-7 | 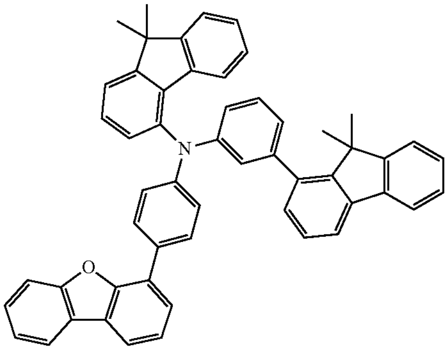 P210 |
| 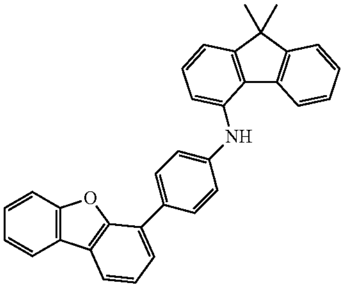 CAS-1933454-49-9 | 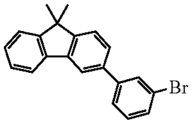 CAS-1417161-08-0 | 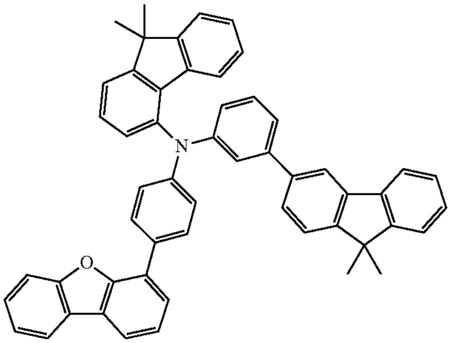 P211 |
| 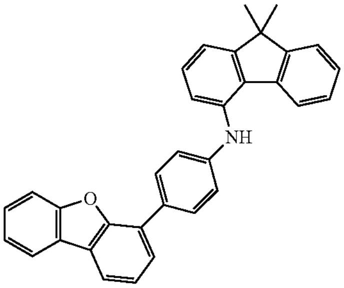 CAS-1933454-49-9 | 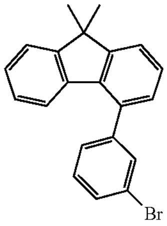 CAS-1860896-40-7 | 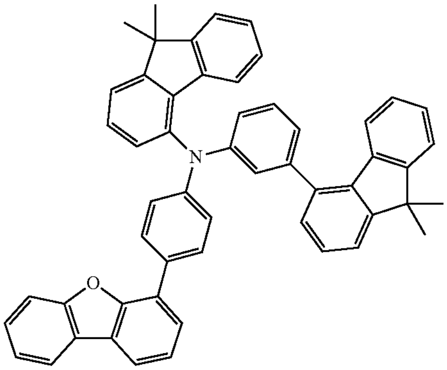 P213 |

-continued
| Reactant 1 | Reactant 2 | Product |
|---|---|---|
| 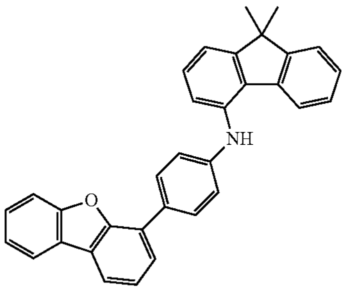 CAS-1933454-49-9 | 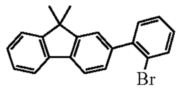 CAS-881912-12-5 | 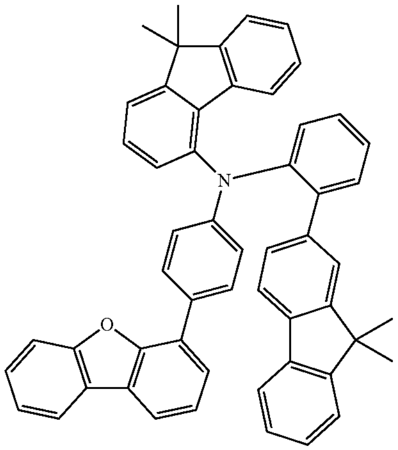 P214 |
| 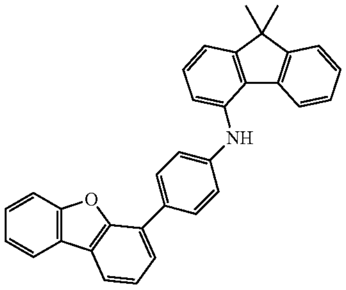 CAS-1933454-49-9 | 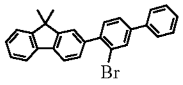 CAS-881912-16-9 | 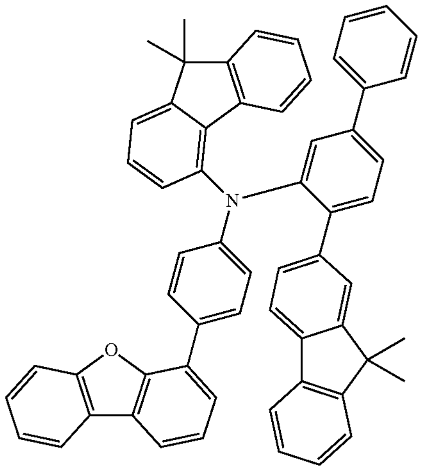 P215 |
| 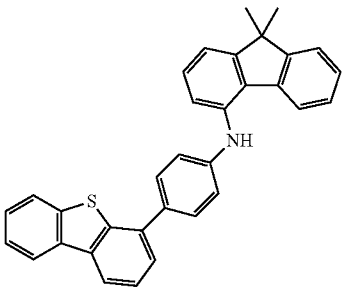 CAS-2089116-67-4 | 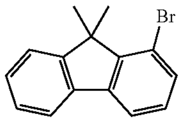 CAS-1225053-54-2 | 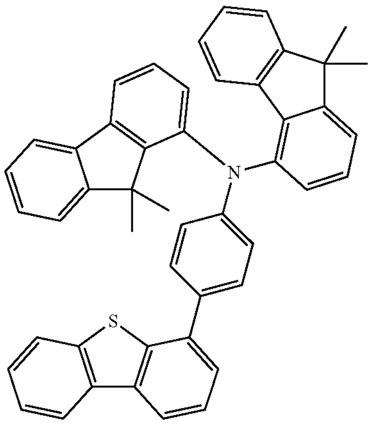 P216 |

-continued
| Reactant 1 | Reactant 2 | Product |
|---|---|---|
| 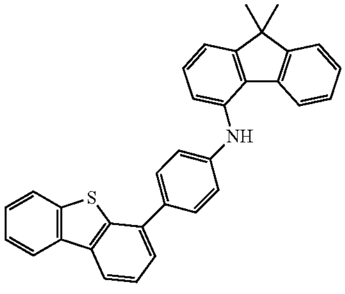<br>CAS-2089116-67-4 | 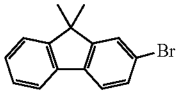<br>CAS-28320-31-2 | 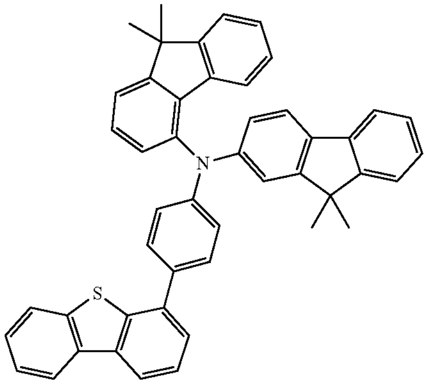<br>P217 |
| 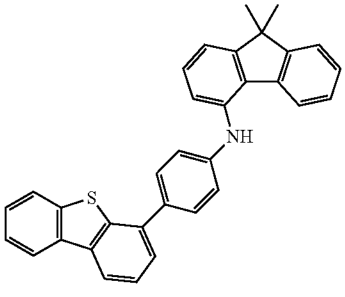<br>CAS-2089116-67-4 | 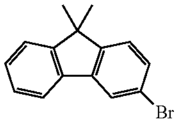<br>CAS-1190360-23-6 | 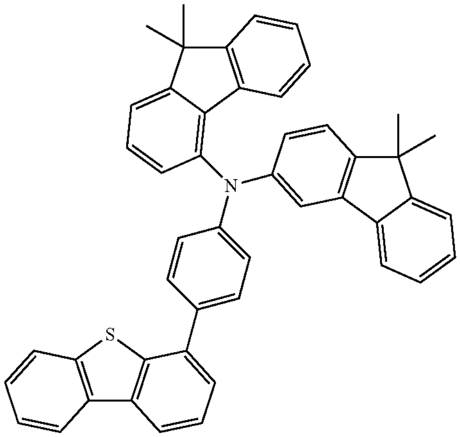<br>P218 |
| 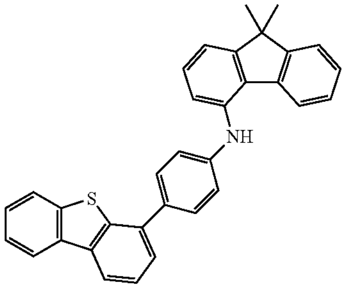<br>CAS-2089116-67-4 | 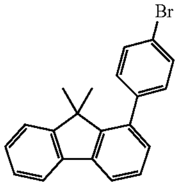<br>CAS-1786416-87-2 | 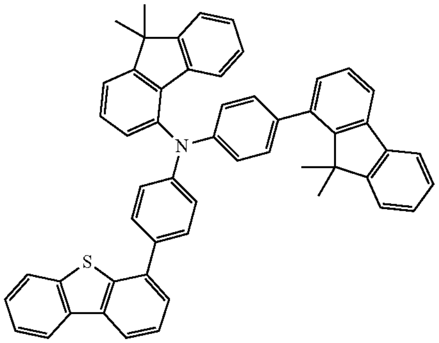<br>P219 |
| 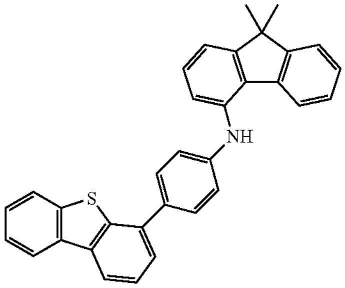<br>CAS-2089116-67-4 | 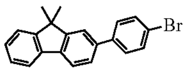<br>CAS-574750-94-0 | 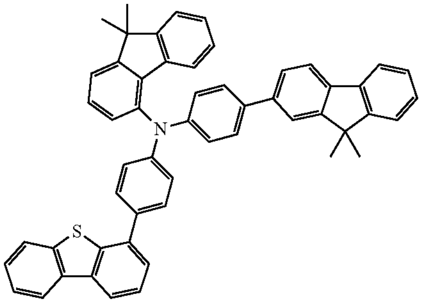<br>P220 |

-continued
| Reactant 1 | Reactant 2 | Product |
| --- | --- | --- |
| 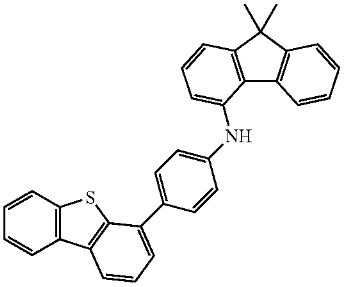 CAS-2089116-67-4 | 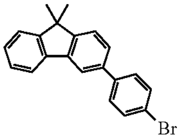 CAS-1421789-06-1 | 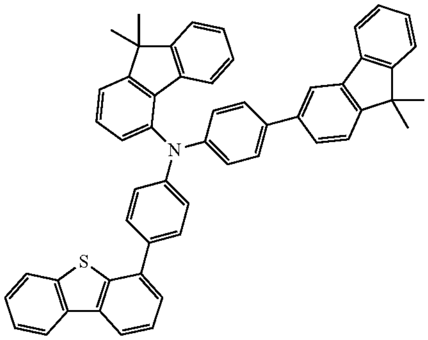 P221 |
| 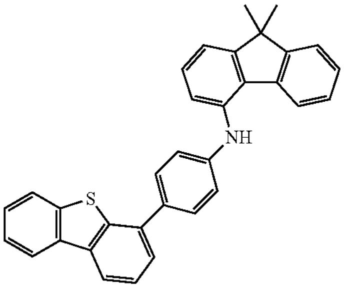 CAS-2089116-67-4 | 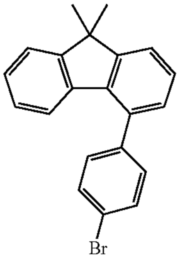 CAS-1860896-38-3 | 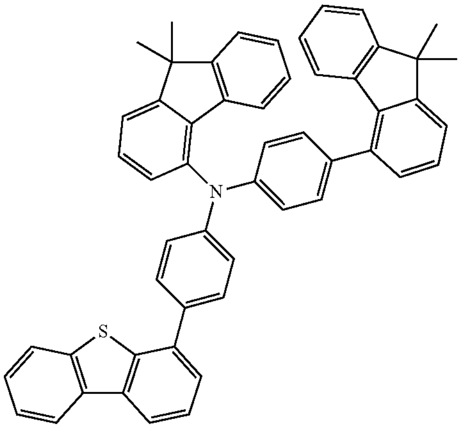 P222 |
| 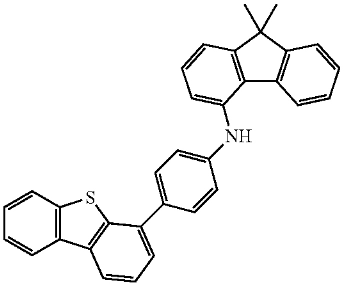 CAS-2089116-67-4 | 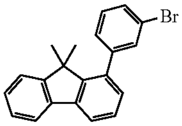 CAS-2035081-41-3 | 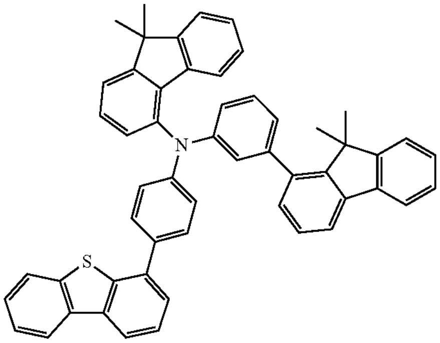 P223 |

-continued
| Reactant 1 | Reactant 2 | Product |
|---|---|---|
| 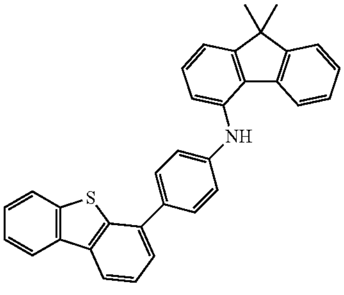 CAS-2089116-67-4 | 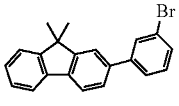 CAS-881912-14-7 | 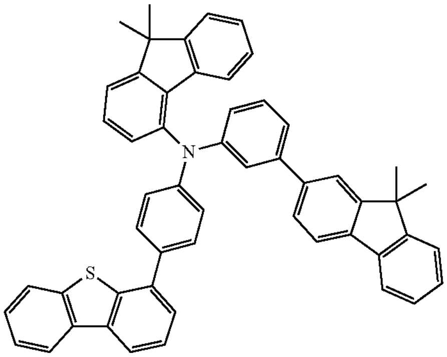 P224 |
| 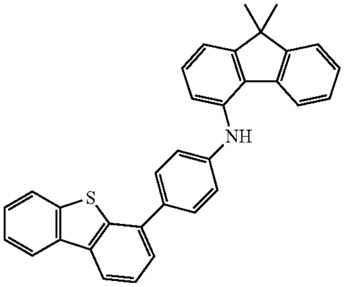 CAS-2089116-67-4 | 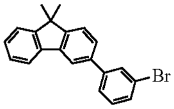 CAS-1417161-08-0 | 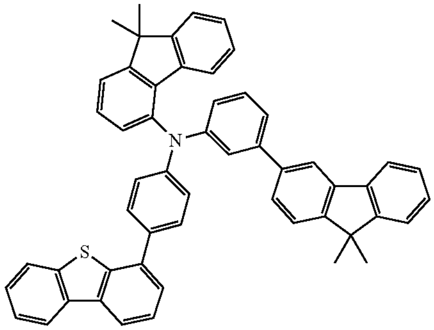 P225 |
| 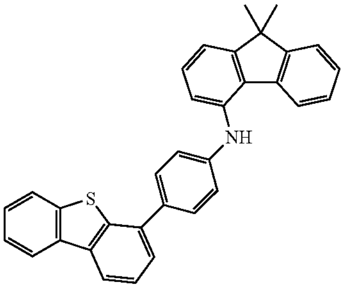 CAS-2089116-67-4 | 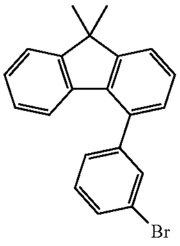 CAS-1860896-40-7 | 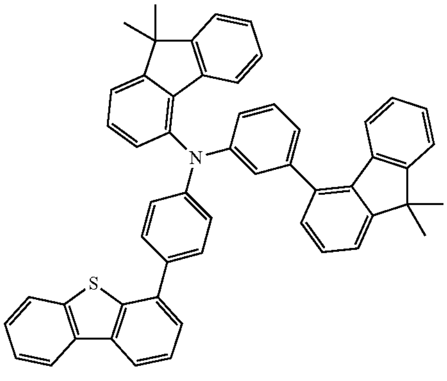 P226 |

-continued
| Reactant 1 | Reactant 2 | Product |
| --- | --- | --- |
| 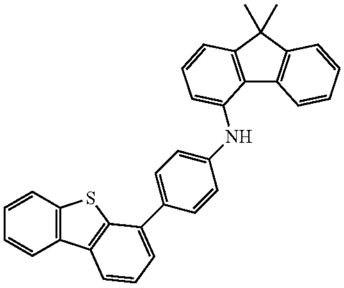<br>CAS-2089116-67-4 | 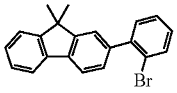<br>CAS-881912-12-5 | 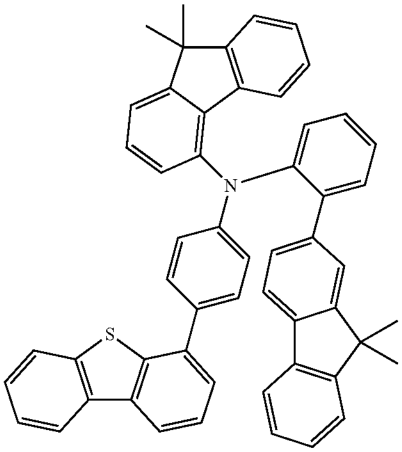<br>P227 |
| 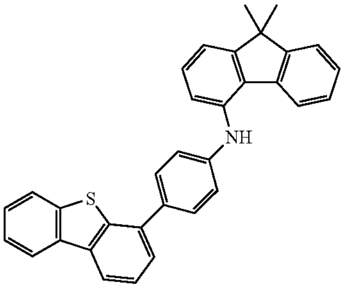<br>CAS-2089116-67-4 | 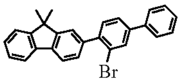<br>CAS-8819112-16-9 | 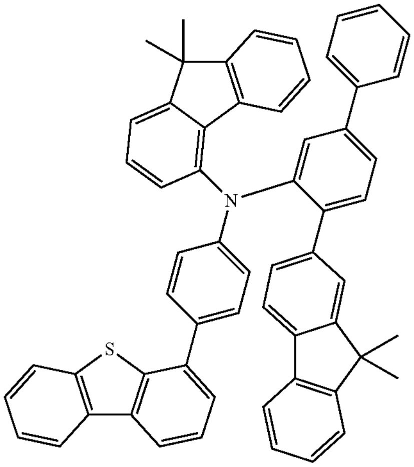<br>P228 |
| 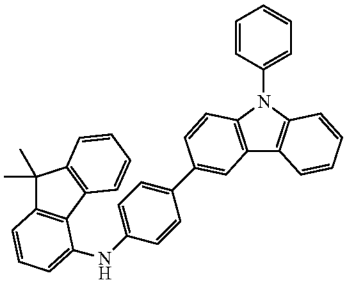<br>S100 | 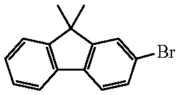<br>CAS-28320-31-2 | 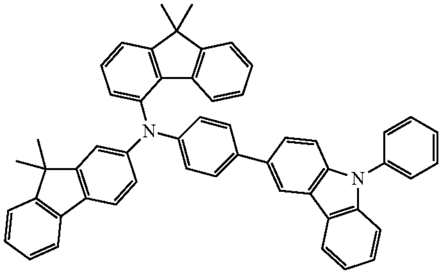<br>P229 |

-continued
| Reactant 1 | Reactant 2 | Product |
| --- | --- | --- |
| 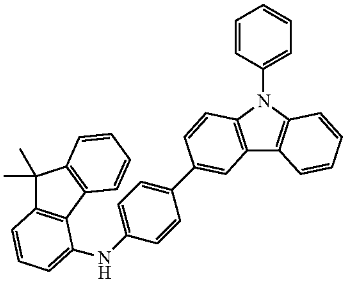 S100 | 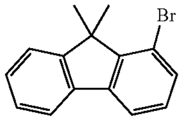 CAS-1225053-54-2 | 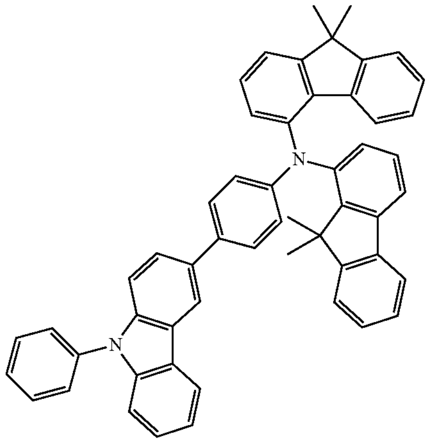 P230 |
| 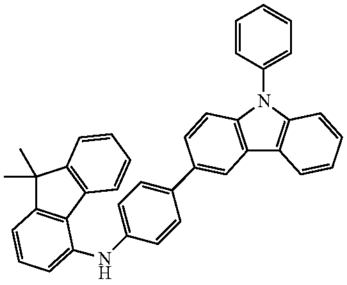 S100 | 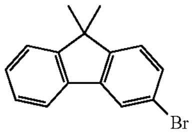 CAS-1190360-23-6 | 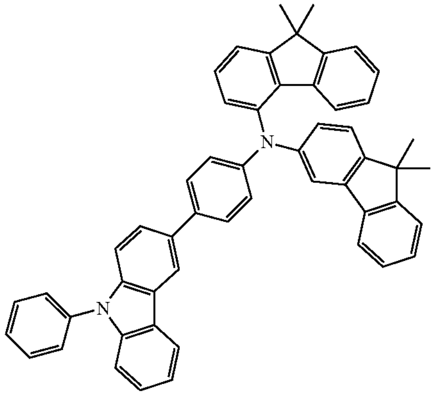 P231 |
| 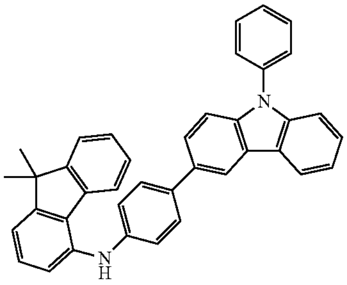 S100 | 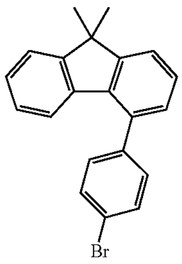 CAS-1860896-38-3 | 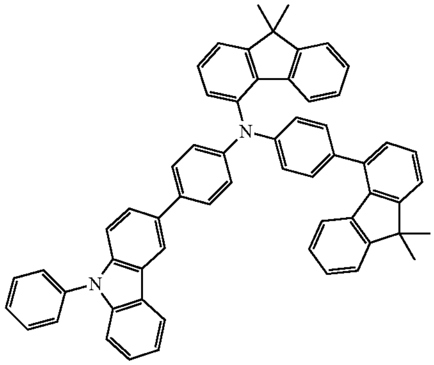 P232 |

-continued
| Reactant 1 | Reactant 2 | Product |
| --- | --- | --- |
| 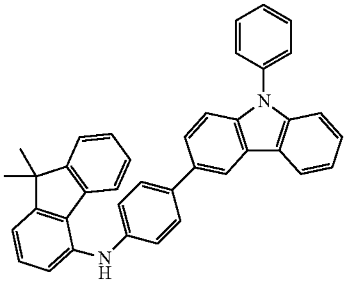 S100 | 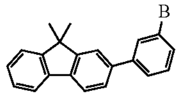 CAS-881912-14-7 | 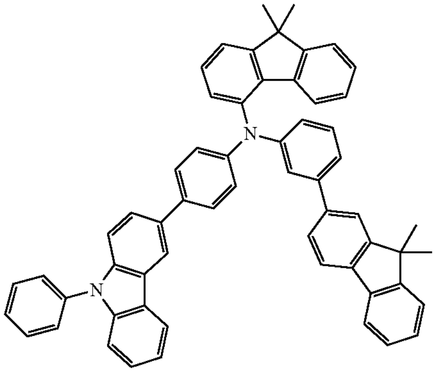 P233 |
| 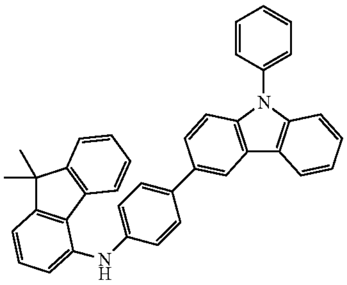 S100 | 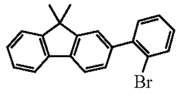 CAS-881912-12-5 | 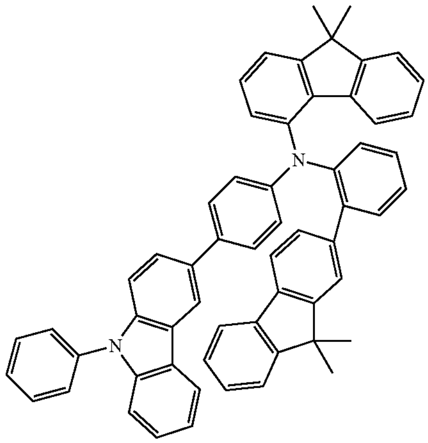 P234 |
| 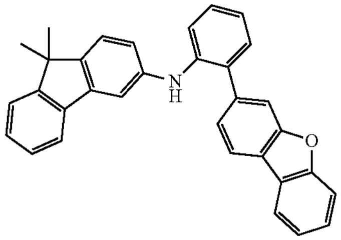 S101 | 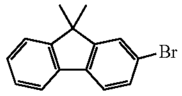 CAS-28320-31-2 | 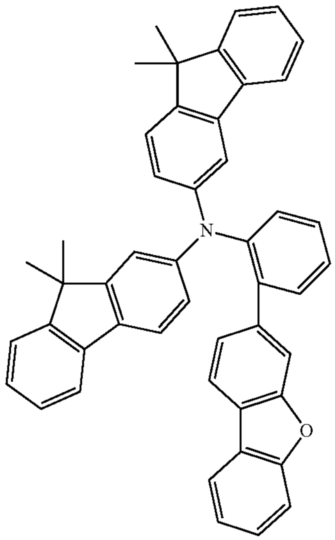 P235 |

-continued
| Reactant 1 | Reactant 2 | Product |
| --- | --- | --- |
| 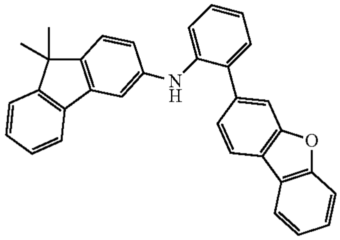<br>S101 | 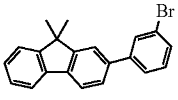<br>CAS-881912-14-7 | 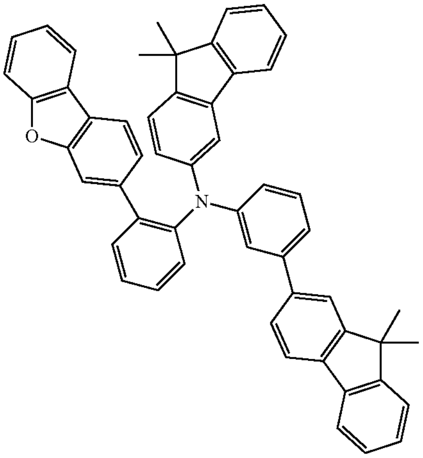<br>P236 |
| 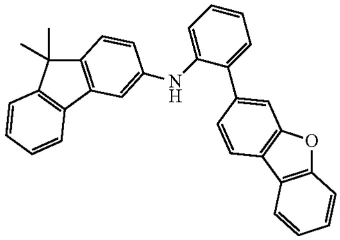<br>S101 | 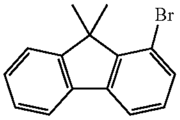<br>CAS-1225053-54-2 | 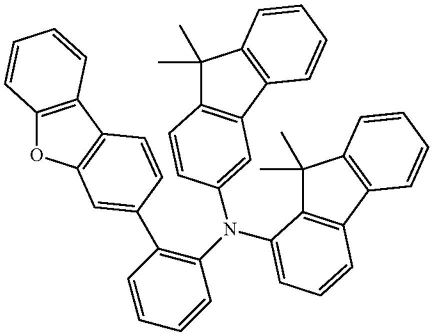<br>P237 |
| 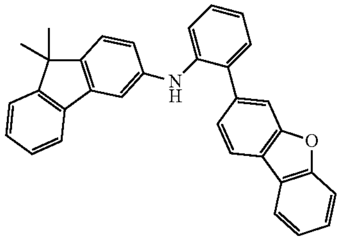<br>S101 | 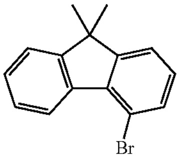<br>CAS-942615-32-9 | 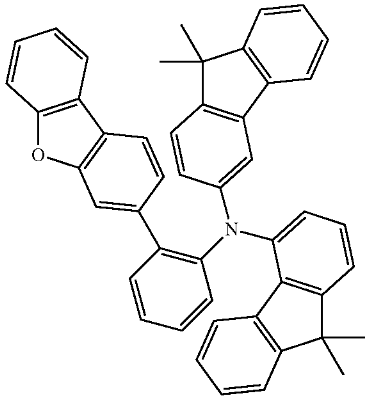<br>P238 |
| 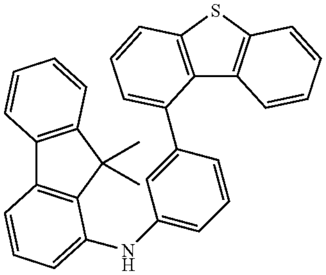<br>S102 | 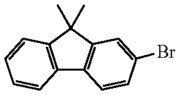<br>CAS-28320-31-2 | 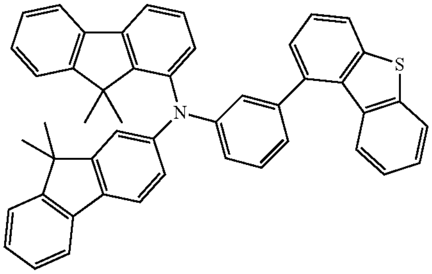<br>P239 |

-continued
| Reactant 1 | Reactant 2 | Product |
| --- | --- | --- |
| 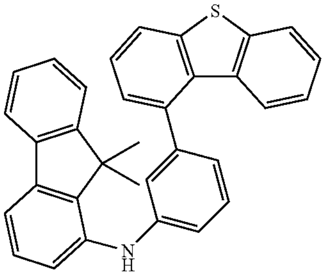<br>S102 | 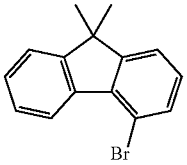<br>CAS-942615-32-9 | 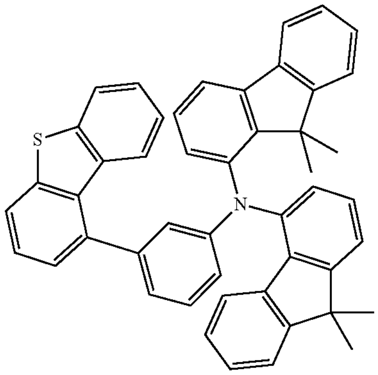<br>P240 |
| 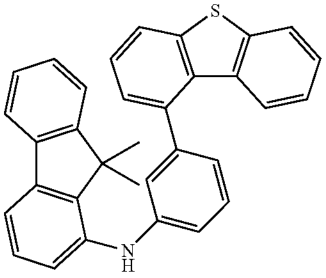<br>S102 | 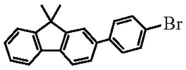<br>CAS-574750-94-0 | 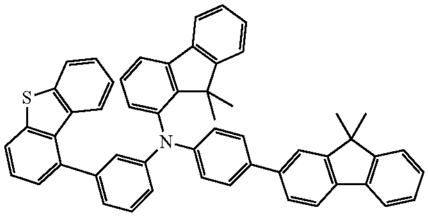<br>P241 |
| 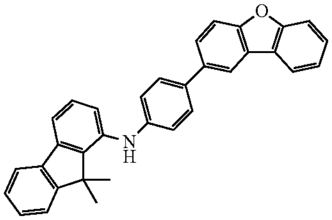<br>S103 | 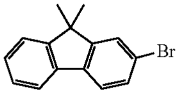<br>CAS-28320-31-2 | 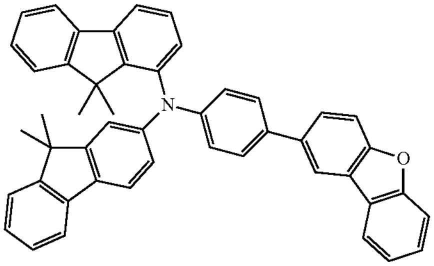<br>P242 |
| 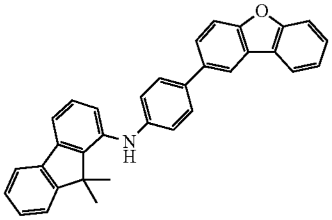<br>S103 | 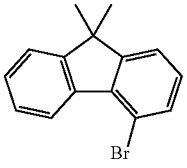<br>CAS-942615-32-9 | 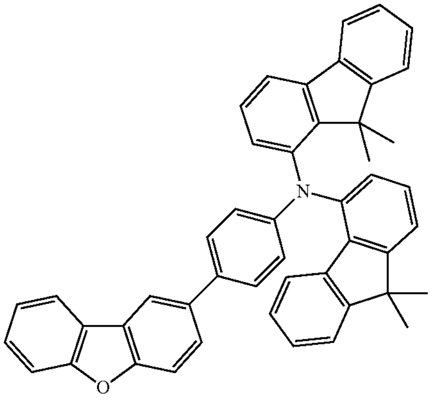<br>P243 |

-continued
| Reactant 1 | Reactant 2 | Product |
| --- | --- | --- |
| 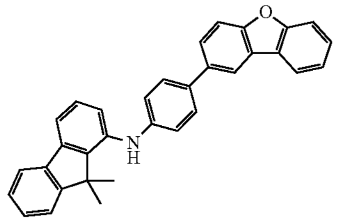 S103 | 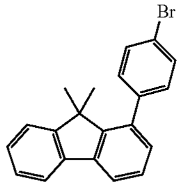 CAS-1786416-87-2 | 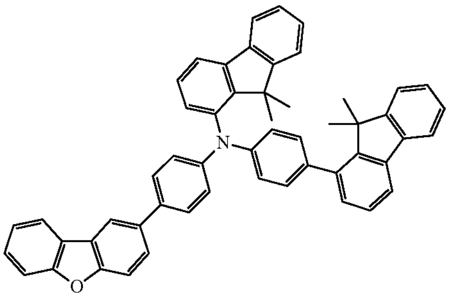 P244 |
| 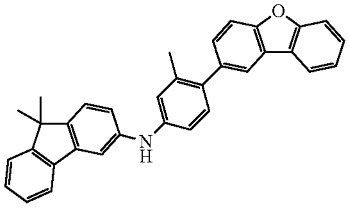 S104 | 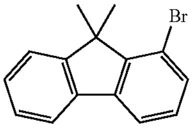 CAS-1225053-54-2 | 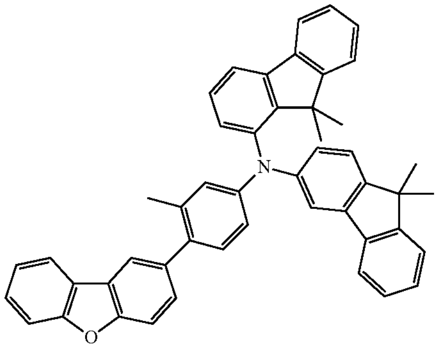 P245 |
| 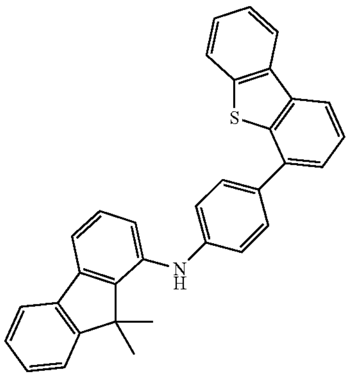 S105 | 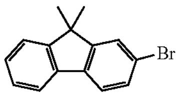 CAS-28320-31-2 | 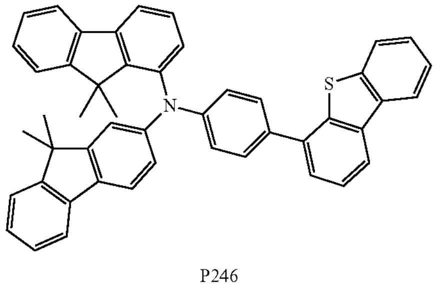 P246 |

-continued
| Reactant 1 | Reactant 2 | Product |
| --- | --- | --- |
| 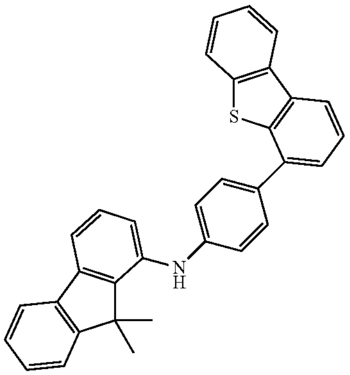 S105 | 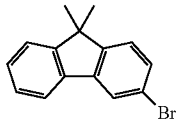 CAS-1190360-23-6 | 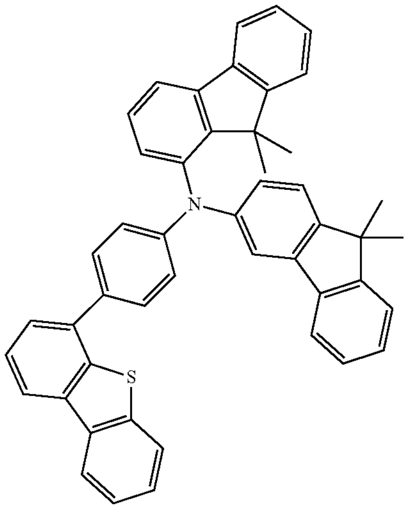 P247 |
| 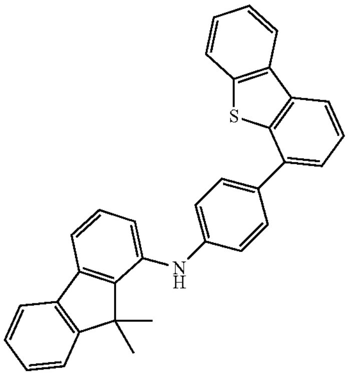 S105 | 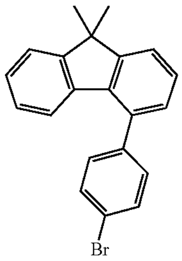 CAS-1860896-38-3 | 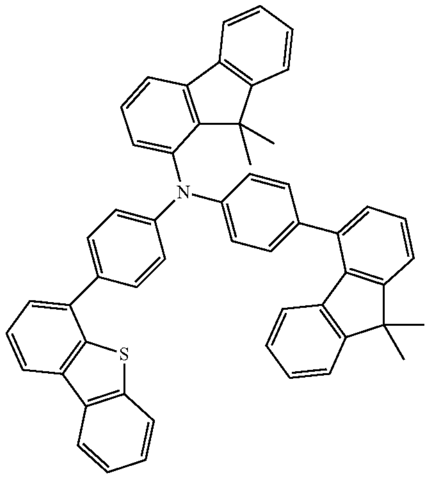 P248 |
| 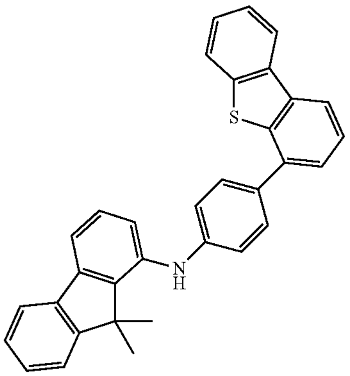 S105 | 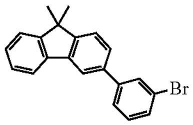 CAS-1417161-08-0 | 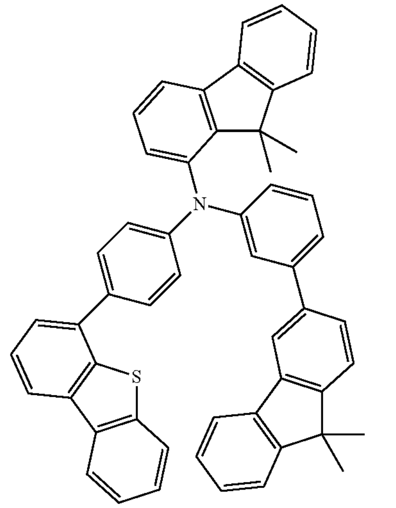 P249 |

-continued
| Reactant 1 | Reactant 2 | Product |
|---|---|---|
| 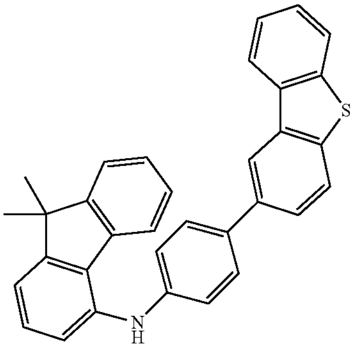<br>S106 | 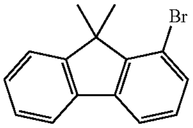<br>CAS-1225053-54-2 | 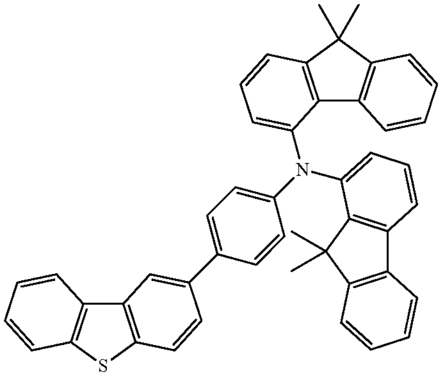<br>P250 |
| 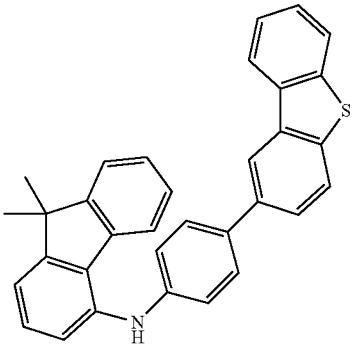<br>S106 | 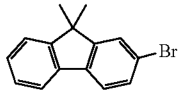<br>CAS-28320-31-2 | 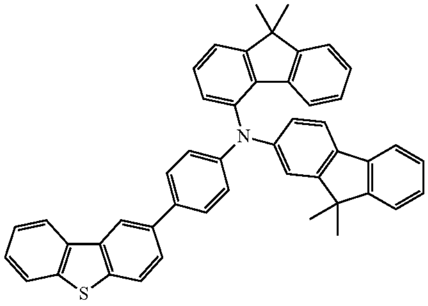<br>P251 |
| 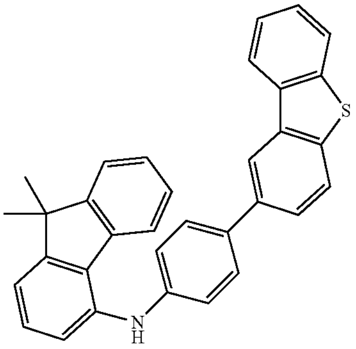<br>S106 | 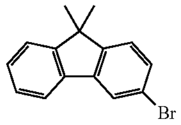<br>CAS-1190360-23-6 | 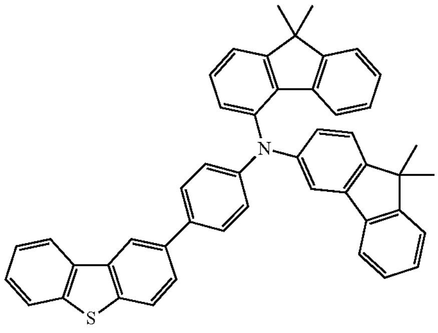<br>P252 |
| 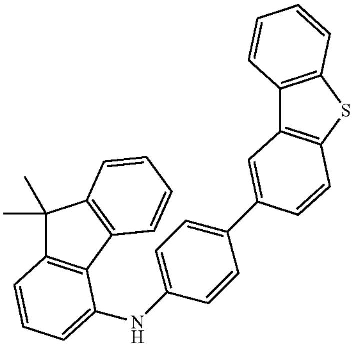<br>S106 | 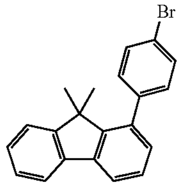<br>CAS-1786416-87-2 | 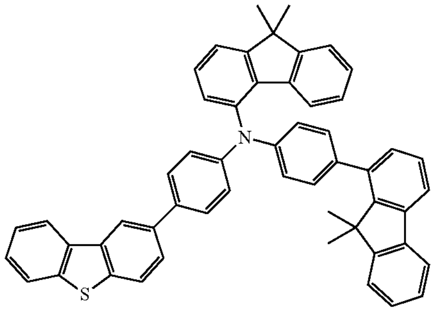<br>P253 |

-continued
| Reactant 1 | Reactant 2 | Product |
|---|---|---|
| 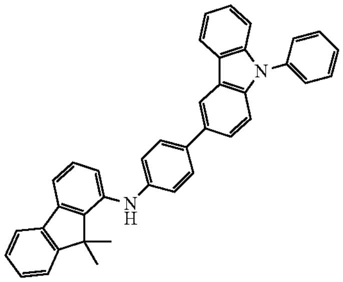 S107 | 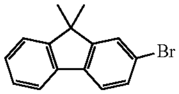 CAS-28320-31-2 | 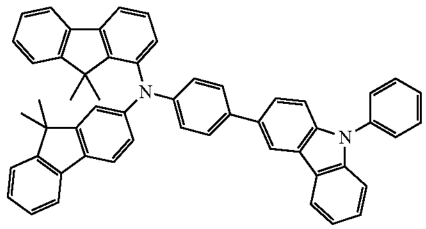 P254 |
| 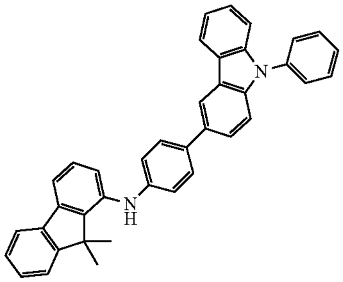 S107 | 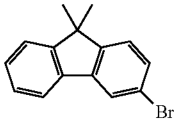 CAS-1190360-23-6 | 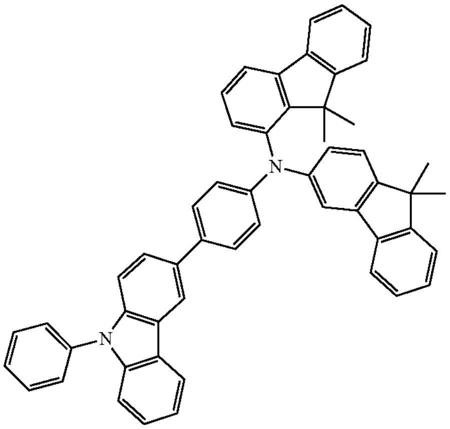 P255 |
| 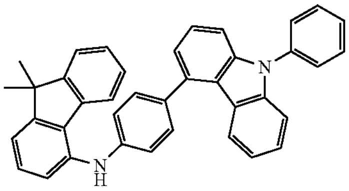 S108 | 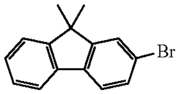 CAS-28320-31-2 | 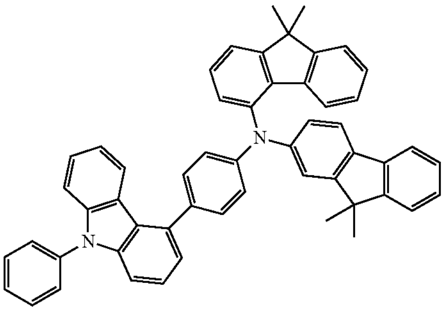 P256 |
| 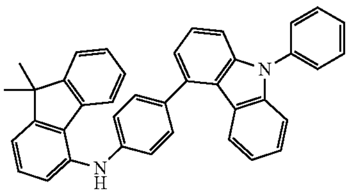 S108 | 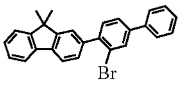 CAS-881912-16-9 | 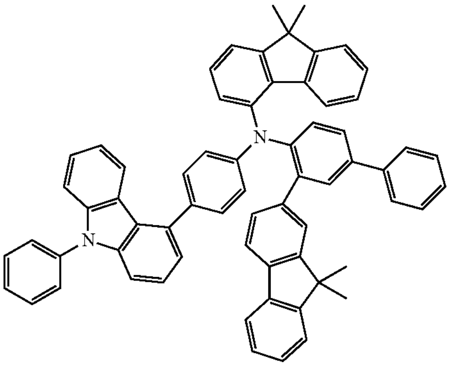 P257 |

-continued
| Reactant 1 | Reactant 2 | Product |
| --- | --- | --- |
| 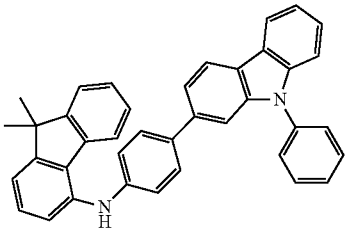 S109 | 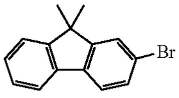 CAS-28320-31-2 | 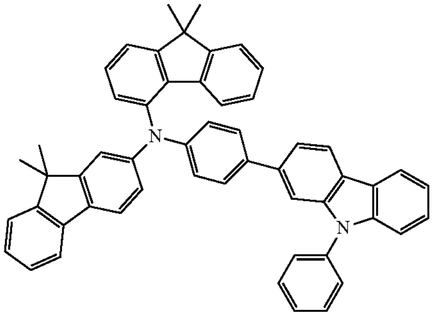 P258 |
| 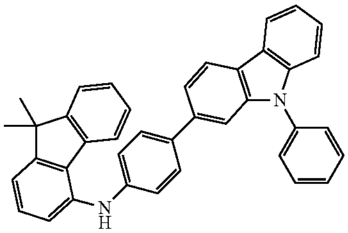 S109 | 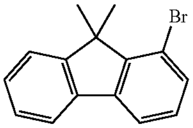 CAS-1225053-54-2 | 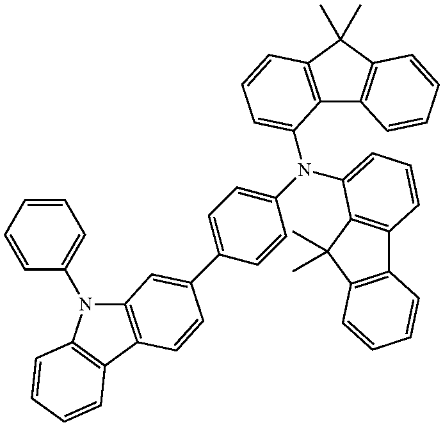 P259 |
| 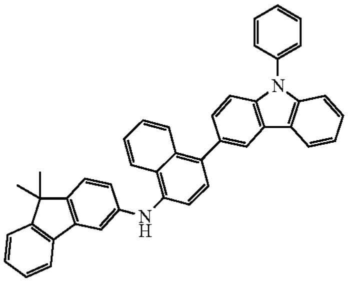 S110 | 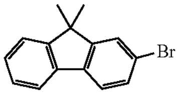 CAS-28320-31-2 | 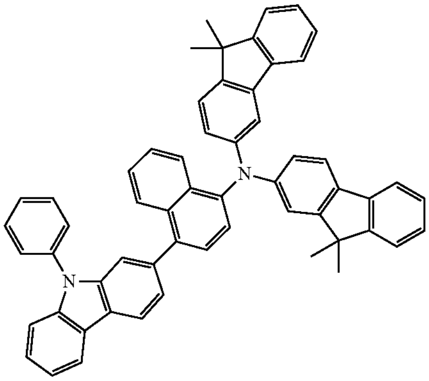 P260 |

-continued
| Reactant 1 | Reactant 2 | Product |
|---|---|---|
| 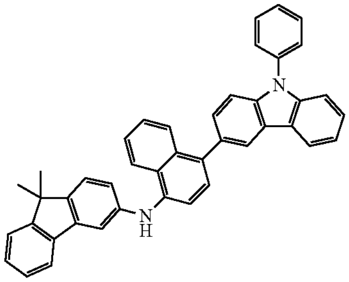 S110 | 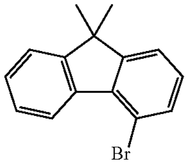 CAS-942615-32-9 | 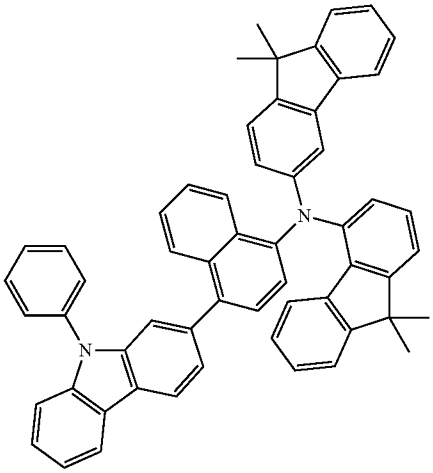 P261 |
| 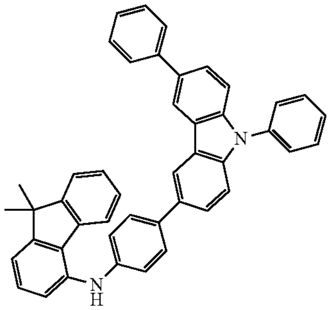 S111 | 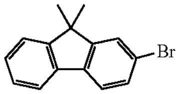 CAS-28320-31-2 | 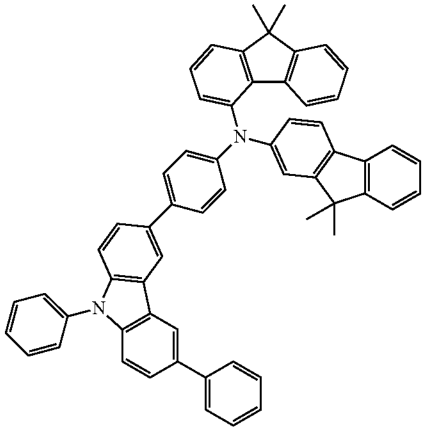 P262 |
| 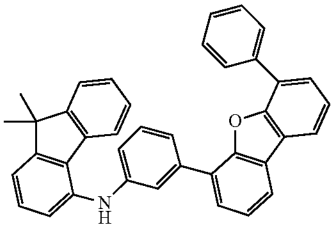 S112 | 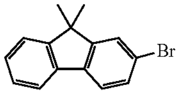 CAS-28320-31-2 | 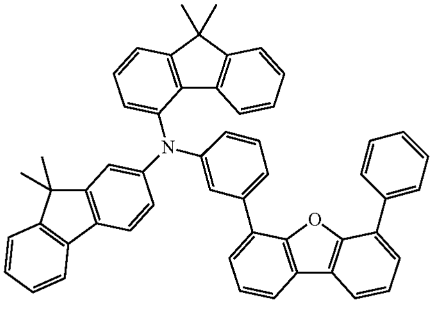 P263 |

-continued
| Reactant 1 | Reactant 2 | Product |
|---|---|---|
| 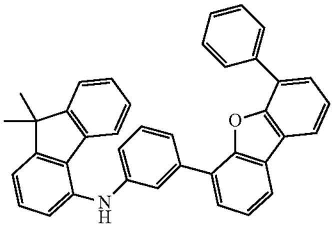 S112 | 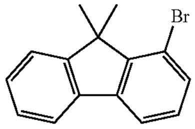 CAS-1225053-54-2 | 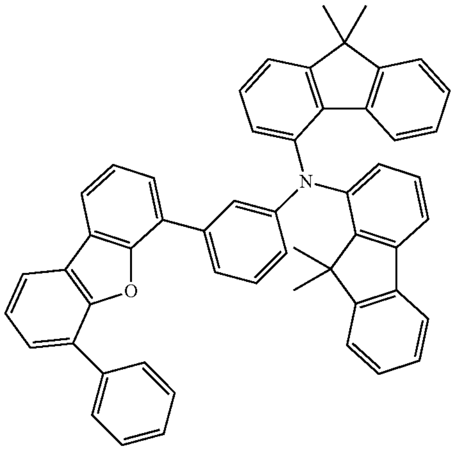 P264 |
| 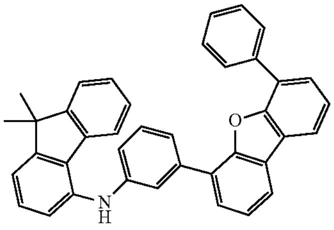 S112 | 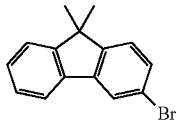 CAS-1190360-23-6 | 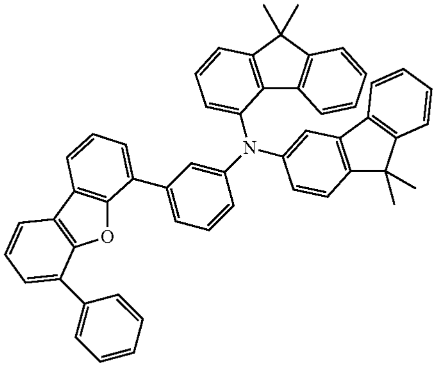 P265 |
| 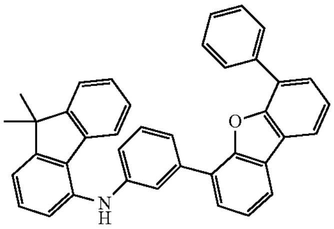 S112 | 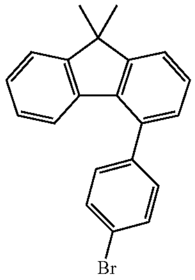 CAS-1860896-38-3 | 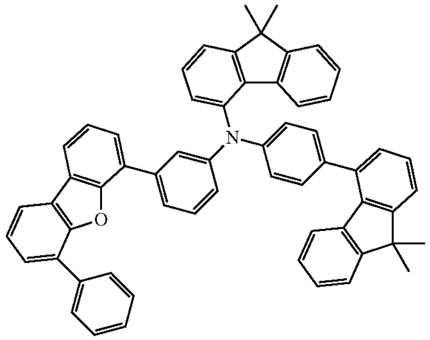 P266 |
| 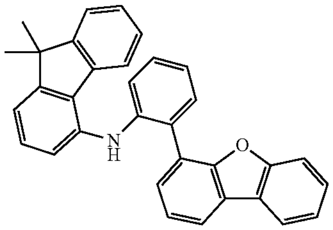 S113 | 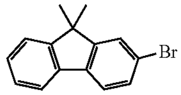 CAS-28320-31-2 | 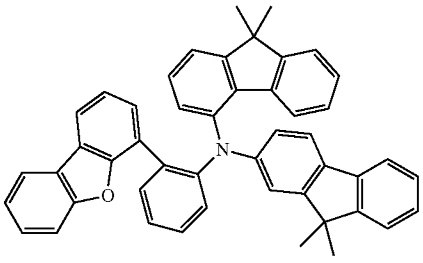 P267 |

-continued
| Reactant 1 | Reactant 2 | Product |
| --- | --- | --- |
| 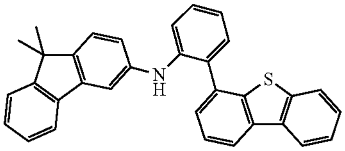 S114 | 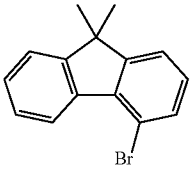 CAS-942615-32-9 | 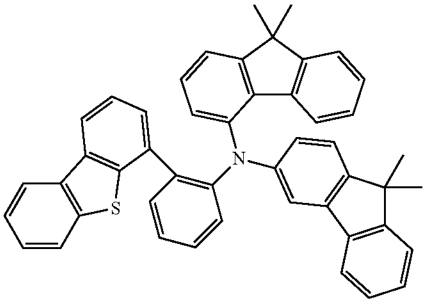 P268 |
| 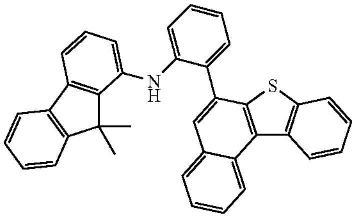 S115 | 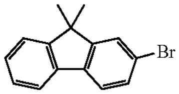 CAS-28320-31-2 | 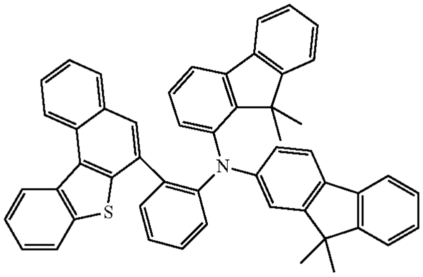 P269 |
| 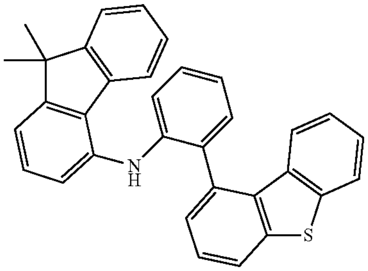 S116 | 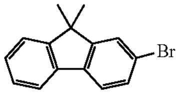 CAS-28320-31-2 | 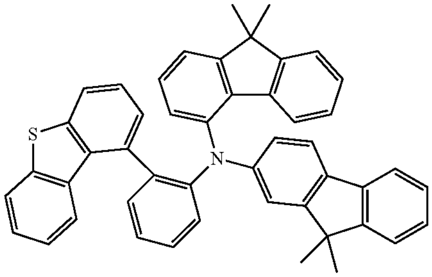 P270 |
| 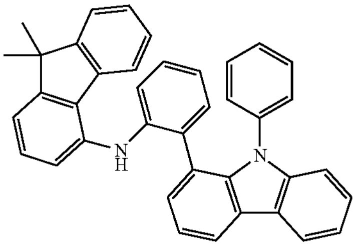 S117 | 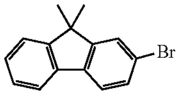 CAS-28320-31-2 | 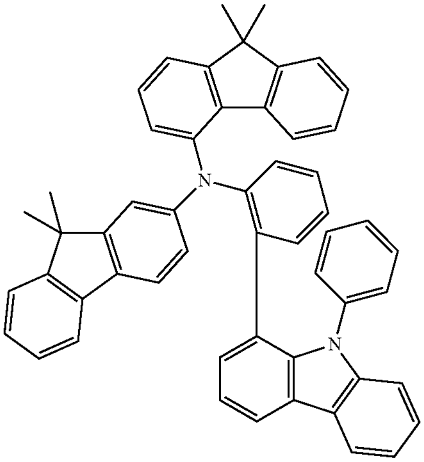 P271 |

-continued
| Reactant 1 | Reactant 2 | Product |
| --- | --- | --- |
| 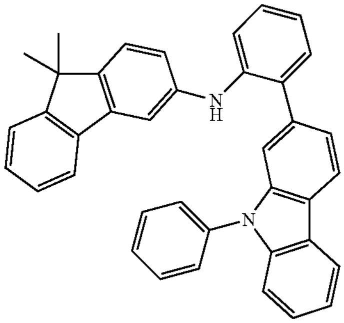 S118 | 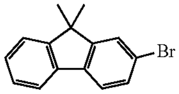 CAS-28320-31-2 | 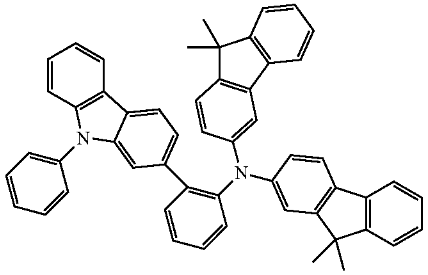 P272 |
| 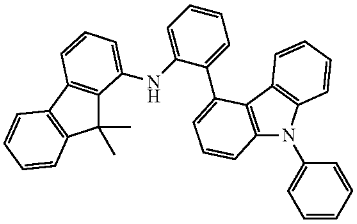 S119 | 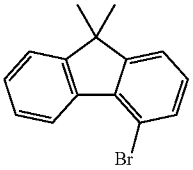 CAS-942615-32-9 | 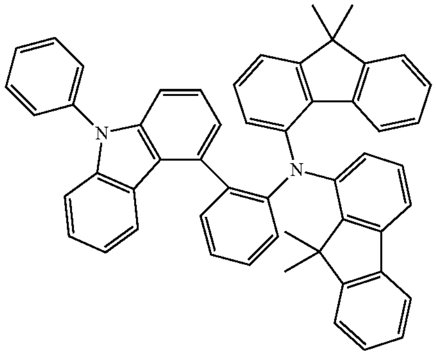 P273 |
| 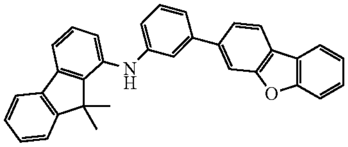 S120 | 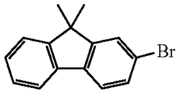 CAS-28320-31-2 | 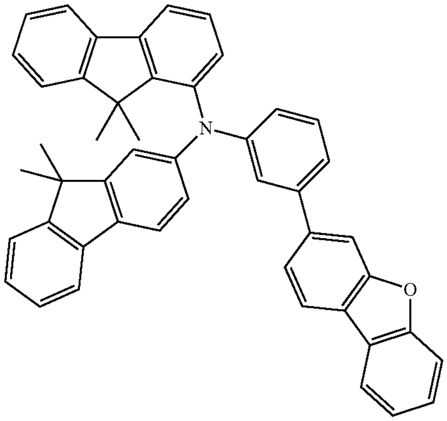 P274 |
| 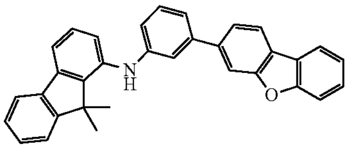 S120 | 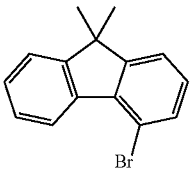 CAS-942615-32-9 | 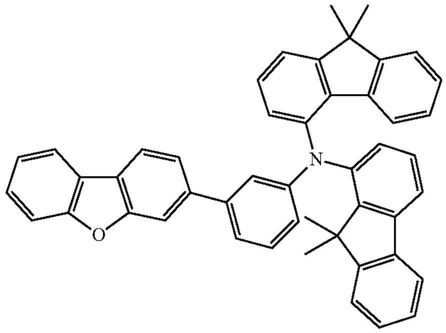 P275 |

-continued
| Reactant 1 | Reactant 2 | Product |
|---|---|---|
| 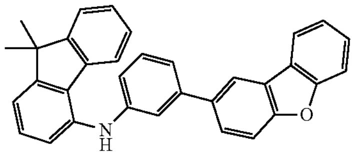<br>S121 | 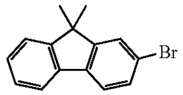<br>CAS-28320-31-2 | 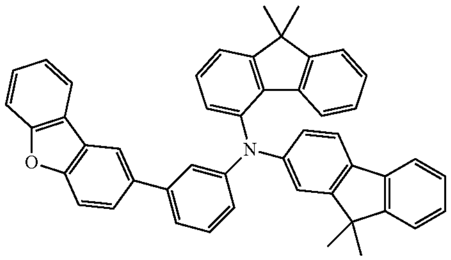<br>P276 |
| 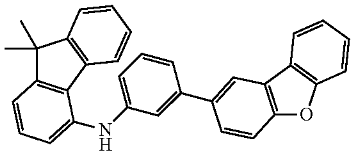<br>S121 | 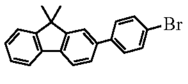<br>CAS-574750-94-0 | 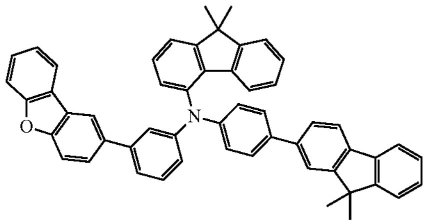<br>P277 |
| 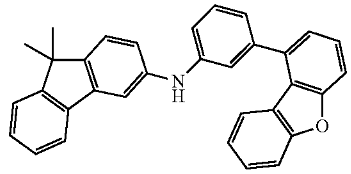<br>S122 | 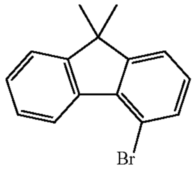<br>CAS-942615-32-9 | 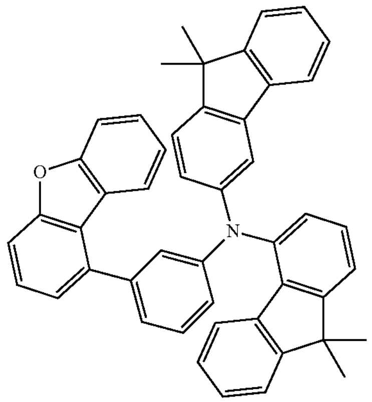<br>P278 |
| 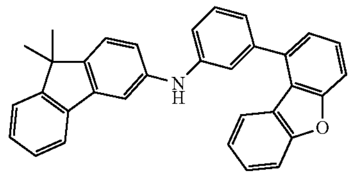<br>S122 | 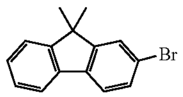<br>CAS-28320-31-2 | 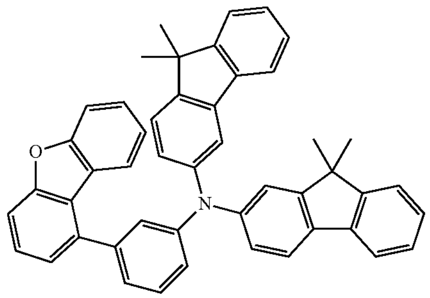<br>P279 |

-continued
| Reactant 1 | Reactant 2 | Product |
| --- | --- | --- |
| 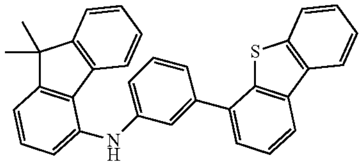 S123 | 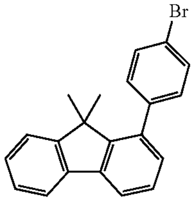 CAS-1786416-87-2 | 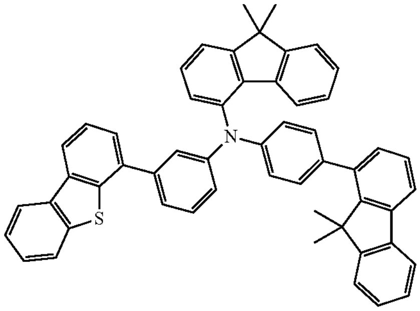 P280 |
| 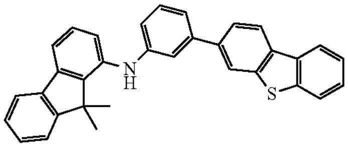 S124 | 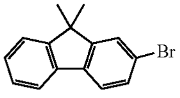 CAS-28320-31-2 | 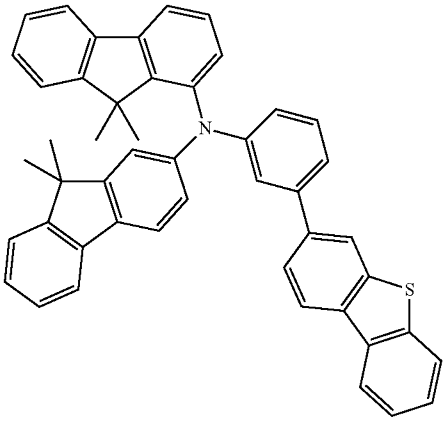 P281 |
| 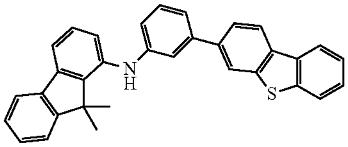 S124 | 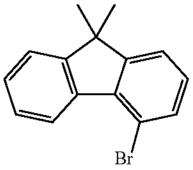 CAS-942615-32-9 | 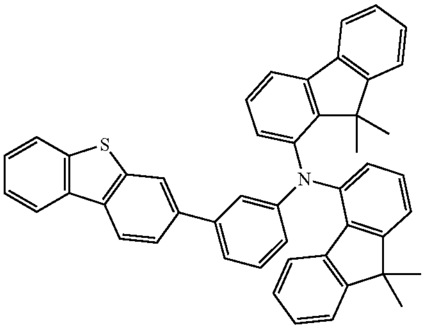 P282 |

-continued
| Reactant 1 | Reactant 2 | Product |
| --- | --- | --- |
| 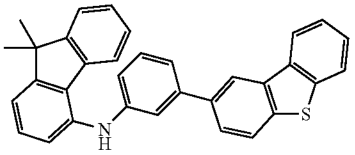<br>S125 | 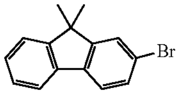<br>CAS-28320-31-2 | 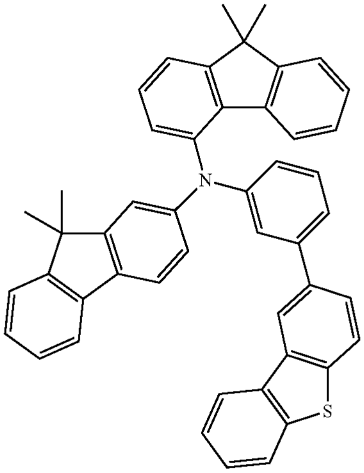<br>P283 |
| 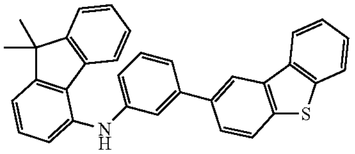<br>S125 | 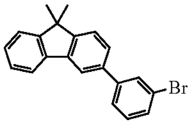<br>CAS-1417161-08-0 | 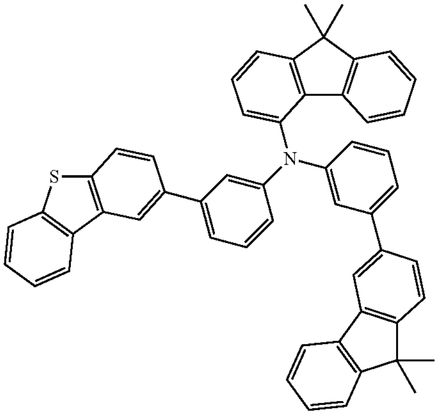<br>P284 |
| 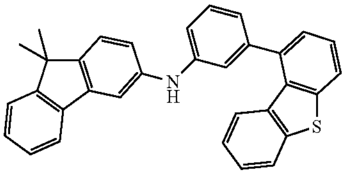<br>S126 | 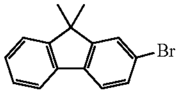<br>CAS-28320-31-2 | 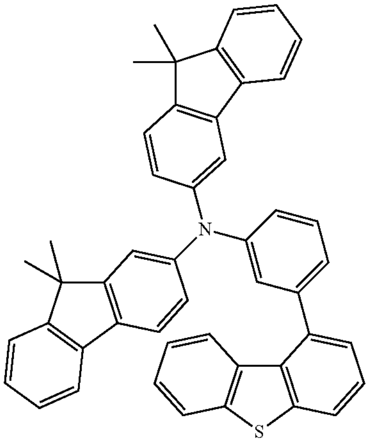<br>P285 |

-continued
| Reactant 1 | Reactant 2 | Product |
|---|---|---|
| 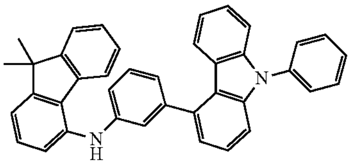 S127 | 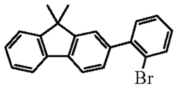 CAS-881912-12-5 | 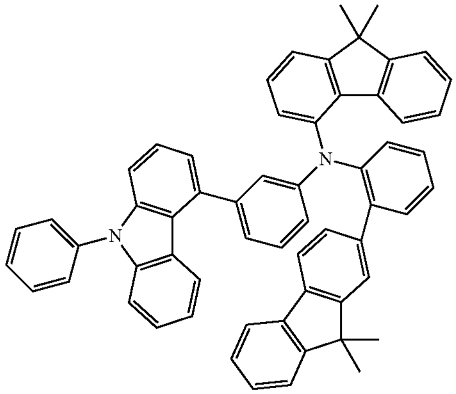 P286 |
| 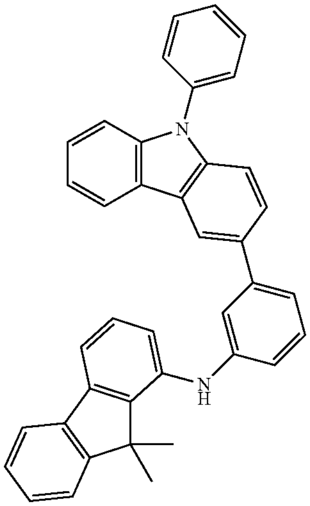 S128 | 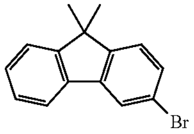 CAS-1190360-23-6 | 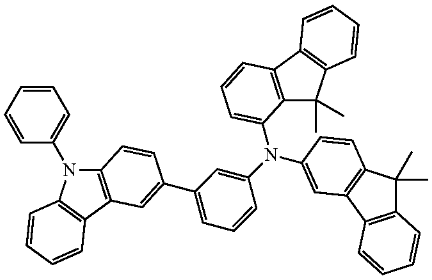 P287 |
| 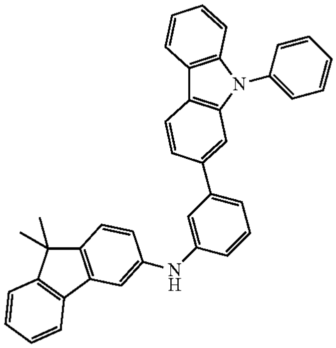 S129 | 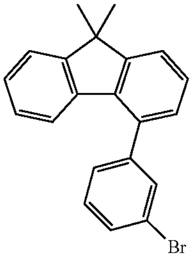 CAS-1860896-40-7 | 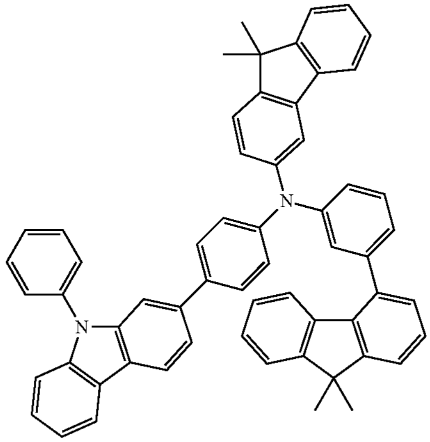 P288 |

-continued
| Reactant 1 | Reactant 2 | Product |
|---|---|---|
| 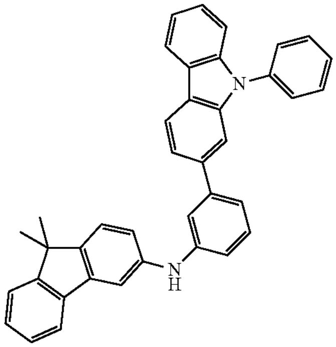 S129 | 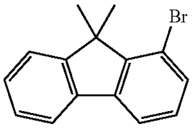 CAS-1225053-54-2 | 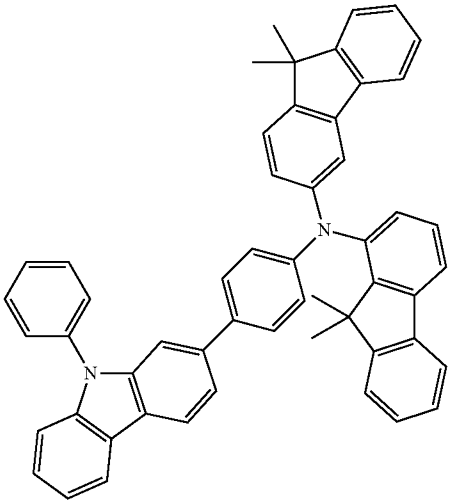 P289 |
| 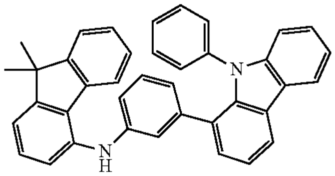 S130 | 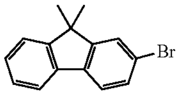 CAS-28320-31-2 | 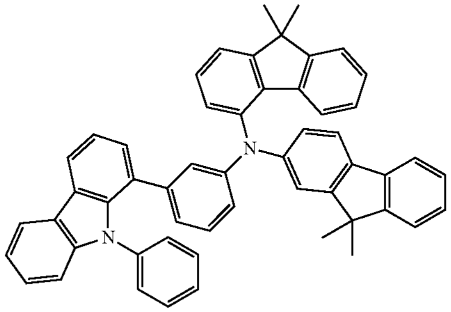 P290 |
| 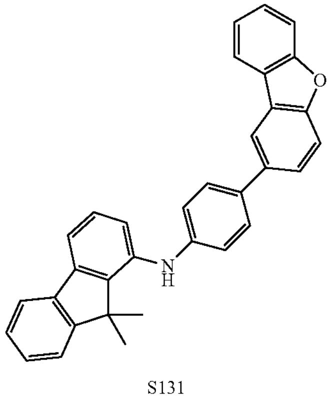 S131 | 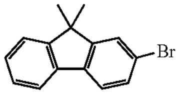 CAS-28320-31-2 | 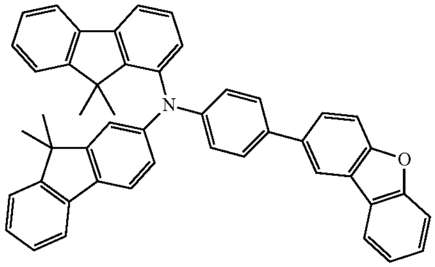 P291 |

-continued
| Reactant 1 | Reactant 2 | Product |
|---|---|---|
| 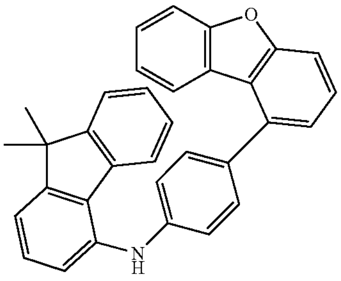 S132 | 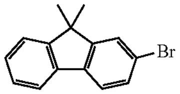 CAS-28320-31-2 | 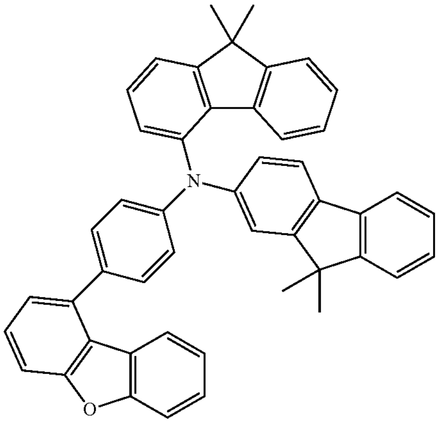 P292 |
| 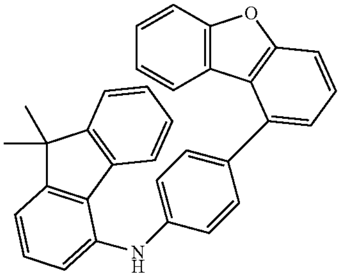 S132 | 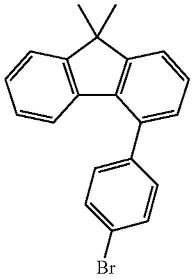 CAS-1860896-38-3 | 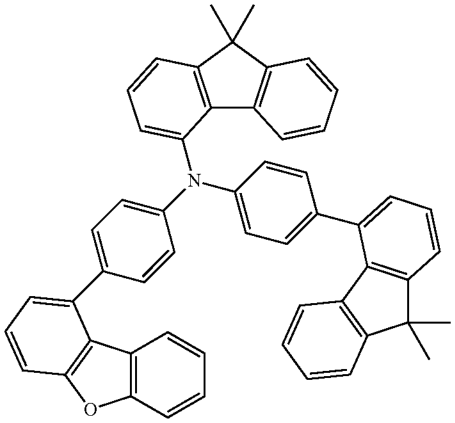 P293 |
| 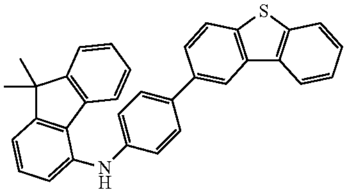 S133 | 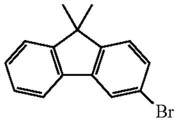 CAS-1190360-23-6 | 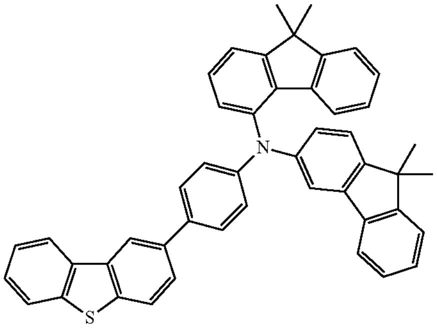 P294 |

-continued
| Reactant 1 | Reactant 2 | Product |
|---|---|---|
| 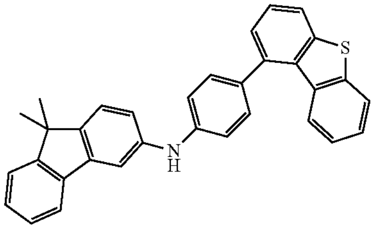 S134 | 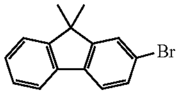 CAS-28320-31-2 | 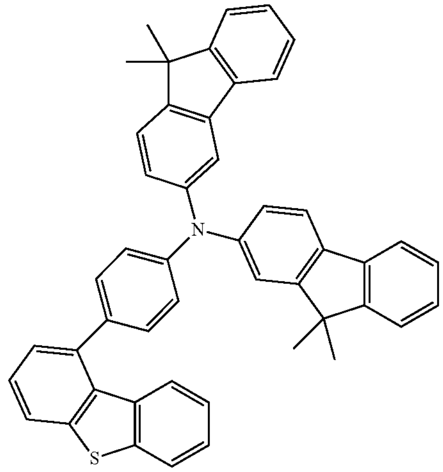 P295 |
| 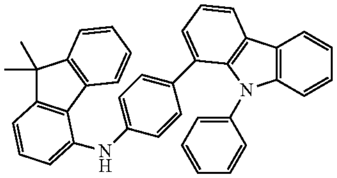 S135 | 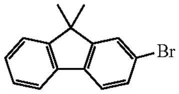 CAS-28320-31-2 | 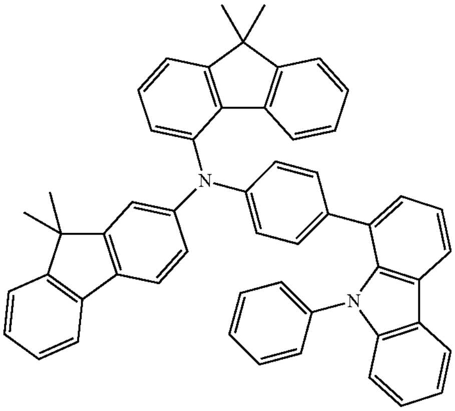 P296 |
| 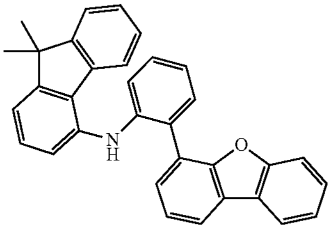 S136 | 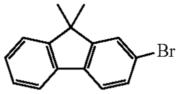 CAS-28320-31-2 | 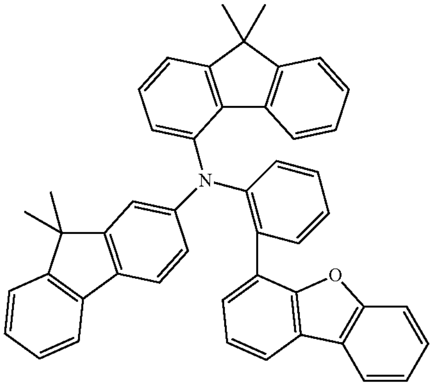 P297 |

-continued
| Reactant 1 | Reactant 2 | Product |
| --- | --- | --- |
| 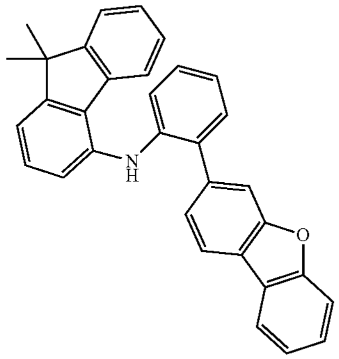 S137 | 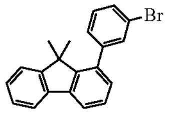 CAS-2035081-41-3 | 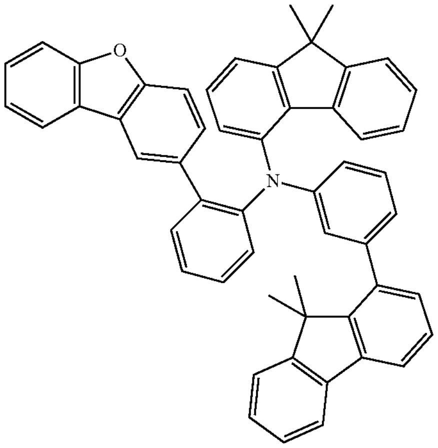 P298 |
| 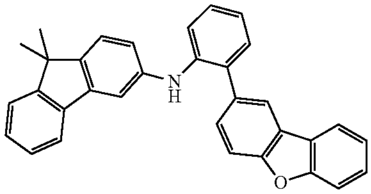 S138 | 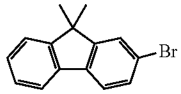 CAS-28320-31-2 | 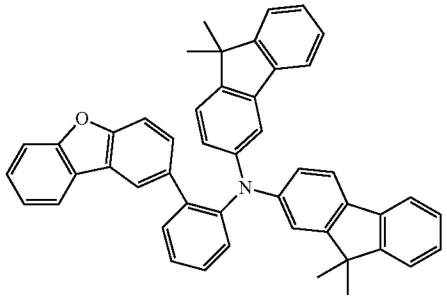 P299 |
| 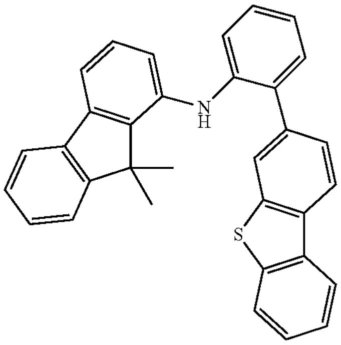 S139 | 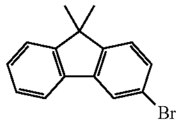 CAS-1190360-23-6 | 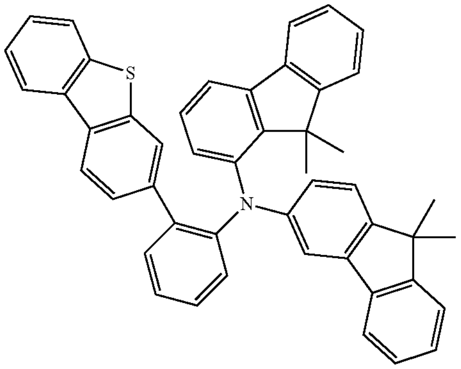 P300 |

-continued
| Reactant 1 | Reactant 2 | Product |
| --- | --- | --- |
| 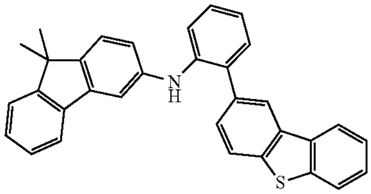<br>S140 | 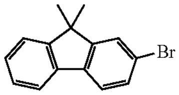<br>CAS-28320-31-2 | 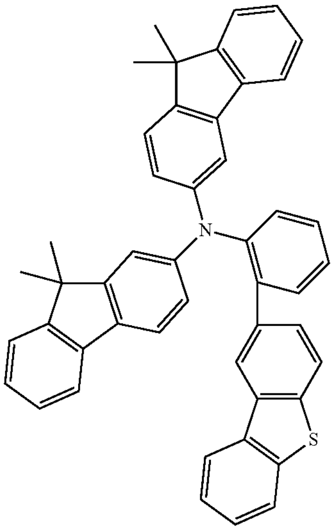<br>P301 |
| 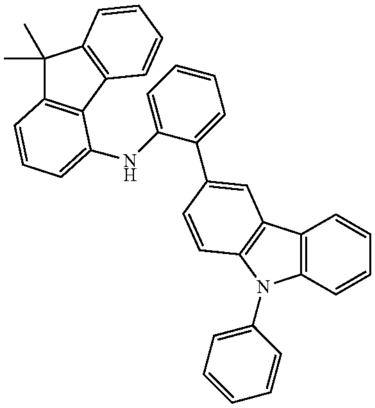<br>S141 | 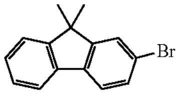<br>CAS-28320-31-2 | 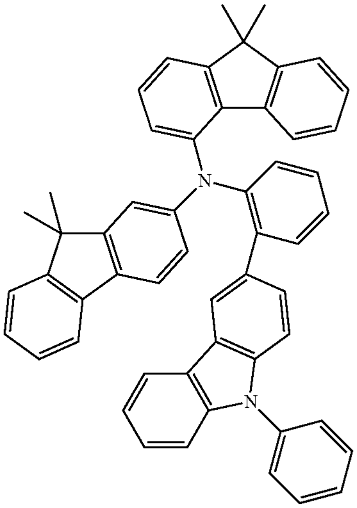<br>P302 |
| 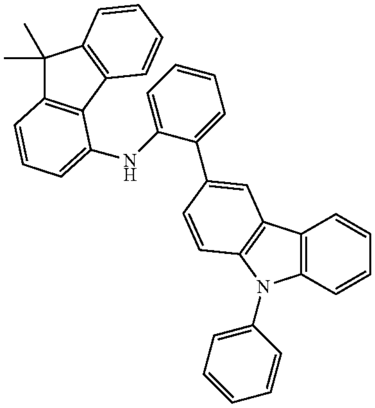<br>S141 | 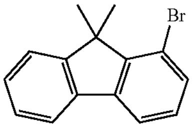<br>CAS-1225053-54-2 | 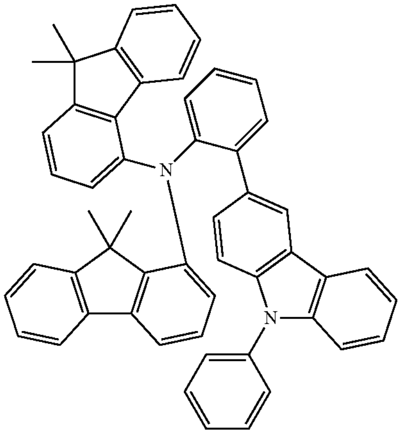<br>P303 |

-continued
| Reactant 1 | Reactant 2 | Product |
| --- | --- | --- |
| 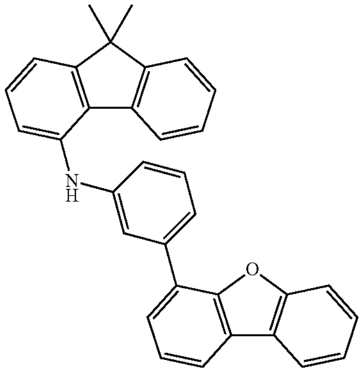 S142 | 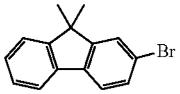 CAS-28320-31-2 | 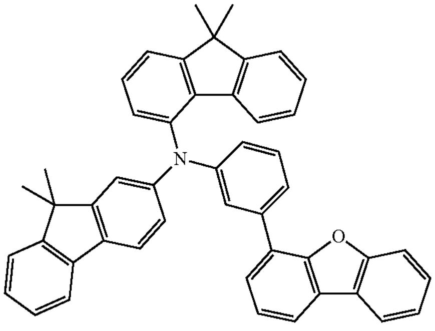 P304 |
| 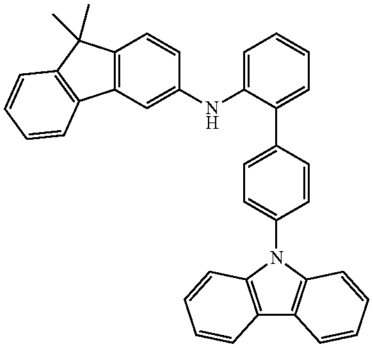 S143 | 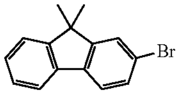 CAS-28320-31-2 | 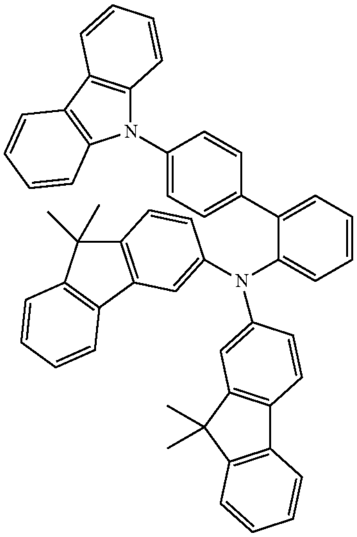 P305 |
| 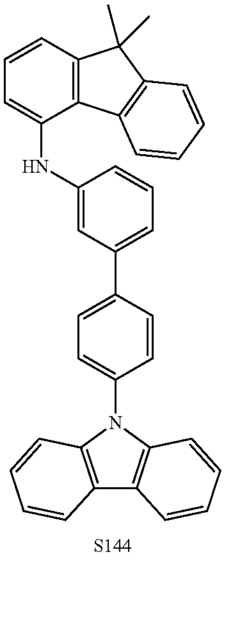 S144 | 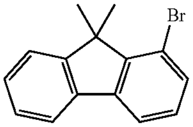 CAS-1225053-54-2 | 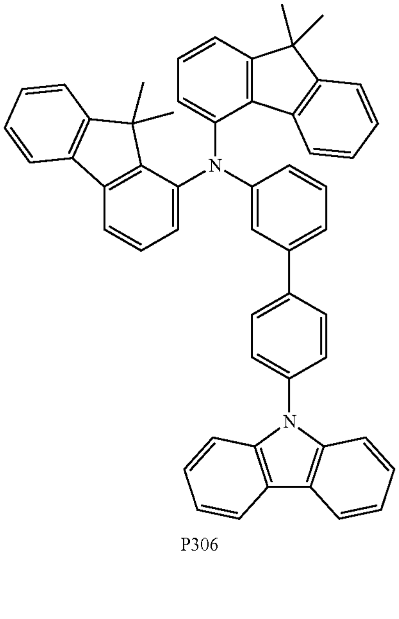 P306 |

-continued
| Reactant 1 | Reactant 2 | Product |
|---|---|---|
| 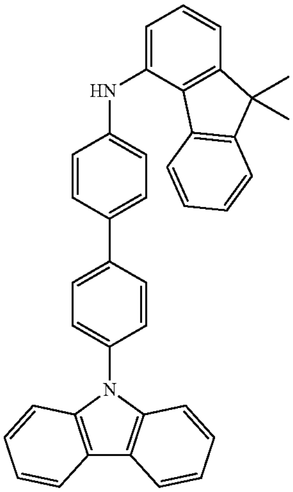<br>S145 | 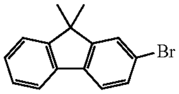<br>CAS-28320-31-2 | 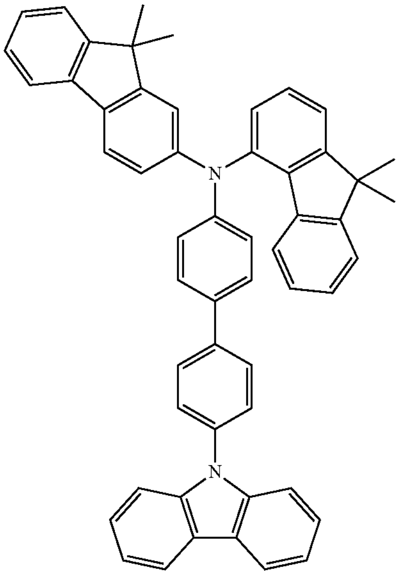<br>P307 |
| 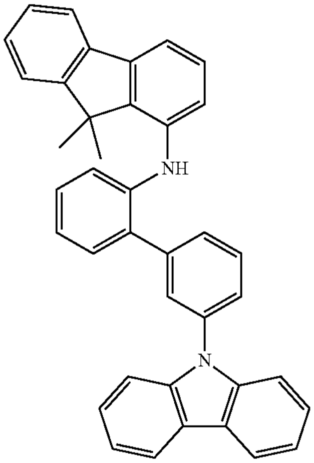<br>S146 | 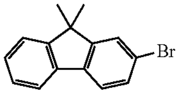<br>CAS-28320-31-2 | 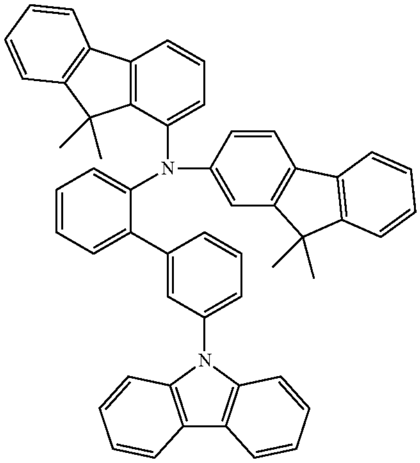<br>P308 |

-continued
| Reactant 1 | Reactant 2 | Product |
| --- | --- | --- |
| 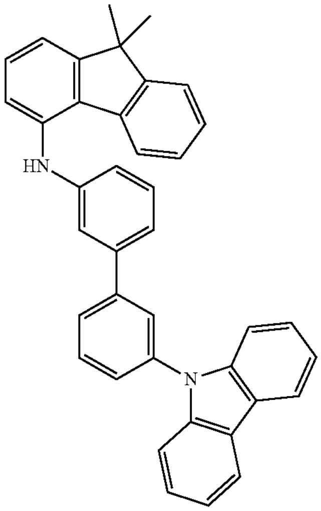 S147 | 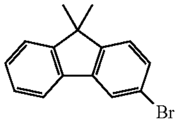 CAS-1190360-23-6 | 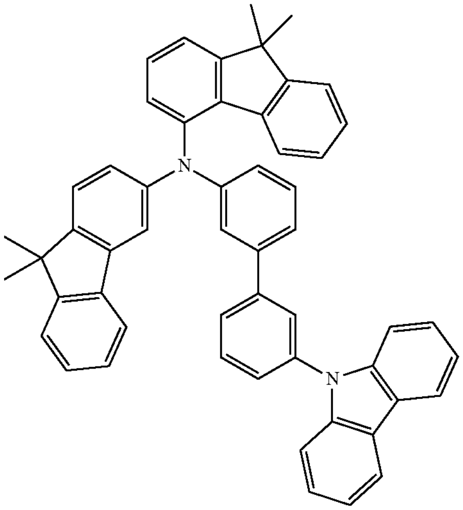 P309 |
| 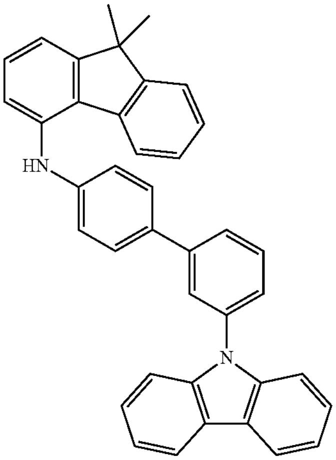 S148 | 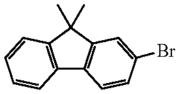 CAS-28320-31-2 | 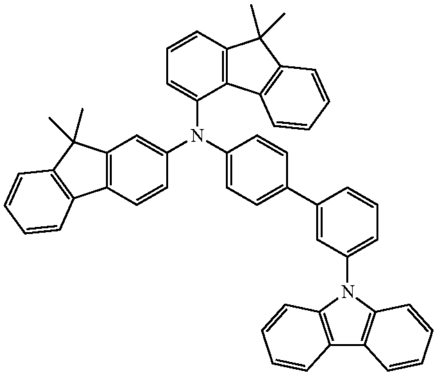 P310 |
| 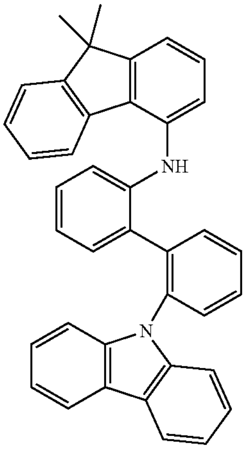 S149 | 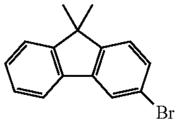 CAS-1190360-23-6 | 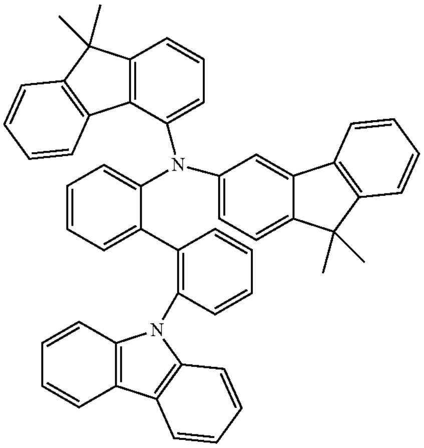 P311 |

-continued
| Reactant 1 | Reactant 2 | Product |
|---|---|---|
| 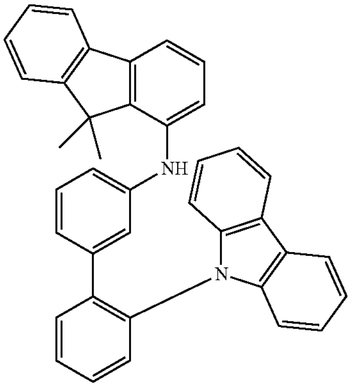 S150 | 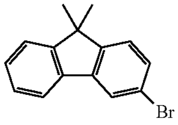 CAS-1190360-23-6 | 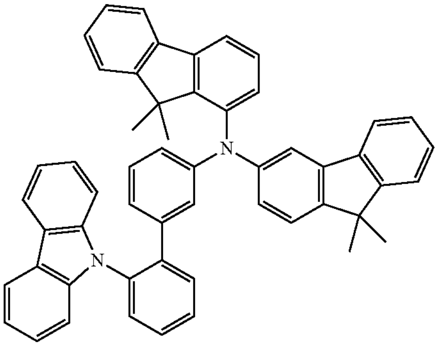 P312 |
| 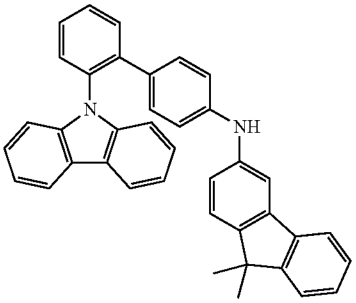 S151 | 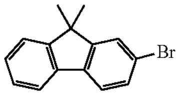 CAS-28320-31-2 | 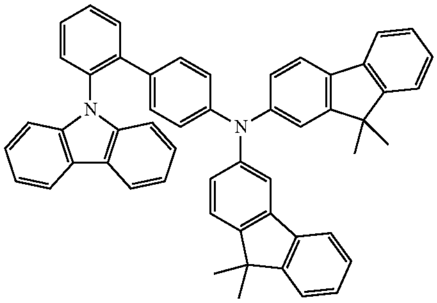 P313 |
| 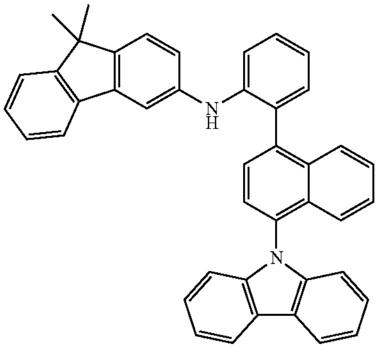 S152 | 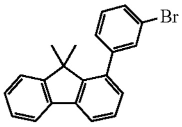 CAS-2035081-41-3 | 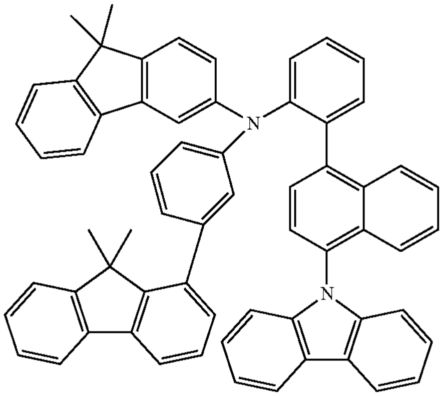 P314 |
| 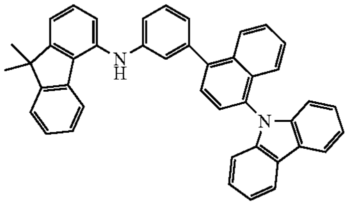 S153 | 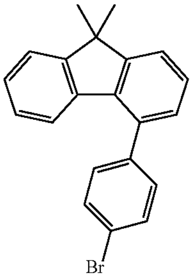 CAS-1860896-38-3 | 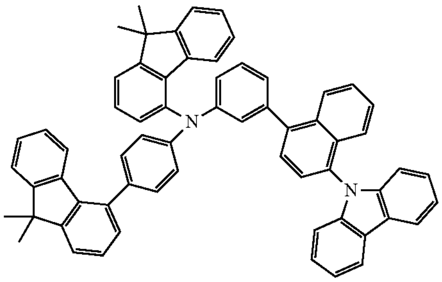 P315 |

-continued
| Reactant 1 | Reactant 2 | Product |
|---|---|---|
| 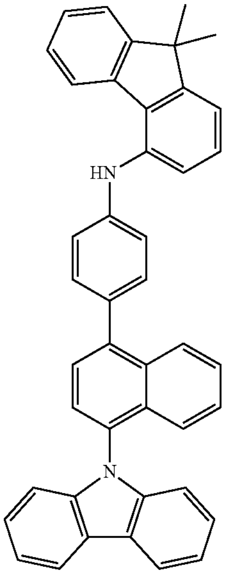 S154 | 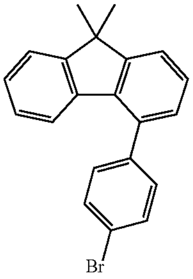 CAS-1860896-38-3 | 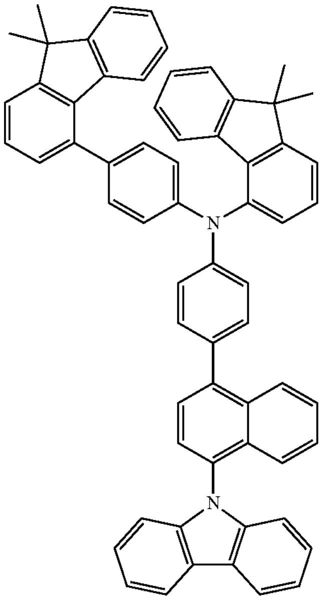 P316 |
| 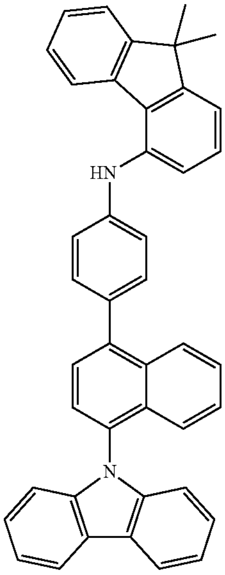 S154 | 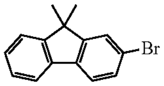 CAS-28320-31-2 | 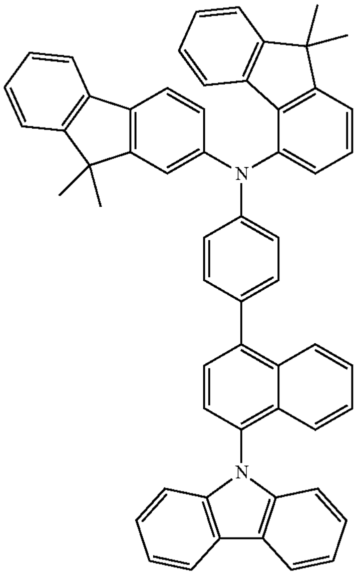 P317 |

-continued
| Reactant 1 | Reactant 2 | Product |
| --- | --- | --- |
| 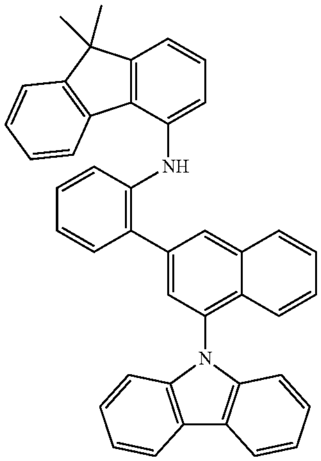 S155 | 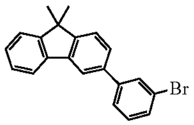 CAS-1417161-08-0 | 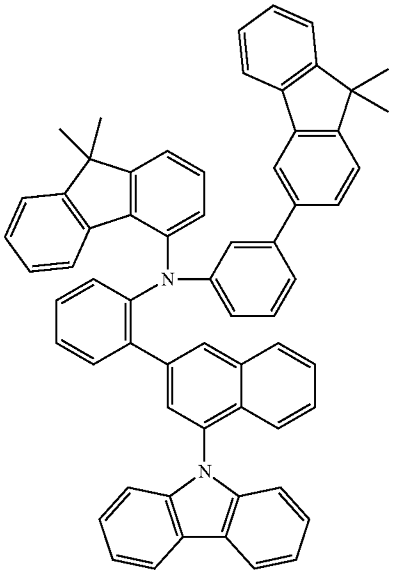 P318 |
| 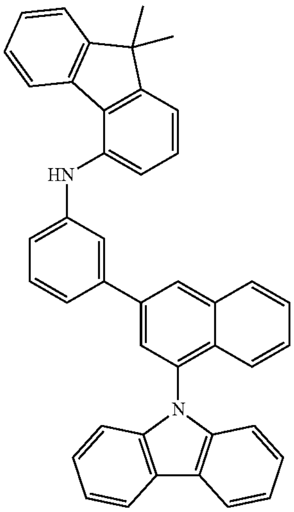 S156 | 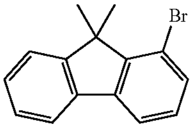 CAS-1225053-54-2 | 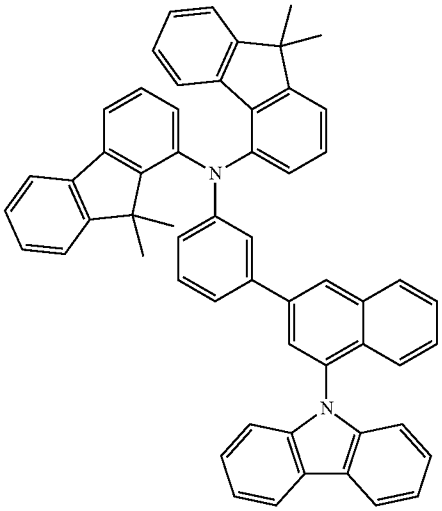 P319 |

-continued
| Reactant 1 | Reactant 2 | Product |
|---|---|---|
| 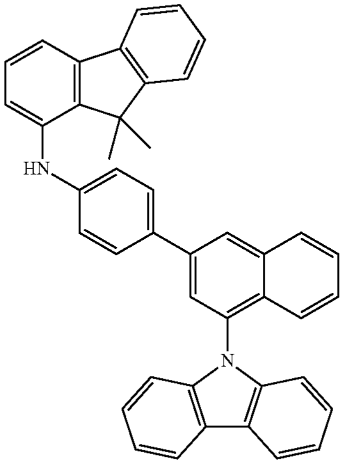 S157 | 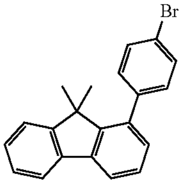 CAS-1786416-87-2 | 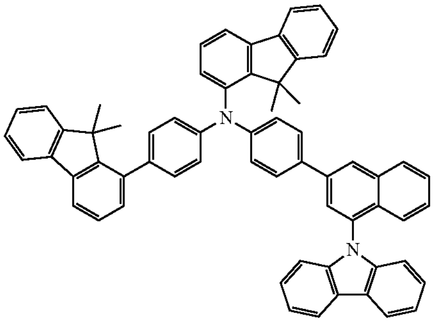 P320 |
| 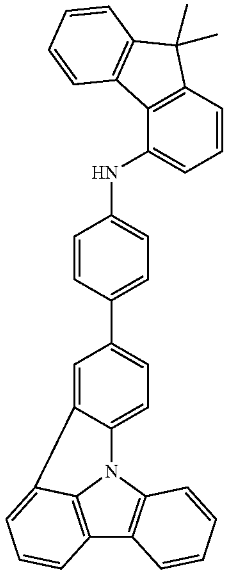 S158 | 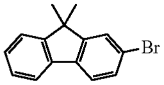 CAS-28320-31-2 | 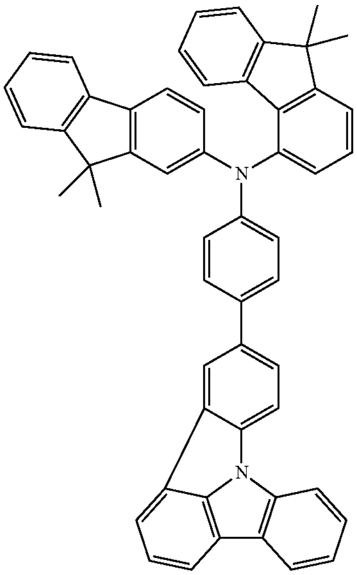 P321 |
| 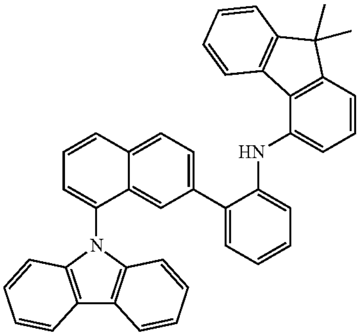 S159 | 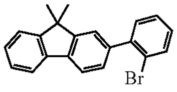 CAS-881912-12-5 | 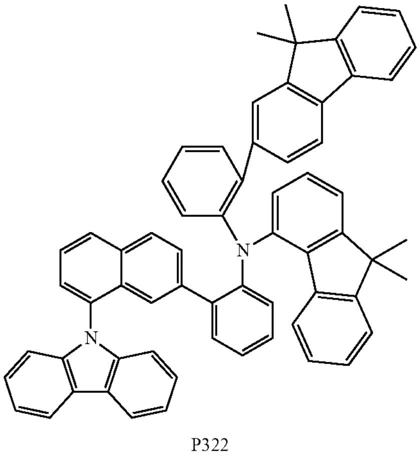 P322 |

-continued
| Reactant 1 | Reactant 2 | Product |
| --- | --- | --- |
| 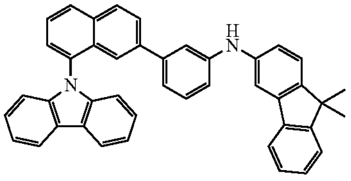 S160 | 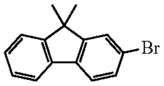 CAS-28320-31-2 | 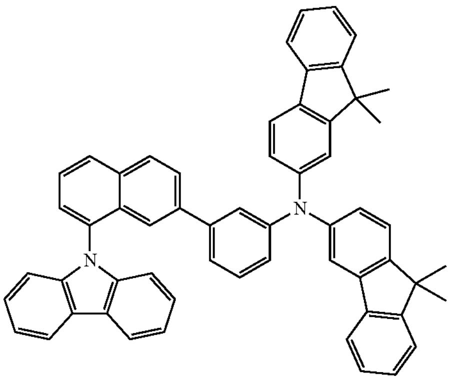 P323 |
| 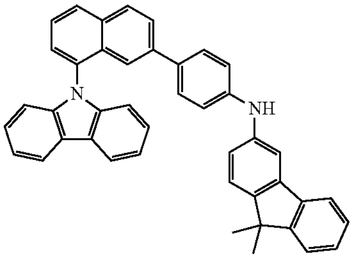 S161 | 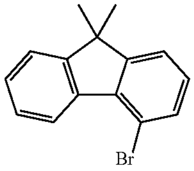 CAS-942615-32-9 | 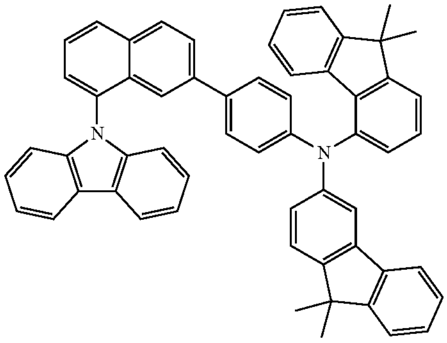 P324 |
| 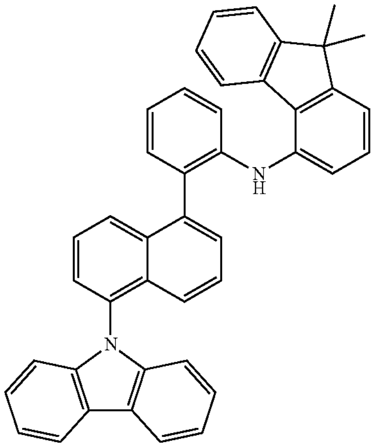 S162 | 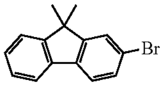 CAS-28320-31-2 | 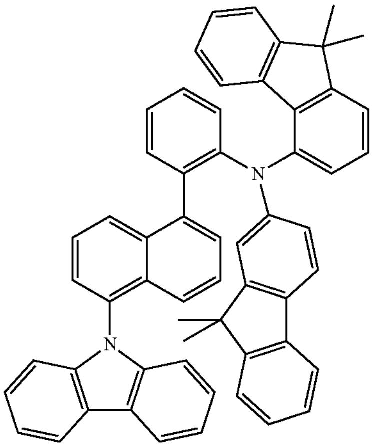 P326 |

-continued
| Reactant 1 | Reactant 2 | Product |
|---|---|---|
| 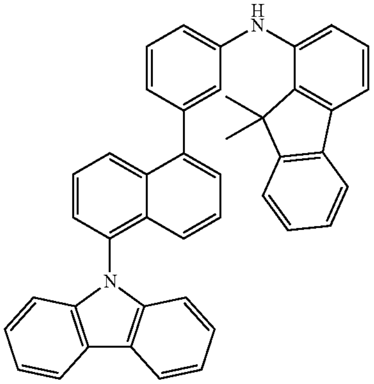 S163 | 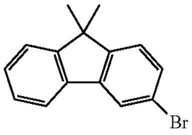 CAS-1190360-23-6 | 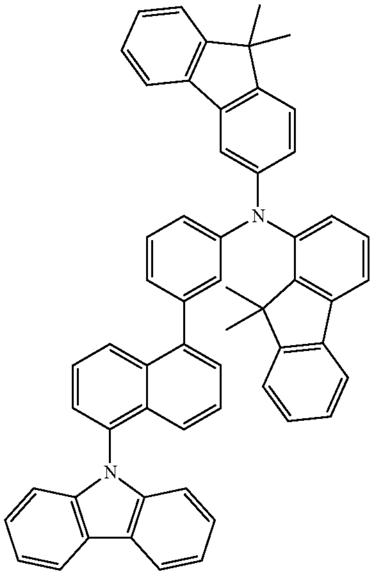 P327 |
| 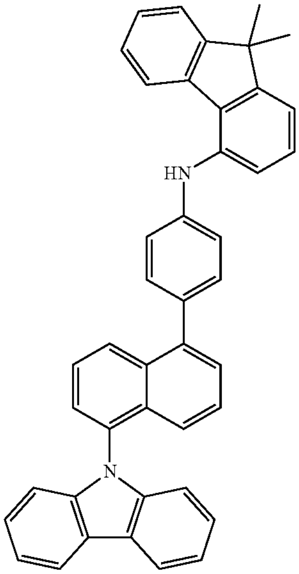 S164 | 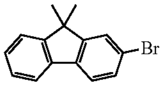 CAS-28320-31-2 | 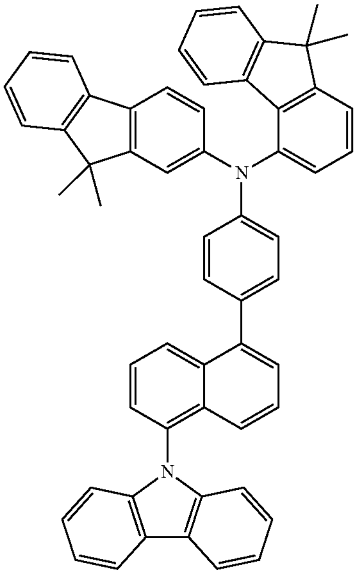 P328 |

-continued
| Reactant 1 | Reactant 2 | Product |
|---|---|---|
| 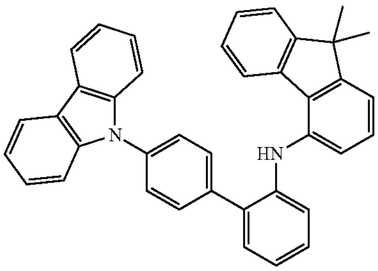 S165 | 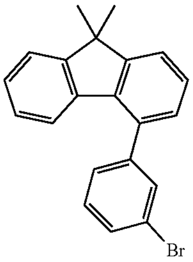 CAS-1860896-40-7 | 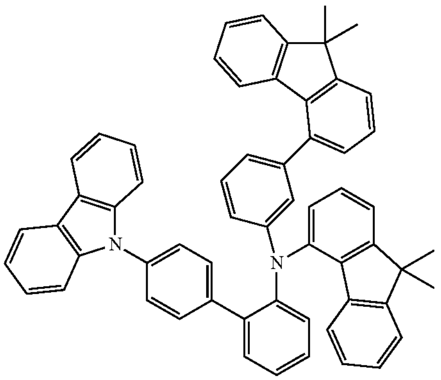 P329 |
| 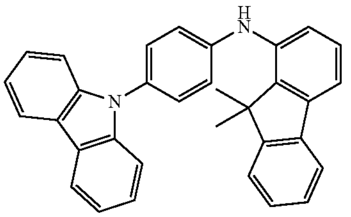 S166 | 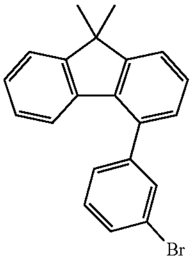 CAS-1860896-40-7 | 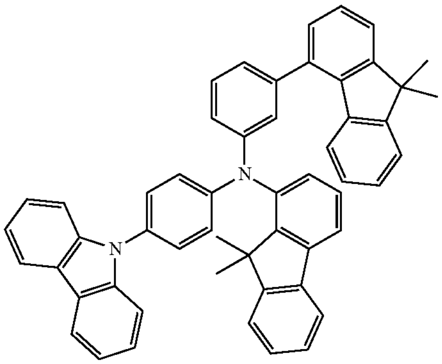 P330 |
| 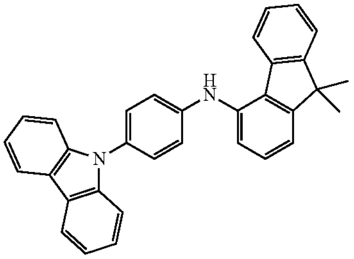 S167 | 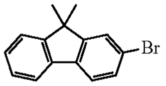 CAS-28320-31-2 | 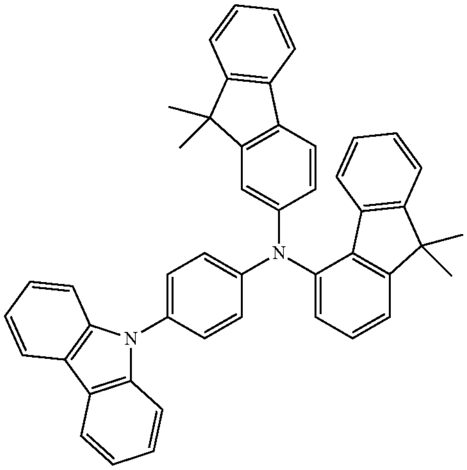 P331 |

-continued
| Reactant 1 | Reactant 2 | Product |
|---|---|---|
| 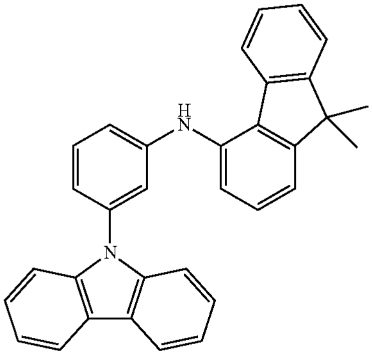 S168 | 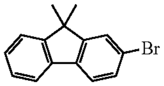 CAS-28320-31-2 | 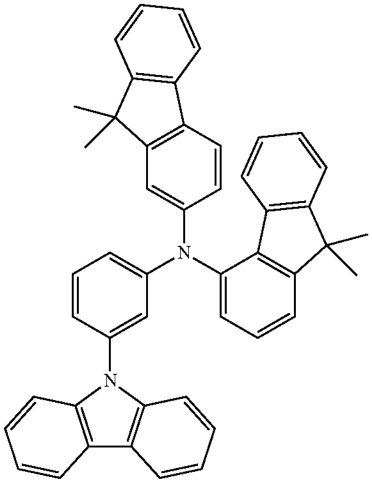 P332 |
| 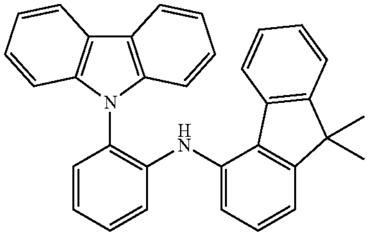 S169 | 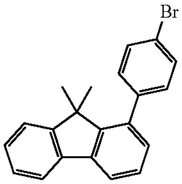 CAS-1786416-87-2 | 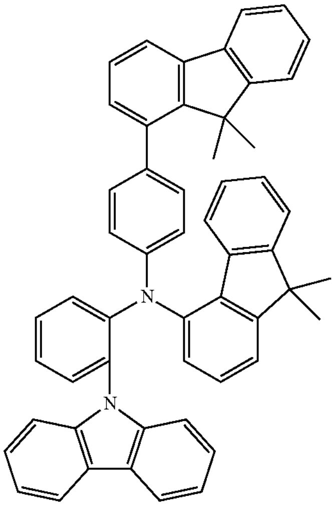 P333 |
| 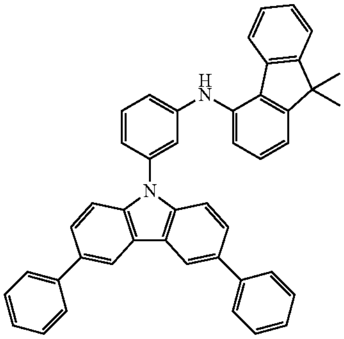 S170 | 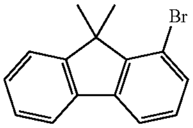 CAS-1225053-54-2 | 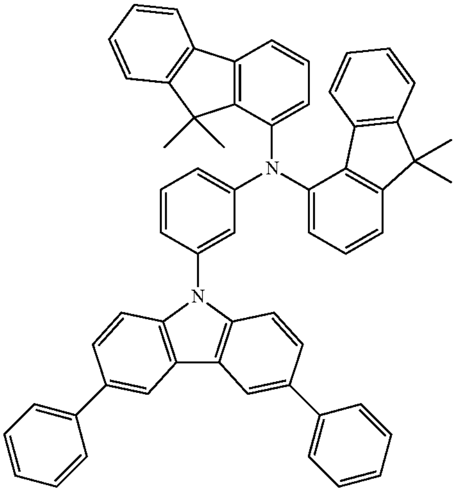 P334 |

-continued
| Reactant 1 | Reactant 2 | Product |
| --- | --- | --- |
| 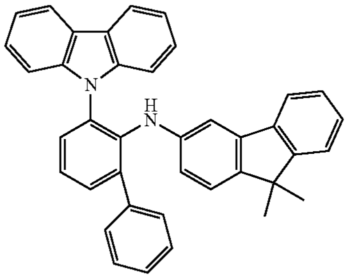 S171 | 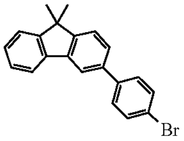 CAS-1421789-06-1 | 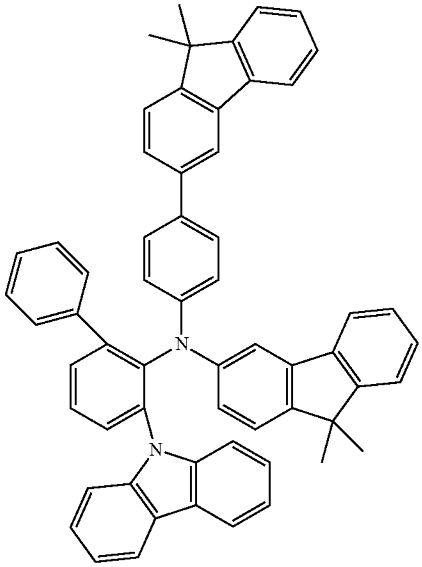 P335 |
| 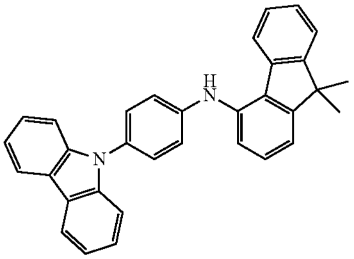 S167 | 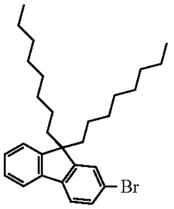 CAS-302554-80-9 | 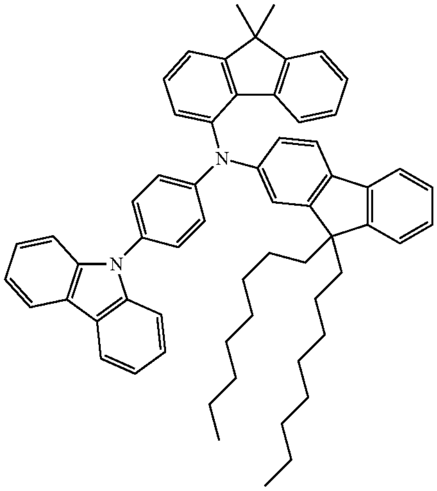 P336 |

-continued
| Reactant 1 | Reactant 2 | Product |
|---|---|---|
| 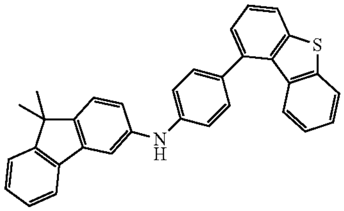 S134 | 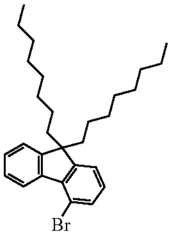 CAS-1469898-60-9 | 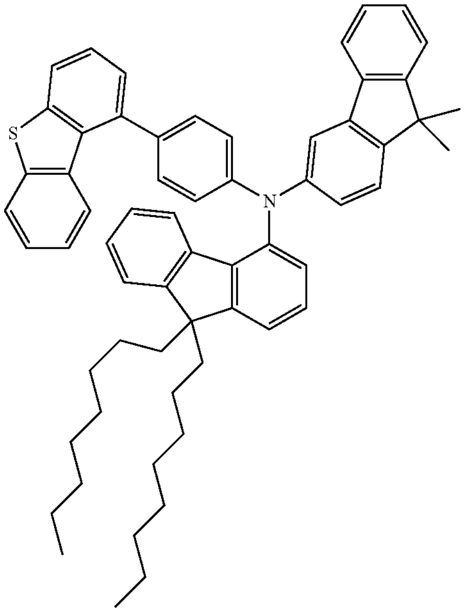 P337 |
| 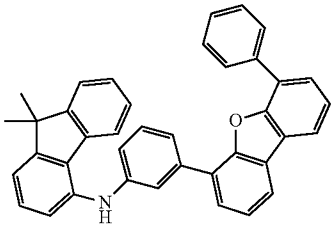 S112 | 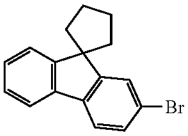 CAS-797056-47-4 | 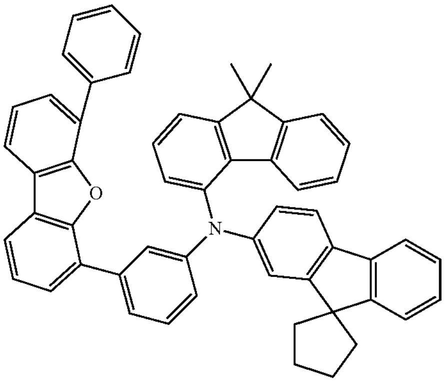 P338 |
| 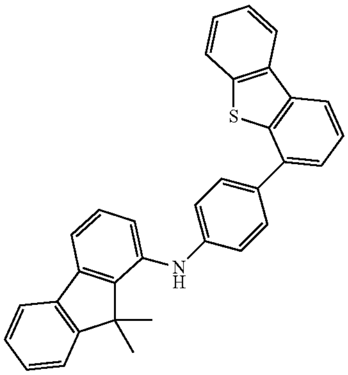 S105 | 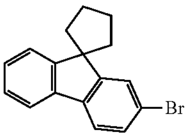 CAS-797056-47-4 | 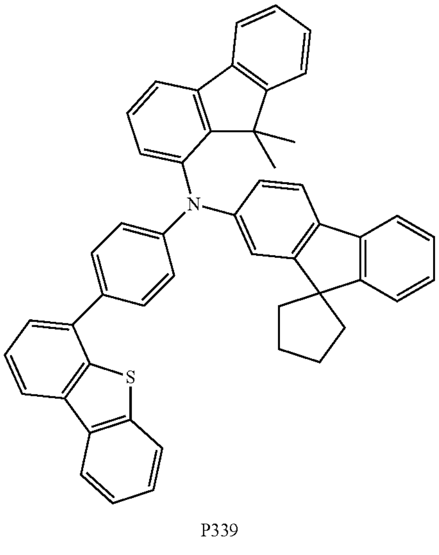 P339 |

-continued

| Reactant 1 | Reactant 2 | Product |
|---|---|---|
| 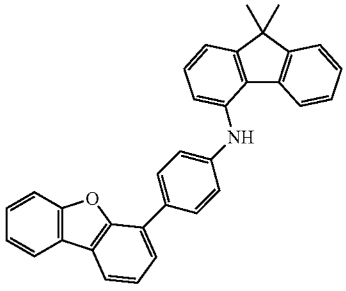 CAS-1933454-49-9 | 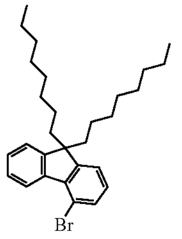 CAS-1469898-60-9 | 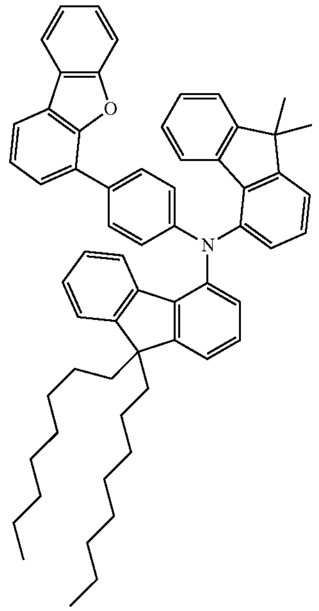 P340 |

B) Device Examples

The OLEDs are produced as follows:

Glass plaques coated with structured ITO (indium tin oxide) of thickness 50 nm are treated prior to coating with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/hole blocker layer (HBL)/electron transport layer (ETL) and finally a cathode. The cathode is formed by an aluminium layer of thickness 100 nm. The exact structure of the OLEDs can be found in Table 1. The materials required for production of the OLEDs are shown in Table 2. The data of the OLEDs are listed in Table 3.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:IV1:TEG1 (55%:35%:10%) mean here that the material IC1 is present in the layer in a proportion by volume of 55%, IV1 in a proportion of 35% and TEG1 in a proportion of 10%.

Analogously, the electron transport layer also consists of a mixture of two materials.

TABLE 1

Structure of the OLEDs

| Ex. | HIL thickness | HTL thickness | EBL thickness | EML thickness | HBL thickness | ETL thickness |
|---|---|---|---|---|---|---|
| C1 | HATCN 5 nm | SpMA1 230 nm | SpMA2 20 nm | IC1:PA1:TEG1 (59%:29%:12%) 30 nm | ST2 10 nm | ST2:LiQ (50%:50%) 30 nm |
| I2 | HATCN 5 nm | SpMA1 230 nm | SpMA2 20 nm | IC1:IV1:TEG1 (59%:29%:12%) 30 nm | ST2 10 nm | ST2:LiQ (50%:50%) 30 nm |
| I2 | HATCN 5 nm | SpMA1 230 nm | SpMA2 20 nm | IC1:IV2:TEG1 (59%:29%:12%) 30 nm | ST2 10 nm | ST2:LiQ (50%:50%) 30 nm |

TABLE 2
| Structural formulae of the materials for the OLEDs |
|---|
| 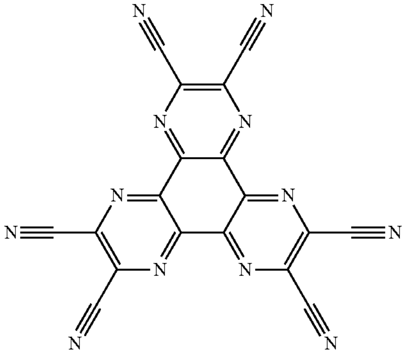 |
| HATCN |
| 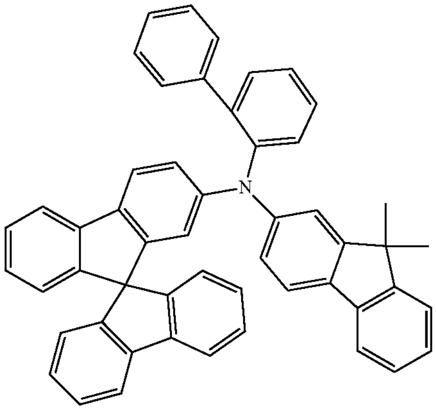 |
| SpMA1 |
| 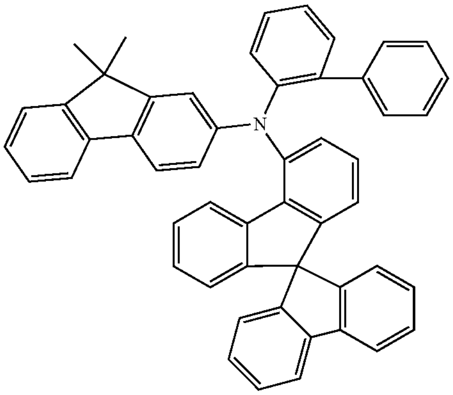 |
| SpMA2 |
TABLE 2-continued
| Structural formulae of the materials for the OLEDs |
|---|
| 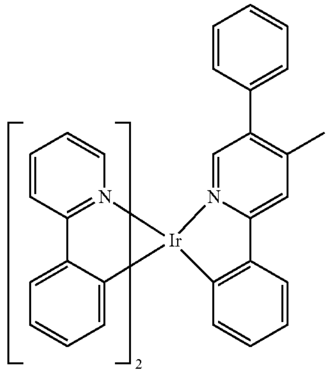 |
| TEG1 |
| 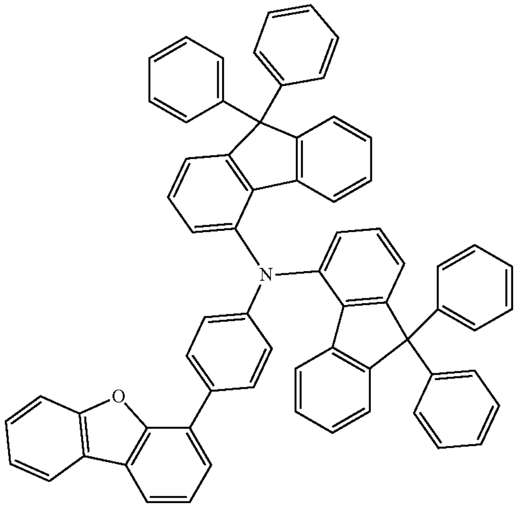 |
| PA1 |
| 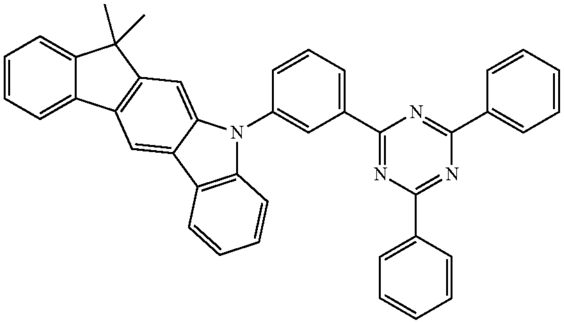 |
| IC1 |

TABLE 2-continued

Structural formulae of the materials for the OLEDs

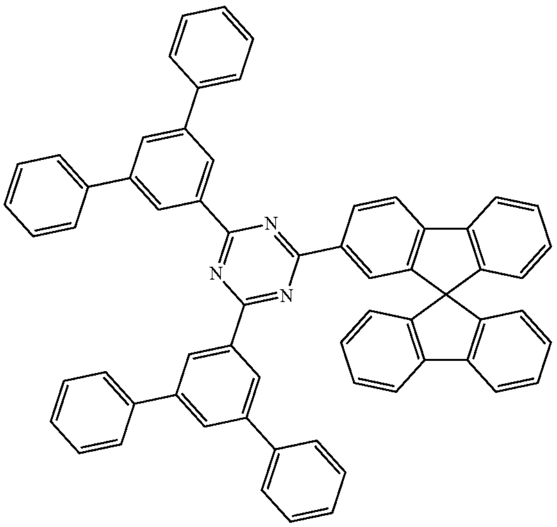

ST2

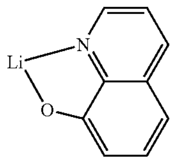

LiQ

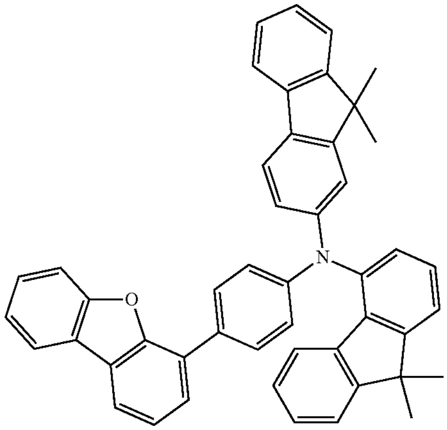

IV1 (P200)

TABLE 2-continued

Structural formulae of the materials for the OLEDs

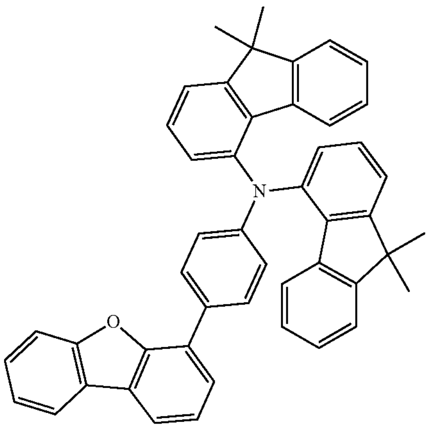

IV2 (P1)

The OLEDs are characterized in a standard manner. For this purpose, the electroluminescence spectra, the current efficiency (CE, measured in cd/A) and the external quantum efficiency (EQE, measured in %) are determined as a function of luminance, calculated from current-voltage-luminance characteristics assuming Lambertian emission characteristics, as is the lifetime. The electroluminescence spectra are determined at a luminance of 1000 cd/m$^2$, and the CIE 1931 x and y colour coordinates are calculated therefrom. The parameter U1000 in Table 3 refers to the voltage which is required for a luminance of 1000 cd/m$^2$. CE1000 and EQE1000 respectively denote the current efficiency and external quantum efficiency that are attained at 1000 cd/m$^2$.

The lifetime LT is defined as the time after which the luminance drops from the starting luminance to a certain proportion L1 in the course of operation with constant current density $j_0$. A figure of L1=80% in Table 3 means that the lifetime reported in the LT column corresponds to the time after which the luminance falls to 80% of its starting value.

The inventive compounds IV1 and IV2 are used in Examples 11 and 12 as matrix material in an emission layer comprising a green triplet emitter. Very good results are obtained for the abovementioned performance data (Table 3a).

TABLE 3a

Data of the OLEDs

| Ex. | U1000 (V) | CE1000 (cd/A) | EQE 1000 (%) | CIE x/y at 1000 cd/m$^2$ | $j_0$ (mA/cm$^2$) | L1 (%) | LT (h) |
|---|---|---|---|---|---|---|---|
| I1 | 3.2 | 73 | 19.5 | 0.33/0.63 | 20 | 80 | 440 |
| I2 | 3.1 | 70 | 19.0 | 0.35/0.62 | 20 | 80 | 700 |

According to the model of examples 11 and 12, by use of further compounds of the invention, as shown in Table 4, OLEDs with excellent performance data are obtained, which demonstrates the broad applicability of the compounds of the invention. The compounds of the invention are notable for a very good lifetime in the examples.

TABLE 4
P6
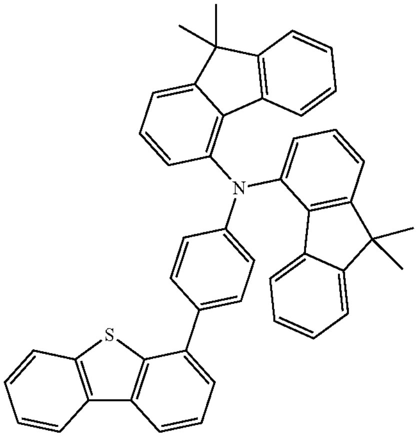 [SMILES: CC1(C)c2ccccc2-c2c(N(c3ccc(-c4cccc5c4sc4ccccc45)cc3)c3cccc4c3-c3ccccc3C4(C)C)cccc21]
P9
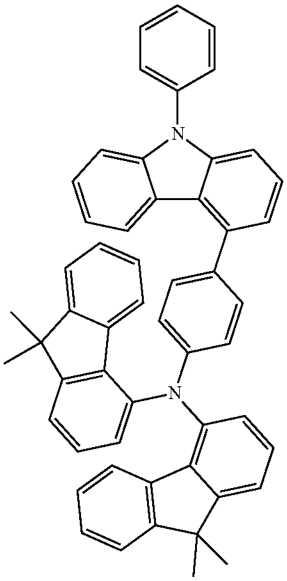 [SMILES: CC1(C)c2ccccc2-c2c(N(c3ccc(-c4cccc5c4c4ccccc4n5-c4ccccc4)cc3)c3cccc4c3-c3ccccc3C4(C)C)cccc21]
P14
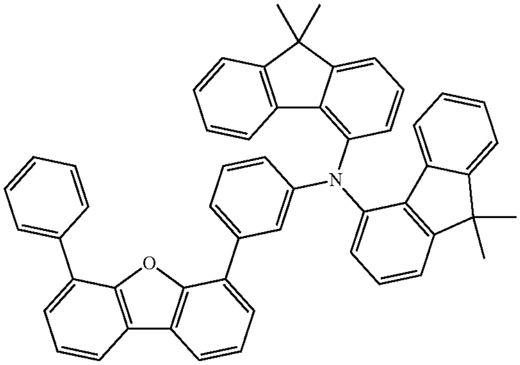 [SMILES: CC1(C)c2ccccc2-c2c(N(c3cccc(-c4cccc5c4oc4c(-c6ccccc6)cccc45)c3)c3cccc4c3-c3ccccc3C4(C)C)cccc21]

TABLE 4-continued
P16
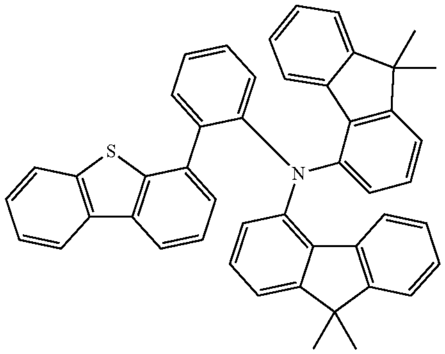 [SMILES: CC1(C)c2ccccc2-c2c(N(c3ccccc3-c3cccc4c3sc3ccccc34)c3cccc4c3-c3ccccc3C4(C)C)cccc21]
P19
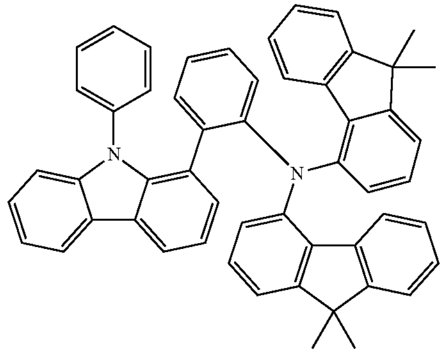 [SMILES: CC1(C)c2ccccc2-c2c(N(c3ccccc3-c3cccc4c5ccccc5n(-c5ccccc5)c34)c3cccc4c3-c3ccccc3C4(C)C)cccc21]
P22
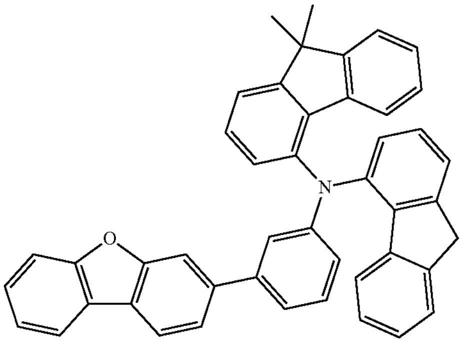 [SMILES: CC1(C)c2ccccc2-c2c(N(c3cccc(-c4ccc5c(c4)oc4ccccc45)c3)c3cccc4c3-c3ccccc3C4)cccc21]
P27
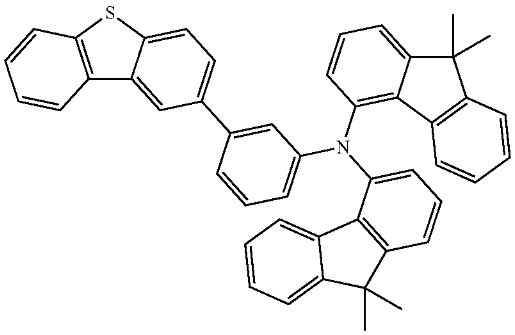 [SMILES: CC1(C)c2ccccc2-c2c(N(c3cccc(-c4ccc5sc6ccccc6c5c4)c3)c3cccc4c3-c3ccccc3C4(C)C)cccc21]

TABLE 4-continued
P46
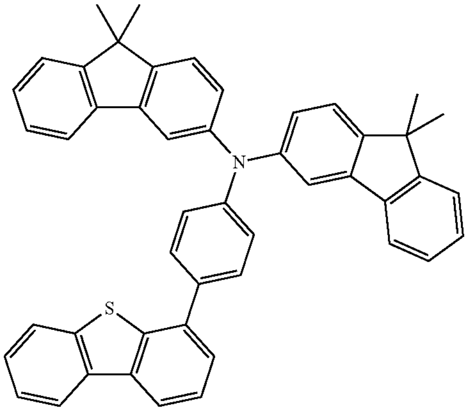 [SMILES: CC1(C)c2ccccc2-c2cc(N(c3ccc(-c4cccc5c4sc4ccccc45)cc3)c3ccc4c(c3)-c3ccccc3C4(C)C)ccc21]
P48
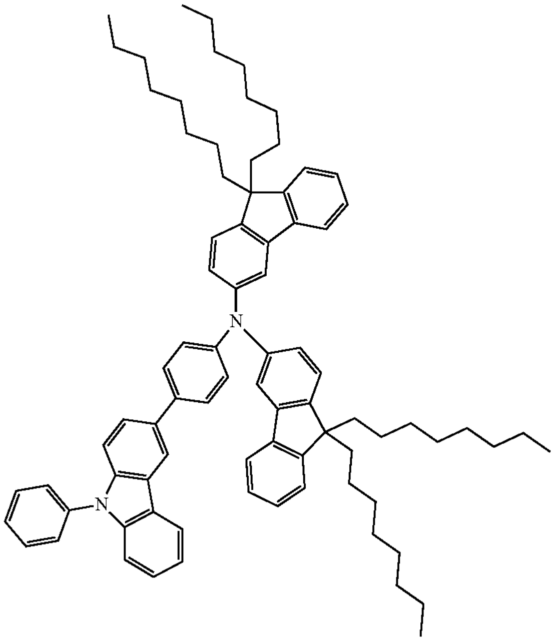 [SMILES: CCCCCCCCC1(CCCCCCCC)c2ccccc2-c2cc(N(c3ccc(-c4ccc5c(c4)c4ccccc4n5-c4ccccc4)cc3)c3ccc4c(c3)-c3ccccc3C4(CCCCCCCC)CCCCCCCC)ccc21]
P50
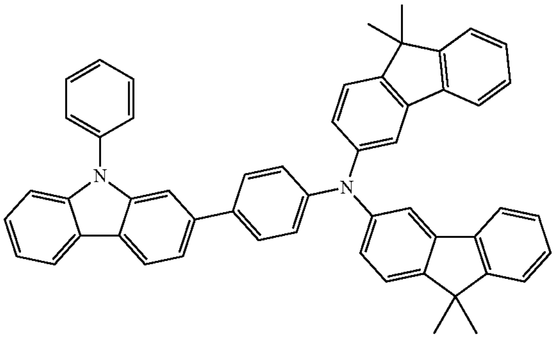 [SMILES: CC1(C)c2ccccc2-c2cc(N(c3ccc(-c4ccc5c6ccccc6n(-c6ccccc6)c5c4)cc3)c3ccc4c(c3)-c3ccccc3C4(C)C)ccc21]

TABLE 4-continued
P61
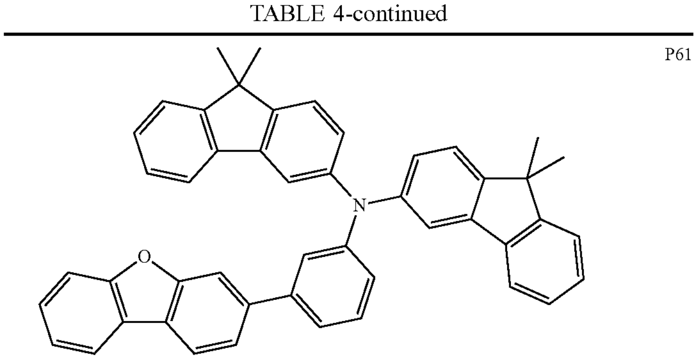
P70
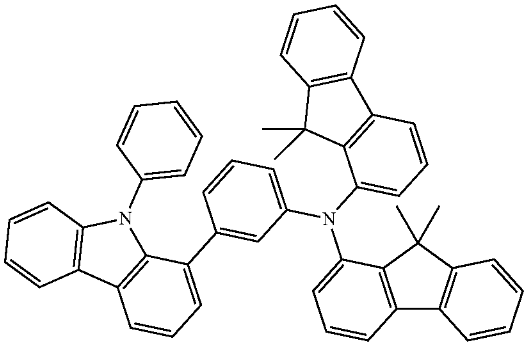 [SMILES: CC1(C)c2ccccc2-c2cccc(N(c3cccc(-c4cccc5c6ccccc6n(-c6ccccc6)c45)c3)c3cccc4c3C(C)(C)c3ccccc3-4)c21]
P74
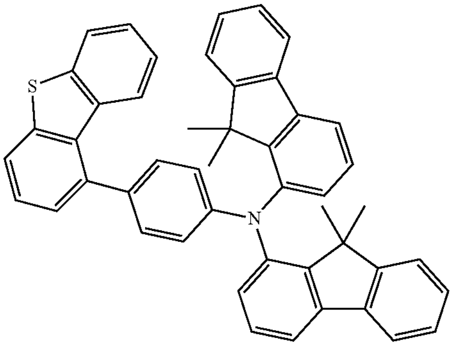 [SMILES: CC1(C)c2ccccc2-c2cccc(N(c3ccc(-c4cccc5sc6ccccc6c45)cc3)c3cccc4c3C(C)(C)c3ccccc3-4)c21]
P85
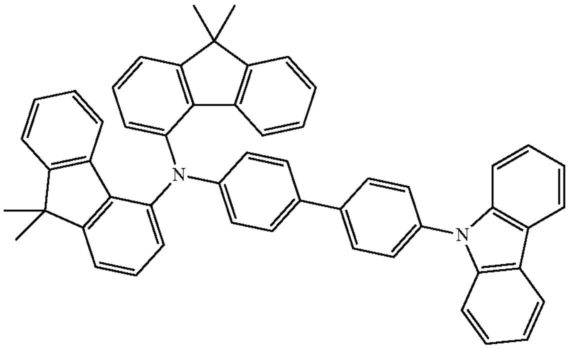 [SMILES: CC1(C)c2ccccc2-c2c(N(c3ccc(-c4ccc(-n5c6ccccc6c6ccccc65)cc4)cc3)c3cccc4c3-c3ccccc3C4(C)C)cccc21]

TABLE 4-continued
P86
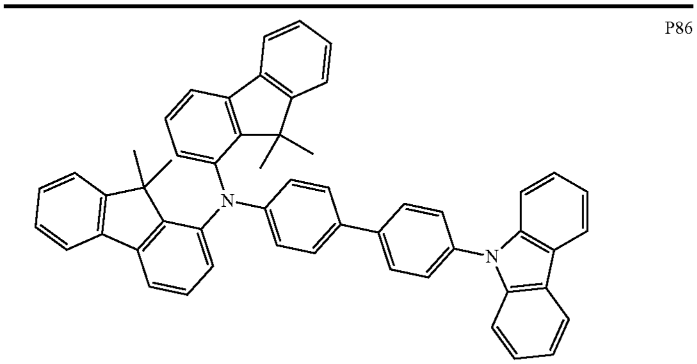
P105
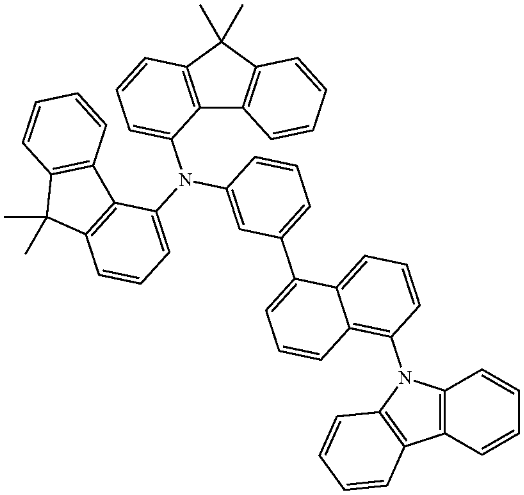 [SMILES: CC1(C)c2ccccc2-c2c(N(c3cccc(-c4cccc5c(-n6c7ccccc7c7ccccc76)cccc45)c3)c3cccc4c3-c3ccccc3C4(C)C)cccc21]
P109
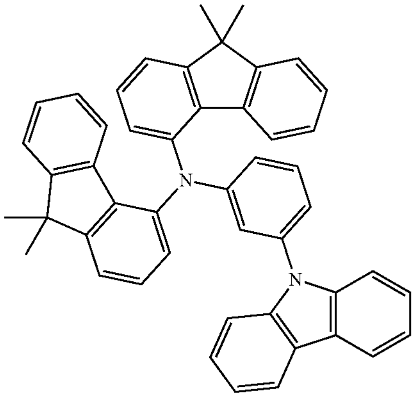 [SMILES: CC1(C)c2ccccc2-c2c(N(c3cccc(-n4c5ccccc5c5ccccc54)c3)c3cccc4c3-c3ccccc3C4(C)C)cccc21]
P113
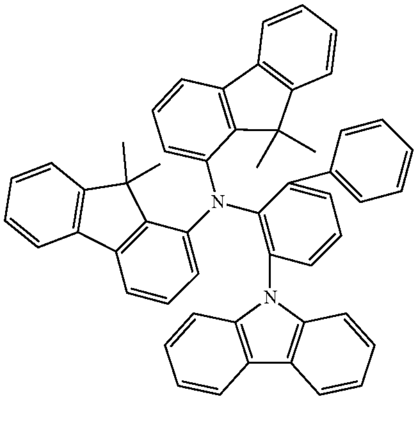 [SMILES: CC1(C)c2ccccc2-c2cccc(N(c3cccc4c3C(C)(C)c3ccccc3-4)c3c(-c4ccccc4)cccc3-n3c4ccccc4c4ccccc43)c21]

TABLE 4-continued
P203
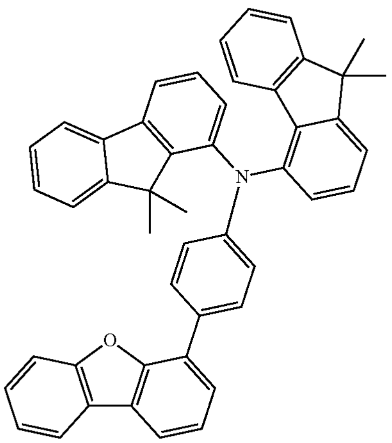 [SMILES: CC1(C)c2ccccc2-c2c(N(c3ccc(-c4cccc5c4oc4ccccc45)cc3)c3cccc4c3C(C)(C)c3ccccc3-4)cccc21]
P205
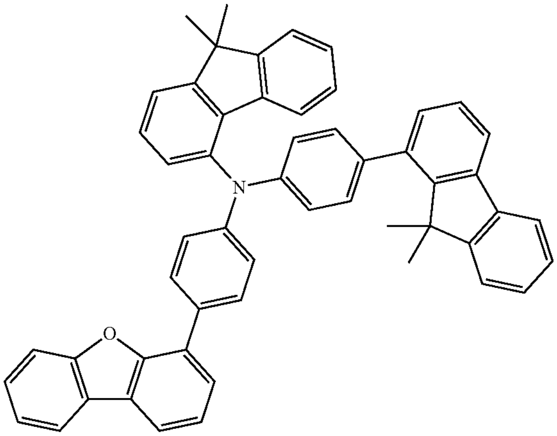 [SMILES: CC1(C)c2ccccc2-c2c(N(c3ccc(-c4cccc5c4C(C)(C)c4ccccc4-5)cc3)c3ccc(-c4cccc5c4oc4ccccc45)cc3)cccc21]
P217
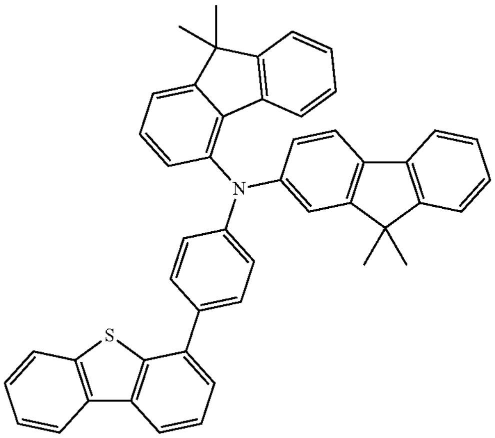 [SMILES: CC1(C)c2ccccc2-c2ccc(N(c3ccc(-c4cccc5c4sc4ccccc45)cc3)c3cccc4c3-c3ccccc3C4(C)C)cc21]

TABLE 4-continued
P226
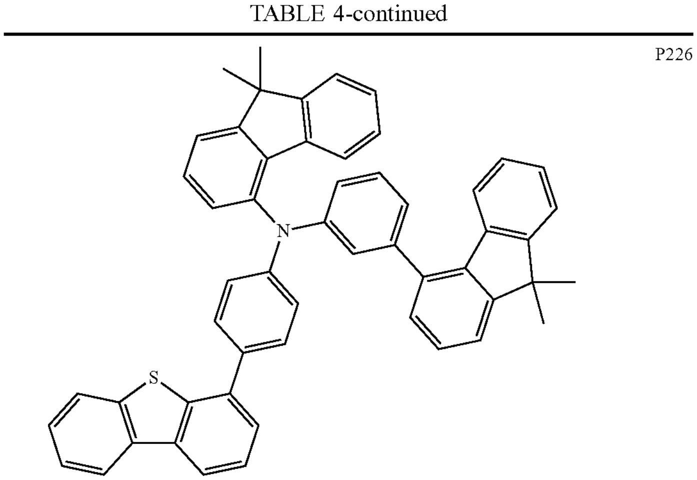
P229
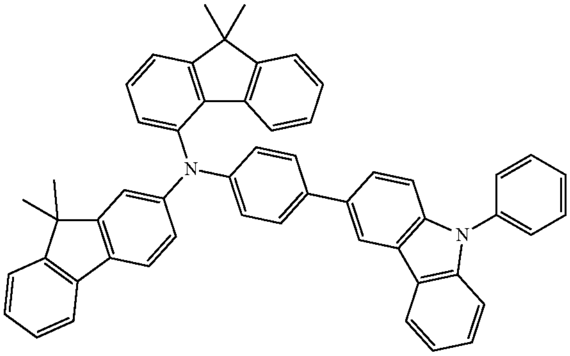 [SMILES: CC1(C)c2ccccc2-c2ccc(N(c3ccc(-c4ccc5c(c4)c4ccccc4n5-c4ccccc4)cc3)c3cccc4c3-c3ccccc3C4(C)C)cc21]
P230
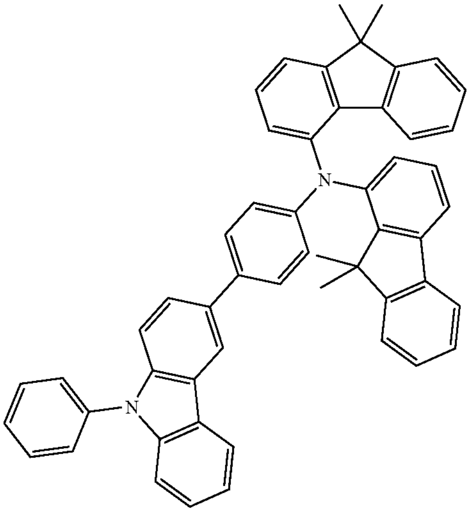 [SMILES: CC1(C)c2ccccc2-c2c(N(c3ccc(-c4ccc5c(c4)c4ccccc4n5-c4ccccc4)cc3)c3cccc4c3C(C)(C)c3ccccc3-4)cccc21]
P237
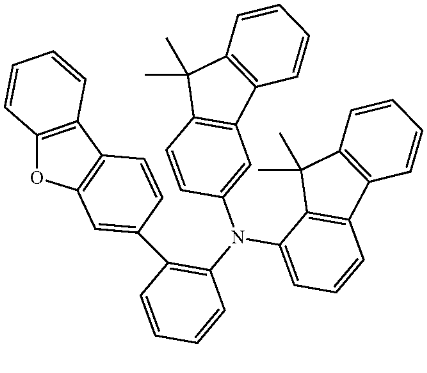 [SMILES: CC1(C)c2ccccc2-c2cc(N(c3ccccc3-c3ccc4c(c3)oc3ccccc34)c3cccc4c3C(C)(C)c3ccccc3-4)ccc21]

TABLE 4-continued
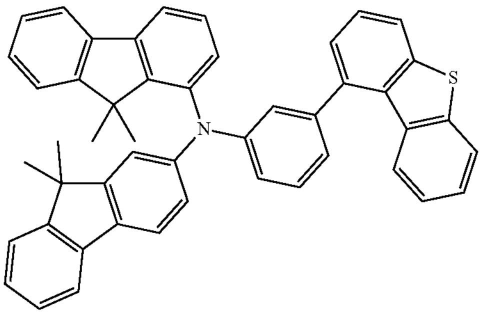 [SMILES: CC1(C)c2ccccc2-c2ccc(N(c3cccc(-c4cccc5sc6ccccc6c45)c3)c3cccc4c3C(C)(C)c3ccccc3-4)cc21]
P239
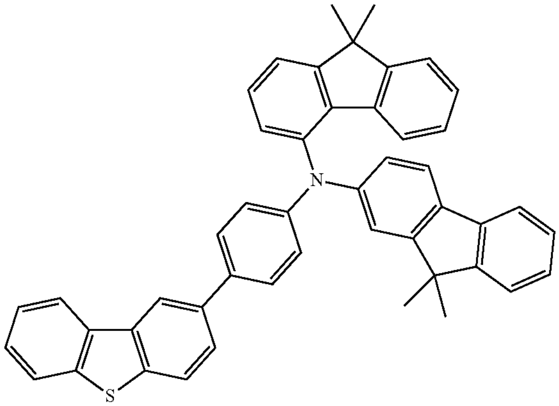 [SMILES: CC1(C)c2ccccc2-c2ccc(N(c3ccc(-c4ccc5sc6ccccc6c5c4)cc3)c3cccc4c3-c3ccccc3C4(C)C)cc21]
P251
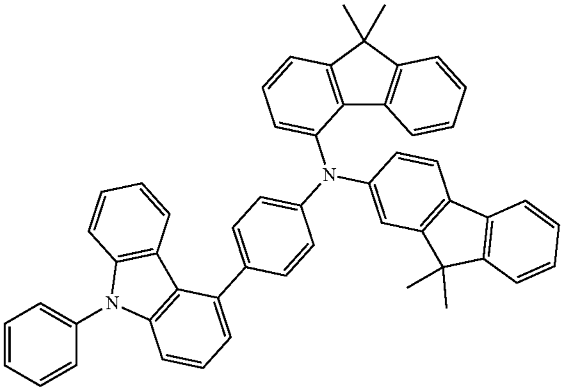 [SMILES: CC1(C)c2ccccc2-c2ccc(N(c3ccc(-c4cccc5c4c4ccccc4n5-c4ccccc4)cc3)c3cccc4c3-c3ccccc3C4(C)C)cc21]
P256
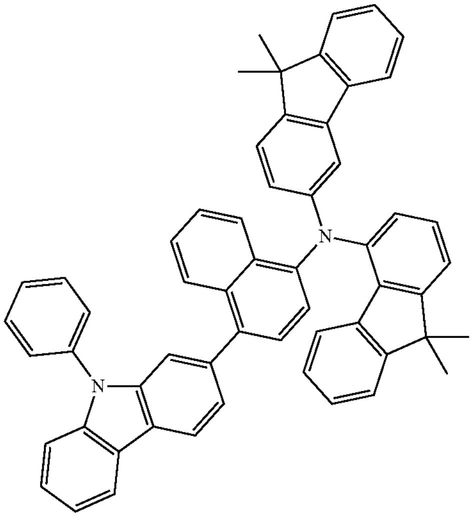 [SMILES: CC1(C)c2ccccc2-c2cc(N(c3cccc4c3-c3ccccc3C4(C)C)c3ccc(-c4ccc5c6ccccc6n(-c6ccccc6)c5c4)c4ccccc34)ccc21]
P261

TABLE 4-continued
P266
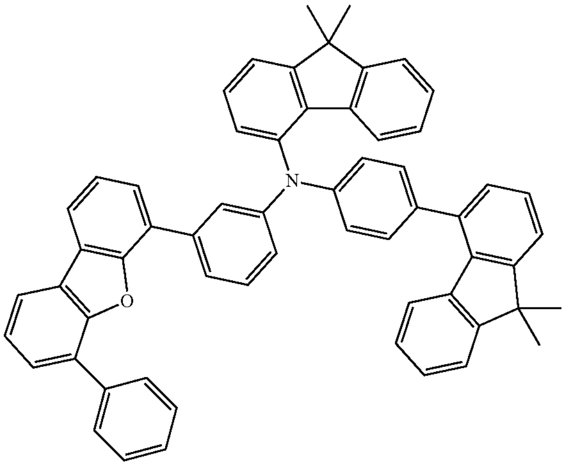 [SMILES: CC1(C)c2ccccc2-c2c(-c3ccc(N(c4cccc(-c5cccc6c5oc5c(-c7ccccc7)cccc56)c4)c4cccc5c4-c4ccccc4C5(C)C)cc3)cccc21]
P273
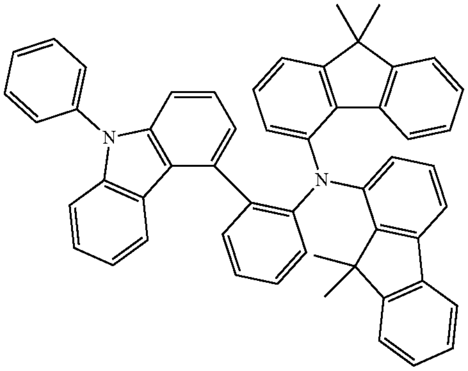 [SMILES: CC1(C)c2ccccc2-c2c(N(c3ccccc3-c3cccc4c3c3ccccc3n4-c3ccccc3)c3cccc4c3C(C)(C)c3ccccc3-4)cccc21]
P281
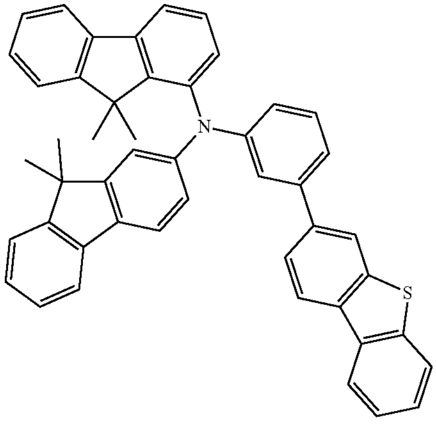 [SMILES: CC1(C)c2ccccc2-c2ccc(N(c3cccc(-c4ccc5c(c4)sc4ccccc45)c3)c3cccc4c3C(C)(C)c3ccccc3-4)cc21]

TABLE 4-continued
P289
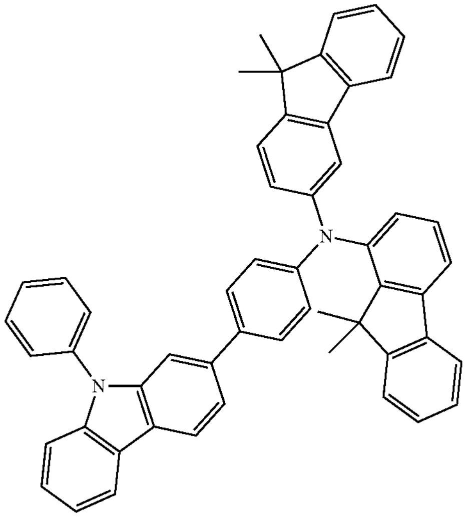 [SMILES: CC1(C)c2ccccc2-c2cc(N(c3ccc(-c4ccc5c6ccccc6n(-c6ccccc6)c5c4)cc3)c3cccc4c3C(C)(C)c3ccccc3-4)ccc21]
P291
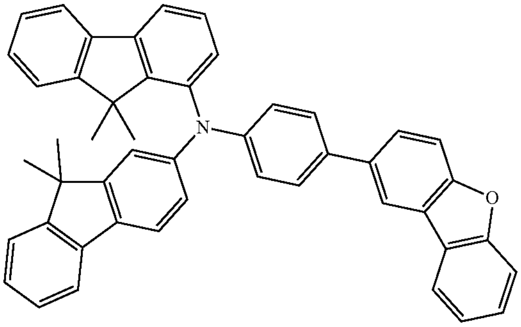 [SMILES: CC1(C)c2ccccc2-c2ccc(N(c3ccc(-c4ccc5oc6ccccc6c5c4)cc3)c3cccc4c3C(C)(C)c3ccccc3-4)cc21]
P298
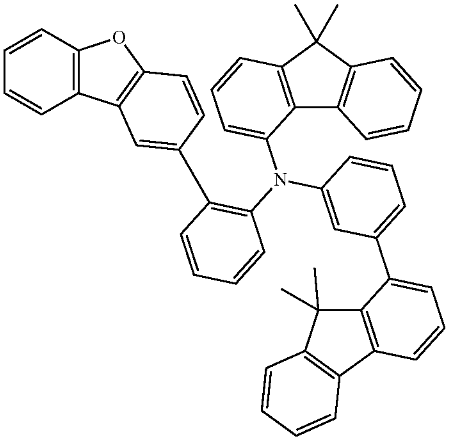 [SMILES: CC1(C)c2ccccc2-c2c(N(c3cccc(-c4cccc5c4C(C)(C)c4ccccc4-5)c3)c3ccccc3-c3ccc4oc5ccccc5c4c3)cccc21]

TABLE 4-continued
P305
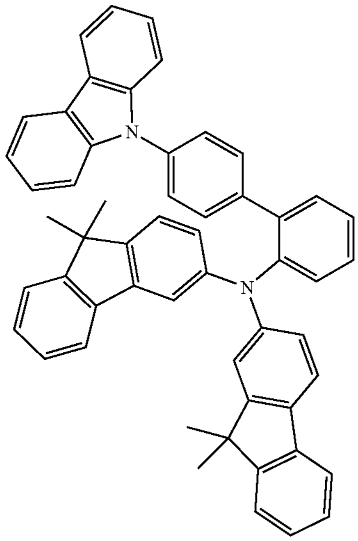 [SMILES: CC1(C)c2ccccc2-c2cc(N(c3ccc4c(c3)C(C)(C)c3ccccc3-4)c3ccccc3-c3ccc(-n4c5ccccc5c5ccccc54)cc3)ccc21]
P314
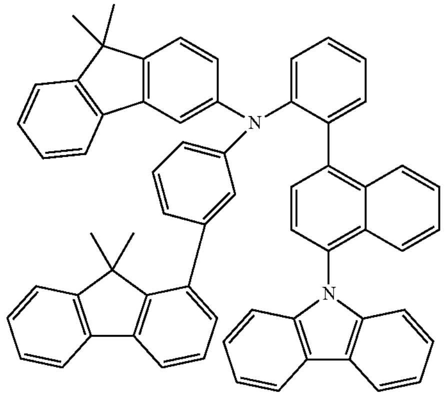 [SMILES: CC1(C)c2ccccc2-c2cc(N(c3cccc(-c4cccc5c4C(C)(C)c4ccccc4-5)c3)c3ccccc3-c3ccc(-n4c5ccccc5c5ccccc54)c4ccccc34)ccc21]
P315
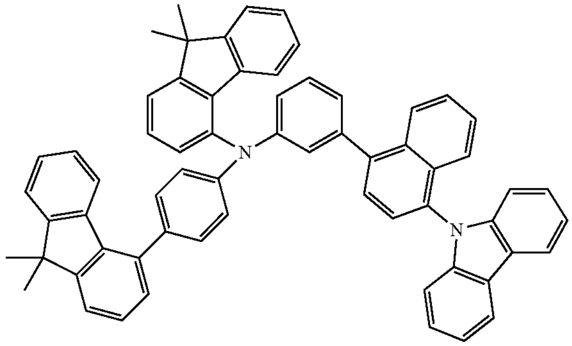 [SMILES: CC1(C)c2ccccc2-c2c(-c3ccc(N(c4cccc(-c5ccc(-n6c7ccccc7c7ccccc76)c6ccccc56)c4)c4cccc5c4-c4ccccc4C5(C)C)cc3)cccc21]

TABLE 4-continued
P321
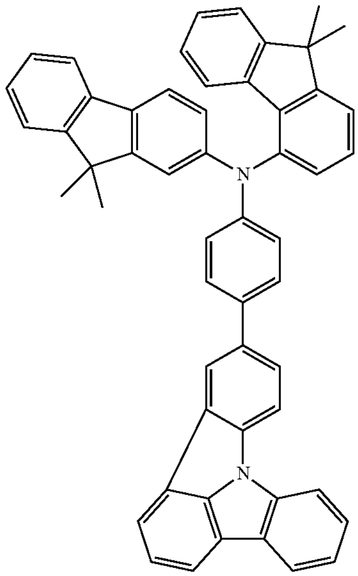 [SMILES: CC1(C)c2ccccc2-c2ccc(N(c3ccc(-c4ccc5c(c4)c4cccc6c7ccccc7n5c64)cc3)c3cccc4c3-c3ccccc3C4(C)C)cc21]
P327
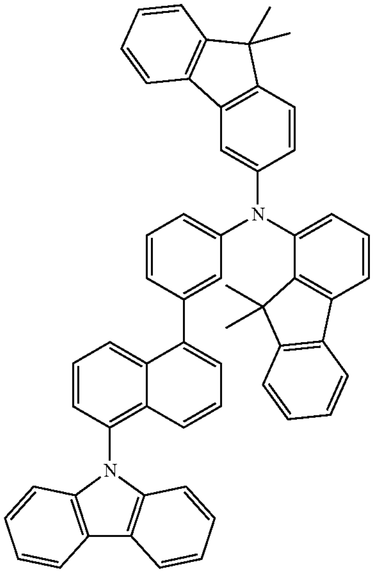 [SMILES: CC1(C)c2ccccc2-c2cc(N(c3cccc(-c4cccc5c(-n6c7ccccc7c7ccccc76)cccc45)c3)c3cccc4c3C(C)(C)c3ccccc3-4)ccc21]
P331
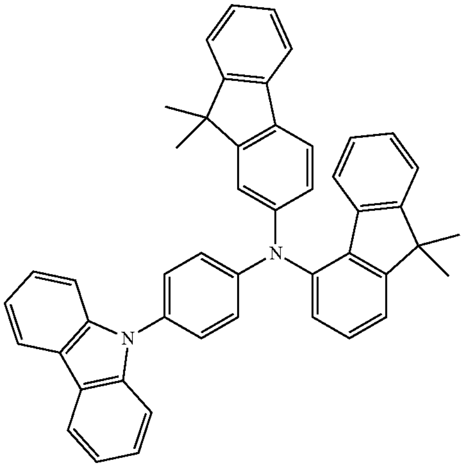 [SMILES: CC1(C)c2ccccc2-c2ccc(N(c3ccc(-n4c5ccccc5c5ccccc54)cc3)c3cccc4c3-c3ccccc3C4(C)C)cc21]

TABLE 4-continued
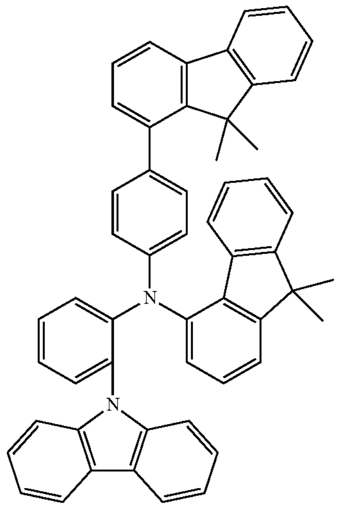 [SMILES: CC1(C)c2ccccc2-c2c(N(c3ccc(-c4cccc5c4C(C)(C)c4ccccc4-5)cc3)c3ccccc3-n3c4ccccc4c4ccccc43)cccc21]
P333
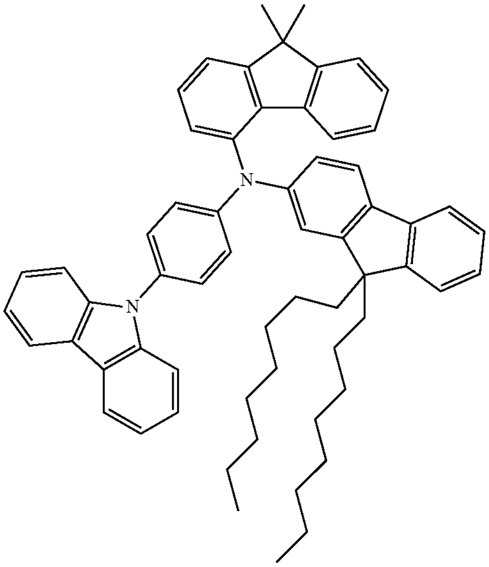 [SMILES: CCCCCCCCC1(CCCCCCCC)c2ccccc2-c2ccc(N(c3ccc(-n4c5ccccc5c5ccccc54)cc3)c3cccc4c3-c3ccccc3C4(C)C)cc21]
P336
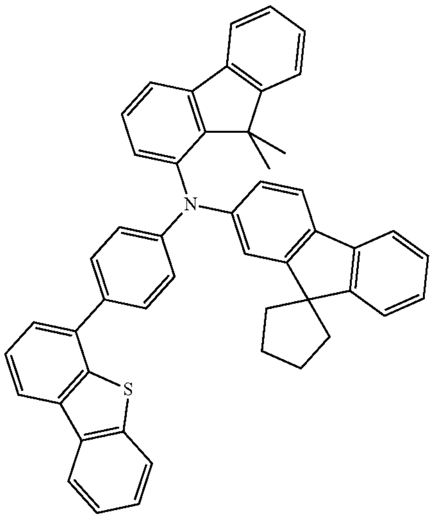 [SMILES: CC1(C)c2ccccc2-c2cccc(N(c3ccc(-c4cccc5c4sc4ccccc45)cc3)c3ccc4c(c3)C3(CCCC3)c3ccccc3-4)c21]
P339

TABLE 4-continued
P340
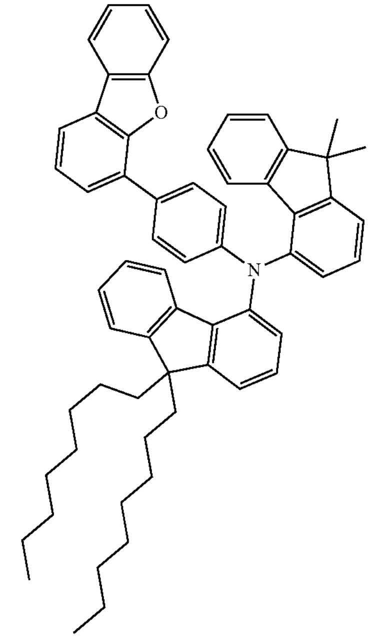 [SMILES: CCCCCCCCC1(CCCCCCCC)c2ccccc2-c2c(N(c3ccc(-c4cccc5c4oc4ccccc45)cc3)c3cccc4c3-c3ccccc3C4(C)C)cccc21]
P204
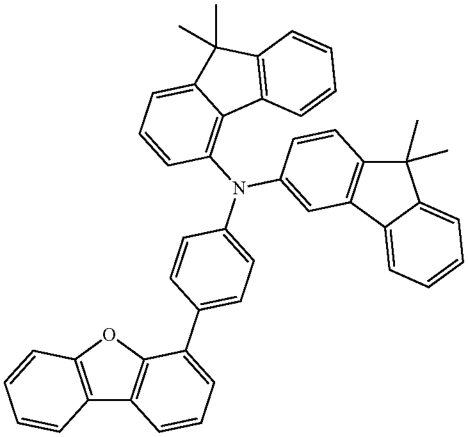 [SMILES: CC1(C)c2ccccc2-c2cc(N(c3ccc(-c4cccc5c4oc4ccccc45)cc3)c3cccc4c3-c3ccccc3C4(C)C)ccc21]
P231
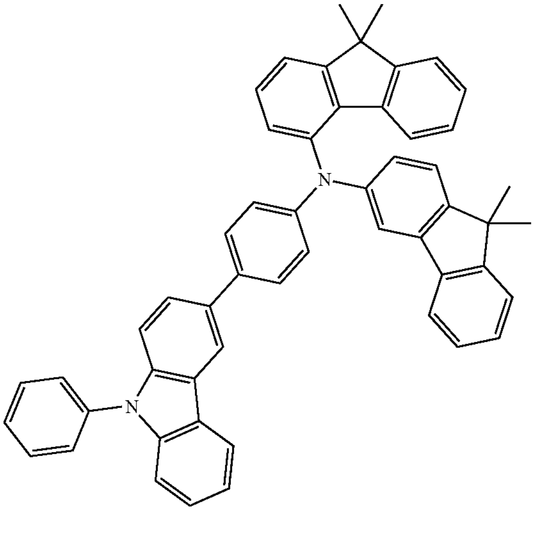 [SMILES: CC1(C)c2ccccc2-c2cc(N(c3ccc(-c4ccc5c(c4)c4ccccc4n5-c4ccccc4)cc3)c3cccc4c3-c3ccccc3C4(C)C)ccc21]

TABLE 4-continued

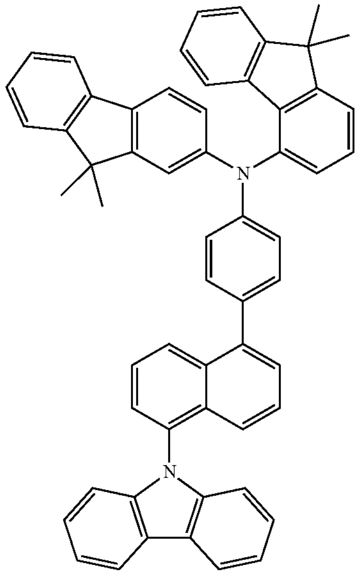 [SMILES: CC1(C)c2ccccc2-c2ccc(N(c3ccc(-c4cccc5c(-n6c7ccccc7c7ccccc76)cccc45)cc3)c3cccc4c3-c3ccccc3C4(C)C)cc21]

P328

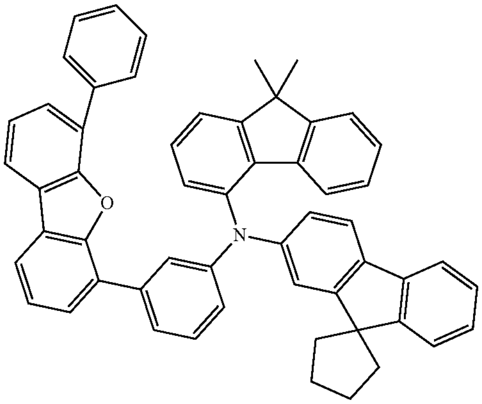 [SMILES: CC1(C)c2ccccc2-c2c(N(c3cccc(-c4cccc5c4oc4c(-c6ccccc6)cccc45)c3)c3ccc4c(c3)C3(CCCC3)c3ccccc3-4)cccc21]

P338

At the same time, good performance data, especially good lifetimes, are likewise achieved.

In the direct comparison of the two compounds PA1 and IV2 in the OLEDs C1 (prior art, with PA1) and 12 (inventive, with IV2), it is found that the OLED comprising the inventive compound IV2 has a much better lifetime, with slightly reduced operating voltage.

TABLE 3b

Data of the OLEDs

| Ex. | U1000 (V) | CIE x/y at 1000 cd/$m^2$ | $j_0$ (mA/$cm^2$) | L1 (%) | LT (h) |
|---|---|---|---|---|---|
| C1 | 3.3 | 0.34/0.62 | 20 | 80 | 250 |
| I2 | 3.1 | 0.35/0.62 | 20 | 80 | 700 |

The invention claimed is:

1. A compound of a formula (I-A-4)

formula (I-A-4)

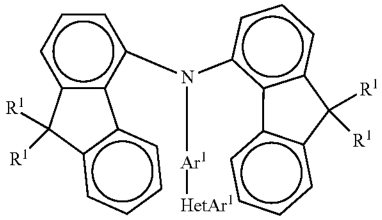

where the free positions on the fluorenyl groups may each be substituted by an $R^2$ radical, and where, in addition:

$R^1$ is the same or different at each instance and is selected from straight-chain alkyl groups having 1 to 20 carbon atoms;

$Ar^1$ is benzene, which may be substituted by one or more $R^4$ radicals;

HetAr[1] is selected from dibenzofuran and dibenzothiophene, which may each be substituted by one or more $R^5$ radicals;

$R^2$ is selected, identically or differently, from H and D;

$R^4$ is selected, identically or differently, from H and D;

$R^5$ is selected, identically or differently, from H and D.

2. The compound according to claim 1, wherein $R^1$ is the same or different at each instance and is selected from straight-chain alkyl groups having 1 to 10 carbon atoms.

3. The compound according to claim 1, wherein $HetAr^1$ is dibenzofuran which may be substituted by one or more $R^5$ radicals.

4. The compound according to claim 1, wherein $R^2$, $R^4$ are H.

5. The compound according to claim 1, wherein the —$Ar^1$-$HetAr^1$ group conforms to the formula (H-1)

Formula (H-1)

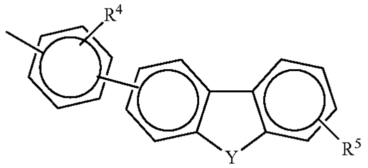

where Y is O S; and where $R^4$ is H;

and where the group is bonded to the nitrogen atom via the free bond.

6. Process for preparing the compound according to claim 1, wherein a compound $HetAr^1$—$Ar^1$—$NH_2$ where the variables that occur are as defined in claim 1 for formula (I-A-4) is reacted with a fluorene having a reactive X group in a Buchwald coupling reaction.

7. An oligomer, polymer or dendrimer containing one or more compounds of formula (I-A-4) according to claim 1, wherein the bond(s) to the polymer, oligomer or dendrimer may be localized at any desired positions substituted by $R^1$, $R^2$, $R^4$ or $R^5$ in formula (I-A-4).

8. A formulation comprising at least one compound according to claim 1 and at least one solvent.

9. A formulation comprising the polymer, oligomer or dendrimer according to claim 7, and at least one solvent.

10. An electronic device comprising at least one compound according to claim 1.

11. The electronic device according to claim 10, wherein the device is an organic electroluminescent device comprising anode, cathode and at least one emitting layer, where it is at least one organic layer of the device selected from emitting layers and hole-transporting layers that comprises the at least one compound.

12. The organic electroluminescent device according to claim 11, comprising anode, cathode and at least one emitting layer, wherein the at least one compound is present in an emitting layer in combination with at least one phosphorescent emitter.

13. The compound according to claim 1, characterized in that $R^2$ is H; and $R^4$ is H; and $R^5$ is H.

14. The compound according to claim 1, characterized in that $R^1$ is methyl.

15. The compound according to claim 1, characterized in that it conforms to one of the following formulae:

P1

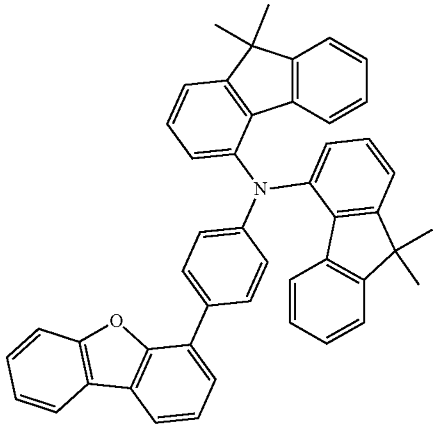

P6

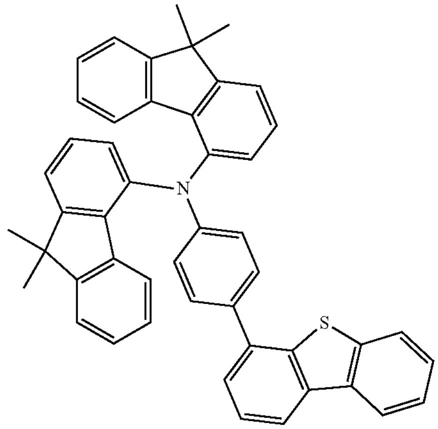

.

* * * * *